US007897601B2

(12) United States Patent
Chackalamannil et al.

(10) Patent No.: US 7,897,601 B2
(45) Date of Patent: Mar. 1, 2011

(54) CANNABINOID RECEPTOR MODULATORS

(75) Inventors: Samuel Chackalamannil, Califon, NJ (US); Mariappan V. Chelliah, Edison, NJ (US); Martin C. Clasby, Plainsboro, NJ (US); Keith A. Eagen, Long Valley, NJ (US); Jack D. Scott, Scotch Plains, NJ (US); Yuguang Wang, Monroe, NJ (US); Yan Xia, Edison, NJ (US); William J. Greenlee, Teaneck, NJ (US)

(73) Assignees: Intervet, Inc., Summit, NJ (US); Intervet International B.V., Boxmeer (NL)

( * ) Notice: Subject to any disclaimer, the term of this patent is extended or adjusted under 35 U.S.C. 154(b) by 690 days.

(21) Appl. No.: 11/653,558

(22) Filed: Jan. 16, 2007

(65) Prior Publication Data

US 2007/0197628 A1 Aug. 23, 2007

Related U.S. Application Data

(60) Provisional application No. 60/760,007, filed on Jan. 18, 2006, provisional application No. 60/846,965, filed on Sep. 25, 2006.

(51) Int. Cl.
*A61K 31/454* (2006.01)
*A61K 31/4035* (2006.01)
*A61K 31/5377* (2006.01)
*C07D 209/46* (2006.01)
*C07D 295/04* (2006.01)
*C07D 401/04* (2006.01)

(52) U.S. Cl. .................. 514/235.2; 514/323; 514/416; 544/109; 546/201; 548/466

(58) Field of Classification Search .................. 514/416, 514/235.2, 323; 548/466; 544/109; 546/201
See application file for complete search history.

(56) References Cited

U.S. PATENT DOCUMENTS

| 4,229,207 | A | 10/1980 | Laanio et al. |
|---|---|---|---|
| 4,839,360 | A | 6/1989 | Sato et al. |
| 4,917,896 | A | 4/1990 | Peck et al. |
| 4,983,597 | A | 1/1991 | Yang et al. |
| 5,073,544 | A | 12/1991 | Peck et al. |
| 5,185,349 | A | 2/1993 | Augelli-Szafran |
| 5,234,895 | A | 8/1993 | Felix |
| 5,306,817 | A | 4/1994 | Thiruvengadam et al. |
| 5,332,817 | A | 7/1994 | Desai et al. |
| 5,464,788 | A | 11/1995 | Bock et al. |
| 5,508,424 | A | 4/1996 | Carmosin et al. |
| 5,561,227 | A | 10/1996 | Thiruvengadam et al. |
| 5,580,883 | A | 12/1996 | Goto et al. |
| 5,624,920 | A | 4/1997 | McKittrick et al. |
| 5,624,941 | A | 4/1997 | Barth et al. |
| 5,631,365 | A | 5/1997 | Rosenblum et al. |
| 5,633,246 | A | 5/1997 | McKittrick et al. |
| 5,656,624 | A | 8/1997 | Vaccaro et al. |
| 5,688,785 | A | 11/1997 | Vaccaro |
| 5,688,787 | A | 11/1997 | Burnett et al. |
| 5,688,990 | A | 11/1997 | Shankar |
| 5,698,548 | A | 12/1997 | Dugar et al. |
| 5,756,470 | A | 5/1998 | Yumibe et al. |
| 5,756,504 | A | 5/1998 | Bock et al. |
| 5,763,444 | A | 6/1998 | Smith et al. |
| 5,767,115 | A | 6/1998 | Rosenblum et al. |
| 5,780,480 | A | 7/1998 | Wai et al. |
| 5,846,966 | A | 12/1998 | Rosenblum et al. |
| 6,093,812 | A | 7/2000 | Thiruvengadam et al. |
| 6,121,319 | A | 9/2000 | Somers |
| 6,147,090 | A | 11/2000 | DeNinno et al. |
| 6,147,250 | A | 11/2000 | Somers |
| 6,207,822 | B1 | 3/2001 | Thiruvengadam et al. |
| 6,369,077 | B1 | 4/2002 | Marquis et al. |
| RE37,721 | E | 5/2002 | Rosenblum et al. |
| 6,391,865 | B1 | 5/2002 | Baroudy et al. |
| 6,432,984 | B1 | 8/2002 | Barth et al. |
| 6,441,001 | B1 | 8/2002 | Watson et al. |
| 6,498,156 | B2 | 12/2002 | Glombik et al. |
| 6,528,529 | B1 | 3/2003 | Brann et al. |
| 6,627,757 | B2 | 9/2003 | Fu et al. |
| 6,642,258 | B1 | 11/2003 | Bourrie et al. |
| 6,703,386 | B2 | 3/2004 | Glombik et al. |
| 6,720,328 | B2 | 4/2004 | Aslanian et al. |

(Continued)

FOREIGN PATENT DOCUMENTS

EP 0230402 4/1993

(Continued)

OTHER PUBLICATIONS

Brettle, Roger, et al., "The Selective Reduction of αβ-Olefinic Amides", Tetrahedron Letters, 1980, pp. 2915-2916, vol. 21. (XP-002441723).

(Continued)

*Primary Examiner*—Taofiq A Solola
(74) *Attorney, Agent, or Firm*—David J. Kerwick

(57) ABSTRACT

A compound having the general structure of Formula (I):

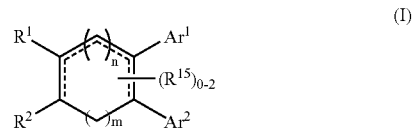

or a pharmaceutically acceptable salt, solvate, or ester thereof, is useful in treating diseases, disorders, or conditions such as obesity, metabolic disorders, addiction, diseases of the central nervous system, cardiovascular disorders, respiratory disorders, and gastrointestinal disorders.

67 Claims, No Drawings

U.S. PATENT DOCUMENTS

| | | | |
|---|---|---|---|
| 6,902,902 | B2 | 6/2005 | Unett et al. |
| 6,982,267 | B2 | 1/2006 | Stamford et al. |
| 7,105,505 | B2 | 9/2006 | Zeng et al. |
| 7,700,597 | B2 | 4/2010 | Gilbert et al. |
| 2001/0006972 | A1 | 7/2001 | Williams |
| 2002/0039774 | A1 | 4/2002 | Kramer et al. |
| 2002/0128252 | A1 | 9/2002 | Glombik et al. |
| 2002/0128253 | A1 | 9/2002 | Glombik et al. |
| 2002/0128476 | A1 | 9/2002 | Marquis, Jr. et al. |
| 2002/0137689 | A1 | 9/2002 | Glombik et al. |
| 2003/0087933 | A1 | 5/2003 | Blanchard et al. |
| 2003/0105028 | A1 | 6/2003 | Ghosal et al. |
| 2003/0109673 | A1 | 6/2003 | Yonghong |
| 2003/0139343 | A1 | 7/2003 | Ramakrishnan |
| 2003/0171588 | A1 | 9/2003 | Kahl et al. |
| 2003/0186960 | A1 | 10/2003 | Lauffer et al. |
| 2004/0063929 | A1 | 4/2004 | Tomiyama et al. |
| 2004/0058820 | A1 | 5/2004 | Hagmann et al. |
| 2004/0106800 | A1 | 6/2004 | Lange et al. |
| 2004/0142377 | A1 | 7/2004 | Unett et al. |
| 2004/0142922 | A1 | 7/2004 | Alanine et al. |
| 2004/0147572 | A1 | 7/2004 | Guba et al. |
| 2004/0167129 | A1 | 8/2004 | Mayweg et al. |
| 2004/0167185 | A1 | 8/2004 | Shankar et al. |
| 2004/0180927 | A1 | 9/2004 | Marquis, Jr. et al. |
| 2004/0235854 | A1 | 11/2004 | Kruse et al. |
| 2004/0254224 | A1 | 12/2004 | Foord et al. |
| 2005/0004178 | A1 | 1/2005 | Unett et al. |
| 2005/0154029 | A1 | 7/2005 | Unett et al. |
| 2005/0187263 | A1 | 8/2005 | Minnich et al. |
| 2005/0187280 | A1 | 8/2005 | Minnich et al. |
| 2007/0197628 | A1 | 8/2007 | Chackalamannil et al. |
| 2007/0203183 | A1 | 8/2007 | Gilbert et al. |
| 2009/0105208 | A1 | 4/2009 | Gilbert et al. |
| 2010/0029607 | A1 | 2/2010 | Gilbert et al. |

FOREIGN PATENT DOCUMENTS

| | | |
|---|---|---|
| EP | 0612745 | 8/1994 |
| EP | 0268222 | 3/1996 |
| JP | 3-200758 | 9/1991 |
| JP | 4-266830 | 9/1992 |
| JP | 4-364175 | 12/1992 |
| NL | 6603256 | 9/1967 |
| WO | WO 88/01131 | 2/1988 |
| WO | WO 93/02048 | 2/1993 |
| WO | WO 94/17038 | 8/1994 |
| WO | WO 95/08532 | 3/1995 |
| WO | WO 95/25443 | 9/1995 |
| WO | WO 96/01656 | 1/1996 |
| WO | WO 97/22597 | 6/1997 |
| WO | WO 98/56820 | 12/1998 |
| WO | WO 99/38498 | 8/1999 |
| WO | WO 00/38721 | 7/2000 |
| WO | WO 00/38727 | 7/2000 |
| WO | WO 00/66558 | 11/2000 |
| WO | WO 01/02372 | 1/2001 |
| WO | WO 01/58869 | 8/2001 |
| WO | WO 01/77320 | 10/2001 |
| WO | WO 01/94385 | 12/2001 |
| WO | WO 02/066464 | 8/2002 |
| WO | WO 02/098853 | 12/2002 |
| WO | WO 03/008559 | 1/2003 |
| WO | WO 03/027637 | 4/2003 |
| WO | WO 03/042174 | 5/2003 |
| WO | WO 03/051850 | 6/2003 |
| WO | WO 03/062392 | 7/2003 |
| WO | WO 03/082190 | 10/2003 |
| WO | WO 03/084942 | 10/2003 |
| WO | WO 2004/000803 | 12/2003 |
| WO | WO 2004/000804 | 12/2003 |
| WO | WO 2004/000805 | 12/2003 |
| WO | WO 2004/005247 | 1/2004 |
| WO | WO 2004/033431 | 4/2004 |
| WO | WO 2004/058255 | 7/2004 |
| WO | WO 2004/071378 | 8/2004 |
| WO | WO 2004/071394 | 8/2004 |
| WO | WO 2004/083388 | 9/2004 |
| WO | WO 2004/085408 | 10/2004 |
| WO | WO 2004/099157 | 11/2004 |
| WO | WO 2005/000775 | 1/2005 |
| WO | WO 2005/011677 | 2/2005 |
| WO | WO 2005/016867 | 2/2005 |
| WO | WO 2005/016870 | 2/2005 |
| WO | WO 2005/020988 | 3/2005 |
| WO | WO 2005/020992 | 3/2005 |
| WO | WO 2005/051937 | 6/2005 |
| WO | WO 2005/077950 | 8/2005 |
| WO | WO 2005/080386 | 9/2005 |
| WO | WO 2006/060461 | 6/2006 |
| WO | WO 2007/018459 | 2/2007 |
| WO | WO 2007/018460 | 2/2007 |
| WO | WO 2007/020502 | 2/2007 |
| WO | WO 2007/029773 | 3/2007 |
| WO | WO 2007/057687 | 5/2007 |
| WO | WO 2007/084319 | 7/2007 |
| WO | WO 2007/084450 | 7/2007 |
| WO | WO 2008/130616 | 10/2008 |
| WO | WO 2009/005645 | 1/2009 |
| WO | WO 2009/005671 | 1/2009 |

OTHER PUBLICATIONS

Gschwend, Heinz W., et al., "Intramolecular [x4-x2]-cycloadditions: Preparative and Kinetic Aspects", Angew. Chem. Internat. Edit. 1972, pp. 294-295, vol. 11, No. 4. (XP-009086254).

Gschwend, Heinz W., et al., "Rates of Intramolecular Diels-Alder Reactions of Pentadienylacrylamides", J. Org. Chem., 1973, pp. 2169-2175, vol. 38, No. 12. (XP-002441724).

Gerson, Fabian, et al., "The Radical Anions of 1,2-Diphenylcyclohexene and Structurally Related Compounds. Conformational ESR and ENDOR Studies", Helvetica Chimica Acta, 1987, pp. 1558-1568, vol. 70, No. 6. (XP-002441721).

Lange, Jos H.M., et al., "Novel 3,4-diarylpyrazolines as potent cannabinoid $CB_1$ receptor antagonists with lower lipophilicity", Bioorganic & Medicinal Chemistry Letters, 2005, pp. 4794-4798, vol. 15, No. 21.

Shea, K.J., et al., Kinetic Investigation of the Type 2 Intramolecular Diels-Alder Cycloaddition, American Chemical Society, 1988, pp. 860-864, vol. 110, No. 3. (XP-002441722).

Chemical Abstracts Service, Columbus, Ohio, US; Zhang J.-H., et al., (XP002441897); Database accession No. 2004:785021; abstract.

Chemical Abstracts Service, Columbus, Ohio, US; Banciu, Mircea D. et al., (XP002441898); Database accession No. 1996:738817; abstract.

Chemical Abstracts Service, Columbus, Ohio, US; Eto, Masashi et al., (XP002441899); Database accession No. 1993:427963; abstract.

Chemical Abstracts Service, Columbus, Ohio, US; Tokita, Sumio, et al., (XP002441900); Database accession No. 1991:228432; abstract.

Chemical Abstracts Service, Columbus, Ohio, US; Dhaon, Madhup K. et al., (XP002441901); Database accession No. 1977:106004; abstract.

Chemical Abstracts Service, Columbus, Ohio, US; Dodds, E.C., et al., (XP002441902); Database accession No. 1955:42823; abstract.

Chemical Abstracts Service, Columbus, Ohio, US; Melles, J.L., (XP002441903); Database accession No. 1953:44564; abstract.

Chemical Abstracts Service, Columbus, Ohio, US; Langer, F., et al., (XP002441904); Database accession No. 1956:24005; abstract.

International Search Report (PCT/US2007/001024), mail date Aug. 21, 2007—8 pages.

PCT Written Opinion of the International Searching Authority for PCT/US2007/001024—8 pages.

Search Report for ROC (Taiwan) Patent Application No. 096101681 (translation) pp. 1-2; Jan. 8, 2010.

Eto, M. et al., "Cycloaddition Behavior of Cyclopentadienone toward Allylic Alcohols. Formation of Hydrophthalide Derivatives via Internal Addition of Alcohol Group to Bridged Carbonyl of *exo* [4+2]π Cycloadducts", *Chemical & Pharmaceutical Bulletin* 41(1):97-107; Pharmaceutical Society of Japan (1993).

Adam, et al., "Recent Advances in the Cannabinoids", Expert Opin. Ther. Patents; (2002), pp. 1475-1489, vol. 12, Issue 10.

Anderson, et al., "The Preparation of β-Substituted Amines from Mixtures of Epoxide Opening Products via a Common Aziridinium Ion Intermediate", Tetrahedron: *Asymmetry*, (1999), pp. 2655-2663, vol. 10.

Bensaid et al., "The Cannabinoid CB1 Receptor Antagonist SR141716 Increases Acrp30 mRNA Expression in Adipose Tissue of Obese fa/fa Rats and in Cultured Adipocyte Cells", Molecular Pharmacology, vol. 63, No. 4, pp. 908-914 (2003).

Bingham, et al, "Over One Hundred Solvates of Sulfathiazole†", Chem. Commun., (2001), pp. 603-604.

Borisy et al, "Systematic Discovery of Multicomponent Therapeutics", PNAS, vol. 100, No. 13, pp. 7977-7982.

Caira, et al., "Preparation and Crystal Characterization of a Polymorph, a Monohydrate, and an Ethyl Acetate Solvate of the Antifungal Fluconazole", Journal of Pharmaceutical Sciences, (2004) pp. 601-611, vol. 93, No. 3.

Chong et al., "Current, New and Future Treatments in Dyslipidaemia and Atherosclerosis"— Drugs, (2000), pp. 55-93, vol. 60, Issue 1.

Fancher et al, "4-Alkyl+(or Aralkyl) 1-Aryl-2-piperazinones", Chemical Therapeutics Research Laboratory, Miles Labs, Inc., Indiana, (1963) vol. 7 pp. 154-158.

Gylling et al., "Serum Sterols During Stanol Ester Feeding in a Mildly Hypercholesterolemic Population"—Journal of Lipid Research, (1999), pp. 593-600, vol. 40.

Huettinger et al., "Hypolipidemic activity of HOE-402 is Mediated by Stimulation of the LDL Receptor Pathway" -Arterioscle. Throm., (1993), PP. 1005-1012, vol. 13.

Japanese Patent No. 03200758, dated Sep. 2, 1991 (English Abstract).

Japanese Patent No. 04026683, dated Jan. 29, 1992 (English Abstract).

Japanese Patent No. 04364175, dated Dec. 16, 1992 (English Abstract).

Josephsohn, Nathan S. et al., "Efficient and Practical AG-Catalyzed Cycloadditions between Arylimines and The Danishefsky Diene", J. Am. Chem. Society, 2003, pp. 4018-4019, vol. 125, No. 14.

Kirkham, "Endogenous cannabinoids: A new target in the treatment of obesity", Am. J. Physiol. Regul. Integr. Comp. Physiol., (2002), pp. R343-R344, vol. 284.

Kvaerno et al., "An in Vitro Assay for Evaluation of Small-Molecule Inhibitors of Cholesterol Absorption", Angew Chem. Int. Ed., (2004), pp. 4653-4656, vol. 43.

Lange et al., "Synthesis, Biological Properties, and Molecular Modeling Investigations of Novel 3,4-Diarylpyrazolines as Potent and Selective CBI Cannabinoid Receptor Antagonists", J. Med. chem., (2004), pp. 627-643, vol. 47.

PCT International Search Report mailed Jul. 30, 2007 for counterpart PCT Application No. PCT/US2007/000705.

International Search Report for PCT/US2005/043281 dated May 19, 2006 for CV06241US01 —5 pages.

Petite et al, The therapeutic applications of annabinoid agonists and antagonists, Ashley Publications, Emerging Drugs (1998) 3:39-53.

Porter et al., "The Endocannabinoid Nervous System: Unique Opportunities for Therapeutic Intervention", Pharmacology and Therapeutics vol. 90, pp. 45-60, 2001.

Ram et al., "Potential Hypolipidemic Agents: Part V¶-Synthesis and Biological Activity of New Ethyl 4-(2-oxoazetidin-4-yl) phenoxyalkanoatesr‡," Indian J. Chem. Sect. B. 29B, (1990), pp. 1134-1137, vol. 12.

Sanofi-Aventis Publication, "A New Approach to Cardiovascular Risk Management" - Bear Stearns Conference, New York (Sep. 2004), pp. 19-24.

Trillou, C.R. et al., "Anti-obesity effect of SR141716, a CB1 receptor antagonist, in diet-induced obese mice" - Am. J. Physiol. Regul. Integr. Comp., Physiol., (2003), pp. R345-R353, vol. 284.

Van Tonder, et al., "Preparation and Physicochemical Characterization of 5 Niclosamide Solvates And 1 Hemisolvate", *AAPS PharmSciTech*, (2004), pp. 1-10, vol. 5, Issue 1.

Weis, Robert et al., "Synthesis of 2-substituted bamipine derivatives", Tetrahedron, (2003), vol. 9 pp. 1395-1402.

Weis, Robert et al., "Synthesis of new 1,2,7 analogs of diphenylpyraline", Tetrahedron, (2003) vol. 9 pp. 1403-1411.

Wikstrom et al., "Synthesis and Pharmacological Testing of 1,2,3,4,10,14b-Hexahydro-6-methoxy-2-methyldibenzo[c,f]pyrazino[1,2-a]azepin and Its Enantiomers in Comparison with the Two Antidepressants Mianserin and Mirtazapine", J. Med. Chem., vol. 45, pp. 3280-3285 (2002).

Vippagunta et al, "Crystalline Solids", Advanced Drug Delivery Reviews 48 (2001) 3-26.

Banciu, M. et al., "Formation of Cyclopent[hi]acephenanthrylene from 1,2-, 1,3-, 1,4- and 2,3-Triphenylenedicarboxylic Acid Derivatives on Flash Vacuum Pyrolysis at >900°C"; *Australian Journal Of Chemistry*, 49(9):965-976 (1996). Abstract was submitted on IDS dated Feb. 23, 2009 as Reference CH; full text is on order and will be submitted shortly.

Tokita, S. et al., "Synthesis of 2,3-Dimethyl-6,7-Diphenyl-1,4,5,8-Tetrahydronaphthalene", *Chemistry Express* 6(3):201-204 (1991). Abstract was submitted on IDS dated Feb. 23, 2009 as Reference CJ; full text is on order and will be submitted shortly.

CANNABINOID RECEPTOR MODULATORS

This application claims the benefit of U.S. Provisional Application No. 60/760,007, filed Jan. 18, 2006 and U.S. Provisional Application No. 60/846,965 filed Sep. 25, 2006.

FIELD OF THE INVENTION

The present invention relates to cannabinoid receptor modulators, particularly, antagonists or inverse agonists of the $CB_1$ receptor, useful for the treatment of obesity, metabolic disorders, addiction, diseases of the central nervous system, cardiovascular disorders, respiratory disorders, and gastrointestinal disorders, pharmaceutical compositions comprising such compounds, and methods of treatment using the compounds and compositions to treat conditions such as obesity, metabolic disorders, addiction, diseases of the central nervous system, cardiovascular disorders, respiratory disorders, and gastrointestinal disorders.

BACKGROUND OF THE INVENTION

The $CB_1$ receptor is one of the most abundant neuromodulatory receptors in the brain, and is expressed at high levels in the hippocampus, cortex, cerebellum, and basal ganglia (e.g., Wilson et al., *Science*, 2002, vol. 296, 678-682). Selective $CB_1$ receptor antagonists, for example pyrazole derivatives such as rimonabant (e.g., U.S. Pat. No. 6,432,984), can be used to treat various conditions, such as obesity and metabolic syndrome (e.g., Bensaid et al., *Molecular Pharmacology*, 2003 vol. 63, no. 4, pp. 908-914; Trillou et al., *Am. J. Physiol. Regul. Integr. Comp. Physiol.* 2002 vol. 284, R345-R353; Kirkham, *Am. J. Physiol. Regul. Integr. Comp. Physiol.* 2002 vol. 284, R343-R344), neuroinflammatory disorders (e.g., Adam, et al., *Expert Opin. Ther. Patents*, 2002, vol. 12, no. 10, 1475-1489; U.S. Pat. No. 6,642,258), cognitive disorders and psychosis (e.g., Adam et al., *Expert Opin. Ther. Pat.*, 2002, vol. 12, pp. 1475-1489), addiction (e.g., smoking cessation; U.S. Patent Publ. 2003/0087933), gastrointestinal disorders (e.g., Lange et al., *J. Med. Chem.* 2004, vol. 47, 627-643) and cardiovascular conditions (e.g., Porter et al., *Pharmacology and Therapeutics*, 2001 vol. 90, 45-60; Sanofi-Aventis Publication, Bear Steams Conference, New York, Sep. 14, 2004, pages 19-24).

However, there is still a need for improved cannabinoid agents, particularly cannabinoid receptor modulators (e.g., antagonists or inverse agonists of the $CB_1$ receptor) with fewer side-effects and improved efficacy. It is therefore an object of the present invention to provide fused bicyclic and spirocyclic cannabinoid receptor modulators useful in the treatment of diseases or conditions mediated by cannabinoid receptors.

SUMMARY OF THE INVENTION

In one embodiment, the present invention is directed to a compound of Formula (I):

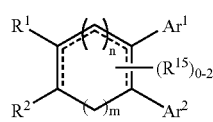

(I)

or a pharmaceutically acceptable salt, solvate, or ester thereof, wherein:

m is 0 or 1, n is 1 or 2, and m+n is 1 or 2;

the dashed lines (═══)in Formula (I) represent single or double bonds as permitted by valence requirements;

$R^1$ is selected from the group consisting of —C(O)—$N(R^{10})_2$, —C(O)—O-alkyl, and —C(O)—$R^{14}$;

$R^2$ is selected from the group consisting of H, unsubstituted alkyl, alkyl substituted with one or more U groups, and -alkylene-$N(R^{10})_2$;

or $R^1$ and $R^2$ together with the carbon atoms to which they are shown attached in Formula (I) form a group Q as shown in Formula (IA):

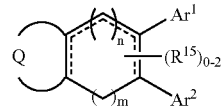

(IA)

wherein Q is selected from the group consisting of:

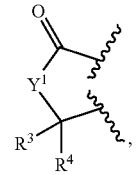

(a)

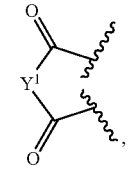

(b)

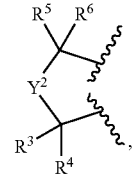

(c)

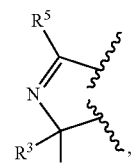

(d)

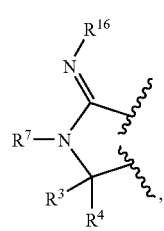

(e)

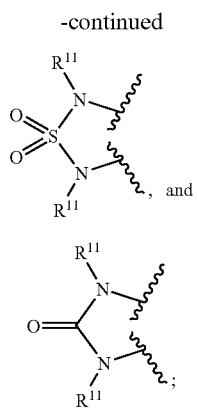

$Y^1$ is —O— or —N($R^7$)—;
$Y^2$ is —O— or —N($R^8$)—;
$R^3$, $R^4$, $R^5$, and $R^6$ are each independently selected from the group consisting of H, —O—$R^9$, $R^{11}$, and —N($R^{16})_2$;
$R^7$ is selected from the group consisting of H, alkyl, arylalkyl, alkenyl, -alkylene-N($R^9)_2$, -alkylene-O—$R^9$, -alkylene-$R^{12}$, —C(O)—$R^{14}$, -alkylene-C(O)H, —C(O)—O—$R^{11}$, and Boc;
$R^8$ is selected from the group consisting of H, -alkylene-$R^{12}$, —C(O)—$R^{17}$, —S($O_2$)—$R^{11}$, —S($O_2$)—$R^{14}$, —C(O)—N($R^{18})_2$, $R^{14}$, and Boc;
with the proviso wherein the group —N($R^{18})_2$, both $R^{18}$ groups taken together with the N atom to which they are bonded form an unsubstituted heterocycloalkyl, heterocycloalkyl substituted with one or more $X^3$ groups, or said substituted or unsubstituted heterocycloalkyl group is fused with aryl, heteroaryl, cycloalkyl or heterocycloalkyl;
$R^9$ is selected from the group consisting of H, TBS, TIPS, Tf and $R^{11}$;
each $R^{10}$ is independently selected from the group consisting of H, unsubstituted alkyl, alkyl substituted with one or more U groups, -alkylene-$R^{12}$, -alkylene-$R^{13}$, -alkylene-$R^{14}$, —C(O)—$R^{14}$, -alkylene-O—$R^9$, $R^{14}$, unsubstituted heterocycloalkyl, heterocycloalkyl substituted with one or more $X^3$ groups, and benzo-fused cycloalkyl;
$R^{11}$ is selected from the group consisting of unsubstituted alkyl, alkyl substituted with one or more U groups, -alkylene-O-alkyl, -alkylene-O-aryl, unsubstituted aryl, and aryl substituted with one or more $X^1$ groups;
$R^{12}$ is selected from the group consisting of unsubstituted aryl and aryl substituted with one or more $X^1$ groups;
$R^{13}$ is selected from the group consisting of unsubstituted heteroaryl and heteroaryl substituted with one or more $X^2$ groups;
$R^{14}$ is selected from the group consisting of unsubstituted cycloalkyl, cycloalkyl substituted with one or more $X^4$ groups unsubstituted alkyl, and alkyl substituted with one or more U groups;
each $R^{15}$ is independently selected from the group consisting of H, —$N_3$, halogen, alkenyl, -alkylene-$R^{12}$, -alkylene-O—$R^9$, -alkylene-N($R^{18})_2$, -alkylene-C(O)H, —OH, —CN, —O-alkyl, —C(O)N($R^{18})_2$, —N($R^{18})_2$, —$NR^{18}$C(O)$R^{18}$, —$NR^{18}$C(O)$_2R^{18}$, —$NR^{18}$C(O)N($R^{18})_2$, —$NR^{18}$S(O)$_2R^{18}$, —O-alkenyl, —C(O)$_2R^{18}$; unsubstituted alkyl, alkyl substituted with one or more U groups, —O-alkylene-C(O)$R^{18}$ or —C(O)$R^{18}$;
with the proviso wherein the group —N($R^{18})_2$, both $R^{18}$ groups taken together with the N atom to which they are bonded form an unsubstituted heterocycloalkyl, heterocycloalkyl substituted with one or more $X^3$ groups, or said substituted or unsubstituted heterocycloalkyl group is fused with aryl, heteroaryl, cycloalkyl or heterocycloalkyl;
$R^{16}$ is selected from the group consisting of $R^9$ and —C(O)—$R^{12}$;
$R^{17}$ is selected from the group consisting of unsubstituted heterocycloalkyl, heterocycloalkyl substituted with one or more $X^3$ groups, -alkylene-$R^{12}$, —O—$R^9$, and $R^{12}$;
each $R^{18}$ is independently selected from the group consisting of H, unsubstituted heterocycloalkyl, heterocycloalkyl substituted with one or more $X^3$ groups, $R^{12}$, $R^{13}$ and $R^{14}$;
with the proviso that when $R^{18}$ is attached to N, then each $R^{18}$ is independently selected from the group consisting of H, unsubstituted heterocycloalkyl, heterocycloalkyl substituted with one or more $W^3$ groups, —C(O)$R^{21}$, $R^{12}$, $R^{13}$ and $R^{14}$;
$R^{19}$ is selected from the group consisting of H, TBS, TIPS, Tf and $R^{21}$;
each $R^{20}$ is independently selected from the group consisting of H, unsubstituted alkyl, alkyl substituted with one or more U groups, -alkylene-$R^{22}$, -alkylene-$R^{23}$, -alkylene-$R^{24}$, —C(O)—$R^{24}$, -alkylene-O—$R^{19}$, $R^{24}$, unsubstituted heterocycloalkyl, heterocycloalkyl substituted with one or more $W^3$ groups, and benzo-fused cycloalkyl;
$R^{21}$ is selected from the group consisting of unsubstituted alkyl, alkyl substituted with one or more U groups, -alkylene-O-alkyl, -alkylene-O-aryl, unsubstituted aryl, aryl substituted with one or more $W^1$ groups; unsubstituted heteroaryl, heteroaryl substituted with one or more $W^2$ groups, unsubstituted cycloalkyl, cycloalkyl substituted with one or more $W^4$ groups, unsubstituted heterocycloalkyl, heterocycloalkyl substituted with one or more $W^3$ groups, —O-alkylene-O—$R^{24}$, —C(O)—O-alkylene-O—$R^{24}$; —C(O)-alkylene-$R^{23}$, —C(O)—$R^{22}$, —C(O)—$R^{24}$, —C(O)—O—$R^{22}$, —C(O)—O—$R^{24}$, —$NHR^{22}$, —$NHR^{24}$—S(O)$_2$—$R^{24}$, and -alkylene-O-alkylene-O—$R^{24}$, with the proviso that —O—O— cannot be formed with $R^{21}$ and the atom said $R^{21}$ is attached to;
$R^{22}$ is selected from the group consisting of unsubstituted aryl and aryl substituted with one or more $W^1$ groups;
$R^{23}$ is selected from the group consisting of unsubstituted heteroaryl and heteroaryl substituted with one or more $W^2$ groups;
$R^{24}$ is selected from the group consisting of alkyl, unsubstituted cycloalkyl, cycloalkyl substituted with one or more $W^4$ groups, unsubstituted alkyl, and alkyl substituted with one or more U groups;
each $R^{25}$ is independently selected from the group consisting of H, $R^{22}$, $R^{23}$, unsubstituted alkyl, alkyl substituted with one or more U groups, unsubstituted cycloalkyl, cycloalkyl substituted with one or more $W^4$ groups, -alkylene-O$R^{19}$, -alkylene-$NR^{19}R^{19}$, -alkylene-$SR^{19}$, -alkylene-$R^{23}$, -alkylene-$R^{22}$, unsubstituted heterocycloalkyl, heterocycloalkyl substituted with one or more $W^3$ groups, -alkylene-heterocycloalkyl, -alkylene-heterocycloalkyl substituted with one or more $W^3$ groups, —C(O)—$R^{24}$, —C(O)—$R^{22}$, —C(O)—$R^{24}$, —C(O)—O—$R^{22}$, —C(O)—O—$R^{24}$, —$NHR^{22}$, —$NHR^{24}$, —S(O)$_2$—$R^{24}$, —C(O)—NH—$R^{22}$ and —C(O)—NH—$R^{24}$;
with the proviso wherein the group —N($R^{25})_2$, both $R^{25}$ groups taken together with the N atom to which they are bonded form an unsubstituted heterocycloalkyl, heterocycloalkyl substituted with one or more $X^3$ groups, or said substituted or unsubstituted heterocycloalkyl group is fused with aryl, heteroaryl, cycloalkyl or heterocycloalkyl;
each $W^1$ is independently selected from the group consisting of halogen, —CN, —OH, —O—S(O)$_2$-haloalkyl, unsubstituted aryl, aryl substituted with one or more Z groups, unsubstituted heteroaryl, heteroaryl substituted with one or more Z groups, and —O-alkyl;

each $W^2$ is independently selected from the group consisting of halogen, unsubstituted aryl, and aryl substituted with one or more Z groups;

each $W^3$ is independently selected from the group consisting of —OH, alkyl, -alkylene-OH, —O-alkyl, —C(O)-alkyl, —C(O)NH$_2$, —NHC(O)alkyl, —NHC(O)H, —NHC(O)—O-alkyl and —C(O)—O-alkyl; or two $W^3$ groups together with the ring carbon atom to which they are attached form a carbonyl group;

each $W^4$ is independently halogen or alkyl;

$Ar^1$ and $Ar^2$ are independently selected from the group consisting of $R^{12}$ and $R^{13}$;

each $X^1$ is independently selected from the group consisting of halogen, —CN, —O—$R^{19}$, —OH, —O—S(O)$_2$-haloalkyl, unsubstituted aryl, aryl substituted with one or more Z groups, unsubstituted heteroaryl, heteroaryl substituted with one or more Z groups, —O-cycloalkyl, —O-cycloalkylalkyl, —O-alkylene-OR$^{19}$, —O-alkylene-C(O)N(R$^{20}$)$_2$, —O-alkylene-O—R$^{19}$, unsubstituted alkyl, alkyl substituted with one or more U groups, unsubstituted —O-alkyl, —O-alkyl substituted with one or more U groups, —O-alkenyl, —O-alkylene-O-alkylene-OR$^{19}$, —O-alkylene-C(O)R$^{24}$, —O-alkylene-C(O)OR$^{19}$, —O-alkyl, —N(R$^{25}$)$_2$, —C(O)alkyl, —C(O)OH, —C(O)O-alkyl, —C(O)O-cycloalkyl, —C(O)N(R$^{25}$)$_2$, —O-alkylene-heterocycloalkyl, —O-alkylene-heterocycloalkyl substituted with one or more $W^3$ groups, unsubstituted heterocycloalkyl, -heterocycloalkyl substituted with one or more $W^3$ groups, —O-alkenylene-O-alkylene-O—R$^{24}$, —O-alkylene-N(R$^{25}$)$_2$, —O-alkylene-C(O)N(R$^{25}$)$_2$, unsubstituted cycloalkyl, cycloalkyl substituted with one or more $W^4$ groups, —S(O)—R$^{24}$, —S(O)$_2$—R$^{24}$, and alkenyl;

with the proviso wherein the group —N(R$^{20}$)$_2$ or —N(R$^{25}$)$_2$ both $R^{20}$ or $R^{25}$ groups taken together with the N atom to which they are bonded form an unsubstituted heterocycloalkyl, heterocycloalkyl substituted with one or more $X^3$ groups, or said substituted or unsubstituted heterocycloalkyl group is fused with aryl, heteroaryl, cycloalkyl or heterocycloalkyl;

each $X^2$ is independently selected from the group consisting of halogen, —CN, —O—R$^{19}$, —OH, —O—S(O)$_2$-haloalkyl, unsubstituted aryl, aryl substituted with one or more Z groups, unsubstituted heteroaryl, heteroaryl substituted with one or more Z groups, —O-cycloalkyl, —O-cycloalkylalkyl, —O-alkylene-OR$^{19}$, —O-alkylene-C(O)N(R$^{20}$)$_2$, —O-alkylene-O—R$^{19}$, unsubstituted alkyl, alkyl substituted with one or more U groups, unsubstituted —O-alkyl, —O-alkyl substituted with one or more U groups, —O-alkenyl, —O-alkylene-O-alkylene-OR$^{19}$, —O-alkylene-C(O)R$^{24}$, —O-alkylene-C(O)OR$^{19}$, —O-alkyl, —N(R$^{25}$)$_2$, —C(O)alkyl, —C(O)OH, —C(O)O-alkyl, —C(O)O-cycloalkyl, —C(O)N(R$^{25}$)$_2$, —O-alkylene-heterocycloalkyl, —O-alkylene-heterocycloalkyl substituted with one or more $W^3$ groups, unsubstituted heterocycloalkyl, -heterocycloalkyl substituted with one or more $W^3$ groups, —O-alkenylene-O-alkylene-O—R$^{24}$, —O-alkylene-N(R$^{25}$)$_2$, —O-alkylene-C(O)N(R$^{25}$)$_2$, unsubstituted cycloalkyl, cycloalkyl substituted with one or more $W^4$ groups, —S(O)—R$^{24}$, —S(O)$_2$—R$^{24}$, and alkenyl;

with the proviso wherein the group —N(R$^{20}$)$_2$ or —N(R$^{25}$)$_2$ both $R^{20}$ or $R^{25}$ groups taken together with the N atom to which they are bonded form an unsubstituted heterocycloalkyl, heterocycloalkyl substituted with one or more $X^3$ groups, or said substituted or unsubstituted heterocycloalkyl group is fused with aryl, heteroaryl, cycloalkyl or heterocycloalkyl;

each $X^3$ is independently selected from the group consisting of —OH, alkyl, -alkylene-OH, —O-alkyl, —C(O)-alkyl, —C(O)NH$_2$, —NHC(O)alkyl, —NHC(O)H, —NHC(O)—O-alkyl and —C(O)—O-alkyl; or two $X^3$ groups together with the ring carbon atom to which they are attached form a carbonyl group;

each $X^4$ is independently halogen or alkyl;

each U is independently selected from the group consisting of —OH, —O-alkyl, —O-aryl, —O-alkylene-aryl, —O-alkylene-O-alkyl, —O-alkylene-O-haloalkyl, —O-alkylene-O-aryl, halogen, —CN, cycloalkyl, heterocycloalkyl, aryl, heteroaryl, OTBS, OTIPS and OTf;

and each Z is independently selected from the group consisting of —OH; —O-alkyl; halogen; alkyl; —CN; —CF$_3$; cycloalkyl; -alkylene-OH; -alkylene-O-alkyl; -alkylene-O-alkyl substituted with one or more groups selected from the group consisting of —OH, —O-alkyl, halogen, —CN, cycloalkyl, heterocycloalkyl, aryl, heteroaryl; -alkylene-O-alkylene-O-alkyl; -alkylene-O-alkylene-O-aryl; -alkylene-O-aryl; and -alkylene-O-aryl substituted with one or more groups selected from the group consisting of halogen, —CN, —OH, —O—S(O)$_2$-haloalkyl, aryl, heteroaryl and —O-alkyl; or two Z groups together with the ring carbon atom to which they are attached form a carbonyl group.

In another embodiment, the present invention is directed to a pharmaceutical composition comprising a therapeutically effective amount of at least one compound of Formula (I), or a pharmaceutically acceptable salt, solvate, or ester thereof, and at least one pharmaceutically acceptable carrier.

In yet another embodiment, the present invention also provides for a method of treating, reducing, or ameliorating metabolic syndrome, obesity, waist circumference, lipid profile, insulin sensitivity, neuroinflammatory disorders, cognitive disorders, psychosis, addictive behavior, gastrointestinal disorders, and cardiovascular conditions by administering an effective amount of at least one compound of Formula (I), or a pharmaceutically acceptable salt, solvate, ester, or stereoisomer thereof, to a patient in need thereof.

In another embodiment, the present invention is directed to a method of treating, reducing, or ameliorating a disease or disorder in a patient, such as metabolic syndrome, obesity, waist circumference, lipid profile, insulin sensitivity, neuroinflammatory disorders, cognitive disorders, psychosis, addictive behavior, gastrointestinal disorders, and cardiovascular conditions. The method comprises administering to the patient an effective amount of at least one compound of Formula (I), or a pharmaceutically acceptable salt, solvate, or ester thereof, in combination with one or more cholesterol lowering agents.

DETAILED DESCRIPTION OF THE INVENTION

In one embodiment, the present invention is directed to a compound of Formula (I), or a pharmaceutically acceptable salt, solvate, ester, or stereoisomer thereof, as described herein.

In another embodiment, the compounds of the present invention, or pharmaceutically acceptable salts, solvates, esters, and stereoisomers thereof have the following Formula (I):

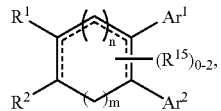

wherein m is 0 or 1, n is 1 or 2, and m+n is 1 or 2;

the dashed lines (═══) in Formula (I) represent single or double bonds as permitted by valence requirements;

$R^1$ is selected from the group consisting of —C(O)—N($R^{10}$)$_2$, —C(O)—O—($C_1$-$C_6$)alkyl, and —C(O)—$R^{14}$;

$R^2$ is selected from the group consisting of H, unsubstituted ($C_1$-$C_6$)alkyl, ($C_1$-$C_6$)alkyl substituted with one or more U groups, and —($C_1$-$C_6$)alkylene-N($R^{10}$)$_2$;

or $R^1$ and $R^2$ together with the carbon atoms to which they are shown attached in Formula (I) form a group Q as shown in Formula (IA):

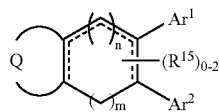

(IA)

wherein Q is selected from the group consisting of:

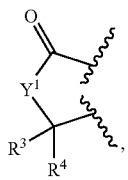 (a)

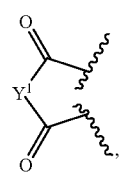 (b)

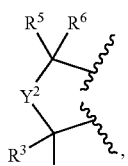 (c)

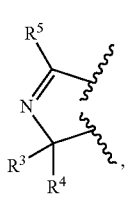 (d)

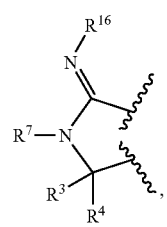 (e)

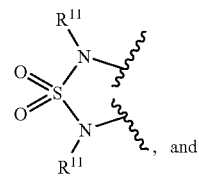 (f)

, and

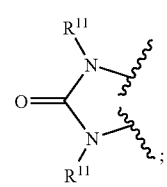 (f)

$Y^1$ is —O— or —N($R^7$)—;

$Y^2$ is —O— or —N($R^8$)—;

$R^3$, $R^4$, $R^5$, and $R^6$ are each independently selected from the group consisting of H, —O—$R^9$, $R^{11}$, and —N($R^{16}$)$_2$;

$R^7$ is selected from the group consisting of H, ($C_1$-$C_6$)alkyl, ($C_6$-$C_{12}$)aryl($C_1$-$C_6$)alkyl, ($C_2$-$C_6$)alkenyl, —($C_1$-$C_6$)alkylene-N($R^9$)$_2$, —($C_1$-$C_6$)alkylene-O—$R^9$, —($C_1$-$C_6$)alkylene-$R^{12}$, —C(O)—$R^{14}$, —($C_1$-$C_6$)alkylene-C(O)H, —C(O)—O—$R^{11}$, and Boc;

$R^8$ is selected from the group consisting of H, —($C_1$-$C_6$)alkylene-$R^{12}$, —C(O)—$R^{17}$, —S($O_2$)—$R^{11}$, —S($O_2$)—$R^{14}$, —C(O)—N($R^{18}$)$_2$, $R^{14}$, and Boc;

with the proviso wherein the group —N($R^{18}$)$_2$, both $R^{18}$ groups taken together with the N atom to which they are bonded form an unsubstituted ($C_3$-$C_5$)heterocycloalkyl, ($C_3$-$C_5$)heterocycloalkyl substituted with one or more $X^3$ groups, or said substituted or unsubstituted ($C_3$-$C_5$)heterocycloalkyl group is fused with ($C_6$-$C_{12}$)aryl, ($C_2$-$C_{10}$)heteroaryl, ($C_3$-$C_7$)cycloalkyl or ($C_3$-$C_5$)heterocycloalkyl;

$R^9$ is selected from the group consisting of H, TBS, TIPS, Tf and $R^{11}$;

each $R^{10}$ is independently selected from the group consisting of H, unsubstituted ($C_1$-$C_6$)alkyl, ($C_1$-$C_6$)alkyl substituted with one or more U groups, —($C_1$-$C_6$)alkylene-$R^{12}$, —($C_1$-$C_6$)alkylene-$R^{13}$, —($C_1$-$C_6$)alkylene-$R^{14}$, —C(O)—$R^{14}$, —($C_1$-$C_6$)alkylene-O—$R^9$, $R^{14}$, unsubstituted ($C_3$-$C_5$)heterocycloalkyl, ($C_3$-$C_5$)heterocycloalkyl substituted with one or more $X^3$ groups, and benzo-fused ($C_3$-$C_7$)cycloalkyl;

$R^{11}$ is selected from the group consisting of unsubstituted ($C_1$-$C_6$)alkyl, ($C_1$-$C_6$)alkyl substituted with one or more U groups, —($C_1$-$C_6$)alkylene-O—($C_1$-$C_6$)alkyl, —($C_1$-$C_6$)alkylene-O—($C_6$-$C_{12}$)aryl, unsubstituted ($C_6$-$C_{12}$)aryl, and ($C_6$-$C_{12}$)aryl substituted with one or more $X^1$ groups;

$R^{12}$ is selected from the group consisting of unsubstituted ($C_6$-$C_{12}$)aryl and ($C_6$-$C_{12}$)aryl substituted with one or more $X^1$ groups;

$R^{13}$ is selected from the group consisting of unsubstituted ($C_2$-$C_{10}$)heteroaryl and ($C_2$-$C_{10}$)heteroaryl substituted with one or more $X^2$ groups;

$R^{14}$ is selected from the group consisting of unsubstituted $(C_3-C_7)$cycloalkyl, $(C_3-C_7)$cycloalkyl substituted with one or more $X^4$ groups unsubstituted $(C_1-C_6)$alkyl and $(C_1-C_6)$ alkyl substituted with one or more U groups;

each $R^{15}$ is independently selected from the group consisting of H, —$N_3$, halogen, $(C_2-C_6)$alkenyl, —$(C_1-C_6)$alkylene-$R^{12}$, —$(C_1-C_6)$alkylene-O—$R^9$, —$(C_1-C_6)$alkylene-N$(R^{18})_2$, —$(C_1-C_6)$alkylene-C(O)H, —OH, —CN, —O—$(C_1-C_6)$alkyl, —C(O)N$(R^{18})_2$, —N$(R^{18})_2$, —NR$^{18}$C(O)R$^{18}$, —NR$^{18}$C(O)$_2$R$^{18}$, —NR$^{18}$C(O)N$(R^{18})_2$, —NR$^{18}$S(O)$_2$R$^{18}$, —O—$(C_2-C_6)$alkenyl, —C(O)$_2$R$^{18}$, unsubstituted $(C_1-C_6)$alkyl, $(C_1-C_6)$alkyl substituted with one or more U groups, —O—$(C_1-C_6)$alkylene-C(O)R$^{18}$, or —C(O)R$^{18}$;

with the proviso wherein the group —N$(R^{18})_2$, both $R^{18}$ groups taken together with the N atom to which they are bonded form an unsubstituted $(C_3-C_5)$heterocycloalkyl, $(C_3-C_5)$heterocycloalkyl substituted with one or more $X^3$ groups, or said substituted or unsubstituted $(C_3-C_5)$heterocycloalkyl group is fused with $(C_6-C_{12})$aryl, $(C_2-C_{10})$heteroaryl, $(C_3-C_7)$cycloalkyl or $(C_3-C_5)$heterocycloalkyl;

$R^{16}$ is selected from the group consisting of $R^9$ and —C(O)—$R^{12}$;

$R^{17}$ is selected from the group consisting of unsubstituted $(C_3-C_5)$heterocycloalkyl, $(C_3-C_5)$heterocycloalkyl substituted with one or more $X^3$ groups, —$(C_1-C_6)$alkylene-$R^{12}$, —O—$R^9$, and $R^{12}$;

each $R^{18}$ is independently selected from the group consisting of H, unsubstituted $(C_3-C_5)$heterocycloalkyl, $(C_3-C_5)$heterocycloalkyl substituted with one or more $X^3$ groups, $R^{12}$, $R^{13}$ and $R^{14}$;

with the proviso that when $R^{18}$ is attached to N, then each $R^{18}$ is independently selected from the group consisting of H, unsubstituted $(C_3-C_5)$heterocycloalkyl, $(C_3-C_5)$heterocycloalkyl substituted with one or more $W^3$ groups, —C(O)R$^{21}$, $R^{12}$, $R^{13}$ and $R^{14}$;

$R^{19}$ is selected from the group consisting of H, TBS, TIPS, Tf and $R^{21}$;

each $R^{20}$ is independently selected from the group consisting of H, unsubstituted $(C_1-C_6)$alkyl, $(C_1-C_6)$alkyl substituted with one or more U groups, —$(C_1-C_6)$alkylene-$R^{22}$, —$(C_1-C_6)$alkylene-$R^{23}$, —$(C_1-C_6)$alkylene-$R^{24}$, —C(O)—$R^{24}$, —$(C_1-C_6)$alkylene-O—$R^{19}$, $R^{24}$, unsubstituted $(C_3-C_5)$heterocycloalkyl, $(C_3-C_5)$heterocycloalkyl substituted with one or more $W^3$ groups, and benzo-fused $(C_3-C_7)$cycloalkyl;

$R^{21}$ is selected from the group consisting of unsubstituted $(C_1-C_6)$alkyl, $(C_1-C_6)$alkyl substituted with one or more U groups, —$(C_1-C_6)$alkylene-O—$(C_1-C_6)$alkyl, —$(C_1-C_6)$alkylene-O—$(C_6-C_{12})$aryl, unsubstituted $(C_6-C_{12})$aryl, and $(C_6-C_{12})$aryl substituted with one or more $W^1$ groups, unsubstituted $(C_2-C_{10})$heteroaryl, $(C_2-C_{10})$heteroaryl substituted with one or more $W^2$ groups, unsubstituted $(C_3-C_7)$cycloalkyl, $(C_3-C_7)$cycloalkyl substituted with one or more $W^4$ groups, unsubstituted $(C_3-C_5)$heterocycloalkyl, $(C_3-C_5)$heterocycloalkyl with one or more $W^3$ groups, —O—$(C_1-C_6)$alkylene-O—$R^{24}$, —C(O)—O—$(C_1-C_6)$alkylene-O—$R^{24}$; —C(O)—$(C_1-C_6)$alkylene —$R^{23}$, —C(O)—$R^{22}$, —C(O)—$R^{24}$, —C(O)—O—$R^{22}$, —C(O)—O—$R^{24}$, —NHR$^{22}$, —NHR$^{24}$, —S(O)$_2$—$R^{24}$ and —$(C_1-C_6)$alkylene-O—$(C_1-C_6)$alkylene-O—$R^{24}$ with the proviso that —O—O— cannot be formed with $R^{21}$ and the atom said $R^{21}$ is attached to;

$R^{22}$ is selected from the group consisting of unsubstituted $(C_6-C_{12})$aryl and $(C_6-C_{12})$aryl substituted with one or more $W^1$ groups;

$R^{23}$ is selected from the group consisting of unsubstituted $(C_2-C_{10})$heteroaryl and $(C_2-C_{10})$heteroaryl substituted with one or more $W^2$ groups;

$R^{24}$ is selected from the group consisting of unsubstituted $(C_3-C_7)$cycloalkyl, $(C_3-C_7)$cycloalkyl substituted with one or more $X^4$ groups, unsubstituted $(C_1-C_6)$alkyl and $(C_1-C_6)$ alkyl substituted with one or more U groups;

each $R^{25}$ is independently selected from the group consisting of H, $R^{22}$, $R^{23}$, unsubstituted $(C_1-C_6)$alkyl, $(C_1-C_6)$alkyl substituted with one or more U groups, unsubstituted $(C_3-C_7)$cycloalkyl, $(C_3-C_7)$cycloalkyl substituted with one or more $W^4$ groups, —$(C_1-C_6)$alkylene-OR$^{19}$, —$(C_1-C_6)$alkylene-NR$^{19}$R$^{19}$, —$(C_1-C_6)$alkylene-SR$^{19}$, —$(C_1-C_6)$alkylene-$R^{23}$, —$(C_1-C_6)$alkylene-$R^{22}$, unsubstituted $(C_3-C_5)$heterocycloalkyl, $(C_3-C_5)$heterocycloalkyl substituted with one or more $W^3$ groups, —$(C_1-C_6)$alkylene-$(C_3-C_5)$heterocycloalkyl, —$(C_1-C_6)$alkylene-$(C_3-C_5)$heterocycloalkyl substituted with one or more $W^3$ groups, —C(O)—$R^{24}$, —C(O)—$R^{22}$, —C(O)—$R^{24}$, —C(O)—O—$R^{22}$, —C(O)—O—$R^{24}$, —NHR$^{22}$, —NHR$^{24}$, —S(O)$_2$—$R^{24}$, —C(O)—NH—$R^{22}$ and —C(O)—NH—$R^{24}$;

with the proviso wherein the group —N$(R^{25})_2$, both $R^{25}$ groups taken together with the N atom to which they are bonded form an unsubstituted $(C_3-C_5)$heterocycloalkyl, $(C_3-C_5)$heterocycloalkyl substituted with one or more $X^3$ groups, or said substituted or unsubstituted $(C_3-C_5)$heterocycloalkyl group is fused with $(C_6-C_{12})$aryl, $(C_2-C_{10})$heteroaryl, $(C_3-C_7)$cycloalkyl or $(C_3-C_5)$heterocycloalkyl;

each $W^1$ is independently selected from the group consisting of halogen, —CN, —OH, —O—S(O)$_2$—$(C_1-C_6)$haloalkyl, unsubstituted $(C_6-C_{12})$aryl, $(C_6-C_{12})$aryl substituted with one or more Z groups, unsubstituted $(C_2-C_{10})$heteroaryl, $(C_2-C_{10})$heteroaryl substituted with one or more Z groups, and —O—$(C_1-C_6)$alkyl;

each $W^2$ is independently selected from the group consisting of halogen, unsubstituted $(C_6-C_{12})$aryl, and $(C_6-C_{12})$aryl substituted with one or more Z groups;

each $W^3$ is independently selected from the group consisting of —OH, $(C_1-C_6)$alkyl, —$(C_1-C_6)$alkylene-OH, —O—$(C_1-C_6)$alkyl, —C(O)—$(C_1-C_6)$alkyl, —C(O)NH$_2$, —NHC(O)$(C_1-C_6)$alkyl, —NHC(O)H, —NHC(O)—O—$(C_1-C_6)$alkyl and —C(O)—O—$(C_1-C_6)$alkyl; or two $W^3$ groups together with the ring carbon atom to which they are attached form a carbonyl group;

each $W^4$ is independently halogen or $(C_1-C_6)$alkyl;

Ar$^1$ and Ar$^2$ are independently selected from the group consisting of $R^{12}$ and $R^{13}$;

each $X^1$ is independently selected from the group consisting of halogen, —CN, —O—$R^{19}$, —OH, —O—S(O)$_2$—$(C_1-C_6)$haloalkyl, unsubstituted $(C_6-C_{12})$aryl, $(C_6-C_{12})$aryl substituted with one or more Z groups, unsubstituted $(C_2-C_{10})$heteroaryl, $(C_2-C_{10})$heteroaryl substituted with one or more Z groups, —O—$(C_3-C_7)$cycloalkyl, —O—$(C_3-C_7)$cycloalkyl$(C_1-C_6)$alkyl, —O—$(C_1-C_6)$alkylene-OR$^{19}$, —O—$(C_1-C_6)$alkylene-C(O)N$(R^{20})_2$, —O—$(C_1-C_6)$alkylene-O—$R^{19}$, unsubstituted $(C_1-C_6)$alkyl, $(C_1-C_6)$alkyl substituted with one or more U groups, unsubstituted —O—$(C_1-C_6)$alkyl, —O—$(C_1-C_6)$alkyl substituted with one or more U groups, —O—$(C_2-C_7)$alkenyl, —O—$(C_1-C_6)$alkylene-O—$(C_1-C_6)$alkylene-OR$^{19}$, —O—$(C_1-C_6)$alkylene-C(O)R$^{24}$, —O—$(C_1-C_6)$alkylene-C(O)OR$^{19}$, —O—$(C_1-C_6)$alkyl, —N$(R^{25})_2$, —C(O)$(C_1-C_6)$alkyl, —C(O)OH, —C(O)—O—$(C_1-C_6)$alkyl, —C(O)O—$(C_3-C_7)$cycloalkyl, —C(O)N$(R^{25})_2$, —O—$(C_1-C_6)$alkylene-$(C_3-C_5)$heterocycloalkyl, —O—$(C_1-C_6)$alkylene-$(C_3-C_5)$heterocycloalkyl substituted with one or more $W^3$ groups, unsubstituted $(C_3\text{-}C_5)$heterocycloalkyl, $-(C_3\text{-}C_5)$heterocycloalkyl substituted with one or more $W^3$ groups, $-O-(C_2\text{-}C_7)$alkenylene-$O-(C_1\text{-}C_6)$alkylene-$O-R^{24}$, $-O-(C_1\text{-}C_6)$alkylene-$N(R^{25})_2$, $-O-(C_1\text{-}C_6)$alkylene-$C(O)N(R^{25})_2$, unsubstituted $(C_3\text{-}C_7)$cycloalkyl, $(C_3\text{-}C_7)$cycloalkyl substituted with one or more $W^4$ groups, $-S(O)-R^{24}$, $-S(O)_2-R^{24}$, and $(C_2\text{-}C_7)$alkenyl;

with the proviso wherein the group $-N(R^{20})_2$ or $-N(R^{25})_2$ both $R^{20}$ or $R^{25}$ groups taken together with the N atom to which they are bonded form an unsubstituted $(C_3\text{-}C_5)$heterocycloalkyl, $(C_3\text{-}C_5)$heterocycloalkyl substituted with one or more $X^3$ groups, or said substituted or unsubstituted $(C_3\text{-}C_5)$heterocycloalkyl group is fused with $(C_6\text{-}C_{12})$aryl, $(C_2\text{-}C_{10})$heteroaryl, $(C_3\text{-}C_7)$cycloalkyl or $(C_3\text{-}C_5)$heterocycloalkyl;

each $X^2$ is independently selected from the group consisting of halogen, $-CN$, $-O-R^{19}$, $-OH$, $-O-S(O)_2-(C_1\text{-}C_6)$haloalkyl, unsubstituted $(C_6\text{-}C_{12})$aryl, $(C_6\text{-}C_{12})$aryl substituted with one or more Z groups, unsubstituted $(C_2\text{-}C_{10})$heteroaryl, $(C_2\text{-}C_{10})$heteroaryl substituted with one or more Z groups, $-O-(C_3\text{-}C_7)$cycloalkyl, $-O-(C_3\text{-}C_7)$cycloalkyl$(C_1\text{-}C_6)$alkyl, $-O-(C_1\text{-}C_6)$alkylene-$OR^{19}$, $-O-(C_1\text{-}C_6)$alkylene-$C(O)N(R^{20})_2$, $-O-(C_1\text{-}C_6)$alkylene-$O-R^{19}$, unsubstituted $(C_1\text{-}C_6)$alkyl, $(C_1\text{-}C_6)$alkyl substituted with one or more U groups, unsubstituted $-O-(C_1\text{-}C_6)$alkyl, $-O-(C_1\text{-}C_6)$alkyl substituted with one or more U groups, $-O-(C_2\text{-}C_7)$alkenyl, $-O-(C_1\text{-}C_6)$alkylene-$O-(C_1\text{-}C_6)$alkylene-$OR^{19}$, $-O-(C_1\text{-}C_6)$alkylene-$C(O)R^{24}$, $-O-(C_1\text{-}C_6)$alkylene-$C(O)OR^{19}$, $-O-(C_1\text{-}C_6)$alkyl, $-N(R^{25})_2$, $-C(O)(C_1\text{-}C_6)$alkyl, $-C(O)OH$, $-C(O)O-(C_1\text{-}C_6)$alkyl, $-C(O)O-(C_3\text{-}C_7)$cycloalkyl, $-C(O)N(R^{25})_2$, $-O-(C_1\text{-}C_6)$alkylene-$(C_3\text{-}C_5)$heterocycloalkyl, $-O-(C_1\text{-}C_6)$alkylene-$(C_3\text{-}C_5)$heterocycloalkyl substituted with one or more $W^3$ groups, unsubstituted $(C_3\text{-}C_5)$heterocycloalkyl, $-(C_3\text{-}C_5)$heterocycloalkyl substituted with one or more $W^3$ groups, $-O-(C_2\text{-}C_7)$alkenylene-$O-(C_1\text{-}C_6)$alkylene-$O-R^{24}$, $-O-(C_1\text{-}C_6)$alkylene-$N(R^{25})_2$, $-O-(C_1\text{-}C_6)$alkylene-$C(O)N(R^{25})_2$, unsubstituted $(C_3\text{-}C_7)$cycloalkyl, $(C_3\text{-}C_7)$cycloalkyl substituted with one or more $W^4$ groups, $-S(O)-R^{24}$, $-S(O)_2-R^{24}$, and $(C_2\text{-}C_7)$alkenyl;

with the proviso wherein the group $-N(R^{20})_2$ or $-N(R^{25})_2$ both $R^{20}$ or $R^{25}$ groups taken together with the N atom to which they are bonded form an unsubstituted $(C_3\text{-}C_5)$heterocycloalkyl, $(C_3\text{-}C_5)$heterocycloalkyl substituted with one or more $X^3$ groups, or said substituted or unsubstituted $(C_3\text{-}C_5)$heterocycloalkyl group is fused with $(C_6\text{-}C_{12})$aryl, $(C_2\text{-}C_{10})$heteroaryl, $(C_3\text{-}C_7)$cycloalkyl or $(C_3\text{-}C_5)$heterocycloalkyl;

each $X^3$ is independently selected from the group consisting of $-OH$, $(C_1\text{-}C_6)$alkyl, $-(C_1\text{-}C_6)$alkylene-$OH$, $-O-(C_1\text{-}C_6)$alkyl, $-C(O)-(C_1\text{-}C_6)$alkyl, $-C(O)NH_2$, $-NHC(O)(C_1\text{-}C_6)$alkyl, $-NHC(O)H$, $-NHC(O)-O-(C_1\text{-}C_6)$alkyl and $-C(O)-O-(C_1\text{-}C_6)$alkyl; or two $X^3$ groups together with the ring carbon atom to which they are attached form a carbonyl group;

each $X^4$ is independently halogen or $(C_1\text{-}C_6)$alkyl;

each U is independently selected from the group consisting of $-OH$, $-O-(C_1\text{-}C_6)$alkyl, $-O-(C_6\text{-}C_{12})$aryl, $-O-(C_1\text{-}C_6)$alkylene-$(C_6\text{-}C_{12})$aryl, $-O-(C_1\text{-}C_6)$alkylene-$O-(C_1\text{-}C_6)$alkyl, $-O-(C_1\text{-}C_6)$alkylene-$O-(C_1\text{-}C_6)$haloalkyl, $-O-(C_1\text{-}C_6)$alkylene-$O-(C_6\text{-}C_{12})$aryl, halogen, $-CN$, $(C_3\text{-}C_7)$cycloalkyl, $(C_3\text{-}C_5)$heterocycloalkyl, $(C_6\text{-}C_{12})$aryl, $(C_2\text{-}C_{10})$heteroaryl, OTBS, OTIPS and OTf;

and each Z is independently selected from the group consisting of $-OH$; $-O-(C_1\text{-}C_6)$alkyl; halogen; $(C_1\text{-}C_6)$alkyl; $-CN$; $-CF_3$; $(C_3\text{-}C_7)$cycloalkyl; $-(C_1\text{-}C_6)$alkylene-$OH$; $-(C_1\text{-}C_6)$alkylene-$O-(C_1\text{-}C_6)$alkyl; $-(C_1\text{-}C_6)$alkylene-$O-(C_1\text{-}C_6)$alkyl substituted with one or more groups selected from the group consisting of $-OH$, $-O-(C_1\text{-}C_6)$alkyl, halogen, $-CN$, $(C_3\text{-}C_7)$cycloalkyl, $(C_3\text{-}C_5)$heterocycloalkyl, $(C_6\text{-}C_{12})$aryl, $(C_2\text{-}C_{10})$heteroaryl; $-(C_1\text{-}C_6)$alkylene-$O-(C_1\text{-}C_6)$alkylene-$O-(C_1\text{-}C_6)$alkyl; $-(C_1\text{-}C_6)$alkylene-$O-(C_1\text{-}C_6)$alkylene-$O-(C_6\text{-}C_{12})$aryl; $-(C_1\text{-}C_6)$alkylene-$O-(C_6\text{-}C_{12})$aryl; and $-(C_1\text{-}C_6)$alkylene-$O-(C_6\text{-}C_{12})$aryl substituted with one or more groups selected from the group consisting of halogen, $-CN$, $-OH$, $-O-S(O)_2-(C_1\text{-}C_6)$haloalkyl, $(C_6\text{-}C_{12})$aryl, $(C_2\text{-}C_{10})$heteroaryl and $-O-(C_1\text{-}C_6)$alkyl; or two Z groups together with the ring carbon atom to which they are attached form a carbonyl group.

The dashed lines (===) in Formula (I) represent bonds which can independently be either a single bond or a double bond. The ring of Formula (I) can contain no double bonds, or one or more double bonds (i.e., one or two double bonds), provided that the resulting compound is stable. Non-limiting examples of compounds of Formula (I) can have one of the following generic formulae, where $R^1$, $R^2$, $R^{15}$, $Ar^1$, and $Ar^2$ are as defined herein:

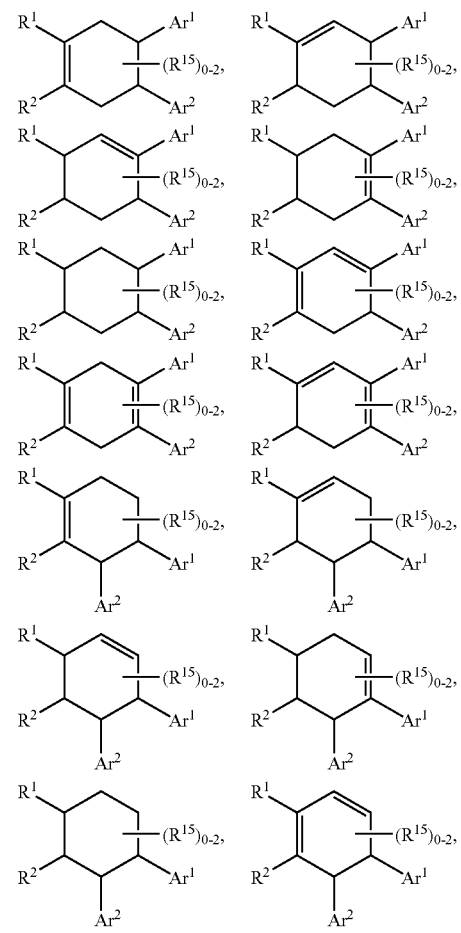

-continued

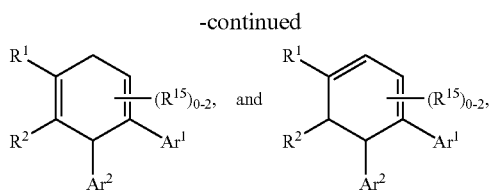

When present, each $R^{15}$ group of Formula (I) can be bonded to any carbon atom of Formula (I) which is capable of substitution. As a non-limiting example, the following generic structure:

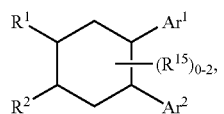

includes the following structures wherein group $R^{15}$, when present, can be bonded to any of the ring carbon atoms. For example, when one $R^{15}$ group is present, the above generic structure includes the following:

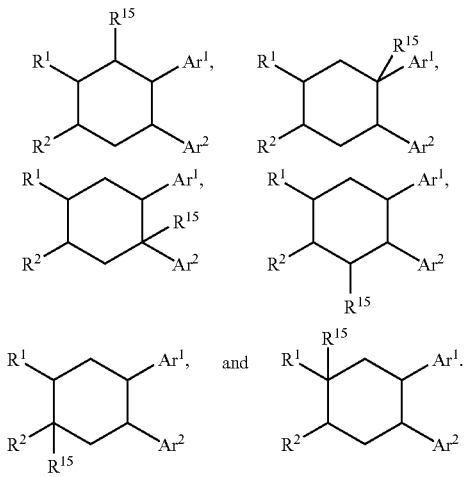

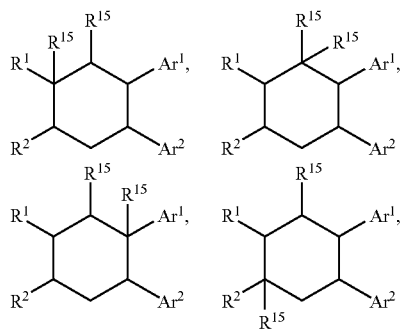

When two $R^{15}$ groups are present, the generic structure above includes the following:

-continued

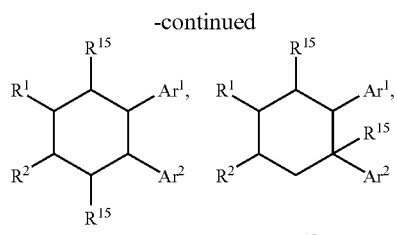
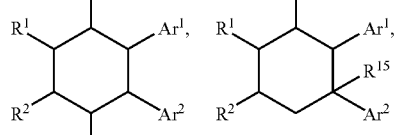
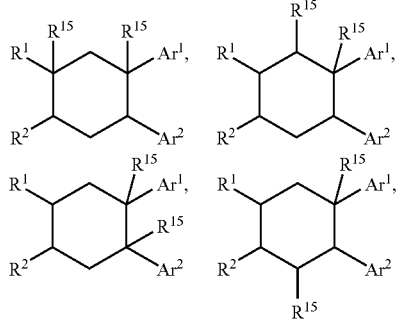
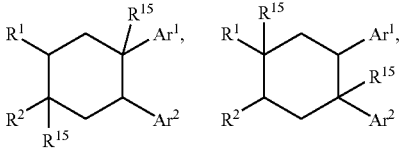
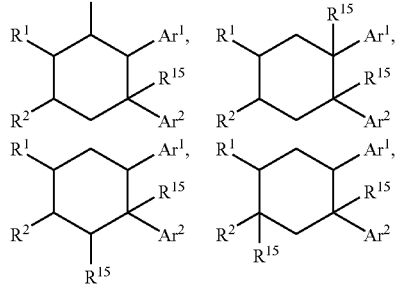
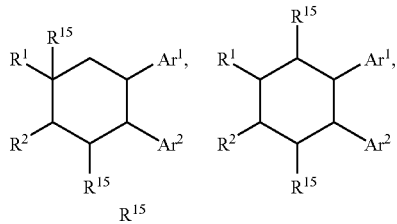
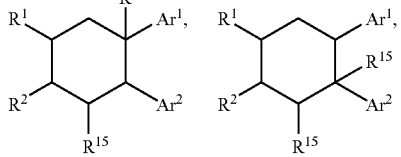
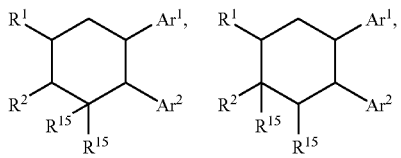
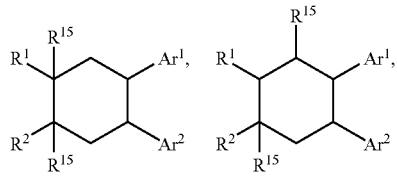

-continued

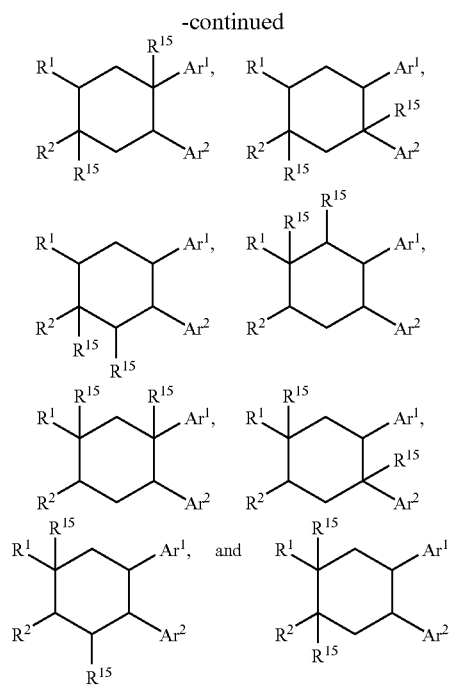

When the six-membered ring of Formula (I) contains one or more double bonds, each $R^{15}$, when present, may be attached to any ring carbon atom to which such substitution is possible.

Similarly, it is contemplated that the compounds of Formula (I) include all possible stable stereoisomers. As a non-limiting example, the following generic structure (wherein each $R^{15}$ is H):

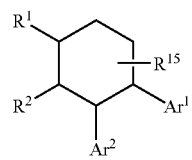

includes the following stereoisomers:

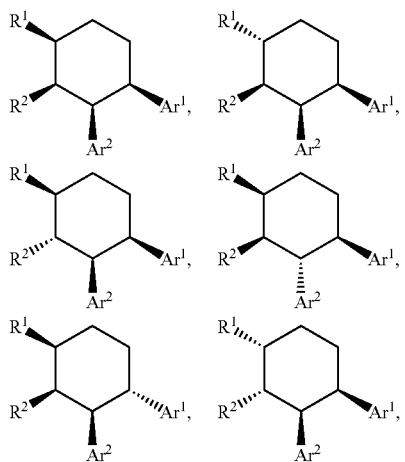

-continued

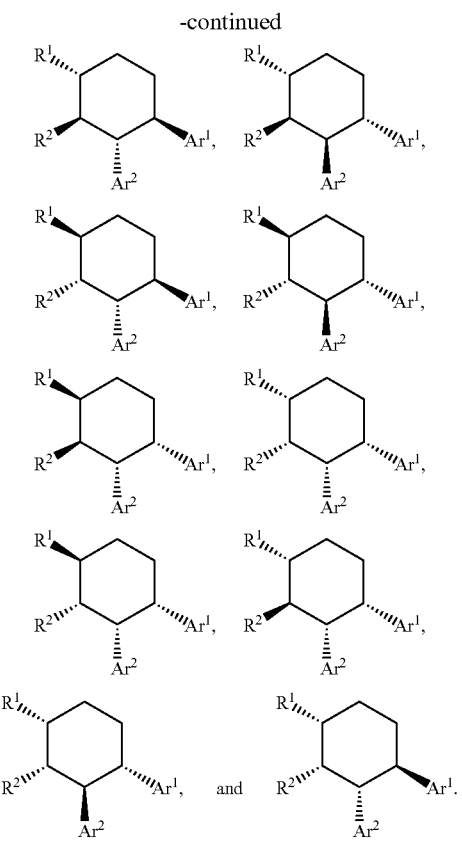

In another embodiment of the compounds of Formula (I), or pharmaceutically acceptable salts, solvates, esters, or stereoisomers thereof, $R^1$ and $R^2$ together with the carbon atoms to which they are shown attached in Formula (I) form a group Q as shown in Formula (IA):

(IA)

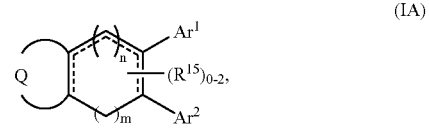

wherein the group Q is selected from the group consisting of:

(a)

(b)

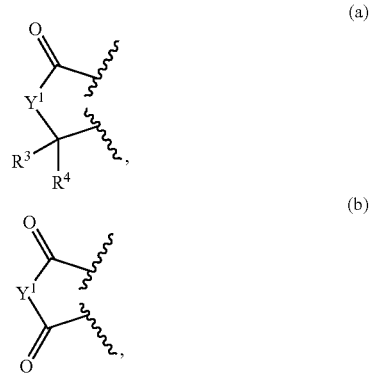

-continued
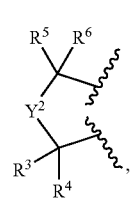 (c)
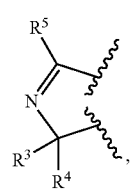 (d)
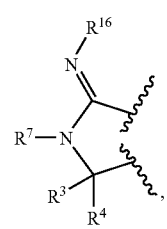 (e)
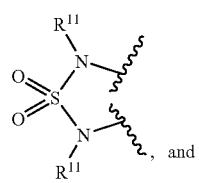 (f)
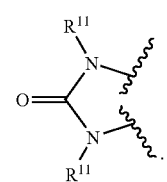 (f)
Thus, the compounds of Formula (IA) of the present invention include the following generic formulae:
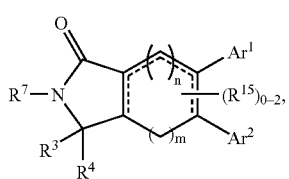 (II-1)
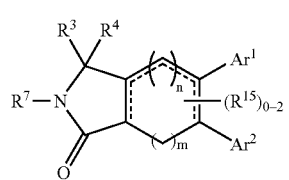 (II-2)
-continued
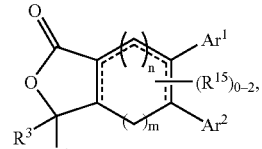 (III-1)
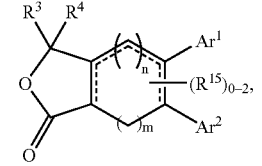 (III-2)
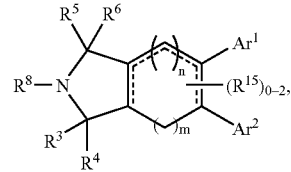 (IV)
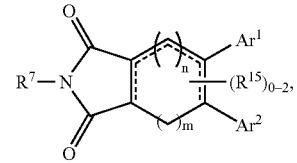 (V)
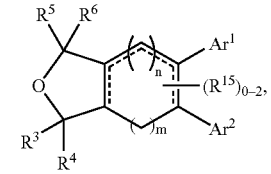 (VI)
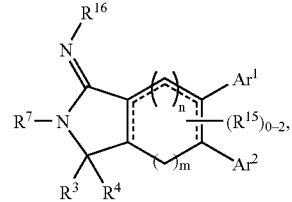 (VII-1)
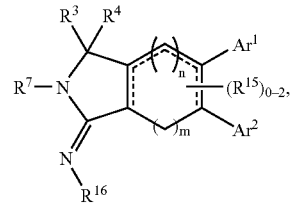 (VII-2)
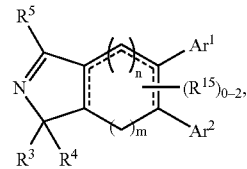 (VIII-1)

-continued

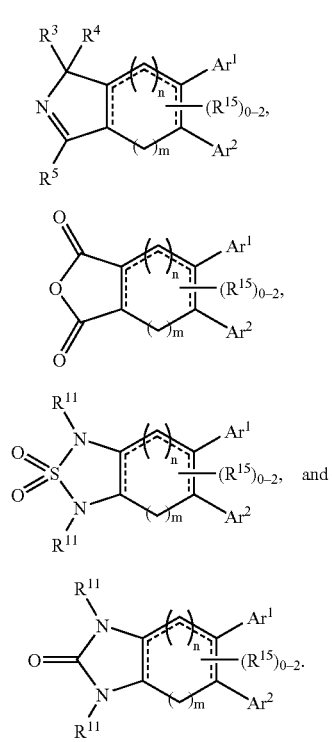

It will be recognized by one of skill in the art that Formulae (VII-1), (VII-2), (VIII-1), and (VIII-2) can describe equivalent tautomeric forms of the same compound (e.g., when $R^5$ of Formulae (VIII-1) or (VIII-2) is —$NHR^{16}$, and $R^7$ of Formulae (VII-1) or (VII-2) is H). Thus, the following structural formulae are considered equivalent:

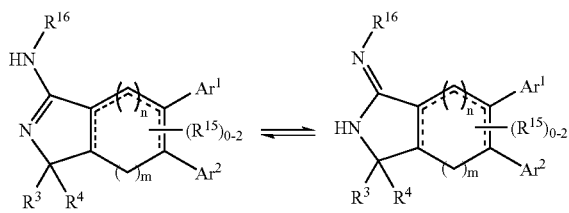

In another embodiment, the compounds of the present invention, or pharmaceutically acceptable salts, solvates, esters, or stereoisomers thereof have the following Formula (II):

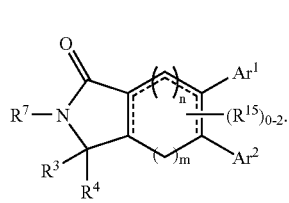

In another embodiment, the compounds of the present invention, or pharmaceutically acceptable salts, solvates, esters, or stereoisomers thereof have the following Formula (IIA):

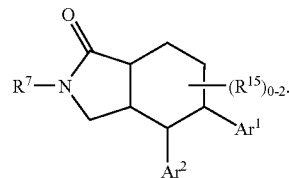

In another embodiment, the compounds of the present invention, or pharmaceutically acceptable salts, solvates, esters, or stereoisomers thereof, have the structure of Formula (IIA), wherein:

$Ar^1$ and $Ar^2$ are independently selected from the group consisting of $R^{12}$ and $R^{13}$;

$R^7$ is selected from the group consisting of H, alkyl, alkenyl, -alkylene-N($R^9$)$_2$, -alkylene-O—$R^9$, -alkylene-$R^{12}$, —C(O)—$R^{14}$, and —C(O)—O—$R^{11}$;

$R^9$ is selected from the group consisting of H and alkyl;

$R^{12}$ is selected from the group consisting of unsubstituted phenyl and phenyl substituted with one or more $X^1$ groups;

$R^{13}$ is selected from the group consisting of unsubstituted pyridyl and pyridyl substituted with one or more $X^2$ groups;

$R^{14}$ is selected from the group consisting of alkyl, unsubstituted cycloalkyl, or cycloalkyl substituted with one or more $X^4$ groups; and $R^{15}$ is selected from the group consisting of H, alkyl, alkenyl, -alkylene-$R^{12}$, and —O-alkenyl.

In another embodiment, the compounds of the present invention, or pharmaceutically acceptable salts, solvates, esters, or stereoisomers thereof, have the structure of Formula (IIA), wherein:

$Ar^1$ is phenyl substituted with one or more $X^1$ groups;

$Ar^2$ is phenyl substituted with one or more $X^1$ groups or pyridyl substituted with one or more $X^2$ groups;

$R^7$ is H; and $R^{15}$ is alkyl.

In another embodiment, the compounds of the present invention, or pharmaceutically acceptable salts, solvates, esters, or stereoisomers thereof have the following Formula (III):

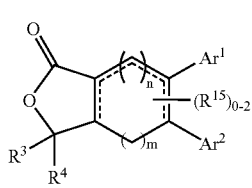

In another embodiment, the compounds of the present invention, or pharmaceutically acceptable salts, solvates, esters, or stereoisomers thereof have the following Formula (IIIA):

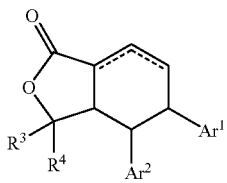
(IIIA)

In another embodiment, the compounds of the present invention, or pharmaceutically acceptable salts, solvates, esters, or stereoisomers thereof, have the structure of Formula (IIIA), wherein:

$Ar^1$ and $Ar^2$ are independently selected from the group consisting of $R^{12}$ and $R^{13}$;

$R^3$ and $R^4$ are each independently H or alkyl;

$R^{12}$ is selected from the group consisting of unsubstituted phenyl and phenyl substituted with one or more $X^1$ groups; and $R^{13}$ is selected from the group consisting of unsubstituted pyridyl and pyridyl substituted with one or more $X^2$ groups.

In another embodiment, the compounds of the present invention, or pharmaceutically acceptable salts, solvates, esters, or stereoisomers thereof, have the structure of Formula (IIIA), wherein:

$R^3$ and $R^4$ are each independently H or —$CH_3$;

$Ar^1$ is unsubstituted phenyl or phenyl substituted with one or more halogens; and $Ar^2$ is selected from the group consisting of unsubstituted phenyl, phenyl substituted with one or more halogens, unsubstituted pyridyl, and pyridyl substituted with one or more $X^2$ groups.

In another embodiment, the compounds of the present invention, or pharmaceutically acceptable salts, solvates, esters, or stereoisomers thereof have the following Formula (IV):

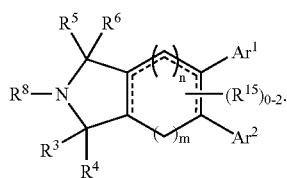
(IV)

In another embodiment, the compounds of the present invention, or pharmaceutically acceptable salts, solvates, esters, or stereoisomers thereof have the following Formula (IVA):

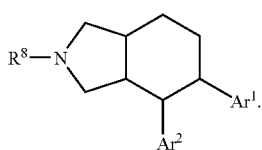
(IVA)

In another embodiment, the compounds of the present invention, or pharmaceutically acceptable salts, solvates, esters, or stereoisomers thereof, have the structure of Formula (IVA), wherein:

$Ar^1$ and $Ar^2$ are independently selected from the group consisting of $R^{12}$ and $R^{13}$;

$R^8$ is selected from the group consisting of -alkylene-$R^{12}$, —C(O)—$R^{17}$, —S($O_2$)—$R^{14}$, —C(O)—N($R^{18}$)$_2$, and $R^{14}$;

$R^9$ is selected from the group consisting of H and alkyl;

$R^{12}$ is selected from the group consisting of unsubstituted phenyl and phenyl substituted with one or more $X^1$ groups;

$R^{13}$ is selected from the group consisting of unsubstituted pyridyl and pyridyl substituted with one or more $X^2$ groups;

$R^{14}$ is selected from the group consisting of alkyl, unsubstituted cycloalkyl, or cycloalkyl substituted with one or more $X^4$ groups; and $R^{17}$ is selected from the group consisting of unsubstituted heterocycloalkyl, heterocycloalkyl substituted with one or more $X^3$ groups, -alkylene-$R^{12}$, —O—$R^9$, and $R^{12}$; and each $R^{18}$ is independently selected from the group consisting of H, $R^{12}$, and $R^{14}$.

In another embodiment, the compounds of the present invention, or pharmaceutically acceptable salts, solvates, esters, or stereoisomers thereof, have the structure of Formula (IVA), wherein:

$R^8$ is selected from the group consisting of —$CH_2$—$R^{12}$, —CH($CH_3$)—$R^{12}$, —C(O)—$R^{17}$, —S($O_2$)—$R^{14}$, —C(O)—N($R^{18}$)$_2$, and $R^{14}$;

$R^9$ is selected from the group consisting of H and alkyl;

$R^{12}$ is selected from the group consisting of unsubstituted phenyl and phenyl substituted with one or more $X^1$ groups;

$R^{14}$ is selected from the group consisting of alkyl, unsubstituted cycloalkyl, or cycloalkyl substituted with one or more $X^4$ groups; and $R^{17}$ is selected from the group consisting of unsubstituted heterocycloalkyl, heterocycloalkyl substituted with one or more $X^3$ groups, —$CH_2$—$R^{12}$, —CH($CH_3$)—$R^{12}$, —O—$R^9$, and $R^{12}$; and each $R^{18}$ is independently H, unsubstituted cycloalkyl, cycloalkyl substituted with one or more $X^4$ groups, unsubstituted aryl, and aryl substituted with one or more $X^1$ groups.

In another embodiment, the compounds of the present invention, or pharmaceutically acceptable salts, solvates, esters, or stereoisomers thereof have the following Formula (V):

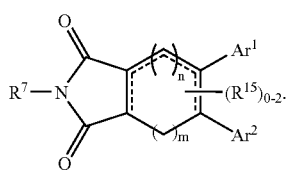
(V)

In another embodiment, the compounds of the present invention, or pharmaceutically acceptable salts, solvates, esters, or stereoisomers thereof have the following Formula (VA):

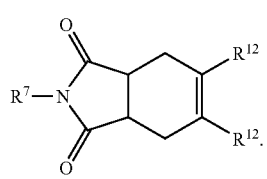

(VA)

In another embodiment, the compounds of the present invention, or pharmaceutically acceptable salts, solvates, esters, or stereoisomers thereof, have the structure of Formula (VA), wherein:
$R^7$ is H or -alkylene-$R^{12}$; and
$R^{12}$ is selected from the group consisting of unsubstituted phenyl and phenyl substituted with one or more $X^1$ groups.

In another embodiment, the compounds of the present invention, or pharmaceutically acceptable salts, solvates, esters, or stereoisomers thereof have the following Formula (VI):

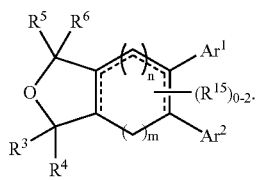

(VI)

In another embodiment, the compounds of the present invention, or pharmaceutically acceptable salts, solvates, esters, or stereoisomers thereof have the following Formula (VIA):

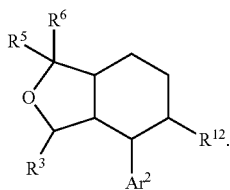

(VIA)

In another embodiment, the compounds of the present invention, or pharmaceutically acceptable salts, solvates, esters, or stereoisomers thereof, have the structure of Formula (VIA), wherein:
$R^3$, $R^5$, and $R^6$ are each independently selected from the group consisting of H, —O—$R^9$, and $R^{11}$;
$R^9$ is H or alkyl;
$R^{11}$ is selected from the group consisting of alkyl, unsubstituted phenyl, and phenyl substituted with one or more $X^1$ groups;
$R^{12}$ is selected from the group consisting of unsubstituted phenyl and phenyl substituted with one or more $X^1$ groups;
$R^{13}$ is selected from the group consisting of unsubstituted pyridyl and pyridyl substituted with one or more $X^2$ groups; and
$Ar^2$ is selected from the group consisting of $R^{12}$ and $R^{13}$.

In another embodiment, the compounds of the present invention, or pharmaceutically acceptable salts, solvates, esters, or stereoisomers thereof have the following Formula (VII):

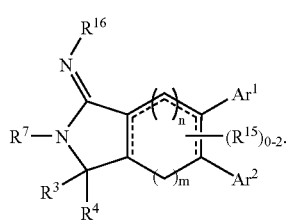

(VII)

In another embodiment, the compounds of the present invention, or pharmaceutically acceptable salts, solvates, esters, or stereoisomers thereof have the following Formula (VIIA):

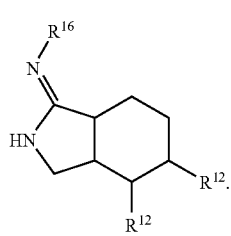

(VIIA)

In another embodiment, the compounds of the present invention, or pharmaceutically acceptable salts, solvates, esters, or stereoisomers thereof, have the structure of Formula (VIIA), wherein:
$R^{16}$ is —C(O)—$R^{12}$; and
$R^{12}$ is selected from the group consisting of unsubstituted phenyl and phenyl substituted with one or more $X^1$ groups.

In another embodiment, the compounds of the present invention, or pharmaceutically acceptable salts, solvates, esters, or stereoisomers thereof have the following Formula (VIII):

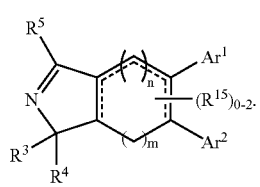

(VIII)

In another embodiment, the compounds of the present invention, or pharmaceutically acceptable salts, solvates, esters, or stereoisomers thereof have the following Formula (VIIIA):

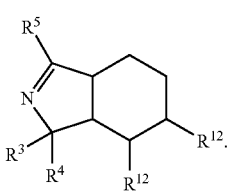

(VIIIA)

In another embodiment, the compounds of the present invention, or pharmaceutically acceptable salts, solvates, esters, or stereoisomers thereof, have the structure of Formula (VIIIA), wherein:

$R^3$, $R^4$, and $R^5$ are each independently H, or —N($R^{16}$)$_2$;

$R^9$ is selected from the group consisting of H and $R^{11}$;

$R^{11}$ is selected from the group consisting of alkyl, unsubstituted aryl, and aryl substituted with one or more $X^1$ groups;

$R^{12}$ is selected from the group consisting of unsubstituted phenyl and phenyl substituted with one or more $X^1$ groups; and $R^{16}$ is selected from the group consisting of $R^9$ and —C(O)—$R^{12}$.

In another embodiment of the compounds of Formula (I), or pharmaceutically acceptable salts, solvates, esters, or stereoisomers thereof, $R^1$ is selected from the group consisting of —C(O)—N($R^{10}$)$_2$, —C(O)—O-alkyl, and —C(O)—$R^{14}$; and $R^2$ is selected from the group consisting of H, alkyl, alkyl substituted with one or more —OH groups, and -alkylene-N($R^{10}$)$_2$.

In another embodiment, the compounds of the present invention, or pharmaceutically acceptable salts, solvates, esters, or stereoisomers thereof have the following Formula (IB):

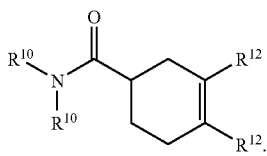

(IB)

In another embodiment, the compounds of the present invention, or pharmaceutically acceptable salts, solvates, esters, or stereoisomers thereof, have the structure of Formula (IB), wherein:

$R^9$ is selected from the group consisting of H and alkyl;

each $R^{10}$ is independently selected from the group consisting of H, alkyl substituted with one or more —OH groups, -alkylene-$R^{12}$, -alkylene-$R^{13}$, -alkylene-$R^{14}$, -alkylene-O—$R^9$, $R^{14}$, and benzo-fused cycloalkyl;

$R^{12}$ is selected from the group consisting of unsubstituted phenyl and phenyl substituted with one or more $X^1$ groups;

$R^{13}$ is selected from the group consisting of unsubstituted heteroaryl and heteroaryl substituted with one or more $X^2$ groups; and $R^{14}$ is selected from the group consisting of alkyl, unsubstituted cycloalkyl, or cycloalkyl substituted with one or more $X^4$ groups.

In another embodiment, the compounds of the present invention, or pharmaceutically acceptable salts, solvates, esters, or stereoisomers thereof have the following Formula (IC):

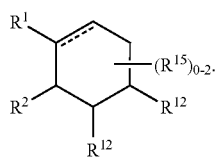

(IC)

In another embodiment, the compounds of the present invention, or pharmaceutically acceptable salts, solvates, esters, or stereoisomers thereof, have the structure of Formula (IC), wherein:

$R^1$ is —C(O)—N($R^{10}$)$_2$ or —C(O)—O-alkyl;

$R^2$ is selected from the group consisting of H, alkyl, alkyl substituted with one or more —OH groups, and -alkylene-N($R^{10}$)$_2$;

each $R^{10}$ is independently selected from the group consisting of H, -alkylene-$R^{12}$, and —C(O)—$R^{14}$;

$R^{12}$ is selected from the group consisting of unsubstituted phenyl and phenyl substituted with one or more $X^1$ groups; and $R^{15}$ is H or —OH.

In another embodiment, the compounds of the present invention, or pharmaceutically acceptable salts, solvates, esters, or stereoisomers thereof have the following Formula (ID):

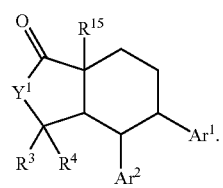

(ID)

In another embodiment, the compounds of the present invention, or pharmaceutically acceptable salts, solvates, esters, or stereoisomers thereof have the following Formula (IE):

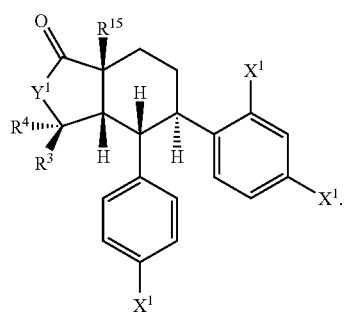

(IE)

In another embodiment, the compounds of the present invention, or pharmaceutically acceptable salts, solvates, esters, or stereoisomers thereof, have the structure of Formula (ID), wherein:

$Y^1$ is NH or N-Boc;

$R^3$ is H or alkyl;

$R^4$ is H or alkyl;

$R^{15}$ is alkyl;

and $Ar^1$ and $Ar^2$ are selected from the group consisting of unsubstituted phenyl and phenyl substituted with one or more $X^1$ groups.

In another embodiment, the compounds of the present invention, or pharmaceutically acceptable salts, solvates, esters, or stereoisomers thereof, have the structure of Formula (ID), wherein:

each $X^1$ is independently selected from the group consisting of halogen, —CN, —OH, —O-cycloalkyl, —O-cycloalkylalkyl, —O-alkylene-OR$^{19}$, —O-alkylene-C(O)N(R$^{20}$)$_2$, —O-alkylene-O—R$^{19}$, unsubstituted alkyl, alkyl substituted with one or more U groups, unsubstituted —O-alkyl, —O-alkyl substituted with one or more U groups, —O-alkenyl—O-alkylene-O-alkylene-OR$^{19}$, —O-alkylene-C(O)R$^{24}$, —O-alkylene-C(O)OR$^{19}$ and —O-alkyl.

In another embodiment, the compounds of the present invention, or pharmaceutically acceptable salts, solvates, esters, or stereoisomers thereof, have the structure of Formula (ID), wherein:

each X$^1$ is independently selected from the group consisting of —OCH$_3$, —OH, —OTf, —CN, —OCH$_2$CH$_3$, —OCH(CH$_3$)$_2$,

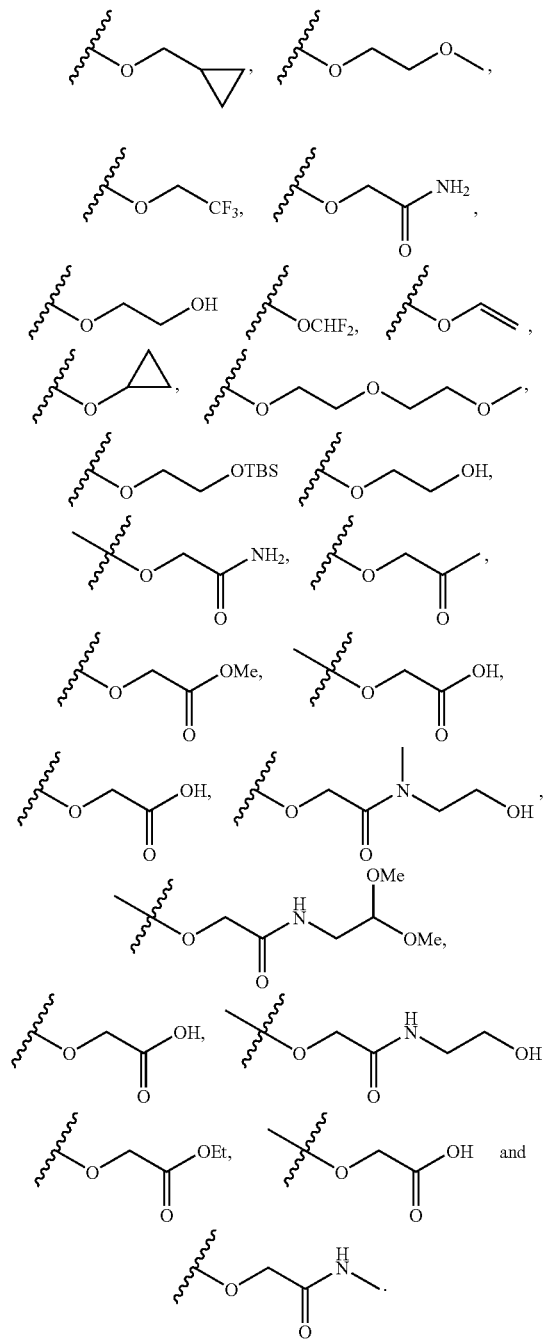

In another embodiment, the compounds of the present invention, or pharmaceutically acceptable salts, solvates, esters, or stereoisomers thereof, have the structure of Formula (ID),

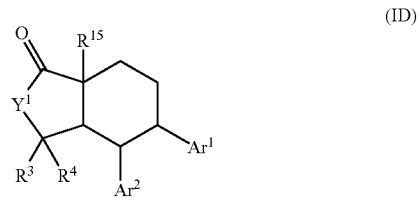

(ID)

or a pharmaceutically acceptable salt, solvate or ester thereof, wherein:

Y$^1$ is NH or N-Boc;
R$^3$ is H or alkyl;
R$^4$ is H or alkyl;
R$^{15}$ is alkyl;
Ar$^1$ and Ar$^2$ are selected from the group consisting of unsubstituted phenyl and phenyl substituted with one or more X$^1$ groups;

and each X$^1$ is independently selected from the group consisting of —OCH$_3$, —OH, —OTf, —CN, —OCH$_2$CH$_3$, —OCH(CH$_3$)$_2$,

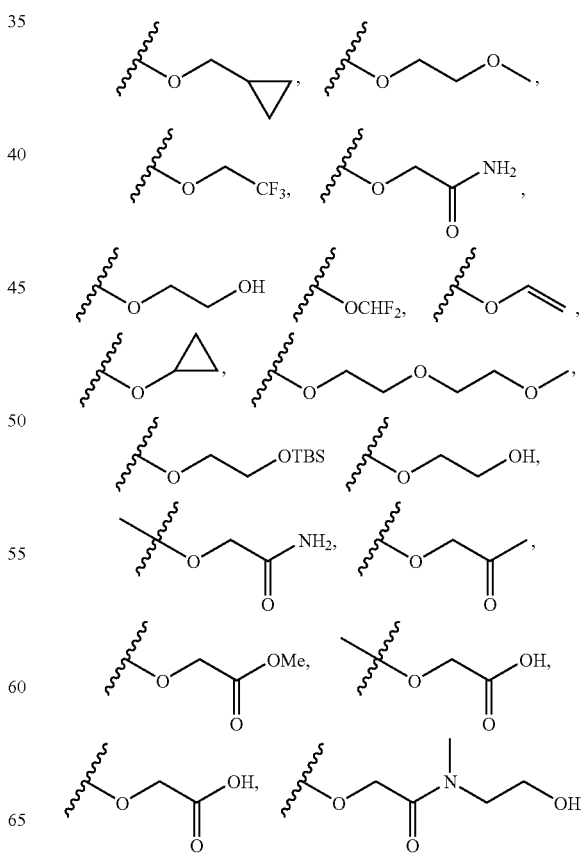

-continued

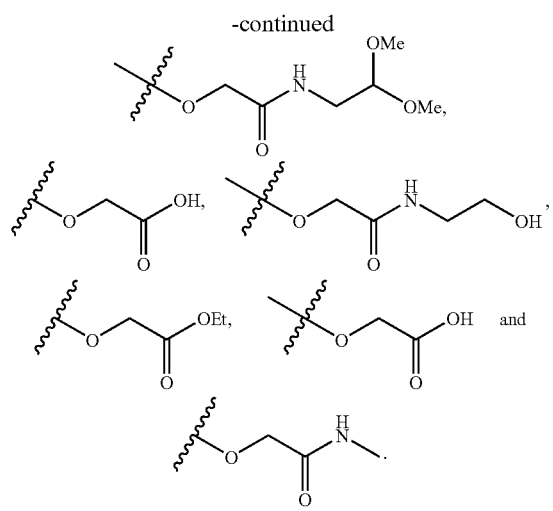

In another embodiment, the compounds of the present invention, or pharmaceutically acceptable salts, solvates, esters, or stereoisomers thereof, have the structure of Formula (IE),

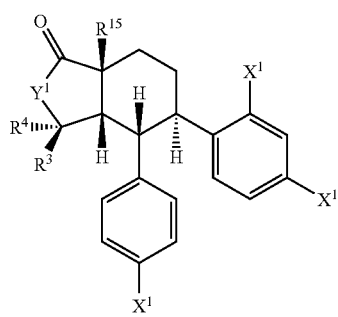
(IE)

or a pharmaceutically acceptable salt, solvate or ester thereof, wherein:
$Y^1$ is NH or N-Boc;
$R^3$ is H or alkyl;
$R^4$ is H or alkyl;
$R^{15}$ is alkyl;
and
each $X^1$ is independently selected from the group consisting of —OCH$_3$, —OH, —OTf, —CN, —OCH$_2$CH$_3$, —OCH(CH$_3$)$_2$,

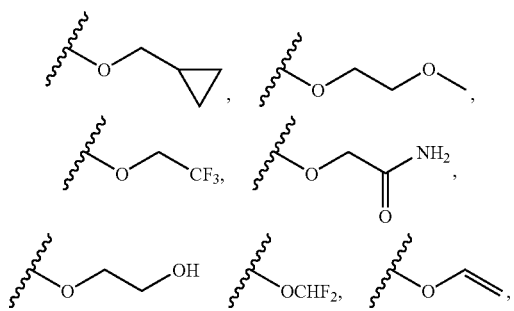

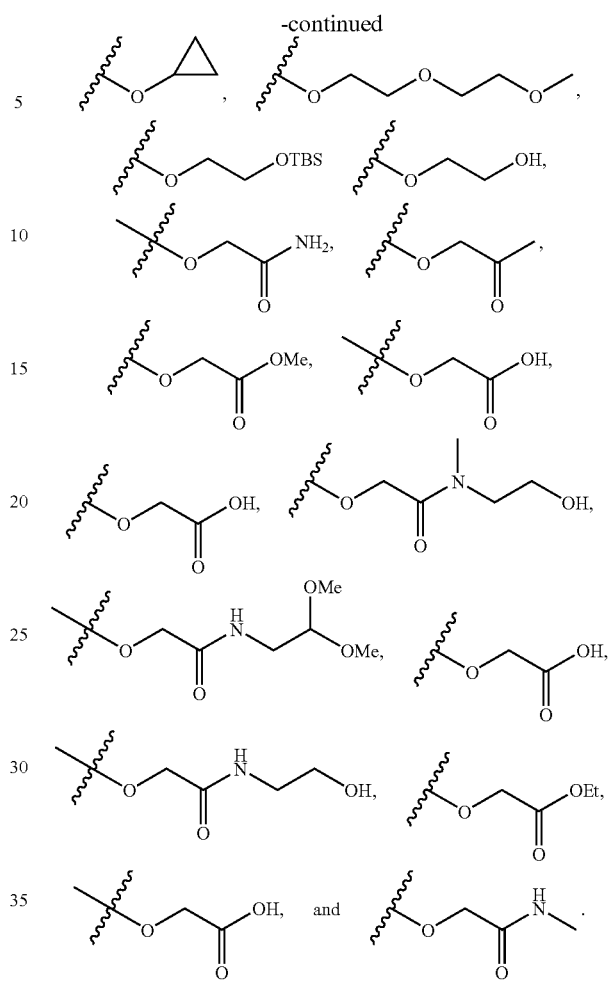

In another embodiment, the compounds of the present invention, or pharmaceutically acceptable salts, solvates, esters, or stereoisomers thereof, have the structure of Formula (I), wherein each $R^{15}$ is independently selected from the group consisting of H, —N$_3$, halogen, alkenyl, -alkylene-$R^{12}$, -alkylene-O—$R^9$, -alkylene-N($R^{18}$)$_2$, -alkylene-C(O)H, —OH, —CN, —O-alkyl, |-C(O)N($R^{18}$)$_2$, —N($R^{18}$)$_2$, —NHC(O)$R^{18}$, —NHC(O)$_2R^{18}$, —N$R^{18}$C(O)N($R^{18}$)$_2$, —NHS(O)$_2R^{18}$, —O-alkenyl, —C(O)$_2R^{18}$, unsubstituted alkyl, alkyl substituted with one or more U groups, —O-alkylene-C(O)$R^{18}$ or —C(O)$R^{18}$; with the proviso wherein the group —N($R^{18}$)$_2$, both $R^{18}$ groups taken together with the N atom to which they are bonded form an unsubstituted heterocycloalkyl, heterocycloalkyl substituted with one or more $X^3$ groups, or said substituted or unsubstituted heterocycloalkyl group is fused with aryl, heteroaryl, cycloalkyl or heterocycloalkyl.

In another embodiment, the compounds of the present invention, or pharmaceutically acceptable salts, solvates, esters, or stereoisomers thereof, have the structure of Formula (I), wherein each $R^{15}$ is independently selected from the group consisting of H, —OH, —OCH$_3$, —OCH$_2$CH$_3$, —CH$_3$, —CH$_2$CH$_3$, —CH$_2$CH$_2$CH$_3$, —N$_3$, —NH$_2$, —CO$_2$H, —CO$_2$CH$_3$, —CH$_2$OH, —CH$_2$CH$_2$OH, —CH$_2$CH$_2$OTBS, —CH$_2$OCH$_3$, —OCH$_2$CH$_2$OH,

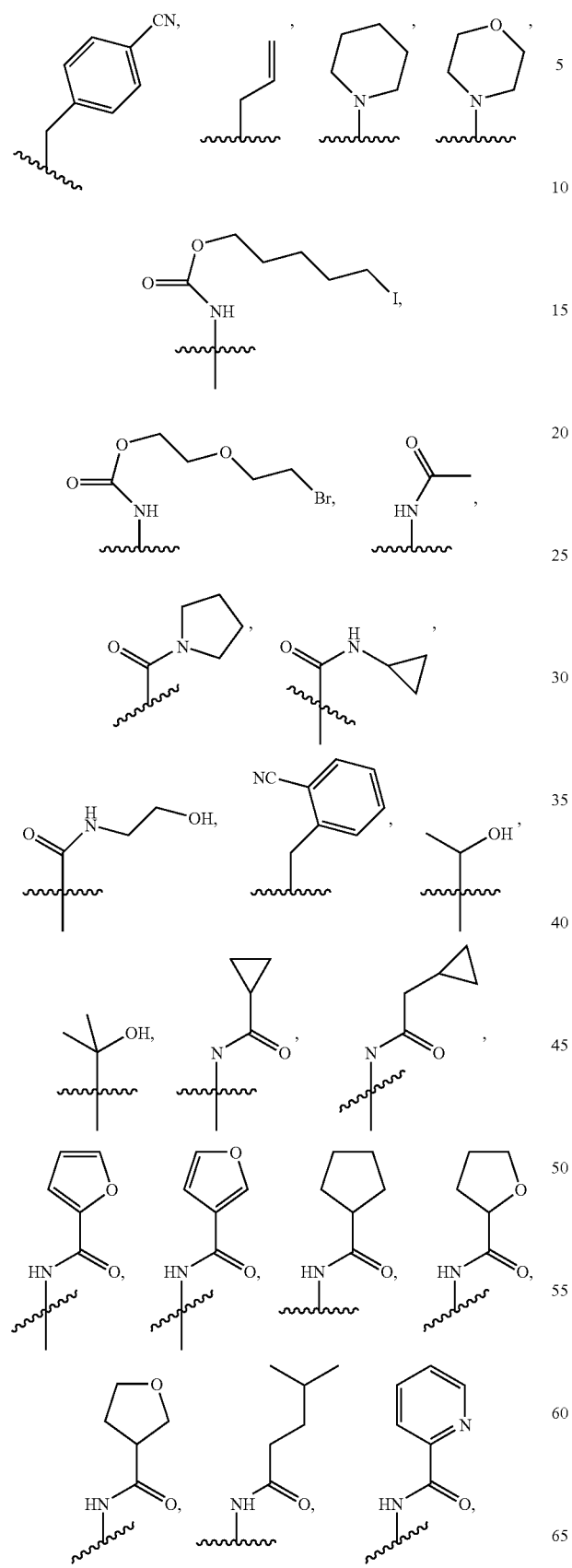
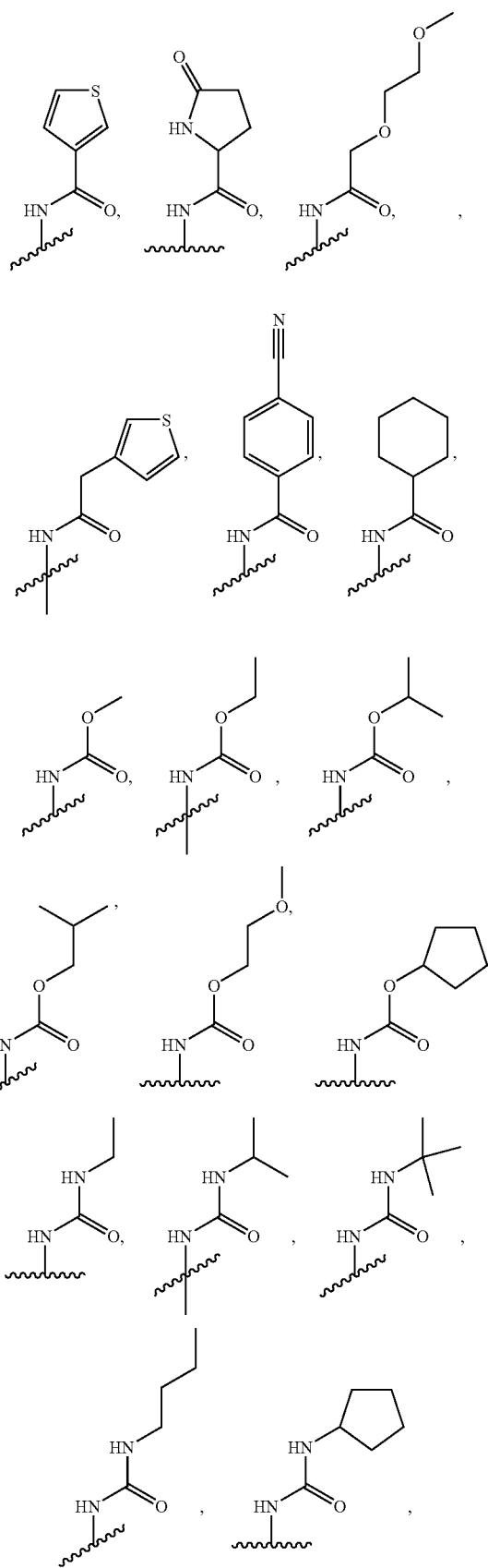

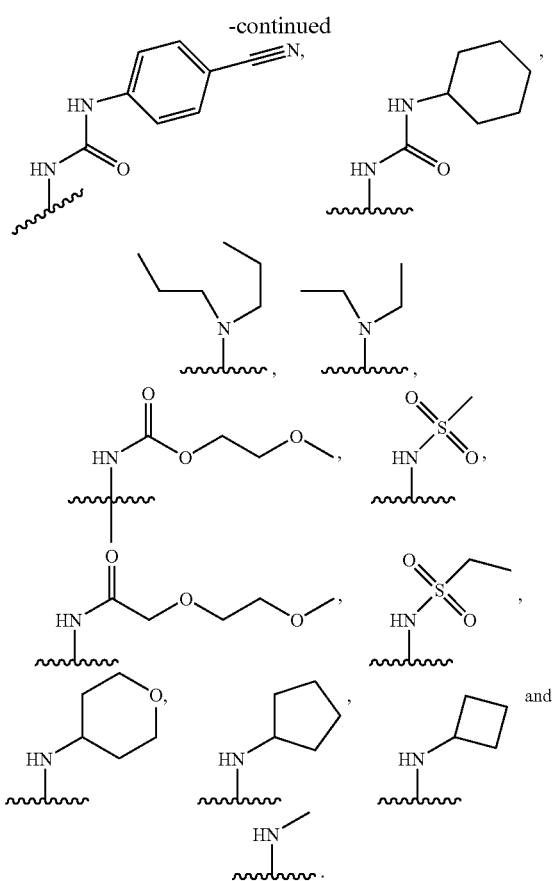

In another embodiment, the compounds of the present invention, or pharmaceutically acceptable salts, solvates, esters, or stereoisomers thereof, have the structure of Formula (I), wherein: $R^3$ and $R^4$ are each independently selected from the group consisting of H, —O—$R^9$, $R^{11}$, and —N($R^{16}$)$_2$.

In another embodiment, the compounds of the present invention, or pharmaceutically acceptable salts, solvates, esters, or stereoisomers thereof, have the structure of Formula (I), wherein each $R^3$ and $R^4$ is independently selected from the group consisting of H, —CH$_3$, —CH$_2$OH, —CH$_2$OCH$_2$CH$_2$OCH$_3$, —CH$_2$OCH$_3$, —CH$_2$OCH$_2$CH$_3$, —CH$_2$OCH$_2$CH$_2$CH$_3$, —CH$_2$CH$_2$OH,

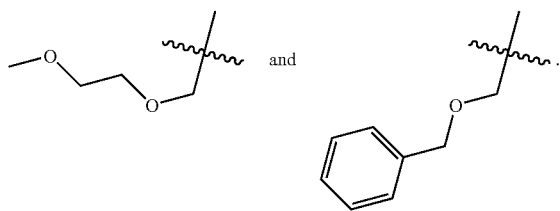

In another embodiment, the compounds of the present invention, or pharmaceutically acceptable salts, solvates, esters, or stereoisomers thereof, have the structure of Formula (I), wherein $R^7$ is selected from the group consisting of H, alkyl, arylalkyl, alkenyl, -alkylene-N($R^9$)$_2$, -alkylene-O—$R^9$, -alkylene-$R^{12}$, —C(O)—$R^{14}$, -alkylene-C(O)H, —C(O)—O—$R^{11}$, and Boc.

In another embodiment, the compounds of the present invention, or pharmaceutically acceptable salts, solvates, esters, or stereoisomers thereof, have the structure of Formula (I), wherein $R^7$ is H, —CH$_3$, Boc,

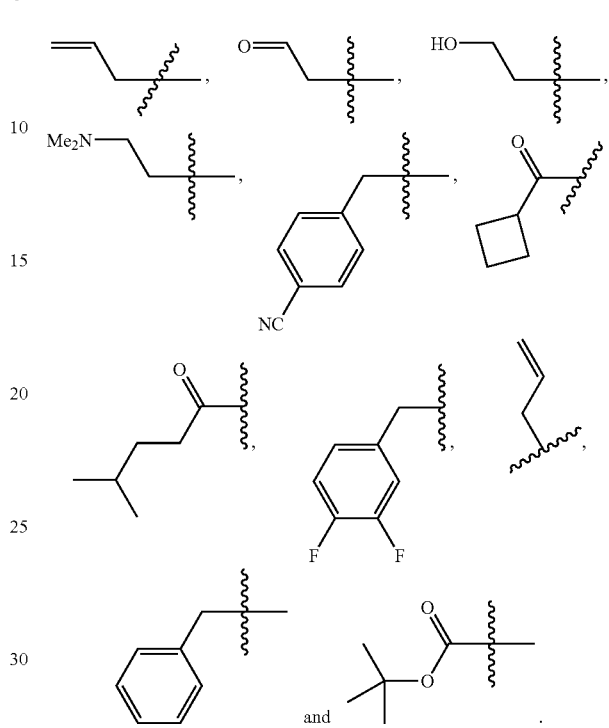

and

In another embodiment, the compounds of the present invention, or pharmaceutically acceptable salts, solvates, esters, or stereoisomers thereof, have the structure of Formula (I), wherein Ar$^1$ is phenyl substituted with one or more $X^1$ groups; and each $X^1$ is independently selected from the group consisting of halogen, —CN, —O—$R^{19}$, —OH, —O—S(O)$_2$- haloalkyl, unsubstituted aryl, aryl substituted with one or more Z groups, unsubstituted heteroaryl, heteroaryl substituted with one or more Z groups, —O-cycloalkyl, —O-cycloalkylalkyl, —O-alkylene-O$R^{19}$, —O-alkylene-C(O)N($R^{20}$)$_2$, —O-alkylene-O—$R^{19}$, unsubstituted alkyl, alkyl substituted with one or more U groups, unsubstituted —O-alkyl, —O-alkyl substituted with one or more U groups, —O-alkenyl, —O-alkylene-O-alkylene-O$R^{19}$, —O-alkylene-C(O)$R^{24}$, —O-alkylene-C(O)O$R^{19}$, —O-alkyl, —N($R^{25}$)$_2$, —C(O)alkyl, —C(O)OH, —C(O)O-alkyl, —C(O)O-cycloalkyl, —C(O)N($R^{25}$)$_2$, —O-alkylene-heterocycloalkyl, —O-alkylene-heterocycloalkyl substituted with one or more W$^3$ groups, unsubstituted heterocycloalkyl, -heterocycloalkyl substituted with one or more W$^3$ groups, —O-alkenylene-O-alkylene-O—$R^{24}$, —O-alkylene-N($R^{25}$)$_2$, —O-alkylene-C(O)N($R^{25}$)$_2$, unsubstituted cycloalkyl, cycloalkyl substituted with one or more W$^4$ groups, —S(O)—$R^{24}$, —S(O)$_2$—$R^{24}$, and alkenyl; with the proviso wherein the group —N($R^{20}$)$_2$ or —N($R^{25}$)$_2$ both $R^{20}$ or $R^{25}$ groups taken together with the N atom to which they are bonded form an unsubstituted heterocycloalkyl, heterocycloalkyl substituted with one or more $X^3$ groups, or said substituted or unsubstituted heterocycloalkyl group is fused with aryl, heteroaryl, cycloalkyl or heterocycloalkyl.

In another embodiment, the compounds of the present invention, or pharmaceutically acceptable salts, solvates, esters, or stereoisomers thereof, have the structure of Formula (I), wherein each $X^1$ is independently selected from the group consisting of Cl, F, —$CH_3$, —$OCH_3$, —$OCH_2CH_3$, —OH, —OTf, —CN, —$OCH_2CH_3$, —$OCH(CH_3)_2$,
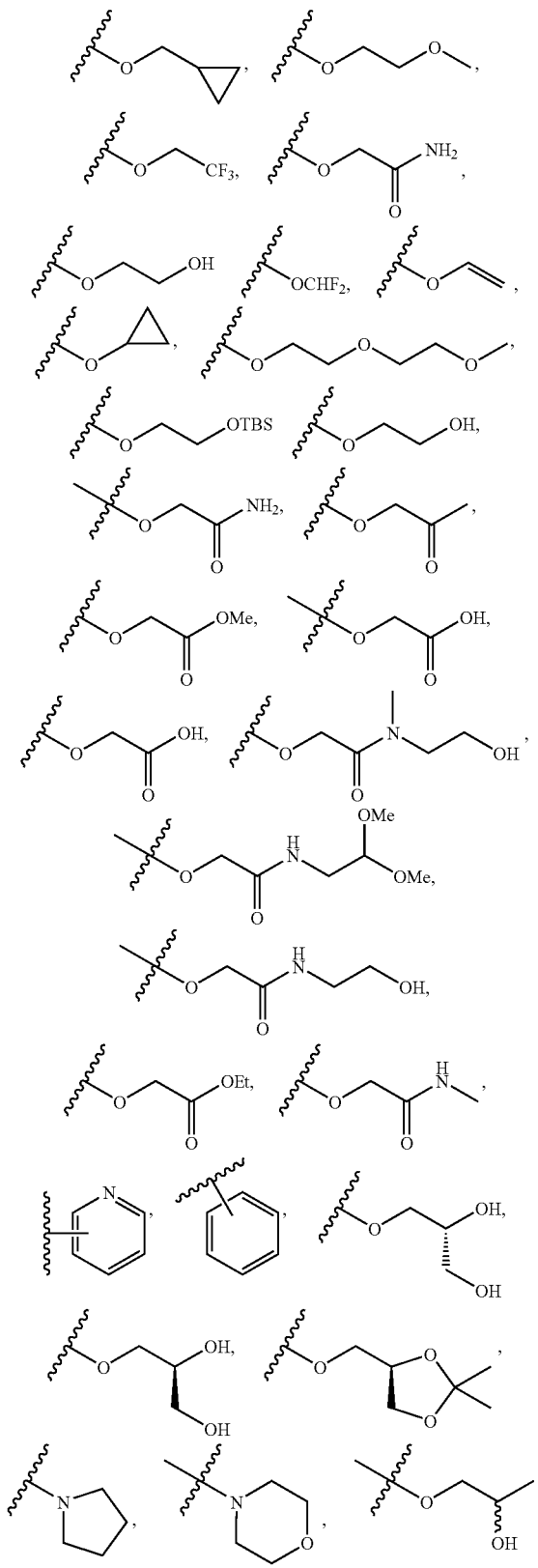
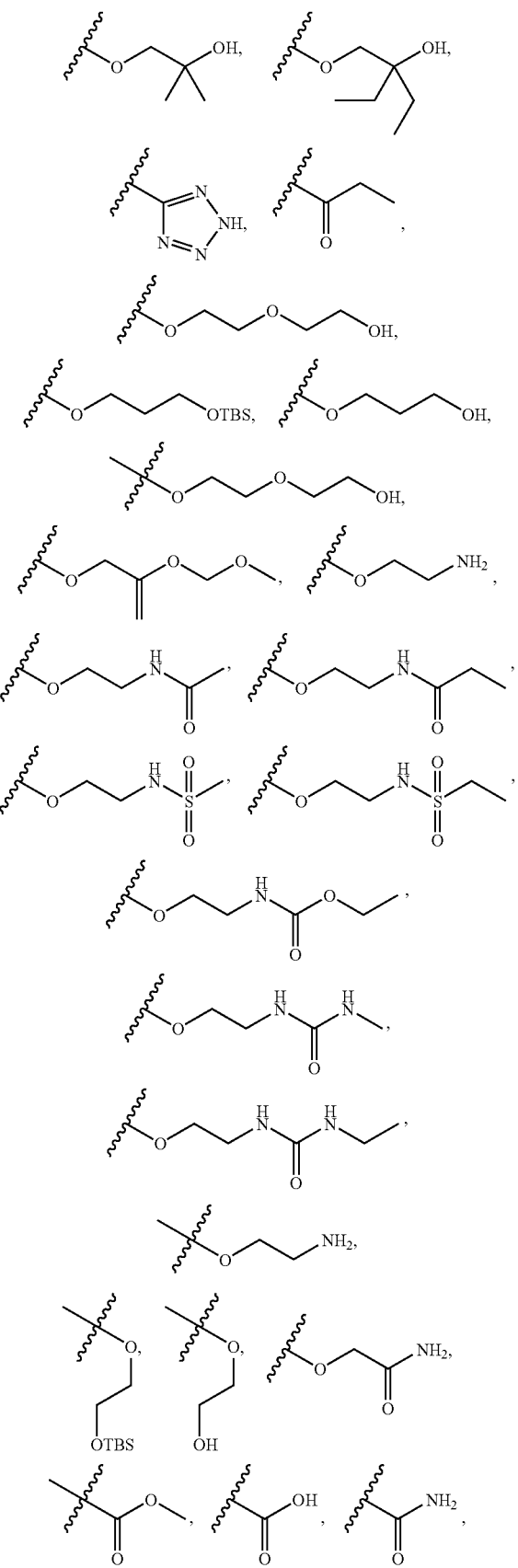

-continued
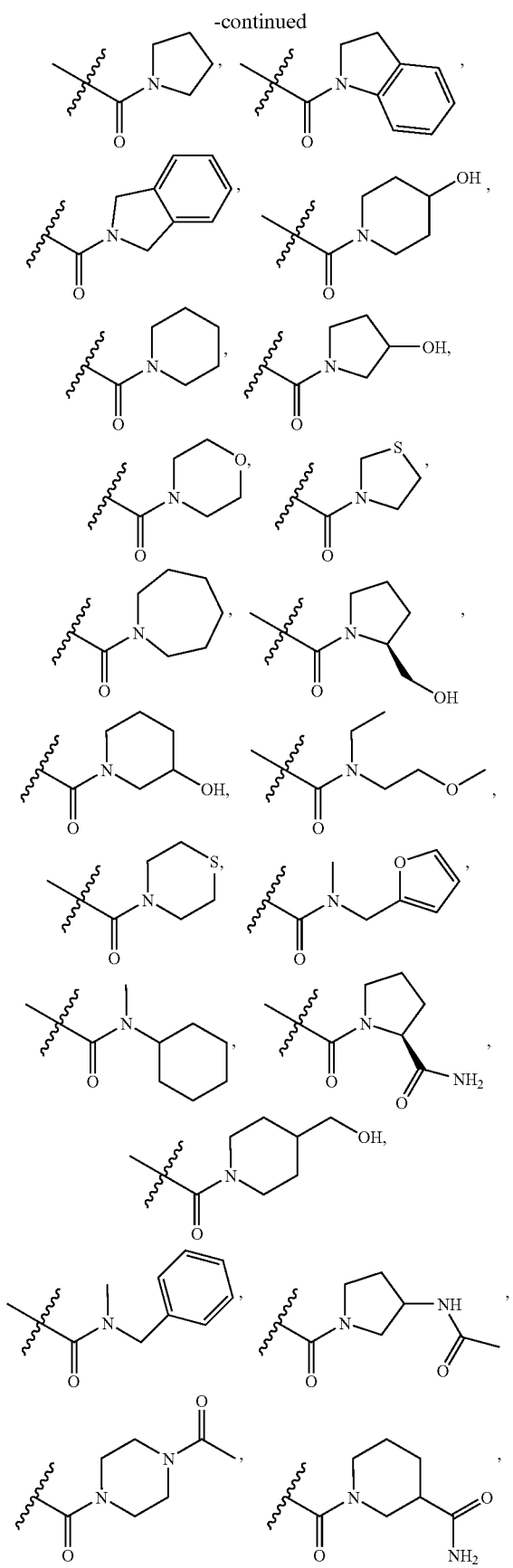
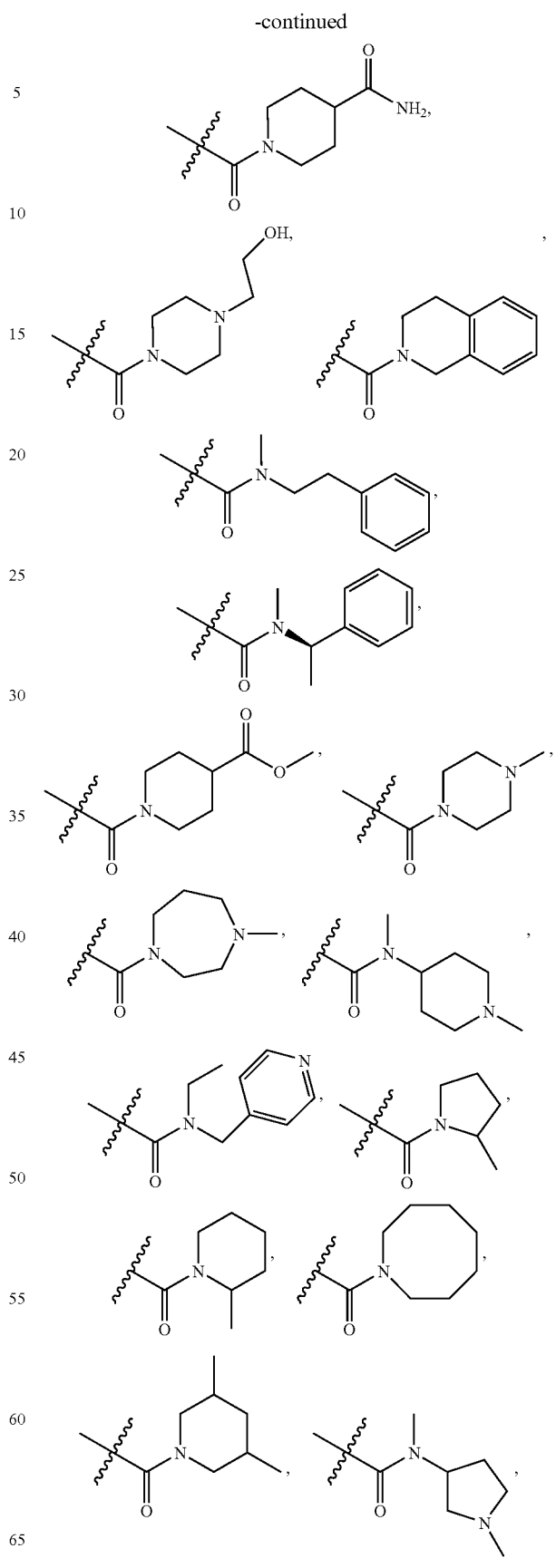

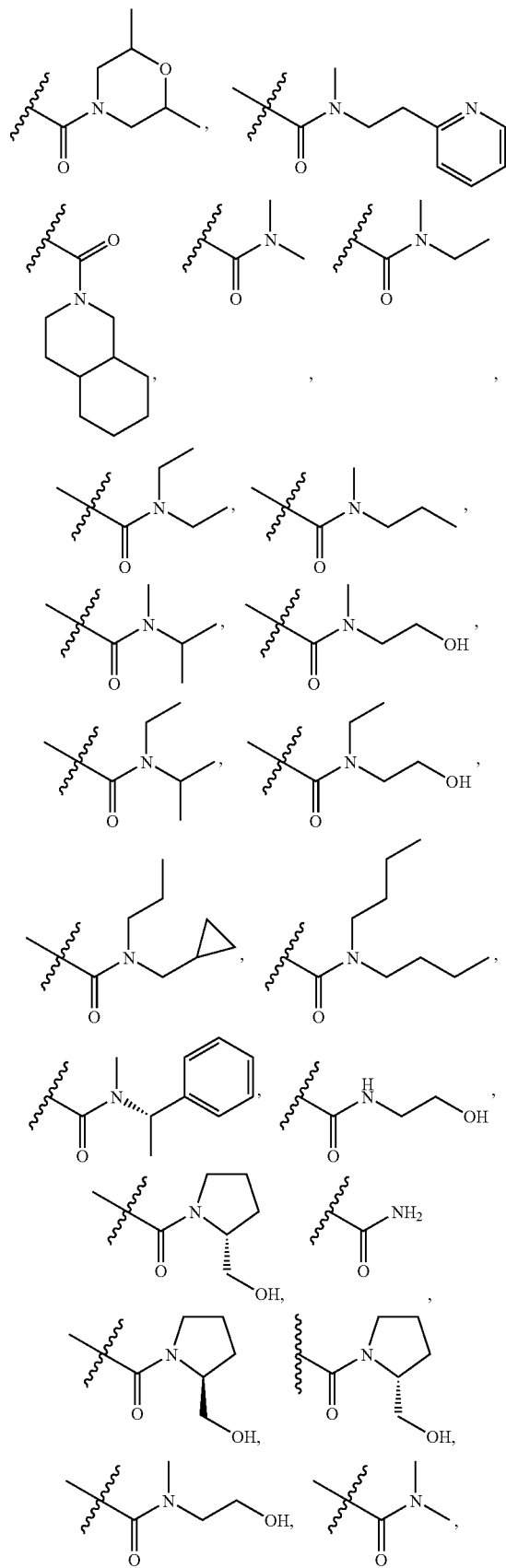
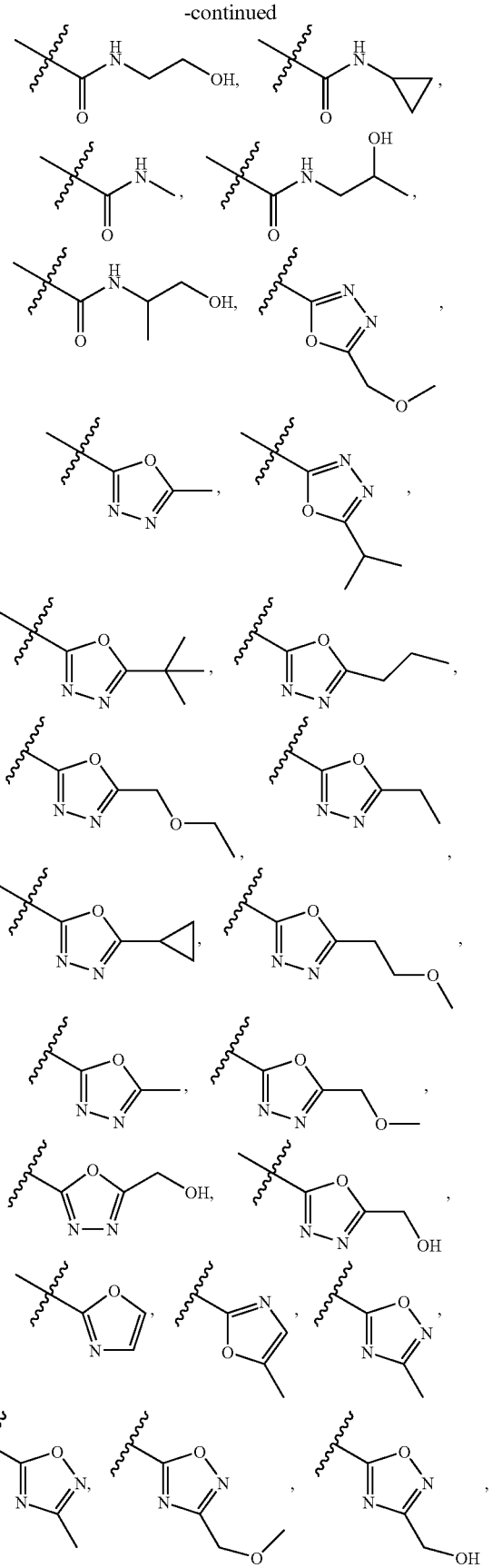

-continued

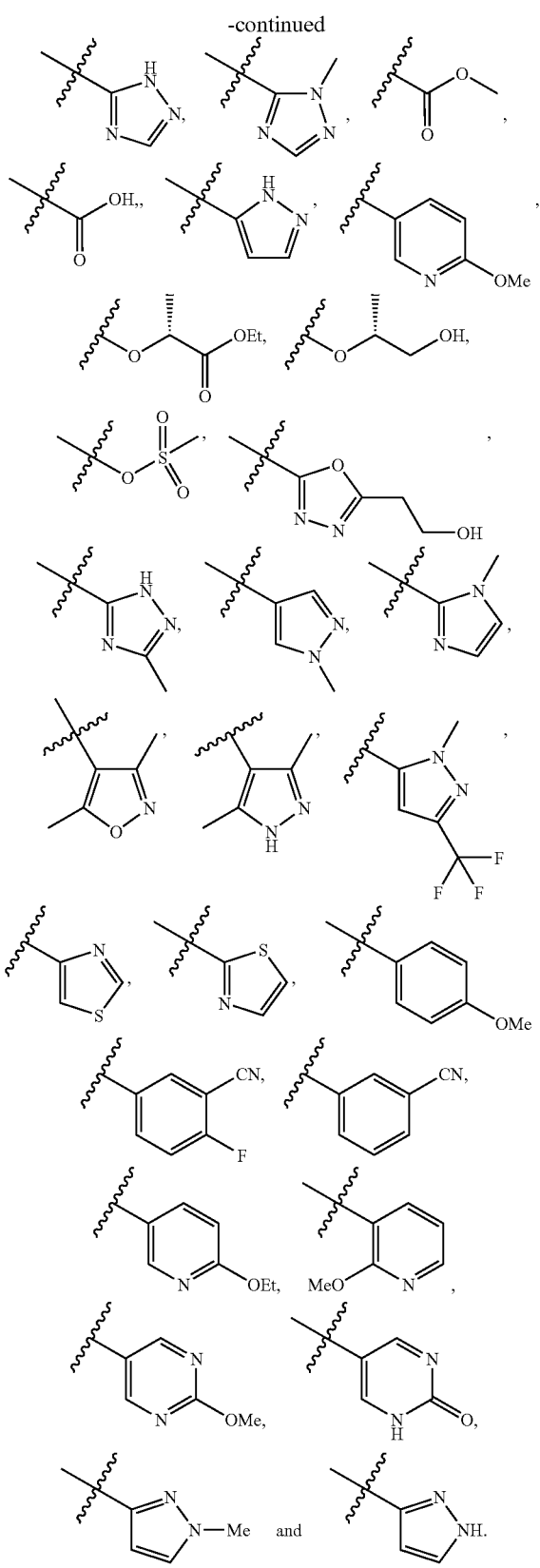

In another embodiment, the compounds of the present invention, or pharmaceutically acceptable salts, solvates, esters, or stereoisomers thereof, have the structure of Formula (I), wherein $Ar^2$ is phenyl substituted with one or more $X^1$ groups or pyridyl substituted with one or more $X^2$ groups; $X^1$ is selected from the group consisting of —OH, —CN, halogen, —OTIPS, —OTf, alkyl, —O-alkyl, —O-alkyl-OH and heteroaryl; and $X^2$ is selected from the group consisting of halogen and cycloalkyl.

In another embodiment, the compounds of the present invention, or pharmaceutically acceptable salts, solvates, esters, or stereoisomers thereof, have the structure of Formula (I), wherein $Ar^2$ is phenyl substituted with one or more $X^1$ groups or pyridyl substituted with one or more $X^2$ groups, $X^1$ is selected from the group consisting of —OH, —CN, Cl, —OTIPS, —CH$_3$, —OCH$_3$, —OCH$_2$CH$_3$, —OTf and

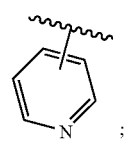

and $X^2$ is selected from the group consisting of Cl, Br and

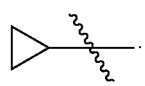

In another embodiment, the compounds of the present invention, or pharmaceutically acceptable salts, esters, or stereoisomers thereof, have the structure of the following Formulas (IF) or (IFa):

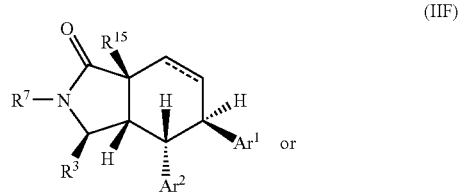
(IIF)

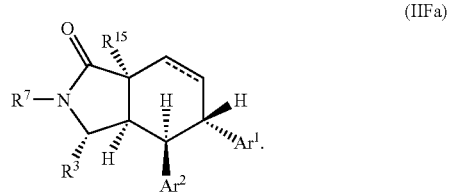
(IIFa)

In another embodiment, the compounds of the present invention, or pharmaceutically acceptable salts, solvates, esters, or stereoisomers thereof, have the structure of the following Formulas (IF) or (IFa):

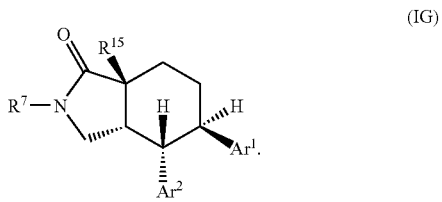
(IG)

In another embodiment, the compounds of the present invention, or pharmaceutically acceptable salts, solvates, esters, or stereoisomers thereof, have the structure of the following Formula (IH):
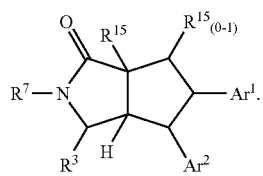
(IH)
An even further embodiment of formula I are those compounds with the following structures
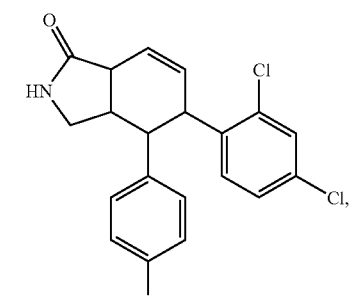
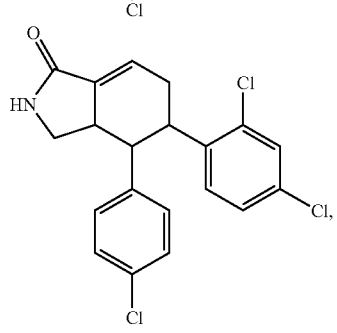
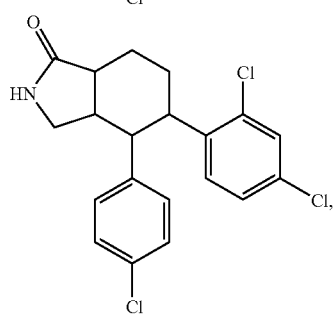
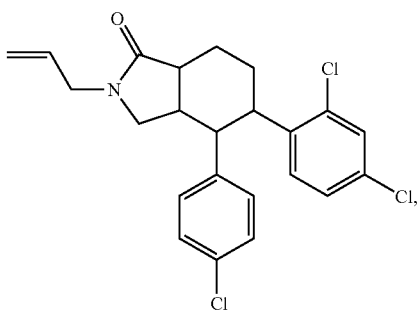
-continued
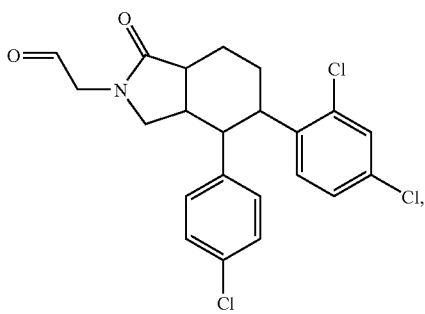
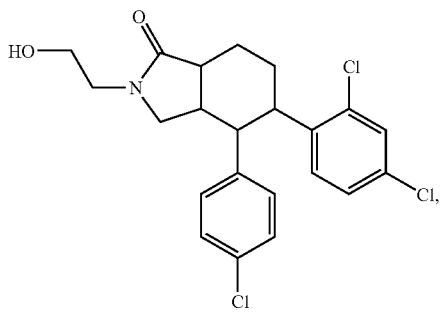
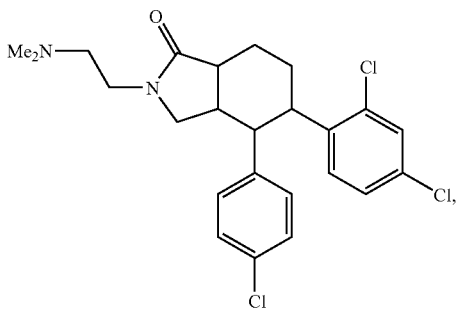
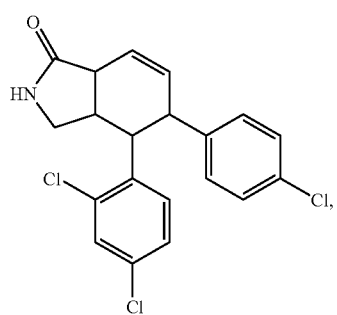
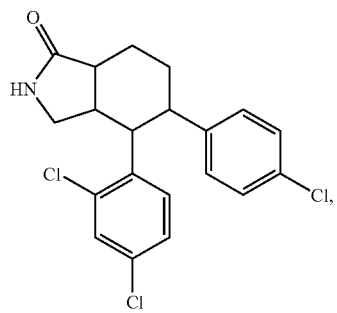

-continued
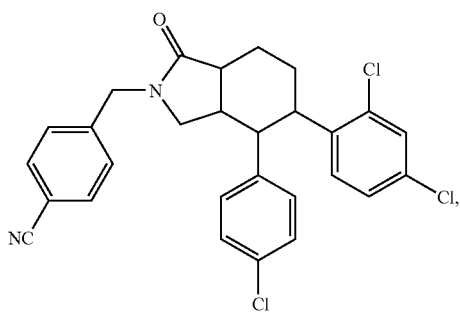
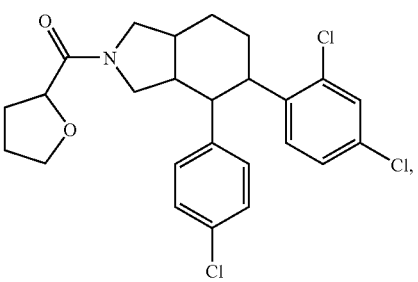
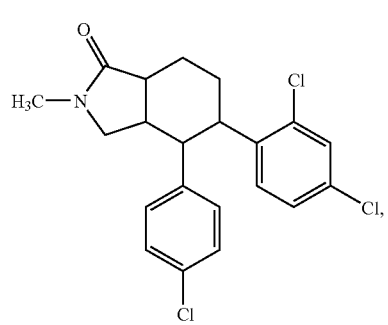
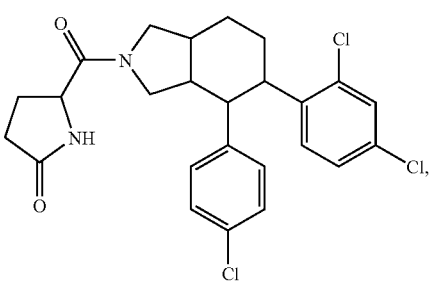
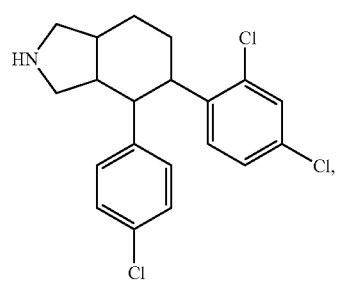
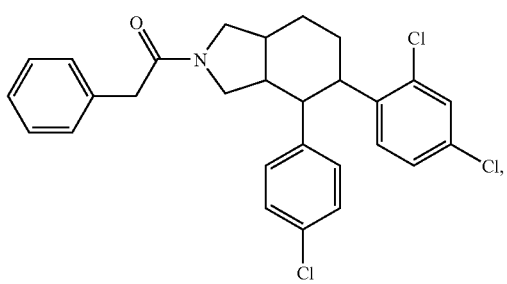
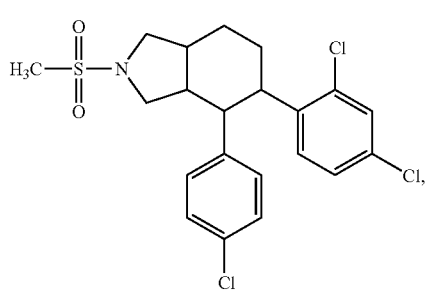
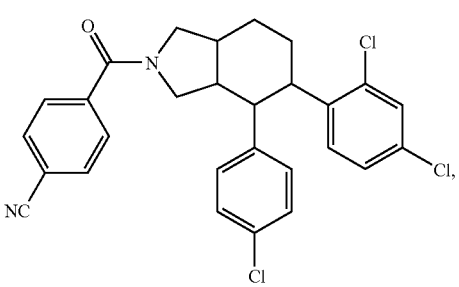
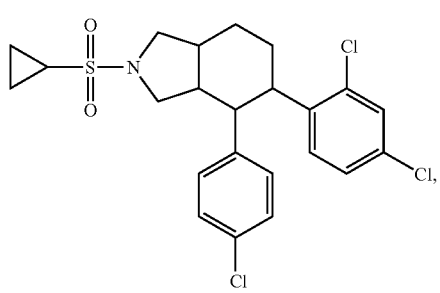
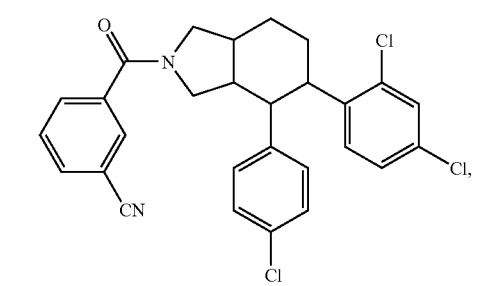

-continued
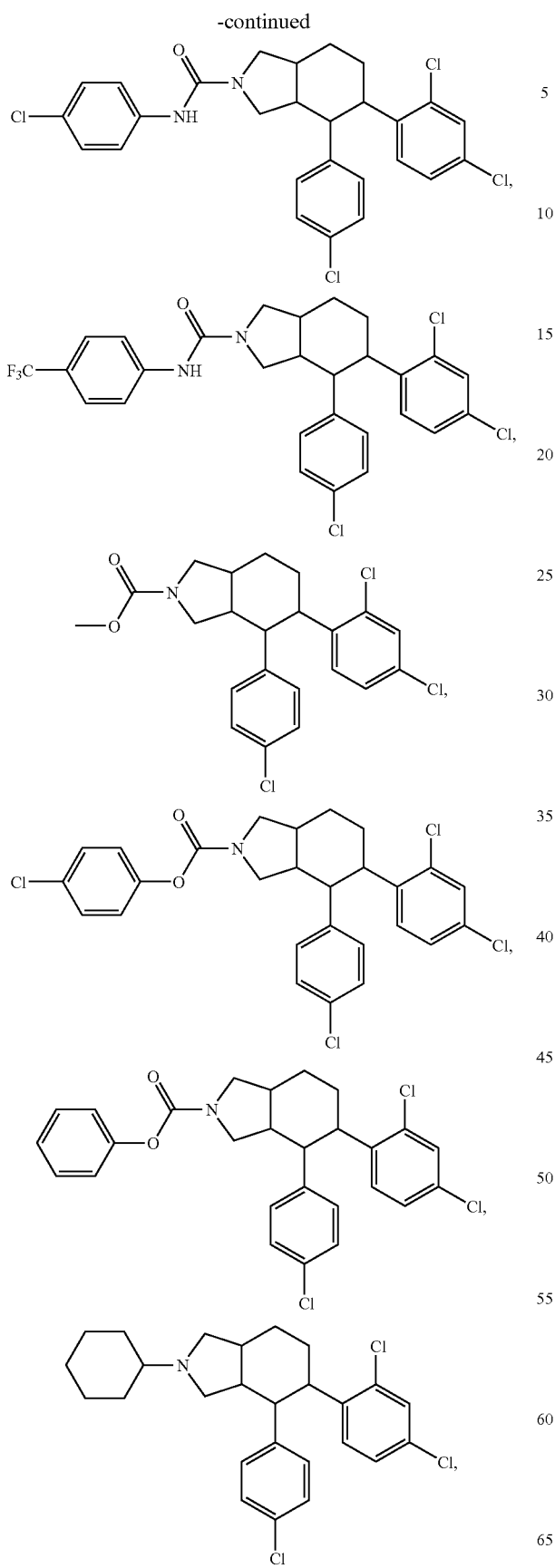
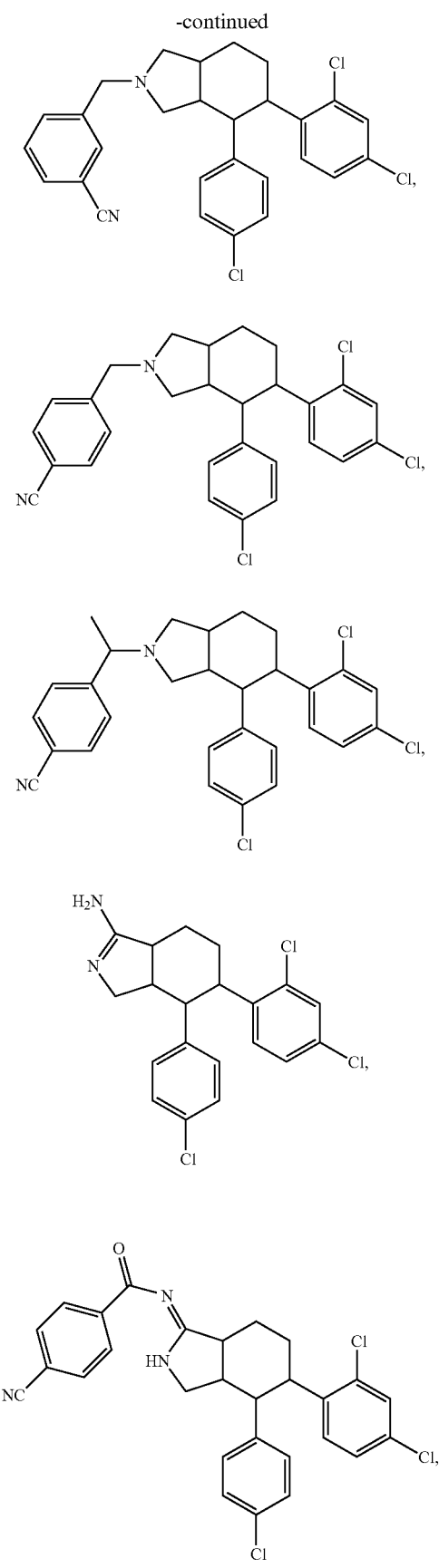

-continued
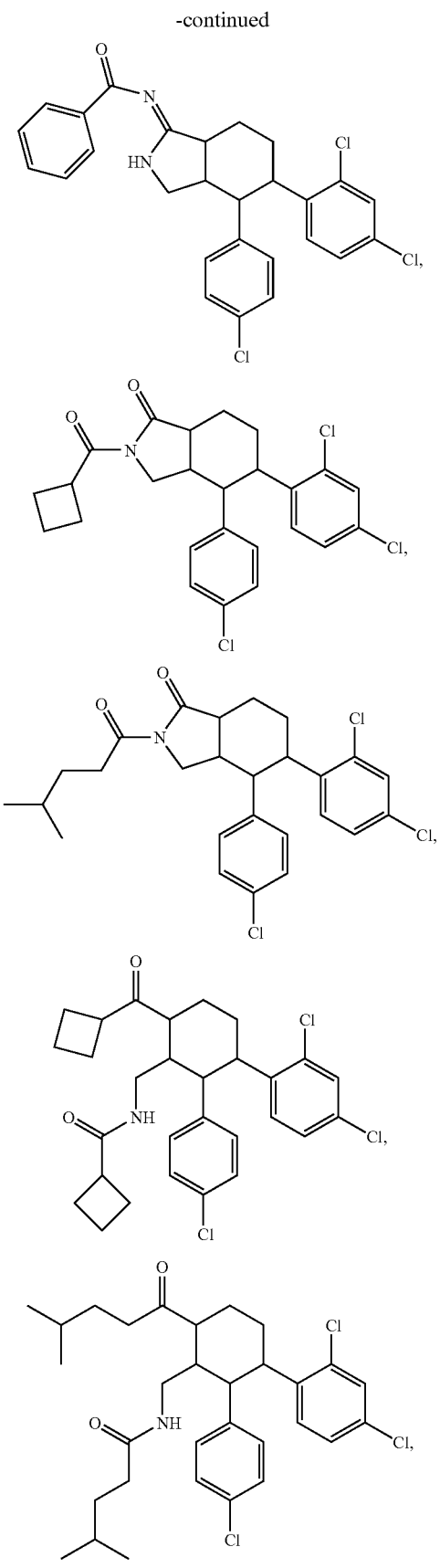
-continued
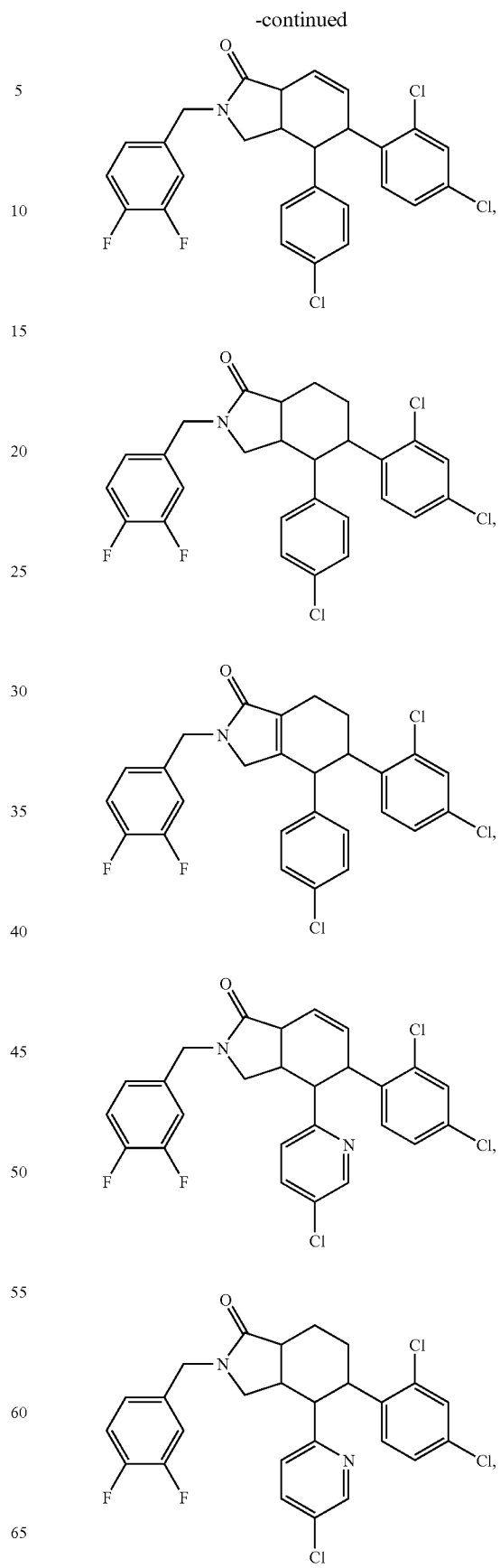

-continued
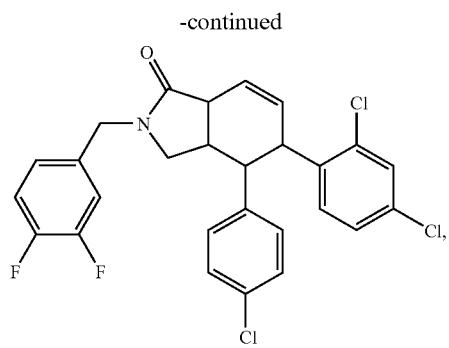
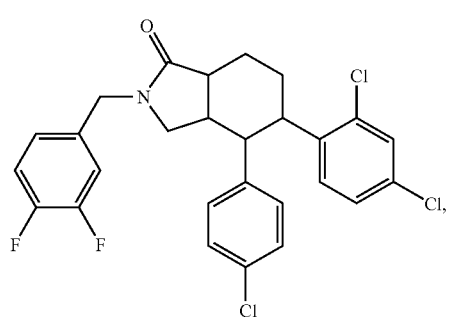
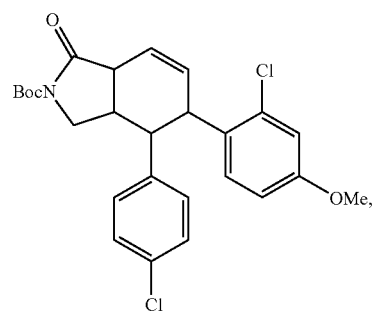
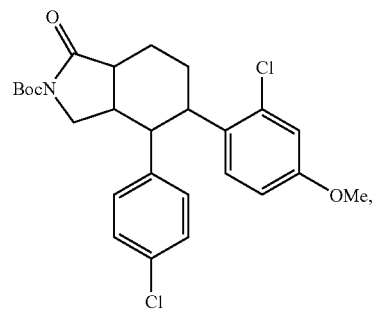
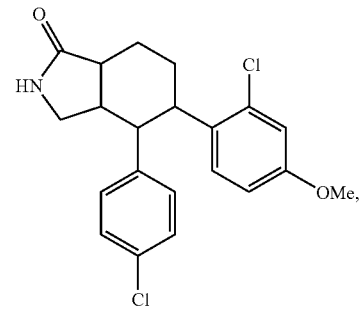
-continued
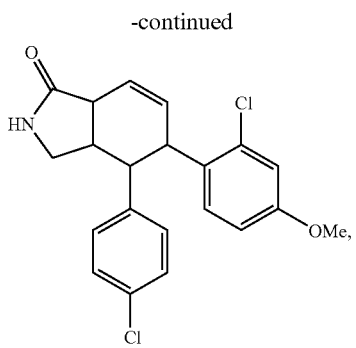
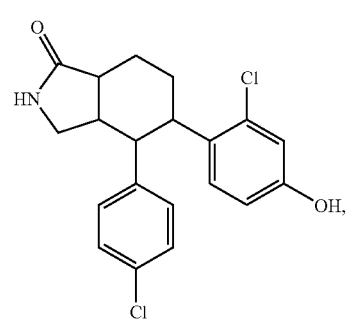
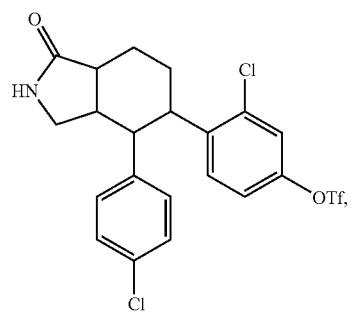
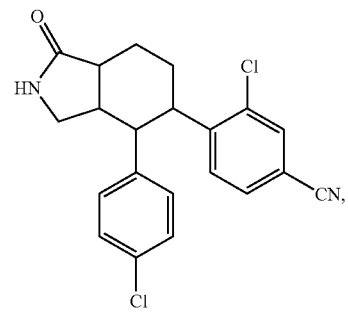
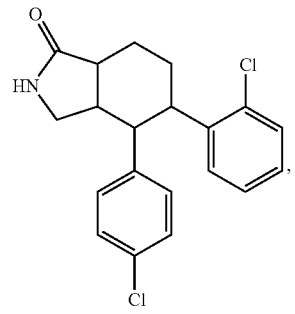

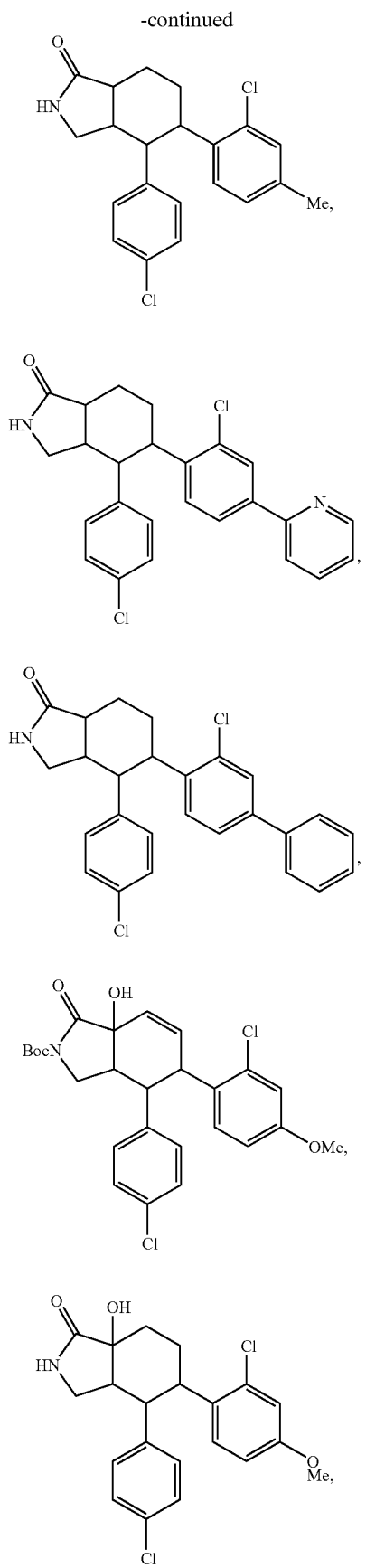
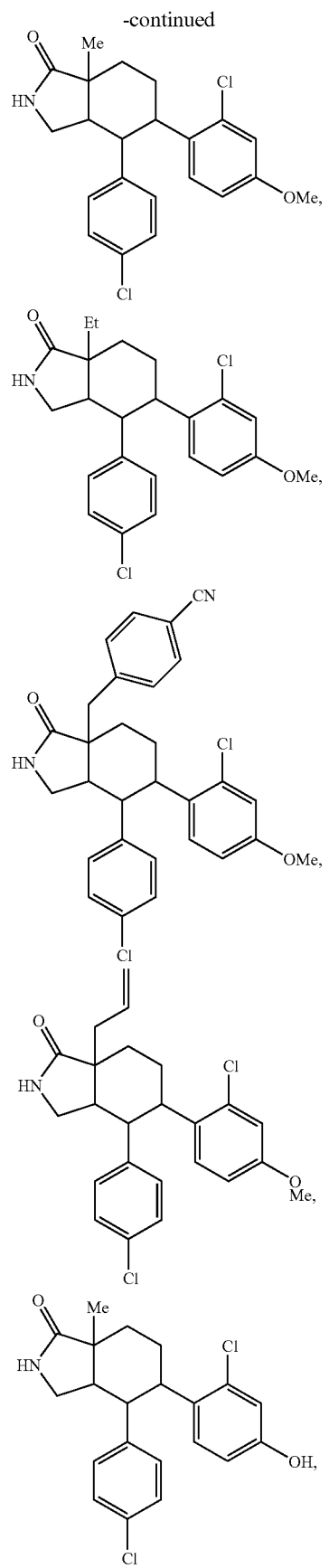

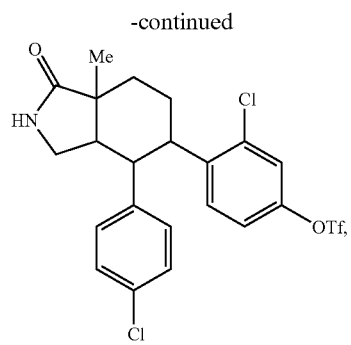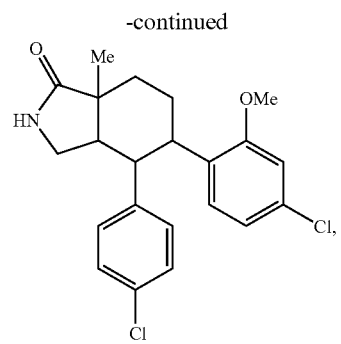

-continued
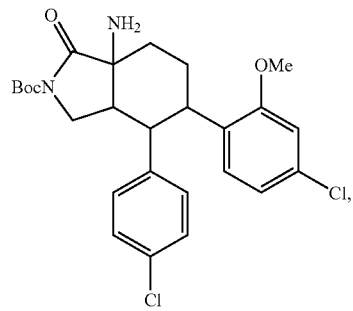
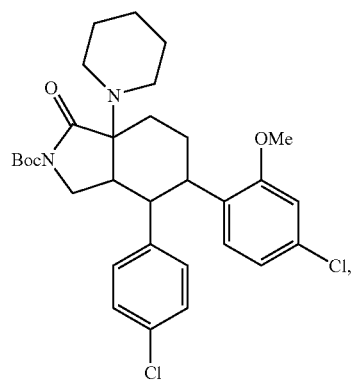
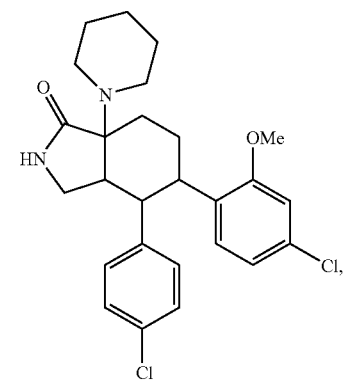
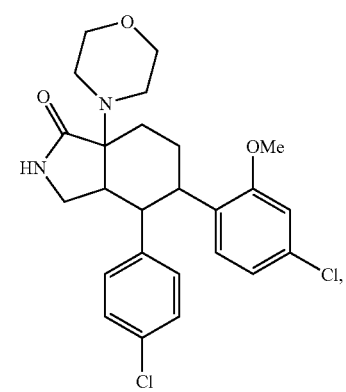
-continued
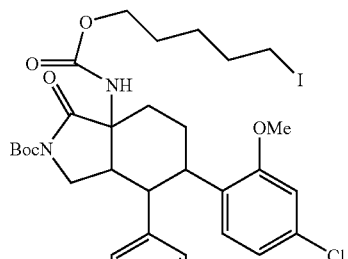
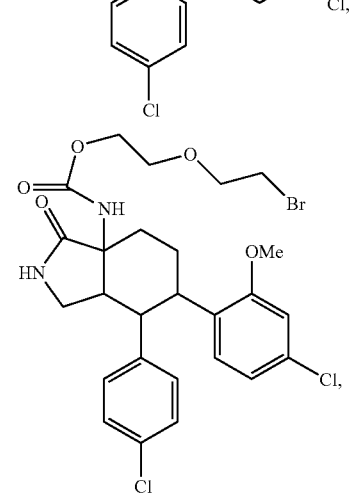

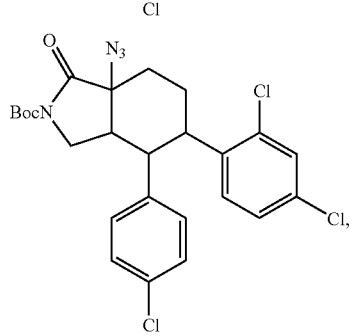

-continued
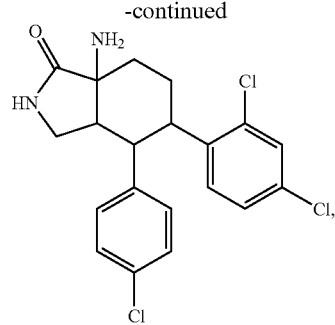
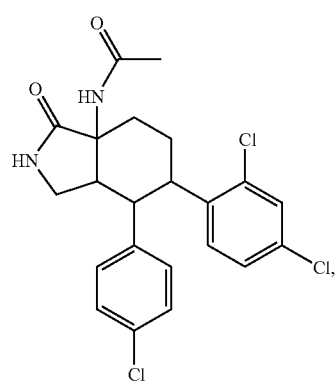
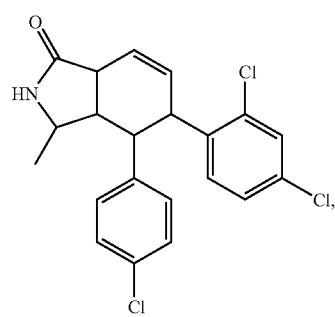
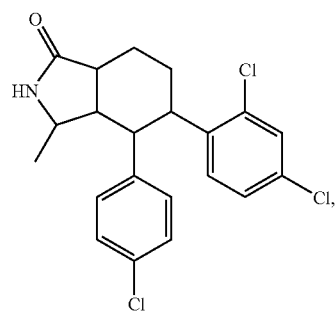
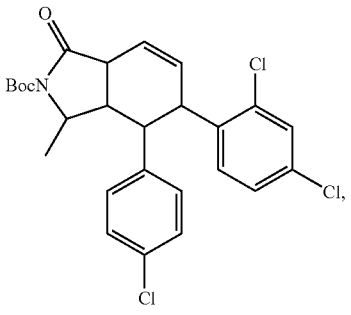
-continued
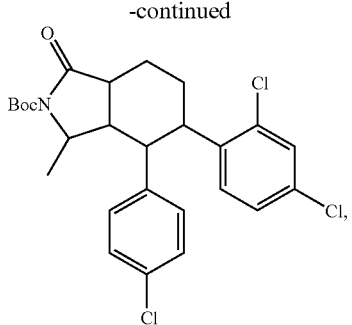
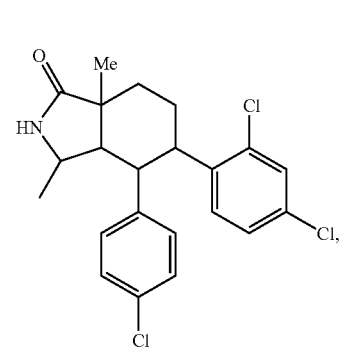
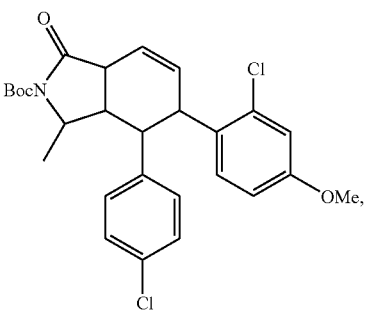
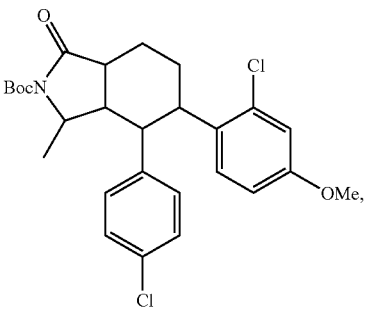
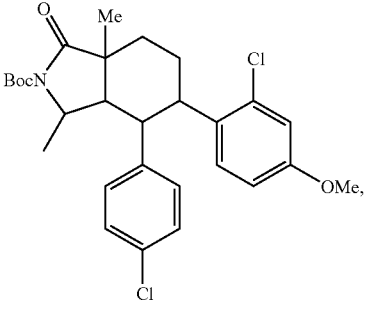

-continued
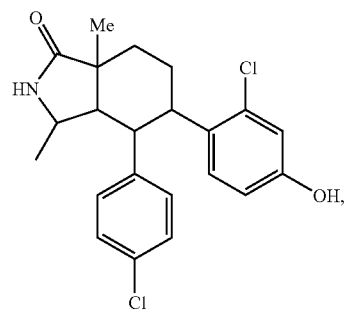
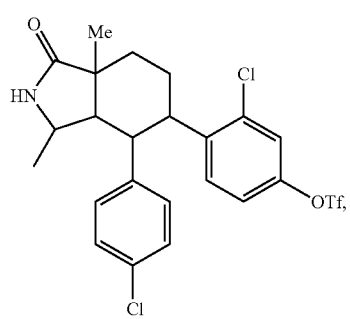
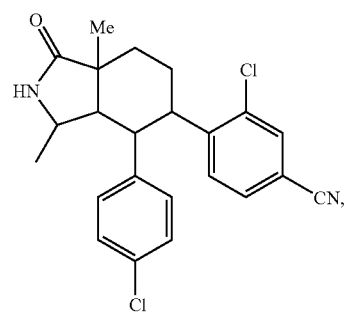
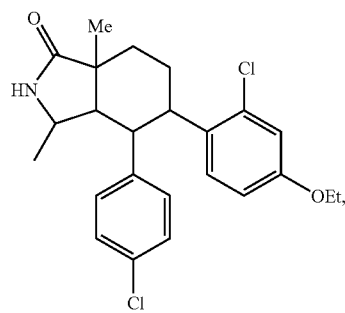
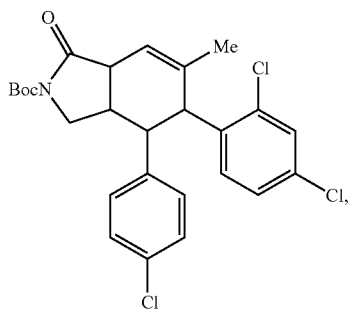
-continued
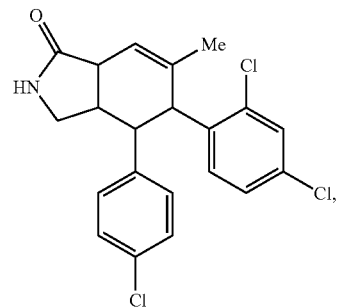
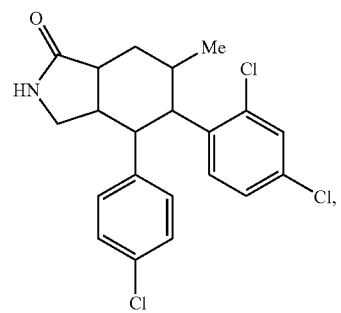
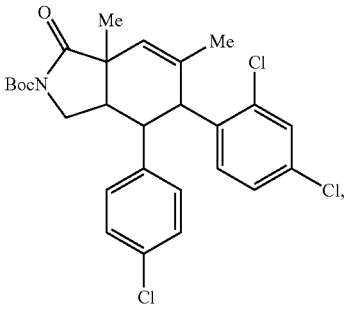
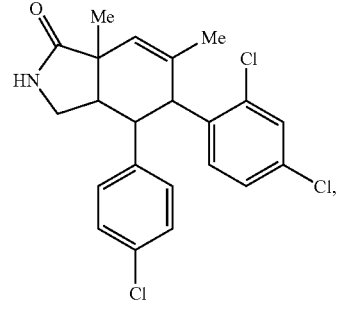
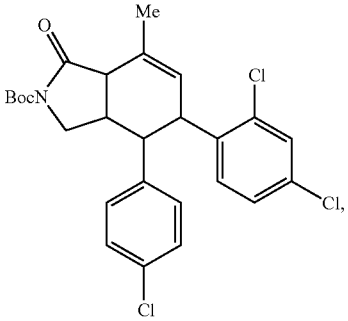

-continued
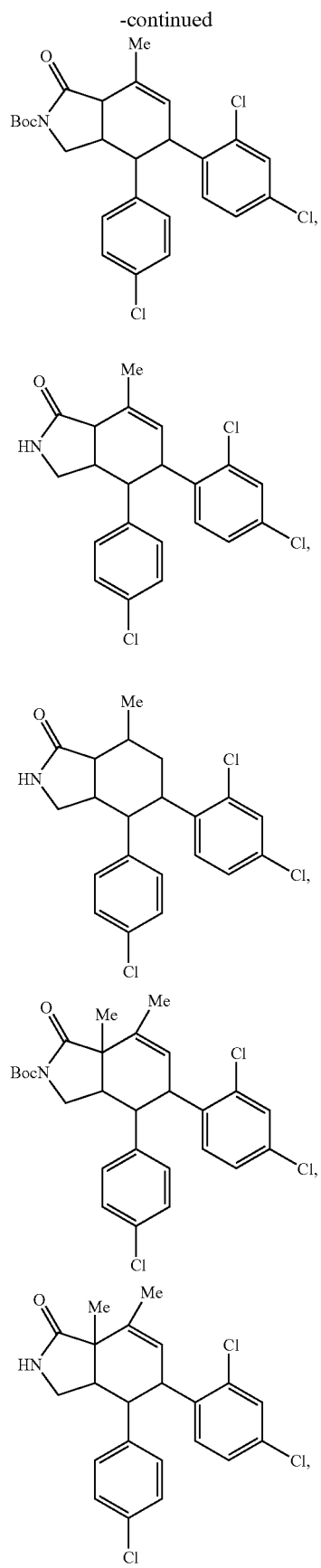
-continued
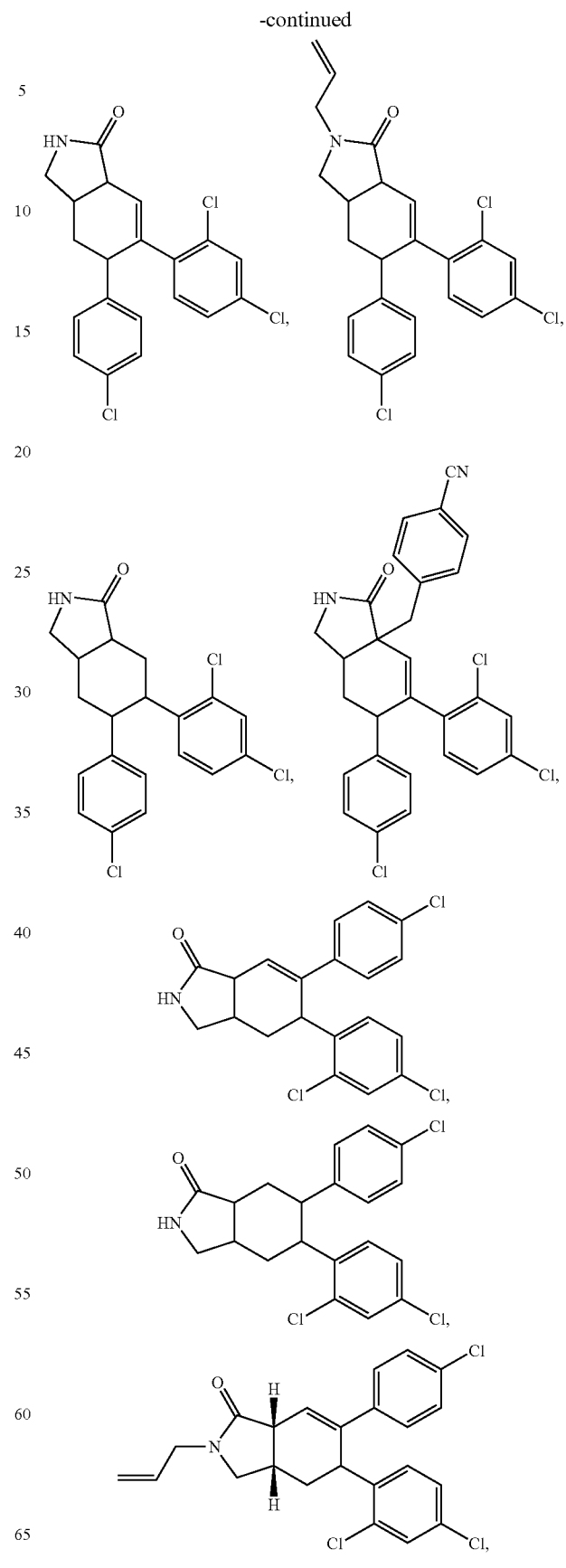

-continued
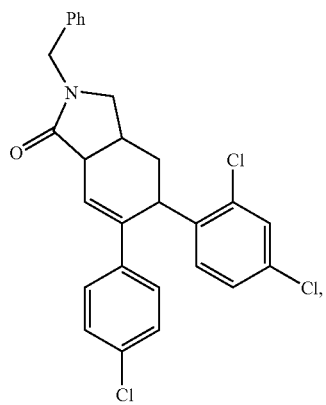
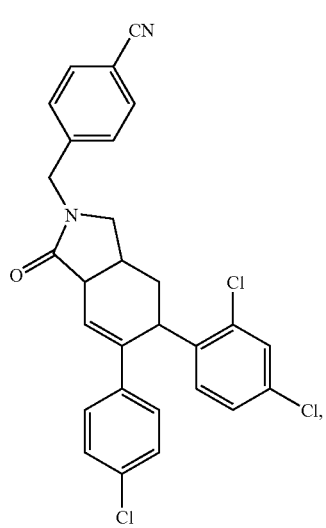
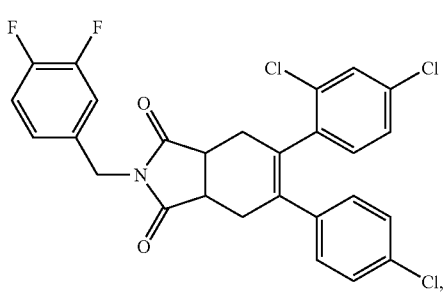
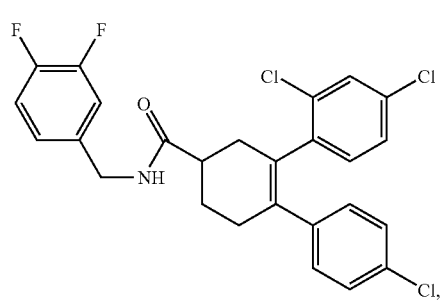
-continued
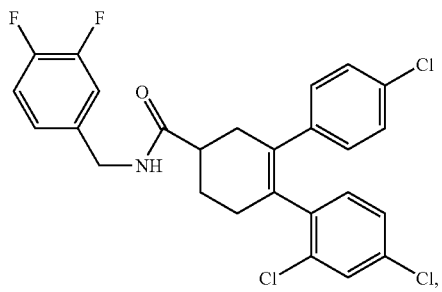
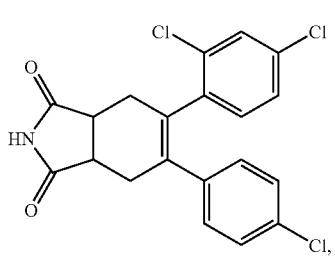
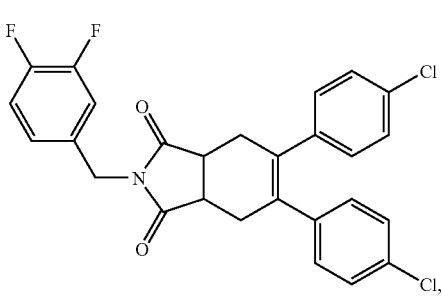
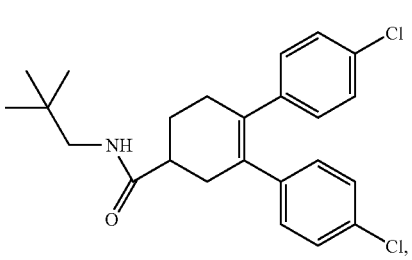
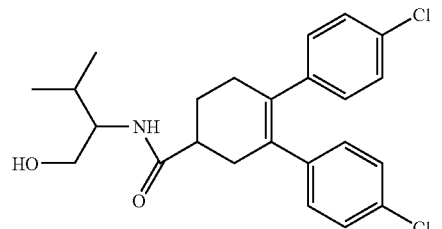
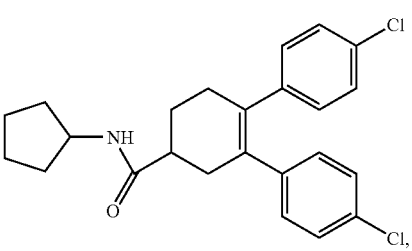

-continued
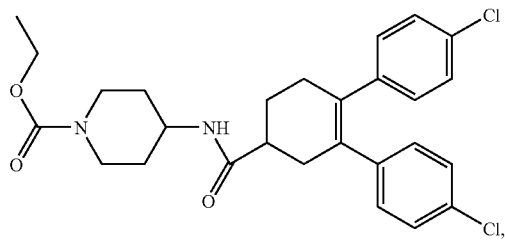
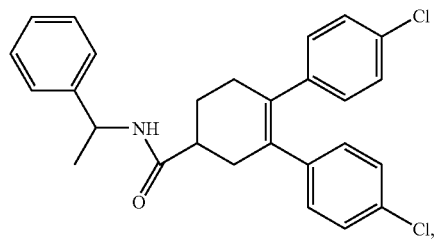
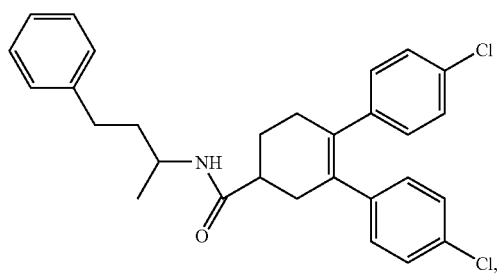
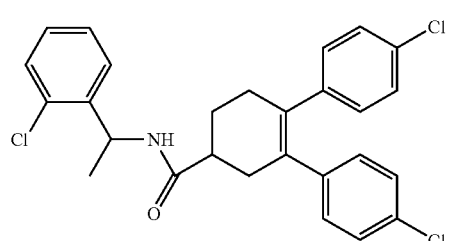
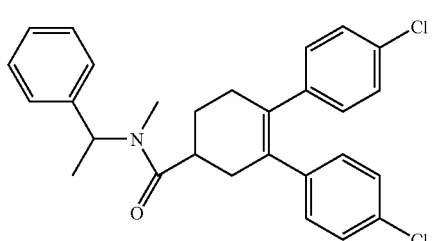
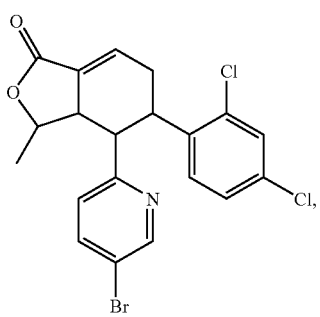
-continued
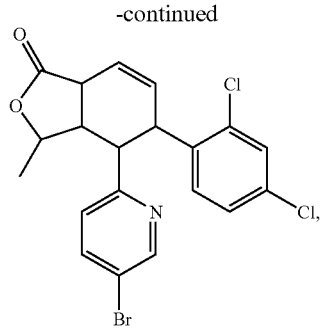
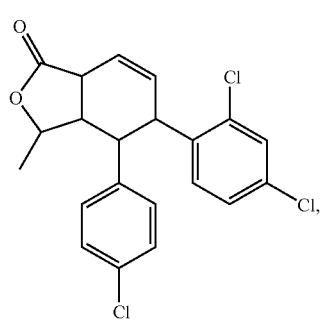
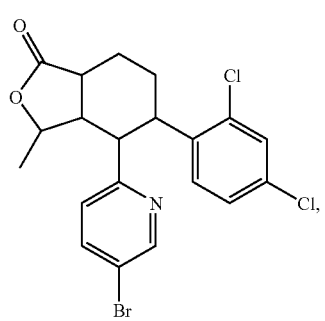
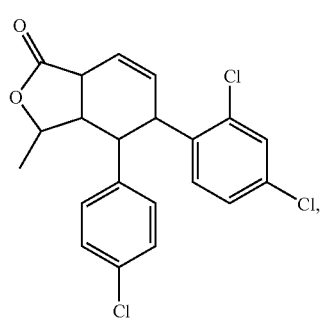
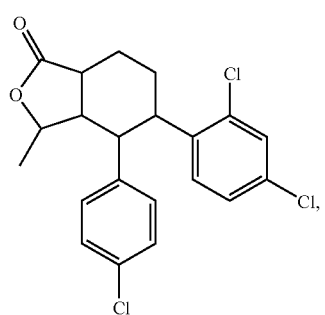

-continued
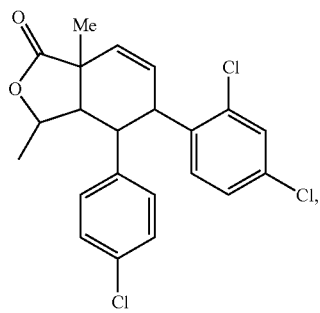
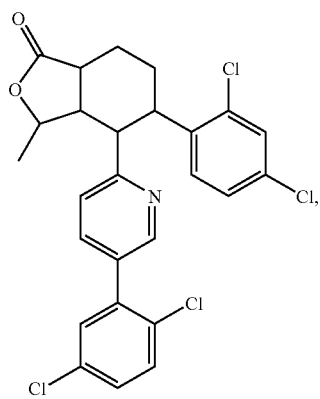
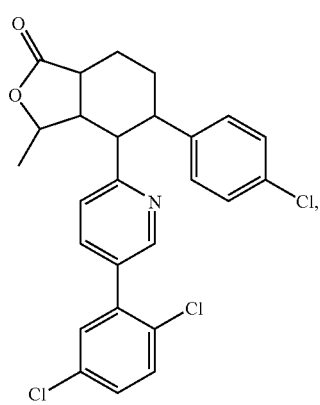
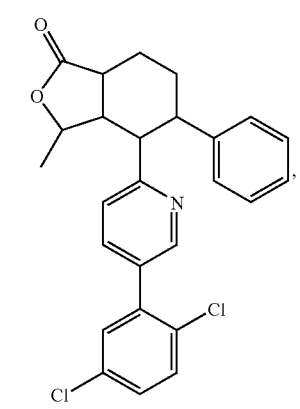
-continued
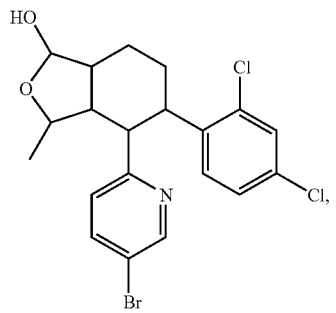
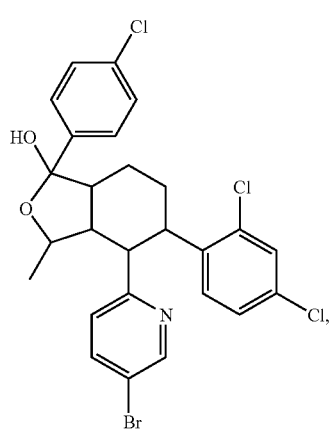
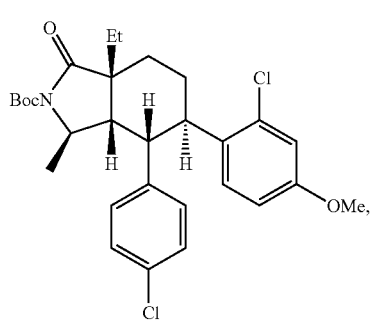

-continued
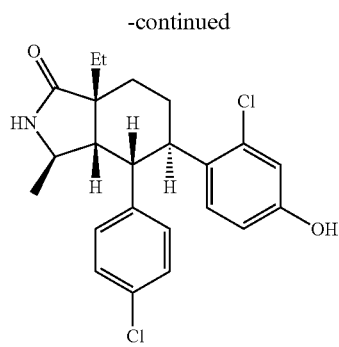
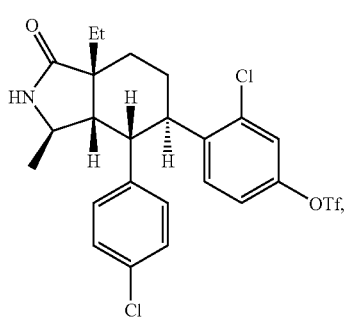
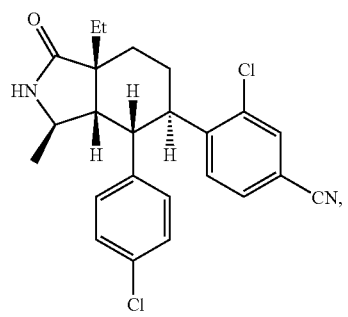
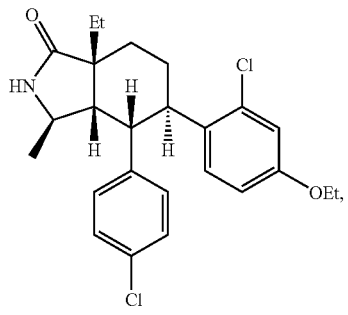
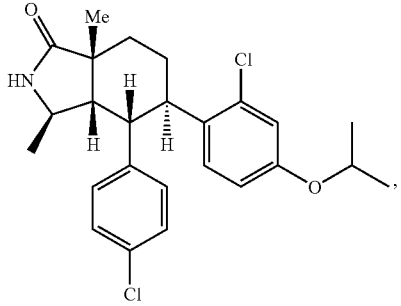
-continued
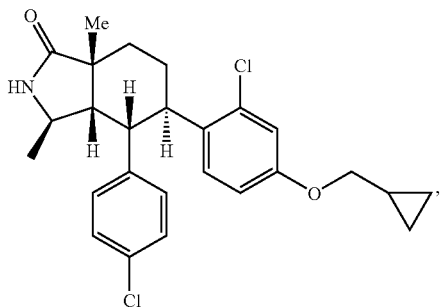
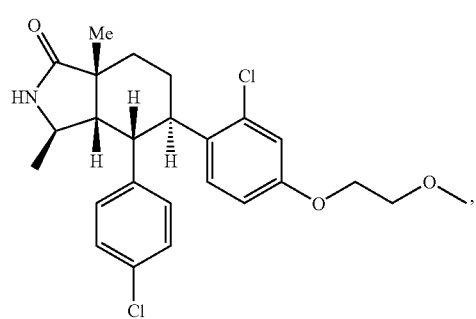
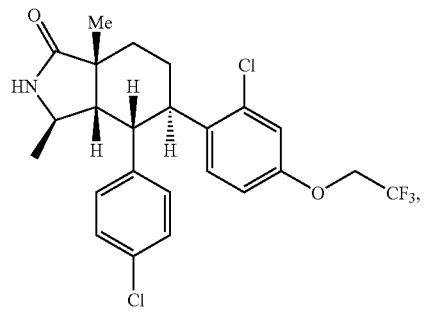
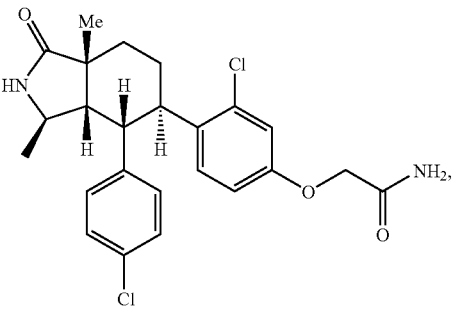

-continued
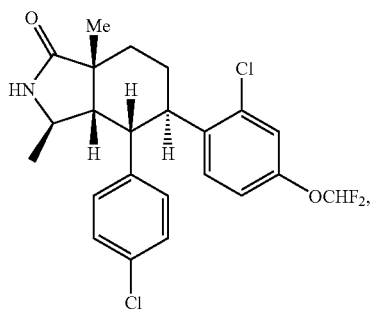
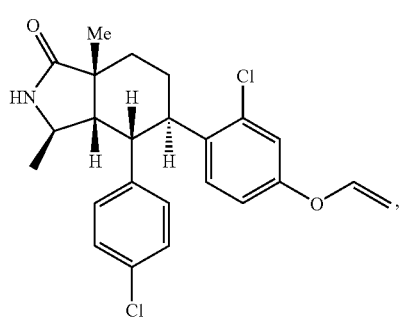
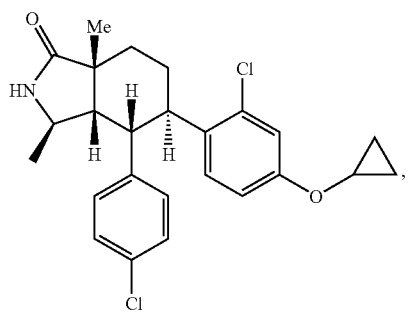
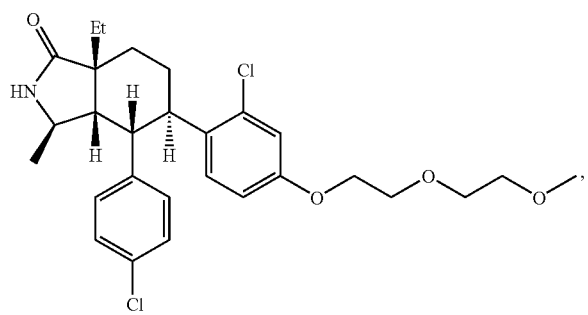
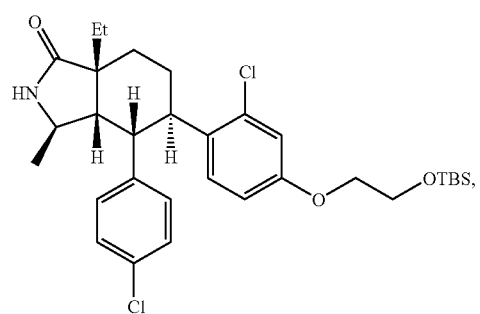
-continued
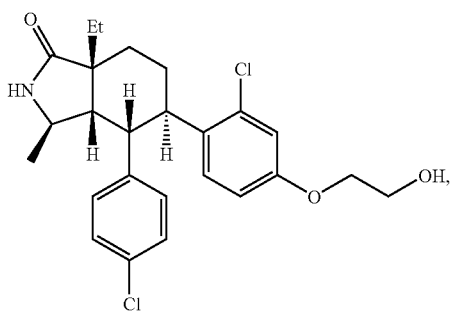
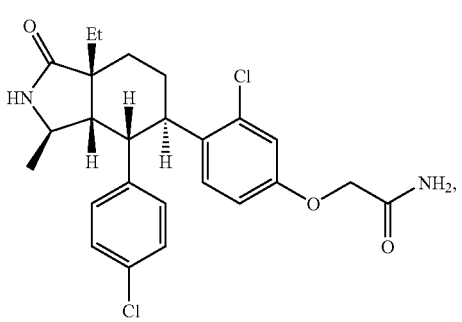
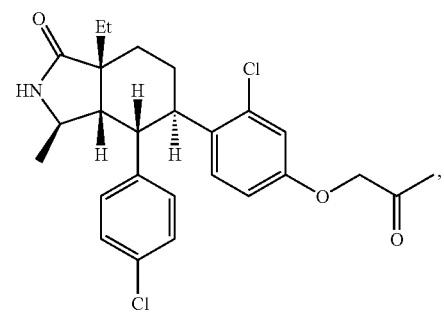
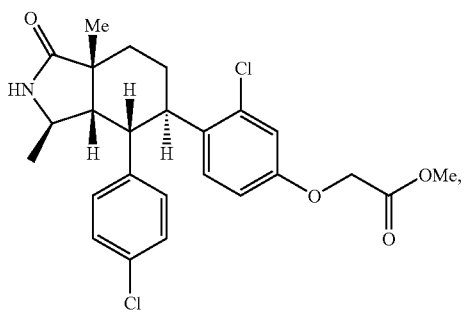
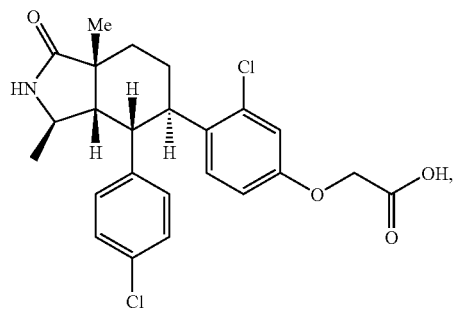

75
-continued
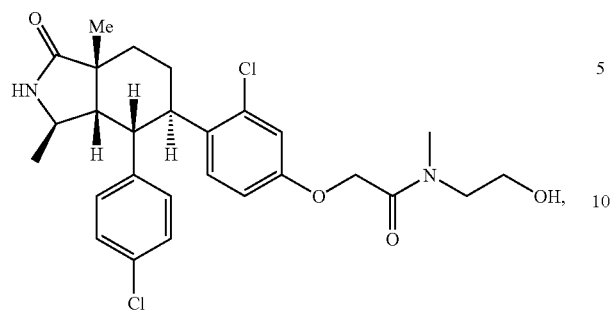
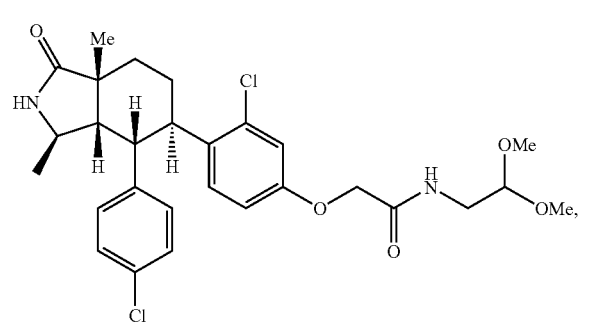
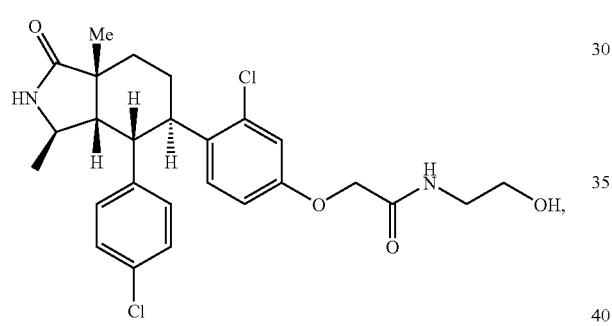
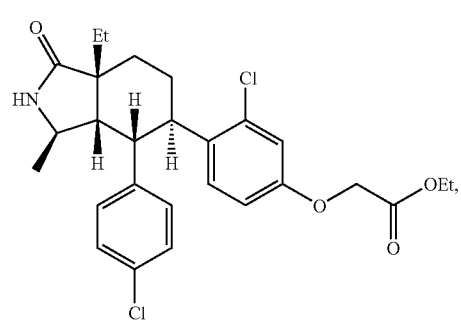
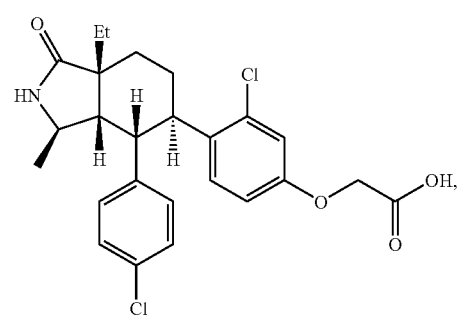
76
-continued
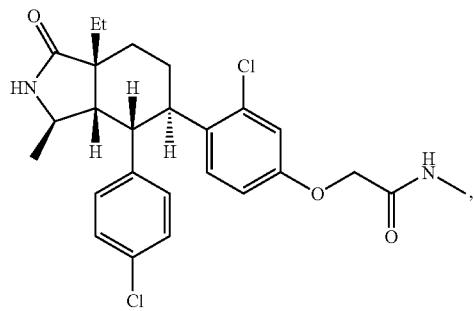
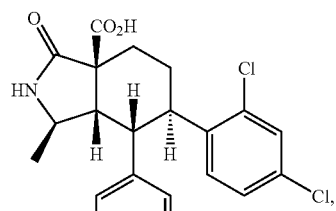
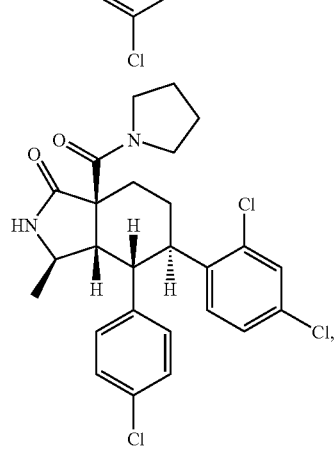
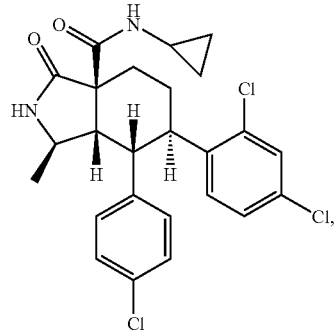
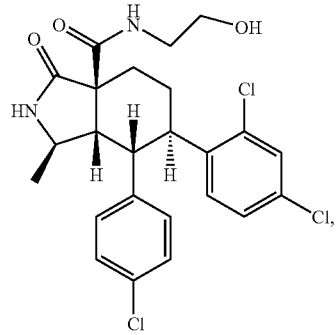

-continued
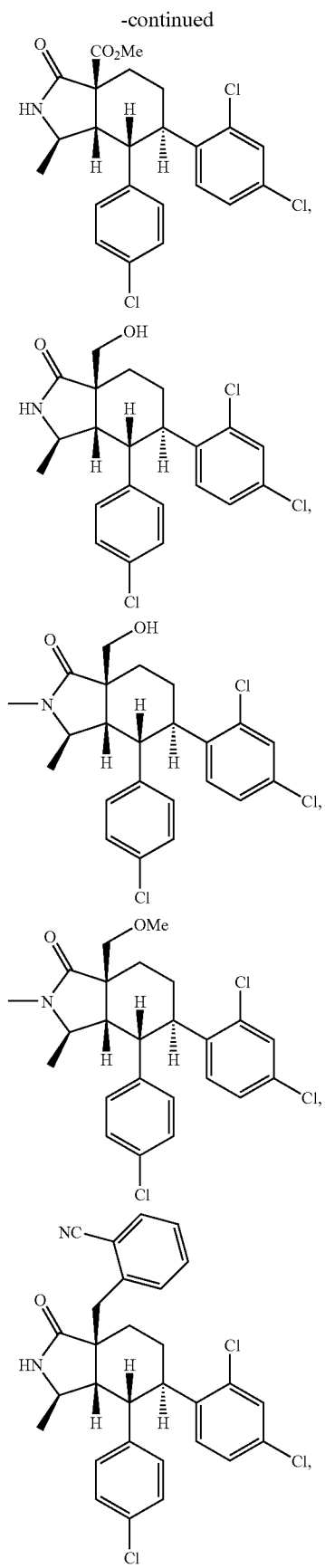
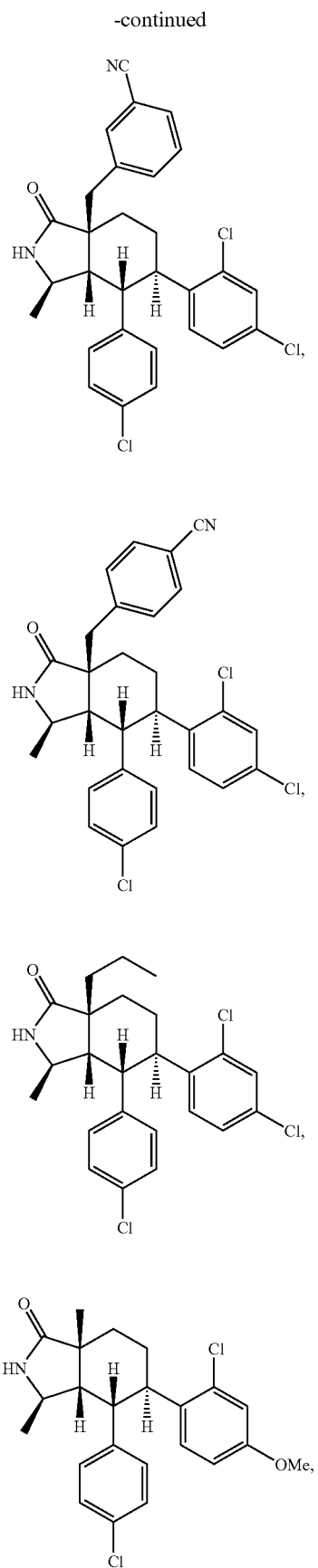

-continued
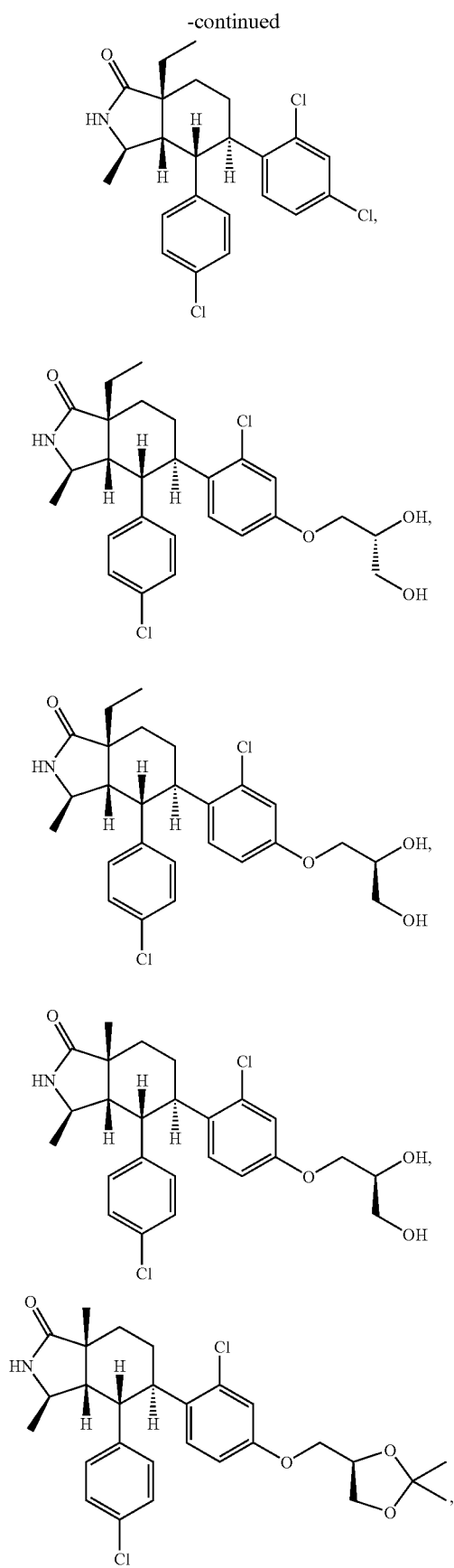
-continued
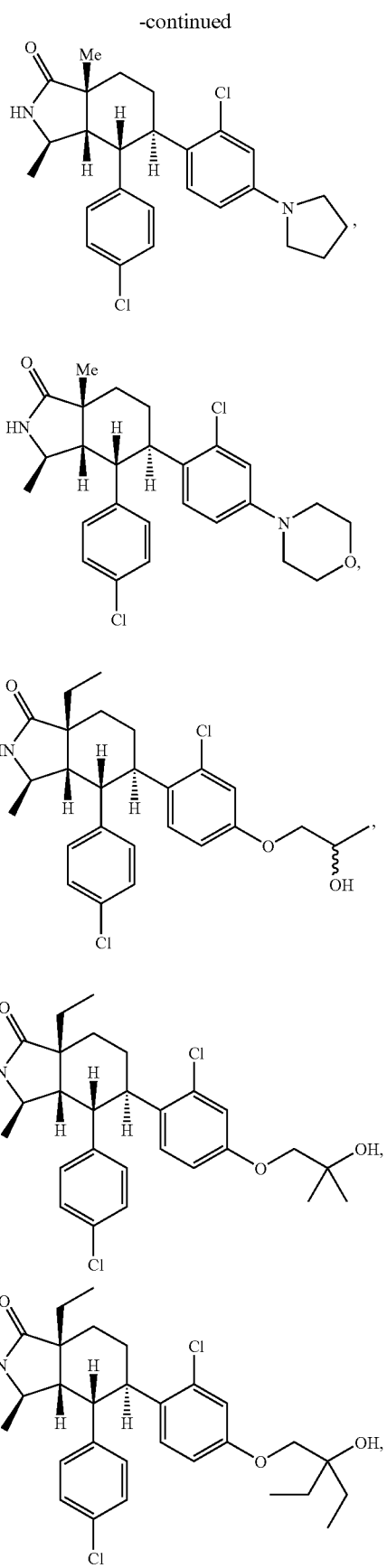

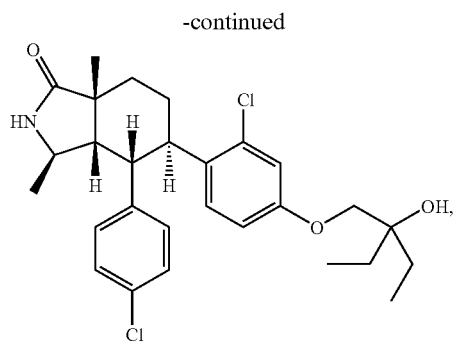
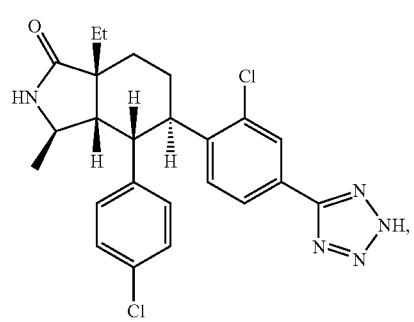
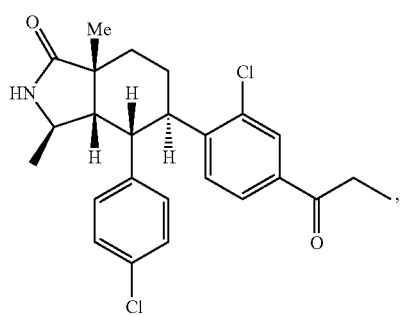
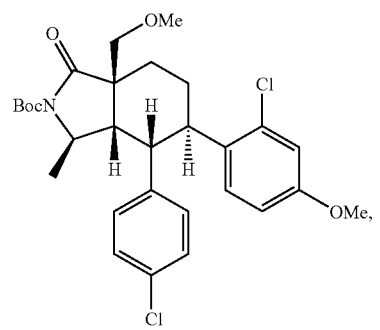
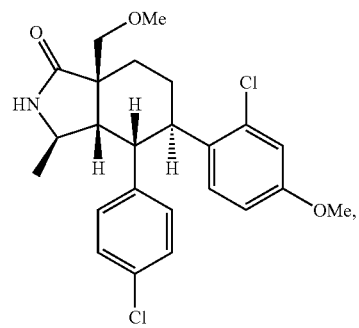
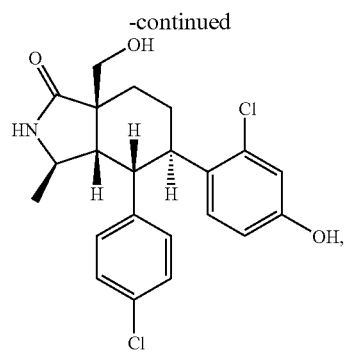
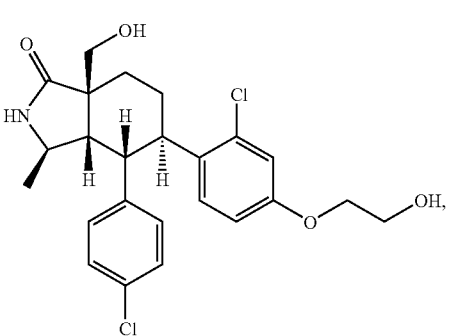
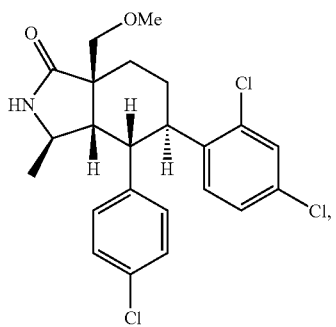
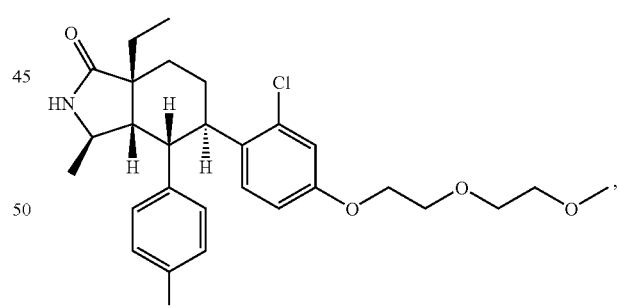
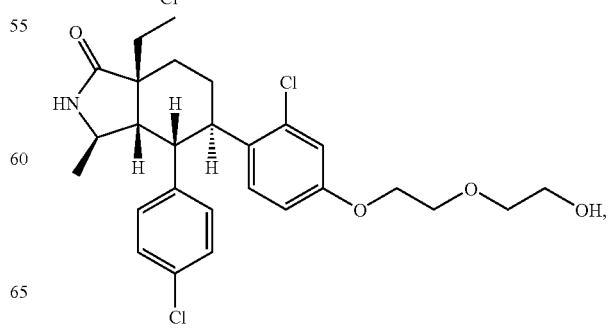

-continued
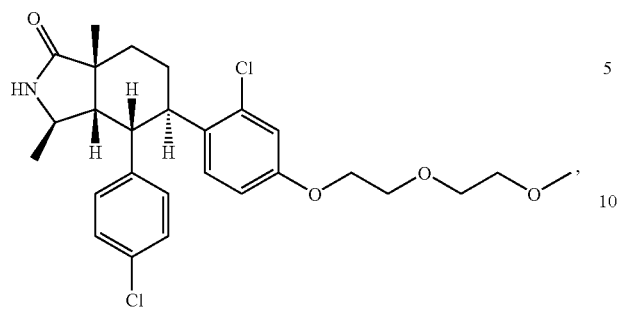
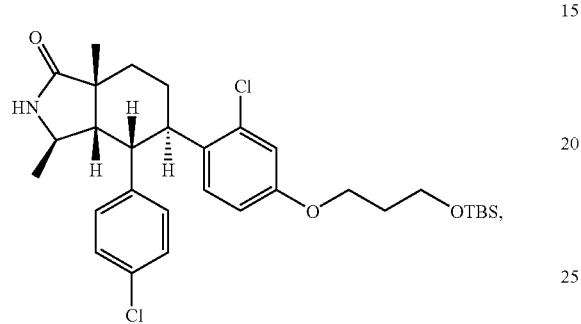
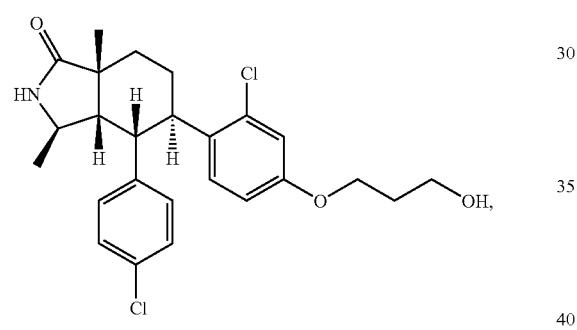
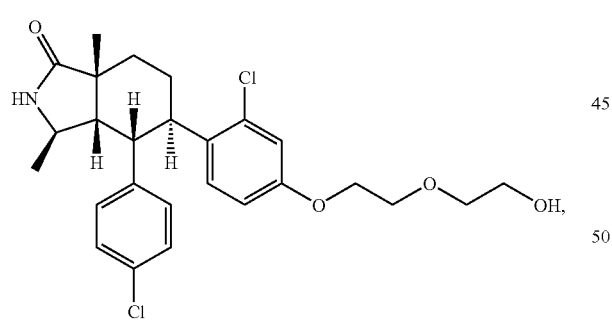
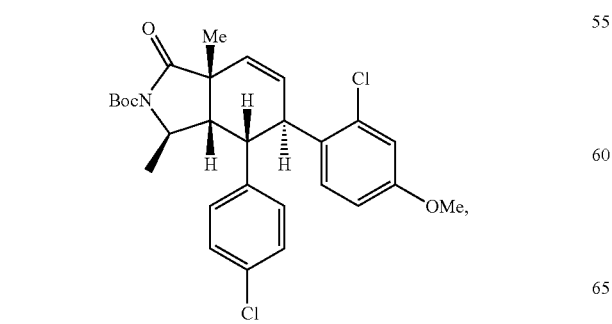
-continued
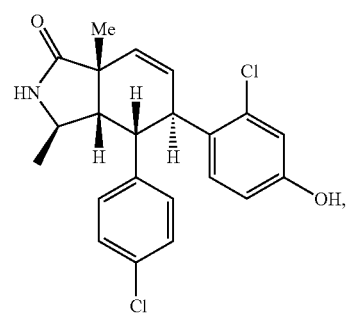
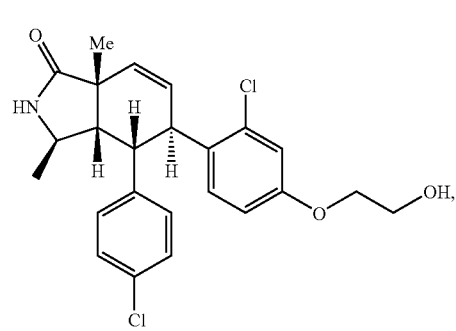
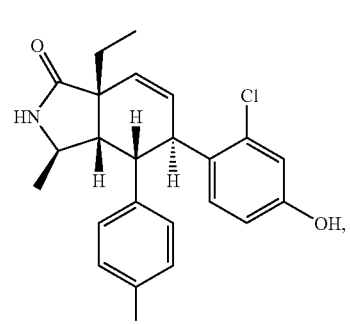
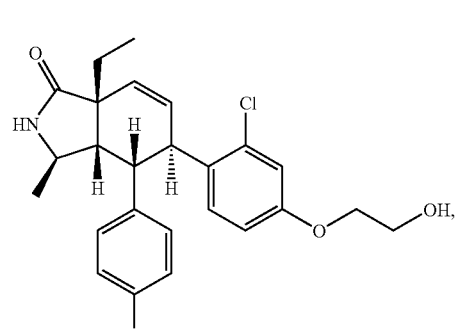

-continued
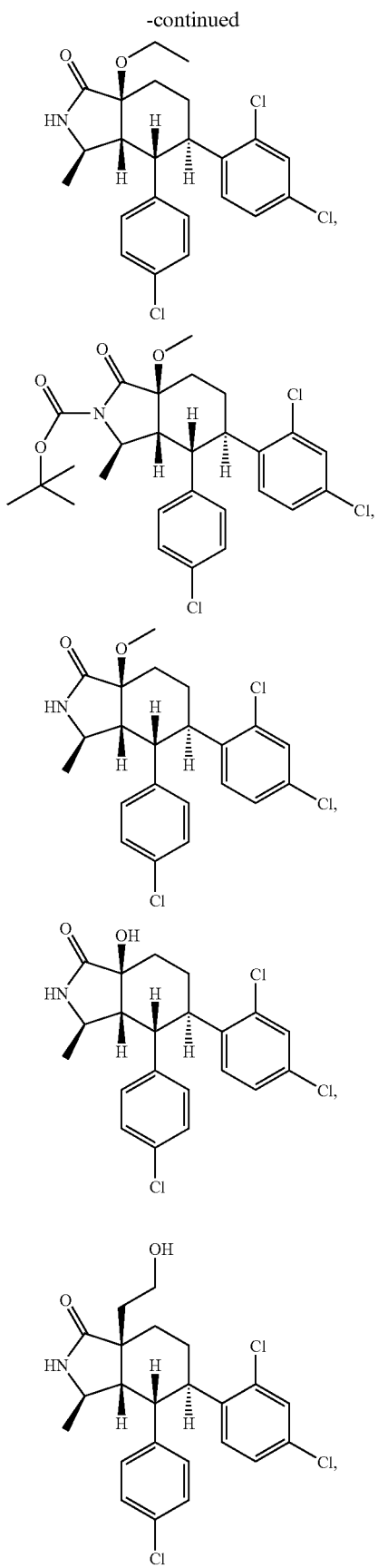
-continued
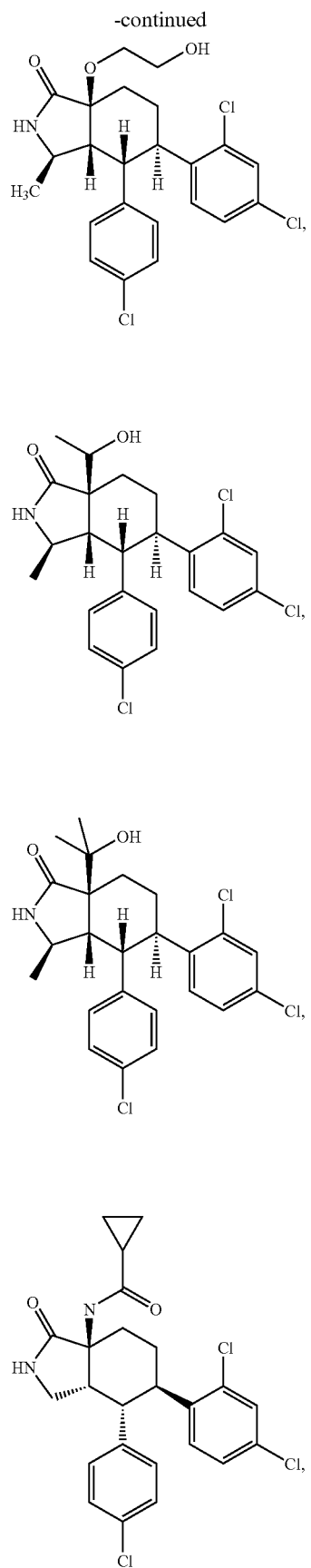

87
-continued
88
-continued
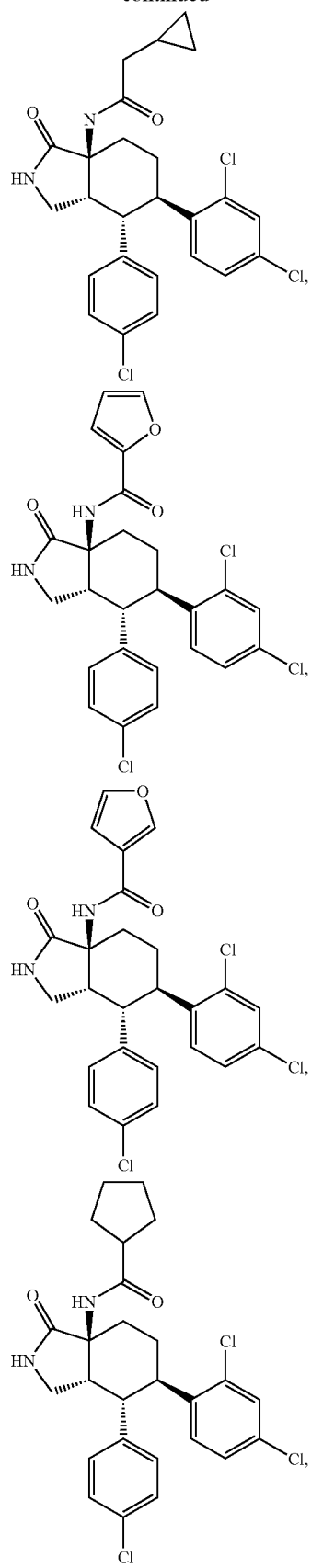
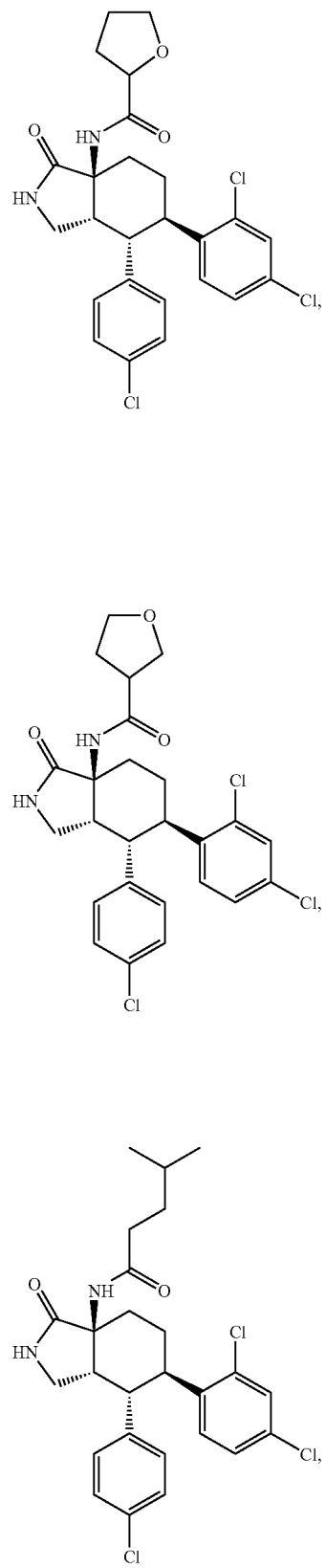

-continued
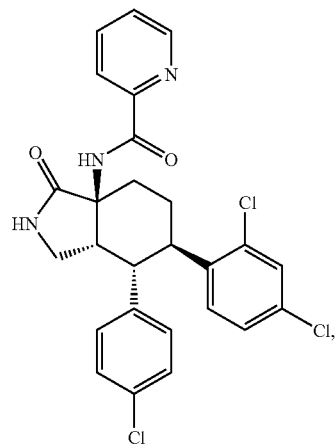
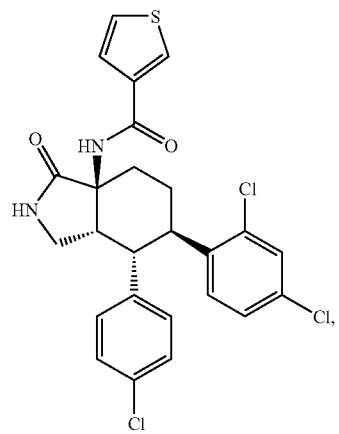
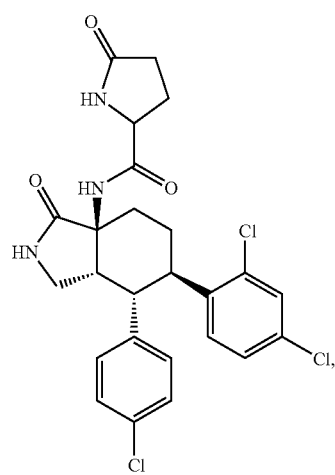
-continued
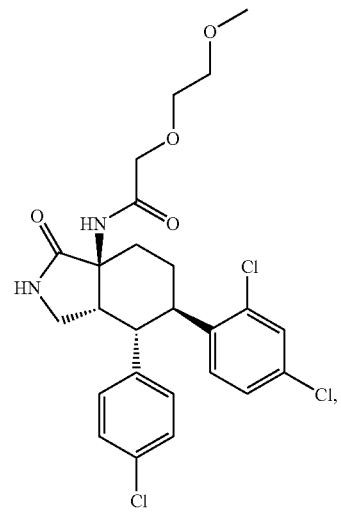
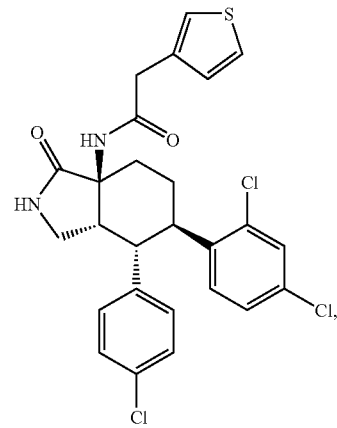
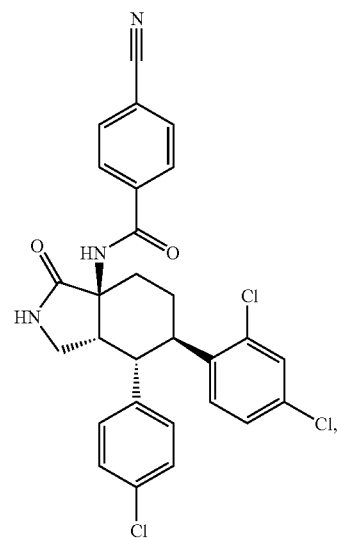

91
-continued
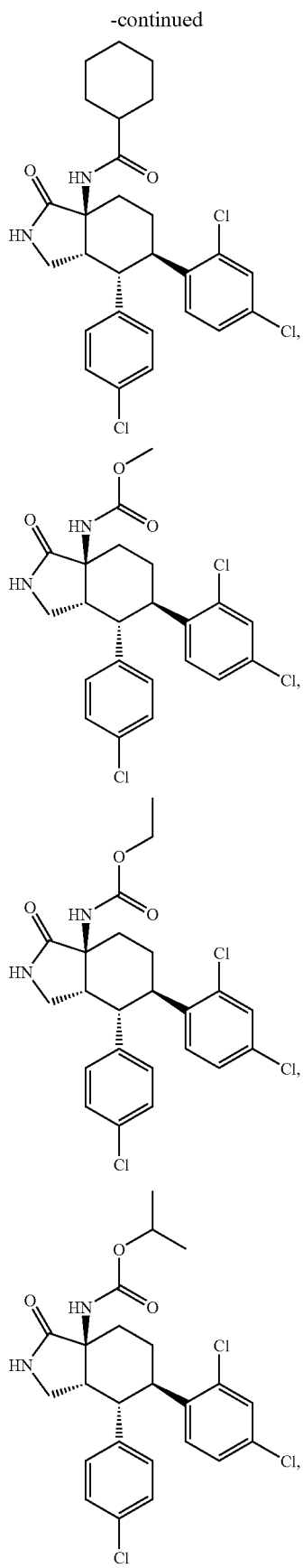
92
-continued
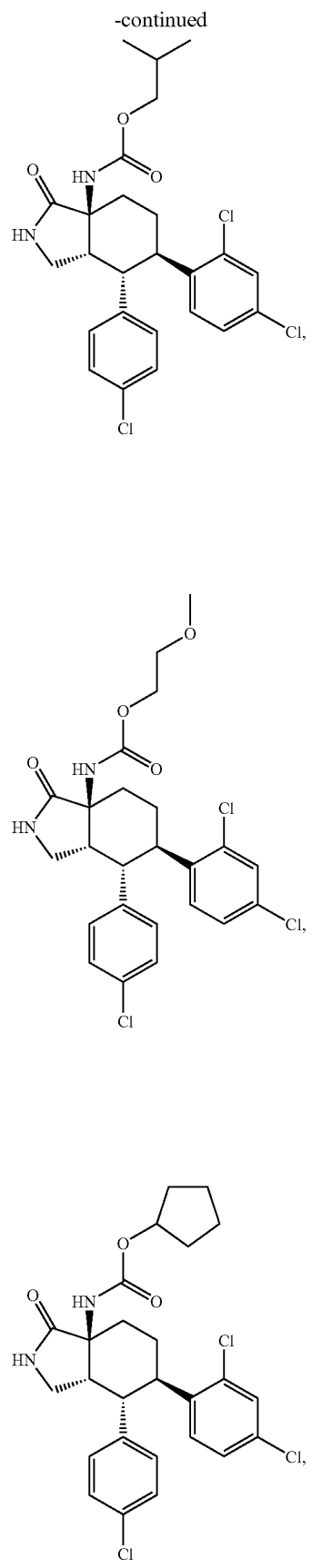

-continued
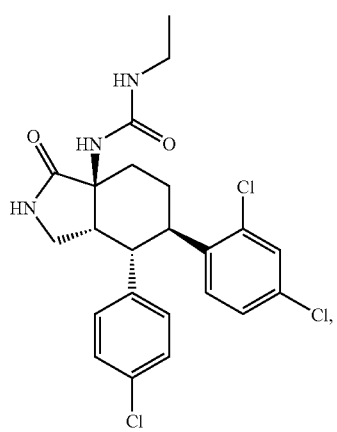
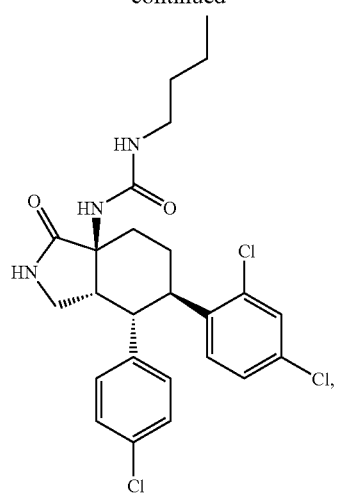
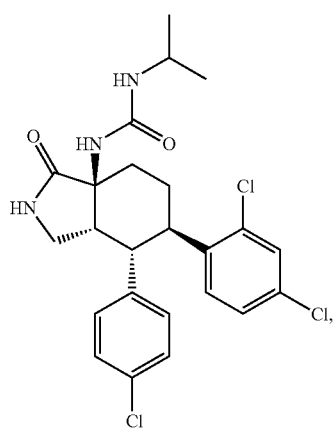
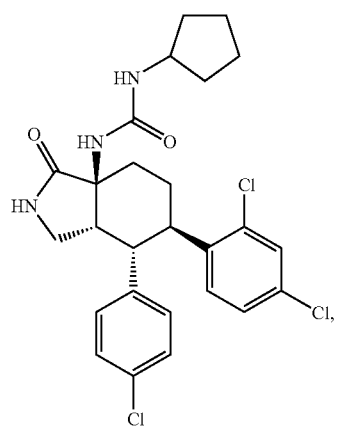
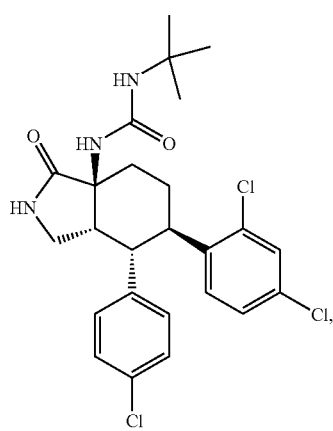
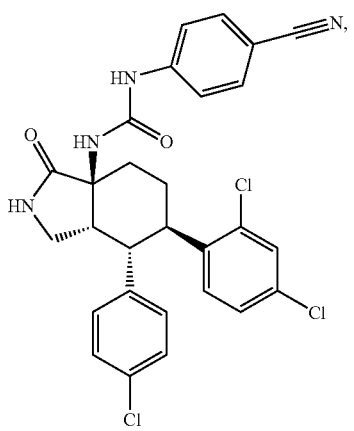

95
-continued
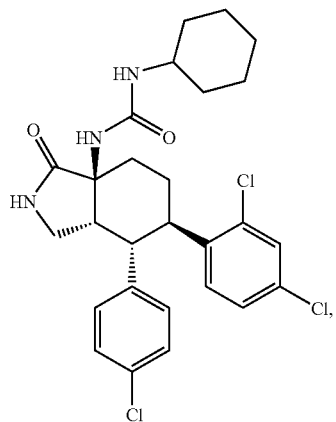
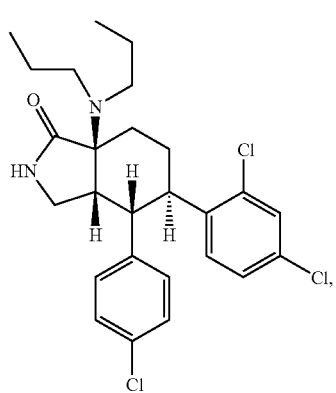
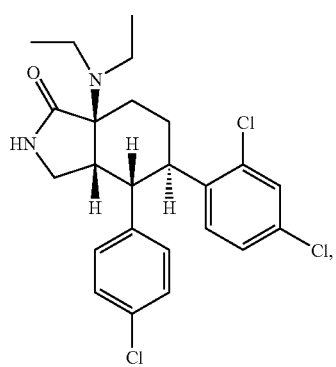
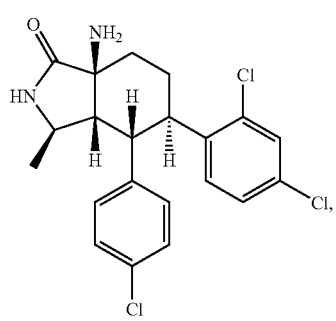
96
-continued
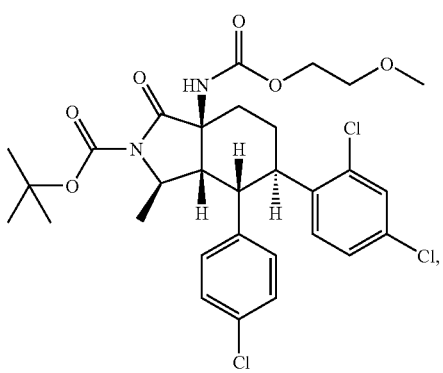
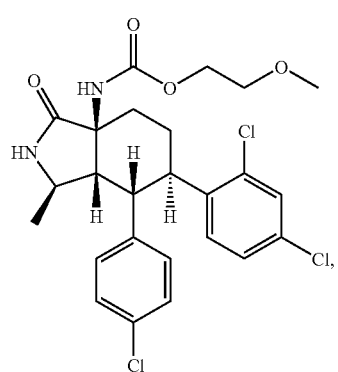
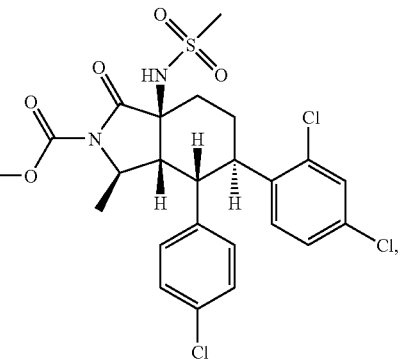
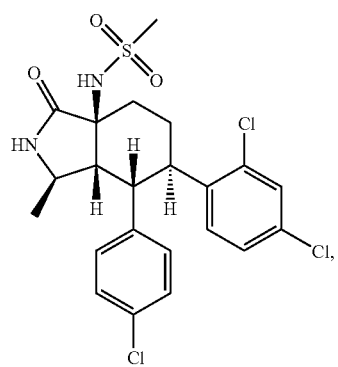

97
-continued
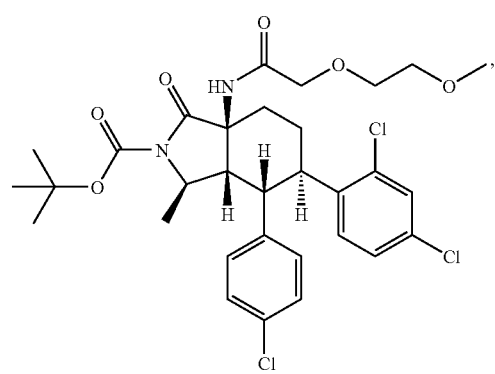
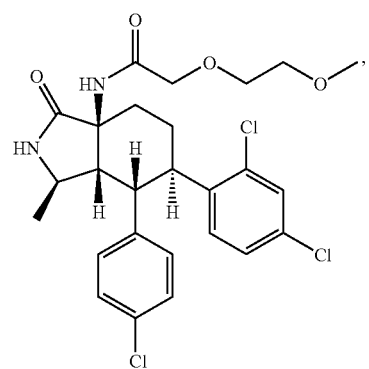
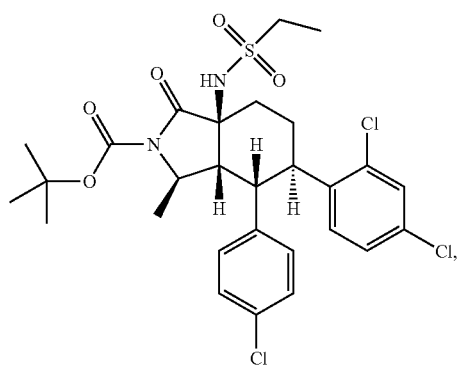
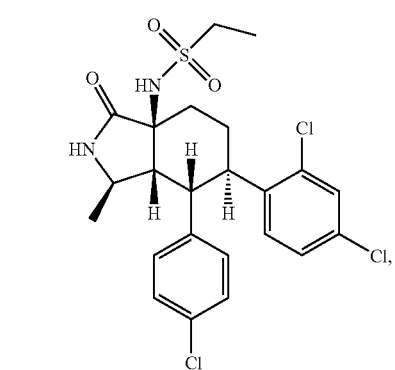
98
-continued
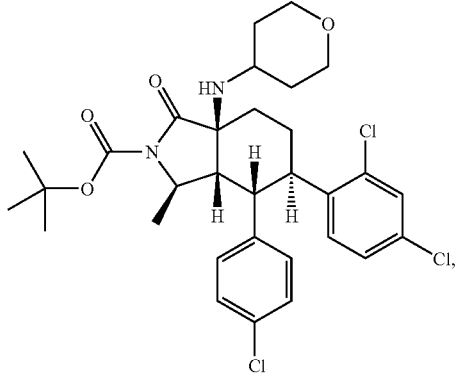
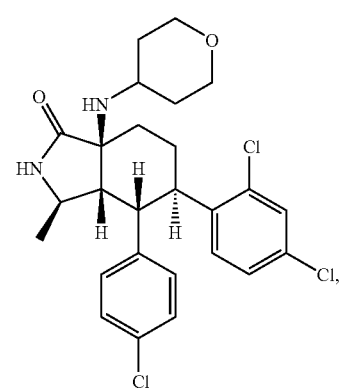
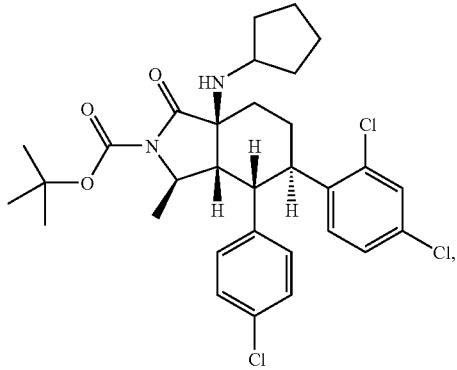
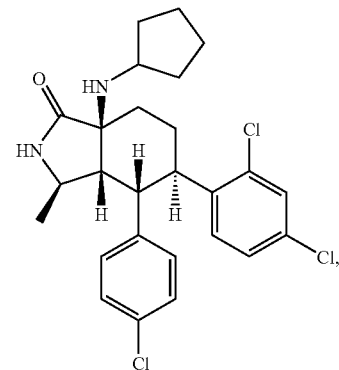

-continued
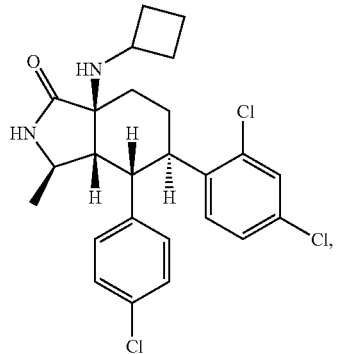
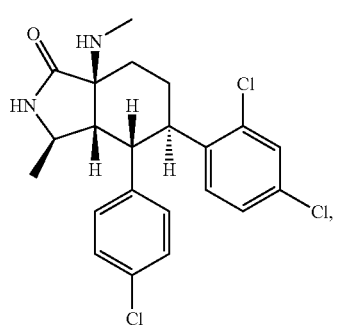
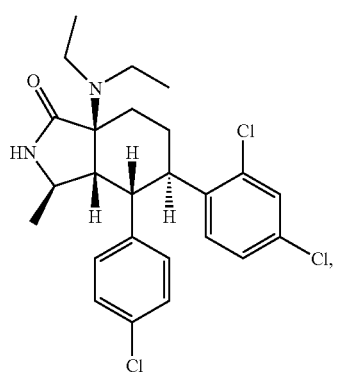
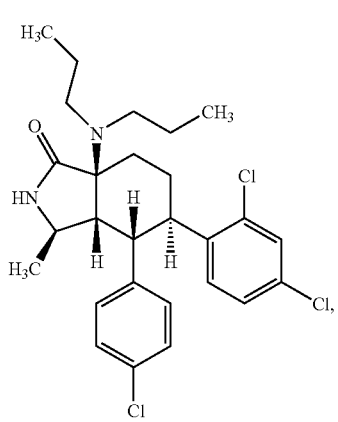
-continued
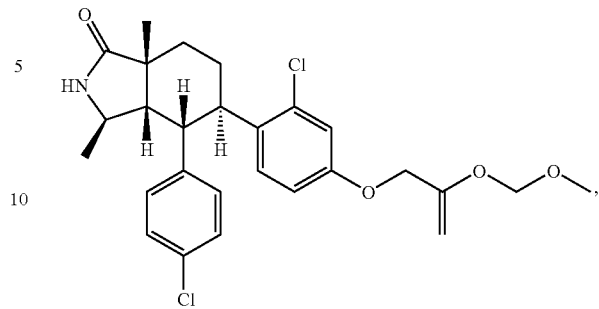
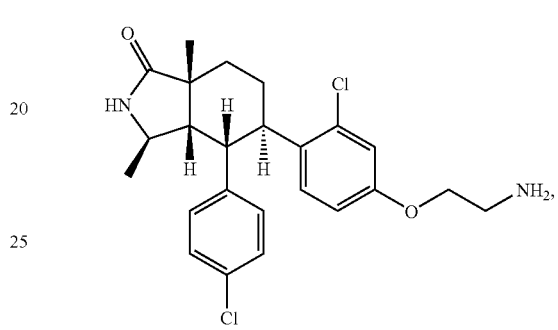
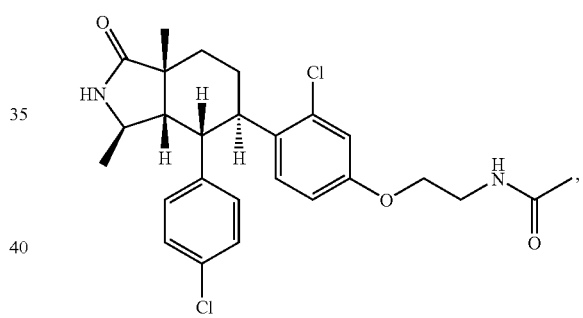
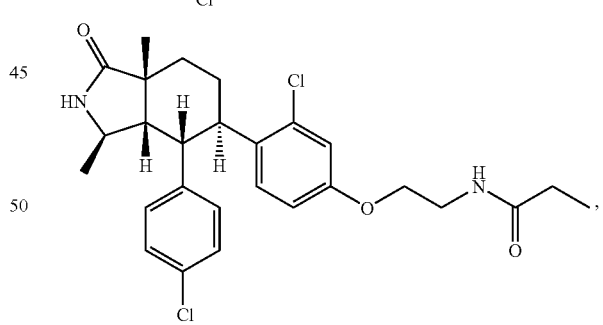
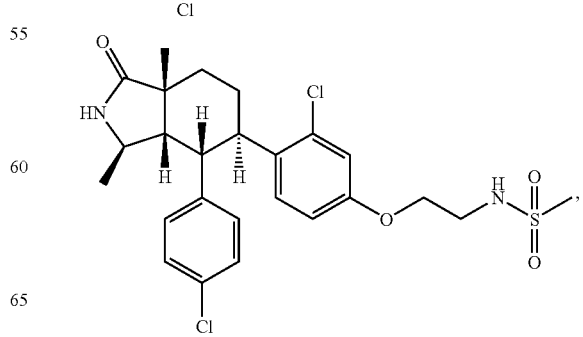

-continued
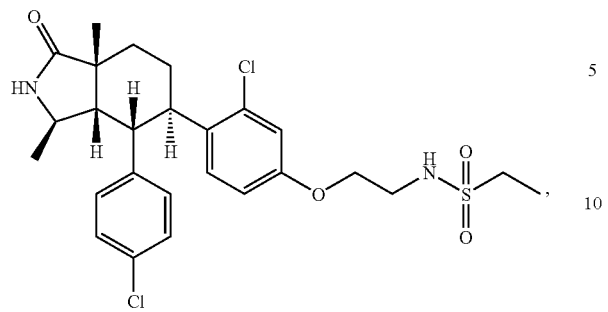
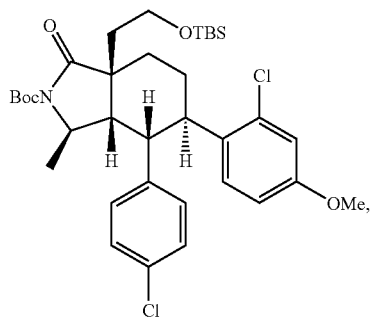
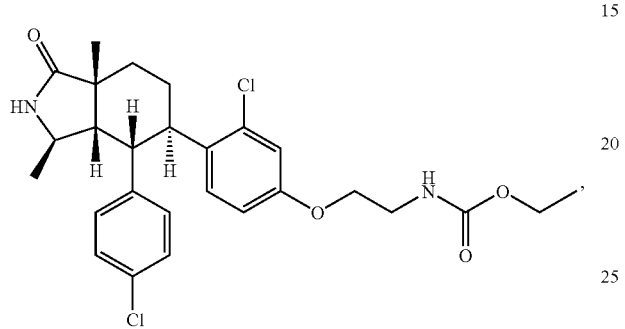
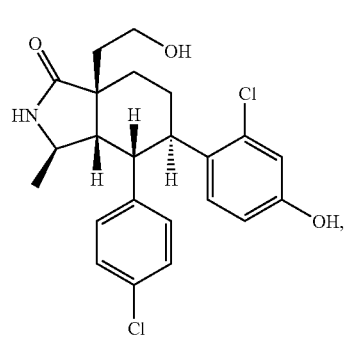
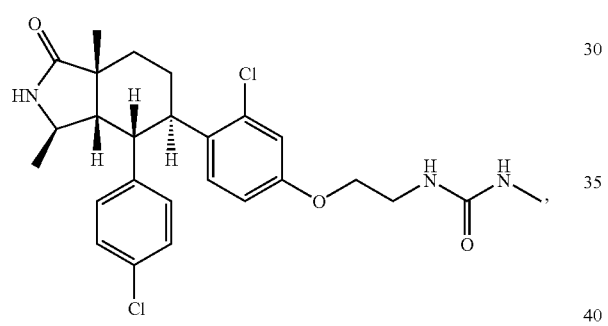
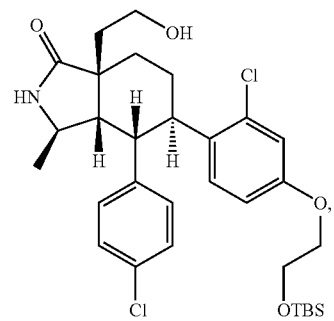
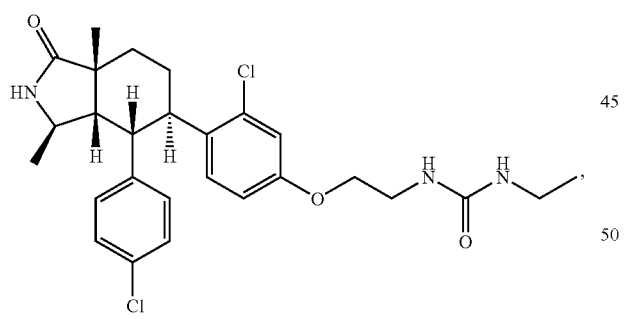
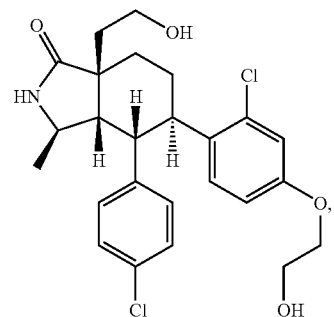

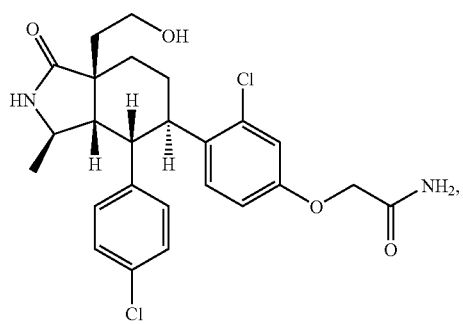

-continued
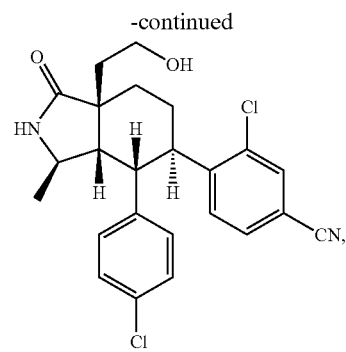
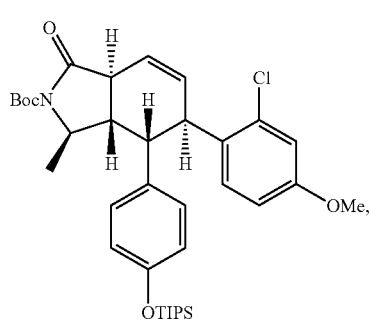
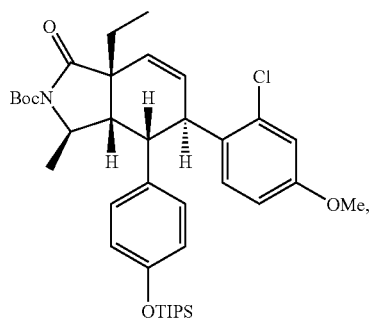
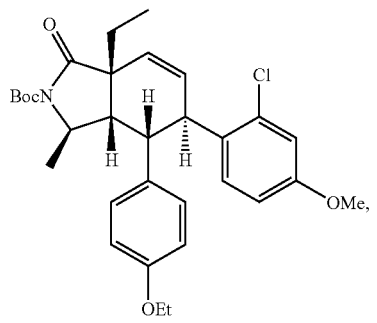
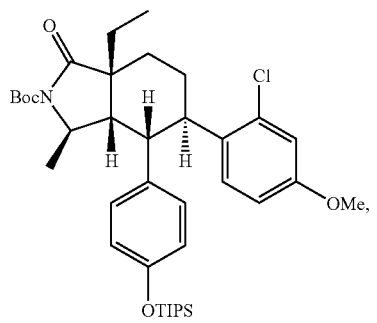
-continued
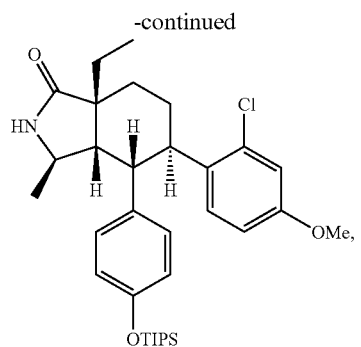
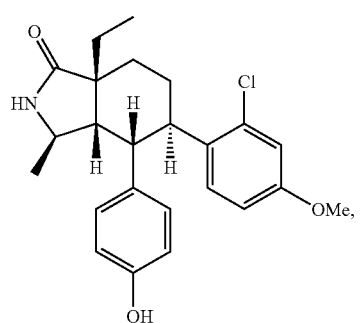
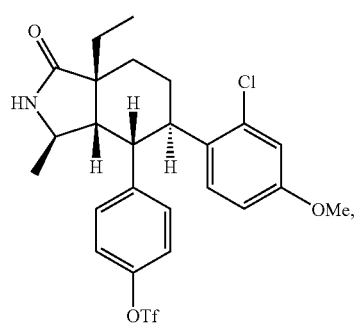
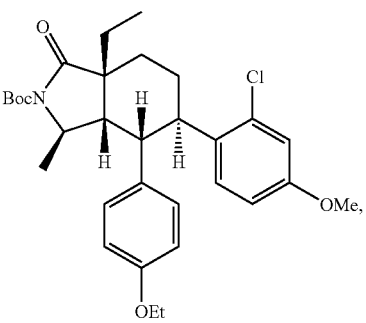
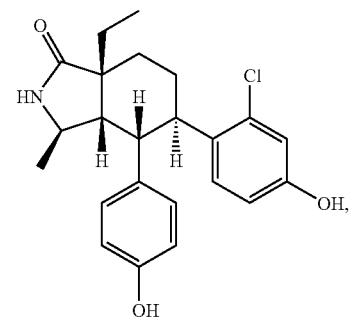

-continued
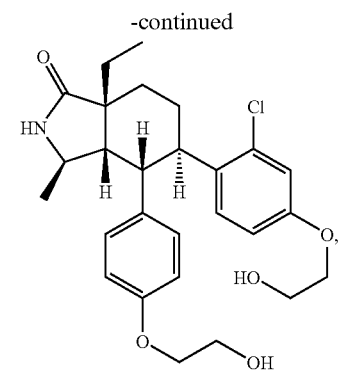
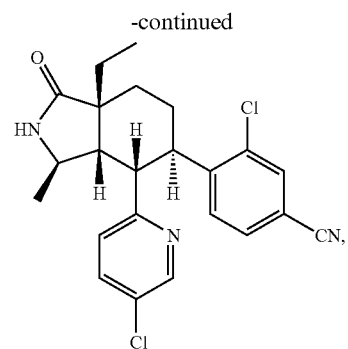
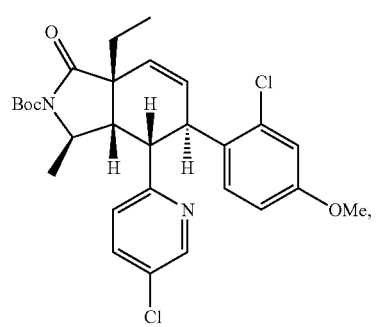
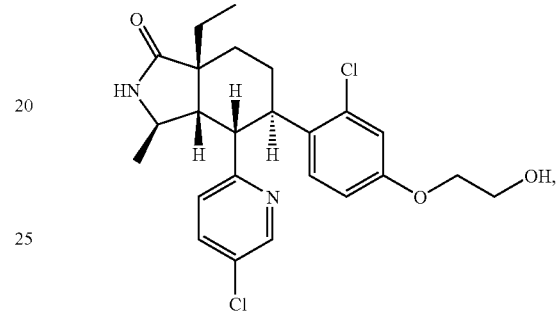
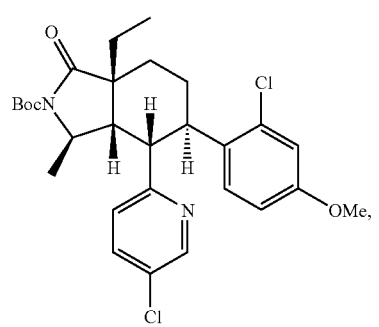
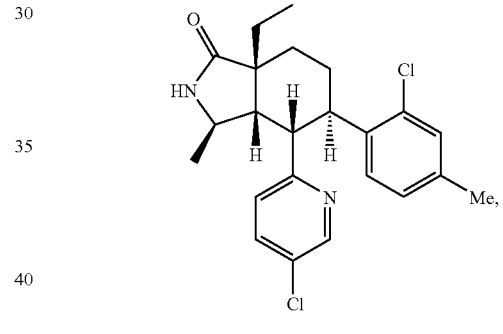
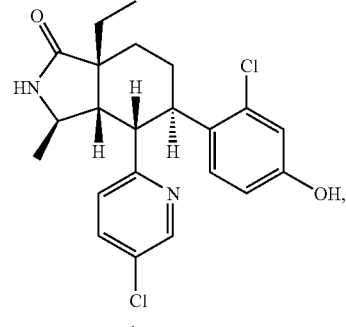
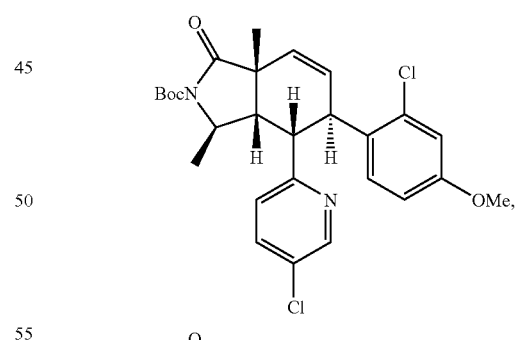
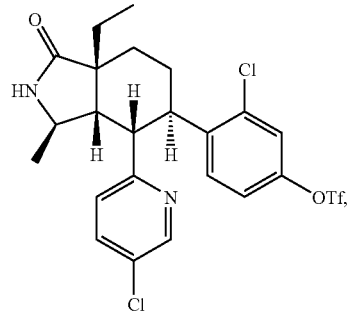
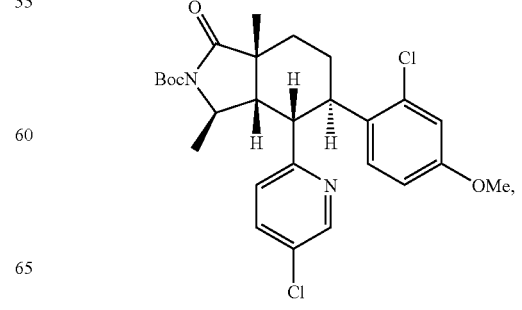

-continued
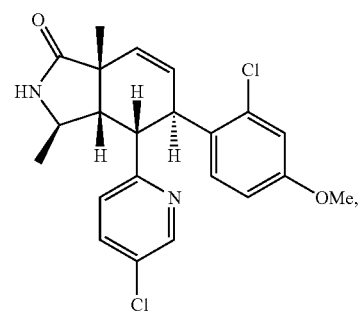
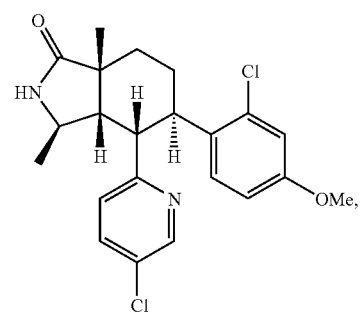
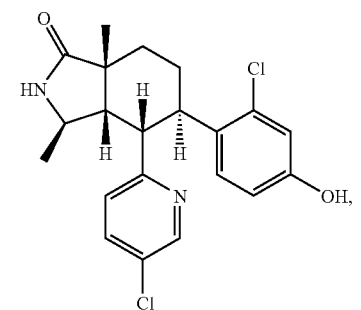
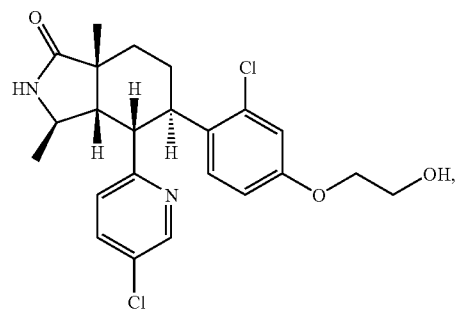
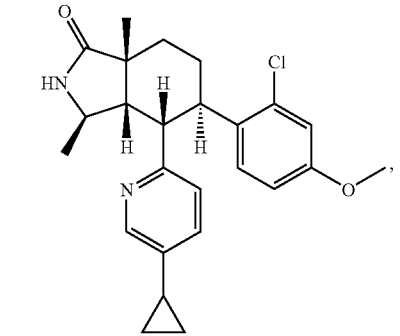
-continued
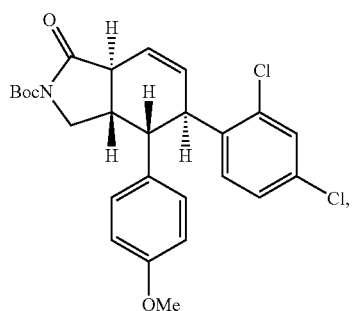
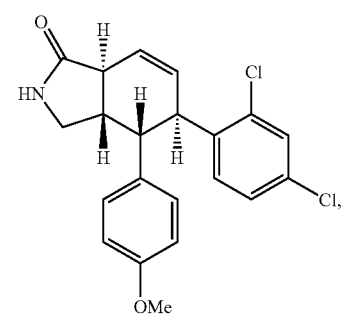
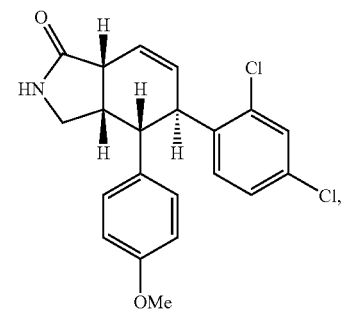
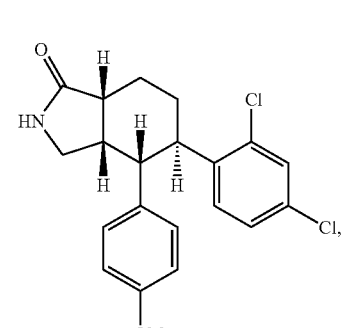
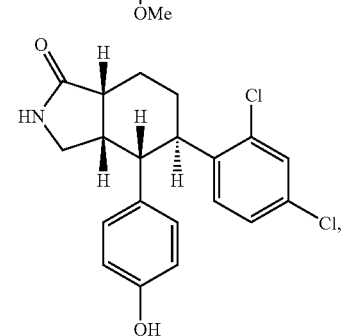

-continued
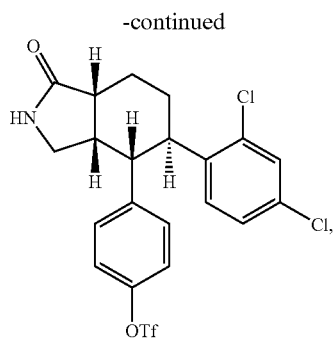
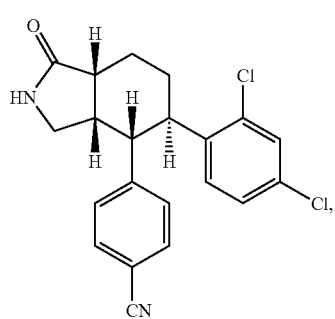
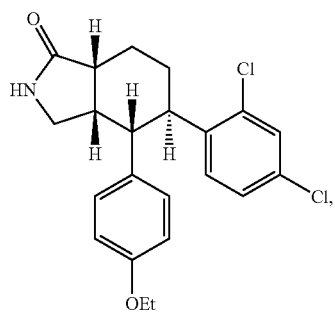
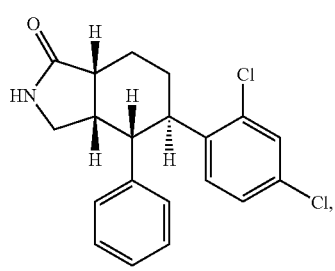
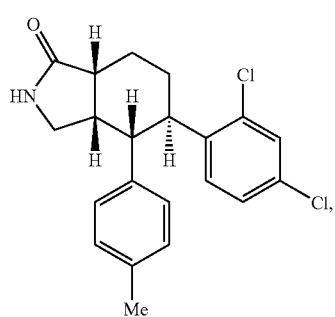
-continued
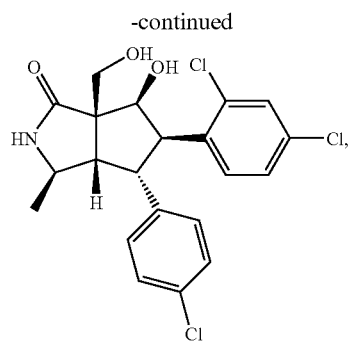
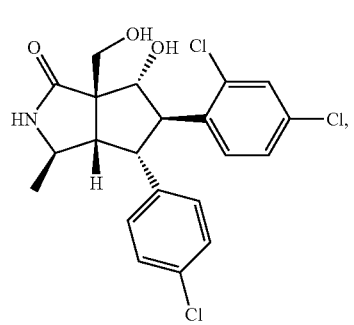
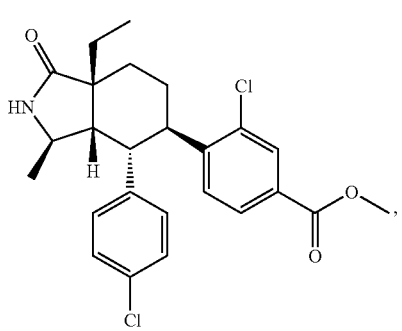
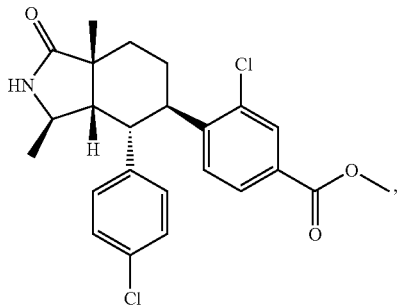
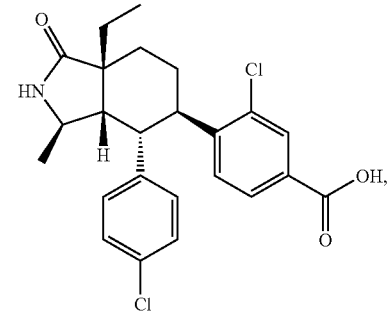

111
-continued
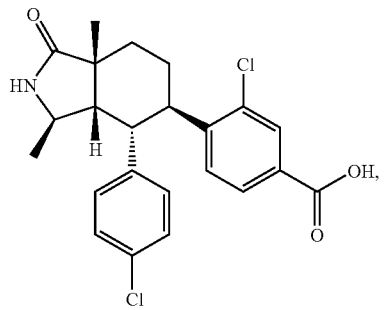
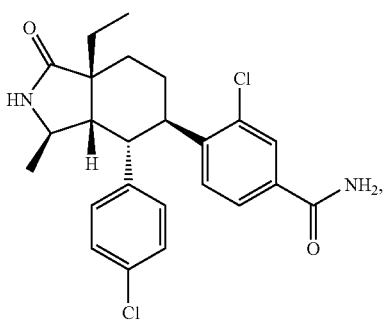
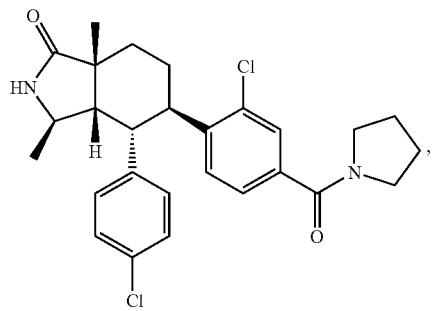
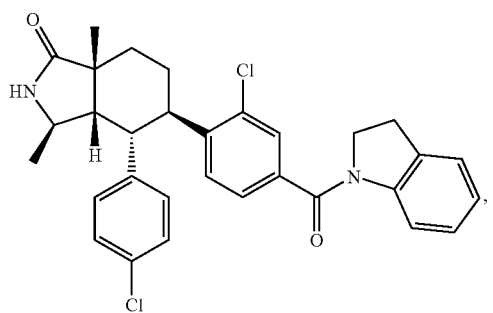
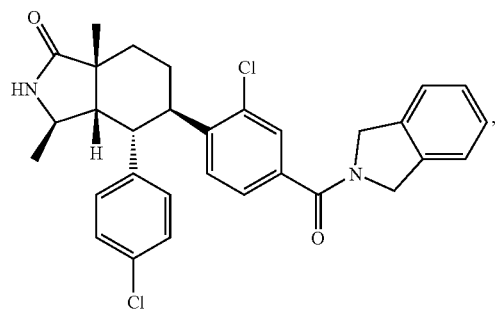
112
-continued
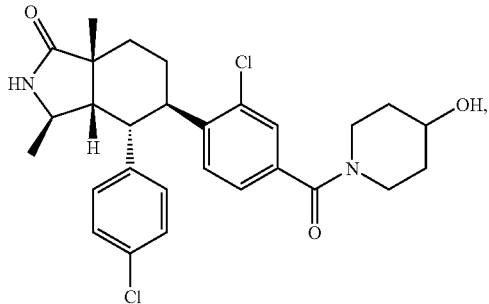
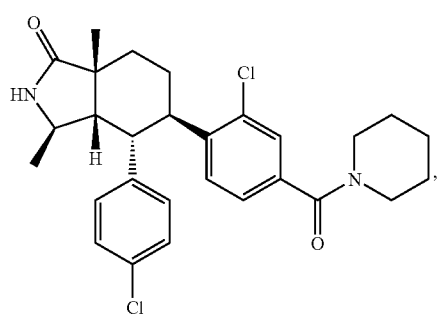
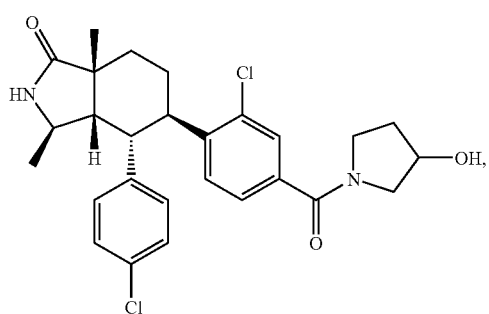
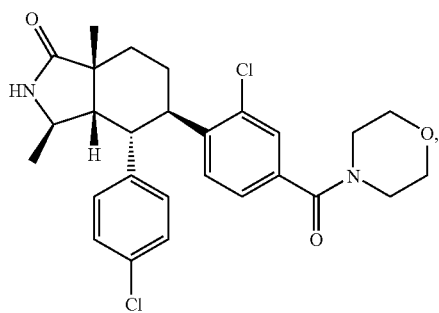
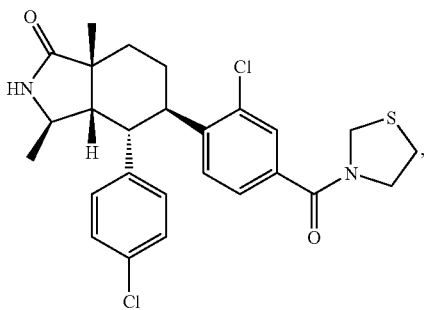

113
-continued
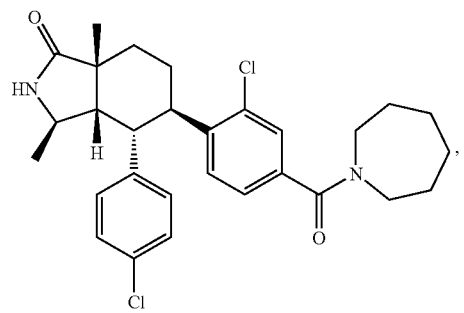
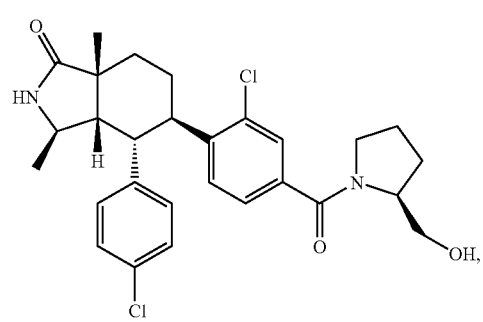
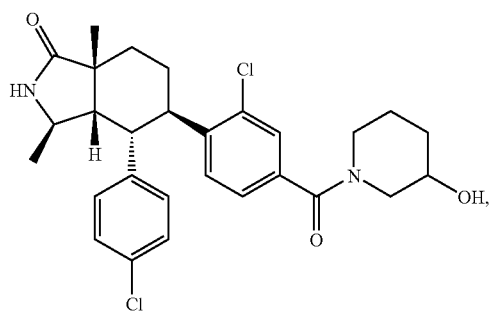
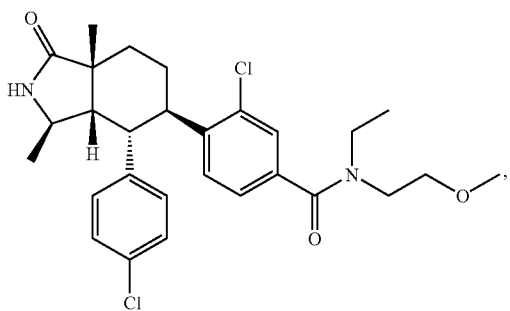
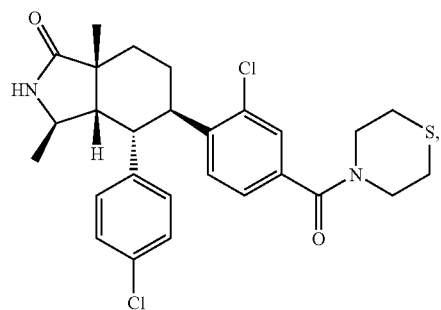
114
-continued
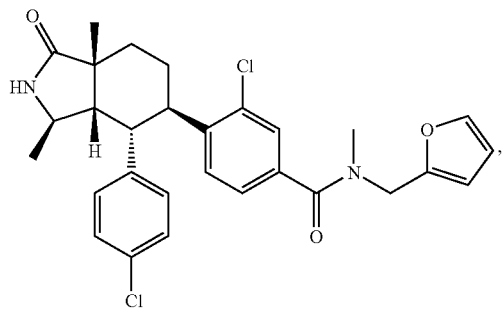
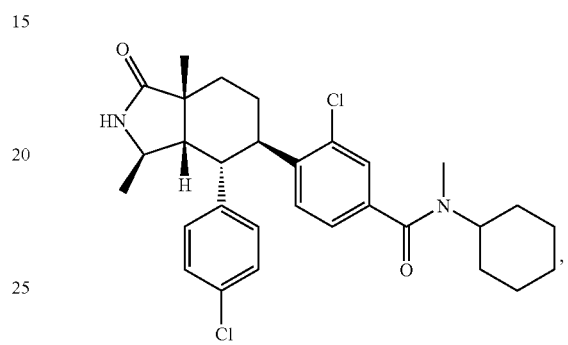
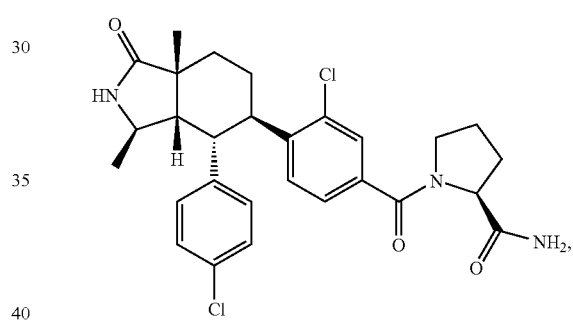
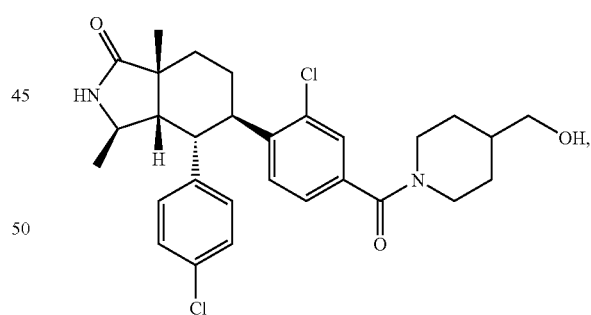
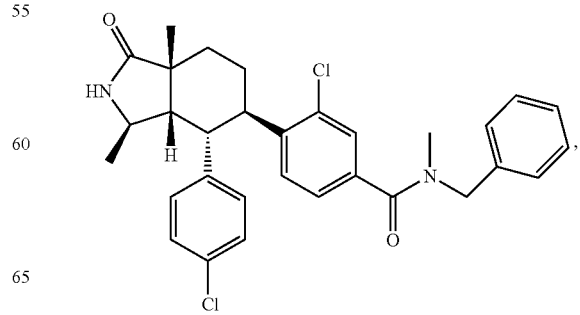

-continued
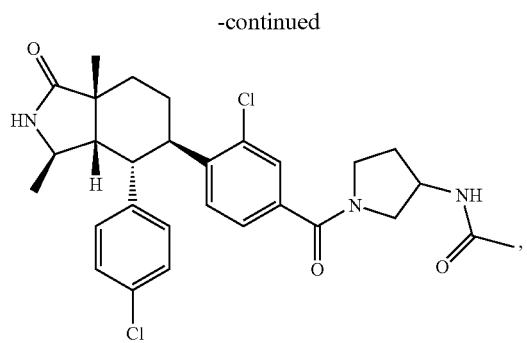
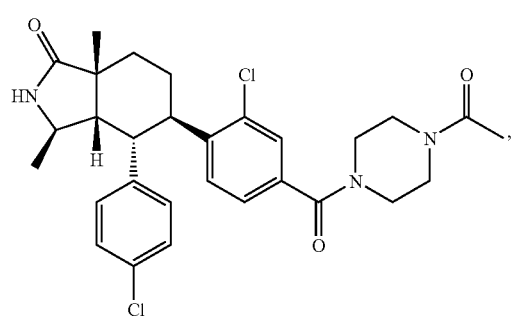
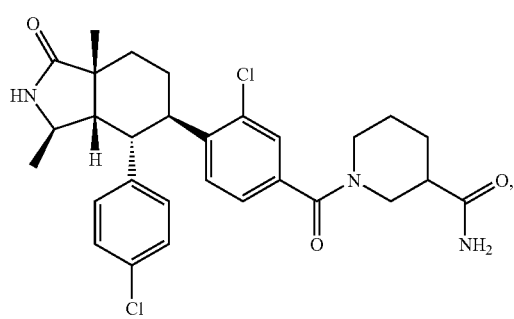
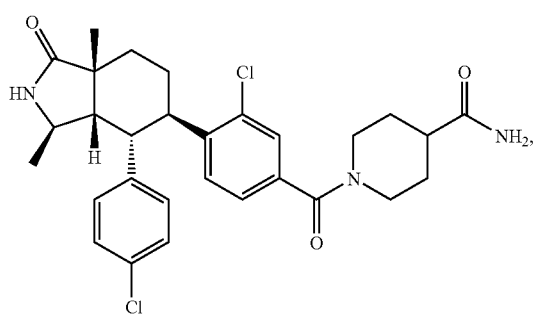
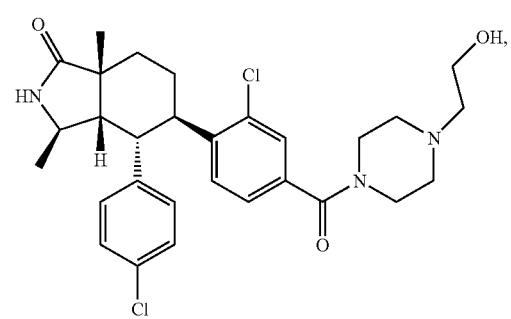
-continued
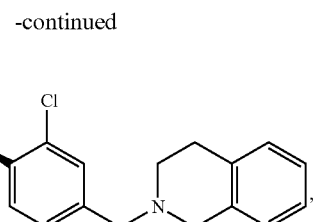
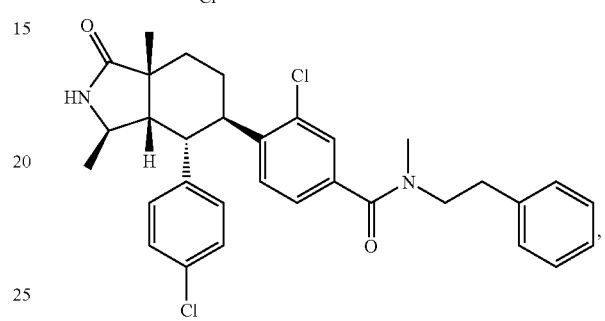
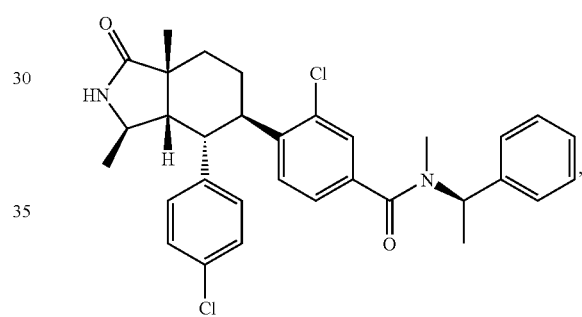
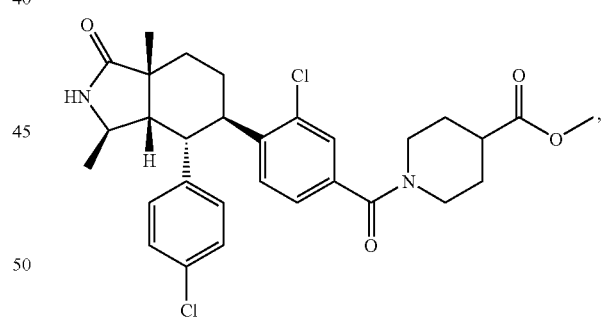
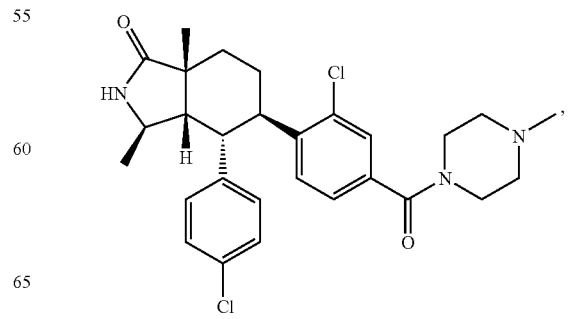

117
-continued
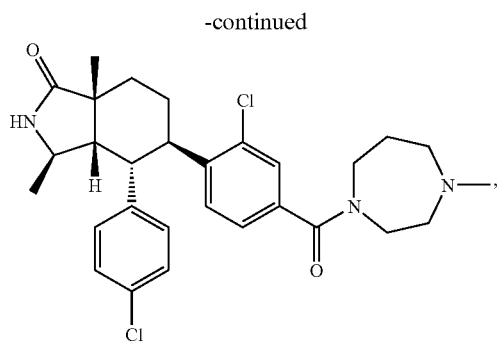
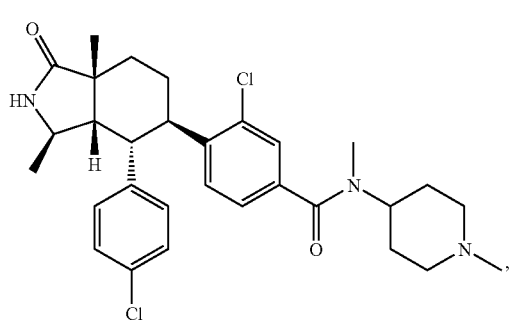
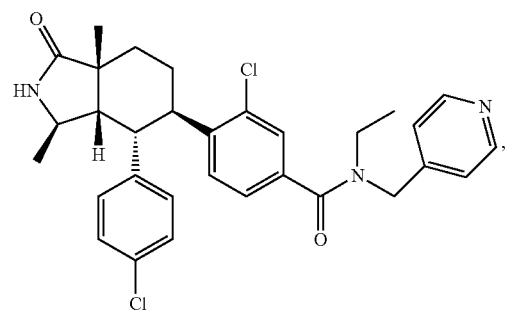
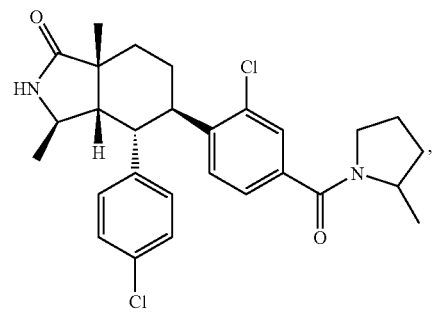
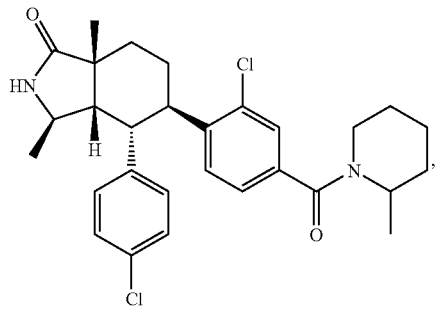
118
-continued
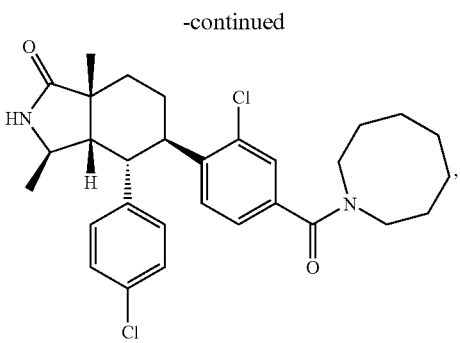
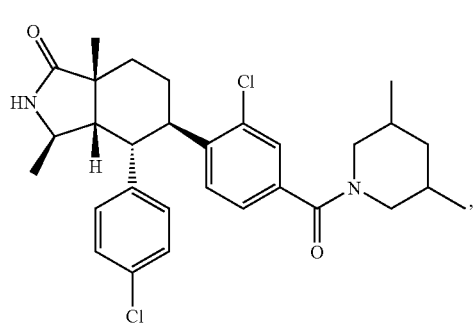
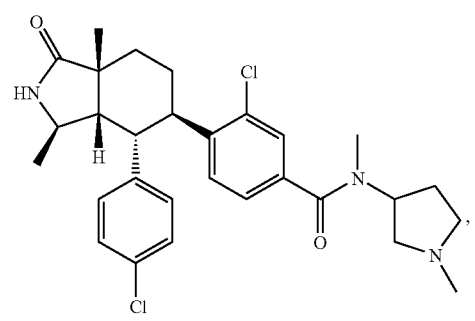
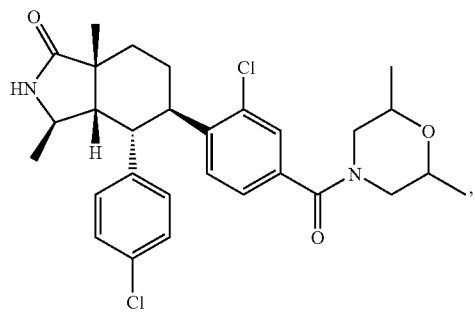
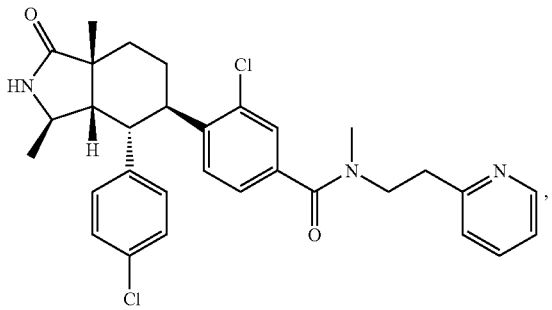

119                                    120
-continued                           -continued
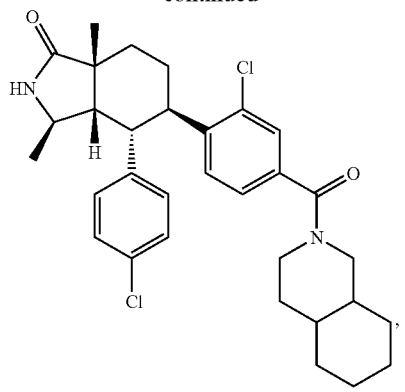
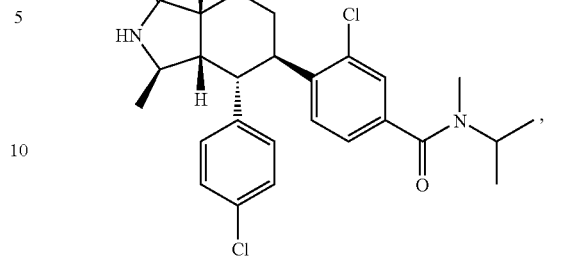
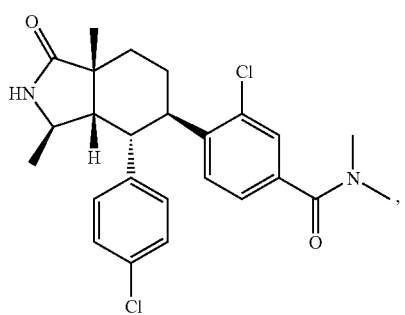
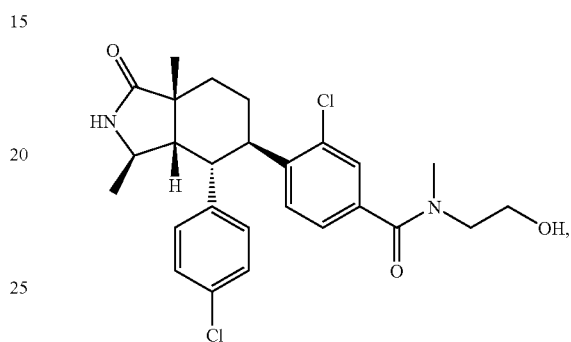
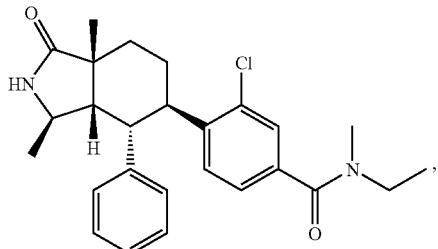
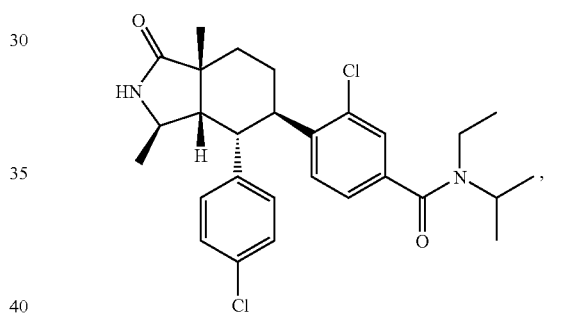
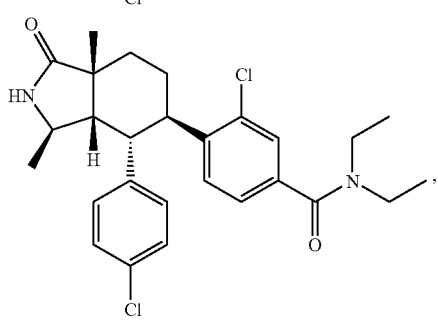

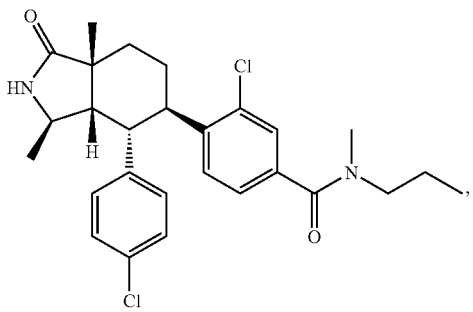

121
-continued
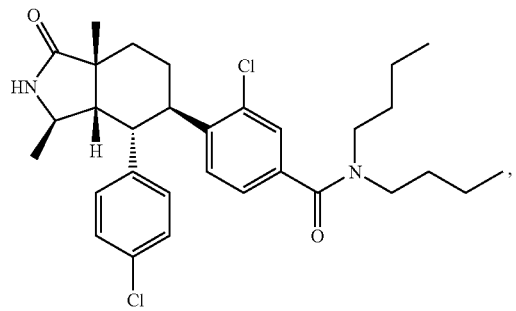
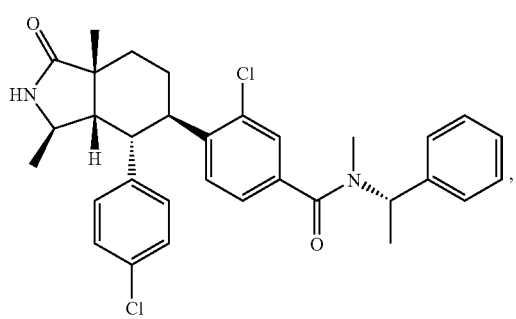
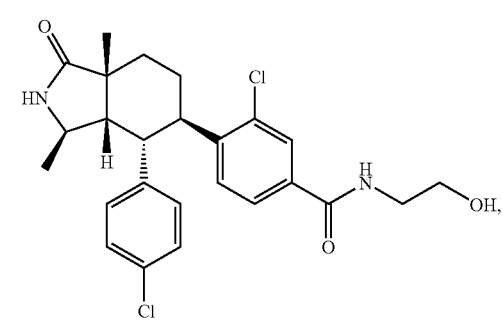
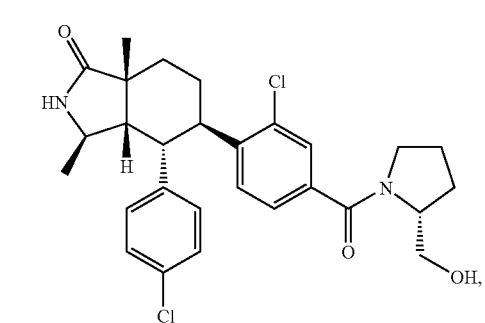
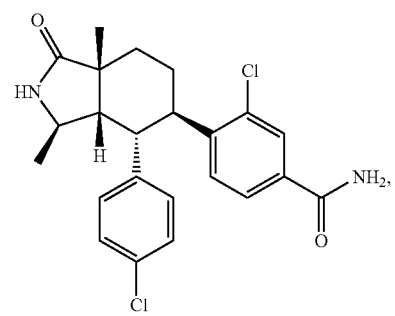
122
-continued
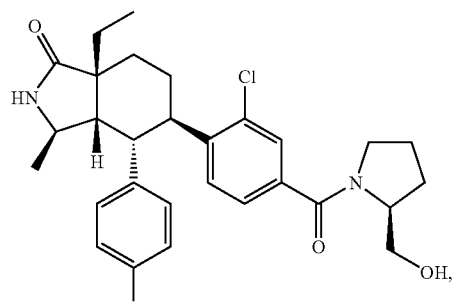
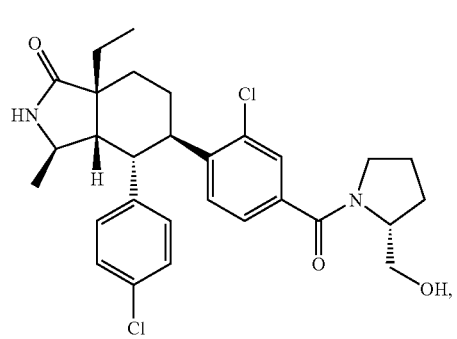
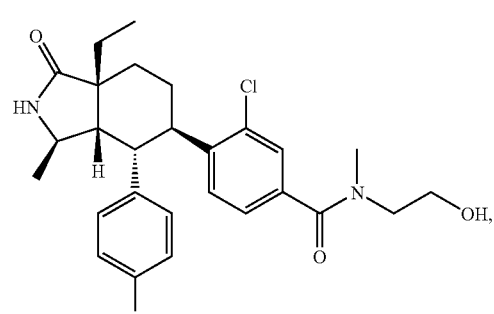
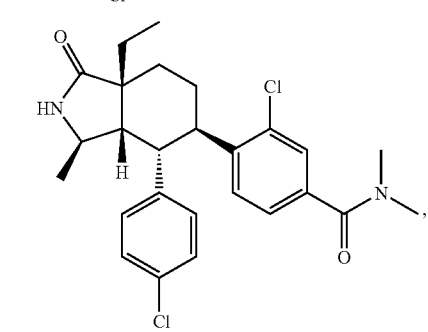
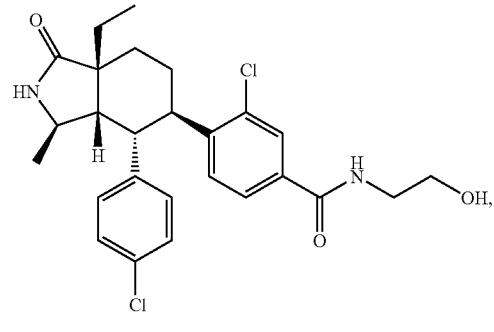

-continued
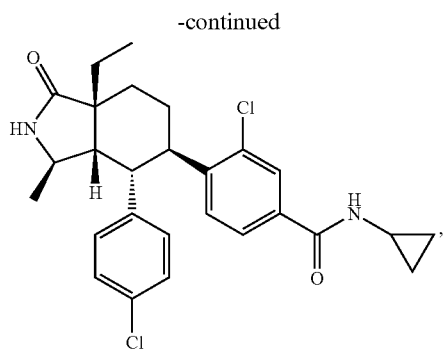
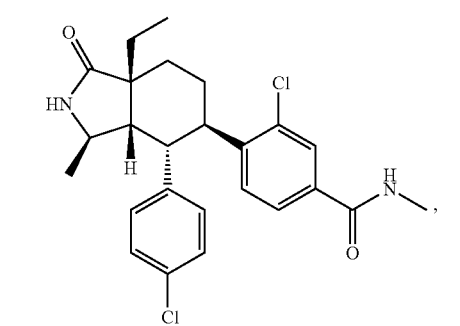
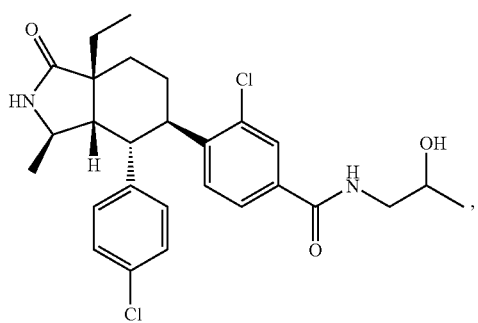
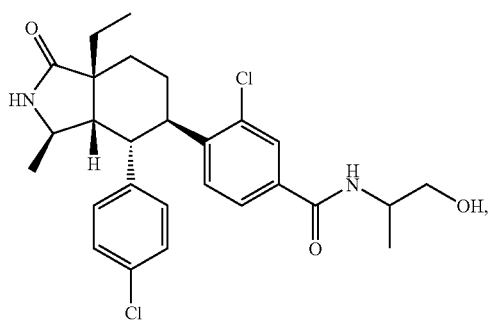
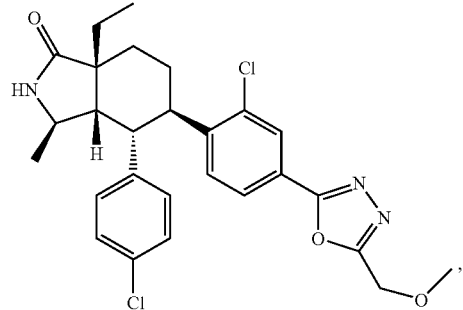
-continued
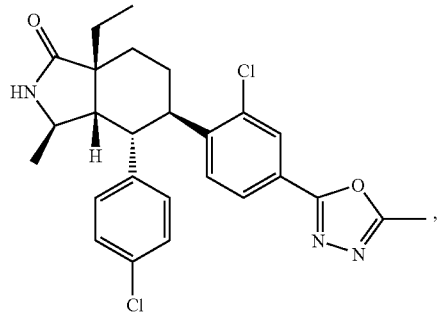
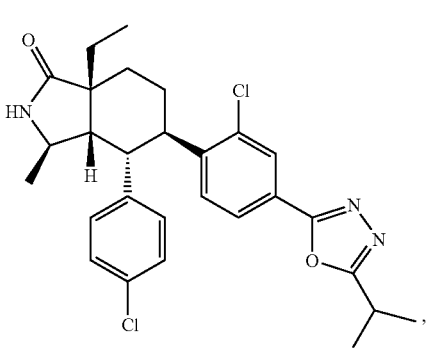
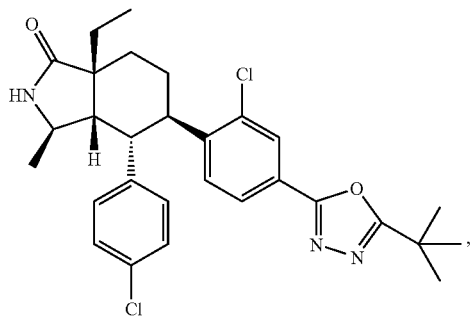
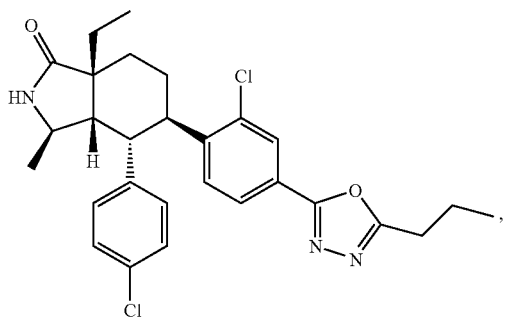
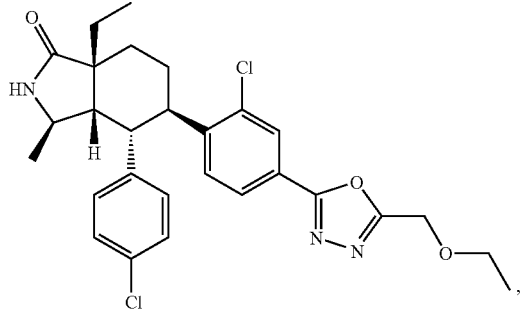

-continued
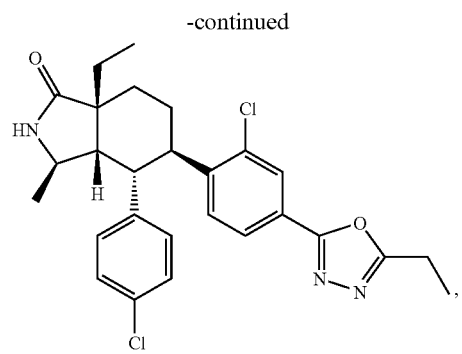
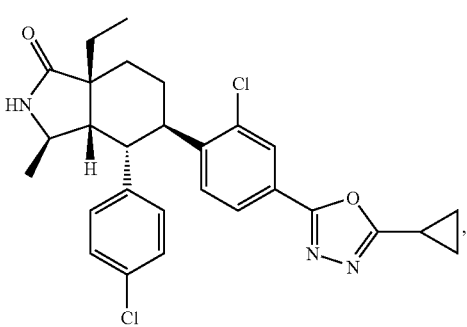
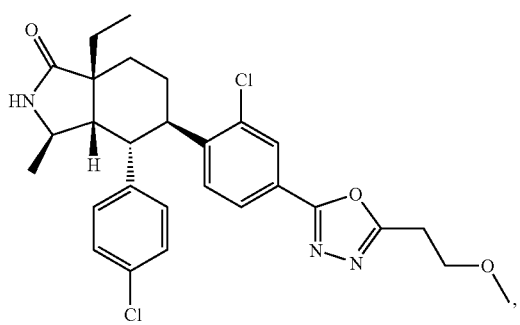
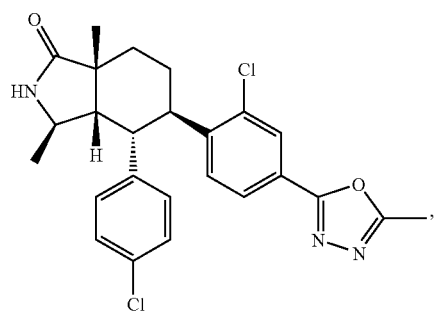
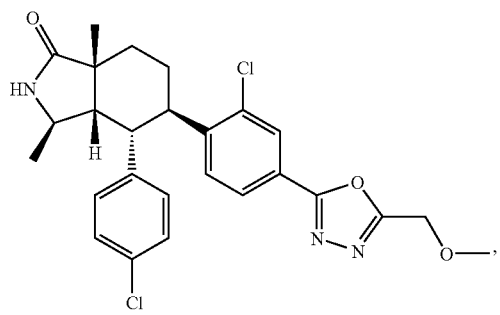
-continued
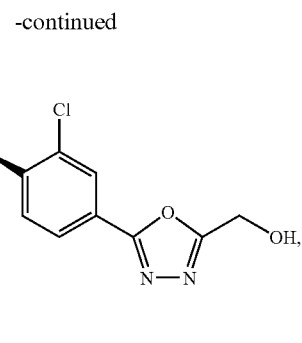
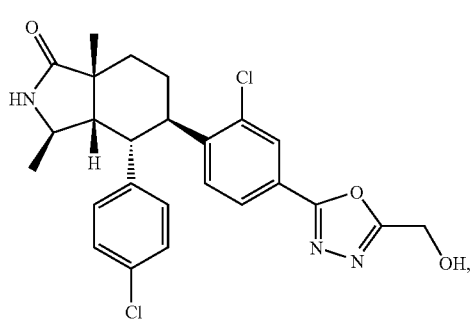
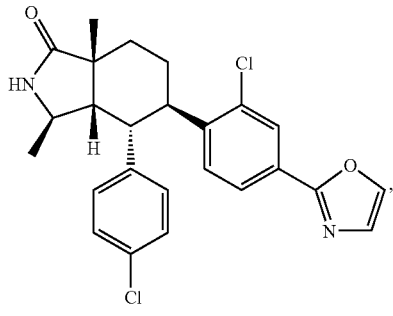
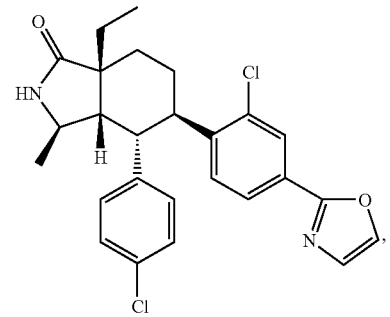
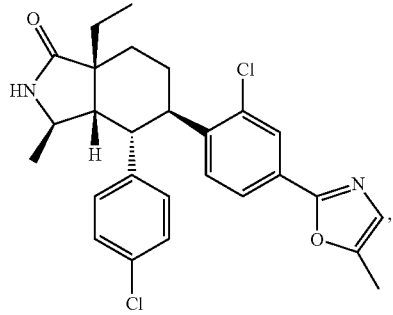

-continued
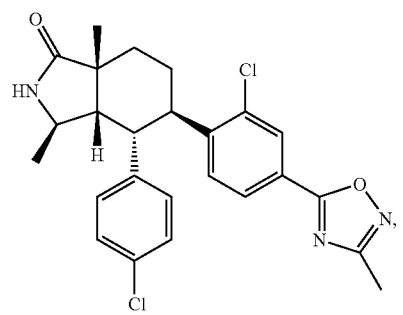
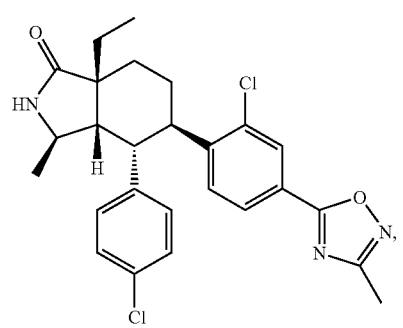
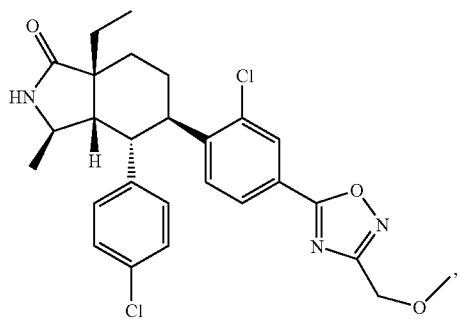
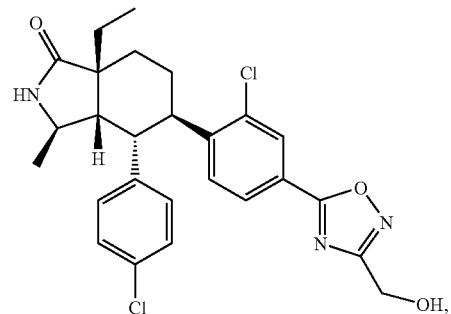
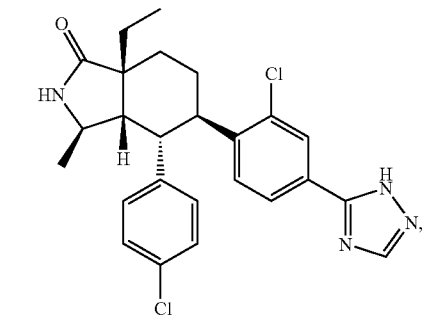
-continued
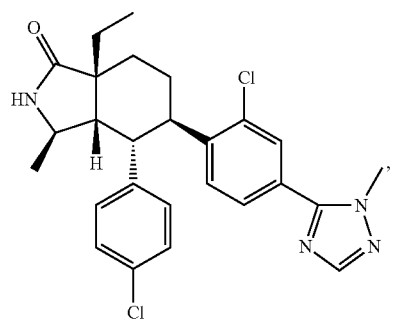
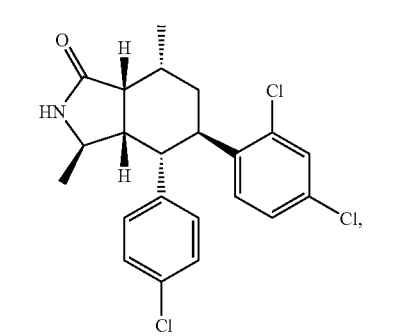
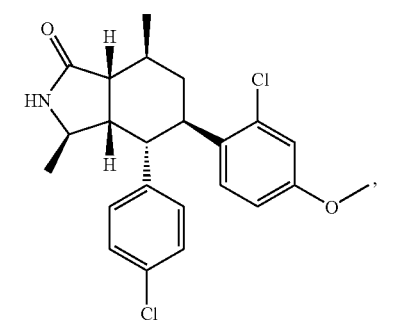

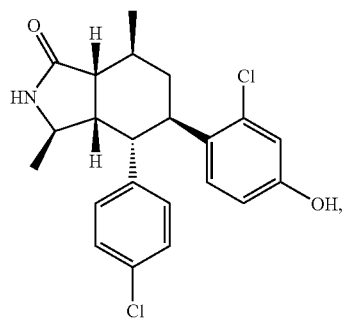
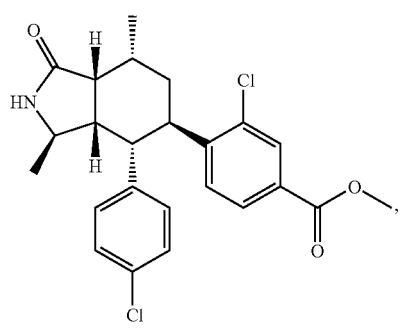
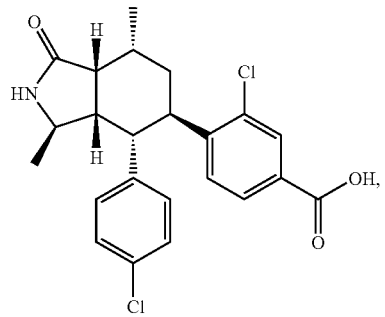
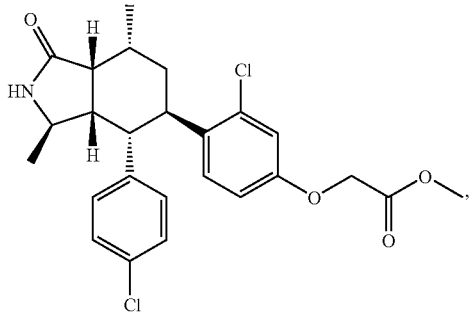
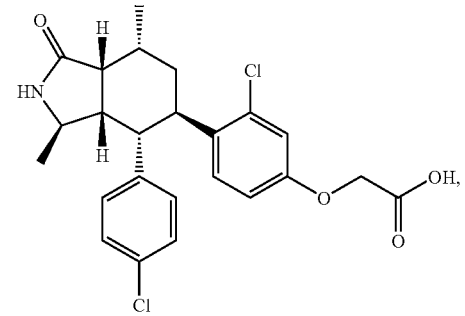
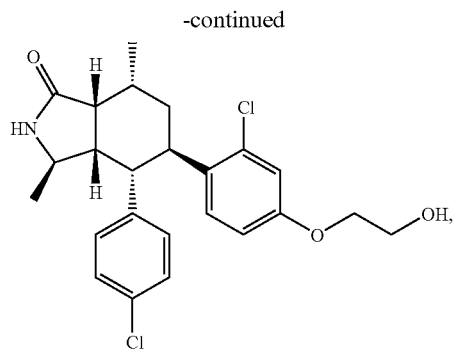
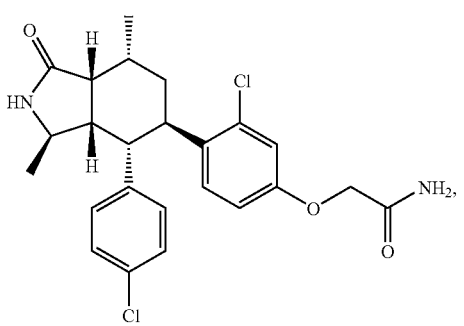
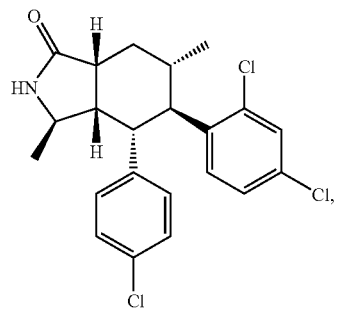
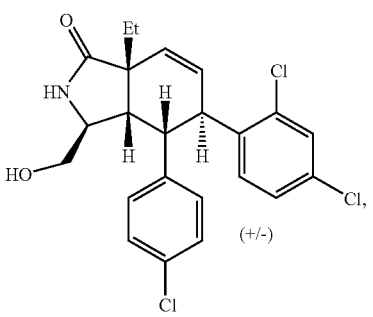
(+/−)
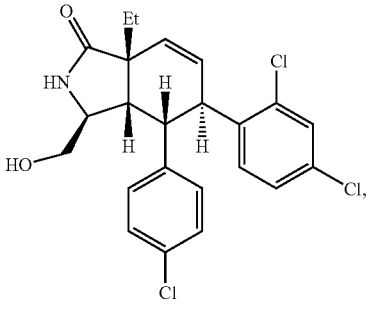

131
-continued
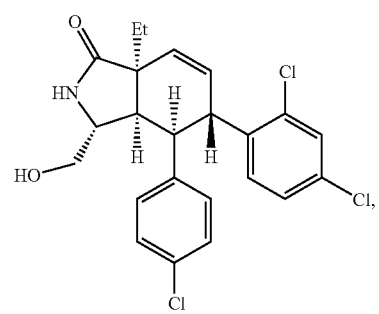
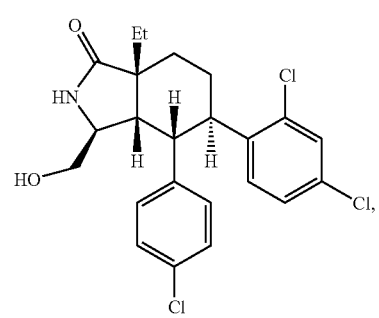
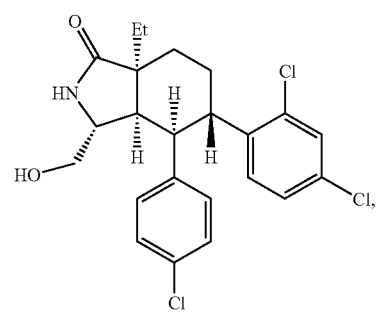
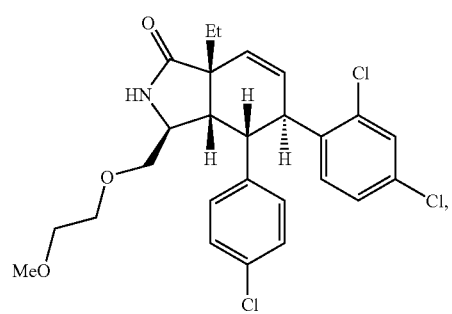
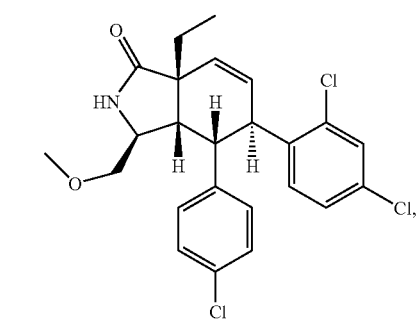
132
-continued
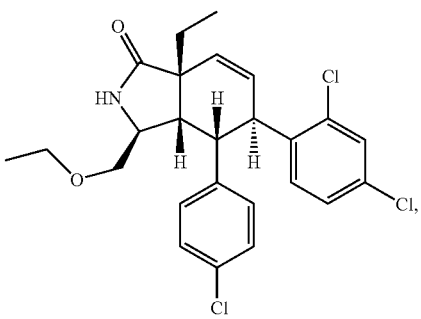
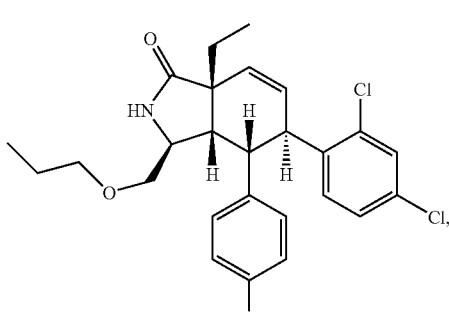
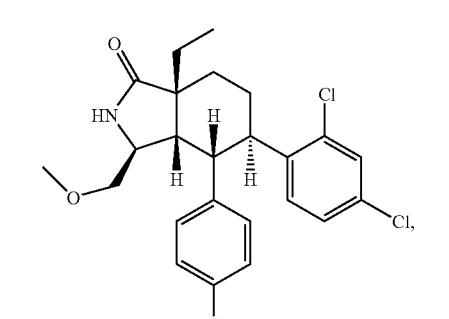
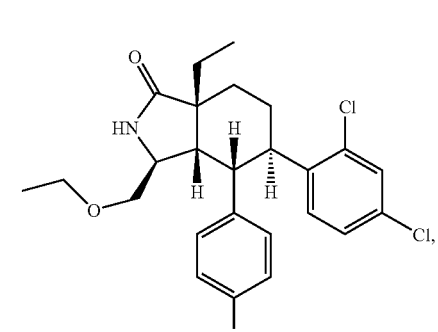
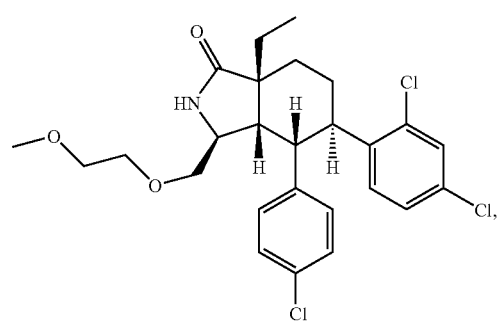

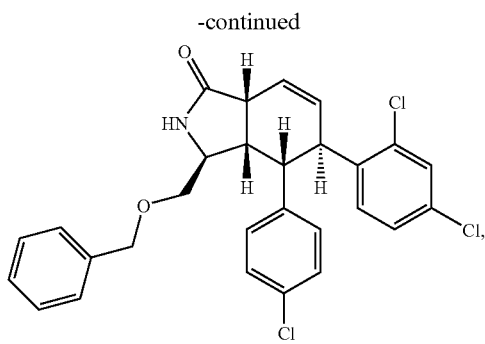
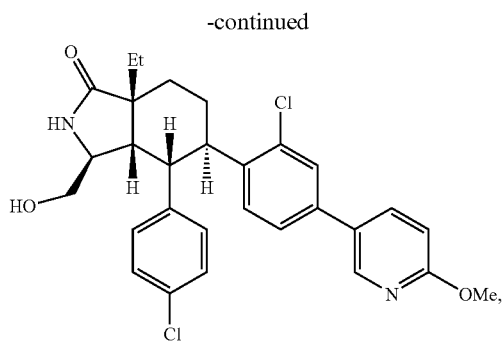
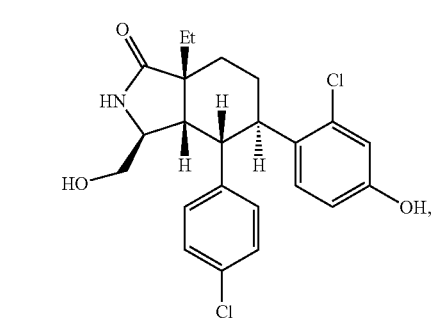
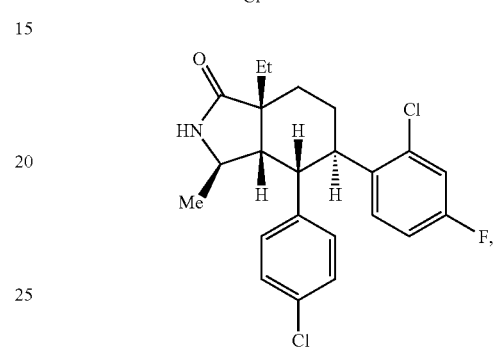
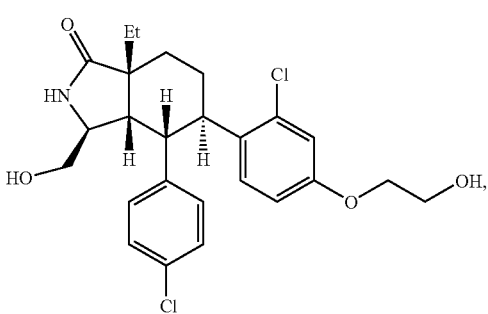
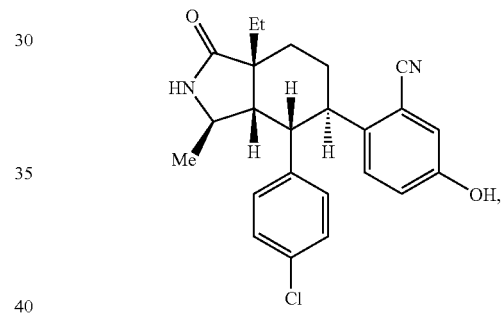
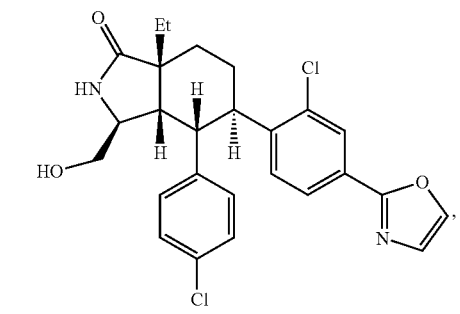
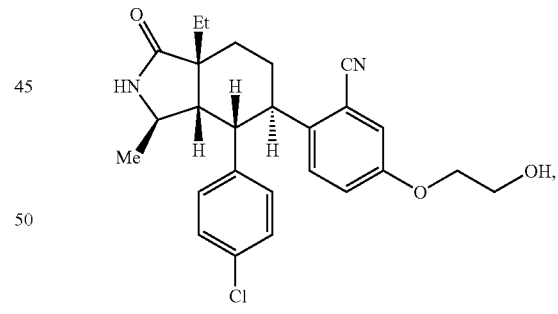
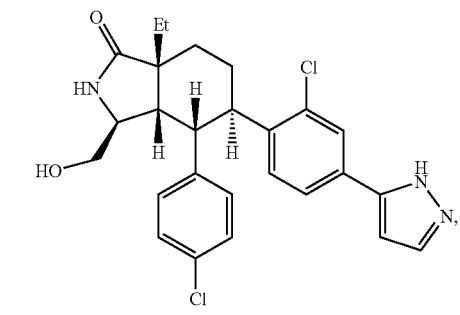
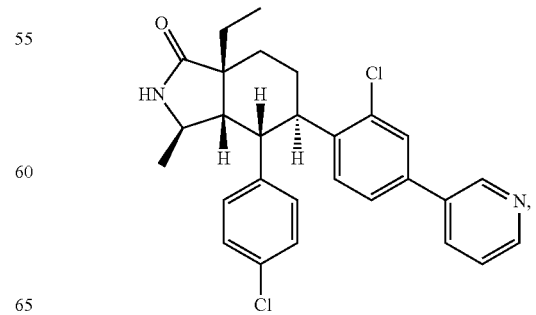

-continued
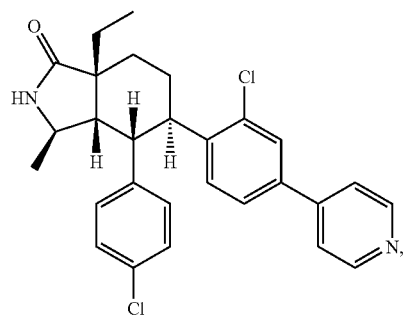
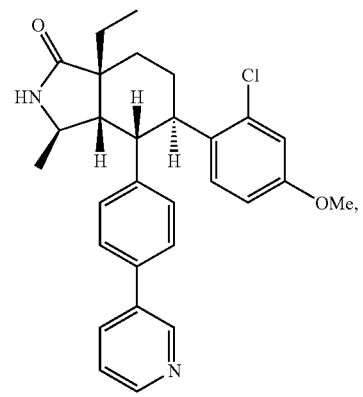
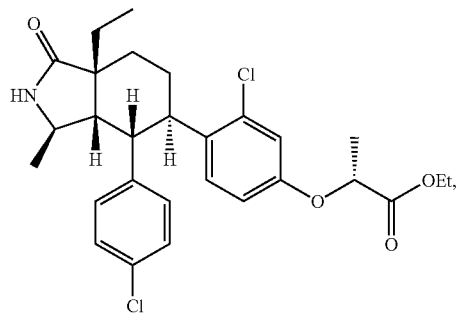
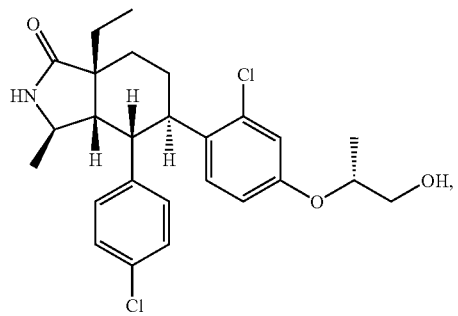
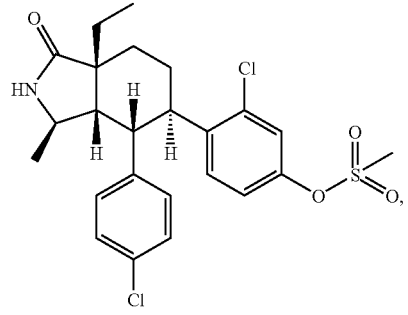
-continued
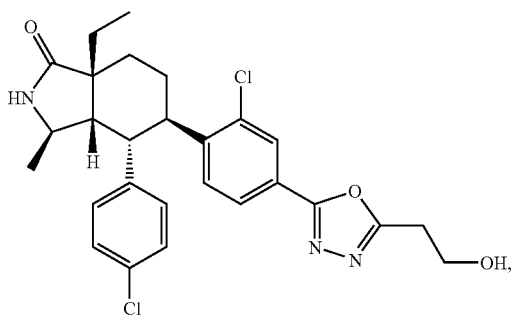
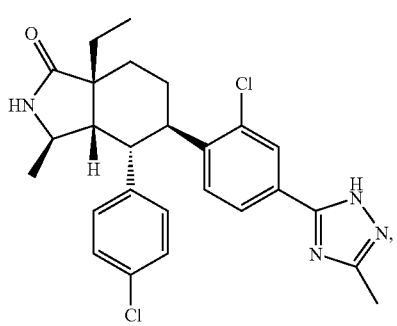
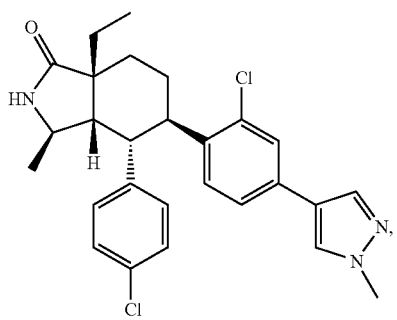
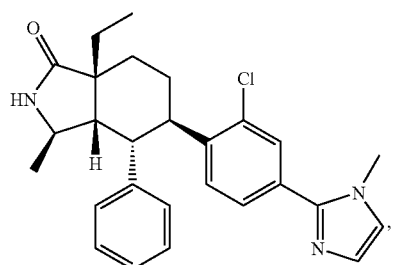
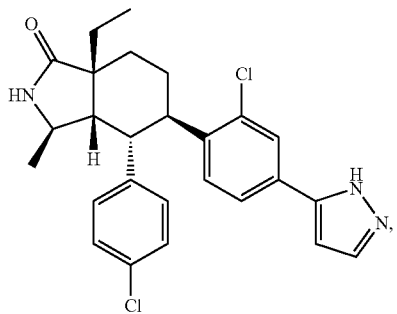

137
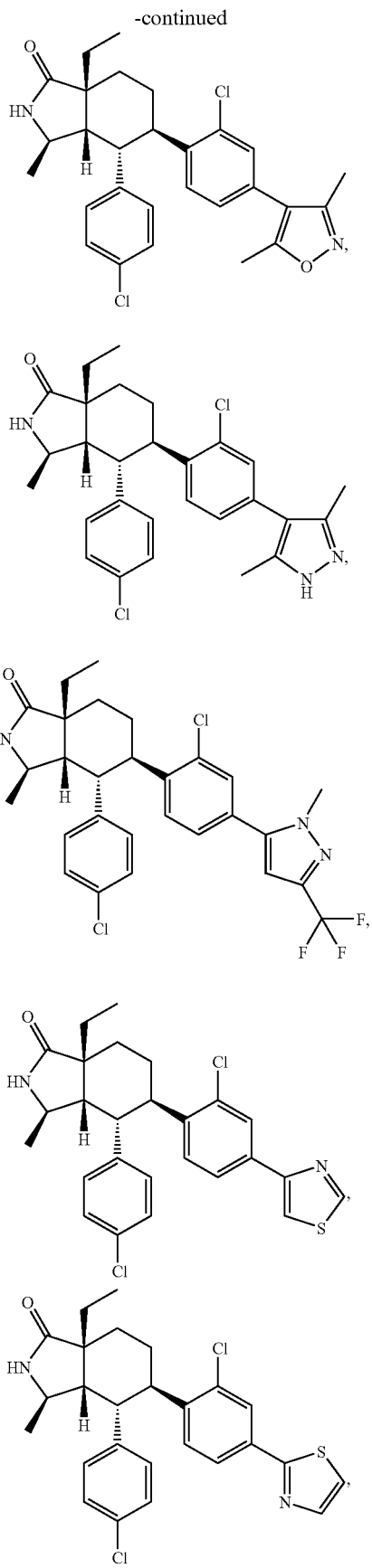
138
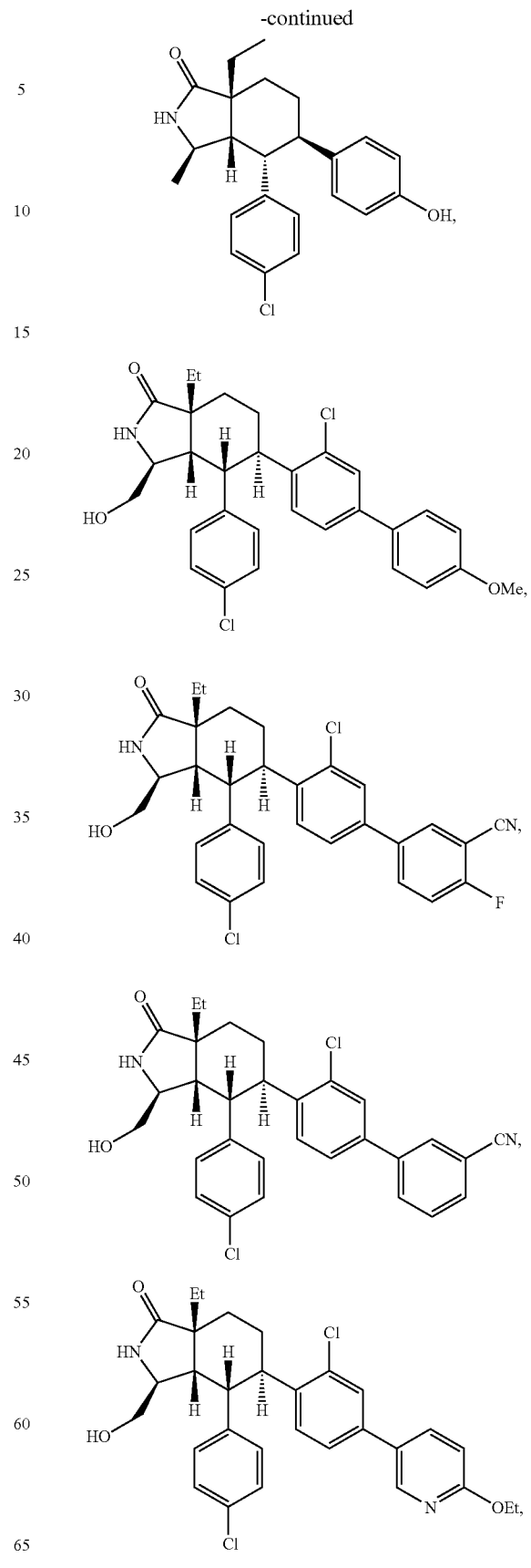

-continued

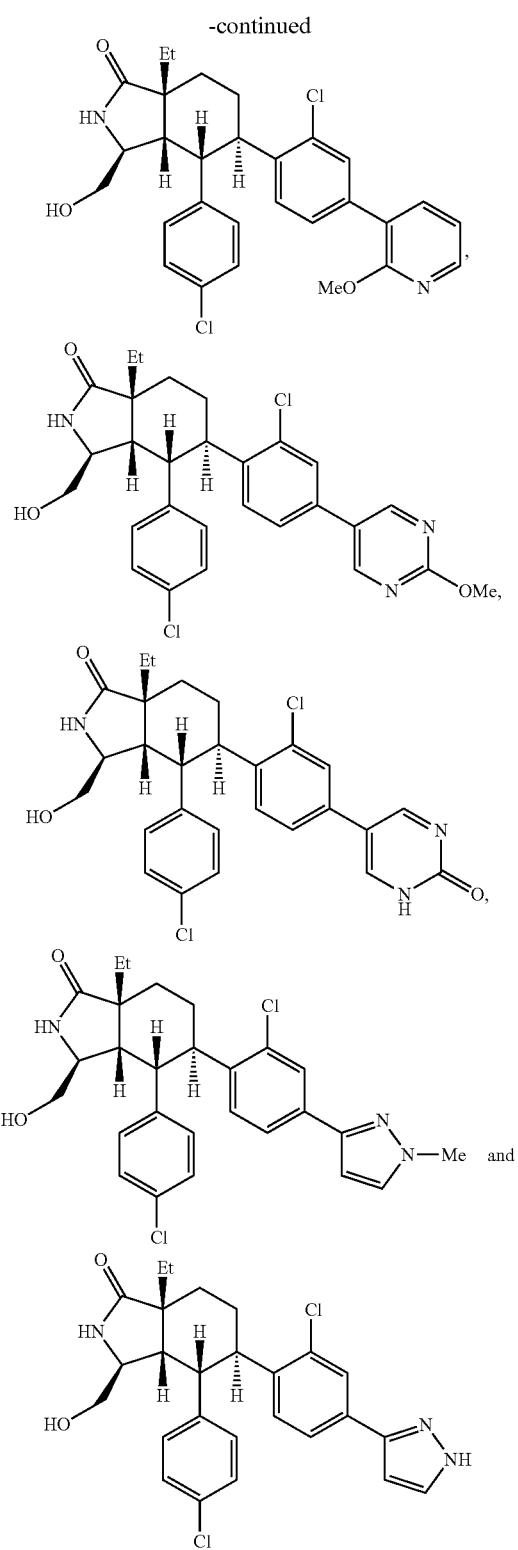

The compounds of the present invention, e.g., according to Formula (I), are preferably purified to a degree suitable for use as a pharmaceutically active substance. That is, the compounds of Formula (I) can have a purity of 95 wt % or more (excluding adjuvants such as pharmaceutically acceptable carriers, solvents, etc., which are used in formulating the compound of Formula (I) into a conventional form, such as a pill, capsule, IV solution, etc. suitable for administration into a patient). More preferably, the purity can be 97 wt % or more, even more preferably, 99 wt % or more. A purified compound of Formula (I) includes a single isomer having a purity, as discussed above, of 95 wt % or more, 97 wt % or more, or 99 wt % or more, as discussed above. For example, the purified compound of Formula (I) can have a purity of 95 wt % or more, 97 wt % or more, or 99 wt % or more.

Alternatively, the purified compound of Formula (I) can include a mixture of isomers, each having a structure according to Formula (I), where the amount of impurity (i.e., compounds or other contaminants, exclusive of adjuvants as discussed above) is 5 wt % or less, 3 wt % or less, or 1 wt % or less. For example, the purified compound of Formula (I) can be an isomeric mixture of compounds of Formula (I), where the ratio of the amounts of the two isomers is approximately 1:1, and the combined amount of the two isomers is 95 wt % or more, 97 wt % or more, or 99 wt % or more.

The variables m and n can represent, respectively, the integers 0 or 1 and 1 or 2, with the proviso that the sum of m and n (i.e., m+n) is 1 or 2. Thus, in one embodiment of the compounds of Formula (I), m is 0 and n is 2, e.g.:

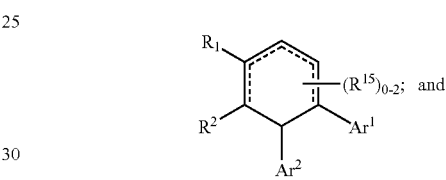

in another embodiment of the compounds of Formula (I), m is 1 and n is 1, e.g.:

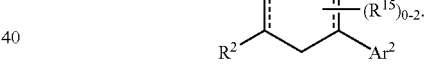

$R^1$ is selected from the group consisting of —C(O)—N$(R^{10})_2$, —C(O)—O-alkyl, and —C(O)—$R^{14}$. The substitutents $R^{10}$ and $R^{14}$ are defined as disclosed herein. The term "alkyl" of —C(O)—O-alkyl includes, for example, lower alkyls such as —$CH_3$, —$CH_2CH_3$, —$CH_2CH_2CH_3$ (n-propyl), —$CH(CH_3)_2$ (i-propyl), —$CH_2CH_2CH_2CH_3$ (n-butyl), —$C(CH_3)_3$ (t-butyl), —$CH(CH_3)$—$CH_2CH_3$ (sec-butyl), —$CH_2CH(CH_3)_2$ (i-butyl), —$CH_2CH_2CH_2CH_2CH_3$ (n-pentyl), —$CH_2C(CH_3)_3$ (neo-pentyl), etc. Thus, —C(O)—O-alkyl includes, for example, —C(O)—O—$CH_3$, —C(O)—O—$CH_2CH_3$, —C(O)—O—$CH_2CH_2CH_3$, —C(O)—O—$CH(CH_3)_2$, —C(O)—O—$CH_2CH_2CH_2CH_3$, —C(O)—O—$C(CH_3)_3$, —C(O)—O—$CH(CH_3)$—$CH_2CH_3$, —C(O)—O—$CH_2CH(CH_3)_2$, —C(O)—O—$CH_2CH_2CH_2CH_2CH_3$, —C(O)—O—$CH_2C(CH_3)_3$, etc. Likewise, —C(O)—N$(R^{10})_2$ includes —C(O)—$NH_2$, —C(O)—NH(alkyl), —C(O)—N(alkyl)$_2$, —C(O)—NH(alkyl-OH), —C(O)—N(alkyl-OH)$_2$, —C(O)—NH-alkylene-$R^{12}$, —C(O)—N(alkyl)-alkylene-$R^{12}$, —C(O)—NH-alkylene-$R^{13}$, —C(O)—N(alkyl)-alkylene-$R^{13}$, —C(O)—NH-alkylene-$R^{14}$, —C(O)—N(alkyl)-alkylene-$R^{14}$, —C(O)—NH—C(O)—$R^{14}$, —C(O)—N(alkyl)-C(O)—$R^{14}$, —C(O)—NH-alkylene-O—$R^9$, —C(O)—N(alkyl)-alkylene-O—$R^9$, —C(O)—NH-heterocycloalkyl optionally substituted on the heterocycloalkyl with one or more $X^3$ groups, —C(O)—N (alkyl)-heterocycloalkyl optionally substituted on the heterocycloalkyl with one or more $X^3$, —C(O)—NH-(benzo-fused cycloalkyl), and —C(O)—N(alkyl)-(benzo-fused cycloalkyl). The terms "alkyl", "alkylene", "benzo-fused cycloalkyl", and "heterocycloalkyl" are as defined herein. The term "alkyl-OH" above refers to an alkyl substituted with one or more —OH groups, for example the groups described below for $R^2$. Each $R^{10}$ of —C(O)—N($R^{10}$)$_2$ can independently include any group defined herein for $R^{10}$, and is not limited to the specific groups and combinations above.

$R^2$ is selected from the group consisting of H, alkyl, alkyl substituted with one or more —OH groups, and -alkylene-N($R^{10}$)$_2$. Alkyl includes, for example, the lower alkyls described above for $R^1$. Alkyl substituted with one or more or more —OH groups includes, for example, —CH$_2$—OH, —CH$_2$CH$_2$—OH, —CH(OH)CH$_3$, —CH(OH)CH$_2$CH$_3$, —CH$_2$CH(OH)CH$_3$, —CH$_2$CH$_2$CH$_2$—OH, —CH(OH)CH$_2$CH$_2$—OH, —CH(OH)CH(OH)CH$_2$—OH, —C(OH)(CH$_3$)$_2$, —CH(CH$_3$)CH$_2$—OH, —CH(OH)CH$_2$CH$_2$CH$_3$, —CH$_2$CH(OH)CH$_2$CH$_3$, —CH$_2$CH$_2$CH(OH)CH$_3$, —CH$_2$CH$_2$CH$_2$CH$_2$—OH, —CH(OH)CH$_2$CH(OH)CH$_3$, etc. Non-limiting examples of the "alkylene" portion of -alkylene-N($R^{10}$)$_2$ include —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, —CH(CH$_3$), —CH(CH$_3$)CH$_2$—, —CH$_2$CH(CH$_3$)—, —CH(CH$_2$CH$_3$)—, —CH(CH$_3$)CH$_2$CH$_2$—, —CH$_2$CH(CH$_3$)CH$_2$—, —CH$_2$CH$_2$CH(CH$_3$)—, —CH(CH$_2$CH$_3$)CH$_2$—, —CH$_2$CH(CH$_2$CH$_3$)—, —CH(CH$_2$CH$_2$CH$_3$)—, —CH(CH$_3$)CH(CH$_3$)—, etc. $R^{10}$ is defined herein, and each $R^{10}$ of -alkylene-N($R^{10}$)$_2$ is independently selected and may be independently combined in any combination with any of the alkylene groups defined herein.

In an alternative embodiment, $R^1$ and $R^2$ together with the carbon atoms to which they are shown attached in Formula (I) form a group Q selected from:

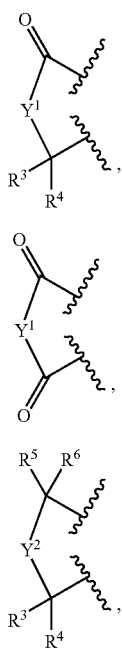

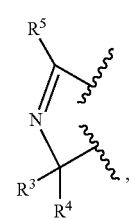

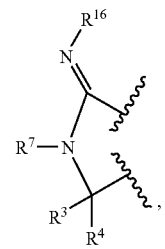

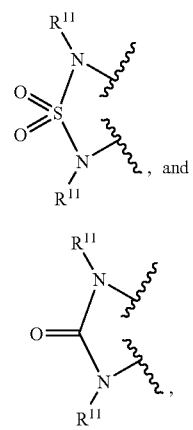

where $Y^1$, $Y^2$, $R^3$, $R^4$, $R^5$, $R^6$, $R^7$, and $R^{16}$ are as defined herein. The various possible bicyclic structures thus formed are described above.

$R^3$, $R^4$, $R^5$, and $R^6$ are each independently selected from the group consisting of H, —O—$R^9$, $R^{11}$, and —N($R^{16}$)$_2$. $R^9$ and $R^{11}$ are as defined herein. For example, —O—$R^9$ can include —OH and —O—$R^{11}$. —O—$R^{11}$ can include, for example, —O—CH$_3$, —O—CH$_2$CH$_3$, —O—CH$_2$CH$_2$CH$_3$, —O—CH(CH$_3$)$_2$, —O—CH$_2$CH$_2$CH$_2$CH$_3$, —O—C(CH$_3$)$_3$, —O—CH(CH$_3$)CH$_2$CH$_3$, —O—CH$_2$CH(CH$_3$)$_2$, —O—CH$_2$CH$_2$CH$_2$CH$_2$CH$_3$, —O—CH$_2$C(CH$_3$)$_3$, —O-phenyl, —O-naphthyl, —O-biphenyl, etc., wherein said phenyl, naphthyl, and biphenyl are unsubstituted or substituted with one or more $X^1$ groups, wherein said $X^1$ is as described herein. Likewise, non-limiting examples of $R^{11}$ include the alkyl groups defined above for $R^1$, as well as unsubstituted or $X^1$ substituted aryls, e.g., phenyl, naphthyl, biphenyl, etc. $R^{16}$ is defined herein, and each $R^{16}$ of —N($R^{16}$)$_2$ may be independently selected. Thus, non-limiting examples of —N($R^{16}$)$_2$ include, for example, —N($R^9$)$_2$ wherein each $R^9$ is independently selected and defined herein and can include H, alkyl, unsubstituted aryl, and aryl substituted with one or more $X^1$ groups in any combination; and —N($R^9$)—C(O)—$R^{12}$ wherein $R^9$ and $R^{12}$ are independently selected and defined herein. Thus, non-limiting examples of —N($R^9$)—C(O)-aryl include —NH—C(O)aryl, —N(alkyl)-C(O)-aryl, —N(aryl)-C(O)-aryl, wherein each "aryl" is e.g., unsubstituted or $X^1$ substituted phenyl, naphthyl, biphenyl, etc., and each "alkyl" is selected from the lower alkyls described for $R^1$ above.

$R^7$ is selected from the group consisting of H, arylalkyl, alkyl, alkenyl, -alkylene-$N(R^9)_2$, -alkylene-O—$R^9$, -alkylene-$R^{12}$, —C(O)—$R^{14}$, -alkylene-C(O)H, and —C(O)—O—$R^{11}$. The term "alkyl" includes, for example, the lower alkyl groups described above for $R^1$. The term "arylalkyl" includes, for example, which may be substituted or unsubstituted, is as defined herein. The term "alkenyl" includes, for example, —CH=$CH_2$, —$CH_2$—CH=$CH_2$, —CH=CH—$CH_3$, —$CH_2$—C($CH_3$)=$CH_2$, and —$CH_2$—CH=$CHCH_3$. The term "-alkylene-$R^{12}$" includes combinations of the "alkylene" groups defined above, and $R^{12}$ groups as defined herein. For example, "-alkylene-$R^{12}$" includes e.g., —$CH_2$-aryl, —$CH_2CH_2$-aryl, —$CH_2CH_2CH_2$-aryl, —$CH_2CH_2CH_2CH_2$-aryl, —$CH_2CH_2CH_2CH_2CH_2$-aryl, —$CH_2CH_2CH_2CH_2CH_2CH_2$-aryl, —CH($CH_3$)-aryl, —CH($CH_3$)$CH_2$-aryl, —$CH_2$CH($CH_3$)-aryl, —CH($CH_2CH_3$)-aryl, —CH($CH_3$)$CH_2CH_2$-aryl, —$CH_2$CH($CH_3$)$CH_2$-aryl, —$CH_2CH_2$CH($CH_3$)-aryl, —CH($CH_2CH_3$)$CH_2$-aryl, —$CH_2$CH($CH_2CH_3$)-aryl, —CH($CH_2CH_3$)-aryl, —CH($CH_3$)CH($CH_3$)-aryl, etc., wherein the "aryl" includes for example phenyl, naphthyl, or biphenyl which may be unsubstituted or substituted with one or more $X^1$ group. Non-limiting examples of the "alkylene" portion of -alkylene-$N(R^9)_2$ include —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, —CH($CH_3$)—, —CH($CH_3$)$CH_2$—, —$CH_2$CH($CH_3$)—, —CH($CH_2CH_3$)—, —CH($CH_3$)$CH_2CH_2$—, —$CH_2$CH($CH_3$)$CH_2$—, —$CH_2CH_2$CH($CH_3$), —CH($CH_2CH_3$)$CH_2$—, —$CH_2$CH($CH_2CH_3$)—, —CH($CH_3$)CH($CH_3$)—, etc. $R^9$ is as defined herein, and each $R^9$ of -alkylene-$N(R^9)_2$ is independently selected and may be independently combined in any combination with any of the alkylene groups defined herein. The term "-alkylene-O—$R^9$" includes, for example, —$CH_2$—O—$R^9$, —$CH_2CH_2$—O—$R^9$, —$CH_2CH_2CH_2$O—$R^9$, —$CH_2CH_2CH_2CH_2$—O—$R^9$, —$CH_2CH_2CH_2CH_2CH_2$—O—$R^9$, —$CH_2CH_2CH_2CH_2CH_2CH_2$—O—$R^9$, —CH($CH_3$)—O—$R^9$, —CH($CH_3$)$CH_2$—O—$R^9$, —$CH_2$CH($CH_3$)—O—$R^9$, —CH($CH_2CH_3$)—O—$R^9$, —CH($CH_3$)$CH_2CH_2$—O—$R^9$, —$CH_2$CH($CH_3$)$CH_2$O—$R^9$, —$CH_2CH_2$CH($CH_3$)O—$R^9$, —CH($CH_2CH_3$)$CH_2$—O—$R^9$, —$CH_2$CH($CH_2CH_3$)O—$R^9$, —CH($CH_2CH_3$)—O—$R^9$, —CH($CH_3$)CH($CH_3$)—O—$R^9$, —CH(O$R^9$)$CH_2$—, etc. Non-limiting examples of -alkylene-$R^{12}$ include for example, —$CH_2$-aryl, —$CH_2CH_2$-aryl, —$CH_2CH_2CH_2$-aryl, —$CH_2CH_2CH_2CH_2$-aryl, —$CH_2CH_2CH_2CH_2CH_2$-aryl, —$CH_2CH_2CH_2CH_2CH_2CH_2$-aryl, —CH($CH_3$)-aryl, —CH($CH_3$)$CH_2$-aryl, —$CH_2$CH($CH_3$)-aryl, —CH($CH_2CH_3$)-aryl, —CH($CH_3$)$CH_2CH_2$-aryl, —$CH_2$CH($CH_3$)$CH_2$-aryl, —$CH_2CH_2$CH($CH_3$)-aryl, —CH($CH_2CH_3$)$CH_2$-aryl, —$CH_2$CH($CH_2CH_3$)-aryl, —CH($CH_2CH_3$)-aryl, —CH($CH_3$)CH($CH_3$)-aryl, etc., wherein the "aryl" includes for example phenyl, naphthyl, or biphenyl which may be unsubstituted or substituted with one or more $X^1$ group. Non-limiting examples of —C(O)—$R^{14}$ include —C(O)-cyclopropyl, —C(O)-cyclobutyl, —C(O)-cyclopentyl, —C(O)-cyclohexyl, —C(O)-cycloheptyl, wherein said cyclopropyl, cyclobutyl, cyclopentyl, cyclohexyl, or cycloheptyl portion are unsubstituted or substituted with one or more $X^4$ groups. Non-limiting examples of —C(O)—O—$R^{11}$ include —C(O)—OH, —C(O)—O—$CH_3$, —C(O)—O—$CH_2CH_3$, —C(O)—O—$CH_2CH_2CH_3$, —C(O)—O—CH($CH_3$)$_2$, —C(O)—O—C($CH_3$)$_3$, —C(O)—O—$CH_2CH_2CH_2CH_3$, —C(O)—O—CH($CH_3$)$CH_2CH_3$, —C(O)—O—$CH_2$CH($CH_3$)$_2$, —C(O)—O-phenyl, —C(O)—O-naphthyl, —C(O)—O-biphenyl, etc., wherein said phenyl, naphthyl, and biphenyl may be unsubstituted or substituted with $X^1$.

$R^8$ is selected from the group consisting of H, -alkylene-$R^{12}$, —C(O)—$R^{17}$, —S($O_2$)—$R^{11}$, —S($O_2$)—$R^{14}$, —C(O)—N($R^{18}$)$_2$, and $R^{14}$. The terms "alkenyl", and "-alkylene-$R^{12}$", for example, are as defined above. The term "—C(O)—$R^{17}$" includes, for example —C(O)-heterocycloalkyl, —C(O)-alkylene-$R^{12}$, —C(O)—O—$R^9$, and —C(O)—$R^{12}$. Thus, —C(O)—$R^{17}$ includes, for example, —C(O)-morpholinyl, —C(O)-piperazinyl, —C(O)-piperidinyl, —C(O)-pyrrolidinyl, —C(O)-tetrahydrofuranyl, —C(O)-tetrahydrofuranyl, —C(O)-thiazolinyl, —C(O)-tetrahydropyranyl, etc.; —C(O)—$CH_2$-aryl, —C(O)—$CH_2CH_2$-aryl, —C(O)—$CH_2CH_2CH_2$-aryl, —C(O)—$CH_2CH_2CH_2CH_2$-aryl, —C(O)—$CH_2CH_2CH_2CH_2CH_2$-aryl, —C(O)—$CH_2CH_2CH_2CH_2CH_2CH_2$-aryl, —C(O)—CH($CH_3$)-aryl, —C(O)—CH($CH_3$)$CH_2$-aryl, —C(O)—$CH_2$CH($CH_3$)-aryl, —C(O)—CH($CH_2CH_3$)-aryl, —C(O)—CH($CH_3$)$CH_2CH_2$-aryl, —C(O)—$CH_2$CH($CH_3$)$CH_2$-aryl, —C(O)—$CH_2CH_2$CH($CH_3$)-aryl, —C(O)—CH($CH_2CH_3$)$CH_2$-aryl, —C(O)—$CH_2$CH($CH_2CH_3$)aryl, —C(O)—CH($CH_2CH_3$)-aryl, —C(O)—CH($CH_3$)CH($CH_3$)-aryl, etc., wherein the term "aryl" includes for example phenyl, naphthyl, or biphenyl which may be unsubstituted or substituted with one or more $X^1$ group; —C(O)—O—H, —C(O)—O—$CH_3$, —C(O)—O—$CH_2CH_3$, —C(O)—O—$CH_2CH_2CH_3$, —C(O)—O—CH($CH_3$)$_2$, —C(O)—O—$CH_2CH_2CH_2CH_3$, —C(O)—O—C($CH_3$)$_3$, —C(O)—O—CH($CH_3$)—$CH_2CH_3$, —C(O)—O—$CH_2$CH($CH_3$)$_2$, —C(O)—O—$CH_2CH_2CH_2CH_2CH_3$, —C(O)—O—$CH_2$C($CH_3$)$_3$, etc., —C(O)—O-phenyl, —C(O)—O-naphthyl, —C(O)—O-biphenyl, wherein said phenyl, naphthyl, and biphenyl portion may be unsubstituted or substituted with one or more $X^1$ group; and —C(O)-phenyl, —C(O)-naphthyl, —C(O)-biphenyl, wherein said phenyl, naphthyl, and biphenyl portion may be unsubstituted or substituted with one or more $X^1$ group. Non-limiting examples of —S($O_2$)—$R^{11}$ include, e.g., —S($O_2$)—$CH_3$, —S($O_2$)—$CH_2CH_3$, —S($O_2$)—$CH_2CH_2CH_3$, —S($O_2$)—CH($CH_3$)$_2$, —S($O_2$)—$CH_2CH_2CH_2CH_3$, —S($O_2$)—C($CH_3$)$_3$, —S($O_2$)—CH($CH_3$)—$CH_2CH_3$, —S($O_2$)—$CH_2$CH($CH_3$)$_2$, —S($O_2$)—$CH_2CH_2CH_2CH_2CH_3$, —S($O_2$)—$CH_2$C($CH_3$)$_3$, etc., —S($O_2$)-phenyl, —S($O_2$)-naphthyl, —S($O_2$)-biphenyl, wherein said phenyl, naphthyl, and biphenyl portion may be unsubstituted or substituted with one or more $X^1$ group. Non-limiting examples of —S($O_2$)—$R^{14}$ include, e.g., —S($O_2$)—$CH_3$, —S($O_2$)—$CH_2CH_3$, —S($O_2$)—$CH_2CH_2CH_3$, —S($O_2$)—CH($CH_3$)$_2$, —S($O_2$)—$CH_2CH_2CH_2CH_3$, —S($O_2$)—C($CH_3$)$_3$, —S($O_2$)—CH($CH_3$)—$CH_2CH_3$, —S($O_2$)—$CH_2$CH($CH_3$)$_2$, —S($O_2$)—$CH_2CH_2CH_2CH_2CH_3$, —S($O_2$)—$CH_2$C($CH_3$)$_3$, etc., and —S($O_2$)-cyclopropyl, —S($O_2$)-cyclobutyl, —S($O_2$)-cyclopentyl, —S($O_2$)-cyclohexyl, —S($O_2$)-cycloheptyl, wherein the cyclopropyl, cyclobutyl, cyclopentyl, cyclohexyl, and cycloheptyl portion thereof may be unsubstituted or substituted with one or more $X^4$ group. $R^8$ also includes $R^{14}$, defined herein, for example cyclopropyl, cyclobutyl, cyclopentyl, cyclohexyl, and cycloheptyl, each of which may be unsubstituted or substituted with one or more $X^4$ group. The term —C(O)—N($R^{18}$)$_2$ includes, for example, —C(O)—$NHR^{18}$, where $R^{18}$ is as defined below.

$R^9$ is selected from the group consisting of H and $R^{11}$, wherein $R^{11}$ is defined as described herein.

$R^{10}$ is selected from the group consisting of H, alkyl substituted with one or more —OH group, -alkylene-$R^{12}$, -alkylene-$R^{13}$, -alkylene-$R^{14}$, —C(O)—$R^{14}$, -alkylene-O—$R^9$, $R^{14}$, unsubstituted heterocycloalkyl, heterocycloalkyl substituted with one or more $X^3$ groups, and benzo-fused cycloalkyl. The terms "alkyl substituted with one or more —OH group" "-alkylene-$R^{12}$", and "—(O)—$R^{14}$" are defined as described herein. Non-limiting examples of -alkylene-$R^{13}$ include -alkylene-heteroaryls wherein the "alkylene" portion thereof includes, e.g., —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, —$CH(CH_3)$—, —$CH(CH_3)CH_2$—, —$CH_2CH(CH_3)$—, —$CH(CH_2CH_3)$—, —$CH(CH_3)CH_2CH_2$—, —$CH_2CH(CH_3)CH_2$—, —$CH_2CH_2CH(CH_3)$—, —$CH(CH_2CH_3)CH_2$—, —$CH_2CH(CH_2CH_3)$—, —$CH(CH_2CH_2CH_3)$—, —$CH(CH_3)CH(CH_3)$—, and the "heteroaryl" portion thereof includes, e.g., azaindolyl, benzimidazolyl, benzofuranyl, benzoazaindolyl, benzothiophenyl, cinnolinyl, furanyl, furazanyl, indolyl, isoquinolyl, phthalazinyl, pyrazinyl, pyridazinyl, pyridyl, pyrimidyl, pyrrolyl, quinolinyl, quinoxalinyl, quinazolinyl, thiophenyl, isoxazolyl, triazolyl, thiazolyl, thiadiazolyl, etc., each of which may be unsubstituted or substituted with one or more $X^2$ groups. Non-limiting examples of -alkylene-$R^{14}$ include -alkylene-cycloalkyls wherein the "alkylene" portion thereof includes, e.g., —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, —$CH(CH_3)$—, —$CH(CH_3)CH_2$—, —$CH_2CH(CH_3)$—, —$CH(CH_2CH_3)$—, —$CH(CH_3)CH_2CH_2$—, —$CH_2CH(CH_3)CH_2$—, —$CH_2CH_2CH(CH_3)$—, —$CH(CH_2CH_3)CH_2$—, —$CH_2CH(CH_2CH_3)$—, —$CH(CH_2CH_2CH_3)$—, —$CH(CH_3)CH(CH_3)$—, and the cycloalkyl portion thereof includes, e.g., cyclopropyl, cyclobutyl, cyclopentyl, cyclohexyl, cycloheptyl, bicyclo[2.2.1]heptyl, adamantyl, etc. each of which may be unsubstituted or substituted with one or more $X^4$ groups. When $R^{10}$ is $R^{14}$, non-limiting examples include e.g., cyclopropyl, cyclobutyl, cyclopentyl, cyclohexyl, cycloheptyl, bicyclo[2.2.1]heptyl, adamantyl, etc. each of which may be unsubstituted or substituted with one or more $X^4$ groups. When $R^{10}$ is unsubstituted heterocycloalkyl or heterocycloalkyl substituted with one or more $X^3$ groups, said heterocycloalkyl may include morpholinyl, piperazinyl, piperidinyl, pyrrolidinyl, tetrahydrofuranyl, tetrahydrofuranyl, thiazolinyl, tetrahydropyranyl, etc. Non-limiting examples of benzo-fused cycloalkyls include the following structures:

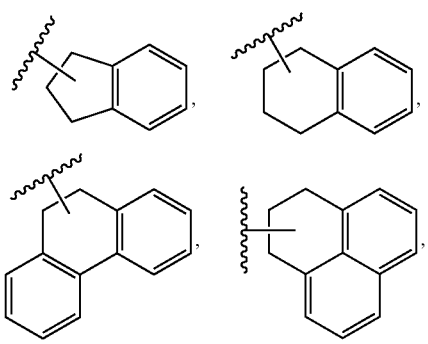

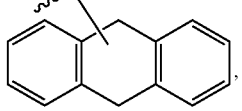

etc. Although the structures above suggest that the benzo-fused cycloalkyl is bonded to the parent structure from the cycloalkyl portion of the group, it is contemplated that the benzo-fused cycloalkyl can be bonded to the parent structure either from the cycloalkyl portion (i.e., from a saturated or $sp^3$ ring carbon, or alternatively from the "benzo" portion (i.e., from an unsaturated or $sp^2$ ring carbon).

$R^{11}$ is selected from the group consisting of unsubstituted alkyl, alkyl substituted with one or more —OH groups, -alkylene-O-alkyl, -alkylene-O-aryl, unsubstituted aryl, and aryl substituted with one or more $X^1$ groups. The terms "alkyl", "alkylene" and "aryl" are as defined herein.

$R^{12}$ is selected from the group consisting of unsubstituted aryl and aryl substituted with one or more $X^1$ groups, wherein the term "aryl" is as defined herein.

$R^{13}$ is selected from the group consisting of unsubstituted heteroaryl and heteroaryl substituted with one or more $X^2$ groups. Non-limiting examples of suitable $R^{13}$ groups include, e.g., azaindolyl, benzimidazolyl, benzofuranyl, benzoazaindolyl, benzothiophenyl, cinnolinyl, furanyl, furazanyl, indolyl, isoquinolyl, phthalazinyl, pyrazinyl, pyridazinyl, pyridyl, pyrimidyl, pyrrolyl, quinolinyl, quinoxalinyl, quinazolinyl, thiophenyl, isoxazolyl, triazolyl, thiazolyl, thiadiazolyl, etc., each of which may be unsubstituted or substituted with one or more $X^2$ groups.

$R^{14}$ is selected from the group consisting of alkyl, unsubstituted cycloalkyl, or cycloalkyl substituted with one or more $X^4$ groups. Non-limiting examples of suitable "alkyl" groups include those defined above. Non-limiting examples of suitable cycloalkyl groups include, for example, cyclopropyl, cyclobutyl, cyclopentyl, cyclohexyl, cycloheptyl, bicyclo[2.2.1]heptyl, adamantyl, etc. each of which may be unsubstituted or substituted with one or more $X^4$ groups.

Each $R^{15}$ is independently selected from the group consisting of H, alkyl, alkenyl, -alkylene-$R^{12}$, —OH, and —O-alkenyl. Non-limiting examples of suitable alkyl, alkenyl, and -alkylene-$R^{12}$ include those defined herein. Non-limiting examples of suitable —O-alkenyl groups include, for example, —O—CH=$CH_2$, —O—$CH_2$—CH=$CH_2$, —O—CH=CH—$CH_3$, —O—$CH_2$—C($CH_3$)=$CH_2$, —O—$CH_2$—CH=$CHCH_3$, etc. There are 0, 1, or 2 $R^{15}$ groups present in the compounds of Formula (I).

$R^{16}$ is selected from the group consisting of $R^9$ and —C(O)—$R^{12}$. Non-limiting examples of suitable $R^9$ and —C(O)—$R^{12}$ groups are defined as disclosed herein.

$R^{17}$ is selected from the group consisting of unsubstituted heterocycloalkyl, heterocycloalkyl substituted with one or more $X^3$ groups, -alkylene-$R^{12}$, —O—$R^9$, and $R^{12}$. Non-limiting examples of suitable heterocycloalkyl, -alkylene-$R^{12}$, —O—$R^9$, and $R^{12}$ groups are defined as disclosed herein.

Each $R^{18}$ is independently selected from the group consisting of H, $R^{12}$, and $R^{14}$ where $R^{12}$ and $R^{14}$ are as defined above.

Each $R^{19}$ is selected from the group consisting of H and $R^{21}$, wherein $R^{21}$ is defined as described herein.

Each $R^{20}$ is selected from the group consisting of H, alkyl substituted with one or more —OH or —O-alkyl groups, -alkylene-R$^{22}$, -alkylene-R$^{23}$, -alkylene-R$^{24}$, —C(O)—R$^{24}$, -alkylene-O—R$^{19}$, R$^{24}$, unsubstituted heterocycloalkyl, heterocycloalkyl substituted with one or more W$^3$ groups, and benzo-fused cycloalkyl. Non-limiting examples of suitable alkyl substituted with one or more —OH or —O-alkyl groups, -alkylene-R$^{22}$, -alkylene-R$^{23}$, -alkylene-R$^{24}$, —C(O)—R$^{24}$, -alkylene-O—R$^{19}$, R$^{24}$, unsubstituted heterocycloalkyl, heterocycloalkyl substituted with one or more W$^3$ groups, and benzo-fused cycloalkyl groups are defined as disclosed herein.

R$^{21}$ is selected from the group consisting of unsubstituted alkyl, alkyl substituted with one or more —OH groups, -alkylene-O-alkyl, -alkylene-O-aryl, unsubstituted aryl, and aryl substituted with one or more W$^1$ groups. Non-limiting examples of suitable unsubstituted alkyl, alkyl substituted with one or more —OH groups, -alkylene-O-alkyl, -alkylene-O-aryl, unsubstituted aryl, and aryl substituted with one or more W$^1$ groups are described herein.

R$^{22}$ is selected from the group consisting of unsubstituted aryl and aryl substituted with one or more W$^1$ groups. Non-limiting examples of suitable unsubstituted aryl and aryl substituted with one or more W$^1$ groups are described herein.

R$^{23}$ is selected from the group consisting of unsubstituted heteroaryl and heteroaryl substituted with one or more W$^2$ groups. Non-limiting examples of suitable unsubstituted heteroaryl and heteroaryl substituted with one or more W$^2$ groups are described herein.

R$^{24}$ is selected from the group consisting of alkyl, unsubstituted cycloalkyl, or cycloalkyl substituted with one or more W$^4$ groups. Non-limiting examples of suitable alkyl, unsubstituted cycloalkyl, or cycloalkyl substituted with one or more W$^4$ groups are described herein.

W$^1$ is independently selected from the group consisting of halogen, —CN, —OH, —O—S(O)$_2$-haloalkyl, unsubstituted aryl, aryl substituted with one or more Z groups, unsubstituted heteroaryl, heteroaryl substituted with one or more Z groups, and —O-alkyl. Non-limiting examples of suitable halogen, —CN, —OH, —O—S(O)$_2$-haloalkyl, unsubstituted aryl, aryl substituted with one or more Z groups, unsubstituted heteroaryl, heteroaryl substituted with one or more Z groups, and —O-alkyl are described herein.

W$^2$ is independently selected from the group consisting of halogen, unsubstituted aryl, and aryl substituted with one or more Z groups. Non-limiting examples of suitable halogens include F, Cl, and Br. Suitable examples of aryl groups include, for example, those described herein.

W$^3$ is —C(O)—O-alkyl. Non-limiting examples of suitable —C(O)—O-alkyl groups include those defined herein. In addition two W$^3$ groups together with the ring carbon atom to which they are attached form a carbonyl group. It is contemplated that a heterocycloalkyl group may be independently substituted with one or more —C(O)—O-alkyl groups and/or one or more carbonyl groups (i.e., one, two, three, four, or five W$^3$ groups).

W$^4$ is independently halogen or alkyl. Non-limiting examples of suitable halogens include F, Cl, and Br. Non-limiting examples of suitable alkyl groups include those described herein.

Ar$^1$ and Ar$^2$ are independently selected from the group consisting of R$^{12}$ and R$^{13}$. Non-limiting examples of suitable R$^{12}$ and R$^{13}$ groups are defined as disclosed herein.

Aryls substituted with one or more X$^1$ groups include, for example mono-substituted, di-substituted, tri-substituted, tetra-substituted aryls, etc, wherein each of the substituents are independently selected from X$^1$. Non-limiting examples include, for example, chlorophenyl, dichlorophenyl, bromophenyl, dibromophenyl, bromo-chlorophenyl, fluorophenyl, difluorophenyl, chloro-fluorophenyl, bromo-fluorophenyl, cyanophenyl, biphenyl, chlorobiphenyl, dichlorobiphenyl, etc. Similarly, heteroaryls substituted with one or more X$^2$ groups include mono-substituted, di-substituted, tri-substituted, tetra-substituted heteroaryls, etc, wherein each of the substitutents are independently selected from X$^2$. Suitable aryls and heteroaryls include any of those disclosed herein.

X$^1$ is independently selected from the group consisting of halogen, —CN, —OH, —O—S(O)$_2$-haloalkyl, unsubstituted aryl, aryl substituted with one or more Z groups, unsubstituted heteroaryl, heteroaryl substituted with one or more Z groups, —O-cycloalkyl, —O-cycloalkylalkyl, —O-alkylene-OR$^{19}$, —O-alkylene-C(O)N(R$^{20}$)$_2$, —O-alkylene-O—R$^{19}$, unsubstituted alkyl, alkyl substituted with one or more U groups, unsubstituted —O-alkyl, —O-alkyl substituted with one or more U groups, —O-alkenyl—O-alkylene-O-alkylene-OR$^{19}$, —O-alkylene-C(O)R$^{24}$, —O-alkylene-C(O)OR$^{19}$, and —O-alkyl. Non-limiting examples of suitable halogens includes, for example F, Cl, and Br. Non-limiting examples of suitable —O—S(O)$_2$-haloalkyls include —O—S(O)$_2$—CH$_2$F, —O—S(O)$_2$—CHF$_2$, —O—S(O)$_2$—CF$_3$, —O—S(O)$_2$—CH$_2$CF$_3$, —O—S(O)$_2$—CF$_2$CF$_3$, —O—S(O)$_2$—CH$_2$Cl, —O—S(O)$_2$—CH$_2$Br, etc. Non-limiting examples of suitable —O-alkyl groups include those described herein.

Non-limiting examples of suitable X$^1$ groups are independently selected from the group consisting of —OCH$_3$, —OH, —OTf, —CN, —OCH$_2$CH$_3$, —OCH(CH$_3$)$_2$,

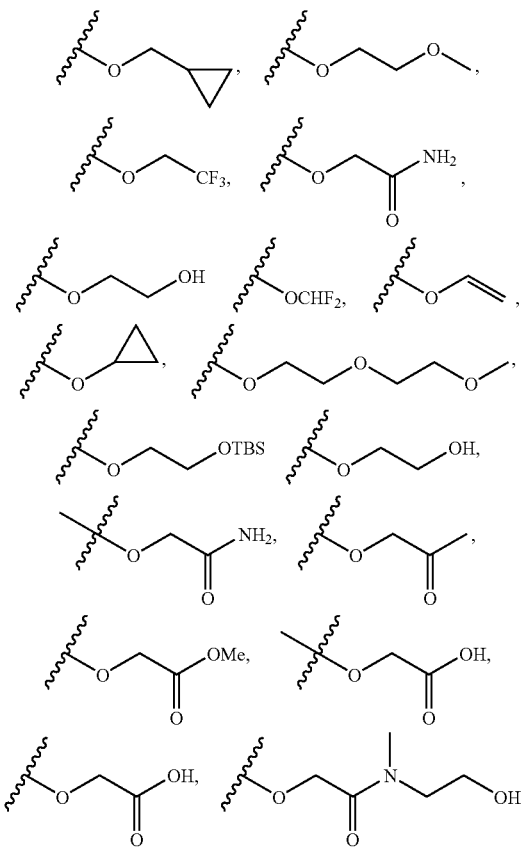

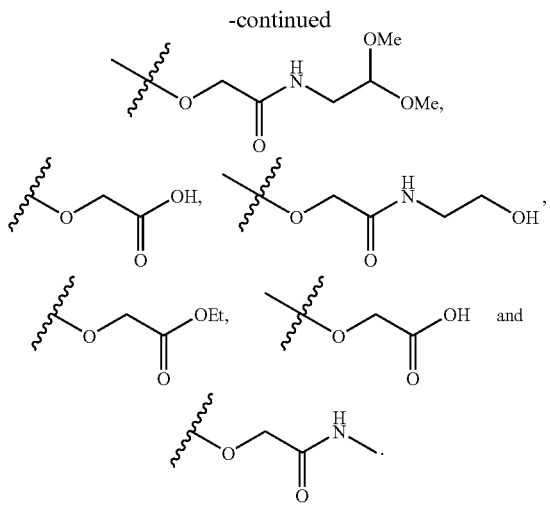

Similarly, $X^2$ is selected from the group consisting of halogen, —CN, unsubstituted aryl, and aryl substituted with one or more Z groups. Non-limiting examples of suitable halogens include F, Cl, and Br. Suitable examples of aryl groups include, for example, those described herein.

$X^3$ is —C(O)—O-alkyl. Non-limiting examples of suitable —C(O)—O-alkyl groups include those defined herein. In addition two $X^3$ groups together with the ring carbon atom to which they are attached form a carbonyl group. It is contemplated that a heterocycloalkyl group may be independently substituted with one or more —C(O)—O-alkyl groups and/or one or more carbonyl groups (i.e., one, two, three, four, or five $X^3$ groups).

$X^4$ is independently halogen or alkyl. Non-limiting examples of suitable halogens include F, Cl, and Br. Non-limiting examples of suitable alkyl groups include those described herein.

U is independently selected from the group consisting of —OH, —O-alkyl and halogen. Non-limiting examples of suitable alkyl and halogen groups include those described herein.

Z is selected from the group consisting of halogen, alkyl, and —CN. Non-limiting examples of halogen and alkyl include those defined herein.

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halogen, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Alkylene" means a divalent group obtained by removal of a hydrogen atom from an alkyl group that is defined above. Non-limiting examples of alkylene include methylene, ethylene (i.e., —CH$_2$CH$_2$— or —CH(CH$_3$)—) and propylene (e.g., including —CH$_2$CH$_2$CH$_2$— and —CH(CH$_3$)CH$_2$—).

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. The term "substituted alkenyl" means that the alkenyl group may be substituted by one or more substitutents which may be the same or different, each substitutent being independently selected from the group consisting of halogen, alkyl, aryl, cycloalkyl, cyano, alkoxy and —S(alkyl). Non-limiting examples of suitable alkenyl groups include ethenyl, propenyl, n-butenyl, 3-methylbut-2-phenyl, n-pentenyl, octenyl and decenyl.

"Alkenylene" means a divalent group obtained by removal of a hydrogen from an alkenyl group that is defined above. Non-limiting examples of alkenylene include —CH=CH—, —C(CH$_3$)=CH—, and —CH=CHCH$_2$—.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substitutents which may be the same or different, each substitutent being independently selected from the group consisting of alkyl, aryl and cycloalkyl.

"Alkynylene" means a difunctional group obtained by removal of a hydrogen from an alkynyl group that is defined above. Non-limiting examples of alkenylene include —C≡C— and —CH$_2$C≡C—.

"Aryl" means an aromatic monocyclic or multicyclic ring system comprising about 6 to about 14 carbon atoms, preferably about 6 to about 10 carbon atoms. The aryl group can be optionally substituted with one or more "ring system substitutents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substitutents" which may be the same or different, and are as defined herein. The prefix aza, oxa or thia before the heteroaryl root name means that at least a nitrogen, oxygen or sulfur atom respectively, is present as a ring atom.

A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl, indazolyl, and the like, in which there is at least one aromatic ring.

"Aralkyl", "arylalkyl", or "-alkylene-aryl" means an arylalkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. A non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substitutents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Halogen" or "halo" means fluorine, chlorine, bromine, or iodine. Preferred are fluorine, chlorine and bromine.

"Haloalkyl" means an alkyl group as defined above wherein one or more hydrogen atoms on the alkyl is replaced by a halo group defined above.

"Ring system substitutent" means a substitutent attached to an aromatic or non-aromatic ring system which, for example, replaces an available hydrogen on the ring system. Ring system substitutents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halogen, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substitutent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

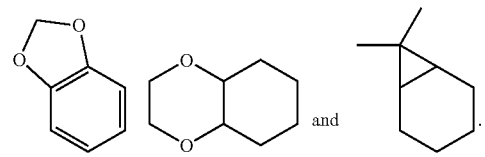

"Heterocyclyl" means a monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Heterocyclyls may be completely saturated, partially unsaturated, or aromatic. Aromatic heterocyclyls are termed "heteroaryl", as defined above. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substitutents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include saturated heterocyclyls, for example piperidyl, pyrrolidinyl, piperazinyl, morpholinyl, thiomorpholinyl, thiazolidinyl, 1,4-dioxanyl, tetrahydrofuranyl, tetrahydrothiophenyl, lactams, lactones, isoxazolyl, 1,2,4-triazolyl, 1,2,4-oxadiazolyl, 1,3,4-oxadiazolyl, 1,2,3-triazolyl and the like. Non-limiting examples of partially unsaturated monocyclic heterocyclyl rings include, for example, thiazolinyl, and the like.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

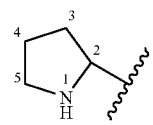

there is no —OH attached directly to carbons marked 2 and 5.

It should also be noted that the compounds of the present invention include tautomers of the compounds of Formula (I).

"Heterocycloalkyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocycloalkyls contain about 5 to about 6 ring atoms. The prefix aza, oxa or thia before the heterocycloalkyl root name means that at least a nitrogen, oxygen or sulfur atom respectively is present as a ring atom. The heterocycloalkyl can be optionally substituted by one or more "ring system substitutents" which may be the same or different, and are as defined herein. The nitrogen or sulfur atom of the heterocycloalkyl can be optionally oxidized to the corresponding N-oxide, S-oxide or S,S-dioxide. Non-limiting examples of suitable monocyclic heterocycloalkyl rings include piperidyl, pyrrolidinyl, piperazinyl, morpholinyl, 1,3-dioxolanyl, tetrahydrofuranyl, tetrahydrothiophenyl and the like.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substitutents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al., *Protective Groups in Organic Synthesis* (1991), Wiley, New York.

When any variable (e.g., aryl, heterocycle, $R^9$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula I or a salt and/or solvate thereof. A discussion of prodrugs is provided in T. Higuchi and V. Stella, *Pro-rugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the diseases or conditions noted below, and thus producing the desired therapeutic, ameliorative, inhibitory or preventative effect.

The compounds of Formula (I) can form salts which are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al., *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $(C_1-C_4)$alkyl, or $(C_1-C_4)$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $(C_1-C_{20})$ alcohol or reactive derivative thereof, or by a 2,3-di-$(C_6-C_{24})$acyl glycerol.

One or more compounds of the invention may also exist as, or optionally converted to, a solvate. Preparation of solvates is generally known. Thus, for example, M. Caira et al., *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al., *AAPS PharmSciTech.*, 5(1), article 12 (2004); and A. L. Bingham et al., *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

Compounds of Formula (I), and salts, solvates, esters and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substitutents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

Polymorphic forms of the compounds of Formula I, and of the salts, solvates, esters and prodrugs of the compounds of Formula I, are intended to be included in the present invention.

The compounds of Formula (I), or pharmaceutically acceptable salts, solvates, or esters thereof according to the invention have pharmacological properties; in particular, the compounds of Formula (I) can be selective $CB_1$ antagonists. The term "selective" means that the compounds of Formula (I) bind to the $CB_1$ receptor more strongly than to other cannabinoid receptors.

The compounds of Formula (I) of the present invention, or pharmaceutically acceptable salts, solvates, or esters thereof are useful in treating diseases or conditions including obesity, metabolic disorders, addiction, diseases of the central nervous system, cardiovascular disorders, respiratory disorders, gastrointestinal disorders, achieving weight reduction, lowering waist circumference, treating dyslipidemia, insulin sensitivity, diabetes mellitus, hypertriglyceridemia, eating disorders, alcoholism, inflammation, psychiatric disorders, migraine, nicotine dependence, Parkinson's disease, psychosis, schizophrenia, sleep disorders, attention deficit hyperactivity disorder, male sexual dysfunction, premature ejaculation, premenstrual syndrome, seizure, epilepsy and convulsion, non-insulin dependent diabetes, dementia, major depressive disorder, bulimia nervosa, drug dependence, septic shock, cognitive disorder, endocrine disorders, eczema, emesis, allergy, glaucoma, hemorrhagic shock, hypertension, angina, thrombosis, atherosclerosis, restenosis, hypertension, acute coronary syndrome, angina pectoris, arrhythmia, heart failure, cerebral ischemia, stroke, myocardial infarction, glomerulonephritis, thrombotic and thromboembolytic stroke, peripheral vascular diseases, neurodegenerative disease, osteoporosis, pulmonary disease, autoimmune disease, hypotension, arthropathy, cancer, demyelinating diseases, Alzheimer's disease, hypoactive sexual desire disorder, bipolar disorder, hyperlipidemia, hypertension, narcotic dependence, Huntington's chorea, pain, multiple sclerosis, anxiety disorder, bone disorders, Paget's disease, rheumatoid arthritis, ulcerative colitis, irritable bowel syndrome, and inflammatory bowel diseases.

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

The compounds of Formula (I), or pharmaceutically acceptable salts, solvates, or esters thereof, can be administered in any suitable form, e.g., alone, or in combination with a pharmaceutically acceptable carrier, excipient or diluent in a pharmaceutical composition, according to standard pharmaceutical practice. The compounds of Formula (I), or pharmaceutically acceptable salts, solvates, or esters thereof, can be administered orally or parenterally, including intravenous, intramuscular, interperitoneal, subcutaneous, rectal, or topical routes of administration.

Pharmaceutical compositions comprising at least one compound of Formula I, or a pharmaceutically acceptable salt, solvate, or ester thereof can be in a form suitable for oral administration, e.g., as tablets, troches, capsules, lozenges, aqueous or oily suspensions, dispersible powders or granules, emulsions, syrups, or elixirs. Oral compositions may be prepared by any conventional pharmaceutical method, and may also contain sweetening agents, flavoring agents, coloring agents, and preserving agents.

The amount of compound of Formula (I), or a pharmaceutically acceptable salt, solvate, or ester thereof, administered to a patient can be determined by a physician based on the age, weight, and response of the patient, as well as by the severity of the condition treated. For example, the amount of compound of Formula I, or a pharmaceutically acceptable salt, solvate, or ester thereof, administered to the patient can range from about 0.1 mg/kg body weight per day to about 60 mg/kg/d, preferably about 0.5 mg/kg/d to about 40 mg/kg/d.

The compounds of Formula I, or pharmaceutically acceptable salts, solvates, or esters thereof, can also be administered in combination with other therapeutic agents. For example one or more compounds of Formula (I), or pharmaceutically acceptable salts, solvates, or esters thereof, can be administered with one or more additional cholesterol lowering agents.

A non-limiting list of cholesterol lowering agents useful in the present invention include HMG CoA reductase inhibitor compounds such as lovastatin (for example MEVACOR® which is available from Merck & Co.), simvastatin (for example ZOCOR® which is available from Merck & Co.), pravastatin (for example PRAVACHOL® which is available from Bristol Meyers Squibb), atorvastatin, fluvastatin, cerivastatin, CI-981, rivastatin (sodium 7-(4-fluorophenyl)-2,6-diisopropyl-5-methoxymethylpyridin-3-yl)-3,5-dihydroxy-6-heptanoate), rosuvastatin calcium (CRESTOR®) from AstraZeneca Pharmaceuticals), pitavastatin (such as NK-104 of Negma Kowa of Japan); HMG CoA synthetase inhibitors, for example L-659,699 ((E,E)-11-[3'R-(hydroxy-methyl)-4'-oxo-2'R-oxetanyl]-3,5,7R-trimethyl-2,4-undecadienoic acid); squalene synthesis inhibitors, for example squalestatin 1; squalene epoxidase inhibitors, for example, NB-598 ((E)-N-ethyl-N-(6,6-dimethyl-2-hepten-4-ynyl)-3-[(3,3'-bithiophen-5-yl)methoxy]benzene-methanamine hydrochloride); sterol (e.g., cholesterol) biosynthesis inhibitors such as DMP-565; nicotinic acid derivatives (e.g., compounds comprising a pyridine-3-carboxylate structure or a pyrazine-2-carboxylate structure, including acid forms, salts, esters, zwitterions and tautomers) such as niceritrol, nicofuranose and acipimox (5-methylpyrazine-2-carboxylic acid 4-oxide); clofibrate; gemfibrazol; bile acid sequestrants such as cholestyramine (a styrene-divinylbenzene copolymer containing quaternary ammonium cationic groups capable of binding bile acids, such as QUESTRAN® or QUESTRAN LIGHT® cholestyramine which are available from Bristol-Myers Squibb), colestipol (a copolymer of diethylenetriamine and 1-chloro-2,3-epoxypropane, such as COLESTID® tablets which are available from Pharmacia), colesevelam hydrochloride (such as WelChol® Tablets (poly (allylamine hydrochloride) cross-linked with epichlorohydrin and alkylated with 1-bromodecane and (6-bromohexyl)-trimethylammonium bromide) which are available from Sankyo), water soluble derivatives such as 3,3-ioene, N-(cycloalkyl)alkylamines and poliglusam, insoluble quaternized polystyrenes, saponins and mixtures thereof; inorganic cholesterol sequestrants such as bismuth salicylate plus montmorillonite clay, aluminum hydroxide and calcium carbonate antacids; ileal bile acid transport ("IBAT") inhibitors (or apical sodium co-dependent bile acid transport ("ASBT") inhibitors) such as benzothiepines, for example the therapeutic compounds comprising a 2,3,4,5-tetrahydro-1-benzothiepine 1,1-dioxide structure such as are disclosed in PCT Patent Application WO 00/38727 which is incorporated herein by reference; AcylCoA:Cholesterol O-acyltransferase ("ACAT") Inhibitors such as avasimibe ([[2,4,6-tris(1-methylethyl)phenyl]acetyl]sulfamic acid, 2,6-bis(1-methylethyl) phenyl ester, formerly known as CI-1011), HL-004, lecimibide (DuP-128) and CL-277082 (N-(2,4-difluorophenyl)-N-[[4-(2,2-dimethylpropyl)phenyl]methyl]-N-heptylurea), and the compounds described in P. Chang et al., "Current, New and Future Treatments in Dyslipidaemia and Atherosclerosis", *Drugs* 2000 July; 60(1); 55-93, which is incorporated by reference herein; Cholesteryl Ester Transfer Protein ("CETP") Inhibitors such as those disclosed in PCT Patent Application No. WO 00/38721 and U.S. Pat. No. 6,147,090, which are incorporated herein by reference; probucol or derivatives thereof, such as AGI-1067 and other derivatives disclosed in U.S. Pat. Nos. 6,121,319 and 6,147,250, herein incorporated by reference; low-density lipoprotein (LDL) receptor activators such as HOE-402, an imidazolidinyl-pyrimidine derivative that directly stimulates LDL receptor activity, described in M. Huettinger et al., "Hypolipidemic activity of HOE-402 is Mediated by Stimulation of the LDL Receptor Pathway", Arterioscler. Thromb. 1993; 13:1005-12, herein incorporated by reference; fish oils containing Omega 3 fatty acids (3-PUFA); natural water soluble fibers, such as psyllium, guar, oat and pectin; plant stanols and/or fatty acid esters of plant stanols, such as sitostanol ester used in BENECOL®) margarine; nicotinic acid receptor agonists (e.g., agonists of the HM74 and HM74A receptor which receptor is described in US 2004/0142377, US 2005/0004178, US 2005/0154029, U.S. Pat. No. 6,902,902, WO 2004/071378, WO 2004/071394, WO 01/77320, US 2003/0139343, WO 01/94385, WO 2004/083388, US 2004/254224, US 2004/0254224, US 2003/0109673 and WO 98/56820) for example those described in WO 2004/033431, WO 2005/011677, WO 2005/051937, US 2005/0187280, US 2005/0187263, WO 2005/077950, WO 2005/016867, and WO 2005/016870; and the substituted azetidinone or substituted β-lactam sterol absorption inhibitors discussed in detail below.

As used herein, "sterol absorption inhibitor" means a compound capable of inhibiting the absorption of one or more sterols, including but not limited to cholesterol, phytosterols (such as sitosterol, campesterol, stigmasterol and avenosterol), 5α-stanols (such as cholestanol, 5α-campestanol, 5α-sitostanol), and/or mixtures thereof, when administered in a therapeutically effective (sterol and/or 5α-stanol absorption inhibiting) amount to a mammal or human.

Substituted Azetidinones of Formula (A)

In one embodiment, substituted azetidinones useful in the compositions, therapeutic combinations and methods of the present invention are represented by Formula (A) below:

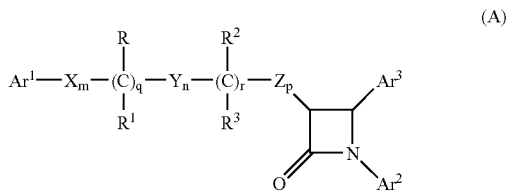

(A)

or pharmaceutically acceptable salts, solvates, or esters of the compounds of Formula (A), wherein, in Formula (A) above:

$Ar^1$ and $Ar^2$ are independently selected from the group consisting of aryl and $R^4$-substituted aryl;

$Ar^3$ is aryl or $R^5$-substituted aryl;

X, Y and Z are independently selected from the group consisting of —$CH_2$—, —CH(lower alkyl)- and —C(lower alkyl)$_2$-;

R and $R^2$ are independently selected from the group consisting of —$OR^6$, —$OC(O)R^6$, —$OC(O)OR^9$ and —$OC(O)NR^6R^7$;

$R^1$ and $R^3$ are independently selected from the group consisting of hydrogen, lower alkyl and aryl;

q is 0 or 1; r is 0 or 1; m, n and p are independently selected from 0, 1, 2, 3 or 4; provided that at least one of q and r is 1, and the sum of m, n, p, q and r is 1, 2, 3, 4, 5 or 6; and provided that when p is 0 and r is 1, the sum of m, q and n is 1, 2, 3, 4 or 5;

$R^4$ is 1-5 substituents independently selected from the group consisting of lower alkyl, —$OR^6$, —$OC(O)R^6$, —$OC(O)OR^9$, —$O(CH_2)_{1-5}OR^6$, —$OC(O)NR^6R^7$, —$NR^6R^7$, —$NR^6C(O)R^7$, —$NR^6C(O)OR^9$, —$NR^6C(O)NR^7R^8$, —$NR^6SO_2R^9$, —$C(O)OR^6$, —$C(O)NR^6R^7$, —$C(O)R^6$, —$S(O)_2NR^6R^7$, $S(O)_{0-2}R^9$, —$O(CH_2)_{1-10}$—$C(O)OR^6$, —$O(CH_2)_{1-10}CONR^6R^7$, -(lower alkylene)$COOR^6$, —CH=CH—$C(O)OR^6$, —$CF_3$, —CN, —$NO_2$ and halogen;

$R^5$ is 1-5 substituents independently selected from the group consisting of —$OR^6$, —$OC(O)R^6$, —$OC(O)OR^9$, —$O(CH_2)_{1-5}OR^6$, —$OC(O)NR^6R^7$, —$NR^6R^7$, —$NR^6C(O)R^7$, —$NR^6C(O)OR^9$, —$NR^6C(O)NR^7R^8$, —$NR^6S(O)_2R^9$, —$C(O)OR^6$, —$C(O)NR^6R^7$, —$C(O)R^6$, —$SO_2NR^6R^7$, $S(O)_{0-2}R^9$, —$O(CH_2)_{1-10}$—$C(O)OR^6$, —$O(CH_2)_{1-10}C(O)NR^6R^7$, -(lower alkylene)$C(O)OR^6$ and —CH=CH—$C(O)OR^6$;

$R^6$, $R^7$ and $R^8$ are independently selected from the group consisting of hydrogen, lower alkyl, aryl and aryl-substituted lower alkyl; and $R^9$ is lower alkyl, aryl or aryl-substituted lower alkyl.

Preferably, $R^4$ is 1-3 independently selected substitutents, and $R^5$ is preferably 1-3 independently selected substitutents.

Certain compounds useful in the therapeutic compositions or combinations of the invention may have at least one asymmetrical carbon atom and therefore all isomers, including enantiomers, diastereomers, stereoisomers, rotamers, tautomers and racemates of the compounds of Formula A-M (where they exist) are contemplated as being part of this invention. The invention includes d and l isomers in both pure form and in admixture, including racemic mixtures. Isomers can be prepared using conventional techniques, either by reacting optically pure or optically enriched starting materials or by separating isomers of a compound of the Formulae A-M. Isomers may also include geometric isomers, e.g., when a double bond is present.

Those skilled in the art will appreciate that for some of the compounds of the Formulae A-M, one isomer may show greater pharmacological activity than other isomers.

Preferred compounds of Formula (A) are those in which $Ar^1$ is phenyl or $R^4$-substituted phenyl, more preferably (4-$R^4$)-substituted phenyl. $Ar^2$ is preferably phenyl or $R^4$-substituted phenyl, more preferably (4-$R^4$)-substituted phenyl. $Ar^3$ is preferably $R^5$-substituted phenyl, more preferably (4-$R^5$)-substituted phenyl. When $Ar^1$ is (4-$R^4$)-substituted phenyl, $R^4$ is preferably a halogen. When $Ar^2$ and $Ar^3$ are $R^4$- and $R^5$-substituted phenyl, respectively, $R^4$ is preferably halogen or —$OR^6$ and $R^5$ is preferably —$OR^6$, wherein $R^6$ is lower alkyl or hydrogen. Especially preferred are compounds wherein each of $Ar^1$ and $Ar^2$ is 4-fluorophenyl and $Ar^3$ is 4-hydroxyphenyl or 4-methoxyphenyl.

X, Y and Z are each preferably —$CH_2$—. $R^1$ and $R^3$ are each preferably hydrogen. R and $R^2$ are preferably —$OR^6$ wherein $R^6$ is hydrogen, or a group readily metabolizable to a hydroxyl (such as —OC(O)$R^6$, —OC(O)O$R^9$ and —OC(O)N$R^6R^7$, defined above).

The sum of m, n, p, q and r is preferably 2, 3 or 4, more preferably 3. Preferred are compounds of Formula (A) wherein m, n and r are each zero, q is 1 and p is 2.

Also preferred are compounds of Formula (A) in which p, q and n are each zero, r is 1 and m is 2 or 3. More preferred are compounds wherein m, n and r are each zero, q is 1, p is 2, Z is —CH$_2$— and R is —O$R^6$, especially when $R^6$ is hydrogen.

Also more preferred are compounds of Formula (A) wherein p, q and n are each zero, r is 1, m is 2, X is —CH$_2$— and $R^2$ is —O$R^6$, especially when $R^6$ is hydrogen.

Another group of preferred compounds of Formula (A) is that in which Ar$^1$ is phenyl or $R^4$-substituted phenyl, Ar$^2$ is phenyl or $R^4$-substituted phenyl and Ar$^3$ is $R^5$-substituted phenyl. Also preferred are compounds in which Ar$^1$ is phenyl or $R^4$-substituted phenyl, Ar$^2$ is phenyl or $R^4$-substituted phenyl, Ar$^3$ is $R^5$-substituted phenyl, and the sum of m, n, p, q and r is 2, 3 or 4, more preferably 3. More preferred are compounds wherein Ar$^1$ is phenyl or $R^4$-substituted phenyl, Ar$^2$ is phenyl or $R^4$-substituted phenyl, Ar$^3$ is $R^5$-substituted phenyl, and wherein m, n and r are each zero, q is 1 and p is 2, or wherein p, q and n are each zero, r is 1 and m is 2 or 3.

Substituted Azetidinones of Formula (B)

In a preferred embodiment, a substituted azetidinone of Formula (A) useful in the compositions, therapeutic combinations and methods of the present invention is represented by Formula (B) (ezetimibe) below:

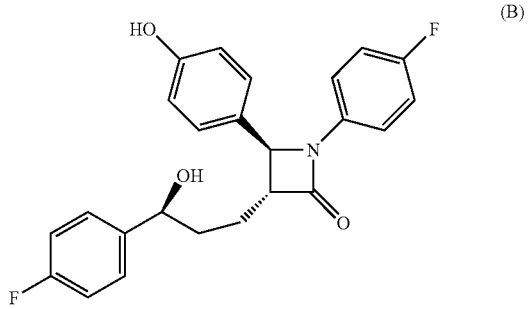

(B)

or pharmaceutically acceptable salts, solvates, or esters of the compound of Formula (B). The compound of Formula (B) can be in anhydrous or hydrated form. A product containing ezetimibe compound is commercially available as ZETIA® ezetimibe formulation from MSP Pharmaceuticals.

Compounds of Formula (A) can be prepared by a variety of methods well known to those skilled in the art, for example such as are disclosed in U.S. Pat. Nos. 5,631,365, 5,767,115, 5,846,966, 6,207,822, 6,627,757, 6,093,812, 5,306,817, 5,561,227, 5,688,785, and 5,688,787, each of which is incorporated herein by reference.

Substituted Azetidinones of Formula (C)

Alternative substituted azetidinones useful in the compositions, therapeutic combinations and methods of the present invention are represented by Formula (C) below:

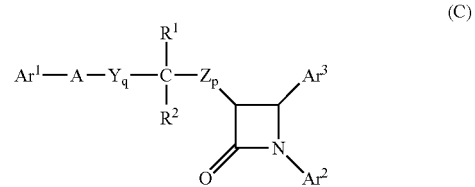

(C)

or a pharmaceutically acceptable salt thereof or a solvate thereof, or an ester thereof, wherein, in Formula (C) above:

Ar$^1$ is $R^3$-substituted aryl;
Ar$^2$ is $R^4$-substituted aryl;
Ar$^3$ is $R^5$-substituted aryl;
Y and Z are independently selected from the group consisting of —CH$_2$—, —CH(lower alkyl)- and —C(lower alkyl)$_2$-;
A is selected from —O—, —S—, —S(O)— or —S(O)$_2$—;
$R^1$ is selected from the group consisting of —O$R^6$, —OC(O)$R^6$, —OC(O)O$R^9$ and —OC(O)N$R^6R^7$;
$R^2$ is selected from the group consisting of hydrogen, lower alkyl and aryl; or $R^1$ and $R^2$ together are =O;
q is 1, 2 or 3;
p is 0, 1, 2, 3 or 4;
$R^5$ is 1-3 substitutents independently selected from the group consisting of —O$R^6$, —OC(O)$R^6$, —OC(O)O$R^9$, —O(CH$_2$)$_{1-5}$O$R^9$, —OC(O)N$R^6R^7$, —N$R^6R^7$, —N$R^6$C(O)$R^7$, —N$R^6$C(O)O$R^9$, —N$R^6$C(O)N$R^7R^8$, —N$R^6$S(O)$_2$-lower alkyl, —N$R^6$S(O)$_2$-aryl, —C(O)N$R^6R^7$, —CO$R^6$, —SO$_2$N$R^6R^7$, S(O)$_{0-2}$-alkyl, S(O)$_{0-2}$-aryl, —O(CH$_2$)$_{1-10}$—C(O)O$R^6$, —O(CH$_2$)$_{1-10}$C(O)N$R^6R^7$, o-halogeno, m-halogeno, o-lower alkyl, m-lower alkyl, -(lower alkylene)-C(O)O$R^6$, and —CH=CH—C(O)O$R^6$;
$R^3$ and $R^4$ are independently 1-3 substitutents independently selected from the group consisting of $R^5$, hydrogen, p-lower alkyl, aryl, —NO$_2$, —CF$_3$ and p-halogeno;
$R^6$, $R^7$ and $R^8$ are independently selected from the group consisting of hydrogen, lower alkyl, aryl and aryl-substituted lower alkyl; and $R^9$ is lower alkyl, aryl or aryl-substituted lower alkyl.

Methods for making compounds of Formula (C) are well known to those skilled in the art. Non-limiting examples of suitable methods are disclosed in U.S. Pat. No. 5,688,990, which is incorporated herein by reference.

Substituted Azetidinones of Formula (D)

In another embodiment, substituted azetidinones useful in the compositions, therapeutic combinations and methods of the present invention are represented by Formula (D):

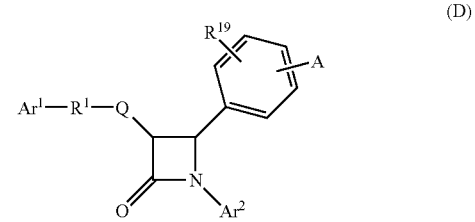

(D)

or a pharmaceutically acceptable salt thereof or a solvate thereof, or an ester thereof, wherein, in Formula (D) above:

A is selected from the group consisting of $R^2$-substituted heterocycloalkyl, $R^2$-substituted heteroaryl, $R^2$-substituted benzo-fused heterocycloalkyl, and $R^2$-substituted benzo-fused heteroaryl;

$Ar^1$ is aryl or $R^3$-substituted aryl;

$Ar^2$ is aryl or $R^4$-substituted aryl;

Q is a bond or, with the 3-position ring carbon of the azetidinone, forms the spiro group

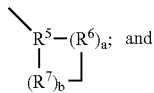 and $R^1$ is selected from the group consisting of:
$(CH_2)_q$—, wherein q is 2-6, provided that when Q forms a spiro ring, q can also be zero or 1;
—$(CH_2)_e$-G-$(CH_2)_r$—, wherein G is —O—, —C(O), phenylene, —$NR^8$— or —$S(O)_{0-2}$—, e is 0-5 and r is 0-5, provided that the sum of e and r is 1-6;
—$(C_2$-$C_6$ alkenylene)-; and
—$(CH_2)_f$—V—$(CH_2)_g$—, wherein V is $C_3$-$C_6$ cycloalkylene, f is 1-5 and g is 0-5, provided that the sum of f and g is 1-6;

$R^5$ is selected from:

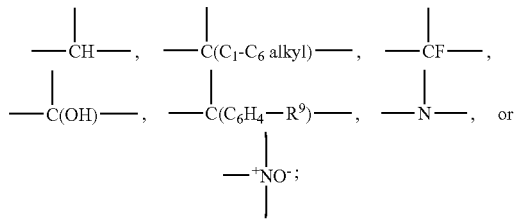

$R^6$ and $R^7$ are independently selected from the group consisting of —$CH_2$—, —$CH(C_1$-$C_6$ alkyl)-, —$C(di-(C_1$-$C_6)$ alkyl), —CH=CH— and —$C(C_1$-$C_6$ alkyl)=CH—; or $R^5$ together with an adjacent $R^6$, or $R^5$ together with an adjacent $R^7$, form a —CH=CH— or a —CH=$C(C_1$-$C_6$ alkyl)-group;

a and b are independently 0, 1, 2 or 3, provided both are not zero; provided that when $R^6$ is —CH=CH— or —$C(C_1$-$C_6$ alkyl)=CH—, a is 1; provided that when $R^7$ is —CH=CH— or —$C(C_1$-$C_6$ alkyl)=CH—, b is 1; provided that when a is 2 or 3, the $R^6$'s can be the same or different; and provided that when b is 2 or 3, the $R^7$'s can be the same or different;

and when Q is a bond, $R^1$ also can be selected from:

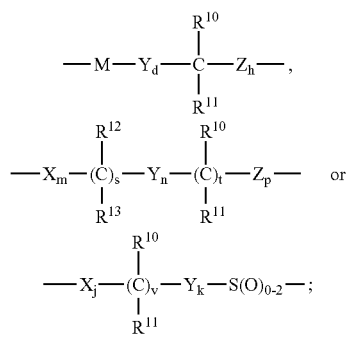

where M is —O—, —S—, —S(O)— or —$S(O)_2$—;

X, Y and Z are independently selected from the group consisting of —$CH_2$—, —$CH(C_1$-$C_6$ alkyl)- and —$C(di-(C_1$-$C_6)$alkyl);

$R^{10}$ and $R^{12}$ are independently selected from the group consisting of —$OR^{14}$, —$OC(O)R^{14}$, —$OC(O)OR^{16}$ and —$OC(O)NR^{14}R^{15}$;

$R^{11}$ and $R^{13}$ are independently selected from the group consisting of hydrogen, $(C_1$-$C_6)$alkyl and aryl; or $R^{10}$ and $R^{11}$ together are =O, or $R^{12}$ and $R^{13}$ together are =O;

d is 1, 2 or 3;

h is 0, 1, 2, 3 or 4;

s is 0 or 1; t is 0 or 1; m, n and p are independently 0-4; provided that at least one of s and t is 1, and the sum of m, n, p, s and t is 1-6; provided that when p is 0 and t is 1, the sum of m, s and n is 1-5; and provided that when p is 0 and s is 1, the sum of m, t and n is 1-5;

v is 0 or 1;

j and k are independently 1-5, provided that the sum of j, k and v is 1-5;

$R^2$ is 1-3 substitutents on the ring carbon atoms selected from the group consisting of hydrogen, $(C_1$-$C_{10})$alkyl, $(C_2$-$C_{10})$alkenyl, $(C_2$-$C_{10})$alkynyl, $(C_3$-$C_6)$cycloalkyl, $(C_3$-$C_6)$cycloalkenyl, $R^{17}$-substituted aryl, $R^{17}$-substituted benzyl, $R^{17}$-substituted benzyloxy, $R^{17}$-substituted aryloxy, halogeno, —$NR^{14}R^{15}$, $NR^{14}R^{15}(C_1$-$C_6$ alkylene)-, $NR^{14}R^{15}C(O)(C_1$-$C_6$ alkylene)-, —$NHC(O)R^{16}$, OH, $C_1$-$C_6$ alkoxy, —$OC(O)R^{16}$, —$C(O)R^{14}$, hydroxy$(C_1$-$C_6)$alkyl, $(C_1$-$C_6)$alkoxy$(C_1$-$C_6)$alkyl, $NO_2$, —$S(O)_{0-2}R^{16}$, —$S(O)_2NR^{14}R^{15}$ and —$(C_1$-$C_6$ alkylene)$C(O)OR^{14}$; when $R^2$ is a substitutent on a heterocycloalkyl ring, $R^2$ is as defined, or $R^2$ is =O or

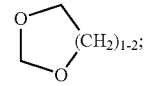

and, where $R^2$ is a substitutent on a substitutable ring nitrogen, $R^2$ is hydrogen, $(C_1$-$C_6)$alkyl, aryl, $(C_1$-$C_6)$alkoxy, aryloxy, $(C_1$-$C_6)$alkylcarbonyl, arylcarbonyl, hydroxy, —$(CH_2)_{1-6}CONR^{18}R^{18}$,

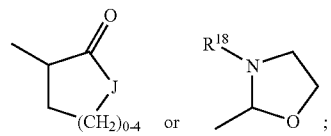

wherein J is —O—, —NH—, —$NR^{18}$— or —$CH_2$—;

$R^3$ and $R^4$ are independently selected from the group consisting of 1-3 substitutents independently selected from the group consisting of $(C_1$-$C_6)$alkyl, —$OR^{14}$, —$OC(O)R^{14}$, —$OC(O)OR^{16}$, —$O(CH_2)_{1-5}OR^{14}$, —$OC(O)NR^{14}R^{15}$, —$NR^{14}R^{14}R^{15}$, —$NR^{14}C(O)R^{15}$, —$NR^{14}C(O)OR^{16}$, —$NR^{14}C(O)NR^{15}R^{19}$, —$NR^{14}S(O)_2R^{16}$, —$C(O)OR^{14}$, —$C(O)NR^{14}R^{15}$, —$C(O)R^{14}$, —$S(O)_2NR^{14}R^{15}$, $S(O)_{0-2}R^{16}$, —$O(CH_2)_{1-10}$—$C(O)OR^{14}$, —$O(CH_2)_{1-10}C(O)NR^{14}R^{15}$, —$(C_1$-$C_6$ alkylene)-$C(O)OR^{14}$, —CH=CH—$C(O)OR^{14}$, —$CF_3$, —CN, —$NO_2$ and halogen;

$R^8$ is hydrogen, $(C_1$-$C_6)$alkyl, aryl $(C_1$-$C_6)$alkyl, —$C(O)R^{14}$ or —$C(O)OR^{14}$;

$R^9$ and $R^{17}$ are independently 1-3 groups independently selected from the group consisting of hydrogen, $(C_1-C_6)$alkyl, $(C_1-C_6)$alkoxy, —C(O)OH, $NO_2$, —$NR^{14}R^{15}$, OH and halogeno;

$R^{14}$ and $R^{15}$ are independently selected from the group consisting of hydrogen, $(C_1-C_6)$alkyl, aryl and aryl-substituted $(C_1-C_6)$alkyl;

$R^{16}$ is $(C_1-C_6)$alkyl, aryl or $R^{17}$-substituted aryl;

$R^{18}$ is hydrogen or $(C_1-C_6)$alkyl; and $R^{19}$ is hydrogen, hydroxy or $(C_1-C_6)$alkoxy.

Methods for making compounds of Formula (D) are well known to those skilled in the art. Non-limiting examples of suitable methods are disclosed in U.S. Pat. No. 5,656,624, which is incorporated herein by reference.

Substituted Azetidinones of Formula (E)

In another embodiment, substituted azetidinones useful in the compositions, therapeutic combinations and methods of the present invention are represented by Formula (E):

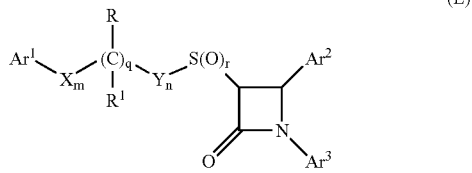

(E)

or a pharmaceutically acceptable salt thereof or a solvate thereof, or an ester thereof, wherein, in Formula (E) above:

$Ar^1$ is aryl, $R^{10}$-substituted aryl or heteroaryl;

$Ar^2$ is aryl or $R^4$-substituted aryl;

$Ar^3$ is aryl or $R^5$-substituted aryl;

X and Y are independently selected from the group consisting of —$CH_2$—, —CH(lower alkyl)- and —C(lower alkyl)$_2$-;

R is —$OR^6$, —$OC(O)R^6$, —$OC(O)OR^9$ or —OC(O)$NR^6R^7$; $R^1$ is hydrogen, lower alkyl or aryl; or R and $R^1$ together are =O;

q is 0 or 1;

r is 0, 1 or 2;

m and n are independently 0, 1, 2, 3, 4 or 5; provided that the sum of m, n and q is 1, 2, 3, 4 or 5;

$R^4$ is 1-5 substitutents independently selected from the group consisting of lower alkyl, —$OR^6$, —$OC(O)R^6$, —$OC(O)OR^9$, —$O(CH_2)_{1-5}OR^6$, —$OC(O)NR^6R^7$, —$NR^6R^7$, —$NR^6C(O)R^7$, —$NR^6C(O)OR^9$, —$NR^6C(O)NR^7R^8$, —$NR^6S(O)_2R^9$, —$C(O)OR^6$, —$C(O)NR^6R^7$, —$C(O)R^6$, —$S(O)_2NR^6R^7$, $S(O)_{0-2}R^9$, —$O(CH_2)_{1-10}C(O)OR^6$, —$O(CH_2)_{1-10}C(O)NR^6R^7$, -(lower alkylene)$C(O)OR^6$ and —CH=CH—$C(O)OR^6$;

$R^5$ is 1-5 substitutents independently selected from the group consisting of —$OR^6$, —$OC(O)R^6$, —$OC(O)OR^9$, —$O(CH_2)_{1-5}OR^6$, —$OC(O)NR^6R^7$, —$NR^6R^7$, —$NR^6C(O)R^7$, —$NR^6C(O)OR^9$, —$NR^6C(O)NR^7R^8$, —$NR^6S(O)_2R^9$, —$C(O)OR^6$, —$C(O)NR^6R^7$, —$C(O)R^6$, —$S(O)_2NR^6R^7$, $S(O)_{0-2}R^9$, —$O(CH_2)_{1-10}C(O)OR^6$, —$O(CH_2)_{1-10}C(O)NR^6R^7$, —$CF_3$, —CN, —$NO_2$, halogen, -(lower alkylene)$C(O)OR^6$ and —CH=CH—$C(O)OR^6$;

$R^6$, $R^7$ and $R^8$ are independently selected from the group consisting of hydrogen, lower alkyl, aryl and aryl-substituted lower alkyl;

$R^9$ is lower alkyl, aryl or aryl-substituted lower alkyl; and $R^{10}$ is 1-5 substitutents independently selected from the group consisting of lower alkyl, —$OR^6$, —$OC(O)R^6$, —OC(O)$OR^9$, —$O(CH_2)_{1-5}OR^6$, —$OC(O)NR^6R^7$, —$NR^6R^7$, —$NR^6C(O)R^7$, —$NR^6C(O)OR^9$, —$NR^6C(O)NR^7R^8$, —$NR^6S(O)_2R^9$, —$C(O)OR^6$, —$C(O)NR^6R^7$, —$C(O)R^6$, —$S(O)_2NR^6R^7$, —$S(O)_{0-2}R^9$, —$O(CH_2)_{1-10}C(O)OR^6$, —$O(CH_2)_{1-10}C(O)NR^6R^7$, —$CF_3$, —CN, —$NO_2$ and halogen.

Methods for making compounds of Formula (E) are well known to those skilled in the art. Non-limiting examples of suitable methods are disclosed in U.S. Pat. No. 5,624,920, which is incorporated herein by reference.

Substituted Azetidinones of Formula (F)

In another embodiment, substituted azetidinones useful in the compositions, therapeutic combinations and methods of the present invention are represented by Formula (F):

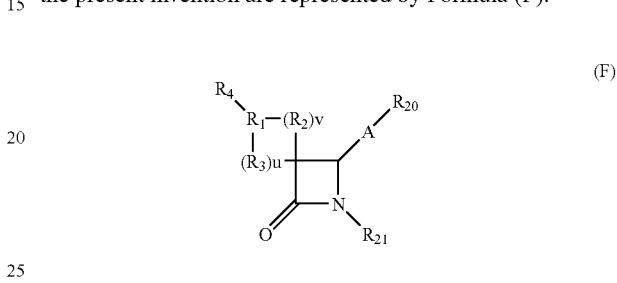

(F)

or a pharmaceutically acceptable salt thereof or a solvate thereof, or an ester thereof, wherein:

$R^1$ is:

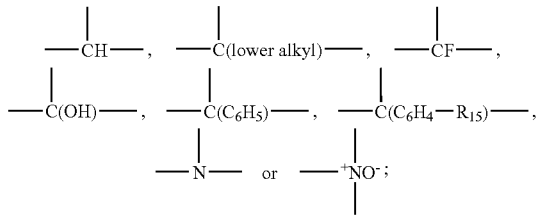

$R^2$ and $R^3$ are independently selected from the group consisting of:

—$CH_2$—, —CH(lower alkyl)-, —C(lower alkyl)$_2$-, —CH=CH— and —C(lower alkyl)=CH—; or $R^1$ together with an adjacent $R^2$, or $R^1$ together with an adjacent $R^3$, form a —CH=CH— or a —CH=C(lower alkyl)- group;

u and v are independently 0, 1, 2 or 3, provided both are not zero; provided that when $R^2$ is —CH=CH— or —C(lower alkyl)=CH—, v is 1; provided that when $R^3$ is —CH=CH— or —C(lower alkyl)=CH—, u is 1; provided that when v is 2 or 3, each $R^2$ can be the same or different; and provided that when u is 2 or 3, each $R^3$ can be the same or different;

$R^4$ is selected from B—$(CH_2)_mC(O)$—, wherein m is 0, 1, 2, 3, 4 or 5; B—$(CH_2)_q$—, wherein q is 0, 1, 2, 3, 4, 5 or 6; B—$(CH_2)_e$—Z—$(CH_2)_r$—, wherein Z is —O—, —C(O)—, phenylene, —$N(R^8)$— or —$S(O)_{0-2}$—, e is 0, 1, 2, 3, 4 or 5 and r is 0, 1, 2, 3, 4 or 5, provided that the sum of e and r is 0, 1, 2, 3, 4, 5 or 6; B—$(C_2-C_6$ alkenylene)-; B—$(C_4-C_6$ alkadienylene)-; B—$(CH_2)_t$—Z—$(C_2-C_6$ alkenylene)-, wherein Z is as defined above, and wherein t is 0, 1, 2 or 3, provided that the sum of t and the number of carbon atoms in the alkenylene chain is 2, 3, 4, 5 or 6; B—$(CH_2)_f$—V—$(CH_2)_g$—, wherein V is $C_3-C_6$ cycloalkylene, f is 1, 2, 3, 4 or 5 and g is 0, 1, 2, 3, 4 or 5, provided that the sum of f and g is 1, 2, 3, 4, 5 or 6; B—$(CH_2)_t$—V—$(C_2-C_6$ alkenylene)- or B—$(C_2-C_6$ alkenylene)-V—(CH$_2$)$_t$—, wherein V and t are as defined above, provided that the sum of t and the number of carbon atoms in the alkenylene chain is 2, 3, 4, 5 or 6; B—(CH$_2$)$_a$—Z—(CH$_2$)$_b$—V—(CH$_2$)$_d$—, wherein Z and V are as defined above and a, b and d are independently 0, 1, 2, 3, 4, 5 or 6, provided that the sum of a, b and d is 0, 1, 2, 3, 4, 5 or 6; or T-(CH$_2$)$_s$—, wherein T is a C$_3$-C$_6$ cycloalkyl and s is 0, 1, 2, 3, 4, 5 or 6; or R$^1$ and R$^4$ together form the group

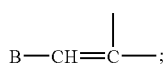

B is selected from indanyl, indenyl, naphthyl, tetrahydronaphthyl, heteroaryl or W-substituted heteroaryl, wherein heteroaryl is selected from the group consisting of pyrrolyl, pyridinyl, pyrimidinyl, pyrazinyl, triazinyl, imidazolyl, thiazolyl, pyrazolyl, thienyl, oxazolyl and furanyl, and for nitrogen-containing heteroaryls, the N-oxides thereof, or

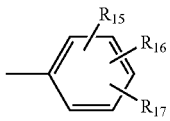

W is 1 to 3 substitutents independently selected from the group consisting of lower alkyl, hydroxy lower alkyl, lower alkoxy, alkoxyalkyl, alkoxyalkoxy, alkoxycarbonylalkoxy, (lower alkoxyimino)-lower alkyl, lower alkanedioyl, lower alkyl lower alkanedioyl, allyloxy, —CF$_3$, —OCF$_3$, benzyl, R$^7$-benzyl, benzyloxy, R$^7$-benzyloxy, phenoxy, R$^7$-phenoxy, dioxolanyl, NO$_2$, —N(R$^8$)(R$^9$), N(R$^8$)(R$^9$)-lower alkylene-, N(R$^8$)(R$^9$)-lower alkylenyloxy-, OH, halogeno, —CN, —N$_3$, —NHC(O)OR$^{10}$, —NHC(O)R$^{10}$, R$^{11}$(O)$_2$SNH—, (R$^{11}$(O)$_2$S)$_2$N—, —S(O)$_2$NH$_2$, —S(O)$_{0-2}$R$^8$, tert-butyldimethyl-silyloxymethyl, —C(O)R$^{12}$, —C(O)OR$^{19}$, —C(O)N(R$^8$)(R$^9$), —CH═CHC(O)R$^{12}$, -lower alkylene-C(O)R$^{12}$, R$^{10}$C(O)(lower alkylenyloxy)-, N(R$^8$)(R$^9$)C(O)(lower alkylenyloxy)- and

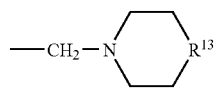

for substitution on ring carbon atoms, and the substitutents on the substituted heteroaryl ring nitrogen atoms, when present, are selected from the group consisting of lower alkyl, lower alkoxy, —C(O)OR$^{10}$, —C(O)R$^{10}$, OH, N(R$^8$)(R$^9$)-lower alkylene-, N(R$^8$)(R$^9$)-lower alkylenyloxy-, —S(O)$_2$NH$_2$ and 2-(trimethylsilyl)-ethoxymethyl;

R$^7$ is 1-3 groups independently selected from the group consisting of lower alkyl, lower alkoxy, —C(O)OH, NO$_2$, —N(R$^8$)(R$^9$), OH, and halogeno;

R$^8$ and R$^9$ are independently selected from H or lower alkyl;

R$^{10}$ is selected from lower alkyl, phenyl, R$^7$-phenyl, benzyl or R$^7$-benzyl;

R$^{11}$ is selected from OH, lower alkyl, phenyl, benzyl, R$^7$-phenyl or R$^7$-benzyl;

R$^{12}$ is selected from H, OH, alkoxy, phenoxy, benzyloxy,

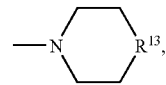

—N(R$^8$)(R$^9$), lower alkyl, phenyl or R$^7$-phenyl;

R$^{13}$ is selected from —O—, —CH$_2$, —NH—, —N(lower alkyl)- or —NC(O)R$^{19}$;

R$^{15}$, R$^{16}$ and R$^{17}$ are independently selected from the group consisting of H and the groups defined for W; or R$^{15}$ is hydrogen and R$^{15}$ and R$^{17}$, together with adjacent carbon atoms to which they are attached, form a dioxolanyl ring;

R$^{19}$ is H, lower alkyl, phenyl or phenyl lower alkyl; and

R$^{20}$ and R$^{21}$ are independently selected from the group consisting of phenyl, W-substituted phenyl, naphthyl, W-substituted naphthyl, indanyl, indenyl, tetrahydronaphthyl, benzodioxolyl, heteroaryl, W-substituted heteroaryl, benzofused heteroaryl, W-substituted benzo-fused heteroaryl and cyclopropyl, wherein heteroaryl is as defined above.

Methods for making compounds of Formula (F) are well known to those skilled in the art. Non-limiting examples of suitable methods are disclosed in U.S. Pat. No. 5,698,548, which is incorporated herein by reference.

Substituted Azetidinones of Formula (G)

In another embodiment, substituted azetidinones useful in the compositions, therapeutic combinations and methods of the present invention are represented by Formulas (GA) and (GB):

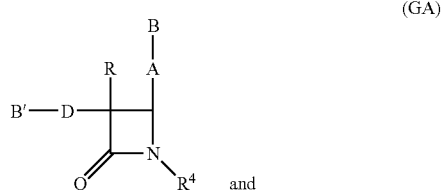

(GA)

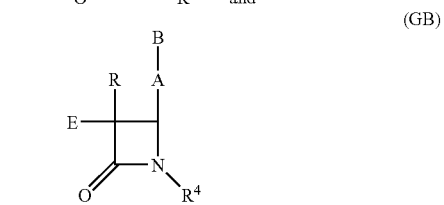

(GB)

or a pharmaceutically acceptable salt, solvate, or ester thereof, wherein:

A is —CH═CH—, —C≡C— or —(CH$_2$)$_p$— wherein p is 0, 1 or 2;

B is

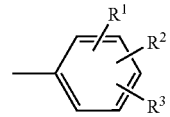

B' is

[structure: phenyl with R1', R2', R3' substituents]

D is —(CH$_2$)$_m$C(O)— or —(CH$_2$)$_q$— wherein m is 1, 2, 3 or 4 and q is 2, 3 or 4;

E is C$_{10}$ to C$_{20}$ alkyl or —C(O)—(C$_9$ to C$_{19}$)-alkyl, wherein the alkyl is straight or branched, saturated or containing one or more double bonds;

R is hydrogen, C$_1$-C$_{15}$ alkyl, straight or branched, saturated or containing one or more double bonds, or B—(CH$_2$)$_r$—, wherein r is 0, 1, 2, or 3;

R$^1$, R$^2$, R$^3$, R$^{1'}$, R$^{2'}$, and R$^{3'}$ are independently selected from the group consisting of hydrogen, lower alkyl, lower alkoxy, carboxy, NO$_2$, NH$_2$, OH, halogeno, lower alkylamino, dilower alkylamino, —NHC(O)OR$^5$, R$^6$(O)$_2$SNH— and —S(O)$_2$NH$_2$;

R$^4$ is

[structure: phenyl with (OR$^5$)$_n$]

wherein n is 0, 1, 2 or 3;

R$^5$ is lower alkyl; and

R$^6$ is OH, lower alkyl, phenyl, benzyl or substituted phenyl wherein the substitutents are 1-3 groups independently selected from the group consisting of lower alkyl, lower alkoxy, carboxy, NO$_2$, NH$_2$, OH, halogeno, lower alkylamino and dilower alkylamino; or a pharmaceutically acceptable salt, solvate, or ester thereof.

Sterol Absorption Inhibitors of Formula (H)

In another embodiment, sterol absorption inhibitors useful in the compositions and methods of the present invention are represented by Formula (H):

[structure of Formula (H): azetidinone with Ar$^1$—R$^1$—Q, R$^{26}$, O—G, Ar$^2$] (H)

or a pharmaceutically acceptable salt, solvate, or ester thereof, wherein, in Formula (H) above, R$^{26}$ is H or OG$^1$;

G and G$^1$ are independently selected from the group consisting of

[sugar/pyranose structures with OR$^5$, OR$^4$, OR$^3$, CO$_2$R$^2$, CH$_2$OR$^6$, OR$^7$, and a larger polysaccharide-type structure with R$^{4a}$O, OR$^{3a}$, R, CH$_2$R$^b$, R$^4$O, OR$^3$, CH$_2$R$^a$]

provided that when R$^{26}$ is H or
OH, G is not H;

R, R$^a$ and R$^b$ are independently selected from the group consisting of H, —OH, halogeno, —NH$_2$, azido, (C$_1$-C$_6$) alkoxy(C$_1$-C$_6$)-alkoxy or —W—R$^{30}$;

W is independently selected from the group consisting of —NH—C(O)—, —O—C(O)—, —O—C(O)—N(R$^{31}$)—, —NH—C(O)—N(R$^{31}$)— and —O—C(S)—N(R$^{31}$)—;

R$^2$ and R$^6$ are independently selected from the group consisting of H, (C$_1$-C$_6$)alkyl, aryl and aryl(C$_1$-C$_6$)alkyl;

R$^3$, R$^4$, R$^5$, R$^7$, R$^{3a}$ and R$^{4a}$ are independently selected from the group consisting of H, (C$_1$-C$_6$)alkyl, aryl(C$_1$-C$_6$)alkyl, —C(O)(C$_1$-C$_6$)alkyl and —C(O)aryl;

R$^{30}$ is selected from the group consisting of R$^{32}$-substituted T, R$^{32}$-substituted-T-(C$_1$-C$_6$)alkyl, R$^{32}$-substituted-(C$_2$-C$_4$) alkenyl, R$^{32}$-substituted-(C$_1$-C$_6$)alkyl, R$^{32}$-substituted-(C$_3$-C$_7$)cycloalkyl and R$^{32}$-substituted-(C$_3$-C$_7$)cycloalkyl(C$_1$-C$_6$)alkyl;

R$^{31}$ is selected from the group consisting of H and (C$_1$-C$_4$) alkyl;

T is selected from the group consisting of phenyl, furyl, thienyl, pyrrolyl, oxazolyl, isoxazolyl, thiazolyl, iosthiazolyl, benzothiazolyl, thiadiazolyl, pyrazolyl, imidazolyl and pyridyl;

R$^{32}$ is independently selected from 1-3 substituents independently selected from the group consisting of halogeno, (C$_1$-C$_4$)alkyl, —OH, phenoxy, —CF$_3$, —NO$_2$, (C$_1$-C$_4$) alkoxy, methylenedioxy, oxo, (C$_1$-C$_4$)alkylsulfanyl, (C$_1$-C$_4$) alkylsulfinyl, (C$_1$-C$_4$)alkylsulfonyl, —N(CH$_3$)$_2$, —C(O)—NH(C$_1$-C$_4$)alkyl, —C(O)—N((C$_1$-C$_4$)alkyl)$_2$, —C(O)—(C$_1$-C$_4$)alkyl, —C(O)—(C$_1$-C$_4$)alkoxy and pyrrolidinylcarbonyl; or R$^{32}$ is a covalent bond and R$^{31}$, the nitrogen to which it is attached and R$^{32}$ form a pyrrolidinyl, piperidinyl, N-methylpiperazinyl, indolinyl or morpholinyl group, or a (C$_1$-C$_4$) alkoxycarbonyl-substituted pyrrolidinyl, piperidinyl, N-methylpiperazinyl, indolinyl or morpholinyl group;

Ar$^1$ is aryl or R$^{10}$-substituted aryl;

Ar$^2$ is aryl or R$^{11}$-substituted aryl;

Q is a bond or, with the 3-position ring carbon of the azetidinone, forms the spiro group

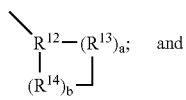 and $R^1$ is selected from the group consisting of
—$(CH_2)_q$—, wherein q is 2-6, provided that when Q forms a spiro ring, q can also be zero or 1;
—$(CH_2)_e$-E-$(CH_2)_r$, wherein E is —O—, —C(O)—, phenylene, —$NR^{22}$— or —$S(O)_{0-2}$—, e is 0-5 and r is 0-5, provided that the sum of e and r is 1-6;
—$(C_2-C_6)$alkenylene-; and
—$(CH_2)_f$—V—$(CH_2)_g$—, wherein V is $C_3-C_6$ cycloalkylene, f is 1-5 and g is 0-5, provided that the sum of f and g is 1-6;
$R^{12}$ is:

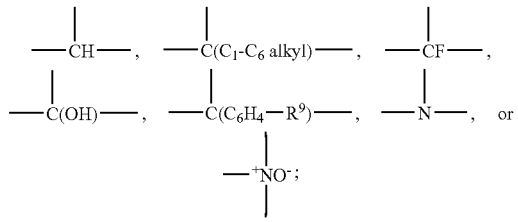

$R^{13}$ and $R^{14}$ are independently selected from the group consisting of
—$CH_2$—, —$CH((C_1-C_6)alkyl)$-, —$C((C_1-C_6)alkyl)_2$, —CH═CH— and —$C((C_1-C_6)$ alkyl)═CH—; or
$R^{12}$ together with an adjacent $R^{13}$, or $R^{12}$ together with an adjacent $R^{14}$, form a —CH═CH— or a —CH═C($C_1-C_6$ alkyl)- group;
a and b are independently 0, 1, 2 or 3, provided both are not zero;
provided that when $R^{13}$ is —CH═CH— or —C($C_1-C_6$ alkyl)═CH—, a is 1;
provided that when $R^{14}$ is —CH═CH— or —C($C_1-C_6$ alkyl)═CH—, b is 1;
provided that when a is 2 or 3, each $R^{13}$ can be the same or different; and
provided that when b is 2 or 3, each $R^{14}$ can be the same or different; and when Q is a bond, $R^1$ also can be:

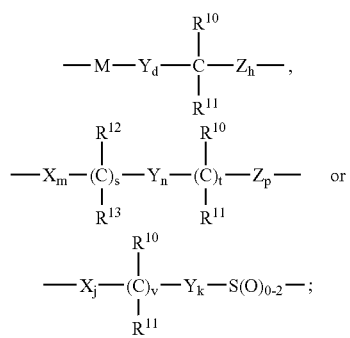

M is —O—, —S—, —S(O)— or —$S(O)_2$—;

X, Y and Z are independently selected from the group consisting of —$CH_2$—, —$CH(C_1-C_6)$alkyl- and —$C((C_1-C_6)alkyl)_2$;
$R^{10}$ and $R^{11}$ are independently selected from the group consisting of 1-3 substitutents independently selected from the group consisting of $(C_1-C_6)$alkyl, —$OR^{19}$, —$OC(O)R^{19}$, —$OC(O)OR^{21}$, —$O(CH_2)_{1-5}OR^{19}$, —$OC(O)NR^{19}R^{20}$, —$NR^{19}R^{20}$, —$NR_{19}C(O)R^{20}$, —$NR^{19}C(O)OR^{21}$, —$NR^{19}C(O)NR^{20}R^{25}$, —$NR^{19}S(O)_2R^{21}$, —$C(O)OR^{19}$, —$C(O)NR^{19}R^{20}$, —$C(O)R^{19}$, —$S(O)_2NR^{19}R^{20}$, $S(O)_{0-2}R^{21}$, —$(CH_2)_{1-10}$—$C(O)OR^{19}$, —$O(CH_2)_{1-10}C(O)NR^{19}R^{20}$, —($C_1-C_6$ alkylene)-$C(O)OR^{19}$, —CH═CH—$C(O)OR^{19}$, —$CF_3$, —CN, —$NO_2$ and halogen;
$R^{15}$ and $R^{17}$ are independently selected from the group consisting of —$OR^{19}$, —$OC(O)R^{19}$, —$OC(O)OR^{21}$ and —$OC(O)NR^{19}R^{20}$;
$R^{16}$ and $R^{18}$ are independently selected from the group consisting of H, $(C_1-C_6)$alkyl and aryl; or $R^{15}$ and $R^{16}$ together are ═O, or $R^{17}$ and $R^{18}$ together are ═O;
 d is 1, 2 or 3;
 h is 0, 1, 2, 3 or 4;
 s is 0 or 1; t is 0 or 1; m, n and p are independently 0-4;
 provided that at least one of s and t is 1, and the sum of m, n, p, s and t is 1-6;
 provided that when p is 0 and t is 1, the sum of m, s and n is 1-5; and provided that when p is 0 and s is 1, the sum of m, t and n is 1-5;
 v is 0 or 1;
 j and k are independently 1-5, provided that the sum of j, k and v is 1-5;
 and when Q is a bond and $R^1$ is

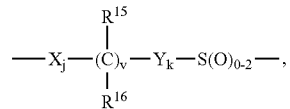

$Ar^1$ can also be pyridyl, isoxazolyl, furanyl, pyrrolyl, thienyl, imidazolyl, pyrazolyl, thiazolyl, pyrazinyl, pyrimidinyl or pyridazinyl;
$R^{19}$ and $R^{20}$ are independently selected from the group consisting of H, $(C_1-C_6)$alkyl, aryl and aryl-substituted $(C_1-C_6)$alkyl;
$R^{21}$ is $(C_1-C_6)$alkyl, aryl or $R^{24}$-substituted aryl;
$R^{22}$ is H, $(C_1-C_6)$alkyl, aryl $(C_1-C_6)$alkyl, —$C(O)R^{19}$ or —$C(O)OR^{19}$;
$R^{23}$ and $R^{24}$ are independently 1-3 groups independently selected from the group consisting of H, $(C_1-C_6)$alkyl, $(C_1-C_6)$alkoxy, —C(O)OH, $NO_2$, —$NR^{19}R^{20}$, —OH and halogeno; and
$R^{25}$ is H, —OH or $(C_1-C_6)$alkoxy.

Methods for making compounds of Formula (H) are well known to those skilled in the art. Non-limiting examples of suitable methods are disclosed in U.S. Pat. No. 5,756,470, which is incorporated herein by reference.

Substituted Azetidinones of Formula (J)

In another embodiment, substituted azetidinones useful in the compositions and methods of the present invention are represented by Formula (J) below:

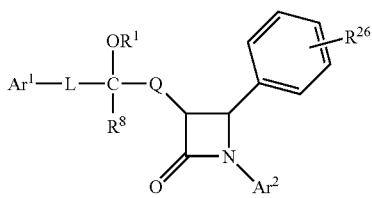

(J)

or a pharmaceutically acceptable salt, solvate, or ester thereof, wherein in Formula (J):

$R^1$ is selected from the group consisting of H, G, $G^1$, $G^2$, —$SO_3H$ and —$PO_3H$;

G is selected from the group consisting of: H,

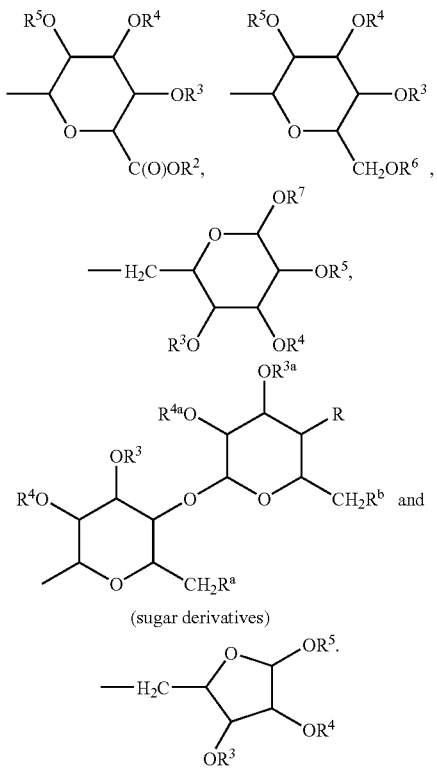

(sugar derivatives)

wherein R, $R^a$ and $R^b$ are each independently selected from the group consisting of H, —OH, halogen, —$NH_2$, azido, $(C_1-C_6)$alkoxy$(C_1-C_6)$alkoxy or —W—$R^{30}$;

W is independently selected from the group consisting of —NH—C(O)—, —O—C(O)—, —O—C(O)—N($R^{31}$)—, —NH—C(O)—N($R^{31}$)— and —O—C(S)—N($R^{31}$)—;

$R^2$ and $R^6$ are each independently selected from the group consisting of H, $(C_1-C_6)$alkyl, acetyl, aryl and aryl$(C_1-C_6)$alkyl;

$R^3$, $R^4$, $R^5$, $R^7$, $R^{3a}$ and $R^{4a}$ are each independently selected from the group consisting of H, $(C_1-C_6)$alkyl, acetyl, aryl$(C_1-C_6)$alkyl, —C(O)$(C_1-C_6)$alkyl and —C(O)aryl;

$R^{30}$ is independently selected from the group consisting of $R^{32}$-substituted T, $R^{32}$-substituted-T-$(C_1-C_6)$alkyl, $R^{32}$-substituted-$(C_2-C_4)$alkenyl, $R^{32}$-substituted-$(C_1-C_6)$alkyl, $R^{32}$-substituted-$(C_3-C_7)$cycloalkyl and $R^{32}$-substituted-$(C_3-C_7)$cycloalkyl$(C_1-C_6)$alkyl;

$R^{31}$ is independently selected from the group consisting of H and $(C_1-C_4)$alkyl;

T is independently selected from the group consisting of phenyl, furyl, thienyl, pyrrolyl, oxazolyl, isoxazolyl, thiazolyl, isothiazolyl, benzothiazolyl, thiadiazolyl, pyrazolyl, imidazolyl and pyridyl;

$R^{32}$ is independently selected from 1-3 substitutents which are each independently selected from the group consisting of H, halogen, $(C_1-C_4)$alkyl, —OH, phenoxy, —$CF_3$, —$NO_2$, $(C_1-C_4)$alkoxy, methylenedioxy, oxo, $(C_1-C_4)$alkylsulfanyl, $(C_1-C_4)$alkylsulfinyl, $(C_1-C_4)$alkylsulfonyl, —$N(CH_3)_2$, —C(O)—NH$(C_1-C_4)$alkyl, —C(O)—N$(C_1-C_4)$alkyl$)_2$, —C(O)—$(C_1-C_4)$alkyl, —C(O)—$(C_1-C_4)$alkoxy and pyrrolidinylcarbonyl; or $R^{32}$ is a covalent bond and $R^{31}$, the nitrogen to which it is attached and $R^{32}$ form a pyrrolidinyl, piperidinyl, N-methylpiperazinyl, indolinyl or morpholinyl group, or a $(C_1-C_4)$ alkoxycarbonyl-substituted pyrrolidinyl, piperidinyl, N-methylpiperazinyl, indolinyl or morpholinyl group;

$G^1$ is represented by the structure:

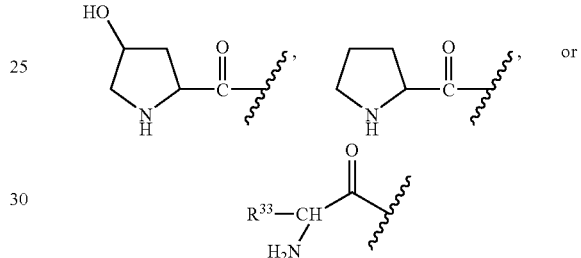

wherein $R^{33}$ is independently selected from the group consisting of unsubstituted alkyl, $R^{34}$-substituted alkyl, $(R^{35})(R^{36})$alkyl-,

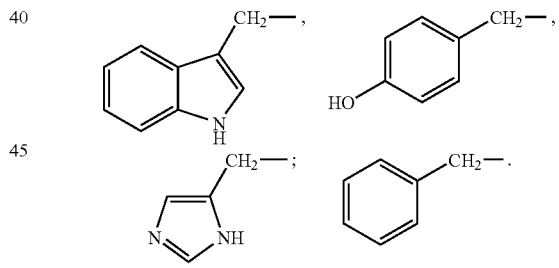

$R^{34}$ is one to three substitutents, each $R^{34}$ being independently selected from the group consisting of HO(O)C—, HO—, HS—, $(CH_3)S$—, $H_2N$—, $(NH_2)(NH)C(NH)$—, $(NH_2)C(O)$— and HO(O)CCH($NH_3^+$)$CH_2SS$—;

$R^{35}$ is independently selected from the group consisting of H and $NH_2$—;

$R^{36}$ is independently selected from the group consisting of H, unsubstituted alkyl, $R^{34}$-substituted alkyl, unsubstituted cycloalkyl and $R^{34}$-substituted cycloalkyl;

$G^2$ is represented by the structure:

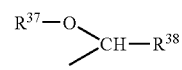

wherein $R^{37}$ and $R^{38}$ are each independently selected from the group consisting of $(C_1-C_6)$alkyl and aryl;

$R^{26}$ is one to five substituents, each $R^{26}$ being independently selected from the group consisting of:
a) H;
b) —OH;
c) —OCH$_3$;
d) fluorine;
e) chlorine;
f) —O-G;
g) —O-G$^1$;
h) —O-G$^2$;
i) —SO$_3$H; and
j) —PO$_3$H;

provided that when $R^1$ is H, $R^{26}$ is not H, —OH, —OCH$_3$ or —O-G;

Ar$^1$ is aryl, $R^{10}$-substituted aryl, heteroaryl or $R^{10}$-substituted heteroaryl;

Ar$^2$ is aryl, $R^{11}$-substituted aryl, heteroaryl or $R^{11}$-substituted heteroaryl;

L is selected from the group consisting of:
a) a covalent bond;
b) $(CH_2)_q$—, wherein q is 1-6;
c) —$(CH_2)_e$-E-$(CH_2)_r$—, wherein E is —O—, —C(O)—, phenylene, —NR$^{22}$— or —S(O)$_{0-2}$—, e is 0-5 and r is 0-5, provided that the sum of e and r is 1-6;
d) —$(C_2-C_6)$alkenylene-;
e) —$(CH_2)_f$—V—$(CH_2)_g$—, wherein V is $C_3-C_6$cycloalkylene, f is 1-5 and g is 0-5, provided that the sum of f and g is 1-6; and
f)

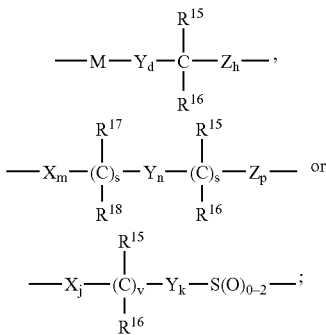

wherein M is —O—, —S—, —S(O)— or —S(O)$_2$—;
X, Y and Z are each independently selected from the group consisting of —CH$_2$—, —CH($C_1-C_6$)alkyl- and —C(($C_1-C_6$)alkyl)$_2$-;
$R^8$ is selected from the group consisting of H and alkyl;
$R^{10}$ and $R^{11}$ are each independently selected from the group consisting of 1-3 substituents which are each independently selected from the group consisting of ($C_1-C_6$)alkyl, —OR$^{19}$, —OC(O)R$^{19}$, —OC(O)OR$^{21}$, —O(CH$_2$)$_{1-5}$OR$^{19}$, —OC(O)NR$^{19}$R$^{20}$, —NR$^{19}$R$^{20}$, —NR$^{19}$C(O)R$^{20}$, —NR$^{19}$C(O)OR$^{21}$, —NR$^{19}$C(O)NR$^{20}$R$^{25}$, —NR$^{19}$S(O)$_2$R$^{21}$, —C(O)OR$^{19}$, —C(O)NR$^{19}$R$^{20}$, —C(O)R$^{19}$, —S(O)$_2$NR$^{19}$R$^{20}$, S(O)$_{0-2}$R$^{21}$, —O(CH$_2$)$_{1-10}$—C(O)OR$^{19}$, —O(CH$_2$)$_{1-10}$—C(O)NR$^{19}$R$^{20}$, —($C_1-C_6$ alkylene)-C(O)OR$^{19}$, —CH=CH—C(O)OR$^{19}$, —CF$_3$, —CN, —NO$_2$ and halogen;

$R^{15}$ and $R^{17}$ are each independently selected from the group consisting of —OR$^{19}$, —OC(O)R$^{19}$, —OC(O)OR$^{21}$, —OC(O)NR$^{19}$R$^{20}$;

$R^{16}$ and $R^{18}$ are each independently selected from the group consisting of H, ($C_1-C_6$)alkyl and aryl; or
$R^{15}$ and $R^{16}$ together are =O, or $R^{17}$ and $R^{18}$ together are =O;

d is 1, 2 or 3;
h is 0, 1, 2, 3 or 4;
s is 0 or 1;
t is 0 or 1;
m, n and p are each independently selected from 0-4;
provided that at least one of s and t is 1, and the sum of m, n, p, s and t is 1-6; provided that when p is 0 and t is 1, the sum of m, n and p is 1-5; and provided that when p is 0 and s is 1, the sum of m, t and n is 1-5;
v is 0 or 1;
j and k are each independently 1-5, provided that the sum of j, k and v is 1-5;
Q is a bond, —$(CH_2)_q$—, wherein q is 1-6, or, with the 3-position ring carbon of the azetidinone, forms the spiro group

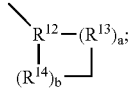

wherein $R^{12}$ is

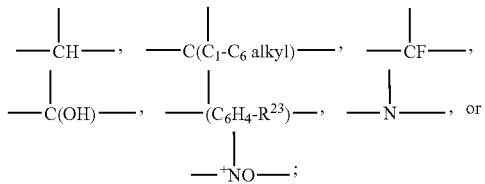

$R^{13}$ and $R^{14}$ are each independently selected from the group consisting of —CH$_2$—, —CH($C_1-C_6$ alkyl)-, —C(($C_1-C_6$)alkyl)$_2$, —CH=CH— and —C($C_1-C_6$ alkyl)=CH—; or $R^{12}$ together with an adjacent $R^{13}$, or $R^{12}$ together with an adjacent $R^{14}$, form a —CH=CH— or a —CH=C($C_1-C_6$ alkyl)- group;

a and b are each independently 0, 1, 2 or 3, provided both are not zero; provided that when $R^{13}$ is —CH=CH— or —C($C_1-C_6$ alkyl)=CH—, a is 1; provided that when $R^{14}$ is —CH=CH— or —C($C_1-C_6$ alkyl)=CH—, b is 1; provided that when a is 2 or 3, each $R^{13}$ can be the same or different; and provided that when b is 2 or 3, each $R^{14}$ can be the same or different;

and when Q is a bond and L is

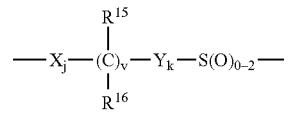

then Ar$^1$ can also be pyridyl, isoxazolyl, furanyl, pyrrolyl, thienyl, imidazolyl, pyrazolyl, thiazolyl, pyrazinyl, pyrimidinyl or pyridazinyl;

$R^{19}$ and $R^{20}$ are each independently selected from the group consisting of H, ($C_1-C_6$)alkyl, aryl and aryl-substituted ($C_1-C_6$)alkyl;

$R^{21}$ is ($C_1-C_6$)alkyl, aryl or $R^{24}$-substituted aryl;

$R^{22}$ is H, $(C_1-C_6)$alkyl, aryl $(C_1-C_6)$alkyl, —C(O)$R^{19}$ or —C(O)O$R^{19}$;

$R^{23}$ and $R^{24}$ are each independently selected from the group consisting of 1-3 substituents which are each independently selected from the group consisting of H, $(C_1-C_6)$alkyl, $(C_1-C_6)$alkoxy, —C(O)OH, $NO_2$, —$NR^{19}R^{20}$, —OH and halogen; and $R^{25}$ is H, —OH or $(C_1-C_6)$alkoxy.

Examples of compounds of Formula (J) which are useful in the methods and combinations of the present invention and methods for making such compounds are disclosed in U.S. patent application Ser. No. 10/166,942, filed Jun. 11, 2002, incorporated herein by reference.

Substituted Azetidinones of Formulae (K)-(M)

An example of a useful substituted azetidinone is one represented by the Formula (K):

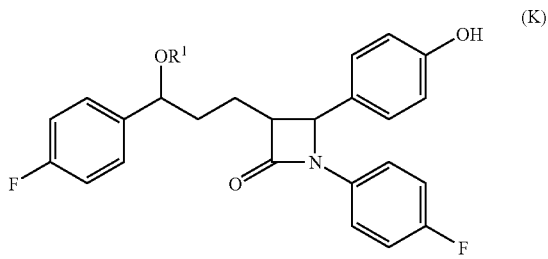

(K)

wherein $R^{11}$ is defined as above.

A more preferred compound is one represented by Formula (L):

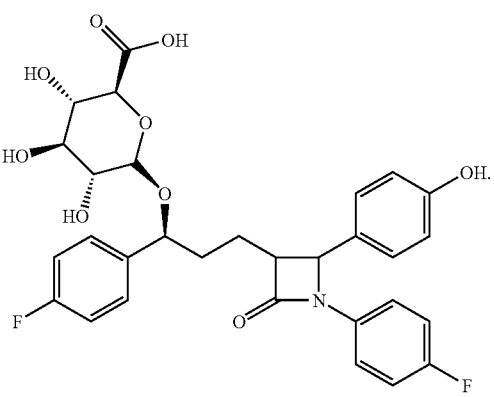

(L)

Another useful compound is represented by Formula (M):

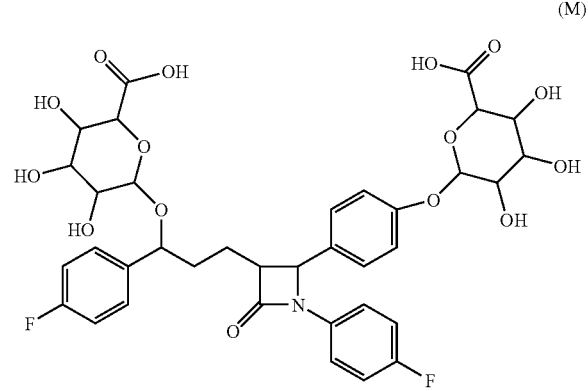

(M)

Other useful substituted azetidinone compounds include N-sulfonyl-2-azetidinones such as are disclosed in U.S. Pat. No. 4,983,597, ethyl 4-(2-oxoazetidin-4-yl)phenoxy-alkanoates such as are disclosed in Ram et al., Indian J. Chem. Sect. B. 29B, 12 (1990), p. 1134-7, diphenyl azetidinones and derivatives disclosed in U.S. Patent Publication Nos. 2002/0039774, 2002/0128252, 2002/0128253 and 2002/0137689, 2004/063929, WO 2002/066464, U.S. Pat. Nos. 6,498,156 and 6,703,386, each of which is incorporated by reference herein.

Other sterol absorption inhibitors useful in the compositions, therapeutic combinations and methods of the present invention are described in WO 2004/005247, WO 2004/000803, WO 2004/000804, WO 2004/000805, WO 0250027, U.S. published application 2002/0137689, and the compounds described in L. Kvaernø et al., Angew. Chem. Int. Ed., 2004, vol. 43, pp. 4653-4656, all of which are incorporated herein by reference. An illustrative compound of Kvaernø et al. is:

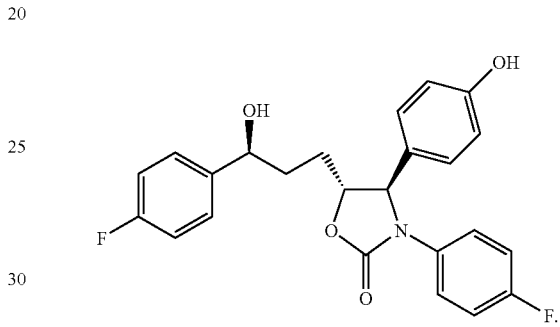

The compounds of Formulae A-M can be prepared by known methods, including the methods discussed above and, for example, in WO 93/02048, U.S. Pat. Nos. 5,306,817 and 5,561,227, herein incorporated by reference, which describe the preparation of compounds wherein —$R^1$-Q- is alkylene, alkenylene or alkylene interrupted by a hetero atom, phenylene or cycloalkylene; WO 94/17038 and U.S. Pat. No. 5,698,548, herein incorporated by reference, describe the preparation of compounds wherein a is a spirocyclic group; WO 95/08532, U.S. Pat. Nos. 5,631,365, 5,767,115, 5,846,966, and U.S. R.E. 37,721, herein incorporated by reference, describe the preparation of compounds wherein —$R^1$-Q- is a hydroxy-substituted alkylene group; PCT/US95/03196, herein incorporated by reference, describes compounds wherein —$R^1$-Q- is a hydroxy-substituted alkylene attached to the $Ar^1$ moiety through an —O— or $S(O)_{0-2}$— group; and U.S. Ser. No. 08/463,619, filed Jun. 5, 1995, herein incorporated by reference, describes the preparation of compounds wherein —$R^1$-Q- is a hydroxy-substituted alkylene group attached to the azetidinone ring by a —$S(O)_{0-2}$— group. Each of the above patents or publications are herein incorporated by reference in their entirety.

The daily dose of the sterol absorption inhibitor(s) administered to the subject can range from about 0.1 to about 1000 mg per day, preferably about 0.25 to about 50 mg/day, and more preferably about 10 mg per day, given in a single dose or 24 divided doses. The exact dose, however, is determined by the attending clinician and is dependent on the potency of the compound administered, the age, weight, condition and response of the patient.

For administration of pharmaceutically acceptable salts of the above compounds, the weights indicated above refer to the weight of the acid equivalent or the base equivalent of the therapeutic compound derived from the salt.

In another embodiment of the present invention, the compositions or therapeutic combinations described above comprise one or more selective $CB_1$ receptor antagonist compounds of Formula (I) in combination with one or more cholesterol biosynthesis inhibitors and/or lipid-lowering compounds discussed below.

Generally, a total daily dosage of cholesterol biosynthesis inhibitor(s) can range from about 0.1 to about 160 mg per day, and preferably about 0.2 to about 80 mg/day in single or 2-3 divided doses.

In another alternative embodiment, the compositions, therapeutic combinations or methods of the present invention can comprise at least one compound of Formula (I), or pharmaceutically acceptable salts, solvates, or esters thereof, and one or more bile acid sequestrants (insoluble anion exchange resins), co-administered with or in combination with the compound of Formula (I), or a pharmaceutically acceptable salt, solvate, or ester thereof, and a substituted azetidinone or a substituted β-lactam discussed above.

Bile acid sequestrants bind bile acids in the intestine, interrupting the enterohepatic circulation of bile acids and causing an increase in the faecal excretion of steroids. Use of bile acid sequestrants is desirable because of their non-systemic mode of action. Bile acid sequestrants can lower intrahepatic cholesterol and promote the synthesis of apo B/E (LDL) receptors that bind LDL from plasma to further reduce cholesterol levels in the blood.

Generally, a total daily dosage of bile acid sequestrant(s) can range from about 1 to about 50 grams per day, and preferably about 2 to about 16 grams per day in single or 2-4 divided doses.

In an alternative embodiment, the compositions or treatments of the present invention can comprise at least one compound of Formula (I), or pharmaceutically acceptable salts, solvates, or esters thereof, and one or more IBAT inhibitors. The IBAT inhibitors can inhibit bile acid transport to reduce LDL cholesterol levels. Generally, a total daily dosage of IBAT inhibitor(s) can range from about 0.01 to about 1000 mg/day, and preferably about 0.1 to about 50 mg/day in single or 2-4 divided doses.

In another alternative embodiment, the compositions or treatments of the present invention can comprise at least one compound of Formula (I), or pharmaceutically acceptable salts, solvates, or esters thereof, and nicotinic acid (niacin) and/or derivatives thereof. Nicotinic acid and its derivatives inhibit hepatic production of VLDL and its metabolite LDL and increases HDL and apo A-1 levels. An example of a suitable nicotinic acid product is NIASPAN® (niacin extended-release tablets) which are available from Kos.

Generally, a total daily dosage of nicotinic acid or a derivative thereof can range from about 500 to about 10,000 mg/day, preferably about 1000 to about 8000 mg/day, and more preferably about 3000 to about 6000 mg/day in single or divided doses.

In another alternative embodiment, the compositions or treatments of the present invention can comprise at least one compound of Formula (I), or pharmaceutically acceptable salts, solvates, or estes thereof, and one or more AcylCoA: Cholesterol O-acyltransferase ("ACAT") Inhibitors, which can reduce LDL and VLDL levels. ACAT is an enzyme responsible for esterifying excess intracellular cholesterol and may reduce the synthesis of VLDL, which is a product of cholesterol esterification, and overproduction of apo B-100-containing lipoproteins. Generally, a total daily dosage of ACAT inhibitor(s) can range from about 0.1 to about 1000 mg/day in single or 2-4 divided doses.

In another alternative embodiment, the compositions or treatments of the present invention can comprise at least one compound of Formula (I), or pharmaceutically acceptable salts, solvates, or esters thereof, and one or more Cholesteryl Ester Transfer Protein ("CETP") Inhibitors. CETP is responsible for the exchange or transfer of cholesteryl ester carrying HDL and triglycerides in VLDL. Pancreatic cholesteryl ester hydrolase (pCEH) inhibitors such as WAY-121898 also can be co-administered with or in combination.

Generally, a total daily dosage of CETP inhibitor(s) can range from about 0.01 to about 1000 mg/day, and preferably about 0.5 to about 20 mg/kg body weight/day in single or divided doses.

In another alternative embodiment, the compositions or treatments of the present invention can comprise at least one compound of Formula (I), or pharmaceutically acceptable salts, solvates, or esters thereof, and probucol or derivatives thereof, which can reduce LDL levels.

Generally, a total daily dosage of probucol or derivatives thereof can range from about 10 to about 2000 mg/day, and preferably about 500 to about 1500 mg/day in single or 2-4 divided doses.

In another alternative embodiment, the compositions or treatments of the present invention can comprise at least one compound of Formula (I), or pharmaceutically acceptable salts, solvates, or esters thereof, and low-density lipoprotein (LDL) receptor activators.

Generally, a total daily dosage of LDL receptor activator(s) can range from about 1 to about 1000 mg/day in single or 2-4 divided doses.

In another alternative embodiment, the compositions or treatments of the present invention can comprise at least one compound of Formula (I), or pharmaceutically acceptable salts, solvates, or esters thereof, and fish oil. Generally, a total daily dosage of fish oil or Omega 3 fatty acids can range from about 1 to about 30 grams per day in single or 2-4 divided doses.

In another alternative embodiment, the compositions or treatments of the present invention can further comprise at least one compound of Formula (I), or pharmaceutically acceptable salts, solvates, or esters thereof, and natural water soluble fibers, such as psyllium, guar, oat and pectin, which can reduce cholesterol levels. Generally, a total daily dosage of natural water soluble fibers can range from about 0.1 to about 10 grams per day in single or 2-4 divided doses.

In another alternative embodiment, the compositions or treatments of the present invention can comprise at least one compound of Formula (I), or pharmaceutically acceptable salts, solvates, or esters thereof, and plant sterols, plant stanols and/or fatty acid esters of plant stanols, such as sitostanol ester used in BENECOL® margarine, which can reduce cholesterol levels. Generally, a total daily dosage of plant sterols, plant stanols and/or fatty acid esters of plant stanols can range from about 0.5 to about 20 grams per day in single or 2-4 divided doses.

In another alternative embodiment, the compositions or treatments of the present invention can comprise at least one compound of Formula (I), or pharmaceutically acceptable salts, solvates, or esters thereof, and antioxidants, such as probucol, tocopherol, ascorbic acid, β-carotene and selenium, or vitamins such as vitamin $B_6$ or vitamin $B_{12}$. Generally, a total daily dosage of antioxidants or vitamins can range from about 0.05 to about 10 grams per day in single or 2-4 divided doses.

In another alternative embodiment, the compositions or treatments of the present invention can comprise at least one compound of Formula (I), or pharmaceutically acceptable salts, solvates, or esters thereof, and monocyte and macrophage inhibitors such as polyunsaturated fatty acids (PUFA), thyroid hormones including throxine analogues such as CGS-26214 (a thyroxine compound with a fluorinated ring), gene therapy and use of recombinant proteins such as recombinant apo E. Generally, a total daily dosage of these agents can range from about 0.01 to about 1000 mg/day in single or 2-4 divided doses.

Also useful with the present invention are compositions or therapeutic combinations that further comprise hormone replacement agents and compositions. Useful hormone agents and compositions for hormone replacement therapy of the present invention include androgens, estrogens, progestins, their pharmaceutically acceptable salts and derivatives thereof. Combinations of these agents and compositions are also useful.

The dosage of androgen and estrogen combinations vary, desirably from about 1 mg to about 4 mg androgen and from about 1 mg to about 3 mg estrogen. Examples include, but are not limited to, androgen and estrogen combinations such as the combination of esterified estrogens (sodium estrone sulfate and sodium equilin sulfate) and methyltestosterone (17-hydroxy-17-methyl-, (17B)-androst-4-en-3-one) available from Solvay Pharmaceuticals, Inc., Marietta, Ga., under the tradename Estratest.

Estrogens and estrogen combinations may vary in dosage from about 0.01 mg up to 8 mg, desirably from about 0.3 mg to about 3.0 mg. Examples of useful estrogens and estrogen combinations include:

(a) the blend of nine (9) synthetic estrogenic substances including sodium estrone sulfate, sodium equilin sulfate, sodium 17α-dihydroequilin sulfate, sodium 17α-estradiol sulfate, sodium 17β-dihydroequilin sulfate, sodium 17α-dihydroequilenin sulfate, sodium 17β-dihydroequilenin sulfate, sodium equilenin sulfate and sodium 17β-estradiol sulfate; available from Duramed Pharmaceuticals, Inc., Cincinnati, Ohio, under the tradename Cenestin;

(b) ethinyl estradiol (19-nor-17α-pregna-1,3,5(10)-trien-20-yne-3,17-diol; available by Schering Plough Corporation, Kenilworth, N.J., under the tradename Estinyl;

(c) esterified estrogen combinations such as sodium estrone sulfate and sodium equilin sulfate; available from Solvay under the tradename Estratab and from Monarch Pharmaceuticals, Bristol, Tenn., under the tradename Menest;

(d) estropipate (piperazine estra-1,3,5(10)-trien-17-one, 3-(sulfooxy)-estrone sulfate); available from Pharmacia & Upjohn, Peapack, N.J., under the tradename Ogen and from Women First Health Care, Inc., San Diego, Calif., under the tradename Ortho-Est; and (e) conjugated estrogens (17α-dihydroequilin, 17α-estradiol, and 17β-dihydroequilin); available from Wyeth-Ayerst Pharmaceuticals, Philadelphia, Pa., under the tradename Premarin.

Progestins and estrogens may also be administered with a variety of dosages, generally from about 0.05 to about 2.0 mg progestin and about 0.001 mg to about 2 mg estrogen, desirably from about 0.1 mg to about 1 mg progestin and about 0.01 mg to about 0.5 mg estrogen. Examples of progestin and estrogen combinations that may vary in dosage and regimen include:

(a) the combination of estradiol (estra-1,3,5(10)-triene-3, 17β-diol hemihydrate) and norethindrone (17β-acetoxy-19-nor-17α-pregn-4-en-20-yn-3-one); which is available from Pharmacia & Upjohn, Peapack, N.J., under the tradename Activella;

(b) the combination of levonorgestrel (d(-)-13β-ethyl-17α-ethinyl-17β-hydroxygon-4-en-3-one) and ethinyl estradial; available from Wyeth-Ayerst under the tradename Alesse, from Watson Laboratories, Inc., Corona, Calif., under the tradenames Levora and Trivora, Monarch Pharmaceuticals, under the tradename Nordette, and from Wyeth-Ayerst under the tradename Triphasil;

(c) the combination of ethynodiol diacetate (19-nor-17α-pregn-4-en-20-yne-3β,17-diol diacetate) and ethinyl estradiol; available from G.D. Searle & Co., Chicago, Ill., under the tradename Demulen and from Watson under the tradename Zovia;

(d) the combination of desogestrel (13-ethyl-11-methylene-18,19-dinor-17α-pregn-4-en-20-yn-17-ol) and ethinyl estradiol; available from Organon under the tradenames Desogen and Mircette, and from Ortho-McNeil Pharmaceutical, Raritan, N.J., under the tradename Ortho-Cept;

(e) the combination of norethindrone and ethinyl estradiol; available from Parke-Davis, Morris Plains, N.J., under the tradenames Estrostep and FemHRT, from Watson under the tradenames Microgestin, Necon, and Tri-Norinyl, from Ortho-McNeil under the tradenames Modicon and Ortho-Novum, and from Wamer Chilcott Laboratories, Rockaway, N.J., under the tradename Ovcon;

(f) the combination of norgestrel ((±)-13-ethyl-17-hydroxy-18,19-dinor-17α-preg-4-en-20-yn-3-one) and ethinyl estradiol; available from Wyeth-Ayerst under the tradenames Ovral and Lo/Ovral, and from Watson under the tradenames Ogestrel and Low-Ogestrel;

(g) the combination of norethindrone, ethinyl estradiol, and mestranol (3-methoxy-19-nor-17α-pregna-1,3,5(10)-trien-20-yn-17-ol); available from Watson under the tradenames Brevicon and Norinyl;

(h) the combination of 17β-estradiol (estra-1,3,5(10)-triene-3,17β-diol) and micronized norgestimate (17α-17-(Acetyloxyl)-13-ethyl-18,19-dinorpregn-4-en-20-yn-3-one3-oxime); available from Ortho-McNeil under the tradename Ortho-Prefest;

(i) the combination of norgestimate (18,19-dinor-17-pregn-4-en-20-yn-3-one, 17-(acetyloxy)-13-ethyl-,oxime, (17(α)-(+)-) and ethinyl estradiol; available from Ortho-McNeil under the tradenames Ortho Cyclen and Ortho Tri-Cyclen; and (j) the combination of conjugated estrogens (sodium estrone sulfate and sodium equilin sulfate) and medroxyprogesterone acetate (20-dione, 17-(acetyloxy)-6-methyl-, (6(α))-pregn-4-ene-3); available from Wyeth-Ayerst under the tradenames Premphase and Prempro.

In general, a dosage of progestins may vary from about 0.05 mg to about 10 mg or up to about 200 mg if microsized progesterone is administered. Examples of progestins include norethindrone; available from ESI Lederle, Inc., Philadelphia, Pa., under the tradename Aygestin, from Ortho-McNeil under the tradename Micronor, and from Watson under the tradename Nor-QD; norgestrel; available from Wyeth-Ayerst under the tradename Ovrette; micronized progesterone (pregn-4-ene-3,20-dione); available from Solvay under the tradename Prometrium; and medroxyprogesterone acetate; available from Pharmacia & Upjohn under the tradename Provera.

In another alternative embodiment, the compositions, therapeutic combinations or methods of the present invention can comprise at least one compound of Formula (I), or pharmaceutically acceptable salts, solvates, or esters thereof, and one or more obesity control medications. Useful obesity control medications include, but are not limited to, drugs that reduce energy intake or suppress appetite, drugs that increase energy expenditure and nutrient-partitioning agents. Suitable obesity control medications include, but are not limited to, noradrenergic agents (such as diethylpropion, mazindol, phenylpropanolamine, phentermine, phendimetrazine, phendamine tartrate, methamphetamine, phendimetrazine and tartrate); serotonergic agents (such as sibutramine, fenfluramine, dexfenfluramine, fluoxetine, fluvoxamine and paroxtine); thermogenic agents (such as ephedrine, caffeine, theophylline, and selective β3-adrenergic agonists); alpha-blocking agents; kainite or AMPA receptor antagonists; leptin-lipolysis stimulated receptors; phosphodiesterase enzyme inhibitors; compounds having nucleotide sequences of the mahogany gene; fibroblast growth factor-10 polypeptides; monoamine oxidase inhibitors (such as befloxatone, moclobemide, brofaromine, phenoxathine, esuprone, befol, toloxatone, pirlindol, amiflamine, sercloremine, bazinaprine, lazabemide, milacemide and caroxazone); compounds for increasing lipid metabolism (such as evodiamine compounds); and lipase inhibitors (such as orlistat). Generally, a total dosage of the above-described obesity control medications can range from 1 to 3,000 mg/day, desirably from about 1 to 1,000 mg/day and more desirably from about 1 to 200 mg/day in single or 2-4 divided doses.

The compositions, therapeutic combinations or methods of the present invention can comprise at least one compound of Formula (I), or pharmaceutically acceptable salts, solvates, or esters thereof, and one or more blood modifiers which are chemically different from the substituted azetidinone and substituted β-lactam compounds (such as compounds II-XIII above) and the lipid modulating agents discussed above, for example, they contain one or more different atoms, have a different arrangement of atoms or a different number of one or more atoms than the sterol absorption inhibitor(s) or lipid modulating agents discussed above. Useful blood modifiers include but are not limited to anti-coagulants (argatroban, bivalirudin, dalteparin sodium, desirudin, dicumarol, lyapolate sodium, nafamostat mesylate, phenprocoumon, tinzaparin sodium, warfarin sodium); antithrombotic (anagrelide hydrochloride, bivalirudin, cilostazol, dalteparin sodium, danaparoid sodium, dazoxiben hydrochloride, efegatran sulfate, enoxaparin sodium, fluretofen, ifetroban, ifetroban sodium, lamifiban, lotrafiban hydrochloride, napsagatran, orbofiban acetate, roxifiban acetate, sibrafiban, tinzaparin sodium, trifenagrel, abciximab, zolimomab aritox); fibrinogen receptor antagonists (roxifiban acetate, fradafiban, orbofiban, lotrafiban hydrochloride, tirofiban, xemilofiban, monoclonal antibody 7E3, sibrafiban); platelet inhibitors (cilostazol, clopidogrel bisulfate, epoprostenol, epoprostenol sodium, ticlopidine hydrochloride, aspirin, ibuprofen, naproxen, sulindae, idomethacin, mefenamate, droxicam, diclofenac, sulfinpyrazone, piroxicam, dipyridamole); platelet aggregation inhibitors (acadesine, beraprost, beraprost sodium, ciprostene calcium, itazigrel, lifarizine, lotrafiban hydrochloride, orbofiban acetate, oxagrelate, fradafiban, orbofiban, tirofiban, xemilofiban); hemorrheologic agents (pentoxifylline); lipoprotein associated coagulation inhibitors; Factor VIIa inhibitors (4H-31-benzoxazin-4-ones, 4H-3,1-benzoxazin-4-thiones, quinazolin-4-ones, quinazolin-4-thiones, benzothiazin-4-ones, imidazolyl-boronic acid-derived peptide analogues TFPI-derived peptides, naphthalene-2-sulfonic acid {1-[3-(aminoiminomethyl)-benzyl]-2-oxo-pyrrolidin-3-(S)-yl}amide trifluoroacetate, dibenzofuran-2-sulfonic acid {1-[3-(aminomethyl)-benzyl]-5-oxo-pyrrolidin-3-yl}-amide, toluene-4-sulfonic acid {1-[3-(aminoiminomethyl)-benzyl]-2-oxo-pyrrolidin-3-(S)-yl}-amide trifluoroacetate, 3,4-dihydro-1H-isoquinoline-2-sulfonic acid {1-[3-(aminoiminomethyl)-benzyl]-2-oxo-pyrrolin-3-(S)-yl}-amide trifluoroacetate); Factor Xa inhibitors (disubstituted pyrazolines, disubstituted triazolines, substituted n-[(aminoiminomethyl)phenyl]propylamides, substituted n-[(aminomethyl)phenyl]propylamides, tissue factor pathway inhibitor (TFPI), low molecular weight heparins, heparinoids, benzimidazolines, benzoxazolinones, benzopiperazinones, indanones, dibasic (amidinoaryl) propanoic acid derivatives, amidinophenyl-pyrrolidines, amidinophenyl-pyrrolines, amidinophenyl-isoxazolidines, amidinoindoles, amidinoazoles, bis-arylsulfonylaminobenzamide derivatives, peptidic Factor Xa inhibitors).

The compositions, therapeutic combinations or methods of the present invention can comprise at least one compound of Formula (I), or pharmaceutically acceptable salts, solvates, or esters thereof, and one or more cardiovascular agents which are chemically different from the substituted azetidinone and substituted β-lactam compounds (such as compounds II-XIII above) and the lipid modulating agents discussed above, for example, they contain one or more different atoms, have a different arrangement of atoms or a different number of one or more atoms than the sterol absorption inhibitor(s) or PPAR receptor activators discussed above. Useful cardiovascular agents include but are not limited to calcium channel blockers (clentiazem maleate, amlodipine besylate, isradipine, nimodipine, felodipine, nilvadipine, nifedipine, teludipine hydrochloride, diltiazem hydrochloride, belfosdil, verapamil hydrochloride, fostedil); adrenergic blockers (fenspiride hydrochloride, labetalol hydrochloride, proroxan, alfuzosin hydrochloride, acebutolol, acebutolol hydrochloride, alprenolol hydrochloride, atenolol, bunolol hydrochloride, carteolol hydrochloride, celiprolol hydrochloride, cetamolol hydrochloride, cicloprolol hydrochloride, dexpropranolol hydrochloride, diacetolol hydrochloride, dilevalol hydrochloride, esmolol hydrochloride, exaprolol hydrochloride, flestolol sulfate, labetalol hydrochloride, levobetaxolol hydrochloride, levobunolol hydrochloride, metalol hydrochloride, metoprolol, metoprolol tartrate, nadolol, pamatolol sulfate, penbutolol sulfate, practolol, propranolol hydrochloride, sotalol hydrochloride, timolol, timolol maleate, tiprenolol hydrochloride, tolamolol, bisoprolol, bisoprolol fumarate, nebivolol); adrenergic stimulants; angiotensin converting enzyme (ACE) inhibitors (benazepril hydrochloride, benazeprilat, captopril, delapril hydrochloride, fosinopril sodium, libenzapril, moexipril hydrochloride, pentopril, perindopril, quinapril hydrochloride, quinaprilat, ramipril, spirapril hydrochloride, spiraprilat, teprotide, enalapril maleate, lisinopril, zofenopril calcium, perindopril erbumine); antihypertensive agents (althiazide, benzthiazide, captopril, carvedilol, chlorothiazide sodium, clonidine hydrochloride, cyclothiazide, delapril hydrochloride, dilevalol hydrochloride, doxazosin mesylate, fosinopril sodium, guanfacine hydrochloride, methyldopa, metoprolol succinate, moexipril hydrochloride, monatepil maleate, pelanserin hydrochloride, phenoxybenzamine hydrochloride, prazosin hydrochloride, primidolol, quinapril hydrochloride, quinaprilat, ramipril, terazosin hydrochloride, candesartan, candesartan cilexetil, telmisartan, amlodipine besylate, amlodipine maleate, bevantolol hydrochloride); angiotensin II receptor antagonists (candesartan, irbesartan, losartan potassium, candesartan cilexetil, telmisartan); anti-anginal agents (amlodipine besylate, amlodipine maleate, betaxolol hydrochloride, bevantolol hydrochloride, butoprozine hydrochloride, carvedilol, cinepazet maleate, metoprolol succinate, molsidomine, monatepil maleate, primidolol, ranolazine hydrochloride, tosifen, verapamil hydrochloride); coronary vasodilators (fostedil, azaclorzine hydrochloride, chromonar hydrochloride, clonitrate, diltiazem hydrochloride, dipyridamole, droprenilamine, erythrityl tetranitrate, isosorbide dinitrate, isosorbide mononitrate, lidoflazine, mioflazine hydrochloride, mixidine, molsidomine, nicorandil, nifedipine, nisoldipine, nitroglycerine, oxprenolol hydrochloride, pentrinitrol, perhexyline maleate, prenylamine, propatyl nitrate, terodiline hydrochloride, tolamolol, verapamil); diuretics (the combination product of hydrochlorothiazide and spironolactone and the combination product of hydrochlorothiazide and triamterene).

The compositions, therapeutic combinations or methods of the present invention can comprise at least one compound of Formula (I), or pharmaceutically acceptable salts, solvates, or esters thereof, and one or more antidiabetic medications for reducing blood glucose levels in a human. Useful antidiabetic medications include, but are not limited to, drugs that reduce energy intake or suppress appetite, drugs that increase energy expenditure and nutrient-partitioning agents. Suitable antidiabetic medications include, but are not limited to, sulfonylurea (such as acetohexamide, chlorpropamide, gliamilide, gliclazide, glimepiride, glipizide, glyburide, glibenclamide, tolazamide, and tolbutamide), meglitinide (such as repaglinide and nateglinide), biguaide (such as metformin and buformin), alpha-glucosidase inhibitor (such as acarbose, miglitol, camiglibose, and voglibose), certain peptides (such as amlintide, pramlintide, exendin, and GLP-1 agonistic peptides), and orally administrable insulin or insulin composition for intestinal delivery thereof. Generally, a total dosage of the above-described antidiabetic medications can range from 0.1 to 1,000 mg/day in single or 2-4 divided doses.

Mixtures of two, three, four or more of any of the pharmacological or therapeutic agents described above can be used in the compositions and therapeutic combinations of the present invention.

Since the present invention relates to treating conditions as discussed above, by treatment with a combination of active ingredients wherein the active ingredients may be administered separately, the invention also relates to combining separate pharmaceutical compositions in kit form. That is, a kit is contemplated wherein two separate units are combined: a pharmaceutical composition comprising at least one selective $CB_1$ receptor antagonist of Formula (I), or a pharmaceutically acceptable salt, solvate, or ester thereof, and a separate pharmaceutical composition comprising at least one cholesterol lowering compound as described above. The kit will preferably include directions for the administration of the separate components. The kit form is particularly advantageous when the separate components must be administered in different dosage forms (e.g., oral and parenteral) or are administered at different dosage intervals.

In yet another embodiment, the present invention provides a method of treating, reducing, or ameliorating a disease or condition selected from the group consisting of metabolic syndrome, obesity, waist circumference, lipid profile, insulin sensitivity, neuroinflammatory disorders, cognitive disorders, psychosis, addictive behavior, gastrointestinal disorders, vascular conditions, hyperlipidaemia, atherosclerosis, hypercholesterolemia, sitosterolemia, vascular inflammation, stroke, diabetes, and cardiovascular conditions, and/or reduce the level of sterol(s) in a patient in need thereof, comprising administering to said patient an effective amount of at least one compound of Formula (I), or a pharmaceutically acceptable salt, solvate, or ester thereof, and one or more cholesterol lowering compound.

The treatment compositions and therapeutic combinations comprising at least one compound of Formula (I) and at least one cholesterol lowering agent can inhibit the intestinal absorption of cholesterol in mammals can be useful in the treatment and/or prevention of conditions, for example vascular conditions, such as atherosclerosis, hypercholesterolemia and sitosterolemia, stroke, obesity and lowering of plasma levels of cholesterol in mammals, in particular in mammals.

In another embodiment of the present invention, the compositions and therapeutic combinations of the present invention can inhibit sterol or 5α-stanol absorption or reduce plasma concentration of at least one sterol selected from the group consisting of phytosterols (such as sitosterol, campesterol, stigmasterol and avenosterol) and/or 5α-stanol (such as cholestanol, 5α-campestanol, 5α-sitostanol), cholesterol and mixtures thereof. The plasma concentration can be reduced by administering to a mammal in need of such treatment an effective amount of at least one treatment composition or therapeutic combination comprising at least one selective $CB_1$ receptor antagonist and at least one cholesterol lowering compound, for example a sterol absorption inhibitor described above. The reduction in plasma concentration of sterols or 5α-stanols can range from about 1 to about 70 percent, and preferably about 10 to about 50 percent. Methods of measuring serum total blood cholesterol and total LDL cholesterol are well known to those skilled in the art and for example include those disclosed in PCT WO 99/38498 at page 11, incorporated by reference herein. Methods of determining levels of other sterols in serum are disclosed in H. Gylling et al., "Serum Sterols During Stanol Ester Feeding in a Mildly Hypercholesterolemic Population", J. Lipid Res. 40: 593-600 (1999), incorporated by reference herein.

The treatments of the present invention can also reduce the size or presence of plaque deposits in vascular vessels. The plaque volume can be measured using (IVUS), in which a tiny ultrasound probe is inserted into an artery to directly image and measure the size of atherosclerotic plaques, in a manner well know to those skilled in the art.

In the Schemes and Experiments below, as well as the specification and claims, the following abbreviations are applicable:

| | |
|---|---|
| rt | room temperature |
| THF | tetrahydrofuran |
| $Et_2O$ | ethyl ether |
| Me | methyl |
| Et | ethyl |
| Bu | Butyl |
| Bn | benzyl |
| Pr | propyl |
| i-Pr | isopropyl |
| Ac | acetyl |
| EtOAc | ethyl acetate |
| $BnOCH_2Cl$ | benzylchloromethylether |
| BuLi | Butyl Lithium |
| DBAD | Di-tert-butyl azodicarboxylate |
| DBU | 1,8-diazabicylco[5.4.0]undec-7-ene |
| DCE | 1,2-dichloroethane |
| DCM | Dichloromethane |
| DMF | N,N-Dimethylformamide |
| DMSO | Methyl sulfoxide |
| HOBT or HOBt | Hydroxybenzotriazole |
| KHMDS | Potassium bis(trimethylsilyl)amide |
| LiHMDS or LHMDS: | Lithium bis(trimethylsilyl)amide |
| $NaB(O_2CCH_3)_3H$ | Sodium triacetoxyborohydride |
| OTf | Triflate or trifluoromethanesulfonate ($CF_3SO_2$—O—) |
| PhSeBr | Phenyl selenium bromide |
| PS | Polymer supported |
| PS-EDC | Polymer supported dimethyl aminopropyl ethylcarbodiimide hydrochloride |
| Py | Pyridine |
| PS-NCO | Polymer supported isocyanate |

| | |
|---|---|
| PS-Tris-NH₂ | Polymer supported trisamine |
| TFA | Trifluoroacetic acid |
| Ti(OiPr)₄ | titanium isopropoxide; |
| TLC | thin layer chromatography |
| TMSI | Trimethylsilyl iodide or iodotrimethylsilane |
| HATU | O-(7-Azabenzotriazole-1-yl)-N,N,N'N'-tetramethyluronium hexafluorophosphate |
| DIPEA | N,N-diisopropylethylamine |
| dppp | 1,3-bis(diphenylphosphino)propane |
| dppf | 1,1'-bis(diphenylphosphino)ferrocene |
| PS-BEMP | 2-tert-Butylimino-2-diethylamino-1,3-dimethyl-perhydro-1,3,2-diaza-phosphorine on polystyrene |
| DMAP: | N,N-dimethylaminopyridine |
| EDCl: | N(3-Dimethylaminopropyl)-N'-ethylcarbodiimide hydrochloride |
| HPLC: | High Performance Liquid Chromatography |
| PhMe: | Toluene |
| MeOH: | Methyl alcohol |
| EtOH: | Ethyl alcohol |
| Trisyl Azide: | 2,4,6-tri-isopropylbenzenesulfonyl azide |
| DEAD: | Diethylazodicarboxylate |
| NMP: | N-Methylpyrrolidinone |
| DMPU: | 1,3-Dimethyl-3,4,5,6-tetrahydro-2(1H)-pyrimidinone |
| Dess-Martin reagent: | 1,1,1-Tris(acetyloxy)-1,1-dihydro-1,2-benziodoxol-3(1H)-one |
| BOM: | Benzyloxymethyl |
| Cbz: | Benzyloxycarbonyl |
| MOM: | Methoxymethyl |
| Tf: | Trifluoromethanesufonyl |
| TIPS: | Triisopropylsilyl |
| TBS or TBDMS: | tert-Butyldimethylsilyl |

EXAMPLES

Preparation of Di(hetero)aryl-isoindol-1-ones

General Scheme A:

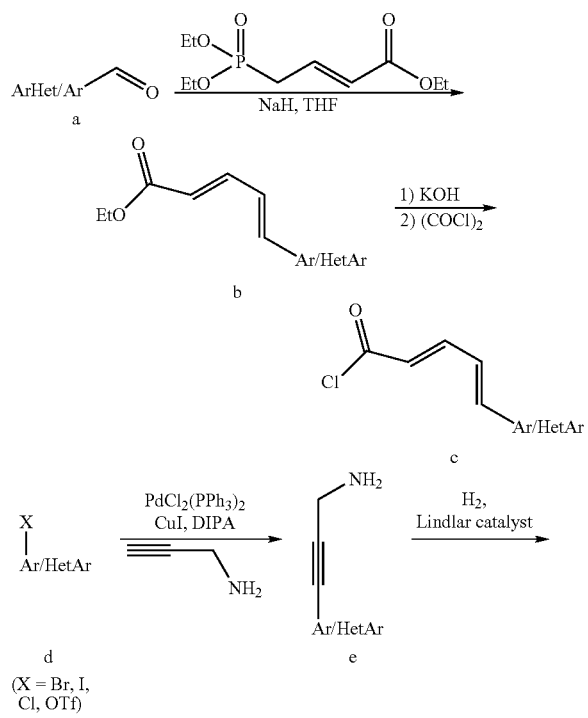

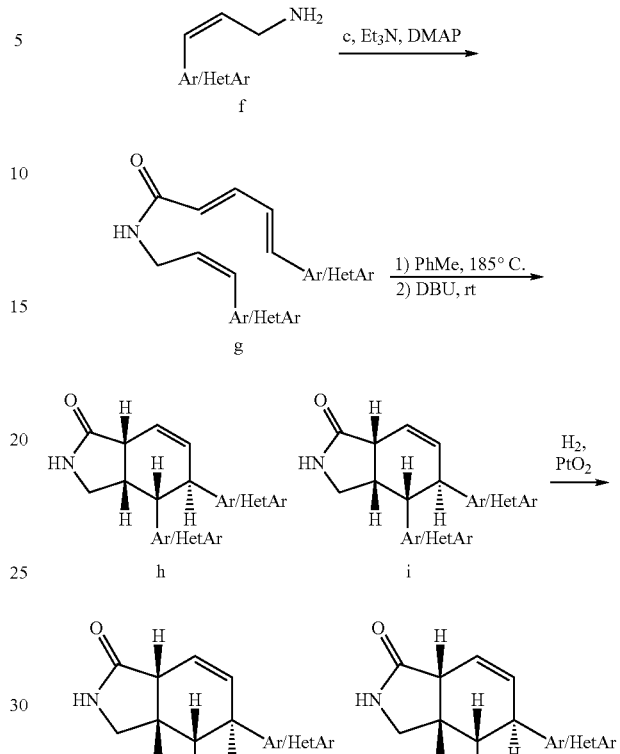

Diaryl-isoindol-1-ones, diheteroaryl-isoindol-1-ones, and aryl-heteroaryl-isoindol-1-ones of Formula (I) can be prepared by a variety of methods, for example by condensing an aryl or heteroaryl substituted diene acid or acid chloride with an aryl or heteroaryl substituted unsaturated amine to form a triene amide, or alternatively condensing a diaryl-, diheteroaryl- or aryl-heteroaryl-substituted diene acid or acid chloride with an unsaturated amine, then cyclizing the resulting triene amide via an intramolecular Diels-Alder reaction to form a di(hetero)aryl-tetrahydro-isoindol-1-one that can be further modified (e.g., by reduction or alklation, etc.) as desired.

Aldehyde a can be reacted with crotyl phosphonate to provide ester b which on saponification followed by reaction with oxalyl chloride gives acid chloride c. Sonagashira coupling [K. Sonogashira et al., Tet, Lett., 4467, (1975)] of aryl or heteroaryl bromide or iodide or chloride or O-triflate d with propargyl amine gives alkynyl amine e, which is reduced to allyl amine f using Lindlar catalyst and hydrogen. Allyl amine f is coupled with acid chloride c to provide amide g. Amide g is subjected to Diels-Alder reaction conditions, and then treated with DBU (i.e., 1,8-diazabicyclo[5.4.0]undec-7-ene) to provide cyclization products h and i. Double bond reduction gives j and k.

Unless expressly indicated otherwise, when compounds or mixtures in any of the following preparations are purified by chromatography, said chromatography is conventional flash chromatography using a silica gel stationary phase.

Preparation of Compounds 1-4

Step 1

Scheme 1:

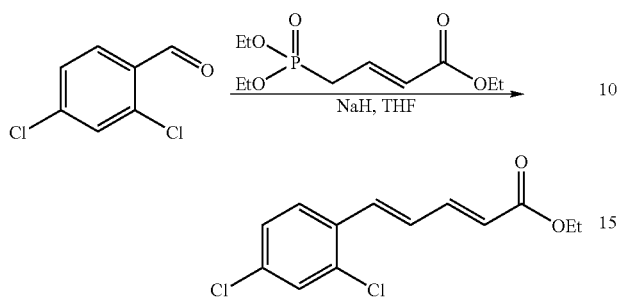

To a suspension of 60% NaH in mineral oil (16 g) in 1 L THF was added triethyl 4-phosphonocrotonate (100 g). The resulting solution was stirred for 2 hr, and then a solution of 2,4-dichlorobenzaldehyde (54 g) in 200 mL THF was added thereto. The mixture was stirred at room temperature for 1 hr. The reaction was quenched by the addition of 1 L of aq. NH$_4$Cl and the THF was evaporated. The mixture was extracted with 4×200 ml ethyl acetate and the combined organic layer washed with water, brine and dried over MgSO$_4$ then evaporated to provide the crude product. This was purified by silica gel chromatography using 5% ethyl acetate-hexanes to give 25.9 g of 5-(2,4-dichloro-phenyl)-penta-2,4-dienoic acid ethyl ester. MS: m/e 271.04 (MH$^+$)

Step 2

Scheme 2:

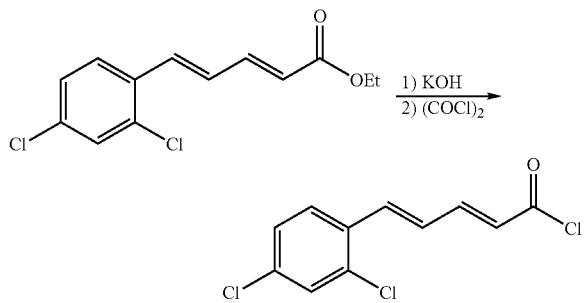

To a solution of 5-(2,4-dichloro-phenyl)-penta-2,4-dienoic acid ethyl ester (25.5 g) in 100 mL each of MeOH and THF was added a solution of KOH (16 g) in 100 mL H$_2$O and the mixture was stirred at room temperature for 2 hr. The mixture was diluted with 300 mL H$_2$O, acidified with 1N HCl and the precipitated product was isolated to provide 23.3 g of acid. To a suspension of the acid (19.5 g) in 400 mL CH$_2$Cl$_2$ at room temperature was added (COCl)$_2$ (20.7 mL) followed by DMF (190 µL) and the mixture was stirred at room temperature for 3 hr. The resultant clear solution was concentrated to provide 5-(2,4-dichloro-phenyl)-penta-2,4-dienoyl chloride. NMR (300 MHz, CDCl$_3$) 7.60 (ddd, J=15.0, 11.2, 0.8 Hz, 1H), 7.54 (d, J=8.4 Hz, 1H), 7.42-7.38 (m, 2H), 7.25-7.21 (m, 1H), 6.85 (ddd, J=15.4, 11.2, 0.8 Hz), 6.20 (d, J=14.8 Hz).

Step 3

Scheme 3:

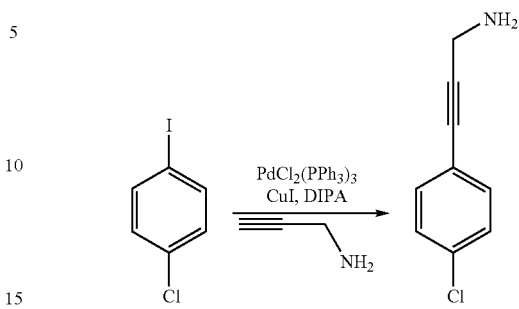

To a solution of 4-chloro iodobenzene (25 g) in 400 mL CH$_2$Cl$_2$ at room temperature was added propargyl amine (13.5 mL), diisopropyl amine (37 mL), CuI (4 g) and Pd(PPh$_3$)$_2$Cl$_2$ (3.7 g). The mixture was stirred overnight at room temperature, diluted with 600 mL EtOAc and filtered through a CELITE pad to remove insoluble materials. The solution washed with water, brine, dried over MgSO$_4$, concentrated and purified by chromatography to provide 14.1 g of 3-(4-chloro-phenyl)-prop-2-ynylamine. MS: m/e 166.1 (MH$^+$)

Step 4

Scheme 4:

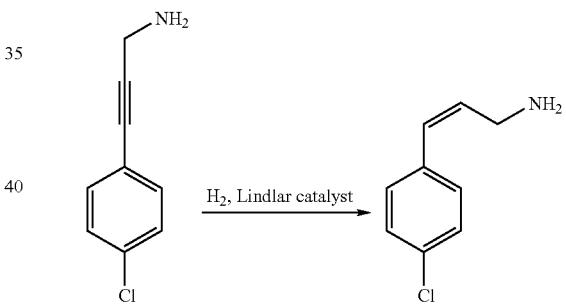

To a solution of 3-(4-chloro-phenyl)-prop-2-ynylamine (14.0 g) in 200 mL each of MeOH and CH$_2$Cl$_2$ was added Et$_3$N (1.2 mL) and Lindlar catalyst (1.4 g) and the resulting suspension was stirred under a H$_2$ balloon. The reaction was followed by TLC (i.e., thin layer chromatography) using 6% methanol-dichloromethane as eluent and once completed, filtered through a CELITE pad, concentrated and purified by chromatography to provide 10.5 g of 3-(4-chloro-phenyl)-allylamine. MS: m/e 168.6 (MH$^+$)

Step 5

Scheme 5:

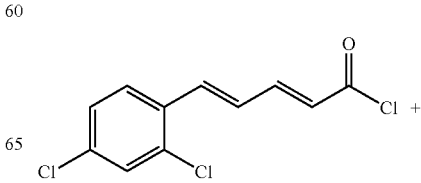

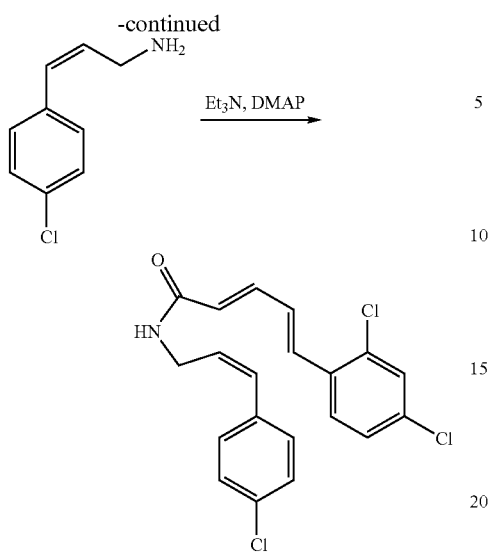

To a solution of 5-(2,4-dichloro-phenyl)-penta-2,4-dienoyl chloride (62.5 mmol) in 300 mL CH$_2$Cl$_2$ at 0° C. was added Et$_3$N (13.0 mL) followed by DMAP (i.e., 4-diaminomethylpyridine) (760 mg). To this was added a solution of 3-(4-chloro-phenyl)-allylamine (10.5 g) in 30 mL CH$_2$Cl$_2$. The mixture was stirred at 0° C. for 1 hr. Then 2 mL of MeOH was added, and the solution was stirred for 10 min. The solution was then diluted with aq. NaHCO$_3$ and extracted with EtOAc. Filtration of solids and concentration of EtOAc layers provided a combined yield of 24.6 g of 5-(2,4-dichloro-phenyl)-penta-2,4-dienoic acid [3-(4-chloro-phenyl)-allyl]-amide. MS: m/e 392.2 (MH$^+$)

Step 6

Scheme 6:

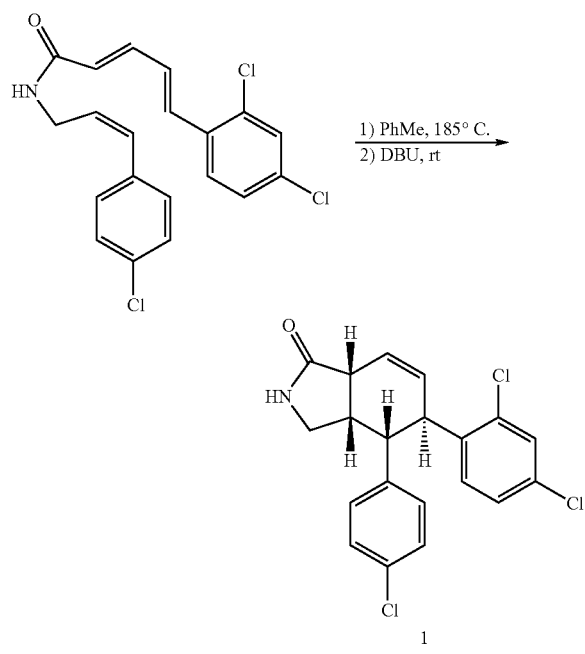

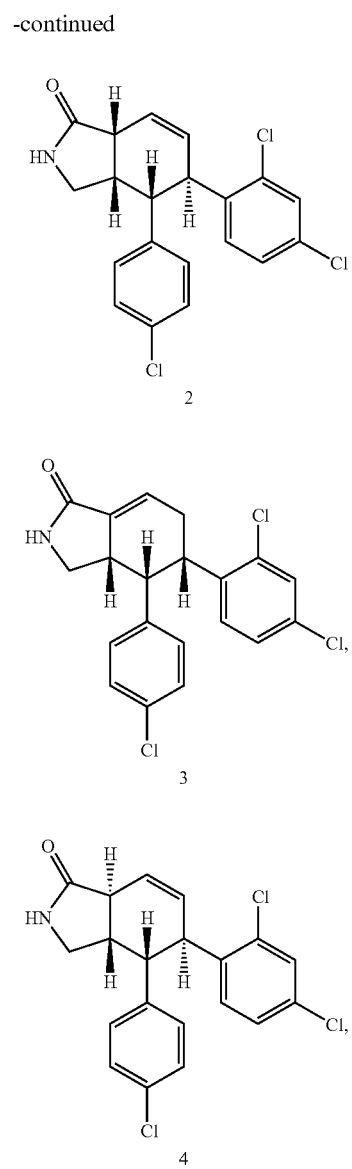

A solution of 5-(2,4-dichloro-phenyl)-penta-2,4-dienoic acid [3-(4-chloro-phenyl)-allyl]-amide (13.6 g) in 1:9 MeOH—CH$_2$Cl$_2$ was filtered through a pad of alumina and concentrated. This solid was taken up in 300 mL of toluene and heated at 185° C. for 10 hr. It was concentrated and stirred with DBU (i.e., 1,8-diazabicyclo[5.4.0]undec-7-ene) (1 g) in 200 mL CH$_2$Cl$_2$ for 1 hr. The mixture was concentrated and chromatographed with 75:25 ethyl acetate-hexanes to provide 8.5 g of a mixture of cyclization products, 1 and 2. The products 3 and 4 were also isolated from these reactions.

One of skill in the art will also recognize that when compounds in the any of the preparative procedures described herein are prepared from racemic starting materials, e.g., as in the preparation of compounds 1 and 2 described above, the resulting products (e.g., compounds 1 and 2) are also racemic mixtures of enantiomers. For example, compound 1:

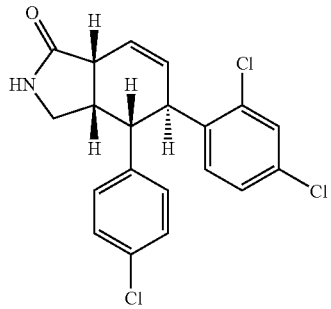

is understood to represent a racemic mixture of the following enantiomers:

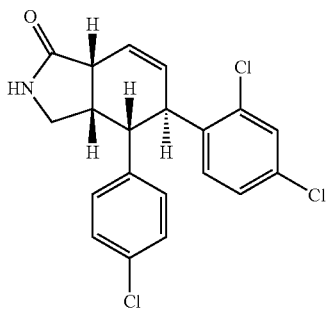

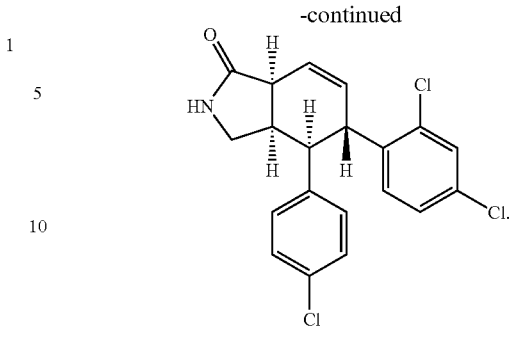

One of skill in the art will also recognize that racemic mixtures of products prepared from racemic starting materials can be separated into the individual enantiomers, e.g., by chiral chromatographic methods. Alternatively, specific enantiomers can be prepared by chiral synthetic methods from chiral starting materials.

The structures disclosed herein are intended to represent relative stereochemistry, i.e., both racemic mixtures and individual enantiomers, rather than absolute stereochemistry, unless there is an express indication that the structure is either intended to represent only a racemic mixture (e.g., by labeling the structure as a "racemic mixture", "D/L", or "+/−") or that the structure is intended to represent a single enantiomer having the indicated absolute stereochemistry (e.g., by expressly labeling the structure with "absolute stereochemistry" or labeling chiral centers with the "R" or "S" designations of the well-known Cahn-Ingold-Prelog system).

Preparation of Compounds 5 and 6

Scheme 7:

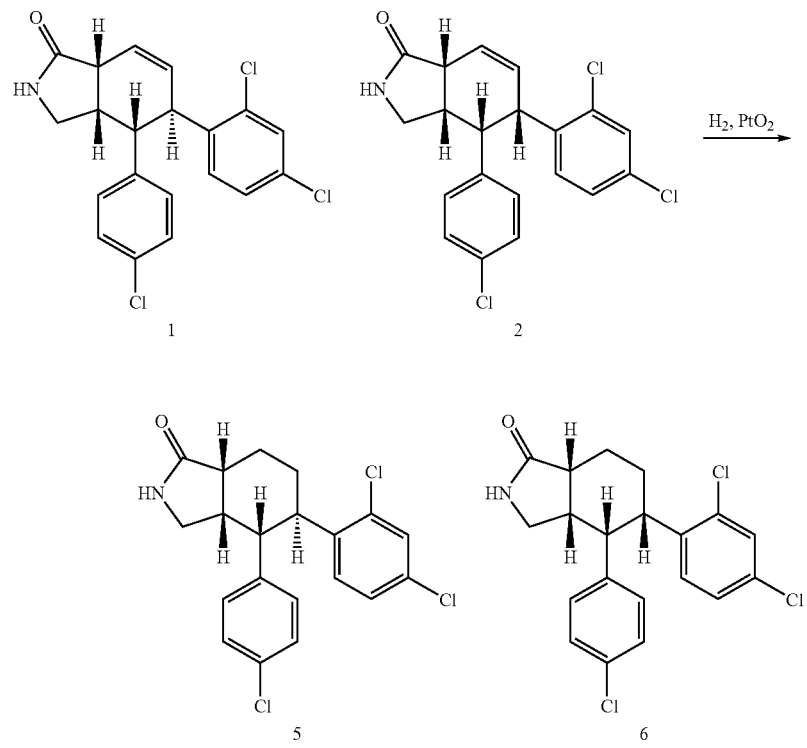

The above mixture of 1 and 2 was taken up in 200 mL EtOAc and stirred with 800 mg of PtO$_2$.H$_2$O under a H$_2$ balloon for 1.5 hr. The mixture was then filtered through a CELITE pad and concentrated. The solution was taken up in a minimum amount of CH$_2$Cl$_2$ and diluted with Et$_2$O and the precipitated solid was filtered to provide 1.93 g of 6. The filtrate was concentrated and purified by chromatography to provide 1.99 g of 5.

Chiral Resolution of 5

Scheme 8:

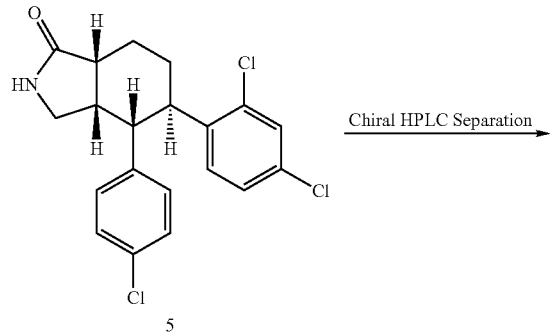

5

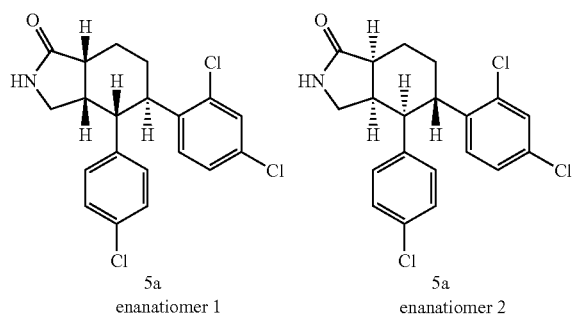

5a enanatiomer 1    5a enanatiomer 2

Compound 5 (25-50 mg) was sonicated in about 1.5 mL of isopropyl alcohol for one minute. After allowing the solution to stand for 30 minutes, about 2.5 mL of hexanes was added and the mixture gently stirred. Once the mixture was allowed to settle for several minutes, the clear solution was decanted off and, after filtration, injected onto a Chiralpac AD preparative HPLC column (5 cm×50 cm) and eluted with 15% isopropyl alcohol in hexanes to obtain 5a and 5b in roughly equal amounts. This process was repeated until the desired quantity of each isomer was obtained. Detection was at 220 nm, and the flow rate was 100 mL/min.

MS for 5a: 394.2 (MH$^+$)
MS for 5b: 394.2 (MH$^+$)

Preparation of Compound 7

Step 1

Scheme 9:

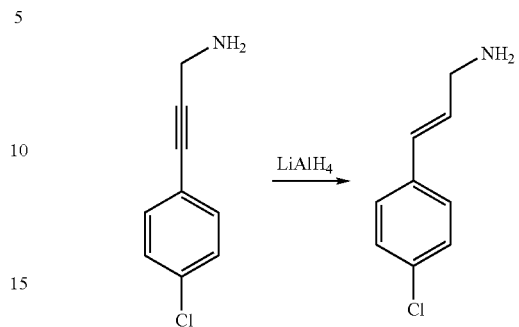

To a solution of 3-(4-chloro-phenyl)-prop-2-ynylamine (2.5 g) in 50 mL of THF at room temperature was added a 1M solution of LiAlH$_4$ in THF (30 mL) and the mixture was heated at reflux for 1 hr. It was cooled to room temperature, and to it was successively added 1.1 mL H$_2$O, 1.1 mL of 15% aq. NaOH and 3.4 mL H$_2$O. The precipitated solid was filtered off and the filtrate was concentrated and purified by chromatography to provide 1.45 g of 3-(4-chloro-phenyl)-allylamine. NMR (400 MHz, CDCl3) 7.26-7.21 (m, 4H), 6.42 (dt, J=16.0, 1.6 Hz, 1H), 6.29-6.22 (m, 1H), 3.44 (dd, J=5.6, 1.6 Hz, 2H)

Step 2

Scheme 10:

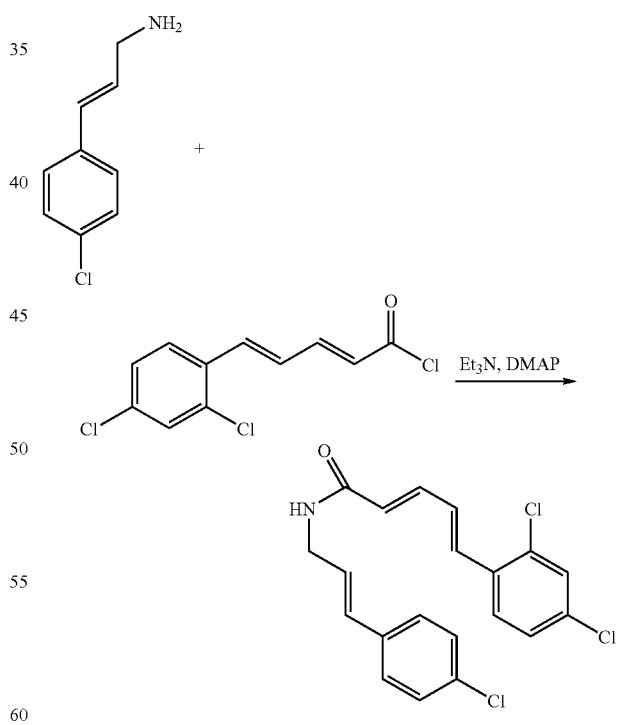

To a solution of 5-(2,4-dichloro-phenyl)-penta-2,4-dienoyl chloride (7.6 mmol) in 30 mL CH$_2$Cl$_2$ at 0° C. was added Et$_3$N (1.6 mL), DMAP (47 mg) followed by a solution of 3-(4-chloro-phenyl)-allylamine (1.4 g) in 10 mL of CH$_2$Cl$_2$. The solution turned into a thick slurry after few minutes. It was stirred for 30 min at 0° C., 30 min at room temperature then diluted with H$_2$O. The solid was filtered and washed with H$_2$O followed by Et$_2$O then dried in a vacuum oven to provide 3.8 g of 5-(2,4-dichloro-phenyl)penta-2,4-dienoic acid [3-(4-chloro-phenyl)-allyl]-amide. MS: m/e 394.02 (MH$^+$)

Step 3

Scheme 11:

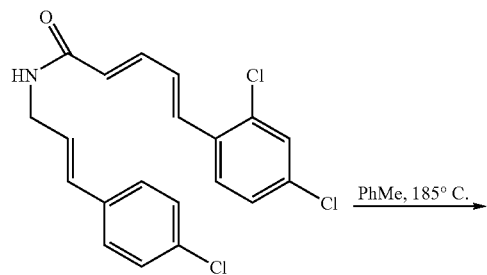

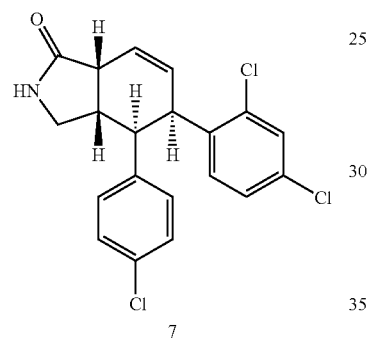

A suspension of 5-(2,4-dichloro-phenyl)-penta-2,4-dienoic acid [3-(4-chloro-phenyl)-allyl]-amide (3.8 g) in 70 mL of toluene was heated in a sealed tube at 185° C. for 6 hr, cooled to room temperature and concentrated to provide 2.8 g of 7. MS: m/e 394.0 (MH$^+$)

Preparation of Compound 8

Scheme 12:

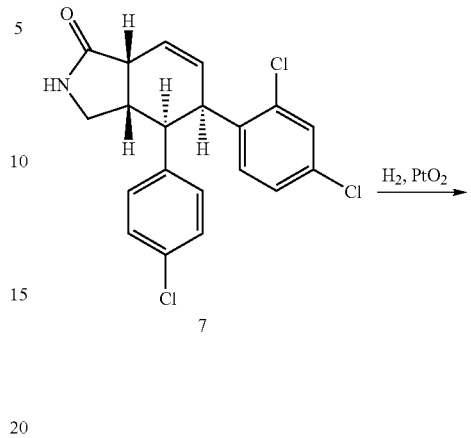

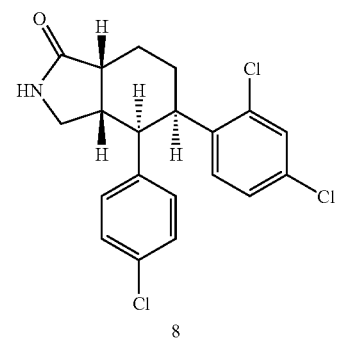

To a solution of 7 (2.8 g) in 70 mL of 1:9 MeOH—CH$_2$Cl$_2$ was added PtO$_2$.H$_2$O (280 mg) and the mixture was stirred under a H$_2$ balloon for 40 min. To the suspension was added activated carbon, then the suspension was filtered through a CELITE pad, concentrated and recrystallized from CH$_2$Cl$_2$/hexanes to provide 1.4 g of 8. MS: m/e 394.03 (MH$^+$)

Preparation of Compounds 9-12

Scheme 13:

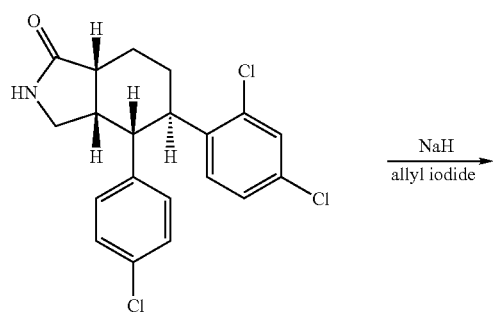

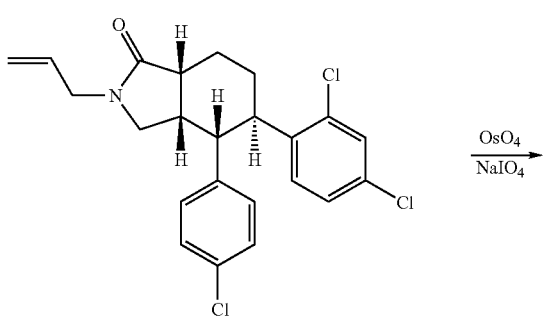

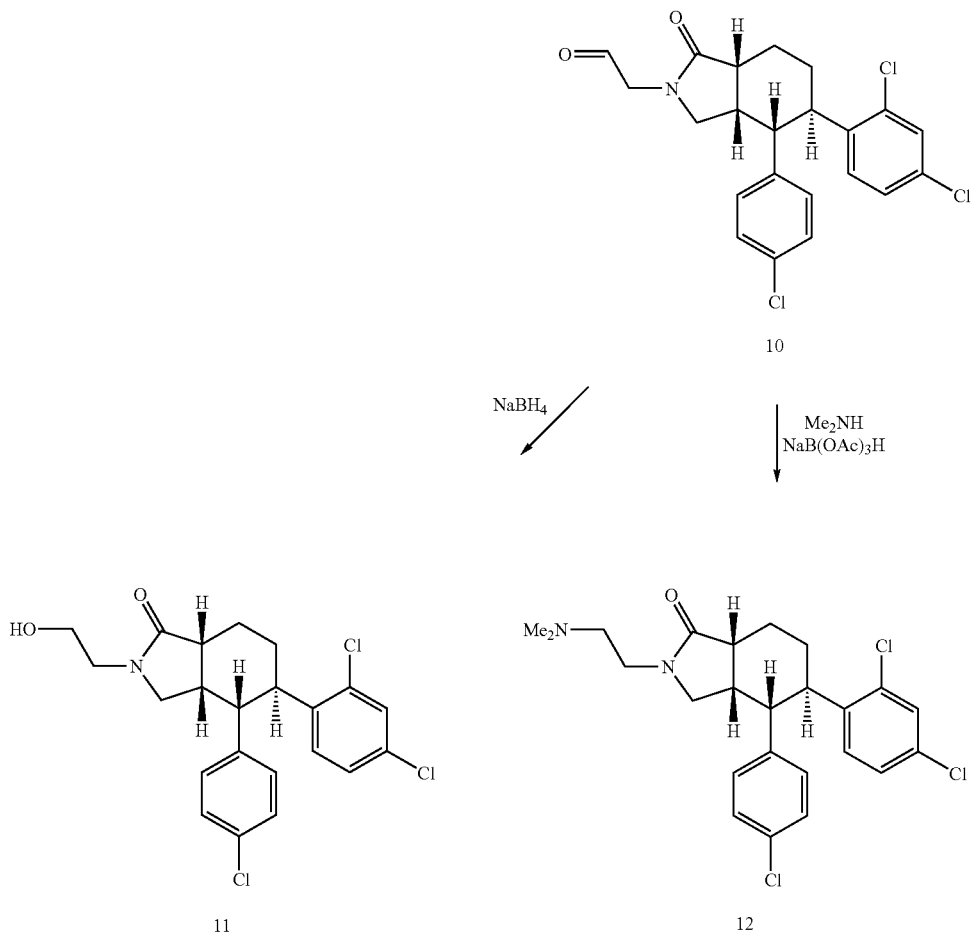

The lactam 5 can be N-alkylated using standard conditions. For example, 5 was N-allylated to give 9 using NaH and allyl iodide. Oxidative cleavage of the double bond followed by reduction or reductive amination gave 11 and 12 respectively as shown in Scheme 12.

Preparation of Compounds 13 and 14

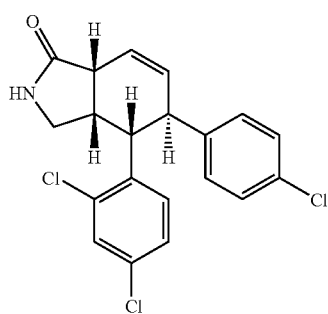

13

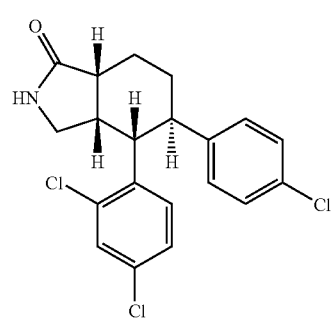

14

Compounds 13 and 14 were prepared by the method of Scheme A using the appropriate starting aldehyde a and iodide d.

It will be recognized by one of ordinary skill in the art that the substituted aryl moieties of the above isoindol-1-ones can be independently replaced with heteroaryl moieties by the appropriate selection of heteroaryl substituted starting materials. For example, a benzaldehyde and/or phenyl iodide could be replaced with the corresponding pyridyl aldehyde or pyridyl halide.

Preparation of Compound 15

Scheme 14

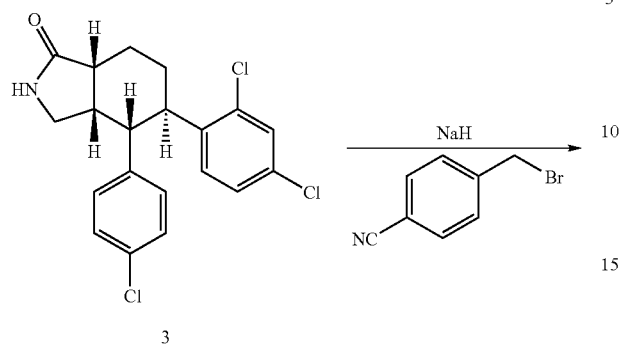

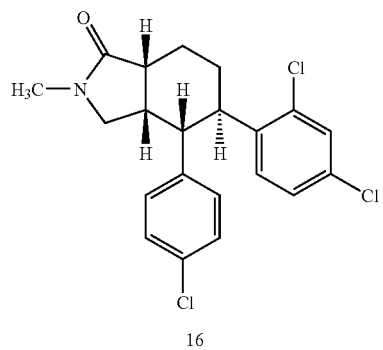

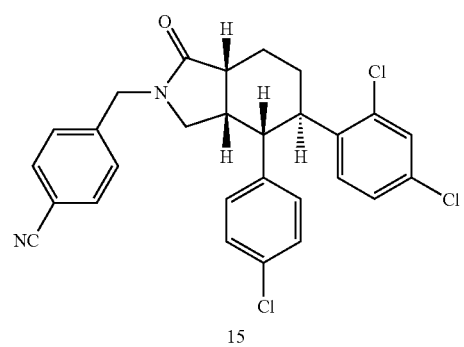

To a solution of 5 (50 mg) in 5 mL DMF at room temperature was added NaH (1.1 equivalent of a 60% dispersion in mineral oil). The solution was then stirred for 20 min. To the stirred solution was added α-bromo-tolunitrile (75 mg) and Bu₄NI (5 mg). After 3 hrs of stirring, an additional portion of NaH (20 mg) was added and the mixture was stirred overnight at room temperature. The solution was then diluted with EtOAc, washed with water, 1N HCl, brine, dried over MgSO₄, filtered and concentrated. The crude product was chromatographed using 10% MeOH in CH₂Cl₂ mixture to provide 40 mg of 15.

MS: 509.3 (MH$^+$)

Preparation of Compound 16

Scheme 15

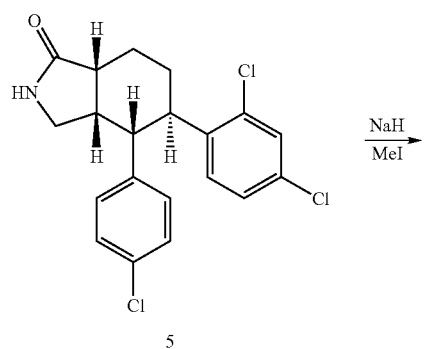

To a solution of 5 (50 mg) in 5 mL DMF at room temperature was added NaH (6 mg of 60% dispersion in mineral oil). The solution was stirred for 20 min. To the stirred solution was added 3 equivalents of CH₃I and the mixture was stirred overnight at room temperature. An additional portion of NaH (20 mg) was then added, and the mixture was heated at 50° C. for 1 day. The solution was then poured into EtOAc and washed with water, 1N HCl and brine, dried over MgSO₄, filtered and evaporated then purified by chromatography using 5% MeOH in CH₂Cl₂ to provide 31 mg of 16.

MS: 406.2 (MH$^+$)

Preparation of N-Substituted-4,5-diphenyl-isoindoles

General Scheme B:

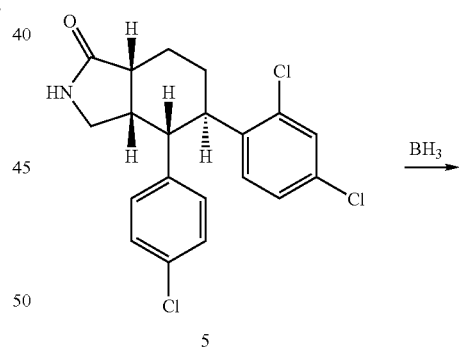

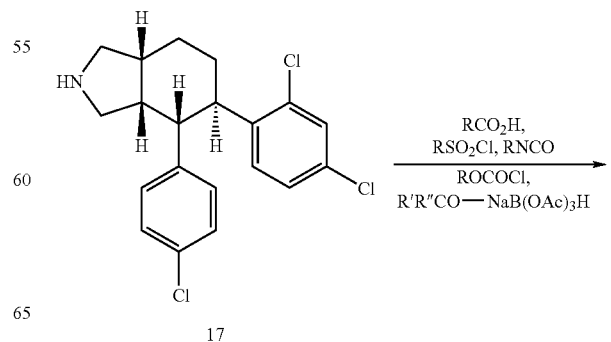

-continued

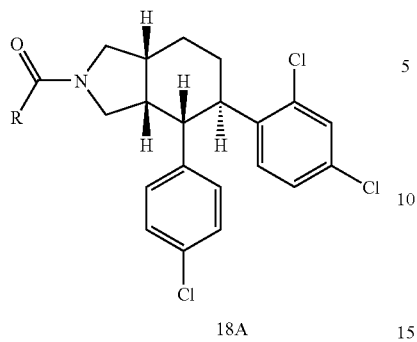

18A

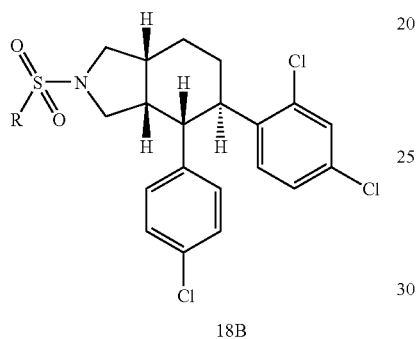

18B

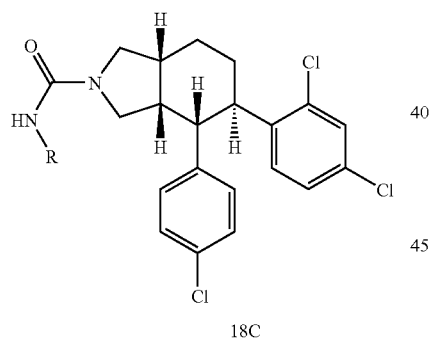

18C

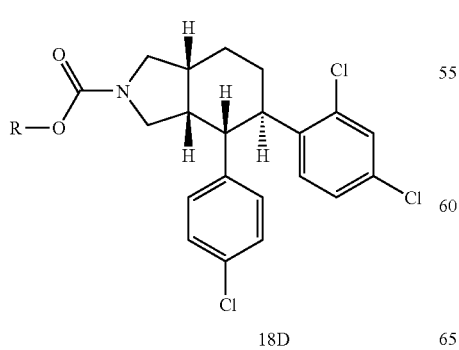

18D

-continued

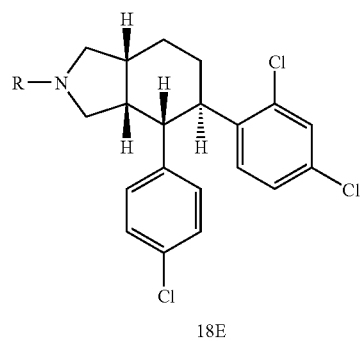

18E

For example, compounds 19 and 20, below, were prepared by reacting compound 17 with methylsulfonyl chloride or cyclopropylsulfonyl chloride, respectively.

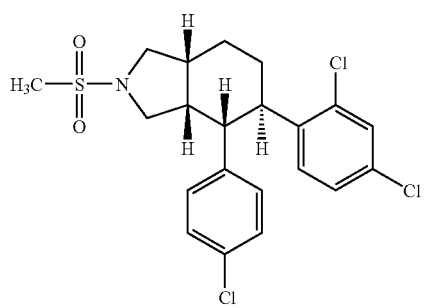

19

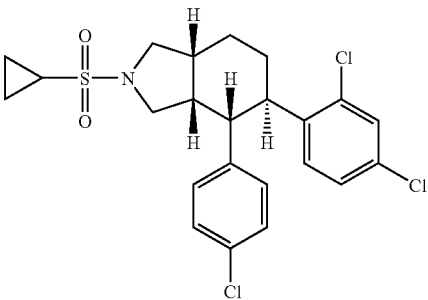

20

Preparation of Compounds 21-36

The following are representative compounds of structure 18A prepared by reacting isoindole 17 with the appropriate carboxylic acid using well-known EDCl and HOBt coupling conditions.

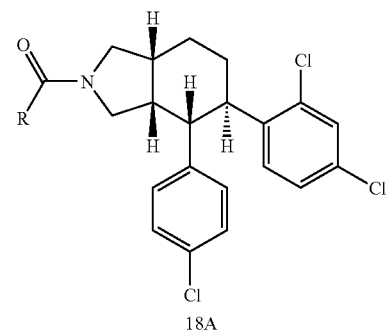

18A

| Example | R | MS (MH+) |
|---|---|---|
| 21 | (tetrahydrofuran-2-yl) | 478.3 |
| 22 | (5-oxopyrrolidin-2-yl) | 491.3 |
| 23 | (benzyl) | 498.3 |
| 24 | (4-cyanophenyl) | 509.3 |
| 25 | (3-cyanophenyl) | 509.3 |

The following are representative compounds of structure 18C prepared by reacting isoindole 17 with the appropriate isocyanate.

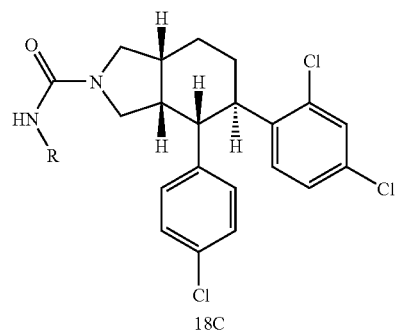

18C

| Compound | R | MS (MH+) |
|---|---|---|
| 26 | (cyclohexyl) | 505.3 |
| 27 | (4-chlorophenyl) | 533.3 |
| 28 | (4-trifluoromethylphenyl) | 567.3 |

The following are representative compounds of structure 18D prepared by reading isoindole 17 with the appropriate chloroformate.

18D

| Compound | R | MS (MH+) |
|---|---|---|
| 29 | -CH₃ | 438.2 |
| 30 | (4-chlorophenyl) | 534.3 |

-continued

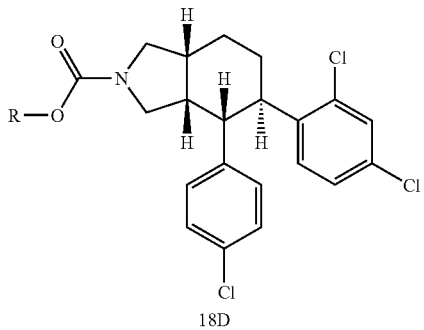

18D

| Compound | R | MS (MH+) |
|---|---|---|
| 31 | 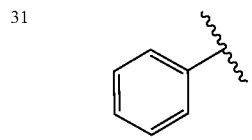 | 500.3 |

The following are some representative compounds of structure 18E prepared by reacting isoindole 17 with the appropriate aldehyde or ketone and sodium triacetoxyborohydride as the reducing agent.

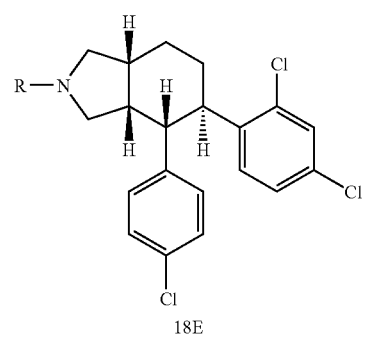

18E

| Compound | R | MS (MH+) |
|---|---|---|
| 32 | 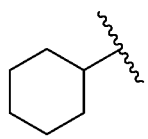 | 462.3 |
| 33 | 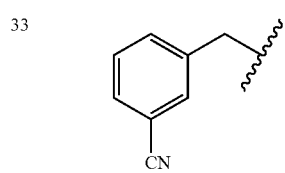 | 495.3 |

-continued

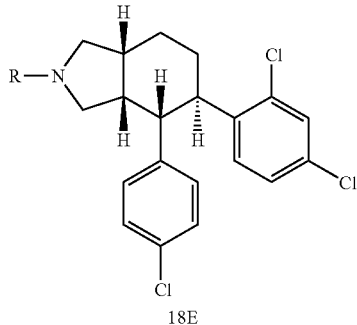

18E

| Compound | R | MS (MH+) |
|---|---|---|
| 34 | 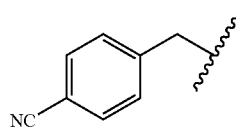 | 495.3 |
| 35 | | 509.3 |
| 36 | 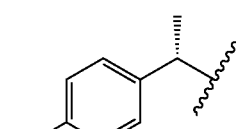 | 509.3 |

It will be recognized by one of ordinary skill in the art that the substituted aryl moieties of the above isoindoles can be independently replaced with heteroaryl moieties by the use of the appropriate heteroaryl substituted starting materials.

It will also be recognized by one of ordinary skill in the art that isoindoles having different substitution patterns of aryl and/or heteroaryl groups on the six-membered ring may be provided by use of the appropriate starting materials. In addition, substitution on the isoindole nitrogen atom may be provided by methods known in the art (e.g., alkylation, acylation, arylation, etc).

Preparation of
Di(hetero)aryl-isoindol-1-ylideneamines

Di(hetero)aryl-isoindol-1-ylideneamines can be prepared by a variety of methods, for example by conversion of an isoindol-1-one to the corresponding amidine, followed by further modification of the amidine, e.g., by acylation.

Preparation of Compounds 37-39

Scheme 16:

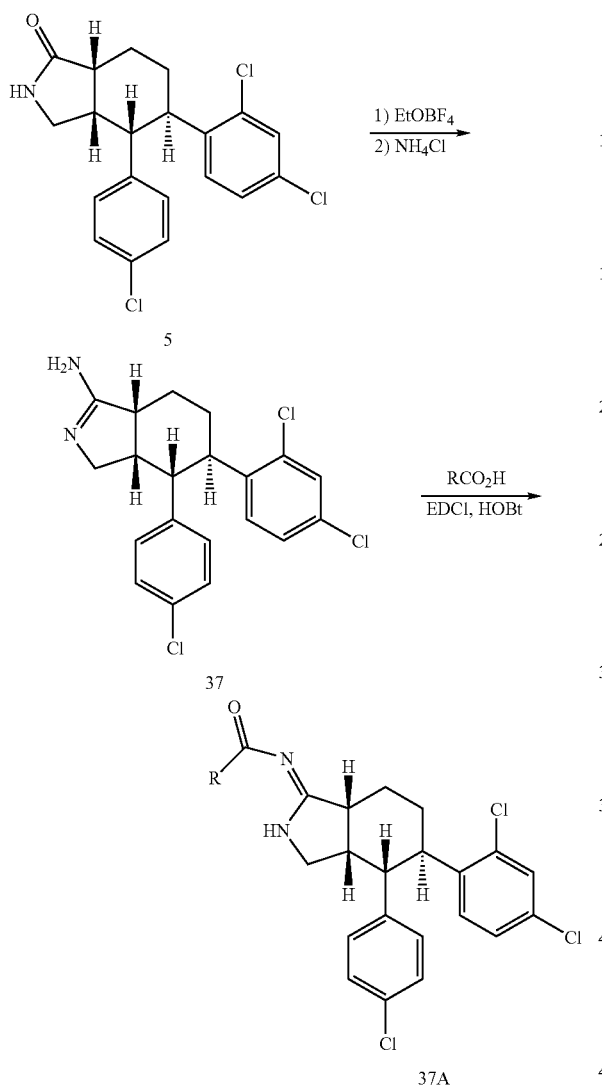

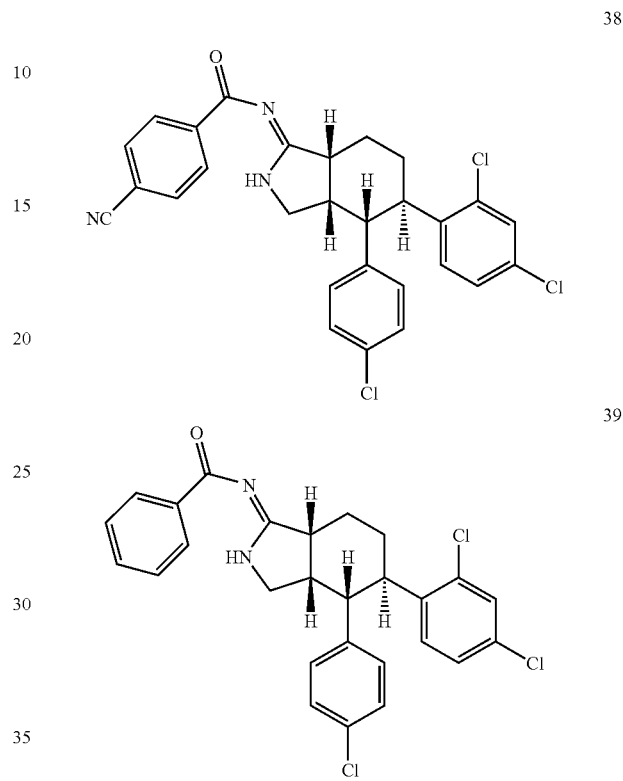

The lactam 5 was converted to amidine 37 which can be coupled with the appropriate carboxylic acid using EDCl/HOBt to provide 37A.

Step 1:

To a solution of 89 mg of 5 in about 3 mL of dichloromethane was added triethyloxonium tetrafluoroborate (2 eq.) and sodium carbonate (2 eq.) and the mixture was stirred under nitrogen for three days. The reaction mixture was poured onto a pH 7 buffer and extracted with dichloromethane three times. The combined extracts were washed with brine, dried with $MgSO_4$, filtered and evaporated to dryness. To the residue in methanol (~4 mL) was added ammonium chloride (10 eq.) and the mixture heated to reflux. After 24 hours the mixture was evaporated to dryness and partitioned between dichloromethane and aq. $K_2CO_3$. The aqueous phase was twice extracted with dichloromethane. The combined organic phases were washed with brine, dried with $MgSO_4$, filtered and evaporated to dryness. Purification by HPLC (C-18 column, elution with water/acetonitrile w/0.1% formic acid) yielded 37 as the formate salt.

MS: 393.2 (MH$^+$)

Preparation of 38 and 39

To 20 mg of 37 (free base) in dichloromethane (1.5 mL) at 0° C. was added 4-cyanobenzoic acid (2 eq.), HOBt (2 eq.) and EDCl (2 eq.) and the mixture was stirred under nitrogen while slowly warming to room temperature. After 24 hours the mixture was poured onto aqueous sodium bicarbonate and extracted three times with ~1% methanol in dichloromethane. The combined extracts were dried with $MgSO_4$, filtered and evaporated to dryness. Purification by flash chromatography (0-50% ethylacetate in hexane) yielded 16 mg of 38.

Compound 39 was prepared using similar conditions, except that benzoic acid was used instead of 4-cycanobezoic acid.

MS for 38: 522.3 (MH$^+$)

MS for 39: 497.3 (MH$^+$)

It will be recognized by one of ordinary skill in the art that the substituted aryl moieties of the above isoindol-1-ylideneamines can be independently replaced with heteroaryl moieties by the appropriate selection of heteroaryl substituted isoindol-1-one starting materials, followed by conversion of the isoindol-1-one to an isoindol-1-ylideneamines, for example as shown above. Furthermore, other substitution patterns on the 6-membered ring of the isoindoles may be obtained by modification of the appropriate isoindol-1-one starting material (e.g., use of a 5,6-di(hetero)aryl-isoindol-1-one starting material rather than a 4,5-di(hetero)aryl-isoindol-1-one).

Preparation of Compounds 40-43

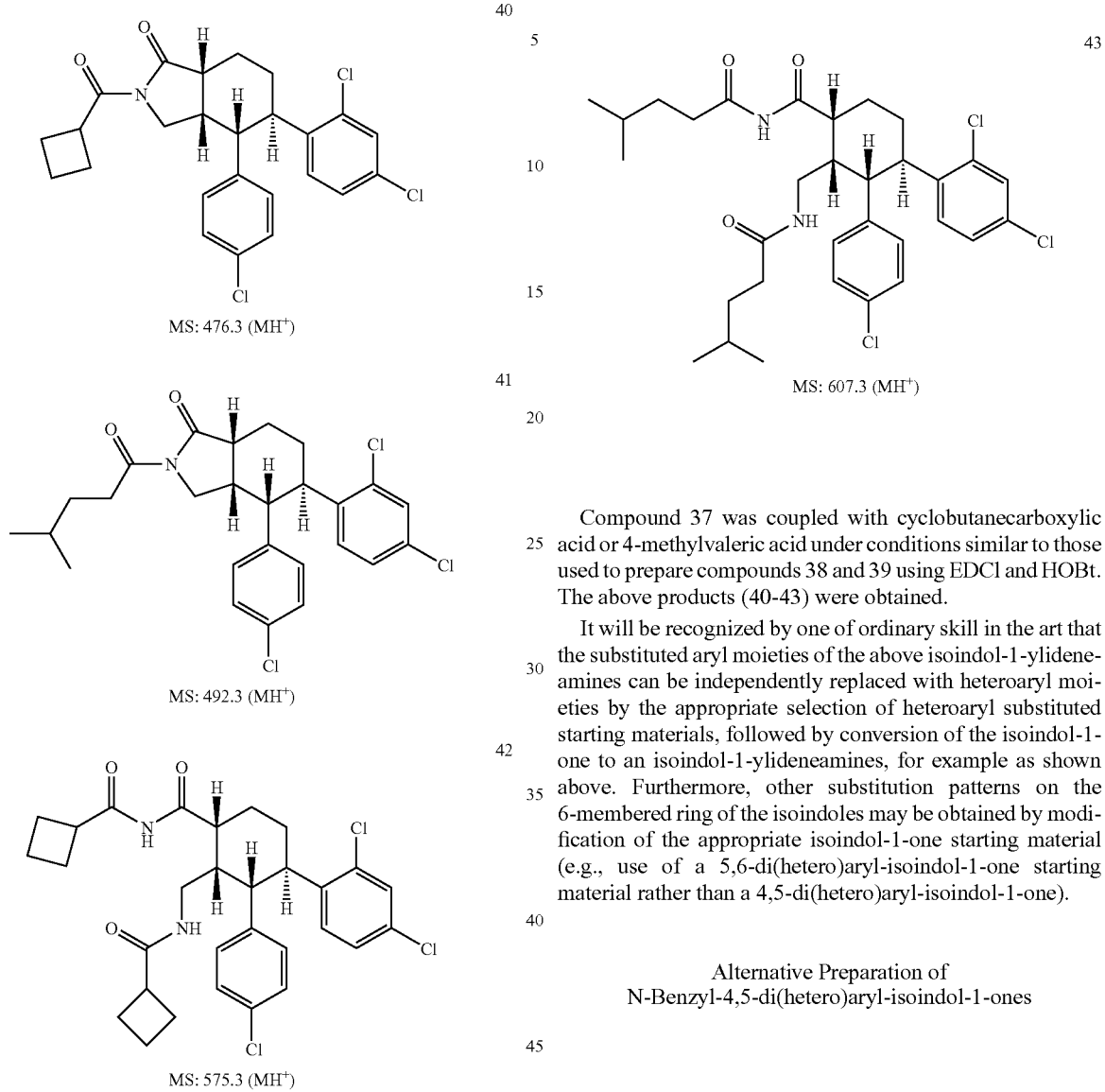

Compound 37 was coupled with cyclobutanecarboxylic acid or 4-methylvaleric acid under conditions similar to those used to prepare compounds 38 and 39 using EDCl and HOBt. The above products (40-43) were obtained.

It will be recognized by one of ordinary skill in the art that the substituted aryl moieties of the above isoindol-1-ylidene-amines can be independently replaced with heteroaryl moieties by the appropriate selection of heteroaryl substituted starting materials, followed by conversion of the isoindol-1-one to an isoindol-1-ylideneamines, for example as shown above. Furthermore, other substitution patterns on the 6-membered ring of the isoindoles may be obtained by modification of the appropriate isoindol-1-one starting material (e.g., use of a 5,6-di(hetero)aryl-isoindol-1-one starting material rather than a 4,5-di(hetero)aryl-isoindol-1-one).

Alternative Preparation of
N-Benzyl-4,5-di(hetero)aryl-isoindol-1-ones

Scheme 17:

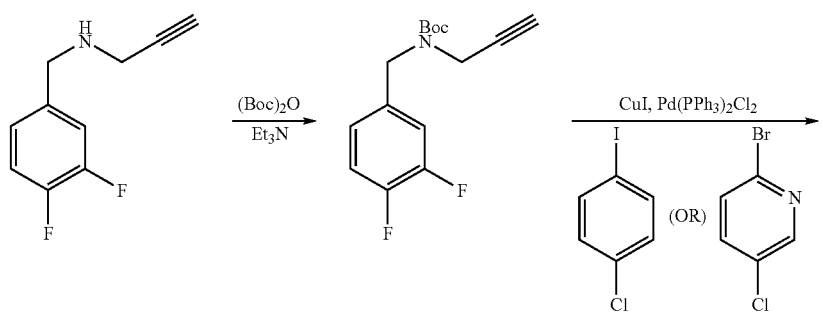

-continued
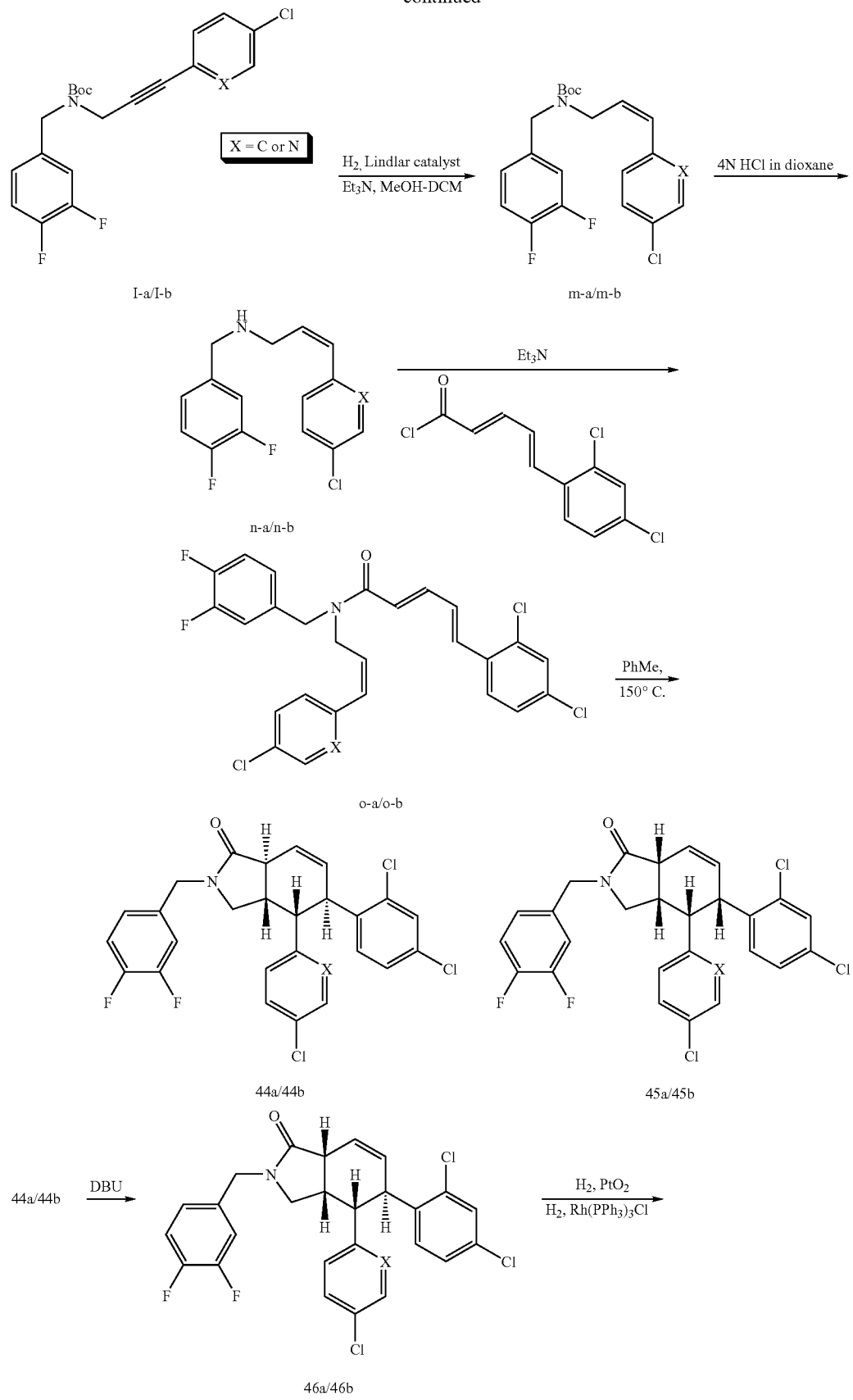

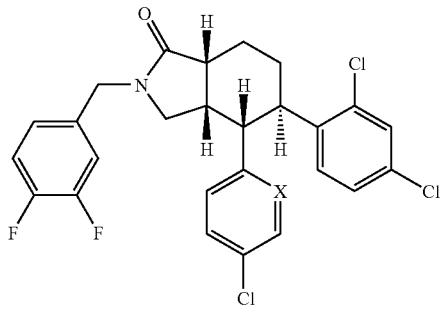

47a/47b

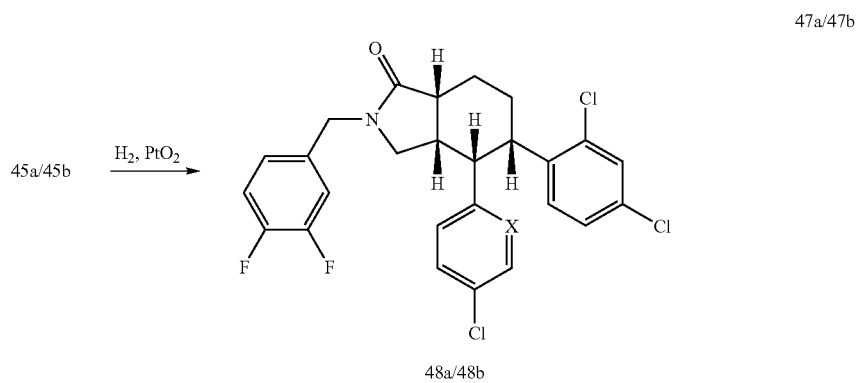

48a/48b

Alternatively, the group attached to the N atom of the desired 4,5-diphenyl-isoindol-1-one was inserted prior to the Diels-Alder reaction, for example as shown in Scheme 17, above. The propargyl amine (3,4-difluoro-benzyl)-prop-2-ynyl-carbamic acid tert-butyl ester was coupled with either 4-chloro iodobenzene or 2-bromo-5-chloro pyridine under Sonagashira conditions to provide l-a/l-b. The resulting alkyne was reduced to the cis-olefin (m-a/m-b) and the Boc group was cleaved under acidic conditions (n-a/n-b). The amine was coupled with 5-(2,4-dichloro-phenyl)-penta-2,4-dienoyl chloride and the Diels-Alder precursor o-a/o-b was thermally cyclized to provide 44a/44b and 45a/45b. The trans-lactam 44a/44b was isomerized to the cis-lactam 46a/46b using DBU, and the double bond was reduced either with $H_2/PtO_2$ or with $H_2/Rh(PPh_3)_3Cl$.

Alternative Preparation of Compounds 49 and 50

Step 1

Scheme 18:

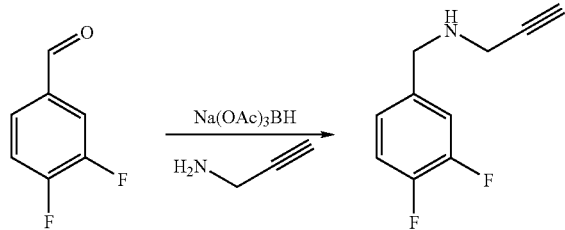

To a solution of 3,4-difluorobenzaldehyde (5 g, 35.2 mmol) in 200 mL dichloroethane was added mono-propargyl amine (4.85 mL, 70.7 mmol, 2 eq.) followed by Na(OAc)$_3$BH (9 g, 42.5 mmol) and the mixture was stirred for 2 days at room temperature. The solution was diluted with 100 mL of dichloromethane, washed with 2×100 mL aq. NaHCO$_3$, 100 mL brine, dried over Na$_2$SO$_4$, filtered and concentrated. The crude product was chromatographed with 20:80 ethyl acetate-hexanes to provide 3.8 g of (3,4-difluoro-benzyl)-prop-2-ynyl-amine as an oil.

MS: 182.15 (MH$^+$)

Step 2

Scheme 19:

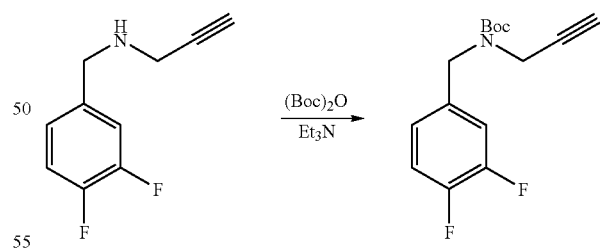

A mixture of (3,4-difluoro-benzyl)-prop-2-ynyl-amine (3.7 g, 20.4 mmol), triethylamine (4.3 mL, 30.9 mmol, 1.5 eq,) and (Boc)$_2$O (6.7 g, 30.7 mmol, 1.5 eq.) in 100 mL dichloromethane was stirred overnight at room temperature. The solution was diluted with 200 mL ether, washed with 2×100 mL aq. NaHCO$_3$, 100 mL brine, dried over MgSO$_4$, filtered, concentrated and chromatographed with 1:9 ethyl acetate-hexanes to provide 6.6 g of (3,4-difluoro-benzyl)-prop-2-ynyl-carbamic acid tert-butyl ester.

MS: 282.13 (MH$^+$)

Step 3

Scheme 20:

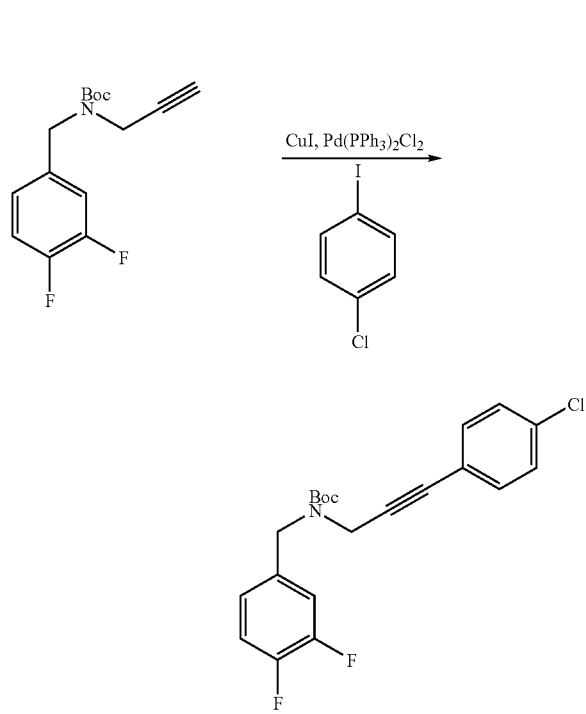

A mixture of (3,4-difluoro-benzyl)-prop-2-ynyl-carbamic acid tert-butyl ester (3.2 g, 11.4 mmol), 4-chloroiodobenzene (4.1 g, 17.2 mmol, 1.5 eq.), Pd(PPh$_3$)$_2$Cl$_2$ (0.4 g. 0.57 mmol, 5 mol %), iPr$_2$NH (4 mL, 28.5 mmol, 2.5 eq.) and CuI (0.435 g, 2.3 mmol, 0.2 eq.) in 100 mL dichloromethane was stirred overnight at room temperature. The solution was diluted with 300 mL ether and filtered through a CELITE pad to remove the insoluble components. The filtrate washed with 2×100 mL 1N HCl, 100 mL brine, dried over MgSO$_4$, filtered, concentrated and chromatographed with 6% ethyl acetate in hexanes to provide 2.6 g of [3-(4-chloro-phenyl)-prop-2-ynyl]-(3,4-difluoro-benzyl)-carbamic acid tert-butyl ester.

MS: 336.10 ([M-$^t$Bu]$^+$)

Step 4

Scheme 21:

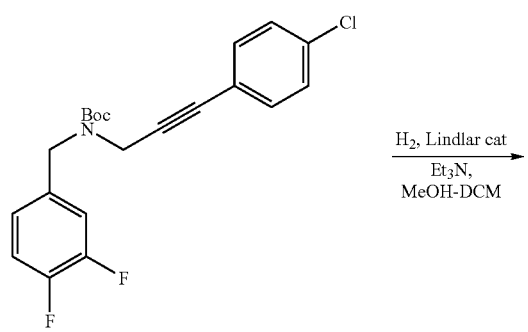

To a solution of [3-(4-chloro-phenyl)-prop-2-ynyl]-(3,4-difluoro-benzyl)-carbamic acid tert-butyl ester (1.05 g, 2.7 mmol) in 20 mL of 1:1 methanol-dichloromethane was added triethylamine (40 µL, 0.1 eq) and Lindlar catalyst (105 mg). The suspension was stirred under a H$_2$ balloon. After 1 hr, an additional 500 mg of Lindlar catalyst was added and the mixture was stirred for another 1.5 hr. The mixture was filtered through a CELITE pad and concentrated to provide the crude product.

The reaction was carried again with 1.5 g of [3-(4-chloro-phenyl)-prop-2-ynyl]-(3,4-difluoro-benzyl)-carbamic acid tert-butyl ester. The resultant crude product was combined with the crude product prepared in the first batch and chromatographed using 6% ethyl acetate-hexanes as solvent to provide 2.04 g of [3-(4-chloro-phenyl)-allyl]-(3,4-difluoro-benzyl)-carbamic acid tert-butyl ester.

MS: 338.11 ([M-$^t$Bu]$^+$)

Step 5

Scheme 22:

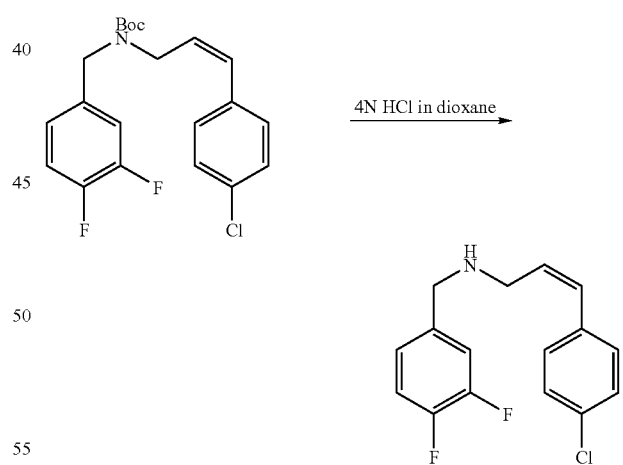

A solution of [3-(4-chloro-phenyl)-allyl]-(3,4-difluoro-benzyl)-carbamic acid tert-butyl ester (2.04 g) in 20 mL of 4N HCl in dioxane was stirred at room temperature for 1 hr. The solution was poured into 150 mL of aq. K$_2$CO$_3$, and extracted with 3×50 mL of ethyl acetate. The combined organic layer was washed with 50 mL brine, dried over Na$_2$SO$_4$, filtered and concentrated to provide 1.49 g of [3-(4-chloro-phenyl)-allyl]-(3,4-difluoro-benzyl)-amine.

MS: 294.12 (MH$^+$)

Step 6

Scheme 23:

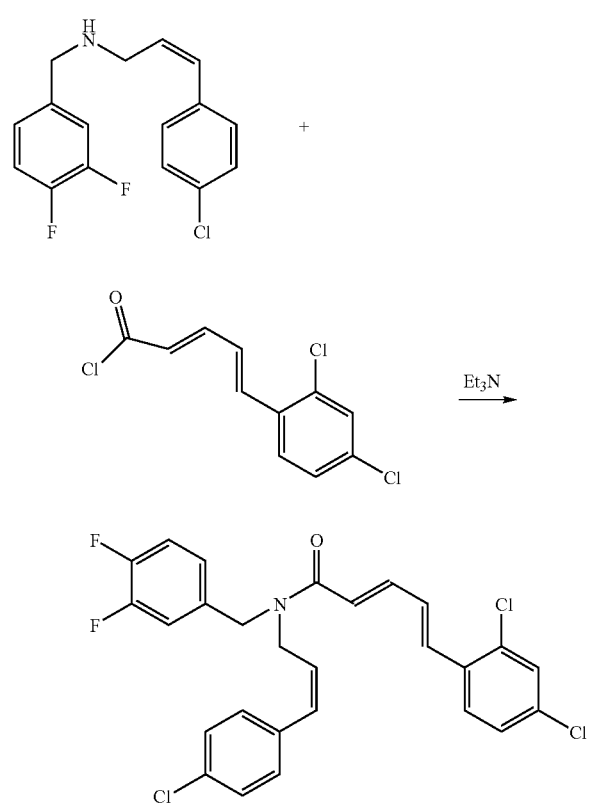

To a solution of [3-(4-chloro-phenyl)-allyl]-(3,4-difluoro-benzyl)-amine (1.49 g, 5.1 mmol), triethylamine (1.06 mL, 7.6 mmol, 1.5 eq.), DMAP (i.e., dimethylaminopyridine) (62 mg, 0.51 mmol, 0.1 eq.) in 15 mL dichloromethane at 0° C. was added a solution of 5-(2,4-dichloro-phenyl)-penta-2,4-dienoyl chloride (6.3 mmol) in 15 mL dichloromethane and stirred for 1 hr. After aqueous work-up, the crude product was purified by chromatography with 20% ethyl acetate-hexanes to provide 2.05 g of 5-(2,4-dichloro-phenyl)-penta-2,4-dienoic acid [3-(4-chloro-phenyl)-allyl]-(3,4-difluoro-benzyl)-amide.

MS: 518.11 (MH$^+$)

Step 7

Scheme 24:

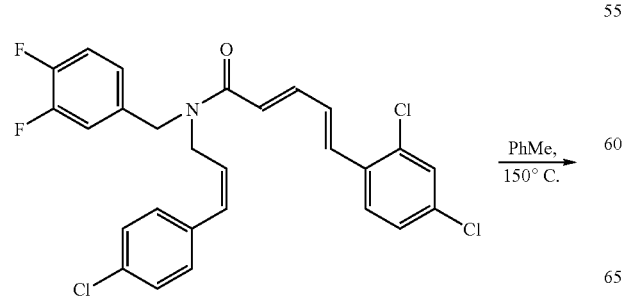

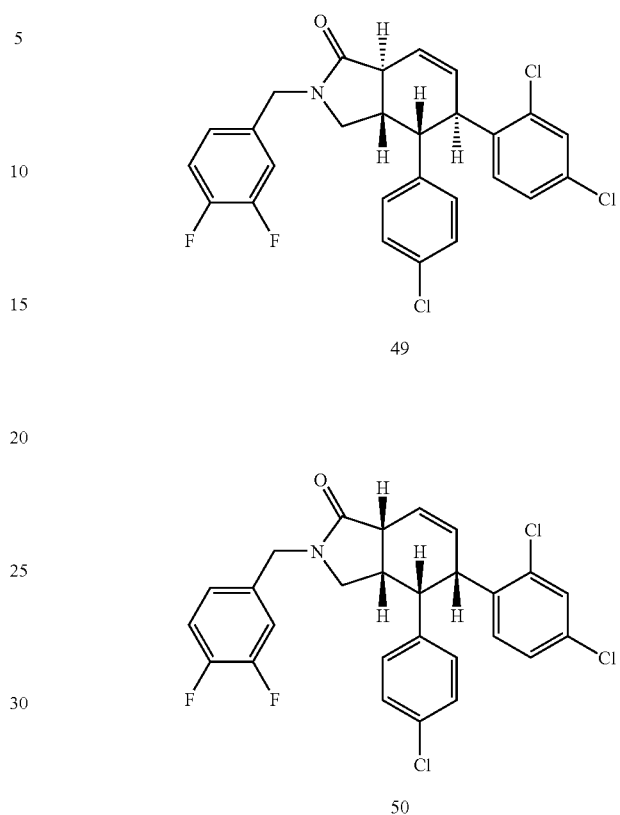

A solution of 5-(2,4-dichloro-phenyl)-penta-2,4-dienoic acid [3-(4-chloro-phenyl)-allyl]-(3,4-difluoro-benzyl)-amide (2.04 g) in 40 mL toluene was heated in a sealed tube at 150° C. for 2 hr. The solution was concentrated and chromatographed with 15% to 30% ethyl acetate in hexanes to provide 720 mg of 49 and 1.1 g of 50.

MS for 49: 518.3 (MH$^+$)

MS for 50: 518.3 (MH$^+$)

Preparation of Compound 51

Scheme 25:

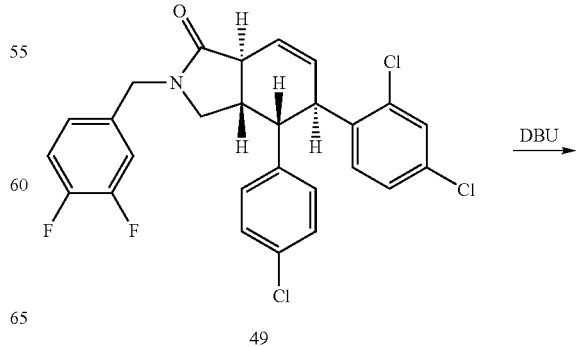

-continued

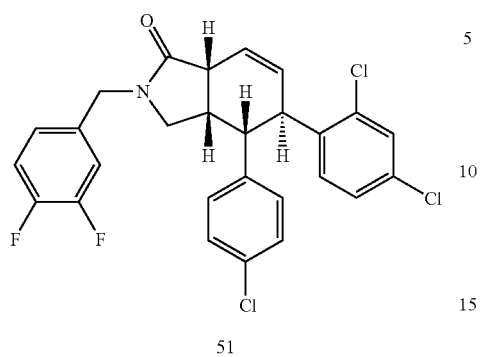

51

A solution of 49 (215 mg, 0.41 mmol) and DBU (63 mg, 0.42 mmol, 1 eq.) in 6 mL dichloromethane was stirred at room temperature for 2 hr, concentrated and chromatographed with 40% ethyl acetate-hexanes to provide 160 mg of 51.

MS: 519.07 (MH⁺)

Preparation of Compound 52

Scheme 26:

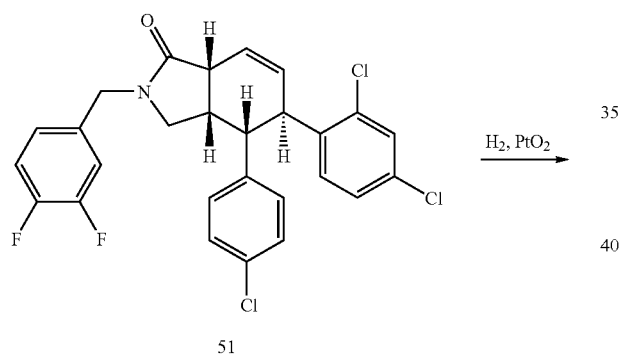

51

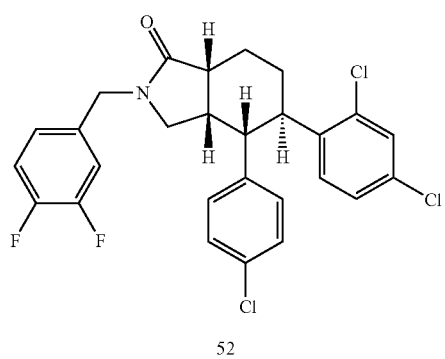

52

To a solution of 51 (105 mg) in 5 mL ethyl acetate was added 10 mg of PtO₂ and the suspension was stirred under a H₂ balloon for 80 min. The solution was then filtered through a CELITE pad, concentrated and chromatographed with 40% to 70% ethyl acetate-hexane to provide 67 mg of 52.

MS: 521.03 (MH⁺)

Preparation of Compounds 53 and 54

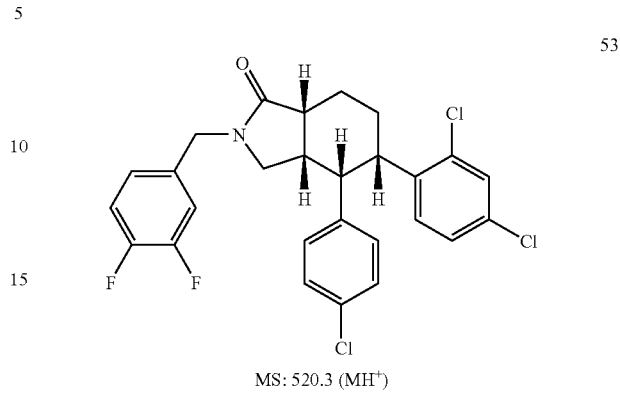

MS: 520.3 (MH⁺)

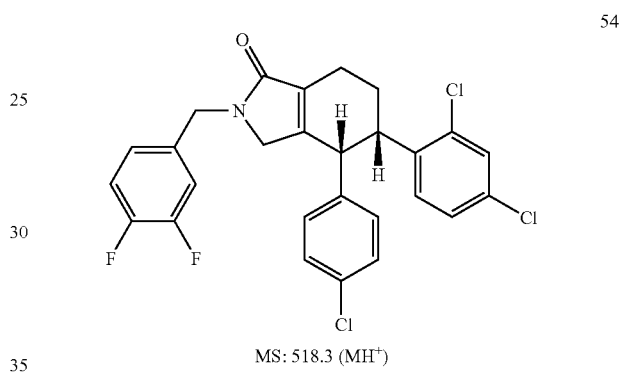

MS: 518.3 (MH⁺)

Using a procedure similar to the procedure described above in Scheme 26, compound 50 was reduced to compound 53. During this reaction, compound 54 was also obtained.

Preparation of Compounds 55-59

The following compounds (X═N) were also prepared using procedures similar to those described above in Scheme 17.

| Compound | MS (MH⁺) |
|---|---|
| 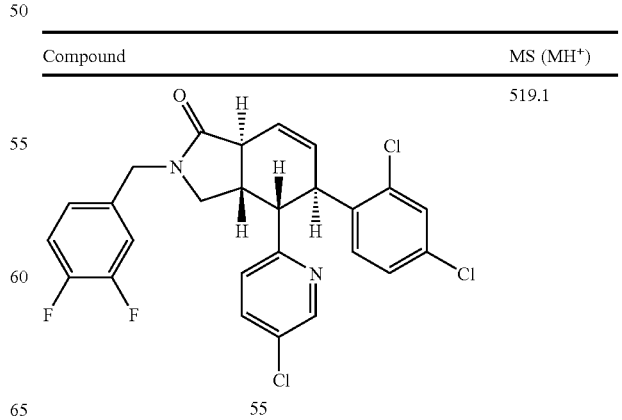 55 | 519.1 |

-continued
| Compound | MS (MH+) |
|---|---|
| 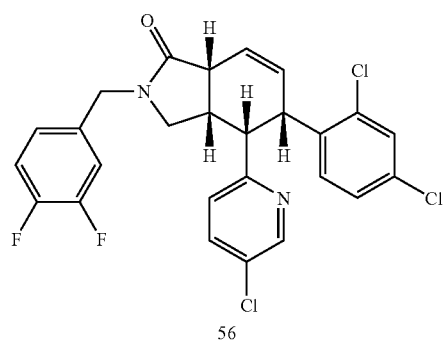 56 | 519.1 |
| 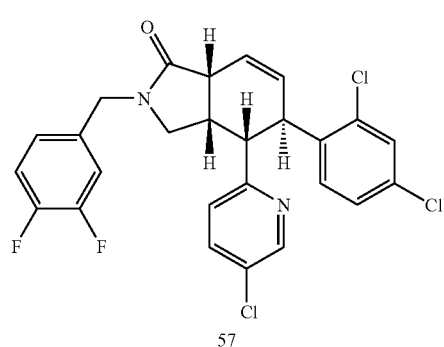 57 | 519.3 |
-continued
| Compound | MS (MH+) |
|---|---|
| 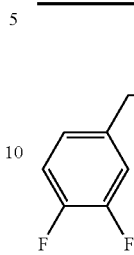 58 | 521.3 |
| 59 | 521.3 |
Preparation of Compounds 60-62
Scheme 27:
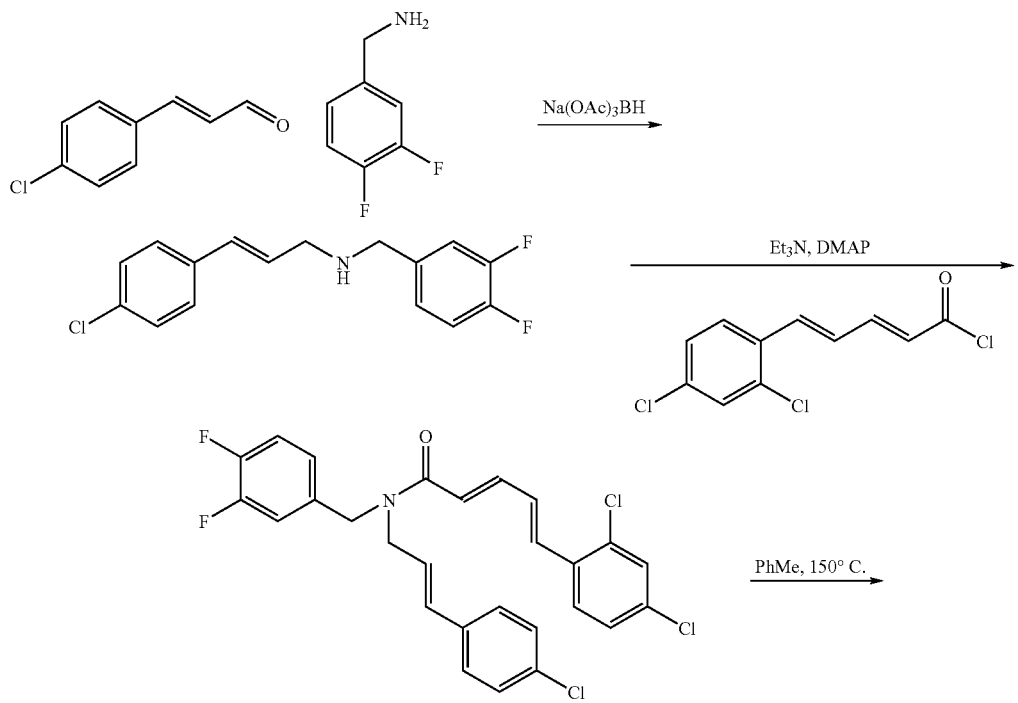

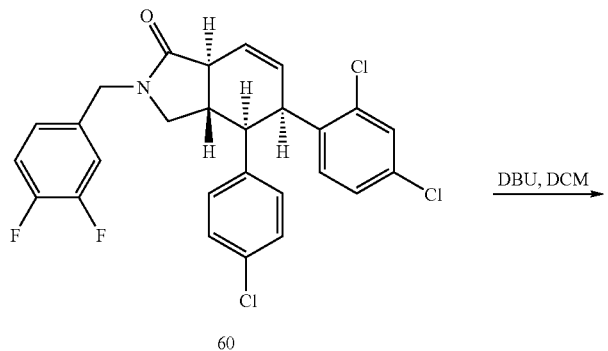

60

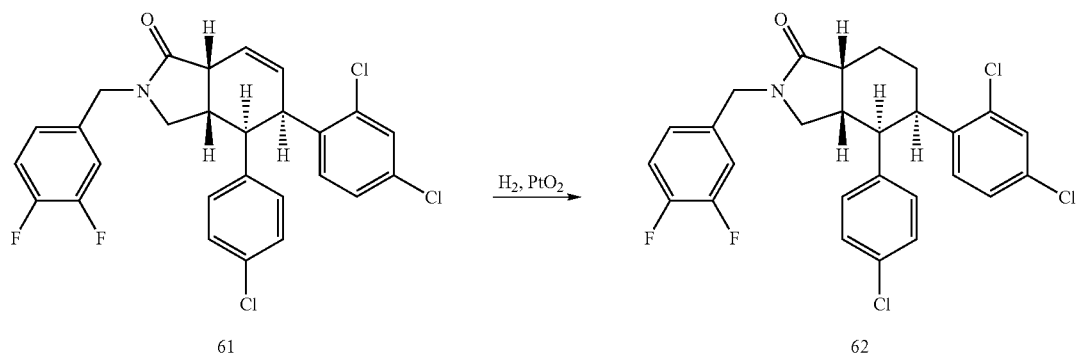

61             62

The cis-diaryl compounds were prepared as shown above. To a solution of 4-chlorocinnamaldehyde (1.45 g, 8.70 mmol) in 100 mL of dichloroethane was added 3,4-difluorobenzylamine followed by sodium triacetoxyborohydride (3.7 g, 17.5 mmol, 2 eq.). The mixture was stirred overnight at room temperature, washed with aq. NaHCO$_3$, brine, dried over MgSO$_4$, filtered, concentrated and chromatographed with 40% ethyl acetate-hexanes to provide 0.84 g of [3-(4-chloro-phenyl)-allyl]-(3,4-difluoro-benzyl)-amine. The [3-(4-chloro-phenyl)-allyl]-(3,4-difluoro-benzyl)-amine was coupled with 5-(2,4-dichloro-phenyl)-penta-2,4-dienoyl chloride to provide 5-(2,4-dichloro-phenyl)-penta-2,4-dienoic acid [3-(4-chloro-phenyl)-allyl]-(3,4-difluoro-benzyl)-amide. When 5-(2,4-dichloro-phenyl)-penta-2,4-dienoic acid [3-(4-chloro-phenyl)-allyl]-(3,4-difluoro-benzyl)-amide was subjected to the Diels-Alder reaction conditions shown above, it gave 60 as the major product. Epimerization of the trans-lactam gave 61 and reduction of the double bond of 61 gave 62.

| Compound | MS (MH$^+$) |
|----------|-------------|
| 60 | 518.18 |
| 61 | 518.06 |
| 62 | 520.05 |

Preparation of Compounds 63-65

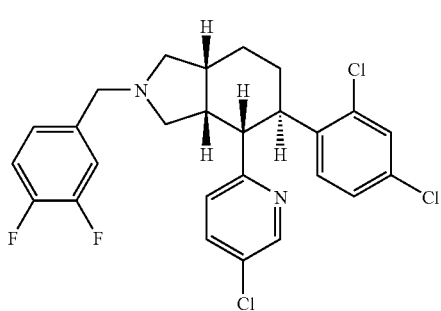

63

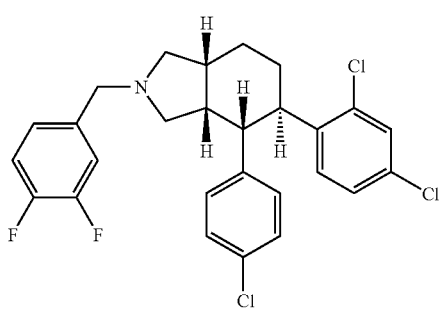

64

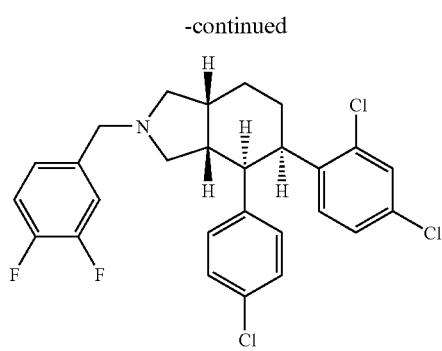

Substituted N-benzyl-4,5-diphenyl-isoindoles 63-65 were prepared by reducing the corresponding lactams. As a representative example, the preparation of 64 is presented below.

Scheme 28

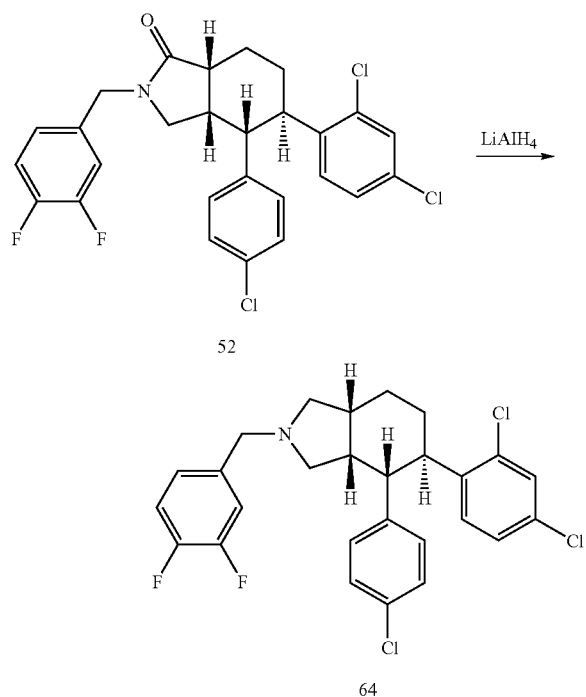

To a solution of 52 (160 mg, 0.31 mmol) in 3 mL THF at was added 0.92 mL of 1M solution of LiAlH$_4$ in THF and the mixture was heated at reflux for 1 hr. The solution was cooled to room temperature and successively added 30 μL water, 30 μL 15% aq. NaOH solution and 90 μL water. The precipitate was filtered off and the filtrate was concentrated and chromatographed with 30% ethyl acetate-hexane to provide 108 mg of 64.

MS: 506.3 (MH$^+$)

Compounds 63 and 65 were prepared using similar procedures from the appropriate starting lactam.

63 [MS: 507.3 (MH$^+$)]
65 [MS: 506.3 (MH$^+$)].

It will be recognized by one of ordinary skill in the art that the substituted aryl moieties of the above isoindoles can be independently replaced with heteroaryl moieties by the use of the appropriate heteroaryl substituted starting materials.

It will also be recognized by one of ordinary skill in the art that isoindoles having different substitution patterns of aryl and/or heteroaryl groups on the six-membered ring may be provided by use of the appropriate starting materials. In addition, substitution on the isoindole nitrogen atom may be provided by methods known in the art (e.g., alkylation, acylation, arylation, etc.).

Preparation of Compounds 66-71

The Diels-Alder reaction (e.g., Scheme 45, Step 3) can also be carried out using a Boc protected intermediate such as [5-(2-chloro-4-methoxy-phenyl)-penta-2,4-dienoyl]-[3-(4-chloro-phenyl)-allyl]-carbamic acid tert-butyl ester as described below in Scheme 29 to give the cyclization products 66 and 67. The trans-lactam 66 can be epimerized to the cis-lactam 68, the double bond reduced and the Boc group cleaved to give 69. Alternatively, 69 can be prepared by first cleaving the Boc group followed by lactam epimerization and double bond reduction.

Scheme 29:

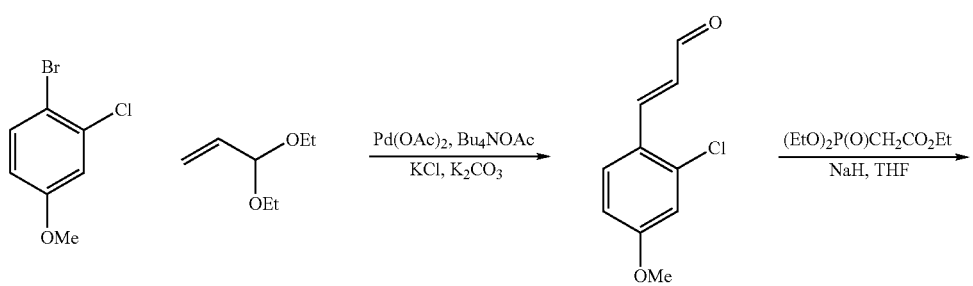

-continued
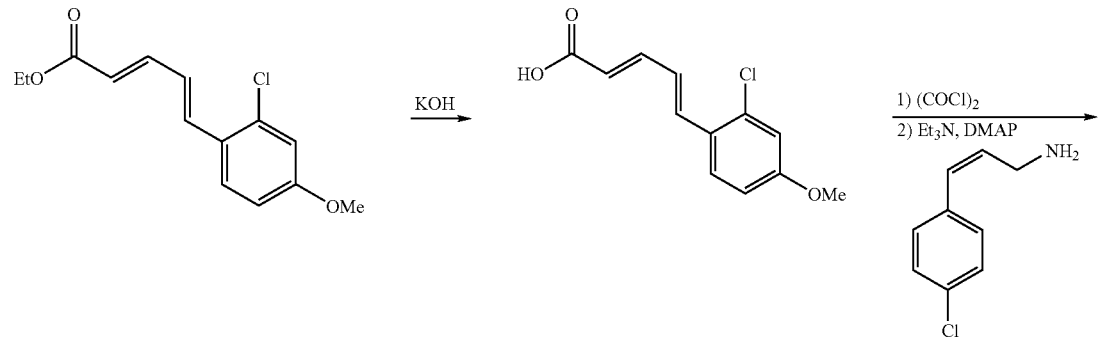
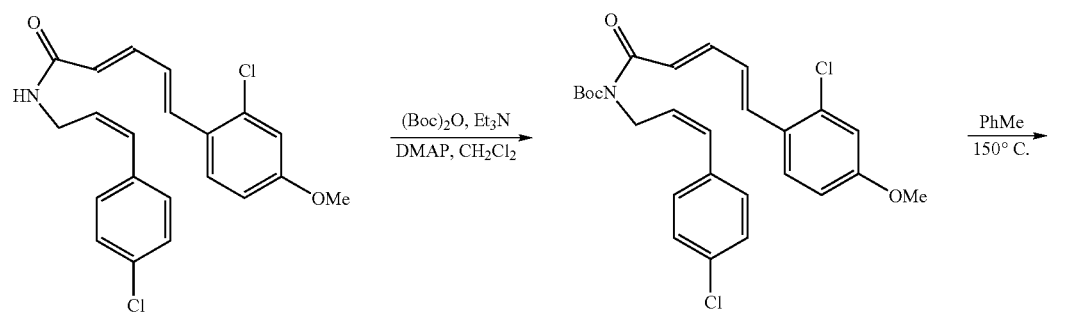
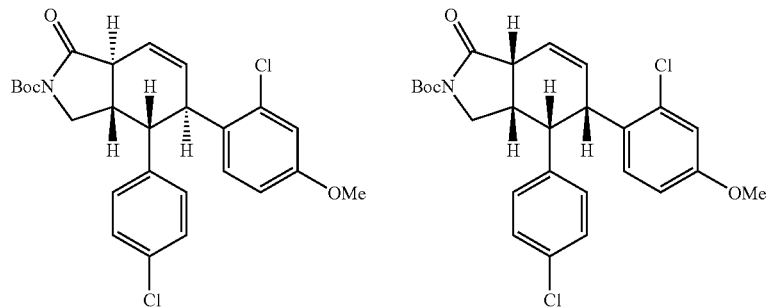
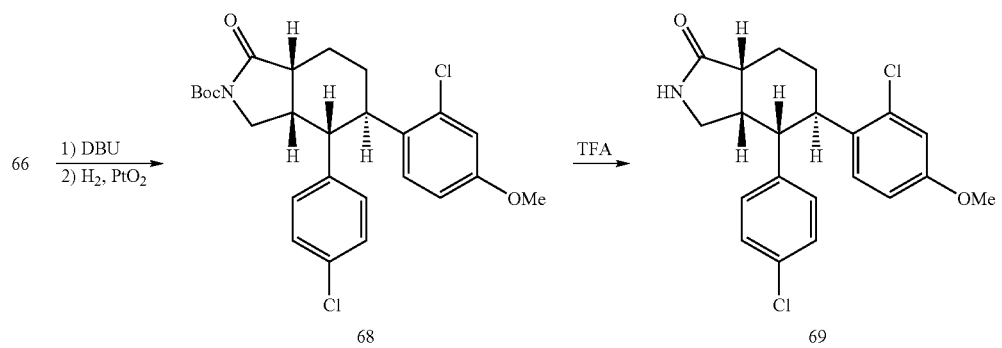

-continued

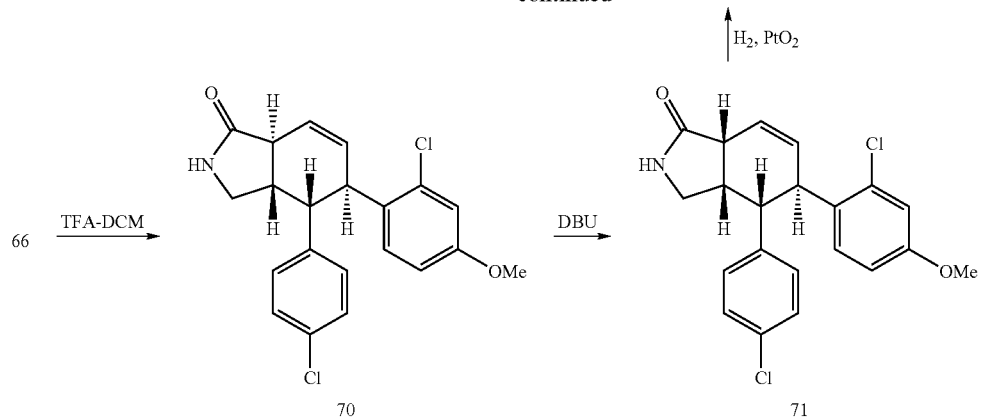

Step 1
Scheme 30:

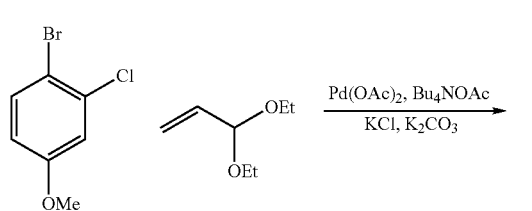

Step 2
Scheme 31:

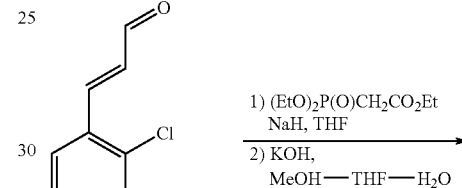

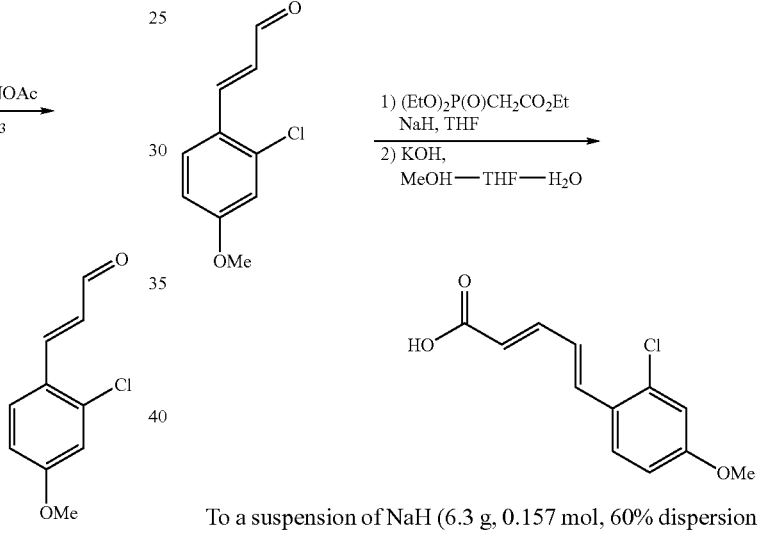

To a mixture of 4-bromo-3-chloro anisole (35 g, 0.159 mol), KCl (11.9 g, 0.160 mol, 1 eq.), $K_2CO_3$ (33 g, 0.238 mol, 1.5 eq) in 400 mL DMF in a sealed tube was added acrolein diethylacetal (73 mL, 0.479 mol, 3 eq.) and $Bu_4NOAc$ (96 g, 0.318 mol, 2 eq.). $N_2$ was bubbled through the mixture and $Pd(OAc)_2$ (1.1 g, 4. mmol, 3 mol %) was added. The reaction mixture was heated in an oil bath for 6 hr at 100° C. then cooled in an ice-bath. 300 mL of water was then added, followed by 500 mL of 1N HCl. The ice-bath was removed and the mixture was stirred for 30 min. The solution was extracted with ethyl acetate once then with diethyl ether 3 times. The combined organic layer washed with water, brine, dried over $MgSO_4$, filtered and concentrated to provide the crude product which was recrystallized from hot ethyl acetate-hexanes to provide 15.5 g of crystalline 3-(2-chloro-4-methoxy-phenyl)-propenal. The mother liquor was concentrated and chromatographed with 10% ethyl acetate to provide another 5.6 g of 3-(2-chloro-4-methoxy-phenyl)-propenal.

To a suspension of NaH (6.3 g, 0.157 mol, 60% dispersion in mineral oil) in 400 mL THF at room temperature was added triethyl phosphonoacetate (29 mL, 0.146 mol) and stirred for 30 min. The solution was cooled in an ice-bath and a solution of 3-(2-chloro-4-methoxy-phenyl)-propenal (22 g, 0.112 mol) in 200 mL THF was added. The mixture was stirred for 1 hr and quenched with the addition of aq. $NH_4Cl$. The THF was evaporated and the slurry was extracted with diethyl ether. The combined organic layer was washed with water, brine, dried over $MgSO_4$, filtered and concentrated to provide the crude 5-(2-chloro-4-methoxy-phenyl)-penta-2,4-dienoic acid ethyl ester.

The crude ester product was taken up in 200 mL each of methanol and THF and then cooled to 0° C. To this mixture was added a solution of KOH (19 g, 0.338 mol, 3 eq.) in 200 mL $H_2O$. The mixture was stirred at room temperature for 1.5 hr and the organic solvent was evaporated. The aqueous layer was diluted with 300 mL $H_2O$ and washed with ether to remove the mineral oil. It was then cooled in an ice-bath and acidified with concentrated HCl to ~pH 2. The thick precipitate was filtered and rinsed with water, then dried in a vacuum oven at 75° C. to provide 26.2 g of 5-(2-chloro-4-methoxy-phenyl)-penta-2,4-dienoic acid.

MS: 239.24 ($MH^+$)

Step 3

Scheme 32:

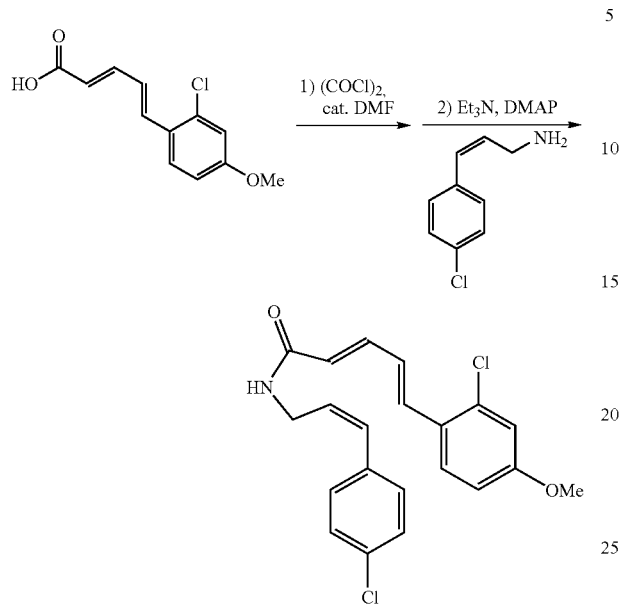

To a suspension of 5-(2-chloro-4-methoxy-phenyl)-penta-2,4-dienoic acid (6 g, 25.1 mmol) in 100 mL dichloromethane at room temperature was added oxalyl chloride (4.4 mL, 50.4 mmol, 2 eq.) followed by DMF (39 µL, 0.51 mmol, 2 mol %). The mixture was stirred for 1 hr and the resultant clear solution was concentrated and evaporated with toluene to provide an acid chloride.

The acid chloride was dissolved in 150 mL dichloromethane, cooled to 0° C., and then triethylamine (5.3 mL, 38.0 mmol, 1.5 eq.), DMAP (310 mg, 2.54 mmol, 0.1 eq.) followed by a solution of 3-(4-chloro-phenyl)-allylamine (5.1 g, 30.2 mmol, 1.2 eq.) in dichloromethane were added. The mixture was stirred for 1 hr at room temperature, diluted with 700 mL ethyl acetate and washed with 1N HCl, aq. NaHCO$_3$ and brine. It was dried over MgSO$_4$, filtered and concentrated to provide 10.1 g of 5-(2-chloro-4-methoxy-phenyl)-penta-2,4-dienoic acid [3-(4-chloro-phenyl)-allyl]-amide.

MS: 388.19 (MH$^+$)

Step 4

Scheme 33:

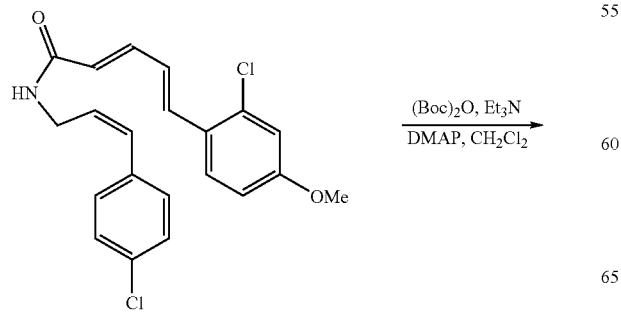

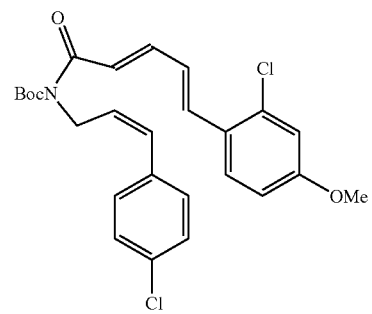

To a suspension of 5-(2-chloro-4-methoxy-phenyl)-penta-2,4-dienoic acid [3-(4-chloro-phenyl)-allyl]-amide (9.8 g, 25 mmol) and (Boc)$_2$O (11 g, 50.4 mmol, 2 eq.) in 150 mL dichloromethane was added triethylamine (3.5 mL, 25.1 mmol, 1 eq.) followed by DMAP (3.1 g, 25.4 mmol, 1 eq.). The mixture was stirred for 1 hr at room temperature, diluted with ether, washed with 1N HCl, aq. NaHCO$_3$, brine, dried over MgSO$_4$, filtered and concentrated to provide 9.8 g of [5-(2-chloro-4-methoxy-phenyl)-penta-2,4-dienoyl]-[3-(4-chloro-phenyl)-allyl]-carbamic acid tert-butyl ester.

Step 5

Scheme 34:

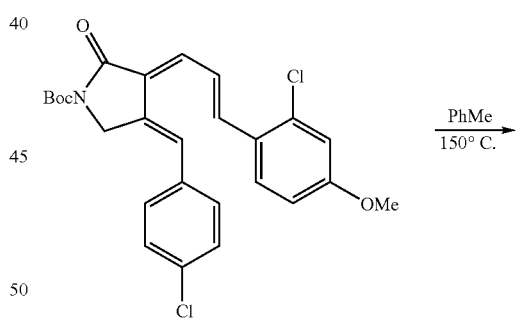

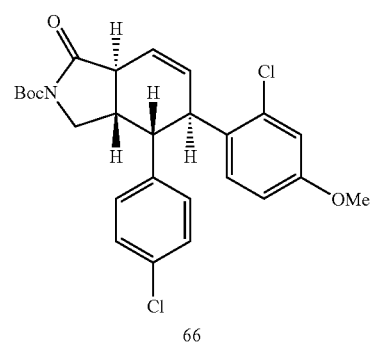

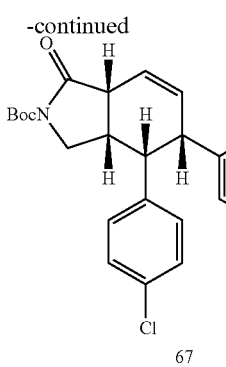

67

A solution of 5-(2-chloro-4-methoxy-phenyl)-penta-2,4-dienoyl]-[3-(4-chloro-phenyl)-allyl]-carbamic acid tert-butyl ester (9.5 g) in 200 mL toluene was heated in a sealed tube at 150° C. for 3 hr. The solution was concentrated and chromatographed with 15% to 30% ethyl acetate-hexanes to provide 4.8 g of 66 and 2.8 g of 67.

MS for 66: 488.3 (MH$^+$)
MS for 67: 488.3 (MH$^+$)

Step 6

Scheme 35:

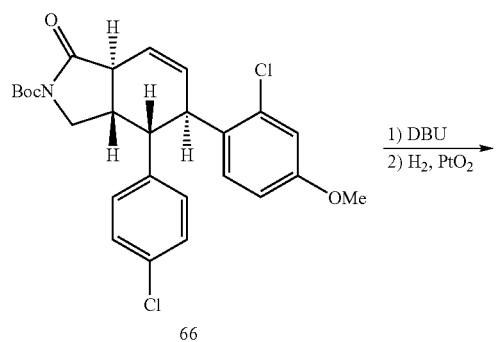

A solution of 66 (690 mg, 1.41 mmol) in 15 mL of dichloromethane was stirred at room temperature with DBU (215 mg, 1.41 mmol, 1 eq.) for 1 hr, concentrated and chromatographed with 20% to 30% ethyl acetate-hexane to provide a mixture of products. This mixture was taken up in 15 mL of 1:1 methanol-dichloromethane and stirred under a H$_2$ balloon with 65 mg of PtO$_2$ for 30 min., then filtered though a CELITE pad, concentrated and chromatographed with 30% ethyl acetate-hexane to provide 34 mg of 68.

MS: 434.2 ([M-$^t$Bu]$^+$)

Step 7

Scheme 36:

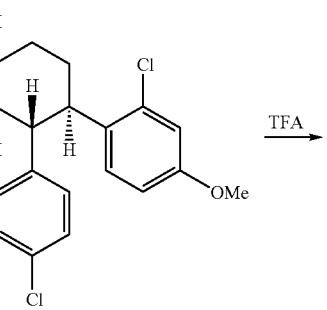

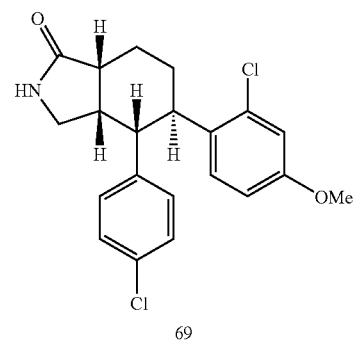

To a flask containing 32 mg of 68 was added 1 mL of TFA (i.e., trifluoroacetic acid). The mixture was stirred for 1 hr at room temperature, then concentrated and chromatographed with 3% methanol-dichloromethane to provide 25 mg of 69.

MS: 390.2 (MH$^+$)

Step 8

Scheme 37:

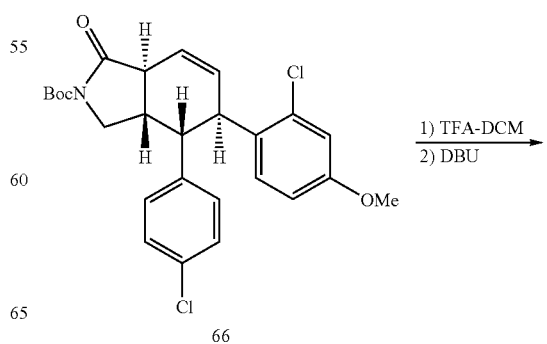

-continued

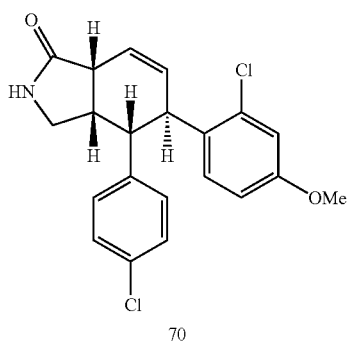
70

To a solution of 66 (2.3 g, 4.71 mmol) in 20 mL dichloromethane at 0° C. was added 20 mL of TFA. The mixture was stirred for 50 min, then concentrated to provide the deprotected product.

The deprotected product was stirred overnight with 720 mg of DBU in 20 mL each of dichloromethane and acetonitrile. After overnight stirring, another 25 mL of acetonitrile and 1.4 g of DBU was added and the mixture was stirred for 2.5 hr. The mixture was diluted with ethyl acetate, washed with 1N HCl, brine, dried over MgSO$_4$, filtered, concentrated and chromatographed with 50% to 60% ethyl acetate-hexane then with 5% methanol-dichloromethane to provide 1.88 g of 71.
MS: 388.2 (MH$^+$)

Alternate Preparation of 69

Scheme 38:

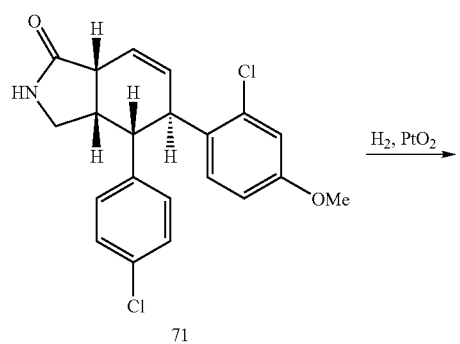

To a solution of 71 (1.8 g) in 50 mL of 1:9 methanol-dichloromethane was added 90 mg of PtO$_2$ and the suspension was stirred under a H$_2$ balloon for 40 min. The mixture was then filtered though a CELITE pad, concentrated and the crude product recrystallized from a hot dichloromethane-hexane mixture to provide 1.1 g of crystalline 69.
MS: 390.2 (MH$^+$)

Preparation of Compounds 72-78

Scheme 39:

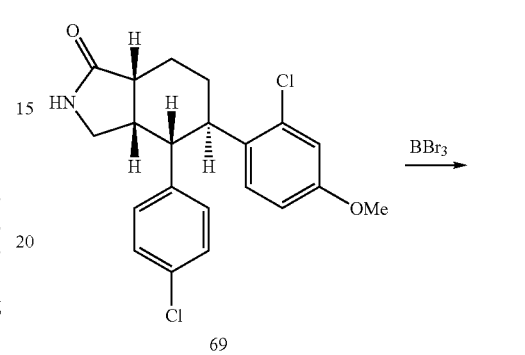
69

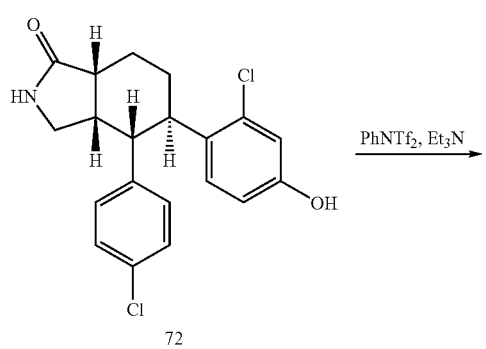
72

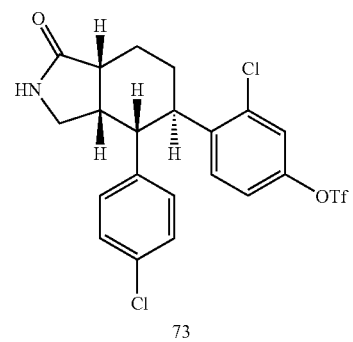
73

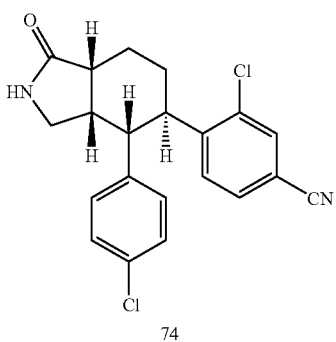
74

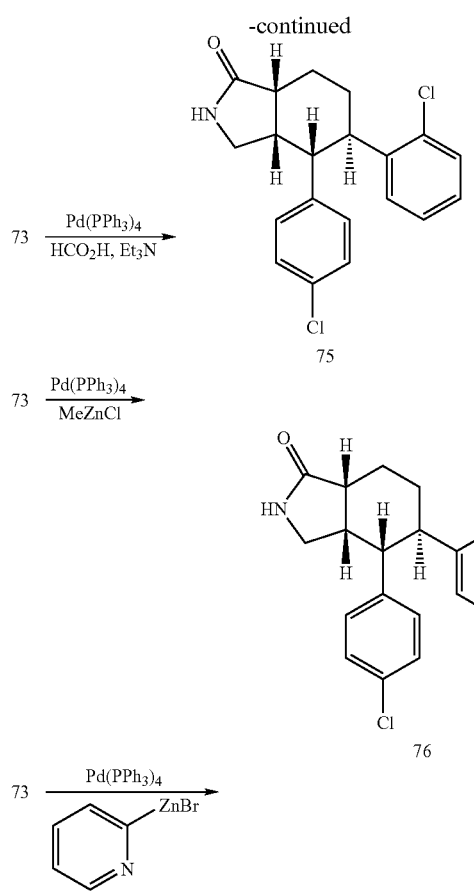

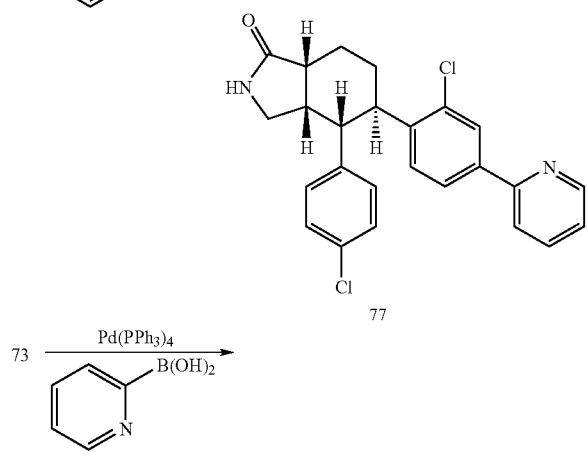

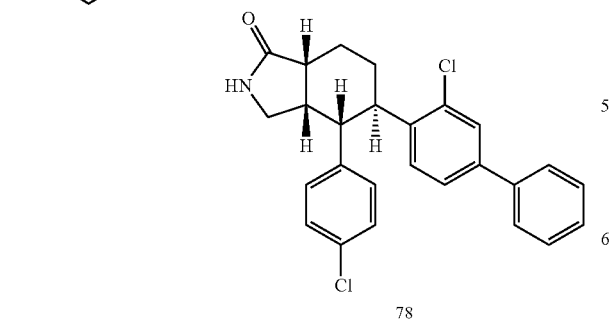

The methoxy functionality at the 5-phenyl group can be converted into a variety of other groups. For example, as shown above, the methoxy group of 69 was hydrolyzed to a hydroxyl 72, which was then converted to the triflate 73. The triflate 73 was converted to the CN derivative 74 using Zn(CN)$_2$ and Pd catalyst or it was reduced to 75 using formic acid and a Pd catalyst. The triflate 73 was reacted with Zn reagents to provide compounds 76 and 77 or with boronic acid to give 78.

Preparation of Compound 72

Scheme 40:

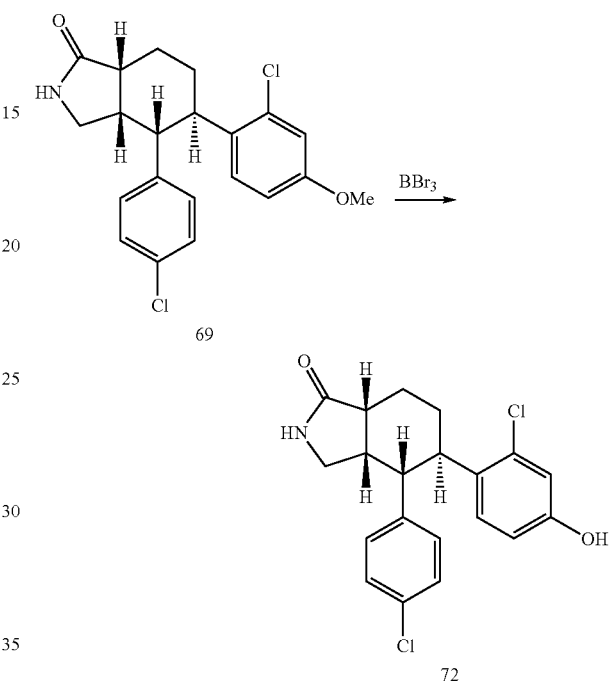

To a solution of 69 (600 mg, 1.54 mmol) in 15 mL dichloromethane was added BBr$_3$ (7.7 mL of a 1M solution in dichloromethane). The mixture was stirred for 1 hr at 0° C. then stirred with 100 mL water for 20 min. The dichloromethane layer was separated and the aqueous phase was extracted with ethyl acetate. The combined organic layer washed with water, brine, dried over MgSO$_4$, filtered, concentrated and chromatographed with 3% to 10% methanol-dichloromethane to provide 535 mg of 72.

MS: 376.2 (MH$^+$)

Preparation of Compound 73

Scheme 41:

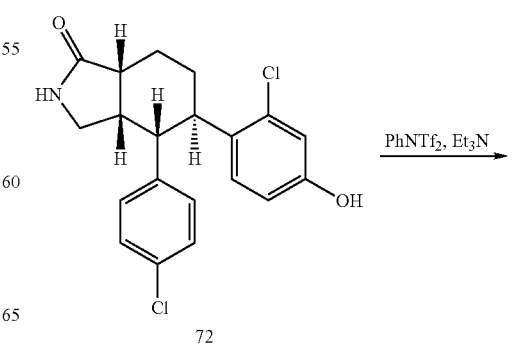

-continued

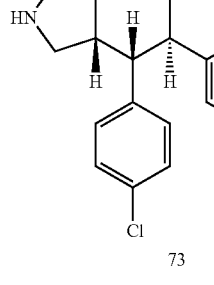
73

To a suspension of 72 (400 mg, 1.1 mmol) in 10 mL acetonitrile was added triethylamine (300 μL, 2.1 mmol, 2 eq.) followed by N-phenyltrifluoromethane sulfonimide (870 mg, 1.5 eq.). The mixture was stirred for 2.5 hr at room temperature and the clear solution was diluted with ethyl acetate, washed twice with aq. NaHCO₃, brine, dried over MgSO₄, filtered, concentrated and chromatographed with 3% methanol-dichloromethane to provide 490 mg of 73.

Preparation of Compound 74

Scheme 42:

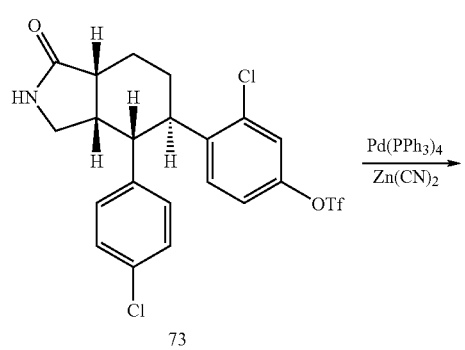

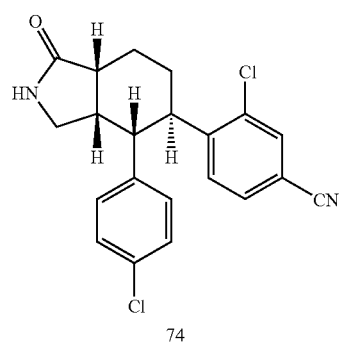
74

A mixture of 73 (62 mg, 0.12 mmol), Zn(CN)₂ (9 mg, 0.08 mmol, 0.6 eq.) and Pd(PPh₃)₄ (14 mg, 0.012 mmol, 0.1 eq.) in 1 mL DMF in a sealed tube was heated at 100° C. for 1 hr. The mixture was diluted with water, washed twice with water, brine, dried over MgSO₄, filtered, concentrated and the crude product was purified by preparative TLC using 80% ethyl acetate-hexane to provide 50 mg of 74.

MS: 385.21 (MH⁺)

Preparation of Compound 75

Scheme 43:

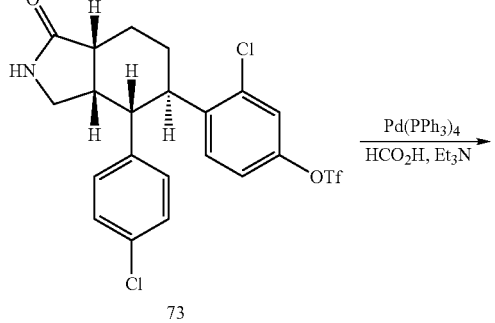
73

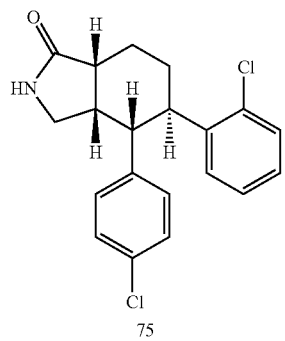
75

A mixture of 73 (50 mg, 0.10 mmol), HCO₂H (19 μL, 0.50 mmol, 5 eq.), triethylamine (70 μL, 0.5 mmol, 5 eq.) and Pd(PPh₃)₄ (6 mg, 5.2 μmol, 5 mol %.) in 1 mL DMF in a sealed tube was heated at 100° C. for 4 hr. The mixture was diluted with ethyl acetate, washed twice with aq. NaHCO₃, brine, dried over MgSO₄, filtered, concentrated and the product was purified by preparative TLC using 3% methanol-dichloromethane to provide 29 mg of 75.

MS: 360.2 (MH⁺)

Preparation of Compound 76

Scheme 44:

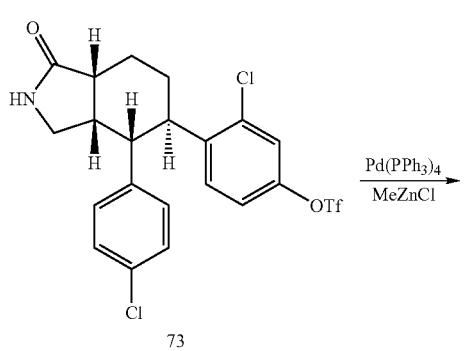
73

-continued

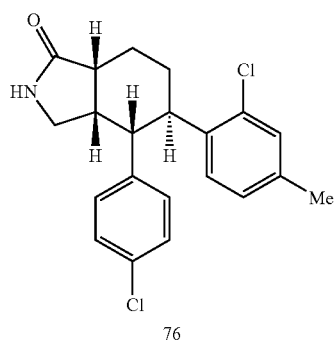

76

A mixture of 73 (50 mg, 0.10 mmol), MeZnCl (0.5 mL of 2M solution, 10 eq.), and Pd(PPh$_3$)$_4$ (6 mg, 5.2 µmol, 5 mol %.) in 1 mL THF in a sealed tube was heated at 80° C. for 4 hr. The mixture was quenched with methanol, diluted with ethyl acetate and washed twice with 1N HCl, brine, dried over MgSO$_4$, filtered and concentrated and the crude product was purified by preparative TLC using 60% ethyl acetate-hexane to provide 26 mg of 76.

MS: 385.21 (MH$^+$)

Preparation of Compound 77

Scheme 45:

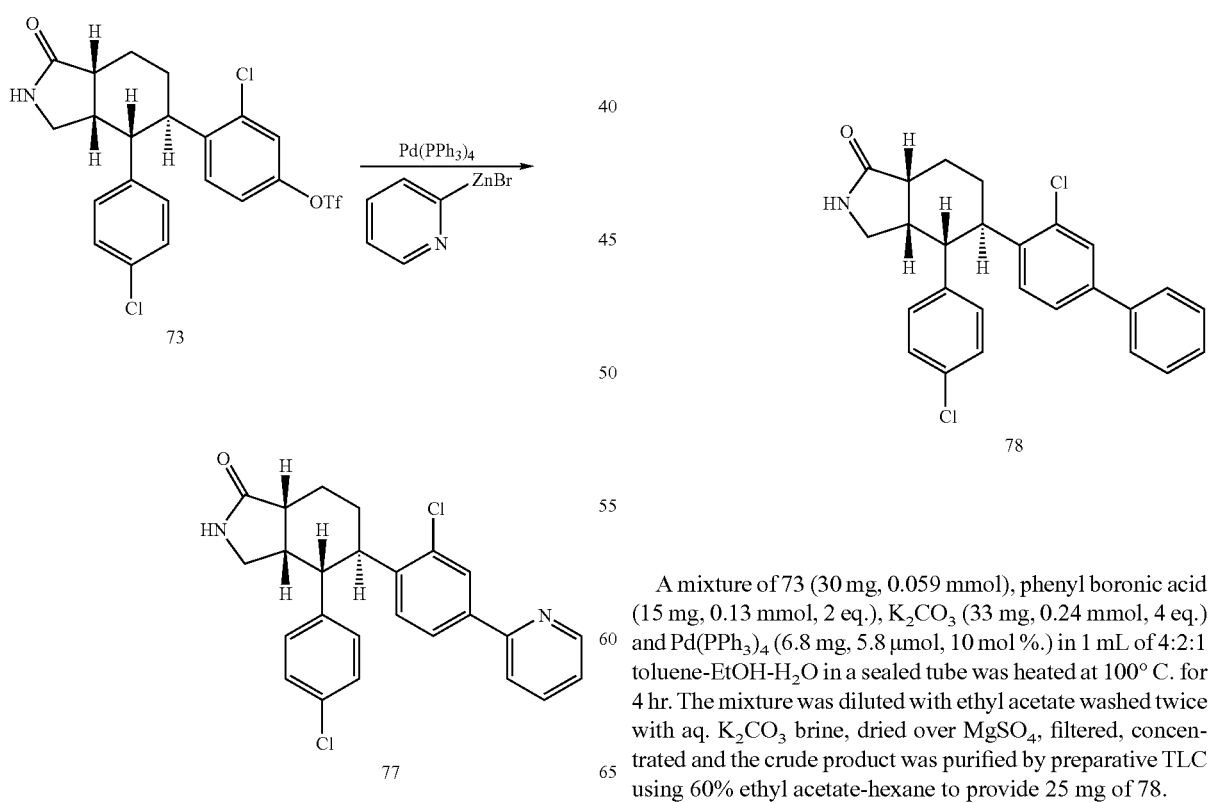

77

A mixture of 73 (30 mg, 0.059 mmol), 2-pyridyl zinc bromide (0.59 mL of 0.5M solution, 5 eq.), and Pd(PPh$_3$)$_4$ (6.8 mg, 5.8 µmol, 10 mol %.) in 0.5 mL THF in a sealed tube was heated at 100° C. for 4 hr. The mixture was diluted with ethyl acetate washed twice with aq. NH$_4$Cl, brine, dried over MgSO$_4$, filtered, concentrated and the crude product was purified by preparative TLC using 3% methanol-dichloromethane to provide 8 mg of 77.

MS: 437.2 (MH$^+$)

Preparation of Compound 78

Scheme 46:

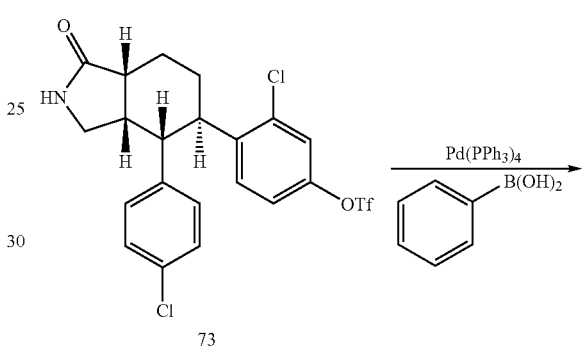

73

78

A mixture of 73 (30 mg, 0.059 mmol), phenyl boronic acid (15 mg, 0.13 mmol, 2 eq.), K$_2$CO$_3$ (33 mg, 0.24 mmol, 4 eq.) and Pd(PPh$_3$)$_4$ (6.8 mg, 5.8 µmol, 10 mol %.) in 1 mL of 4:2:1 toluene-EtOH-H$_2$O in a sealed tube was heated at 100° C. for 4 hr. The mixture was diluted with ethyl acetate washed twice with aq. K$_2$CO$_3$ brine, dried over MgSO$_4$, filtered, concentrated and the crude product was purified by preparative TLC using 60% ethyl acetate-hexane to provide 25 mg of 78.

MS: 436.2 (MH$^+$)

Preparation of Compounds 79-86
Scheme 47:
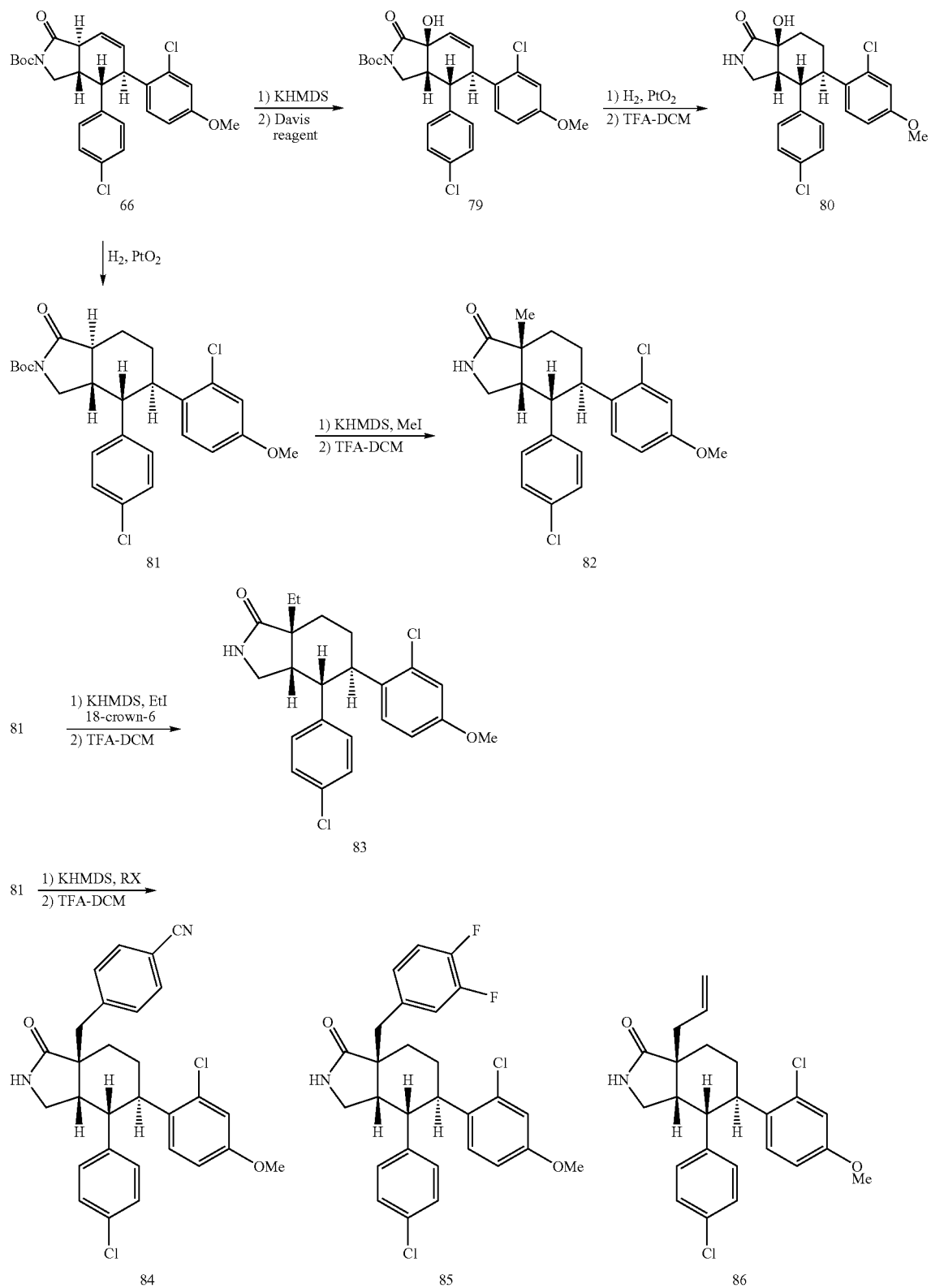

The 7a-position of the isoindolone can be functionalized as shown above in Scheme 47 by reacting the enolate with the appropriate electrophiles. For example, a hydroxy functionality was introduced in 66 by generating the potassium enolate followed by reaction with oxaziridine. Double-bond reduction followed by deprotection of the Boc group gave 80. Alternatively, the double bond was reduced before generating the enolate (e.g., reduction of 66 to form 81). Compound 81 was subsequently reacted with MeI and TFA to give 82. Alkylation, e.g., ethylation with KHMDS/18-crown-6 and EtI, gave 83. In a similar fashion, 81 was converted to 84, 85 and 86 by reacting the enolate with the appropriate optionally substituted benzyl bromide or allyl iodide.

Preparation of Compound 79

Scheme 48:

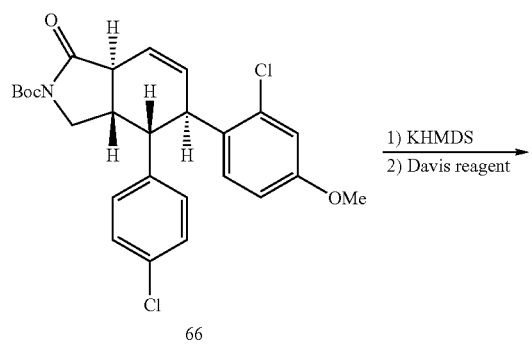

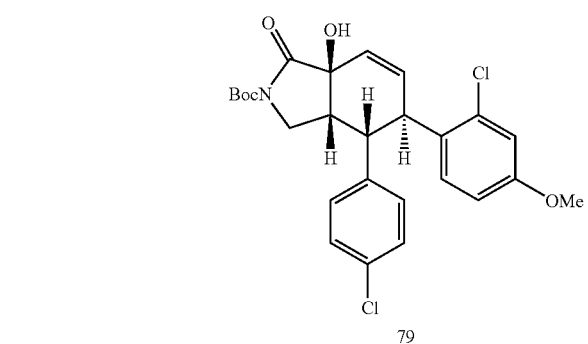

To a solution of 66 (44 mg, 0.090 mmol) in 1 mL THF at −78° C. was added a 0.5 M solution of KHMDS (i.e., potassium bis(trimethylsilyl)amide) in toluene (0.27 mL, 1.5 eq.). The solution was stirred for 10 min at −78° C., 10 min at 0° C., and then cooled back to −78° C. To the cooled solution was then added a solution of (1S)-(+)-(camphorsulfonyl)oxaziridine (Davis reagent) (31 mg, 0.135 mmol, 1.5 eq.) in 0.5 mL THF and stirred for 2 hr. The solution was then quenched by the addition of aq. NH₄Cl. Extraction with ethyl acetate followed by chromatographic purification using 1% methanol-dichloromethane gave 30 mg of 79.

MS: 504.3 (MH⁺)

Preparation of Compound 80

Scheme 49:

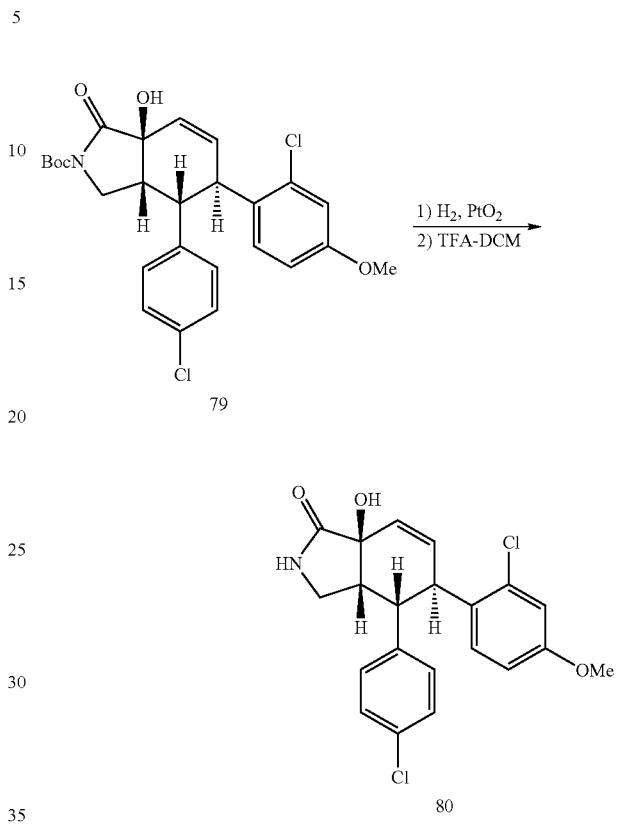

A suspension of 79 (30 mg) and PtO₂ (3 mg) in 2 mL ethyl acetate was stirred under H₂ balloon for 2 hr. The mixture was filtered through a CELITE pad, concentrated and stirred with 1 mL each of TFA (i.e., trifluoroacetic acid) and dichloromethane at 0° C. for 1 hr. The solution was concentrated and purified by preparative TLC using 3% methanol-dichloromethane to provide 24 mg of 80.

MS: 406.2 (MH⁺)

Preparation of Compound 81

Scheme 50:

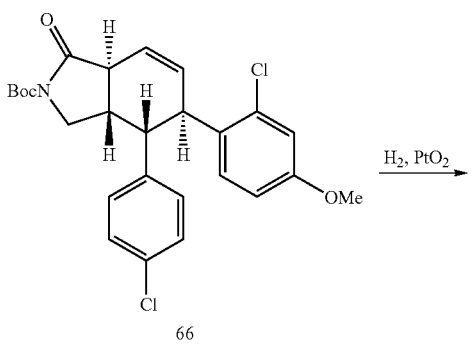

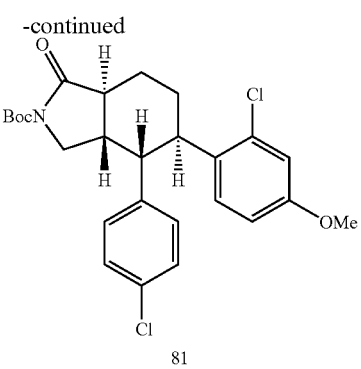

81

A suspension of 66 (230 mg) and PtO$_2$ (23 mg) in 5 mL of ethyl acetate was stirred under H$_2$ balloon for 30 min, filtered and evaporated to provide 230 mg of 81.

MS: 490.3 (MH$^+$)

Preparation of Compound 82

Scheme 51:

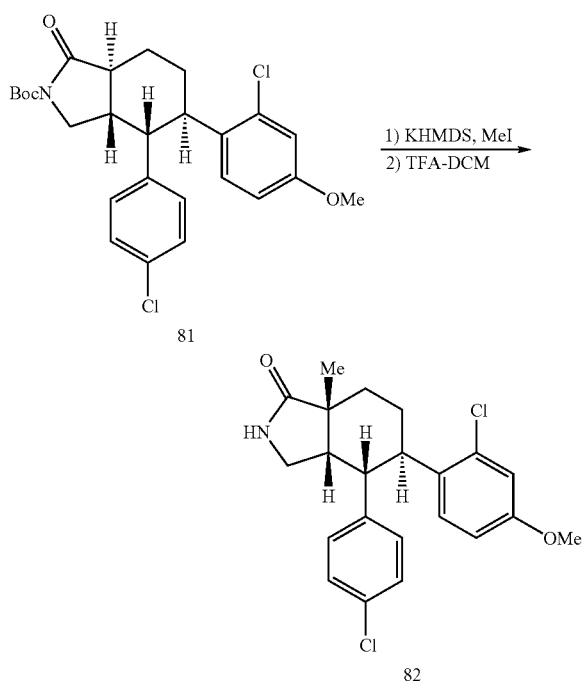

To a solution of 81 (30 mg, 0.061 mmol) in 1 mL of THF at −78° C. was added a 0.5 M solution of KHMDS (0.15 mL, 0.075 mmol, 1.2 eq.) in toluene and the mixture was stirred for 20 min. To the mixture was added MeI (19 μL, 0.305 mmol, 5 eq.), and it was then stirred for 10 min. and quenched with aqueous NH$_4$Cl. After extracting the mixture with ethyl acetate, the crude product was purified by preparative TLC using 30% ethyl acetate-hexane to provide 11 mg of the methylated product. The methylated product was stirred with 0.5 mL each of TFA and dichloromethane at 0° C. for 1 hr, concentrated and evaporated with toluene to provide 8 mg of 82.

MS: 404.2 (MH$^+$)

Preparation of Compound 83

Scheme 52:

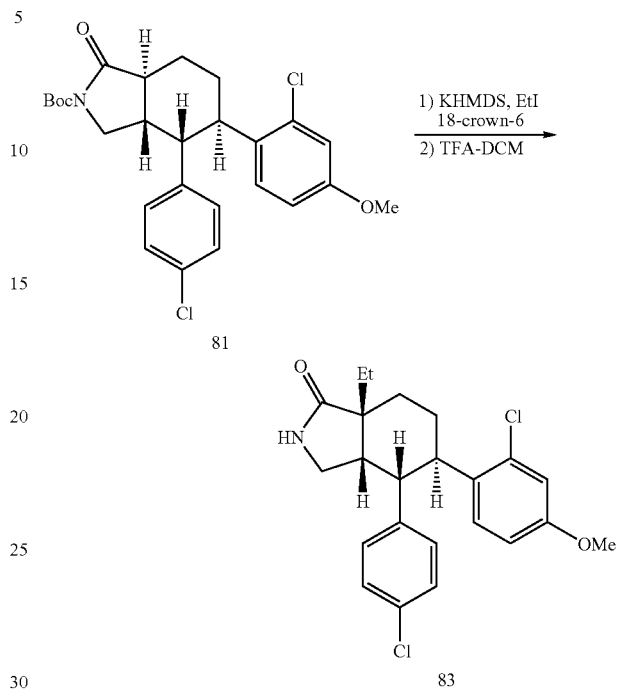

To 50 mg of 81 in 1.5 mL of dry THF was added 18-crown-6 (1.5 eq.). The mixture was degassed and, at −78° C. under argon, potassium bis(trimethylsilyl)amide (1.5 eq., 306 μL of a 0.5 M solution in toluene) was added. After stirring for twenty minutes, iodoethane (1.5 eq.) was added. The mixture was quenched with aqueous ammonium chloride and extracted with ethyl acetate three times. The combined organic extracts were washed with brine, dried with magnesium sulfate, filtered and evaporated to dryness. Purification by flash chromatography (0-25% ethyl acetate in hexane) yielded 30 mg of the ethylated product.

To a solution of the ethylated product prepared as described above in 1.5 mL of dichloromethane at 0° C. was added 1 mL of trifluoroacetic acid and the mixture was stirred under nitrogen for one hour. The mixture was evaporated to dryness and the residue was dissolved in toluene, evaporated to dryness then dissolved in diethyl ether and again evaporated to dryness yielding 23 mg of 83.

MS: 418.2 (MH$^+$)

Intermediate 81 was converted to 84, 85 and 86 using a procedure similar to the procedure used to prepare 82 except that 4-cyanobenzyl bromide, 3,4-difluorobenzyl bromide, and allyl bromide, respectively, were used instead of methyl iodide.

| Compound | MS (MH$^+$) |
| --- | --- |
| 84 | 505.3 |
| 85 | 516.3 |
| 86 | 430.2 |

Preparation of Compounds 87-91

Scheme 54:

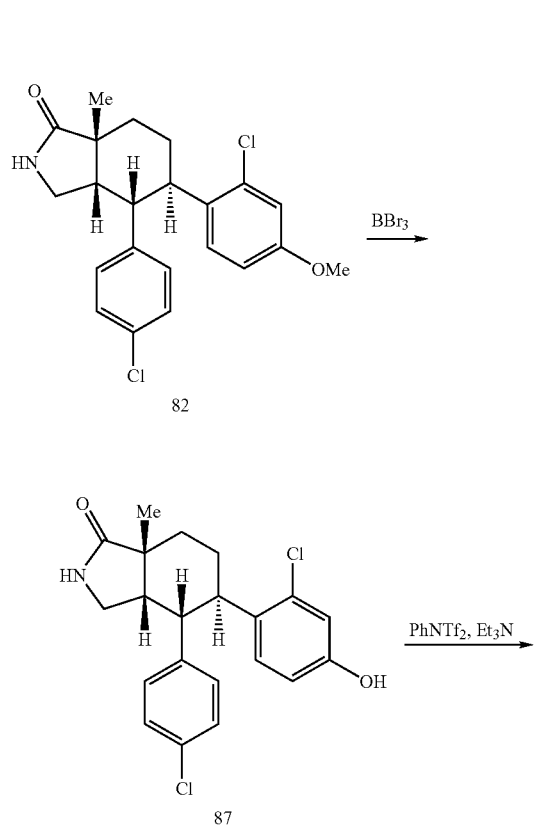

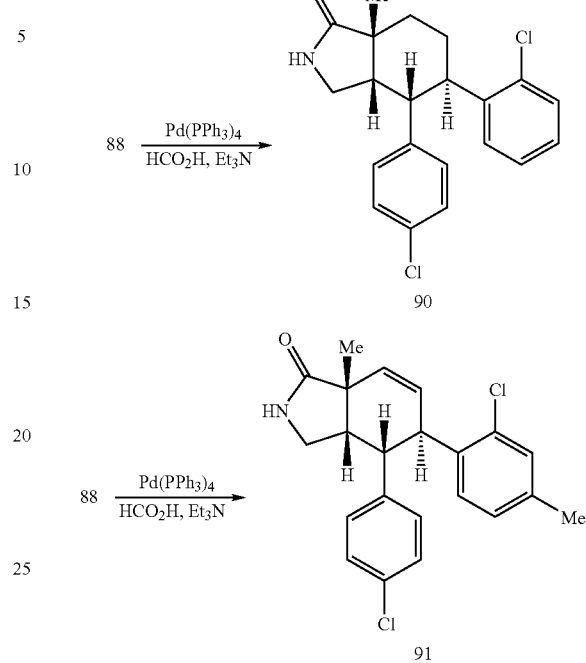

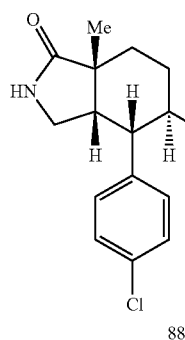

Using procedures similar to the preparation of compounds 72 and 73, 82 was converted to 87 and triflate 88. Also using procedures similar to the transformation of the triflate functionality of 73 to compounds 74, 75, and 76, compound 88 was converted to compounds 89, 90 and 91.

| Compound | MS (MH+) |
|---|---|
| 87 | 390.2 |
| 88 | 522.3 |
| 89 | 399.2 |
| 90 | 374.2 |
| 91 | 388.2 |

Compound 89 was also resolved using chiral HPLC conditions

Chiral Resolution of 89

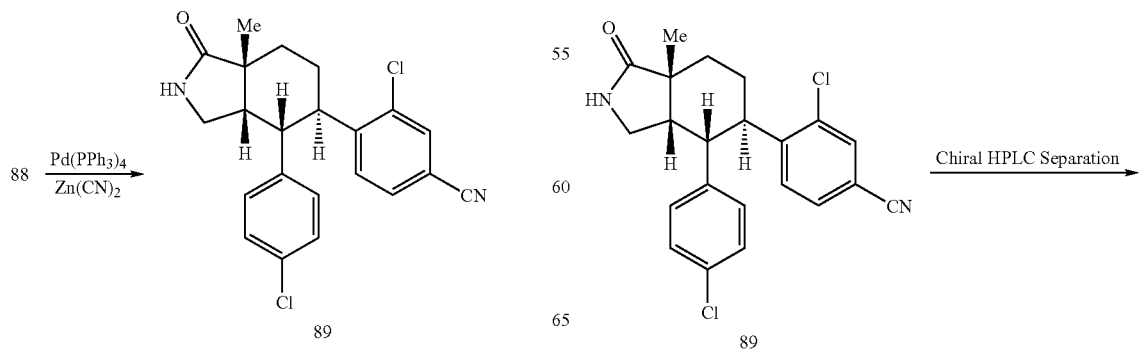

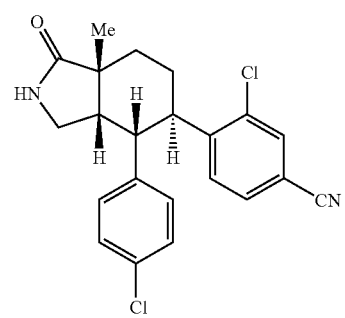

89A
enantiomer 1

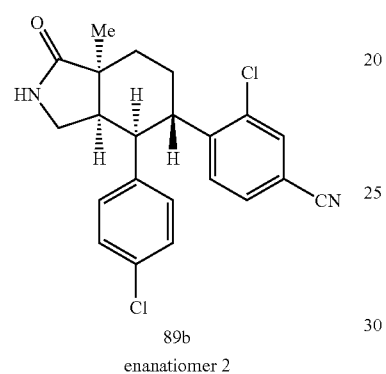

89b
enantiomer 2

A solution of 89 (~550 mg) in 4 ml of 1:1 iso-propyl alcohol and hexanes was injected into a Chiralpac AD preparative HPLC column (5 cm×50 cm) and eluted with 15% isopropyl alcohol in hexanes to obtain 149 mg of 89A and 230 mg of 89B.

MS for 89A: 399.2 (MH$^+$)

MS for 89B: 399.2 (MH$^+$)

Preparation of Compounds 92-95

Scheme 54

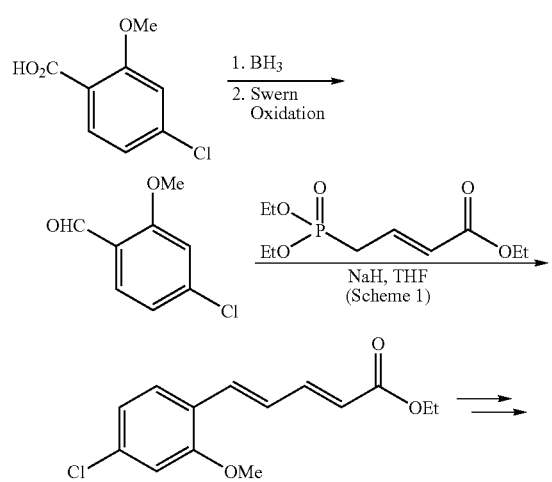

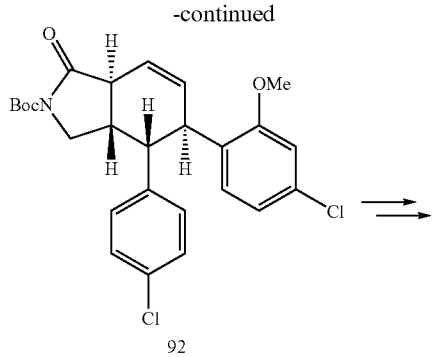

92

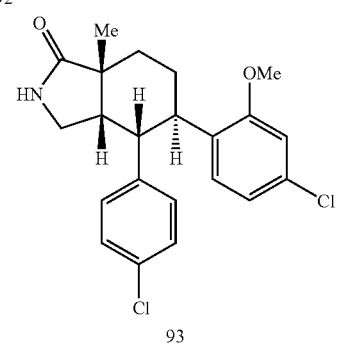

93

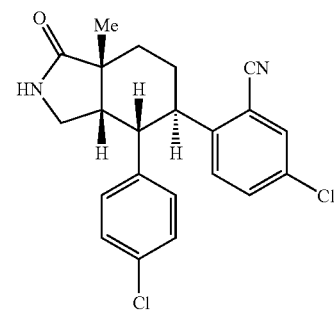

94

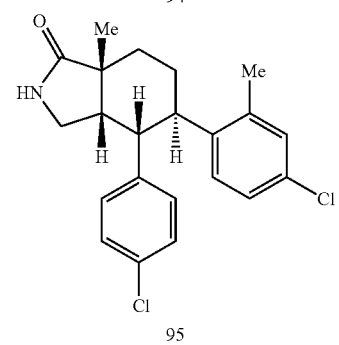

95

Using procedures similar to those used to prepare compounds 66, 82, 89, and 91 and using appropriate starting materials as shown in Scheme 54, compounds 92, 93, 94, and 95 were prepared.

| Compound | MS (MH$^+$) |
| --- | --- |
| 93 | 404.2 |
| 94 | 399.2 |
| 95 | 388.2 |

Preparation of Compounds 96-107
Scheme 55:
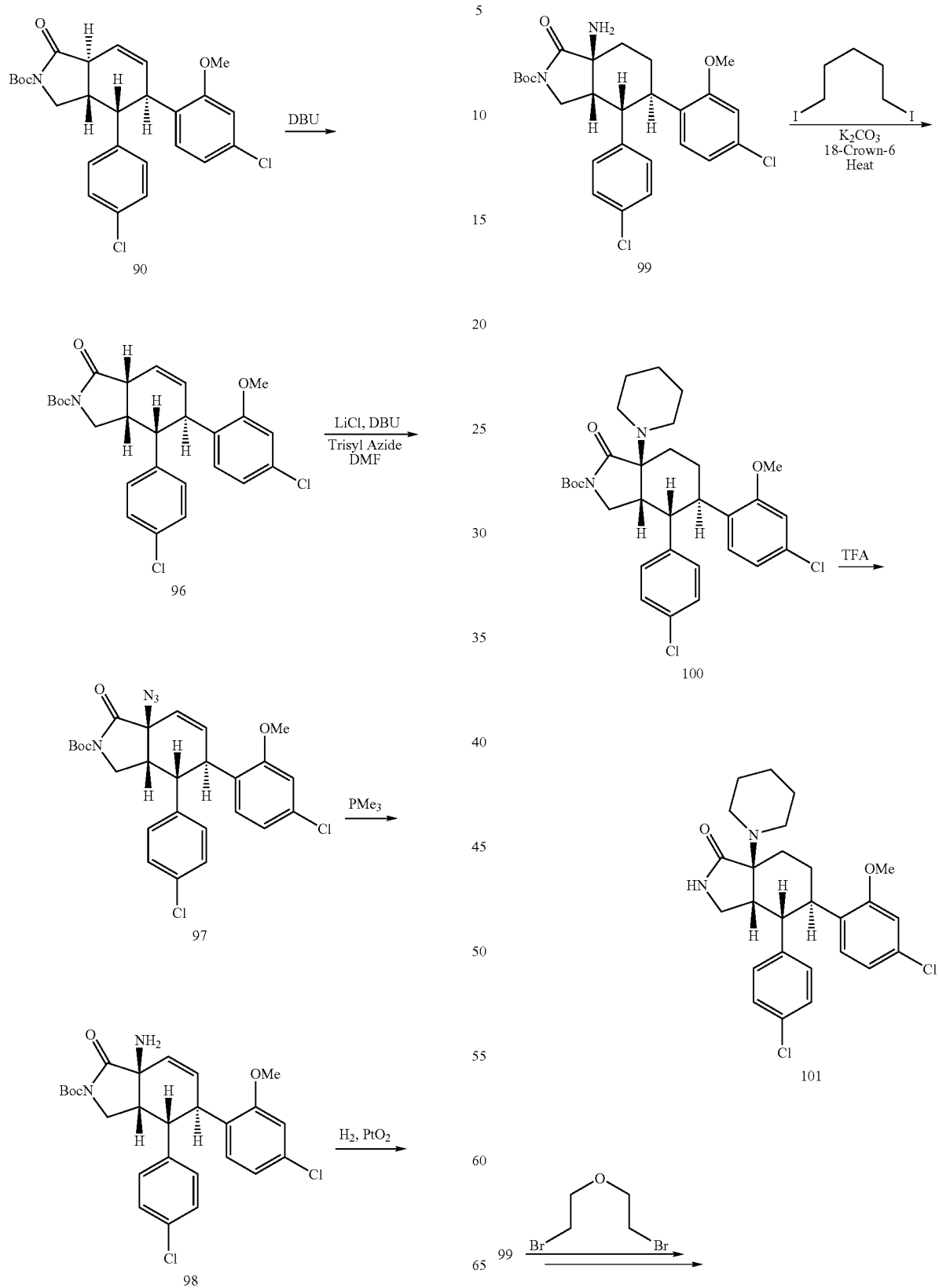

-continued

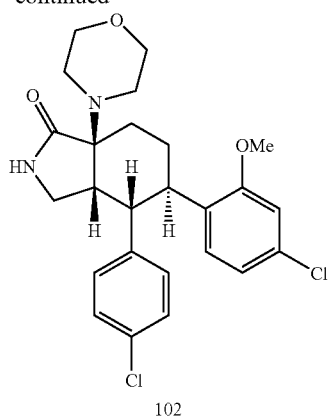
102

Step 1

Compound 90 was converted to compound 96 using procedures similar to those shown in Scheme 25.

Step 2

Scheme 56:

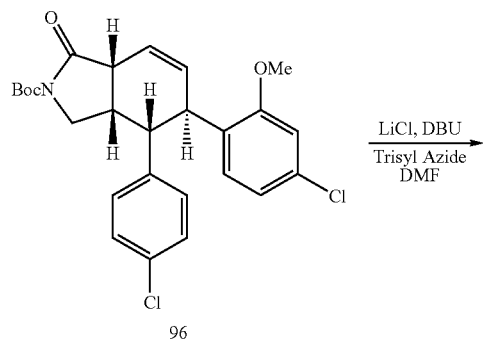

To a solution of compound 96 (30 mg, 0.064 mmol), LiCl (35 mg, 0.826 mmol, 6.5 eq.), and 2,4,6-triisopropylbenzenesulfonyl azide (45 mg, 0.15 mmol, 2.3 eq.) in 1 mL DMF under argon atmosphere at room temperature was added DBU (19 µL, 0.13 mmol, 2 eq.). The solution was stirred for 0.5 hr at room temperature and diluted with ethyl acetate. The solution washed with $NH_4Cl$ (sat.), dried over $MgSO_4$, filtered, and concentrated. The residue was subjected to preparative TLC purification ($SiO_2$, 3:2 hexane/EtOAc) to afford 97 as a white solid (25 mg, 74%). LCMS: m/e 529.3 ($MH^+$)

Step 3

Scheme 57:

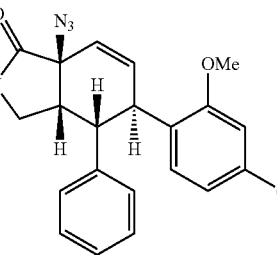
97

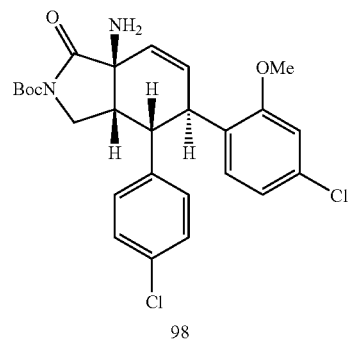
98

To a solution of compound 97 (171 mg, 0.323 mmol) in 7 mL $EtOAc-H_2O$ (10-1) under argon atmosphere at room temperature was added $PMe_3$ (650 µL, 1 M in THF, 0.65 mmol, 2 eq.). The solution was stirred for 4 hr at room temperature. The solution was concentrated. The residue was chromatographed with 3% methanol-dichloromethane to afford 98 as an off-white solid (145 mg, 89%).

Step 4

Compound 98 was converted to compound 99 using procedures similar to those shown in Scheme 50.

Step 5

Scheme 58:

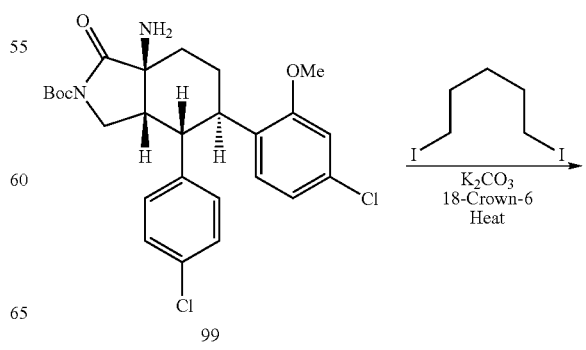
99

-continued

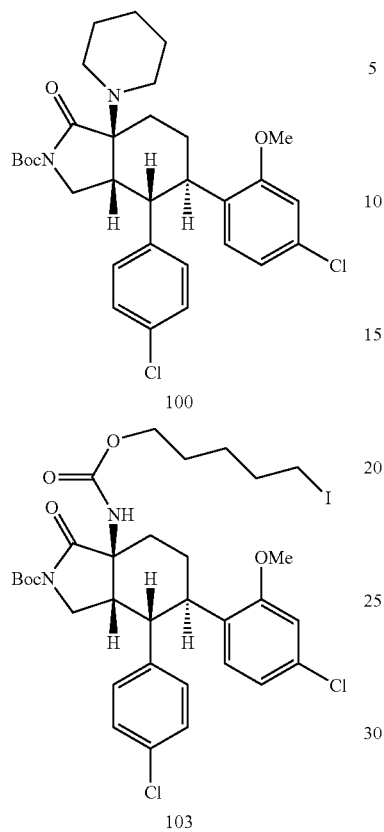

100

103

A mixture of compound 99 (50 mg, 0.10 mmol), 18-crown-6 (52 mg, 2 eq.), K$_2$CO$_3$ (82 mg, 6 eq.), and 1,5-diiodopentane (29 µL, 2 eq.) in 2 mL MeCN was heated for 19 hr at 90° C. The mixture was filtered. The filtrate was dissolved in EtOAc, washed with NH$_4$Cl (sat.), dried over MgSO$_4$, filtered, and concentrated. The residue was subjected to preparative TLC purification (SiO$_2$, 3:2 hexane/EtOAc) to afford 97f (10 mg, 18%). Also isolated was compound 103 (18 mg, 24%).

Step 6

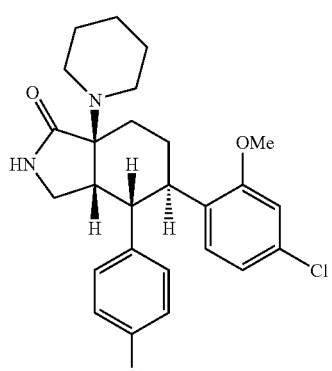

101

LCMS: m/e 473.3 (MH$^+$)

-continued

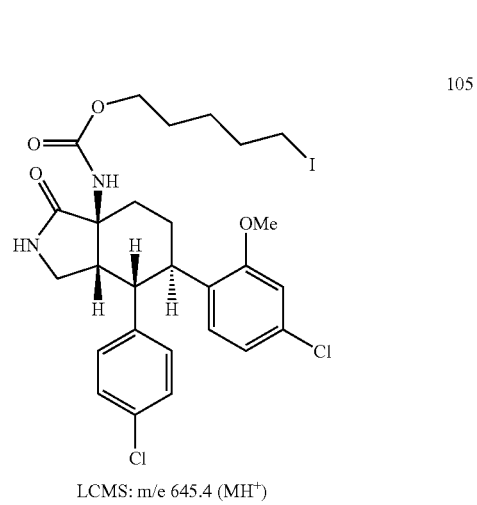

105

LCMS: m/e 645.4 (MH$^+$)

Compounds 100 and 103 were converted to compounds 101 and 105 using procedures similar to those shown in Scheme 36.

Scheme 59:

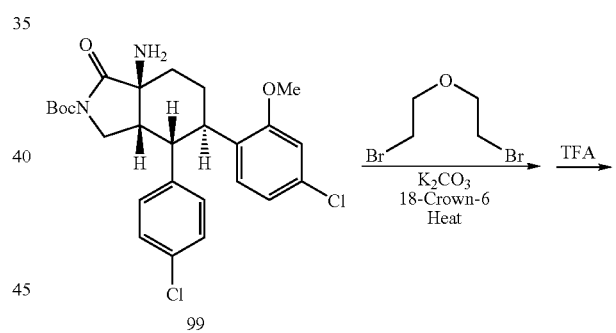

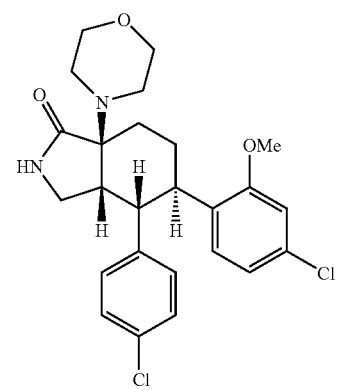

LCMS: m/e 475.3 (MH$^+$)
102

-continued

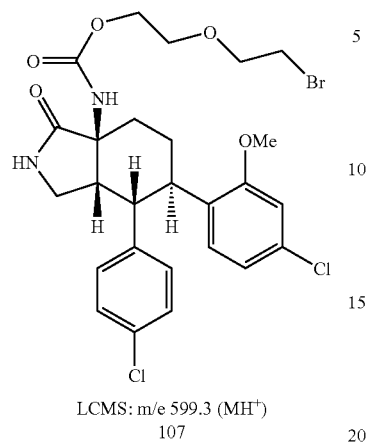

LCMS: m/e 599.3 (MH$^+$)
107

Compounds 102 and 107 were similarly prepared as shown above in Scheme 60.

The amine functionally at the 7a-position can also be introduced in a slightly modified sequence as presented in the following scheme. Intermediate 108, which was prepared using a procedure similar to the preparation of 66, was treated with KHMDS followed by trisyl azide to give the azido derivative 109. Reduction of the azide followed by cleavage of the BOC group afforded the amine 111 which was converted to the amide 112. The amine can be similarly converted to various analogs such as sulfonamides, carbamates, ureas etc. using standard literature procedures.

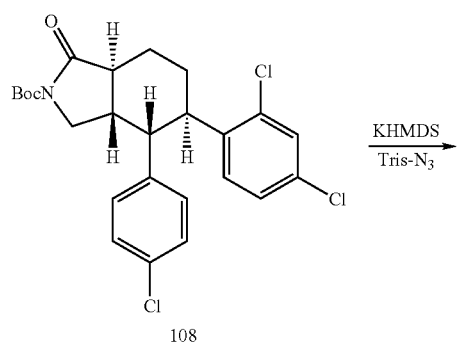
108

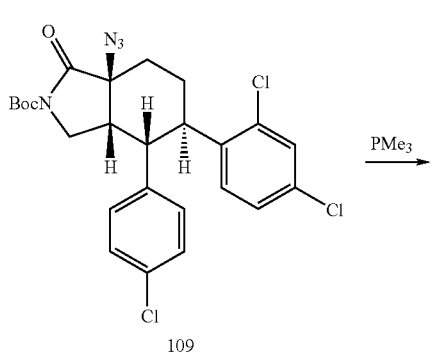
109

-continued

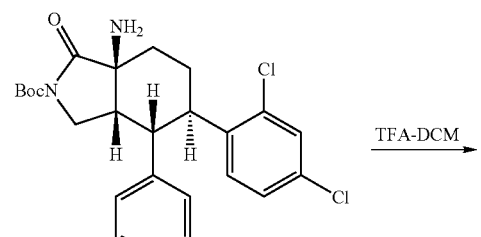
110

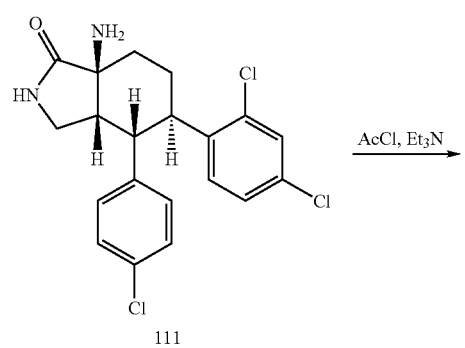
111

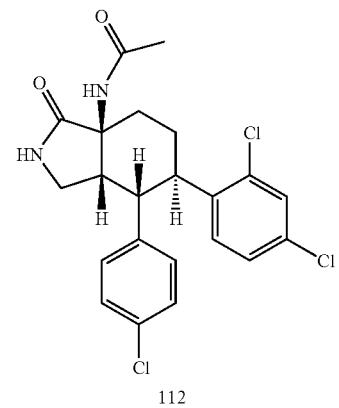
112

Preparation of Compound 109

Scheme 60:

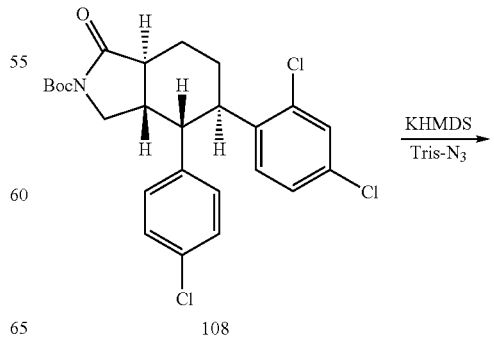
108

-continued

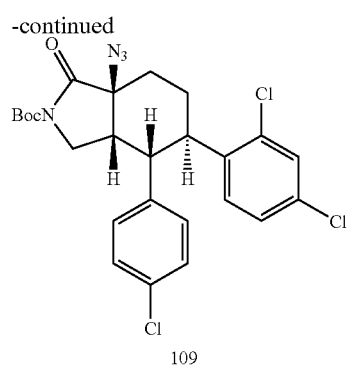

109

To 1.0 g of 108 in 10 mL of dry THF at 0° C. was added 1.3 eq. of potassium hexamethyldisilyl amide (0.5M solution in toluene) and the mixture stirred for 20 minutes then cooled to −78° C. A cooled (−78° C.) solution of Tris-N$_3$ (1.5 eq.) in 2.5 ml of THF was added followed, after two minutes, by acetic acid (3 eq.). The reaction was immediately warmed to room temperature using a warm water bath then stirred for 1.5 hours. The mixture was evaporated to dryness, dissolved in 10 mL of dichloromethane and washed with water, aq. NaHCO$_3$, and brine, then dried with MgSO$_4$, filtered and evaporated to dryness. Purification by flash chromatography with 0% to 15% ethyl acetate-hexanes yielded 864 mg of 109.

MS: 479.3 (MH$^+$).

Preparation of Compound 110

Scheme 61:

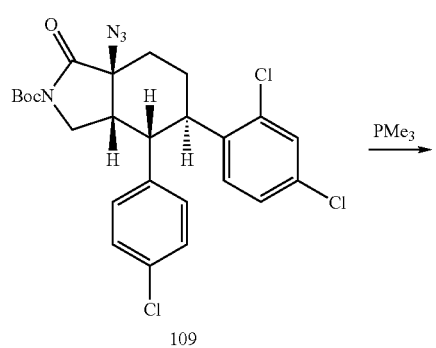

109

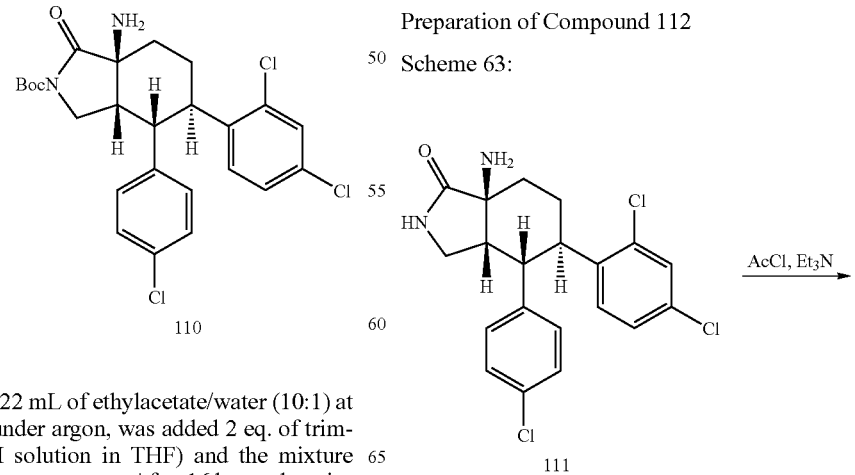

To 860 mg of 109 in 22 mL of ethylacetate/water (10:1) at 0° C., after degassing under argon, was added 2 eq. of trimethyl phosphine (1.0M solution in THF) and the mixture warmed slowly to room temperature. After 16 hours the mixture was evaporated to dryness, then toluene was added to the residue and the mixture evaporated to dryness. Purification by flash chromatography with 0% to 2.5% methanol-dichloromethane yielded 575 mg of 110.

MS: 392.2 (MH$^+$)

Preparation of Compound 111

Scheme 62:

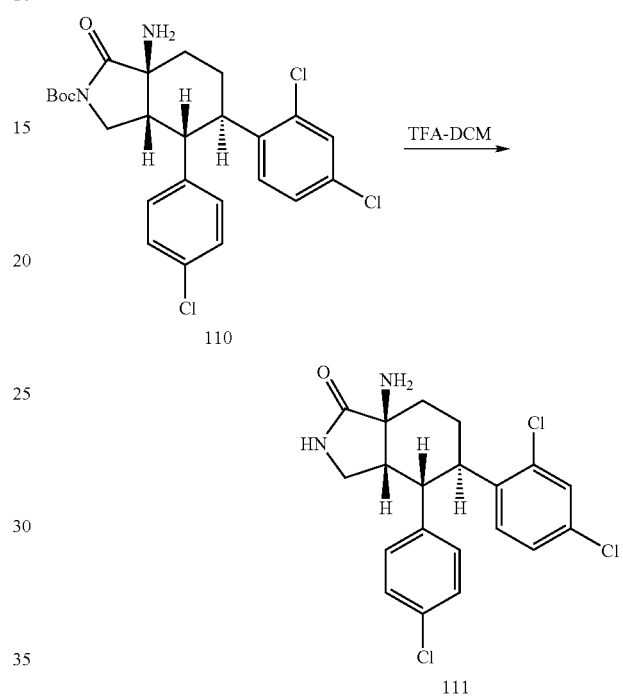

To 565 mg of 110 in 5 mL of dichloromethane at 0° C. was added 2 mL of trifluoroacetic acid and the mixture was stirred under a N$_2$ atmosphere. After two hours the reaction mixture was poured onto aq. NaHCO$_3$ and extracted with dichloromethane three times. The combined extracts were dried with MgSO$_4$, filtered and evaporated to dryness yielding 465 mg of 111.

MS: 409.2 (MH$^+$)

Preparation of Compound 112

Scheme 63:

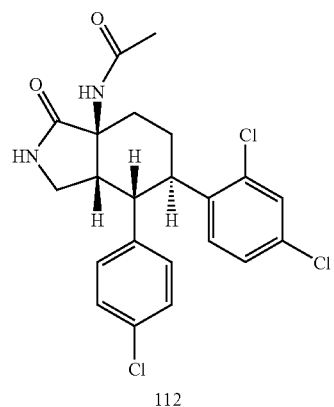

112

To 20 mg of 111 in 1.5 mL pyridine at 0° C. was added 3 eq. of acetyl chloride and the mixture was warmed to room temperature while stirring under a $N_2$ atmosphere. The reaction mixture was poured onto aq. ammonium chloride and extracted with ethylacetate three times. The combined extracts were washed with water twice and brine once, dried with $MgSO_4$, filtered and evaporated to dryness yielding 17 mg of 112 after purification by flash chromatography with 0% to 2.5% methanol-dichloromethane.

MS: 451.2 ($MH^+$)

Preparation of Compounds 113-117

Scheme 64:

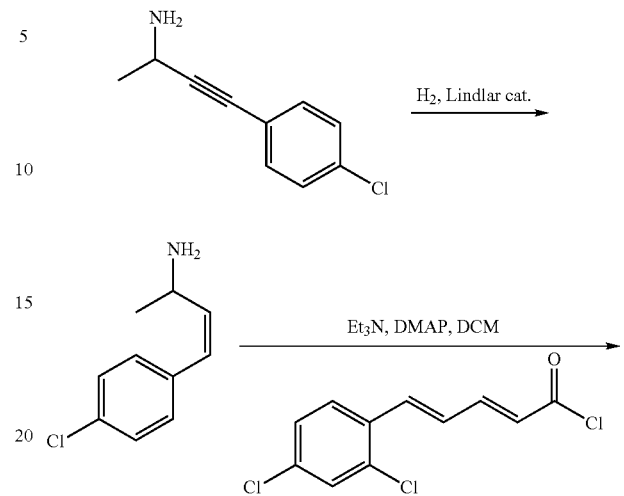

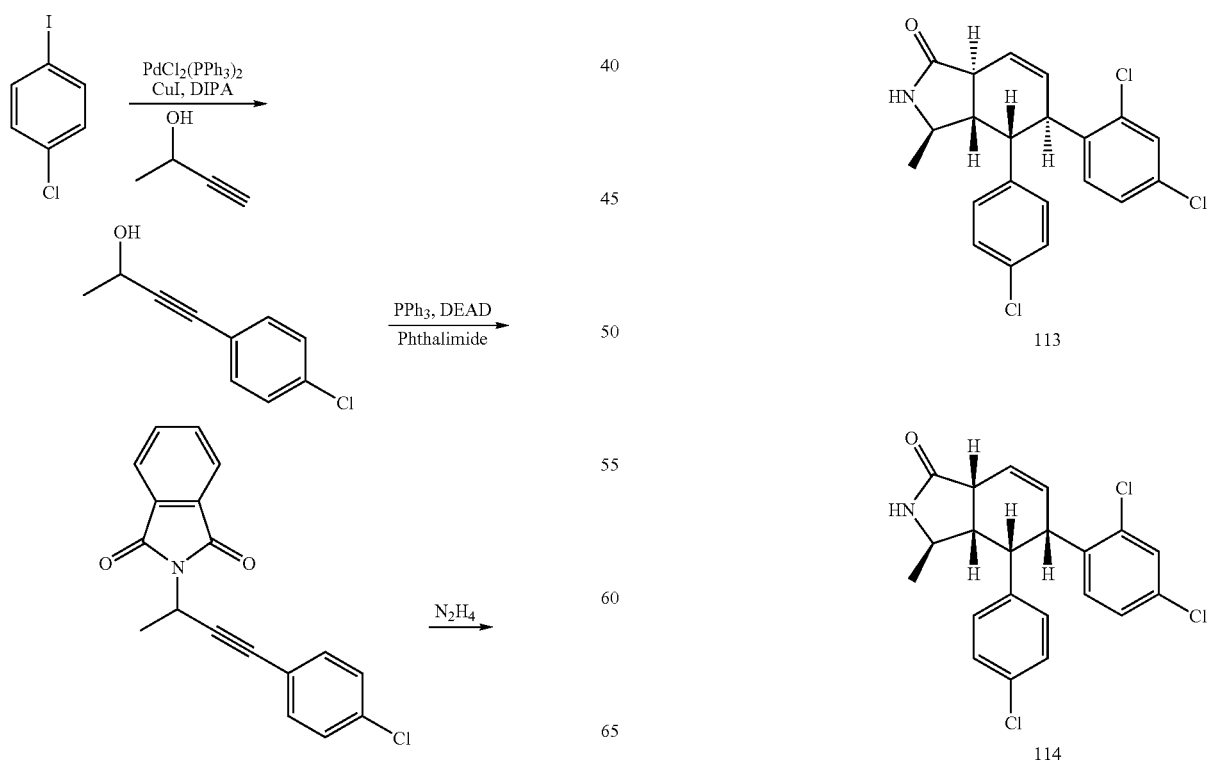

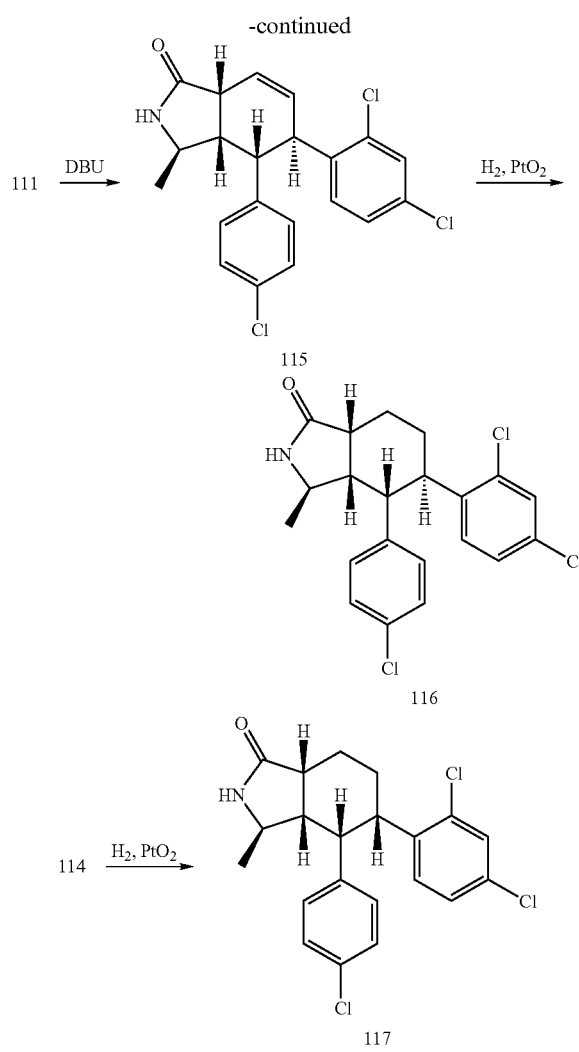

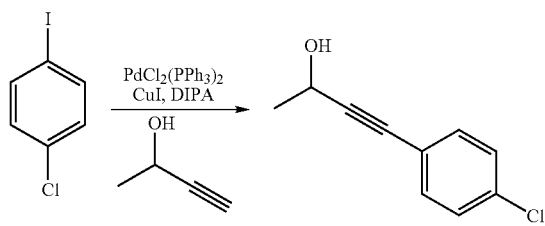

The C₃ position of the lactam can be substituted with various groups by starting with an appropriately functionalized propargyl amine. For example, a methyl group can be introduced at the C₃ position as described above in Scheme 64.

Step 1

Scheme 65:

insoluble components of the mixture were filtered off and the filtrate washed with 1N HCl and brine, dried over MgSO₄, filtered, concentrated and chromatographed with 20% ethyl acetate-hexane to provide 7.6 g of 4-(4-chloro-phenyl)-but-3-yn-2-ol.

Step 2

Scheme 66:

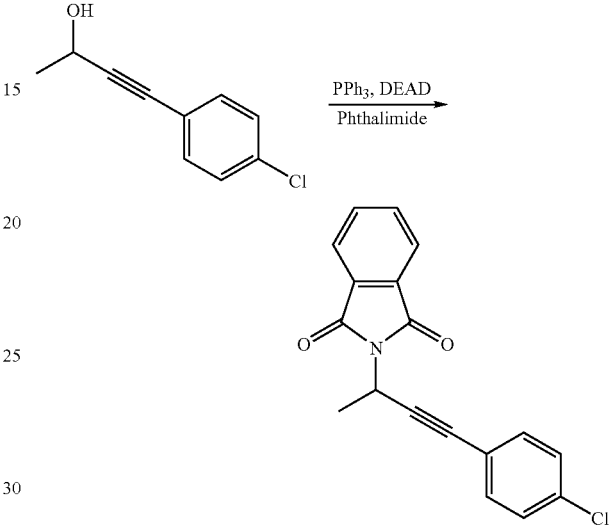

To a solution of 4-(4-chloro-phenyl)-but-3-yn-2-ol (3 g, 16.6 mmol), phthalimide (3.7 g, 25.2 mmol, 1.5 eq.) and PPh₃ (4.8 g, 18.3 mmol, 1.1 eq.) in 100 mL of THF cooled to 0° C. with an ice bath was added dropwise DEAD (i.e., diethyl azodicarboxylate) (3.1 mL, 19.9 mmol, 1.2 eq.). The ice-bath was removed and the mixture was stirred overnight at room temperature. The THF was evaporated and the residue was stirred with 200 mL of 1:1 ether-hexane mixture for 1 hr. The precipitate was filtered off and the filtrate was concentrated and chromatographed with 15% ethyl acetate-hexane to provide 4.1 g of 2-[3-(4-chloro-phenyl)-1-methyl-prop-2-ynyl]-isoindole-1,3-dione.

MS: 310.09 (MH⁺)

Step 3

Scheme 67:

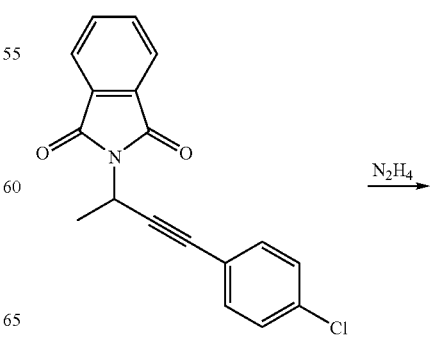

To a solution of 4-chloro iodobenzene (10 g, 42 mmol), 3-butyn-2-ol (6.6 mL, 84 mmol, 2 eq.), and iPr₂NH (14.8 mL, 105 mmol, 2.5 eq.) in 200 mL dichloromethane was added CuI (1.6 g, 8.4 mmol, 0.2 eq.) followed by Pd(PPh₃)₂Cl₂ (1.5 g, 2.1 mmol, 5 mol %). The mixture was stirred for 1.5 hr at room temperature, concentrated and diluted with ether. The -continued

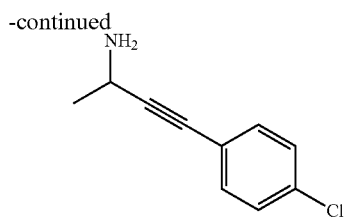

To a solution of 2-[3-(4-chloro-phenyl)-1-methyl-prop-2-ynyl]-isoindole-1,3-dione (4.1 g, 13.2 mmol) in 20 mL of dichloromethane was added 30 mL of methanol followed by hydrazine (4.2 mL, 133 mmol, 10 eq.). The mixture was stirred for 1 hr, filtered, concentrated and chromatographed with 3% methanol-dichloromethane to provide 1.5 g of 3-(4-chloro-phenyl)-1-methyl-prop-2-ynylamine.

MS: 163.21 (MH+)

Step 4

Scheme 68:

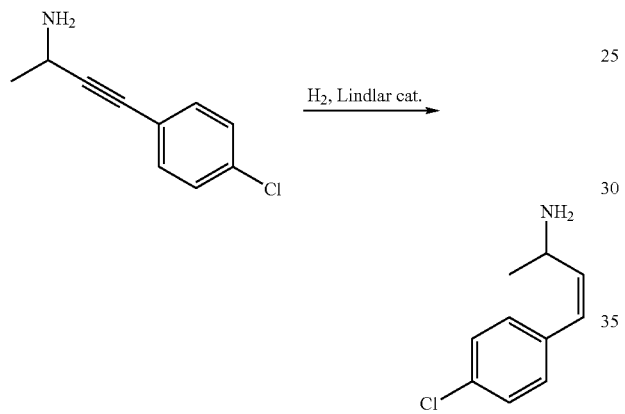

A mixture of 3-(4-chloro-phenyl)-1-methyl-prop-2-ynylamine (1.5 g, 8.4 mmol), triethylamine (0.12 mL, 0.86 mmol, 0.1 eq.) and Lindlar catalyst (150 mg) in 40 mL of 1:1 methanol-dichloromethane was stirred for 1 hr, filtered through a CELITE pad and concentrated to provide 1.5 g of 3-(4-chloro-phenyl)-1-methyl-allylamine.

Compound 3-(4-chloro-phenyl)-1-methyl-allylamine was converted to 5-(2,4-dichloro-phenyl)-penta-2,4-dienoic acid [3-(4-chloro-phenyl)-1-methyl-allyl]-amide using procedures similar to those described in Scheme 5, above. Compound 5-(2,4-dichloro-phenyl)-penta-2,4-dienoic acid [3-(4-chloro-phenyl)-1-methyl-allyl]-amide was converted to compounds 113 and 114 using the Diels-Alder conditions similar to those described above in Scheme 6. Compound 115 was prepared by the isomerization of compound 113 using procedures similar to those described in Scheme 6. Compound 116 was prepared by the reduction of compound 115 using procedures similar to those described in Scheme 7. Compound 117 was prepared by the reduction of compound 114 using procedures similar to those described in Scheme 7.

| Compound | MS (MH+) |
|---|---|
| 113 | 406.2 |
| 114 | 406.2 |
| 115 | 406.2 |
| 116 | 408.1 |
| 117 | 408.2 |

Preparation of Compounds 118-119

Scheme 69

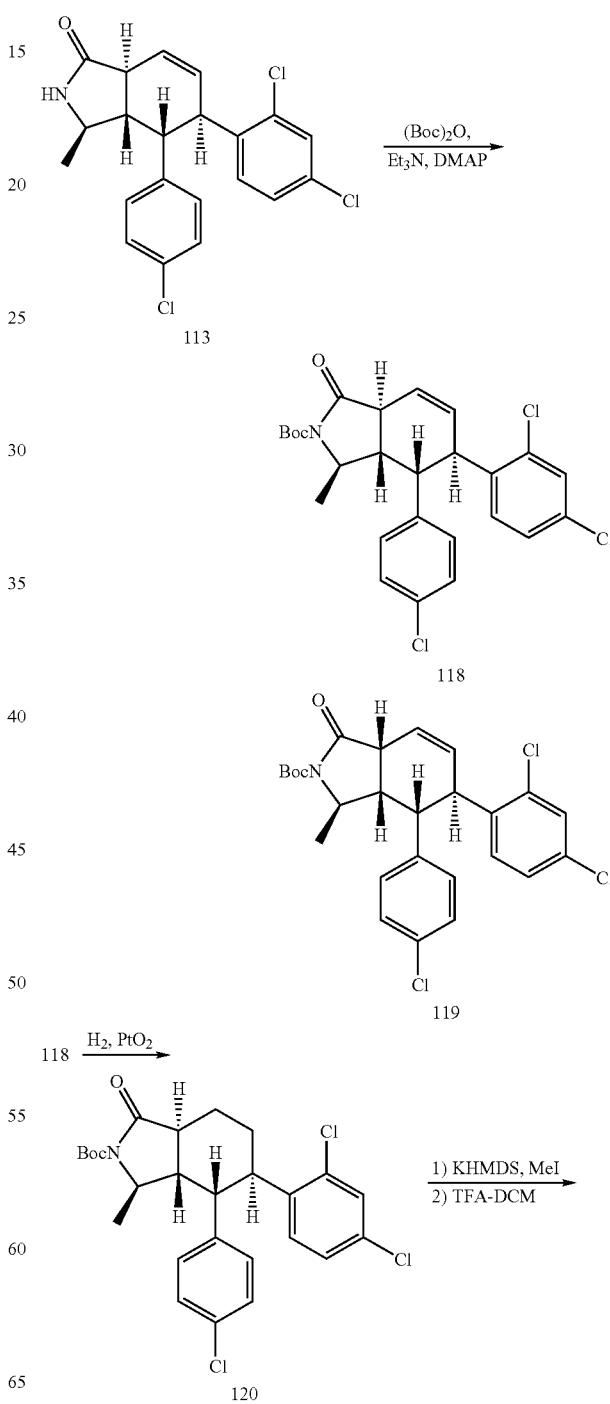

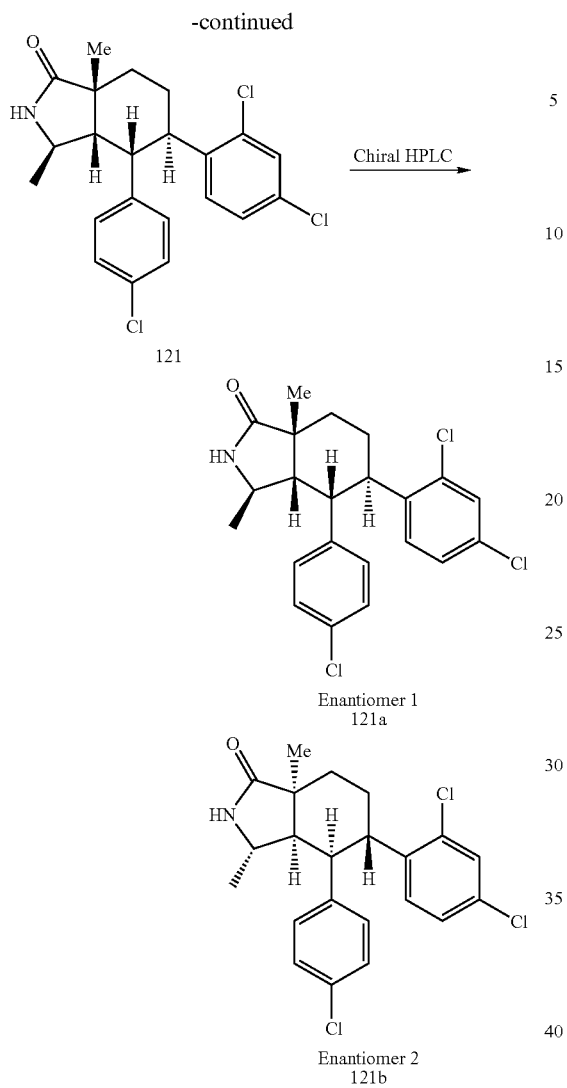

Enantiomer 1
121a

Enantiomer 2
121b

Intermediate 113 from the above synthesis was further transformed into 7a-methyl analog 121 as described in the following scheme. This was also further resolved into the single enantiomers 121a and 121b.

Preparation of Compounds 118 and 119

Scheme 70:

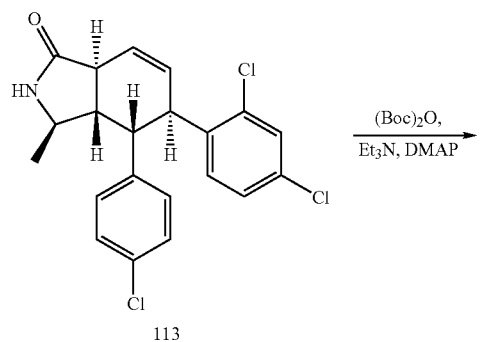

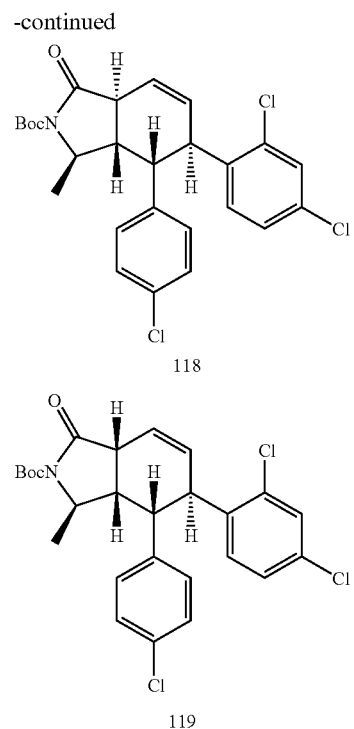

To a solution of 113 (500 mg, 1.23 mmol) (Boc)$_2$O (2.8 g, 12.8 mmol, 10 eq.), Et$_3$N (345 μL, 2.48 mmol, 2 eq.) in 5 mL each of dichloromethane and acetonitrile was added DMAP (300 mg, 2.46 mmol, 2 eq.) and the mixture was stirred overnight at room temperature. The solution was diluted with ether, washed with 1N HCl, aq. NaHCO$_3$, and brine, dried over MgSO$_4$, filtered, evaporated and chromatographed with 0% to 20% ethyl acetate-hexanes to provide 220 mg of 118 and 330 mg of 119.

MS for 118: 450.2 (M$^+$-$^t$Bu)

MS for 119: 450.2 (M$^+$-$^t$Bu)

Compound 118 was converted to compound 120 using a procedure similar to the conversion of 66 to 81. Conversion of 120 to 121 was achieved using a procedure similar to the conversion of 81 to 82. Also, 121 was resolved using chiral HPLC conditions as described below to obtain the single enantiomers 121a and 121b.

Scheme 71:

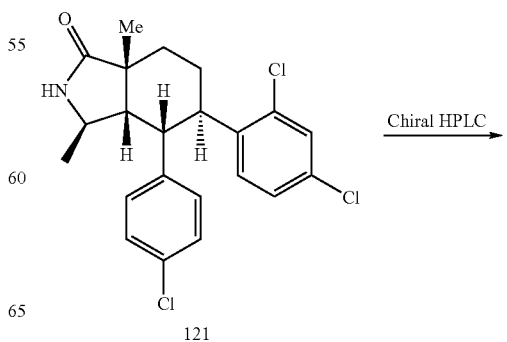

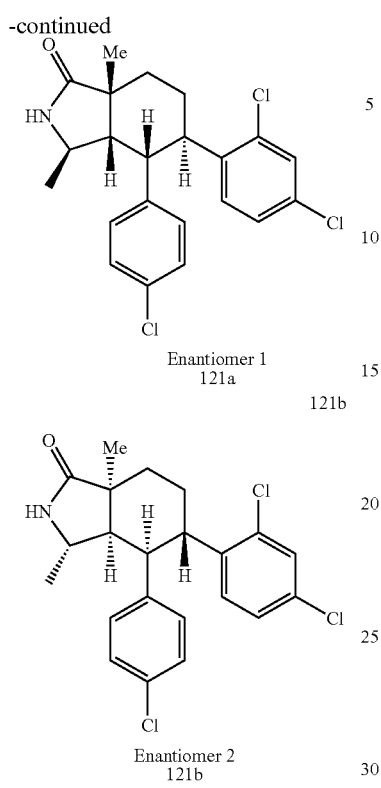

Enantiomer 1
121a

Enantiomer 2
121b

About 40 mg of 121 was dissolved in isopropanol and injected onto a 5×50 cm CHIRALPAK AD column and eluted with 10% isopropanol in hexane at 100 mL/min, using a 220 nm UV detector. 15 mg each of 121a (enantiomer 1) and 121b (enantiomer 2) was obtained. Retention times were 19.8 minutes and 25.4 minutes, respectively MS for 120: 510.3 (MH+)
MS for 121: 422.2 (MH+)
MS for 121a: 422.2 (MH+)
MS for 121b: 422.2 (MH+)

Scheme 72:

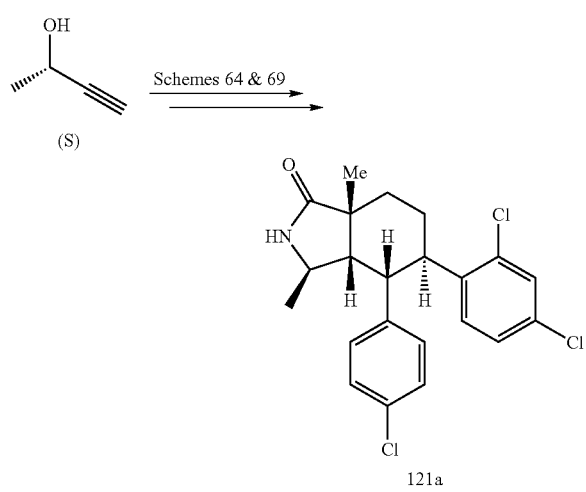

121a

In the above preparation of 121, racemic starting materials were employed and the individual enantiomers were resolved using chiral HPLC conditions. Alternatively, these chiral $C_3$-substituted analogs were synthesized as a single enantiomer by starting with 3-butyn-2(S)-ol as shown in Schemes 64 and 69.

Scheme 72a

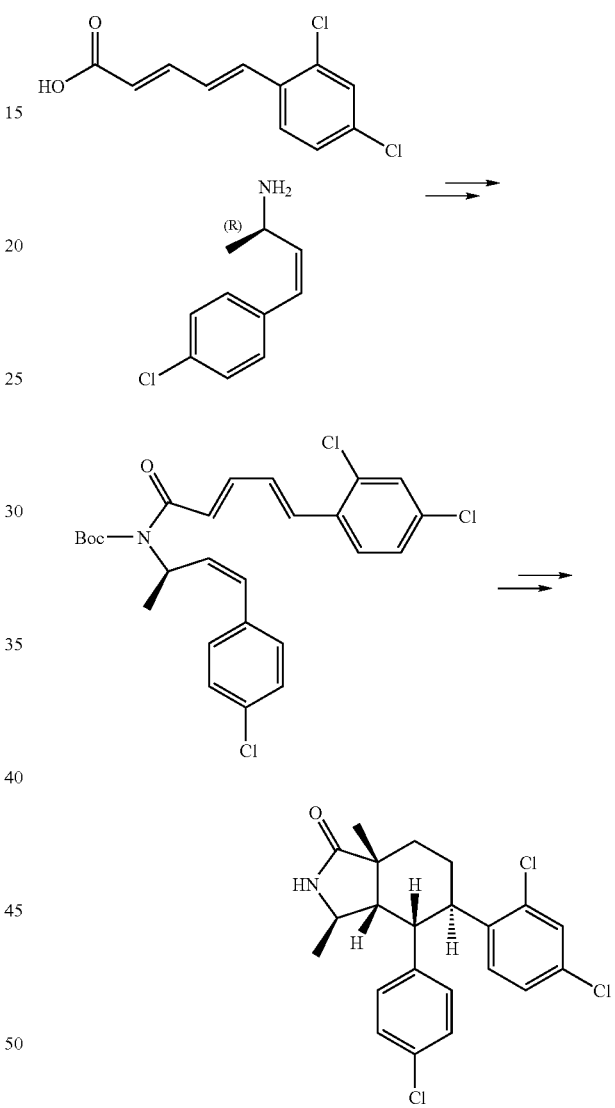

For example, 3-(4-chloro-phenyl)-1-methyl-allylamine (prepared, e.g., by the method of Scheme 7) was reacted with 5-(2,4-dichloro-phenyl)-penta-2,4-dienoic acid using the method of, e.g., Scheme 29, to provide [3-(4-chloro-phenyl)-1-methyl-propyl]-[5-(2,4-dichloro-phenyl)-penta-2,4-dienoyl]-carbamic acid tert-butyl ester. [3-(4-Chloro-phenyl)-1-methyl-propyl]-[5-(2,4-dichloro-phenyl)-penta-2,4-dienoyl]-carbamic acid tert-butyl ester was then cyclized (e.g., using the method of Scheme 47) to provide 4-(4-Chloro-phenyl)-5-(2,4-dichloro-phenyl)-3,7a-dimethyl-octahydro-isoindol-1-one.

Preparation of Compounds 122-131
Scheme 73:
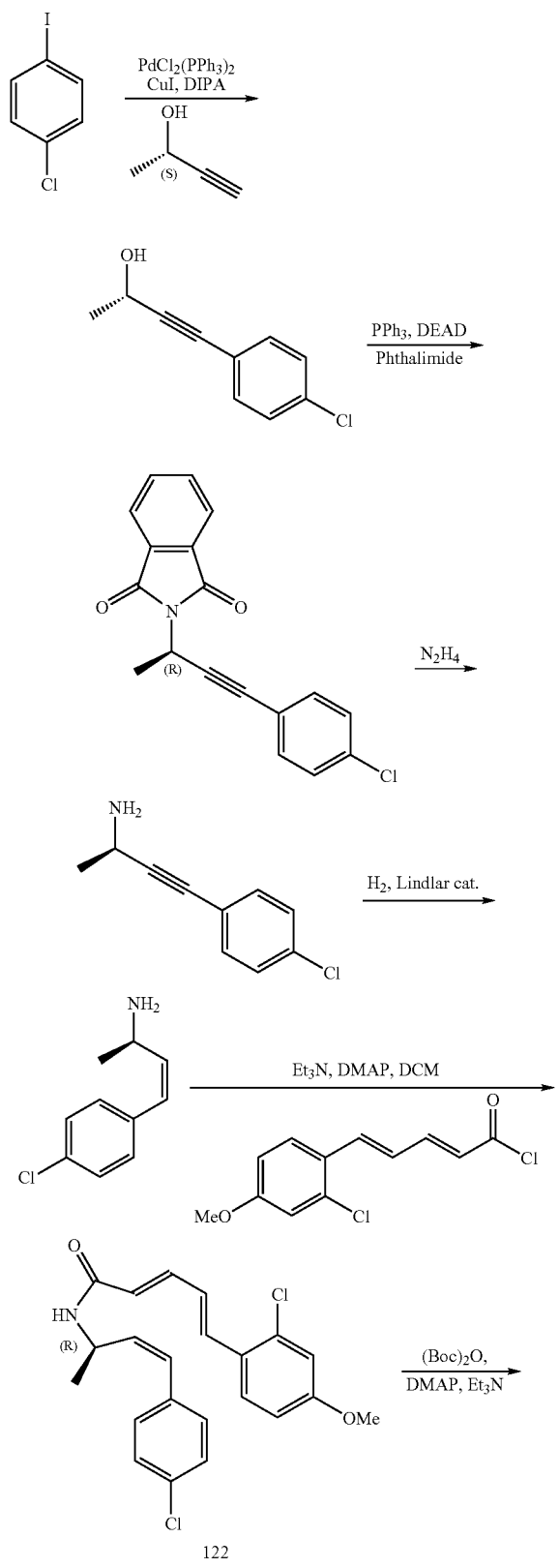
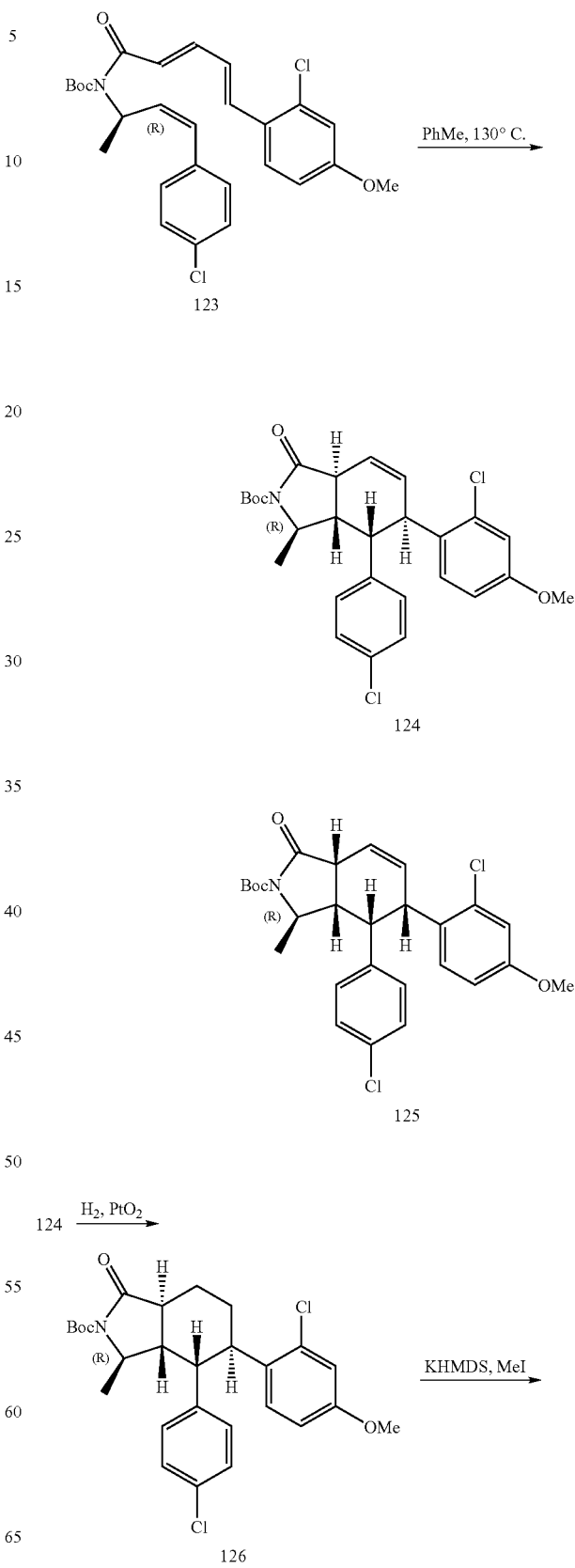

-continued

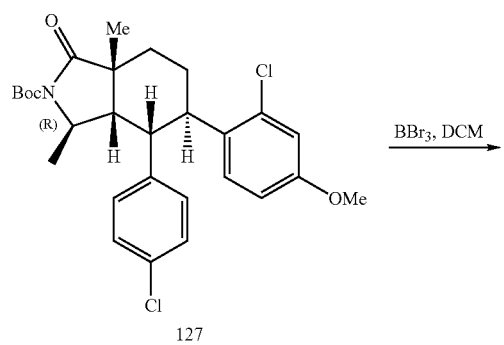
127

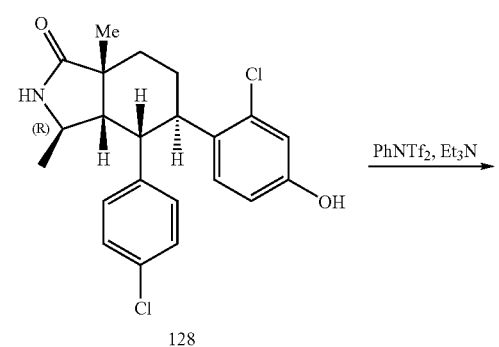
128

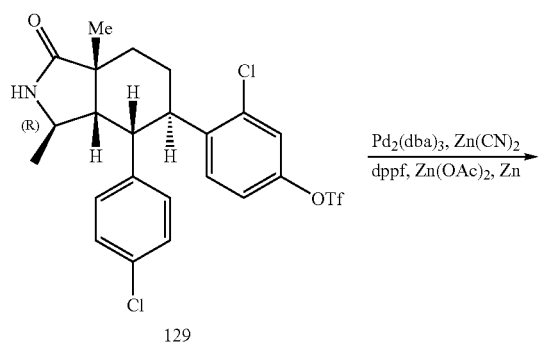
129

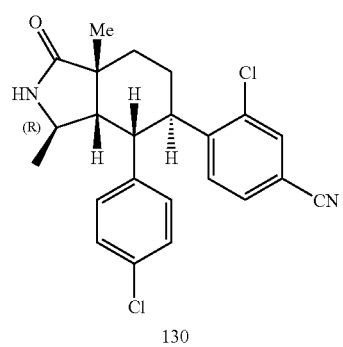
130

Another example of chiral synthesis of the compounds of the present invention is presented above in Scheme 73 for the preparation of 130 and 131 in an optically active form starting with optically active 3-butyn-2(S)-ol.

Preparation of Compound 122

Amide 122 was prepared using a procedure similar to that used to prepare the amide from which 113 was prepared, except that optically active 3-butyn-2(S)-ol was used instead of racemic 3-butyn-2-ol.

Preparation of Compound 123

Scheme 74:

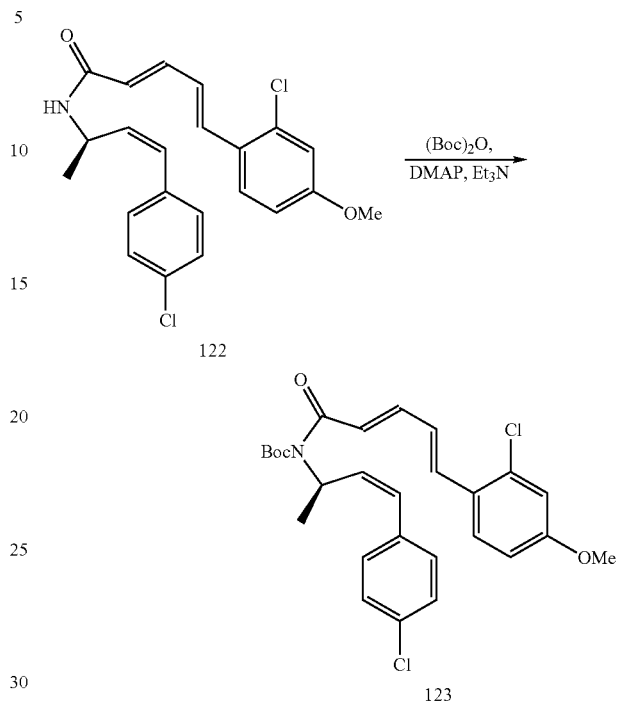

To a suspension of 122 (10 g, 24.8 mmol), (Boc)$_2$O (10.9 g, 2 eq.) in 100 mL dichloromethane at room temperature was added Et$_3$N (3.5 mL, 1 eq) followed by DMAP (3.1 g, 1 eq) and the suspension was stirred at room temperature. After two hours another 2 equivalents of (Boc)$_2$O was added and the mixture was stirred overnight. The solution was concentrated to half of its volume, diluted with ethyl acetate, washed with 1N HCl, aq. NaHCO$_3$ and brine, dried over MgSO$_4$, filtered and concentrated to give a crude product. The crude product was suspended in MeOH—CH$_2$Cl$_2$ mixture and diluted with diethyl ether. The solid was filtered off and rinsed with diethyl ether. The filtrate was concentrated and chromatographed with 0% to 10% ethyl acetate-hexanes to provide 9.5 g of 123.

MS: 502.3 (MH$^+$)

Preparation of Compounds 124 and 125

Scheme 74

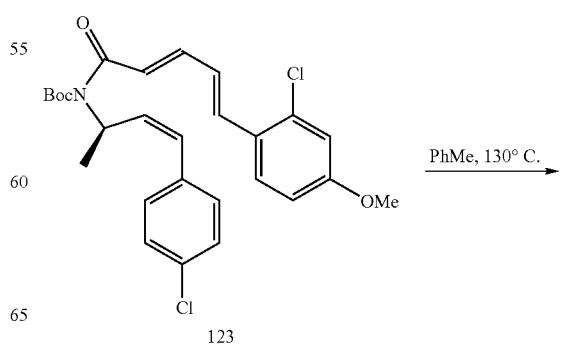
123

-continued

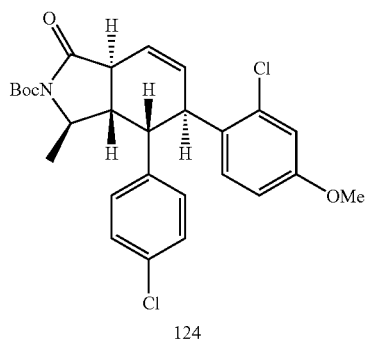

124

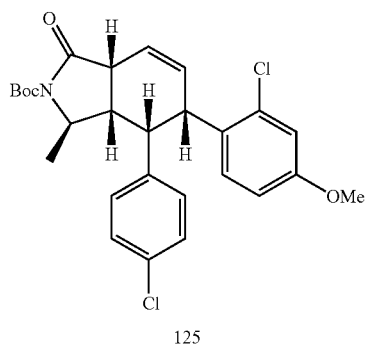

125

A solution of 123 (9.5 g) in 100 mL of toluene was heated in a sealed tube at 130° C. for 2 hr. The solution was concentrated and chromatographed with 0% to 20% ethyl acetate-hexanes to provide 4.3 g of 124 and 3.1 g of 125.

MS for 124: 502.3 (MH$^+$)

MS for 125: 502.3 (MH$^+$)

Preparation of Compound 126

Scheme 75

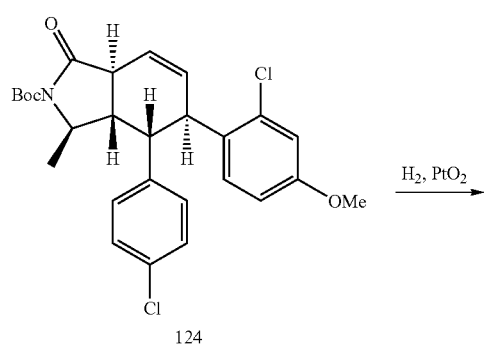

-continued

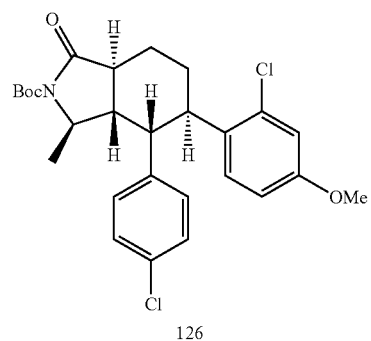

126

A suspension of 124 (4.3 g) and platinum oxide hydrate (215 mg, 5 wt %) in 100 mL of ethyl acetate was stirred under a hydrogen balloon for 30 min, filtered through a CELITE pad and concentrated to provide 4.15 g of 126.

MS: 504.3 (MH$^+$)

Preparation of Compound 127

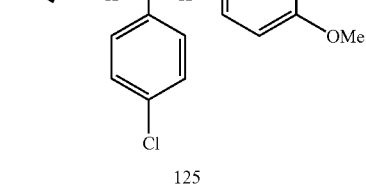

126

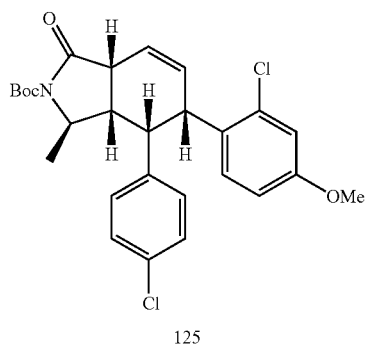

127

To a solution of 126 (600 mg, 1.19 mmol) in 7 mL of THF at −78° C., degassed under vacuum, was added a THF solution of 0.5M 1M LHMDS (i.e., lithium hexamethyldisilazide) (3.6 mL, 1.8 mmol, 1.5 eq.) and stirred for 20 min. To this solution was added methyl iodide (0.37 mL, 5.94 mmol, 1.5 eq.), stirred for 10 min, quenched with aq. NH$_4$Cl and THF was evaporated. The mixture was extracted with ethyl acetate, the combined organic layer washed with brine, dried over MgSO$_4$, filtered, concentrated and chromatographed with 0% to 15% ethyl acetate in hexanes to provide 470 mg of 127.

MS: 518.3 (MH$^+$)

Preparation of Compound 128

Scheme 77:

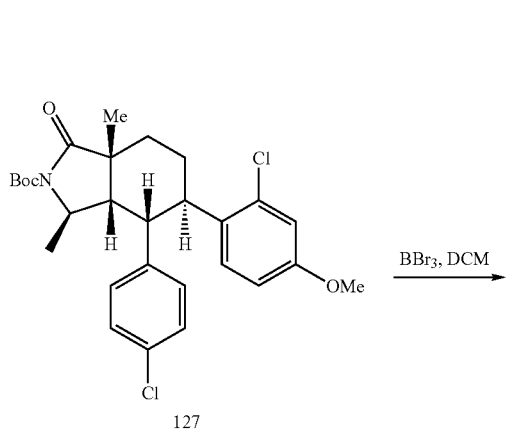

127

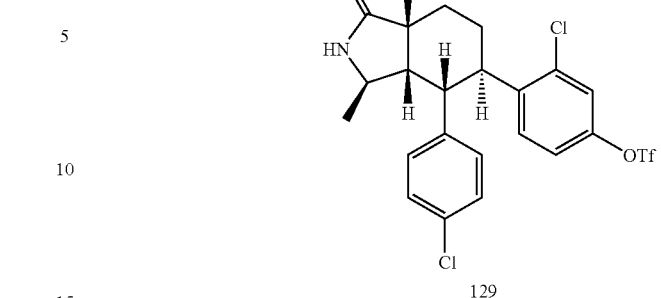

To a solution of 127 (460 mg, 0.89 mmol) in 5 mL dichloromethane at room temperature was added a dichloromethane solution of 1M BBr₃ (4.5 mmol, 5 eq.) and the mixture was stirred at room temperature for 2 hr. The solution was diluted with water, stirred for few minutes, the organic layer separated and the aqueous layer extracted twice with dichloromethane. The combined organic layer washed with brine, dried over MgSO₄, filtered and concentrated to provide 380 mg 128.

MS: 404.2 (MH⁺)

Preparation of Compound 129

Scheme 78:

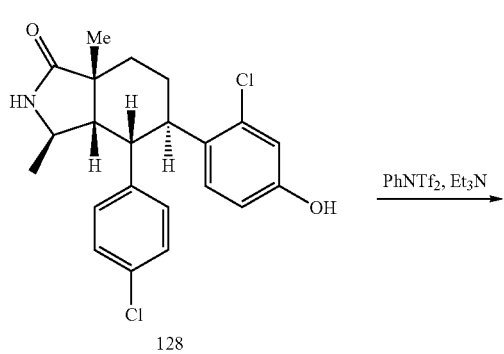

128

To a solution of 128 (330 mg, 0.82 mmol) in 5 mL each of dichloromethane and acetonitrile was added triethyl amine (0.23 mL, 1.65 mmol, 2 eq) followed by N-phenyltrifluoromethane sulfonimide (440 mg, 1.23 mmol, 1.5 eq.). The mixture was stirred for 1.5 hr, diluted with ethyl acetate washed twice with aq. NaHCO₃, brine, dried over MgSO₄, filtered, concentrated and chromatographed with 0% to 3% methanol-dichloromethane to provide 370 mg of 129.

MS: 536.3 (MH⁺)

Preparation of Compound 130

Scheme 79:

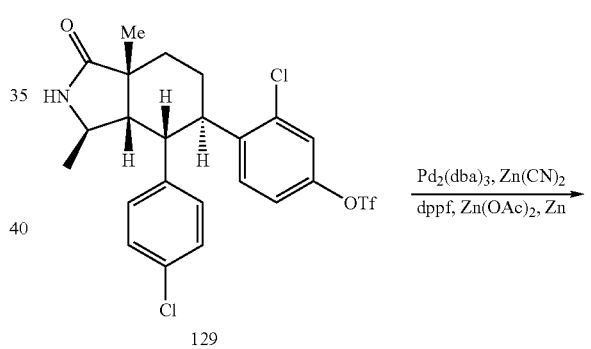

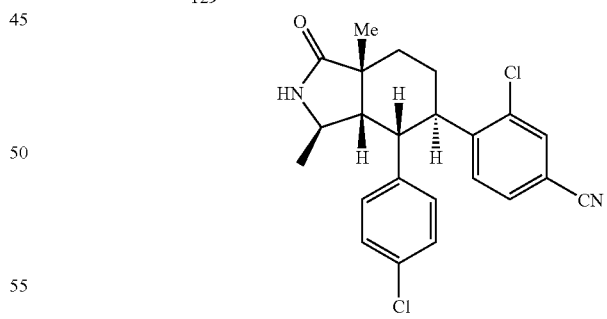

130

A mixture of 129 (150 mg, 0.28 mmol), Pd₂(dba)₃ (13 mg, 0.014 mmol, 5 mol %), dppf (i.e., diphenylphosphine-ferrocene complex) (19.5 mg, 0.035 mmol, 12.5 mol %), Zn(OAc)₂ (14 mg, 0.088 mmol, 0.3 eq.), Zn dust (5.5 mg, 0.084 mmol, 0.3 eq.), Zn(CN)₂ (23 mg, 0.20 mmol, 07 eq) in 2 mL of DMF in a sealed tube was bubbled with argon and heated in an oil-bath at 100° C. for 1 hr. The solution was diluted with ethyl acetate, washed with ferrous ammonium sulfate, brine, dried over MgSO₄, filtered, concentrated and chromatographed with 0% to 3% methanol-dichloromethane to provide 120 mg 130.

MS: 413.2 (MH⁺)

Preparation of Compound 131

Scheme 80:

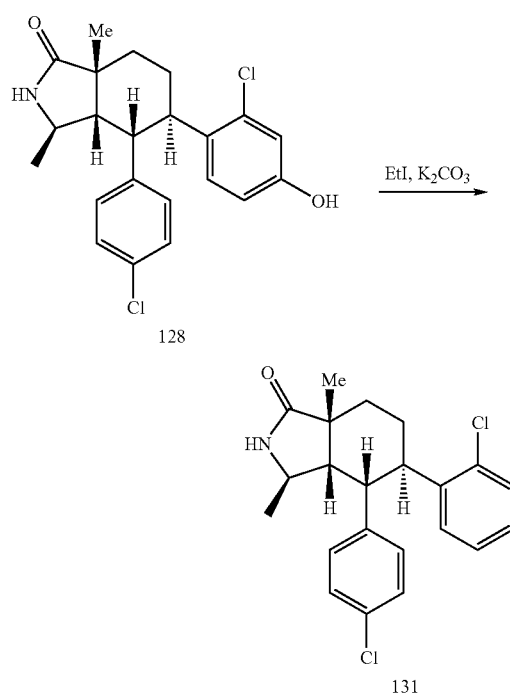

A mixture of 128 (40 mg, 0.10 mmol), K₂CO₃ (69 mg, 0.50 mmol, 5 eq.) and iodomethane (0.04 mL, 050 mmol, 5 eq.) in 2 mL of acetone was heated overnight in a sealed tube at 50° C. The mixture was diluted with water, extracted three times with ethyl acetate, combined organic layer washed with brine, dried over MgSO4, filtered and evaporated to provide 47 mg of 131.

MS: 432.2 (MH⁺)

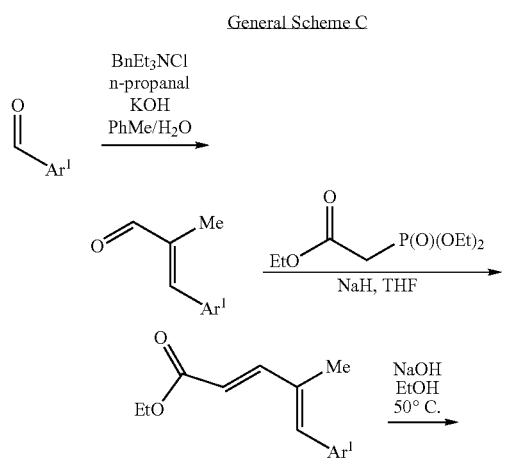

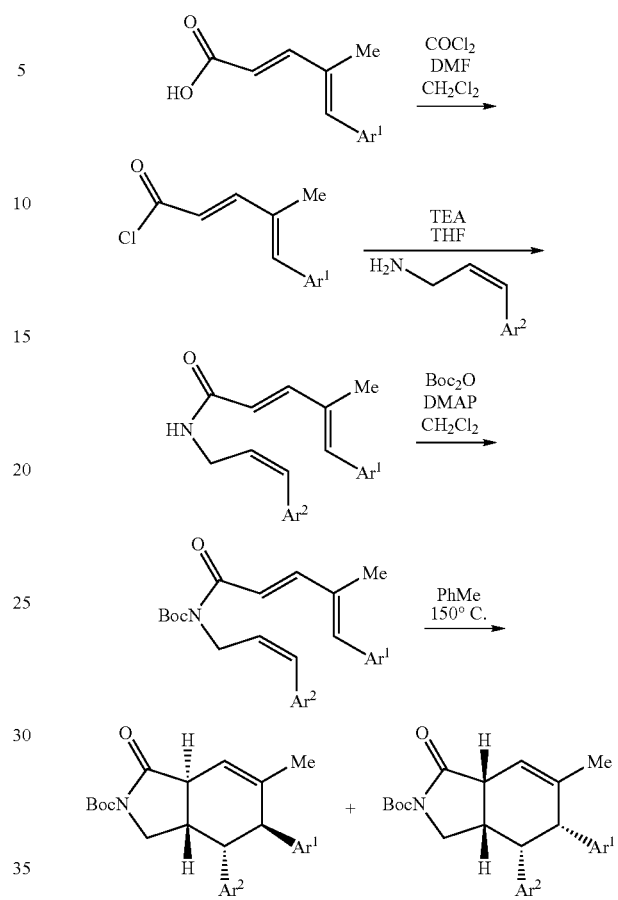

Preparation of Compounds 132 and 133

Step 1

Preparation of 3-(2,4-Dichlorophenyl)-2-methylpropenal

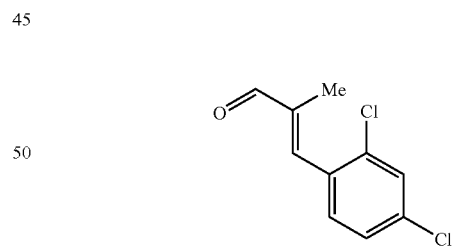

2,4-dichlorobenzaldehyde (26.26 g, 0.15 mol) was dissolved in toluene (200 mL), and then KOH (8.4 g, 1 eq) in water (183 mL) was added followed by BnEt₃NCl. The mixture was cooled to 0° C. and n-propanal (26.15 g, 0.45 mol, 3 eq) in toluene (50 mL) was added dropwise. The mixture was allowed to warm to room temperature and stirred overnight. The organic layer was separated and washed successively with water, brine, dried (MgSO₄), and concentrated under reduced pressure. The resulting residue was purified by silica gel chromatography (0-1-2-3% EtOAc in hexanes) to give 17.56 g of 3-(2,4-dichlorophenyl)-2-methylpropenal.

Step 2

Preparation of 5-(2,4-Dichlorophenyl)-4-methylpenta-2,4-dienoic Acid Ethyl Ester

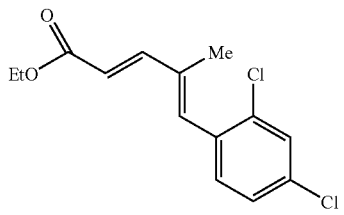

Sodium hydride (4.88 g of a 60% dispersion in mineral oil, 1.5 eq, 0.122 mol) was suspended in THF (442 mL). To this suspension was added a solution of diethoxyphosphorylactic acid ethyl ester (27.5 g, 0.122 mol, 1.5 eq) in THF (10 mL), dropwise. After 10 minutes a solution of 3-(2,4-dichlorophenyl)-2-methylpropenal (17.56 g, 0.082 mol) in THF (50 mL) was added, dropwise. After stirring for 4 hours the mixture was added to $NH_4Cl_{(sat)}$ and extracted with EtOAc. The combined organic extracts were dried ($MgSO_4$), concentrated under reduced pressure to give a residue that was purified by silica gel chromatography (0-2.5-5% EtOAc in hexanes) to give 20.9 g of 5-(2,4-dichlorophenyl)-4-methylpenta-2,4-dienoic acid ethyl ester.

Step 3

Preparation of 5-(2,4-Dichlorophenyl)-4-methylpenta-2,4-dienoic Acid

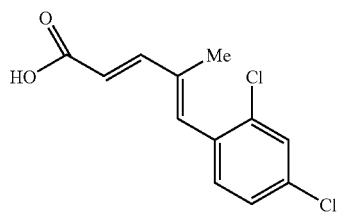

5-(2,4-Dichlorophenyl)-4-methylpenta-2,4-dienoic acid ethyl ester (2.37 g, 0.083 mol) was suspended in EtOH (50 mL). 2 N NaOH (13 mL, 3 eq) was added and the mixture was heated at 50° C. for 1 hour. The mixture was cooled to room temperature and acidified to pH 1. The resulting solid was collected to give 2 g of 5-(2,4-dichlorophenyl)-4-methylpenta-2,4-dienoic acid.

Step 4

5-(2,4-Dichlorophenyl)-4-methylpenta-2,4-dienoic acid [3-(4-chlorophenyl)allyl]amide

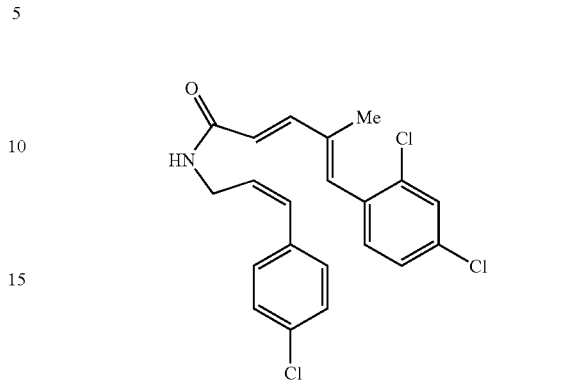

5-(2,4-Dichlorophenyl)-4-methylpenta-2,4-dienoic acid (1 g, 0.0039 mol) was suspended in $CH_2Cl_2$ (10 mL). Oxalyl chloride (0.5 mL, 1.5 eq) was added, followed by 1 drop of DMF. After 2 hours the volatiles were removed, the residue taken up in THF (10 mL), and the mixture cooled to 0° C. A mixture of 3-(4-chlorophenyl)allylamine (0.7 g, 1.1 eq, 0.0042 mol, prepared as shown in Scheme 4) and $Et_3N$ (0.82 mL, 0.0042 mol, 1.5 eq) in THF (5 mL) was added dropwise. After 1 hour, TLC analysis showed complete conversion of the starting materials and the mixture was then diluted with EtOAc. The organic layer washed with $NH_4Cl_{(sat)}$, dried ($MgSO_4$), and concentrated under reduced pressure. The resulting residue was purified by silica gel chromatography (0-10-20-30-40% EtOAc in hexanes) to give 1.25 g of 5-(2,4-dichlorophenyl)-4-methylpenta-2,4-dienoic acid [3-(4-chlorophenyl)allyl]amide.

Step 5

Preparation of [3-(4-Chlorophenyl)allyl]-[5-(2,4-dichlorophenyl)-4-methylpenta-2,4-dienoyl]carbamic acid tert-butyl ester

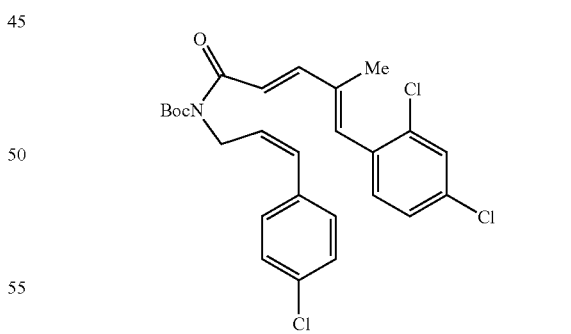

5-(2,4-Dichlorophenyl)-4-methylpenta-2,4-dienoic acid [3-(4-chlorophenyl)allyl]amide (1.25 g, 0.0032 mol) was dissolved in $CH_2Cl_2$ (20 mL). To this mixture was added, $Et_3N$ (0.443 mL, 1 eq), $Boc_2O$ (1.39 g, 2 eq), and DMAP (0.39 g, 1 eq). After stirring for 16 hours, the mixture was diluted with $CH_2Cl_2$, washed with $NH_4Cl_{(sat)}$, and dried ($MgSO_4$). Silica gel chromatography (5% EtOAc in hexanes) gave 1.43 g of [3-(4-Chlorophenyl)allyl]-[5-(2,4-dichlorophenyl)-4-methylpenta-2,4-dienoyl]carbamic acid tert-butyl ester.

Step 6

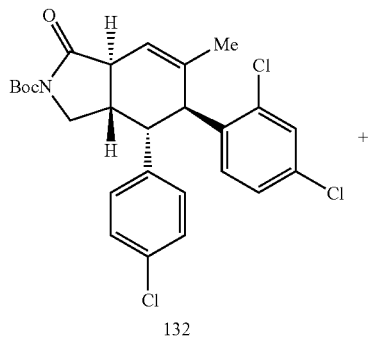

132

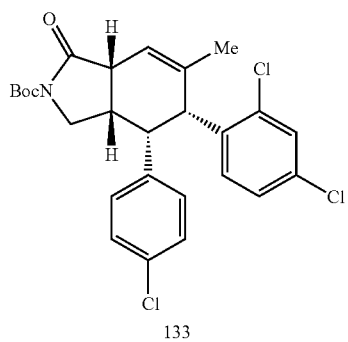

133

[3-(4-Chlorophenyl)allyl]-[5-(2,4-dichlorophenyl)-4-methylpenta-2,4-dienoyl]carbamic acid tert-butyl ester (1.25 g, 0.00247 mol) was dissolved in toluene (60 mL) and heated at 150° C. for 2.5 hours. The mixture was concentrated and the residue purified by silica gel chromatography (5-15-20-40% EtOAc in hexanes) to give, in order of elution, 0.46 g of 132 LCMS: 452 (MH$^+$-Bu$^t$), and 0.46 g of 133 LCMS: 452 (MH$^+$-Bu$^t$).

General Scheme D

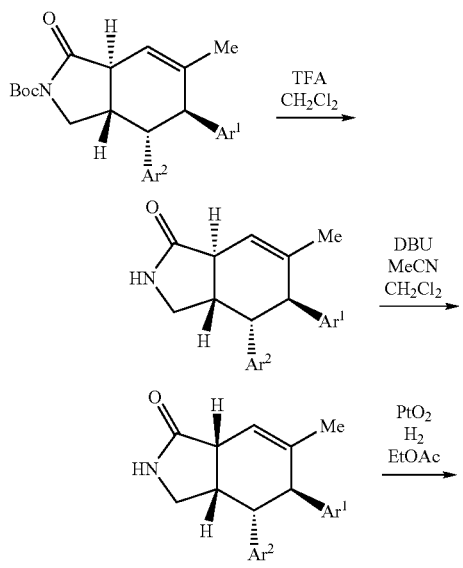

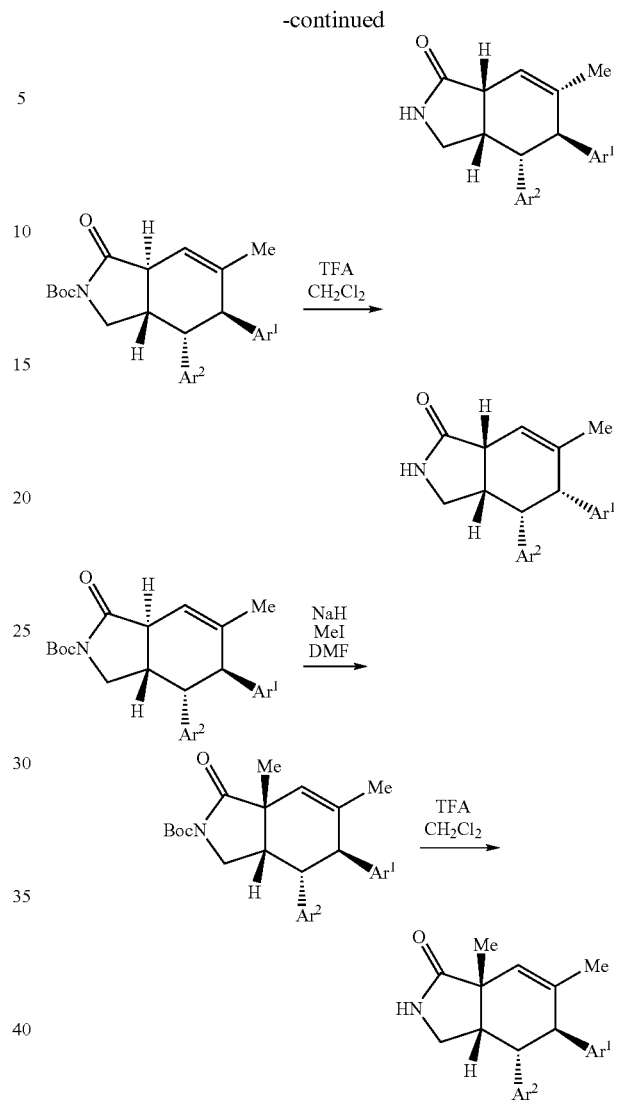

Preparation of Compound 134

134

Compound 132 (120 mg, 0.000236 mol) was dissolved in CH$_2$Cl$_2$ (2 mL) and cooled to 0° C. TFA (i.e., trifluoroacetic acid (2 mL)) was added and the mixture was stirred for 30 min. Removal of volatiles gave 105 mg of the compound 134. LCMS: 406.2, 408.2 (MH$^+$)

Preparation of Compound 135

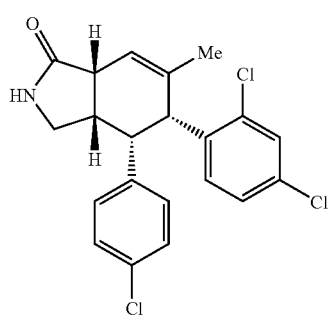

Starting from compound 133, compound 135 was produced using a procedure similar to the procedure used to prepare 134. LCMS: 406.2, 408.2 (MH+)

Preparation of Compound 136

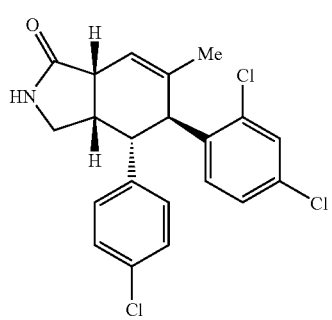

Compound 134 (100 mg, 0.000246 mol) was suspended in MeCN/CH$_2$Cl$_2$ (2 mL/2 mL), DBU (0.111 mL, 3 eq) was added and the mixture stirred for 4 hours. The mixture was diluted with EtOAc and washed with NH$_4$Cl$_{(sat)}$, the organic layer was dried (MgSO$_4$) and concentrated under reduced pressure to give 40 mg of 136. LCMS: 406.2, 408.2 (MH+)

Preparation of Compound 137.

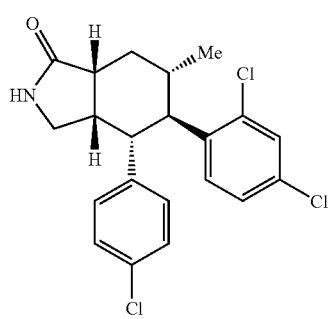

Compound 136 (30 mg, 0.000074 mol) was dissolved in EtOAc. PtO$_2$ (3 mg) was added and the mixture stirred under 1 atm of H$_2$ for 4 hours. The catalyst was removed by filtration through a pad of CELITE and the filtrate was concentrated to give 29 mg of compound 137. LCMS: 408.2, 410.2 (MH+)

Preparation of Compound 138

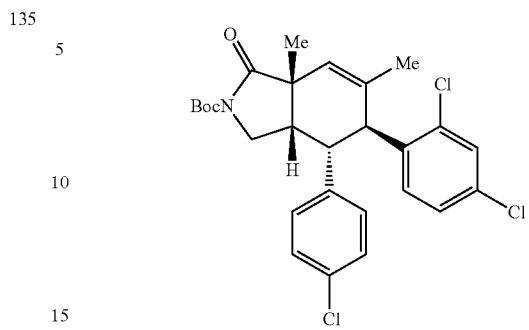

Compound 132 (100 mg, 0.000197 mol) was dissolved in DMF (1 mL), MeI (0.246 mL, 20 eq). NaH (11.8 mg of a 60% dispersion in mineral oil, 1.5 eq) was then added. After stirring for 2 hours, the reaction was quenched with NH$_4$Cl$_{(sat)}$, extracted with EtOAc, and the combined organic extracts were dried (MgSO$_4$) and concentrated under reduced pressure. The resulting residue was purified using silica gel chromatography to give 80 mg of compound 138. LCMS: 466.3 (MH+-Bu$^t$).

Preparation of Compound 139

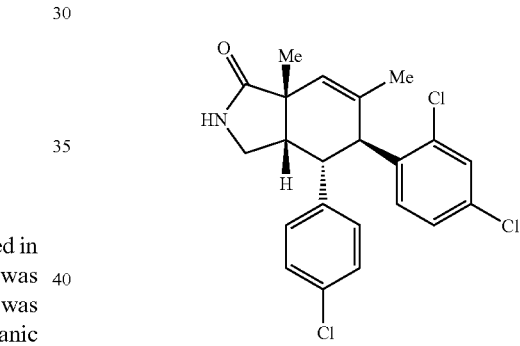

Compound 138 (80 mg, 0.000154 mol) was dissolved in CH$_2$Cl$_2$ (5 mL) and cooled to 0° C. TFA (5 mL) was added and the mixture was stirred for 30 min. Removal of volatiles followed by silica gel chromatography (0-30-50-70% EtOAc in hexanes) gave 35 mg of compound 139. LCMS: 420.2 (MH+)

Preparation of Compounds 140 and 141

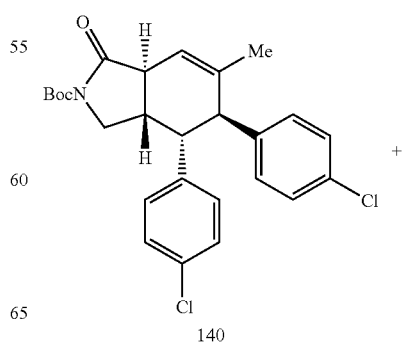

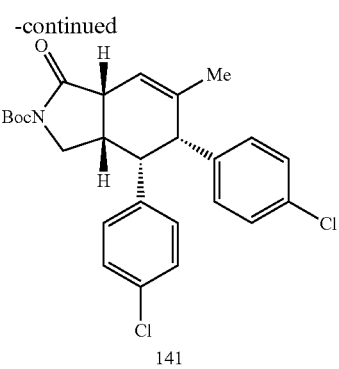

141

Using procedures similar to those employed for the synthesis of compounds 132 and 133, compounds 140 (LCMS: 416.2 (MH$^+$-Bu$^t$)) and 141 (LCMS: 416.2 (MH$^+$-Bu$^t$)) were synthesized.

Preparation of Compound 142

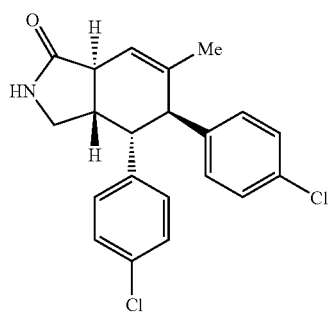

142

Compound 142 was prepared from compound 140 using a procedure similar to that employed for the synthesis of compound 134.

Compound 142 LCMS: 372.2 (MH$^+$).

Preparation of Compound 143

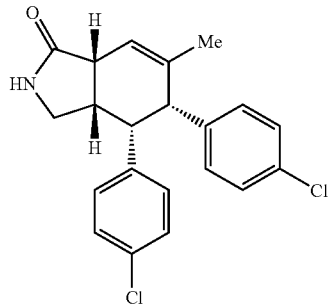

143

Compound 143 was prepared from compound 141 using a procedure similar to that employed for the synthesis of compound 134.

Compound 143 LCMS: 372.2 (MH$^+$).

Preparation of Compound 144

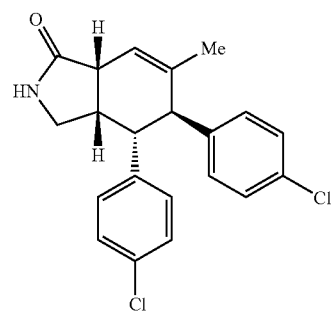

144

Compound 144 was prepared from compound 142 using a procedure similar to that employed for the synthesis of compound 136.

Compound 144 LCMS: 372.2 (MH$^+$).

Preparation of Compound 145

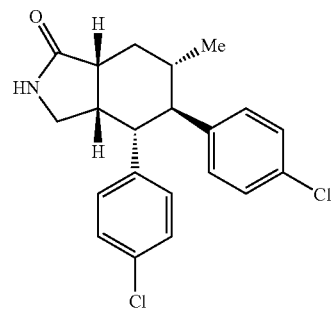

145

Compound 145 was prepared from compound 144 using a procedure similar to that employed for the synthesis of compound 137.

Compound 145, LCMS: 374.2 (MH$^+$).

Preparation of Compound 146

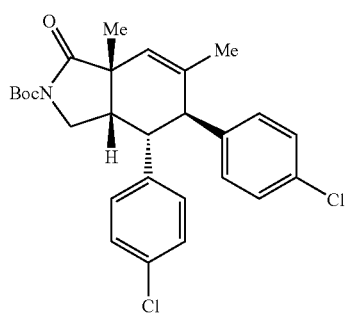

146

Compound 146 was prepared from compound 140 using a procedure similar to that employed for the synthesis of compound 138.

Compound 146 LCMS: 430.2 (MH$^+$-Bu$^t$).

Preparation of Compound 147

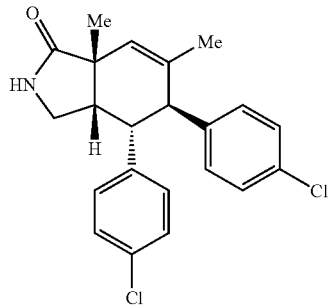

Compound 147 was prepared from compound 146 using a procedure similar to that employed for the synthesis of compound 139.

Compound 147 LCMS: 386.2 (MH$^+$).

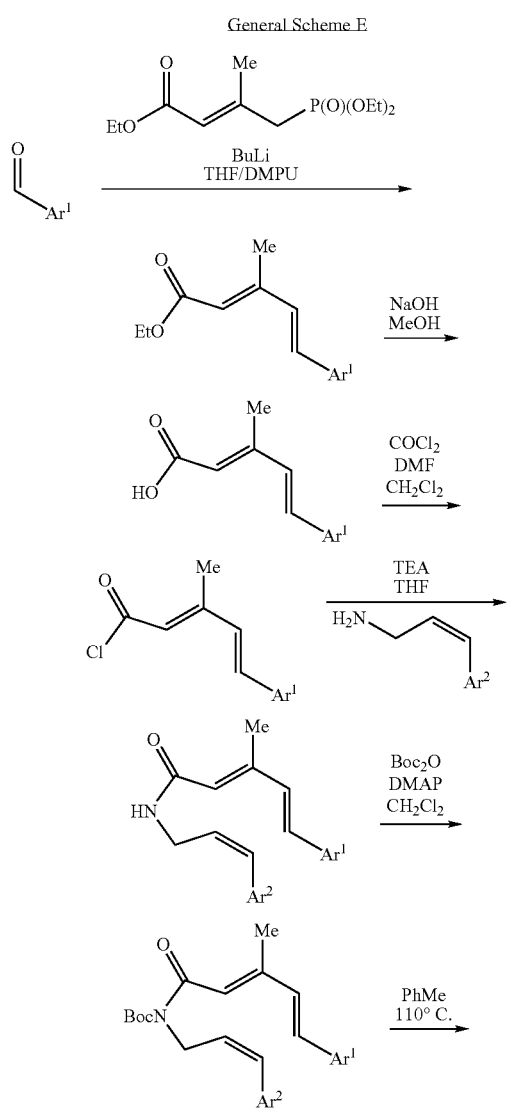

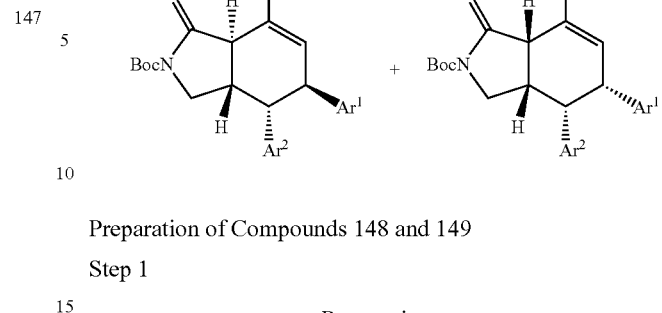

Preparation of Compounds 148 and 149

Step 1

Preparation 5-(2,4-Dichlorophenyl)-3-methylpenta-2,4-dienoic Acid Ethyl Ester

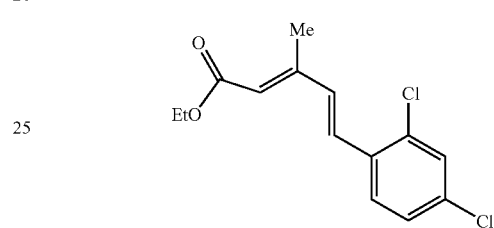

Triethyl 3-methyl-4-phosphonocrotonate (34.24 g, 0.129 mol, 1.3 eq) was dissolved in THF/DMPU (100 mL/200 mL) and the mixture was cooled to −78° C. BuLi (51.8 mL of a 2.5M solution in hexanes, 1.3 eq) was added dropwise. The mixture was stirred for 20 min and then a solution of 2,4-dichlorobenzaldehyde (17.6 g, 0.1 mol) in THF/DMPU (20 mL/40 mL) was added dropwise. The resulting mixture was stirred for 1 hour and then allowed to warm to room temperature. NH$_4$Cl$_{(sat)}$ was added and the mixture extracted with EtOAc. The organic layers were washed with, water, brine, and dried (MgSO$_4$). Removal of solvent under reduced pressure followed by silica gel chromatography (0-1-2-3% EtOAc in hexanes) gave 23.3 g of 5-(2,4-dichlorophenyl)-3-methylpenta-2,4-dienoic acid ethyl ester.

Step 2

Preparation 5-(2,4-Dichlorophenyl)-3-methylpenta-2,4-dienoic Acid

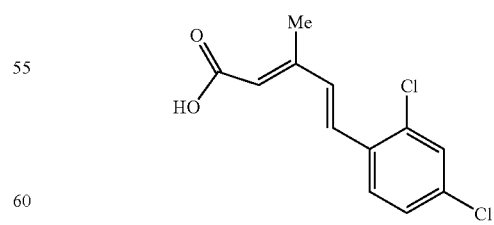

5-(2,4-Dichlorophenyl)-3-methylpenta-2,4-dienoic acid ethyl ester (5 g, 0.0184 mol) was dissolved in THF (125 mL). Water (50 mL), MeOH (50 mL), and NaOH (18.44 mL of a 2M solution in water, 2 eq) were then added. After 6 hours, TLC analysis showed complete conversion of the starting materials and the mixture was acidified to pH 1 by addition of 6N HCl. The resulting solid was collected to give 4.24 g of 5-(2,4-dichlorophenyl)-3-methylpenta-2,4-dienoic acid.

Step 3

Preparation of [3-(4-Chlorophenyl)allyl]-[5-(2,4-dichlorophenyl)-3-methylpenta-2,4-dienoyl]carbamic Acid Tert-Butyl Ester

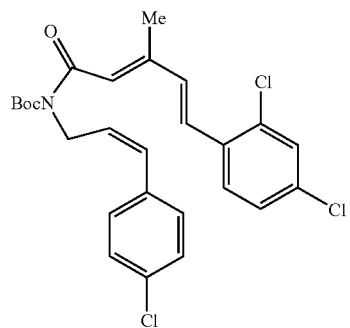

5-(2,4-Dichlorophenyl)-3-methylpenta-2,4-dienoic acid (4.24 g, 0.0165 mol) was suspended in CH$_2$Cl$_2$ (40 mL), oxalyl chloride (2.12 mL, 1.5 eq) was added followed by 1 drop of DMF. After 2 hours the volatiles were removed, the residue taken up in THF (34 mL), and the mixture cooled to 0° C. A mixture of 3-(4-chlorophenyl)allylamine (3.2 g, 1.1 eq, Scheme 4) and Et$_3$N (3.6 mL, 1.5 eq) in THF (20 mL) was added dropwise. After 1 hour, TLC analysis showed complete conversion of the starting materials and the mixture was then diluted with EtOAc. The organic layer washed with NH$_4$Cl$_{(sat)}$, dried (MgSO$_4$), and concentrated under reduced pressure, and the resulting residue was taken up in CH$_2$Cl$_2$ (100 mL). To this mixture was added Et$_3$N (2.3 mL, 1 eq), Boc$_2$O (7.17 g, 2 eq), and DMAP (2 g, 1 eq). After stirring for 16 hours, the mixture was diluted with CH$_2$Cl$_2$, washed with NH$_4$Cl$_{(sat)}$, and dried (MgSO$_4$). Silica gel chromatography (0-2-4% EtOAc in hexanes) gave 5.8 g of [3-(4-chlorophenyl)allyl]-[5-(2,4-dichlorophenyl)-3-methylpenta-2,4-dienoyl]carbamic acid tert-butyl ester.

Step 4

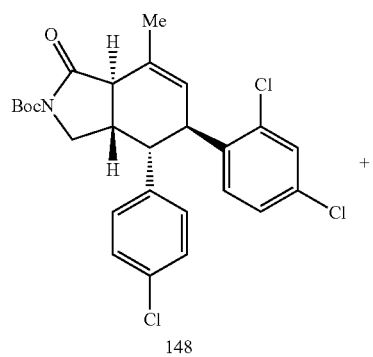

148

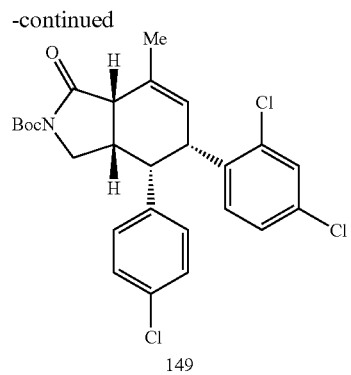

149

[3-(4-Chlorophenyl)allyl]-[5-(2,4-dichlorophenyl)-3-methylpenta-2,4-dienoyl]carbamic acid tert-butyl ester (5.8 g, 0.011 mol) was dissolved in toluene (350 mL) and heated at 110° C. for 3 hours. The mixture was concentrated and the residue purified by silica gel chromatography (0-2.5-5-10-40% EtOAc in hexanes) to give, in order of elution, 2.4 g of compound 148 LCMS: 452 (MH$^+$-Bu$^t$), and 2.2 g of compound 149 LCMS: 452 (MH$^+$-Bu$^t$).

General Scheme F

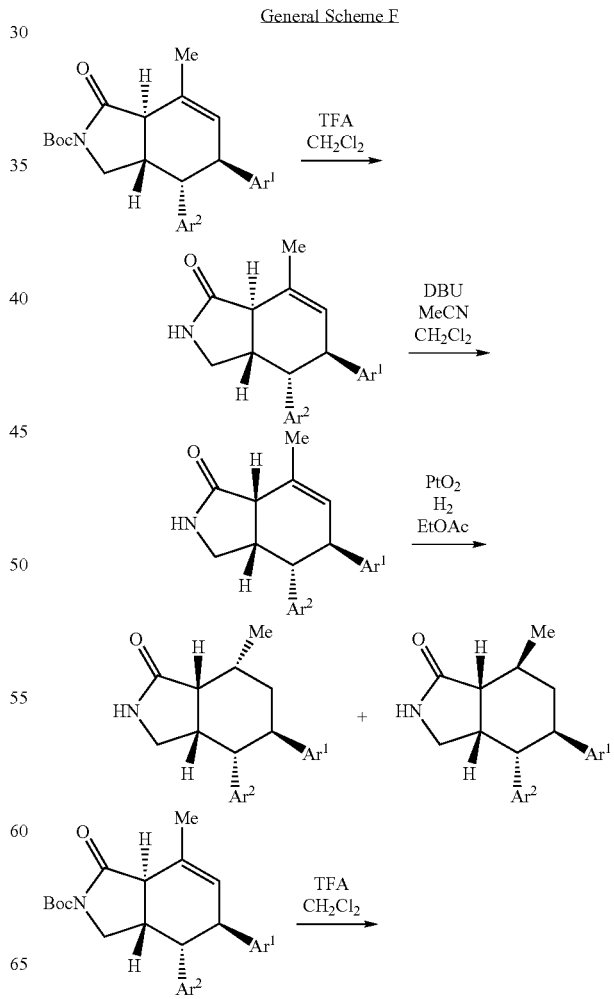

General Scheme F

Preparation of Compound 151

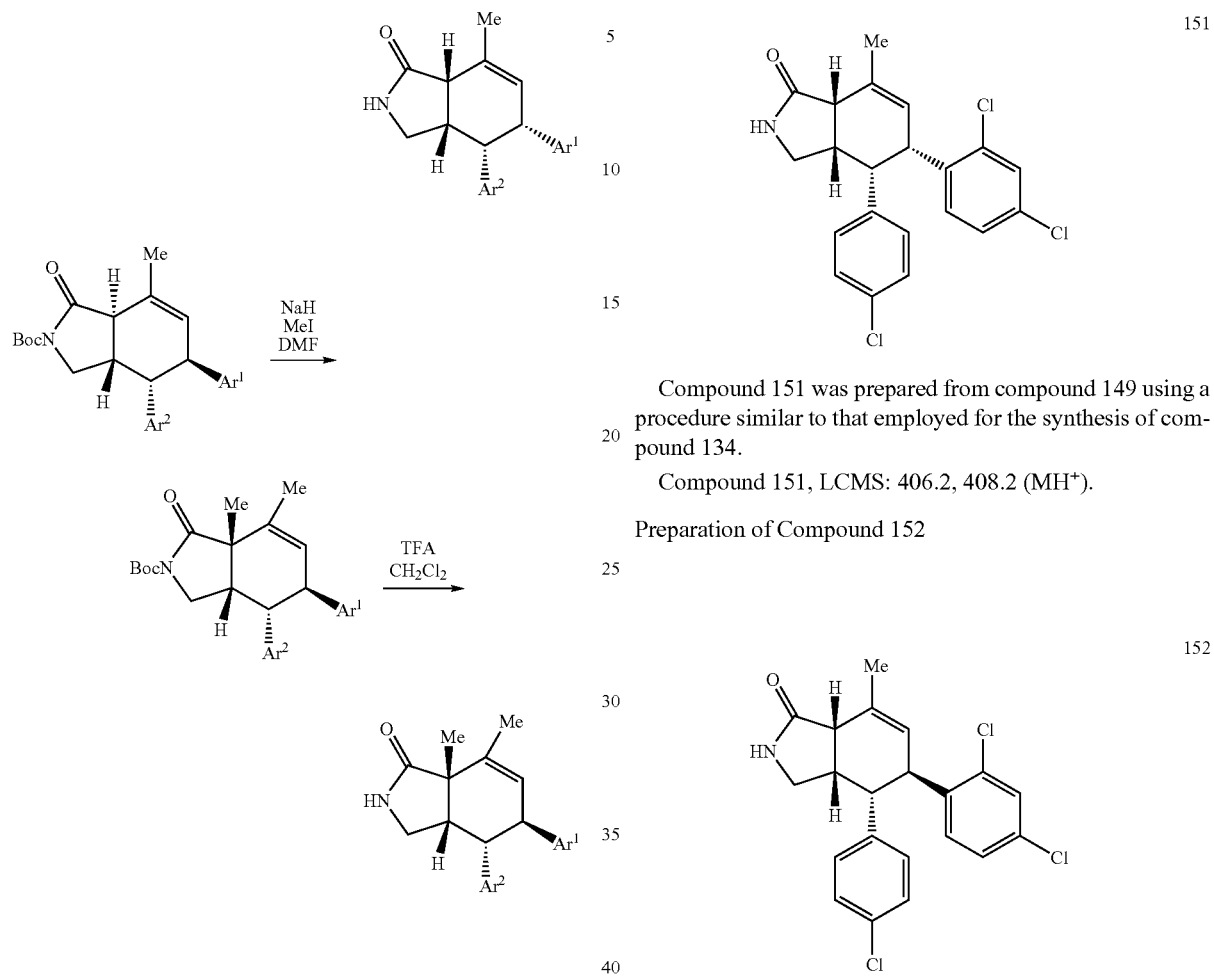

Compound 151 was prepared from compound 149 using a procedure similar to that employed for the synthesis of compound 134.

Compound 151, LCMS: 406.2, 408.2 (MH⁺).

Preparation of Compound 152

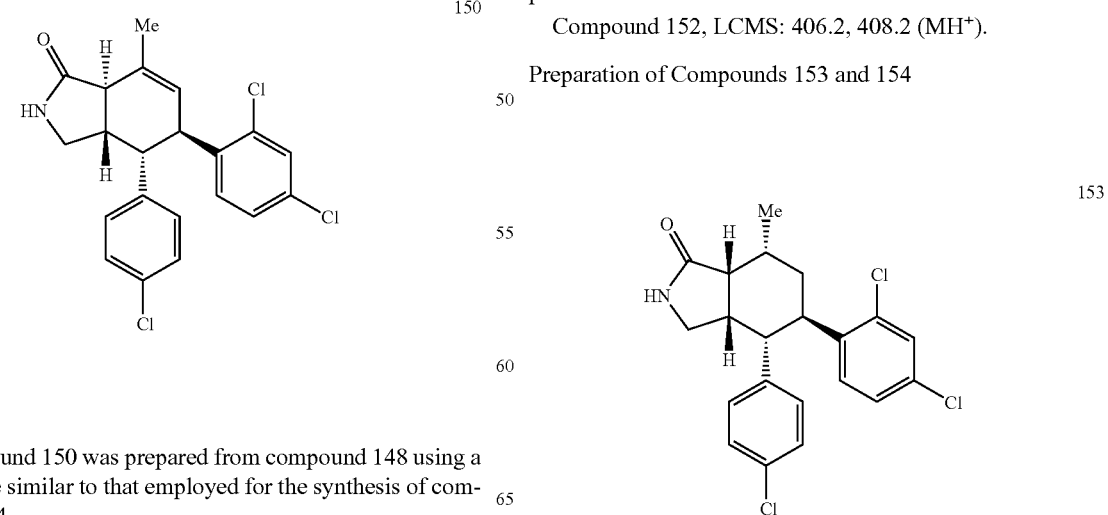

Preparation of Compound 150

Compound 150 was prepared from compound 148 using a procedure similar to that employed for the synthesis of compound 134.

Compound 150, LCMS: 406.2, 408.2 (MH⁺).

Compound 152 was prepared from compound 150 using a procedure similar to that employed for the synthesis of compound 136.

Compound 152, LCMS: 406.2, 408.2 (MH⁺).

Preparation of Compounds 153 and 154

299

-continued

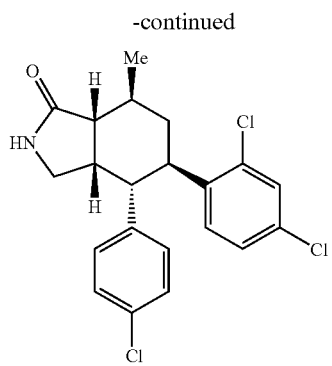

154

Compounds 153 and 154 were prepared by the hydrogenation of compound 152 using a procedure similar to that employed for the synthesis of compound 137.

Compound 153, LCMS: 408.2, 410.2 (MH⁺).
Compound 154, LCMS: 408.2, 410.2 (MH⁺).

Preparation of Compound 155

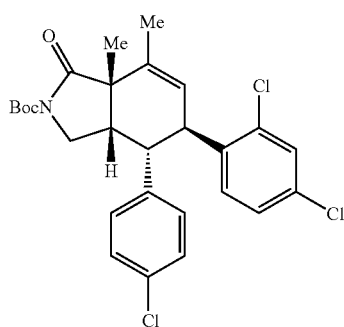

155

Compound 155 was prepared from compound 148 using a procedure similar to that employed for the synthesis of compound 138.

Compound 155, LCMS: 466.3 (MH⁺-Buᵗ).

Preparation of Compound 156

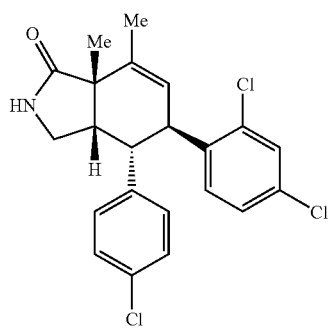

156

Compound 156 was prepared from compound 155 using a procedure similar to that employed for the synthesis of compound 139.

Compound 156, LCMS: 420.2 (MH⁺).

300

Preparation of 5,6-Di(hetero)aryl-isoindol-1-ones

General Scheme G:

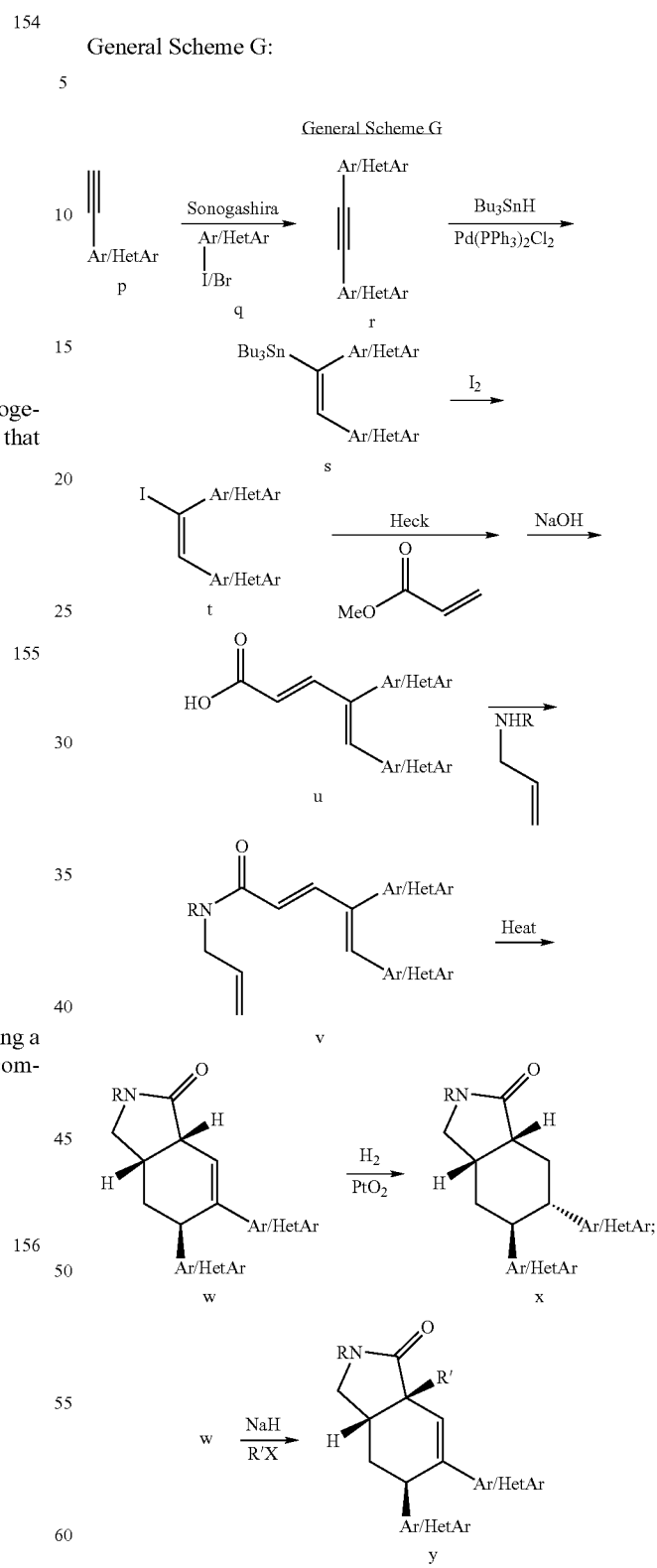

Substituted 5,6-Di(hetero)aryl-isoindol-1-ones may be prepared by procedures shown in General Scheme G, above. An aryl or heteroaryl alkyne p can be coupled by the Sonogashira reaction to an aryl or heteroaryl iodide or bromide q to give the alkyne r. Palladium catalyzed addition of tributyltin hydride followed by treatment with iodine gives the vinyl iodide t. Heck coupling reaction with methyl acrylate followed by hydrolysis gives the dienoic acid u which was converted to the allylamide v either through the acid chloride or by EDCl (i.e., 1-ethyl-3-(3-dimethylaminopropyl)carbodiimide) coupling. Intramolecular Diels-Alder reaction gave product w which can be converted to product x by hydrogenation or product y by alkylation.

Preparation of Compounds 157 and 158

Step 1

Scheme 81:

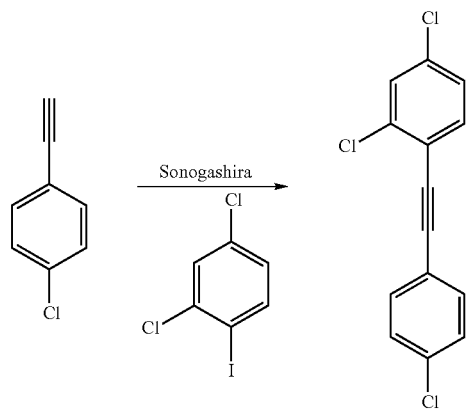

A mixture of 1-chloro-4-ethynyl-benzene (2.71 g, 0.020 mol), 2,4-dichloro-1-iodo-benzene (3.23 mL, 0.024 mol), PdCl$_2$(PPh$_3$)$_2$ (0.10 g, 1.4 mmol), CuI (1.44 g, 7.6 mmol), and diisopropylamine (7 mL) in DCM (i.e., dichloromethane) (100 mL) was stirred at room temperature for 16 h. The mixture was filtered through CELITE. The filtrate was concentrated in vacuo. The residue was chromatographed (SiO$_2$, hexane) to afford 2,4-dichloro-1-(4-chloro-phenylethynyl)-benzene as a white solid (3.23 g, 87%).

Step 2

Scheme 82:

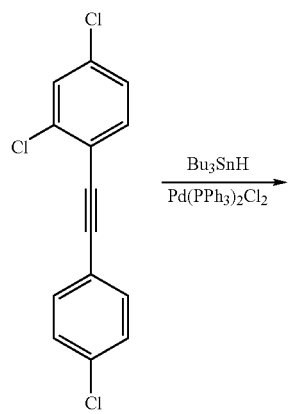

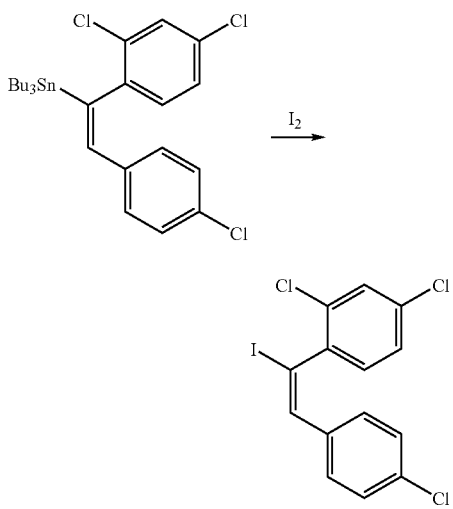

Tributyltin hydride (2.7 mL, 10 mmol) was added to a mixture of 2,4-dichloro-1-(4-chloro-phenylethynyl)-benzene (2.01 g, 7.13 mmol) and PdCl$_2$(PPh$_3$)$_2$ (0.45 g, 0.64 mmol) in THF (70 mL) at room temperature and stirred for 1 h. Iodine crystals (2.7 g, 11 mmol) were added to the mixture at room temperature and stirred for 30 min. The mixture was then stirred with sodium thiosulfate aqueous solution and KF aqueous solution. The mixture was filtered through CELITE. The organic layer of the filtrate was separated and concentrated in vacuo. The residue was chromatographed (SiO$_2$, hexane) to afford 2,4-dichloro-1-[2-(4-chloro-phenyl)-1-iodo-vinyl]-benzene as a light yellow solid (2.43 g, 83%).

Step 3

Scheme 83:

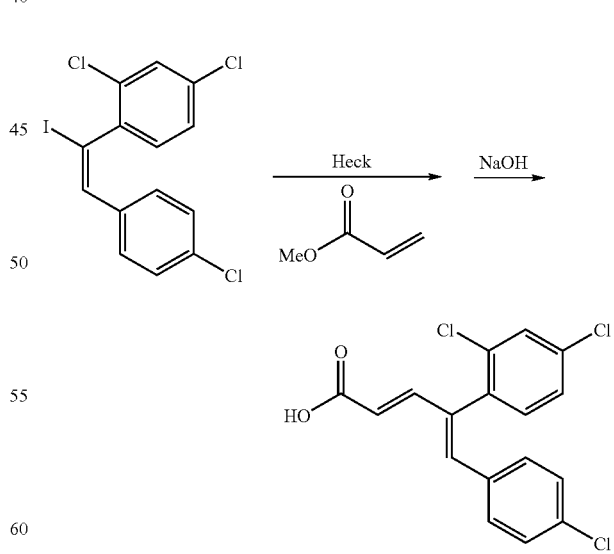

To a solution of 2,4-dichloro-1-[2-(4-chloro-phenyl)-1-iodo-vinyl]-benzene (270 mg, 0.66 mmol) in DMF (6 mL) was added methyl acrylate (0.30 mL, 3.3 mmol), Et$_3$N (0.30 mL, 2.2 mmol), and Pd(PPh$_3$)$_2$Cl$_2$ (46 mg, 0.07 mmol). The mixture was stirred at 100° C. for 16 h. The mixture was filtered through CELITE. The filtrate was concentrated in vacuo. The mixture was diluted with EtOAc and washed with NH₄Cl (sat.). The organic layer was dried (MgSO₄) and concentrated in vacuo. Flash chromatography of the residue on a silica gel column with EtOAc-hexane (5-95) as eluent gave the methyl ester (98 mg, 40%) as a clear oil.

To a solution of the methyl ester (98 mg, 0.27 mmol) in THF-MeOH (3 mL, 1-1) was added NaOH (1.5 mL, 10%). The mixture was stirred at room temperature for 1 h. The mixture was diluted with water and the organics were evaporated. The aqueous mixture was diluted with water, acidified with 10% HCl, and extracted with CH₂Cl₂. The organic layer washed with brine, dried (MgSO₄), and concentrated in vacuo to give 5-(4-chloro-phenyl)-4-(2,4-dichloro-phenyl)-penta-2,4-dienoic acid (82 mg, 87%) as an off-white solid.

Step 4

Scheme 84:

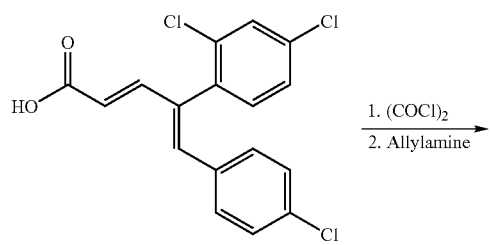

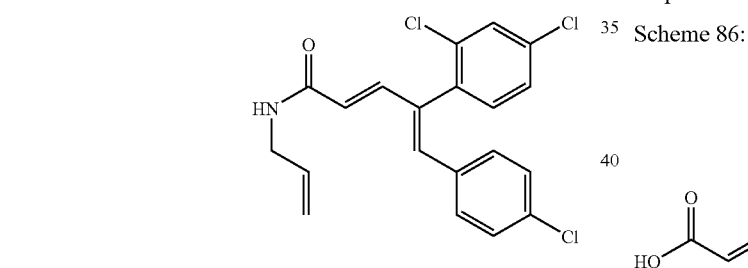

The 5-(4-chloro-phenyl)-4-(2,4-dichloro-phenyl)-penta-2,4-dienoic acid was converted to 5-(4-chloro-phenyl)-4-(2,4-dichloro-phenyl)-penta-2,4-dienoic acid allylamide in a manner similar to the procedure used to prepare amide g in General Scheme A.

Step 5

Scheme 85:

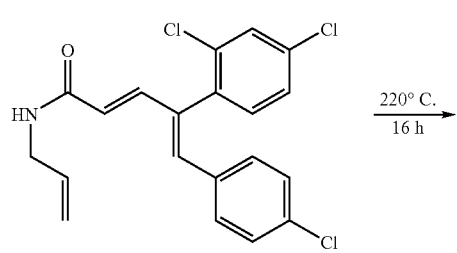

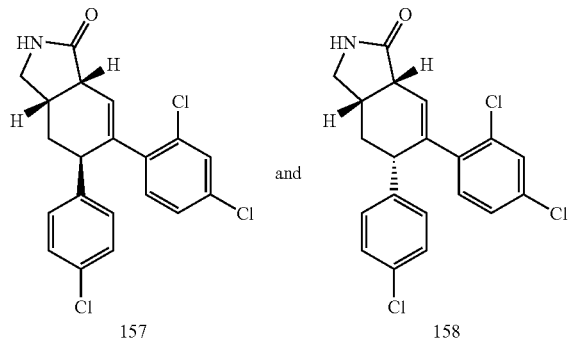

The 5-(4-chloro-phenyl)-4-(2,4-dichloro-phenyl)-penta-2,4-dienoic acid allylamide (55 mg) and dihydroquinone (4 mg) were dissolved in o-xylene and heated in a closed pressure tube at 220° C. under nitrogen for 16 h. After cooling to room temperature, the solution was diluted with EtOAc and hexanes, washed with 10% NaOH and brine, dried (MgSO₄), and concentrated. The residue was chromatographed (SiO₂, 9:1-2:1 CH₂Cl₂/EtOAc) to give 157 as a white solid (12 mg, 22%), LCMS: m/e 392 (MH⁺), and 158 as a white solid (2 mg, 4%), LCMS: m/e 392 (MH⁺).

Preparation of Compounds 159 and 160

Step 1

Scheme 86:

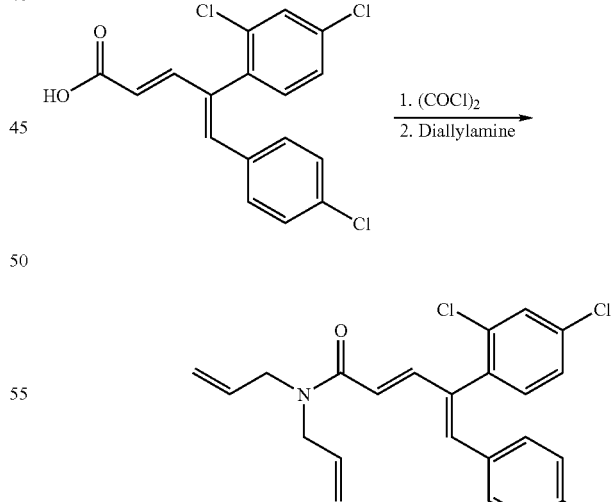

The 5-(4-chloro-phenyl)-4-(2,4-dichloro-phenyl)-penta-2,4-dienoic acid was also converted to 5-(4-chloro-phenyl)-4-(2,4-dichloro-phenyl)-penta-2,4-dienoic acid diallylamide in a manner similar to the procedure used to prepare amide g in General Scheme A.

Step 2:

Scheme 87:

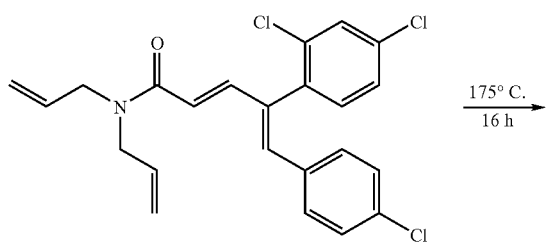

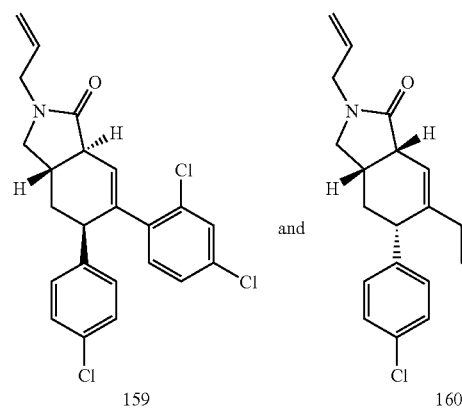

The 5-(4-chloro-phenyl)-4-(2,4-dichloro-phenyl)-penta-2,4-dienoic acid diallylamide (39 mg) and dihydroquinone (2 mg) was dissolved in toluene and heated in a closed pressure tube at 175° C. under nitrogen for 16 h. After cooling to room temperature, the solution was diluted with EtOAc and hexanes, washed with 10% NaOH and brine, dried (MgSO$_4$), and concentrated. The residue was chromatographed (SiO$_2$, 4:1-3:2 hexane/EtOAc) to give 159 as an off-white solid (15 mg, 38%), LCMS: m/e 432 (MH$^+$), and 160 as an off-white solid (12 mg, 30%), LCMS: m/e 432 (MH$^+$).

Preparation of Compound 161

Scheme 88:

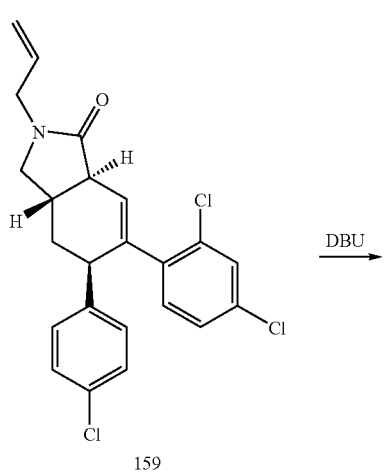

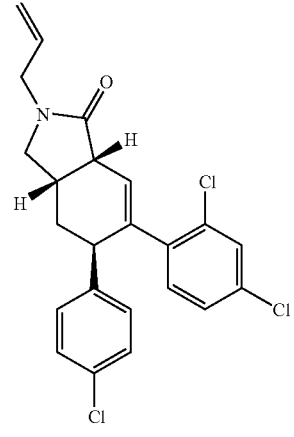

Compound 159 (12 mg) and 1 drop of DBU (i.e., 1,8-diazabicyclo[5.4.0]undec-7-ene) were dissolved in CH$_2$Cl$_2$ (2 mL) and stirred at room temperature for 1 h. The solution was concentrated. The residue was chromatographed (SiO$_2$, 4:1-3:2 hexane/EtOAc) to give 161 as an off-white resin (7 mg, 58%), LCMS: m/e 432 (MH$^+$).

Preparation of Compound 162

Scheme 89:

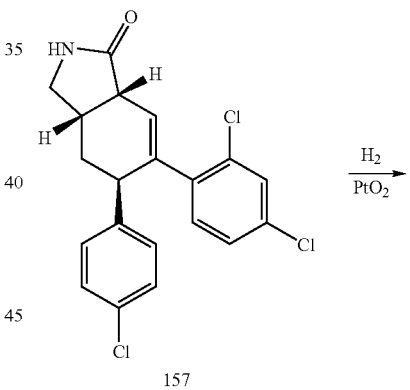

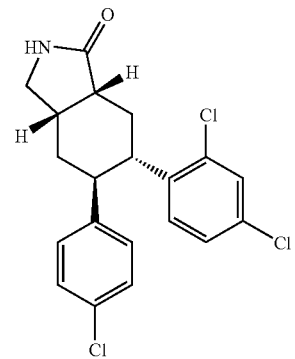

Compound 157 was converted to 162 in a manner similar to that used to prepare compounds 5 and 6 in Scheme 7. LCMS: m/e 394 (MH$^+$).

Preparation of Compound 163

Scheme 90:

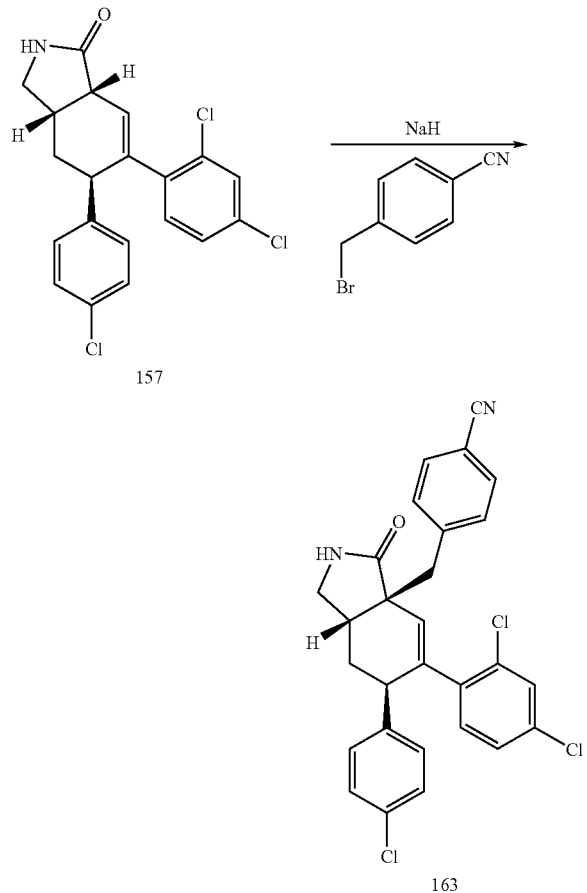

To a solution of 157 (31 mg, 0.079 mmol) and p-cyanobenzylbromide (46 mg, 0.24 mmol) in DMF (6 mL) was added NaH (31 mg, 0.79 mmol, 60% in mineral oil) at room temperature and the mixture was stirred at room temperature for 16 h. The mixture was concentrated in vacuo. The residue was diluted with EtOAc and washed with $NH_4Cl$ (sat.). The organic layer was dried ($MgSO_4$) and concentrated in vacuo. Chromatography of the residue on a preparative silica gel plate with EtOAc-hexane (40-60) as eluent gave 163 (10 mg, 25%) as a white solid. LCMS: m/e 507 ($MH^+$).

Alternative Preparation of 5,6-Diphenyl-isoindol-1-ones

General Scheme H:

General Scheme H:

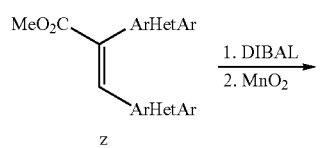

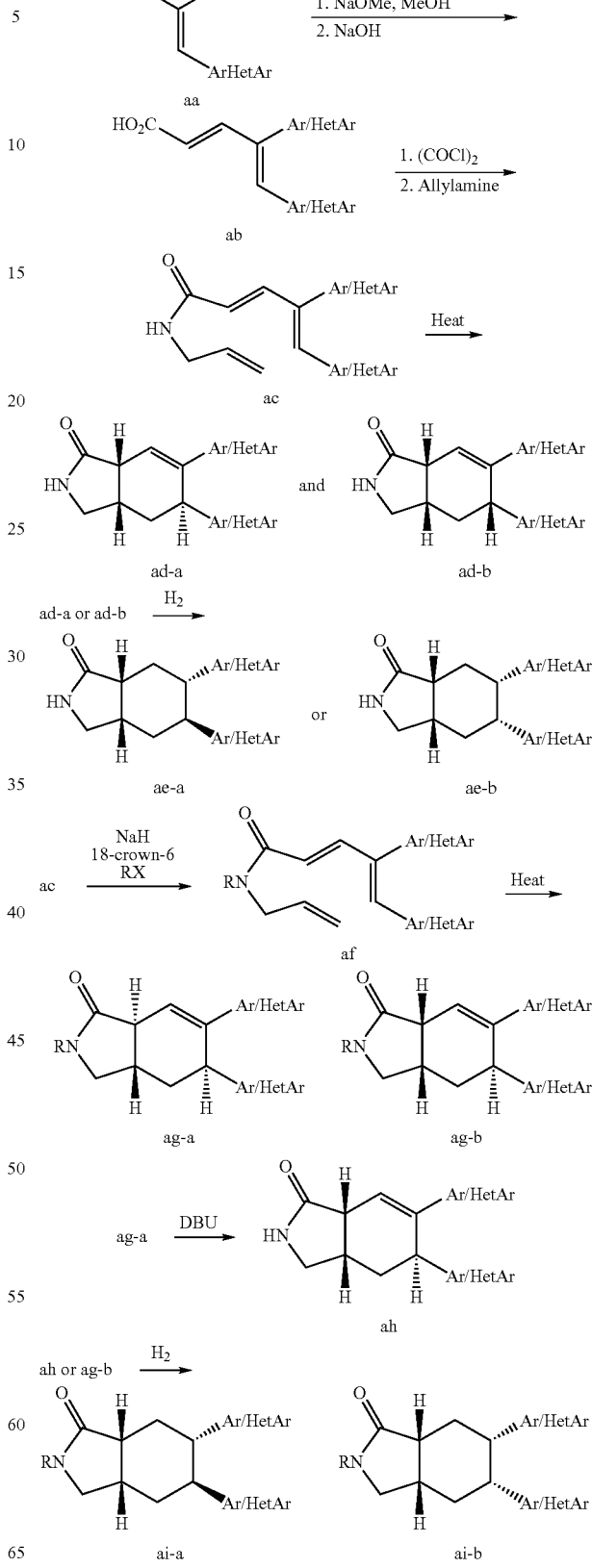

An alternative method for preparing substituted 5,6-diphenyl-isoindol-1-ones is shown in General Scheme H, above. The bis aryl or heteroaryl substituted ester z may be prepared by a procedure similar to the procedure published in *Acta Chem Scand,* 1993, 47, 1112 (herein incorporated by reference in its entirety) and converted to the dienoic acid ab by well known procedures as shown in General Scheme H. The dienoic acid ab was then converted to the target compounds using procedures similar to those used in General Scheme G.

Preparation of Compounds 164-170

Scheme 91:

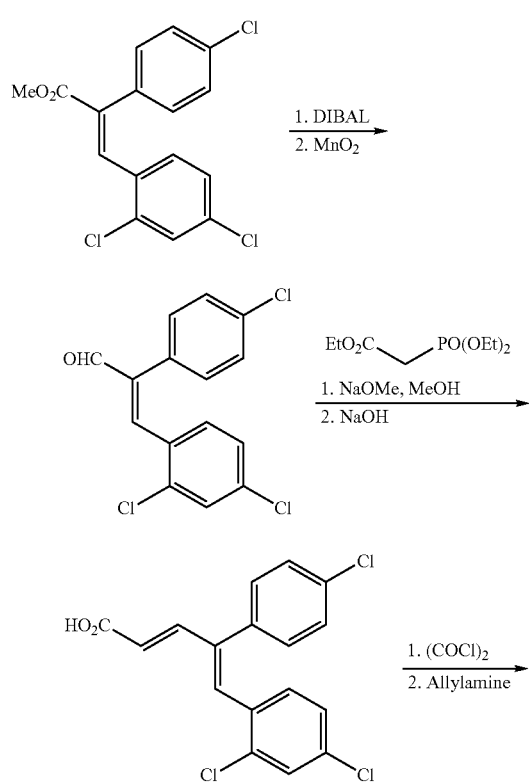

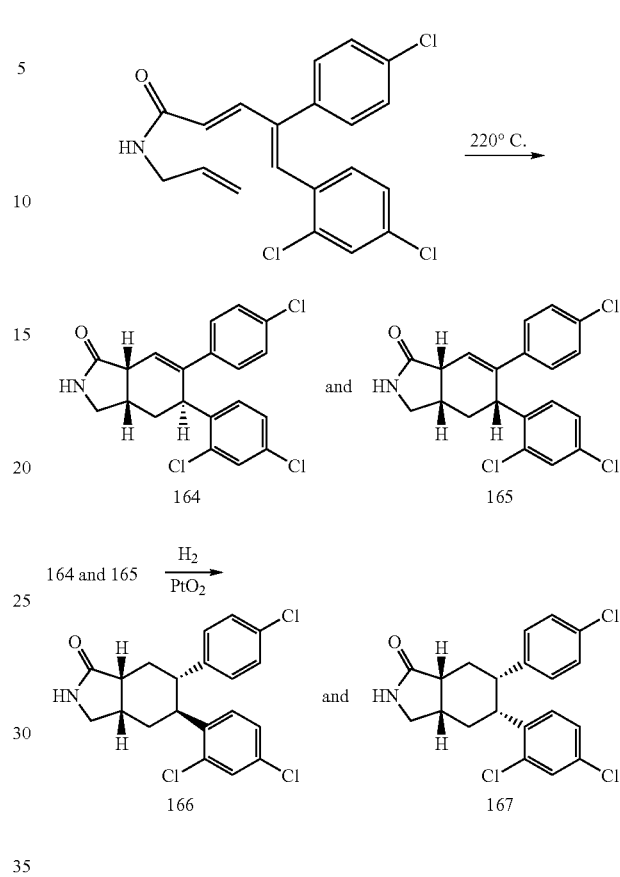

2-(4-Chloro-phenyl)-3-(2,4-dichloro-phenyl)-acrylic acid methyl ester was prepared by a reported procedure (*Acta Chem Scand,* 1993, 47, 1112; herein incorporated by reference in its entirety) and converted to the dienoic acid 4-(4-chloro-phenyl)-5-(2,4-dichloro-phenyl)-penta-2,4-dienoic acid by well known procedures as shown in Scheme 92. Compounds 164 and 166 were prepared from 4-(4-chlorophenyl)-5-(2,4-dichloro-phenyl)-penta-2,4-dienoic acid using procedures similar to those used to prepare compounds 157, 158, and 162.

General Scheme I:

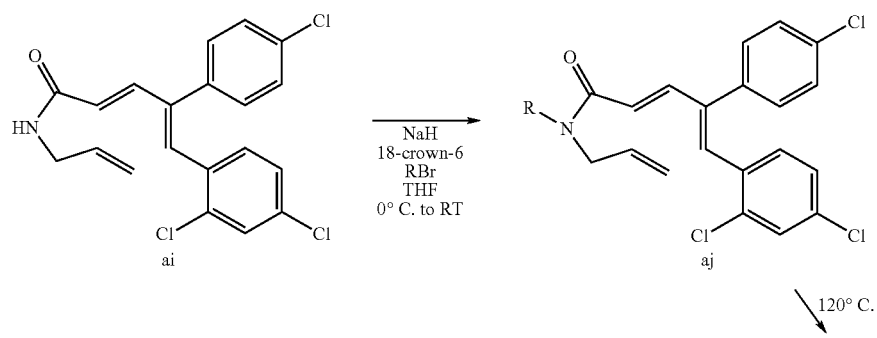

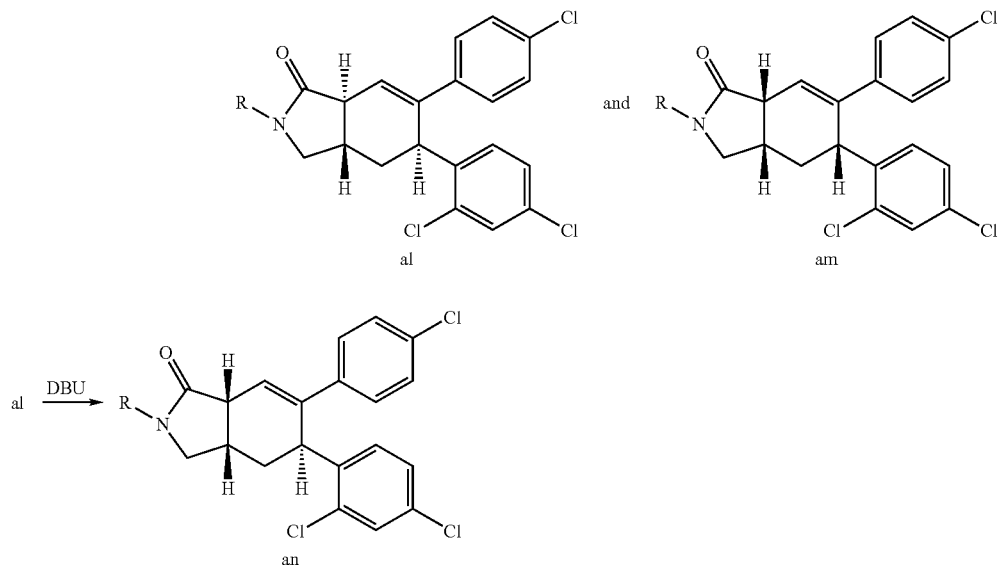
The amide ai was also alkylated to give aj which was converted to compounds 168-171 as shown in General Scheme I.
| Compound # | Compound | LCMS m/e (MH⁺) |
|---|---|---|
| 168 | | 432 |
| 169 | | 482 |

-continued
| Compound # | Compound | LCMS m/e (MH+) |
|---|---|---|
| 170 | 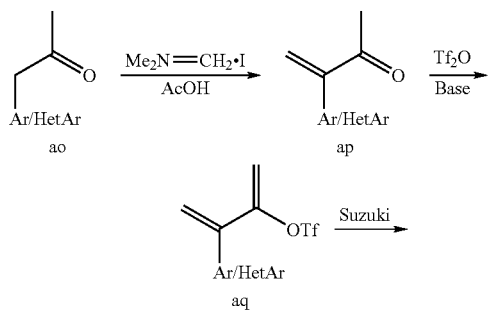 | 507 |
| 171 | | 507 |
Preparation of 5,6-Di(hetero)aryl-isoindol-1,3-diones or 3,4-Di(hetero)aryl-cyclohex-3-ene Carboxylic Amides
General Scheme J:
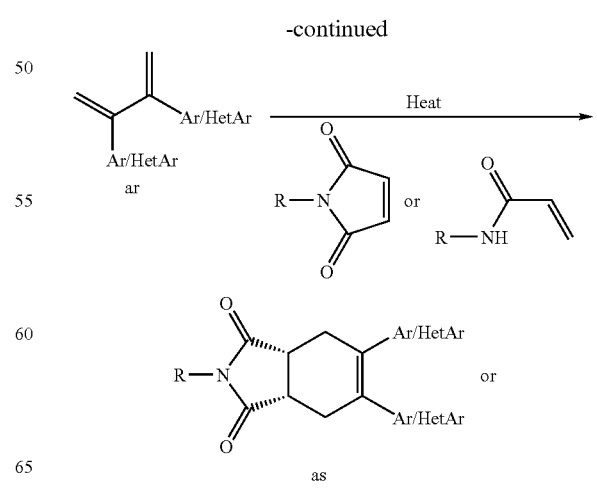

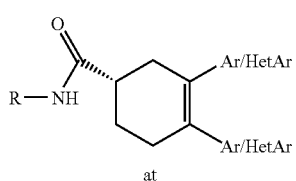

Di(hetero)aryl-isoindol-1,3-diones or 3,4-di(hetero)aryl-cyclohex-3-ene carboxylic amides can be prepared by various methods, for example by the intermolecular Diels-Alder reaction of a diaryl-, diheteroaryl-, or aryl-heteroaryl-substituted diene with a pyrrole-2,5-dione or an acrylamide derivative, for example as shown in General Scheme J, above.

Preparation of Compounds 172-175

Scheme 92:

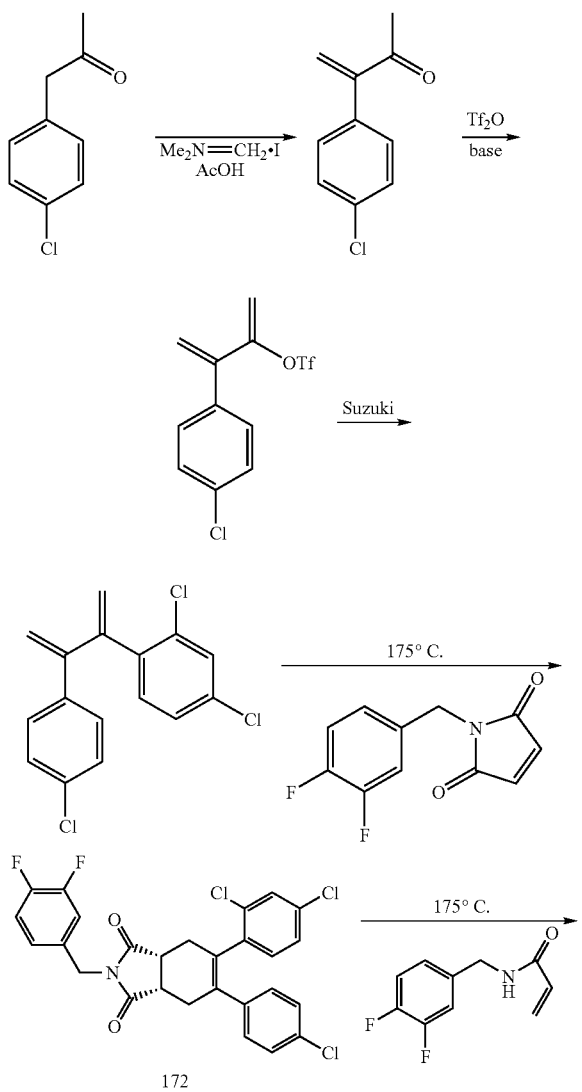

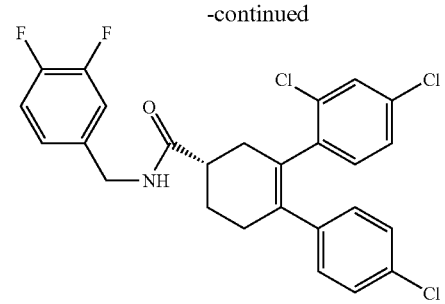

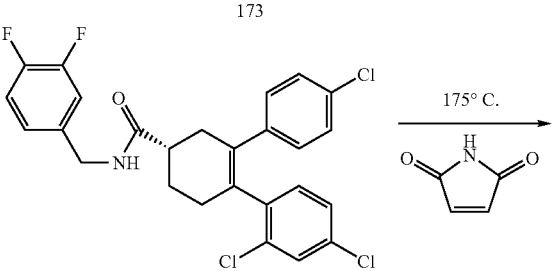

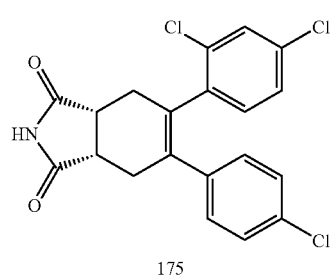

Compounds 172-175 were prepared by converting the commercially available ketone 1-(4-chloro-phenyl)-propan-2-one to 3-(4-chloro-phenyl)-but-3-en-2-one with Eschenmoser's salt. 3-(4-Chloro-phenyl)-but-3-en-2-one was then converted to trifluoro-methanesulfonic acid 2-(4-chloro-phenyl)-1-methylene-allyl ester with triflic anhydride and a hindered pyridine base. Suzuki coupling gave 2,4-dichloro-1-[2-(4-chloro-phenyl)-1-methylene-allyl]-benzene. Diels-Alder reaction of 2,4-dichloro-1-[2-(4-chloro-phenyl)-1-methylene-allyl]-benzene with the different dienophiles shown above in Scheme 93 gave compounds 172-175.

Step 1:

1-(4-Chloro-phenyl)-propan-2-one (8.6 g, 51 mmol) and Eschenmoser's salt (12.3 g, 66.3 mmol) were dissolved in glacial acetic acid and heated in a closed pressure tube at 125° C. under nitrogen for 1 h. After cooling to room temperature, the solution was concentrated. The residue was dissolved in EtOAc, washed with saturated NaHCO$_3$ aqueous solution, dried (MgSO$_4$), concentrated, and chromatographed (SiO$_2$, 39:1-19:1 hexane/EtOAc) to give 3-(4-chloro-phenyl)-but-3-en-2-one as yellow oil (3.92 g, 43%).

Step 2:

Triflic anhydride (0.23 mL, 1.4 mmol) was added to a mixture of 3-(4-chloro-phenyl)-but-3-en-2-one (189 mg, 1.04 mmol) and 2,6-di-t-butyl-4-methylpyridine (0.32 g, 1.6 mmol) in CH$_2$Cl$_2$ (10 mL) and refluxed for 16 h. After cooling to room temperature, the solution washed with 10% HCl solution and saturated NH$_4$Cl aqueous solution, dried (MgSO$_4$), concentrated, and chromatographed (SiO$_2$, hexanes) to give trifluoro-methanesulfonic acid 2-(4-chloro-phenyl)-1-methylene-allyl ester as a clear oil (136 mg, 41%).

Step 3

Scheme 93:

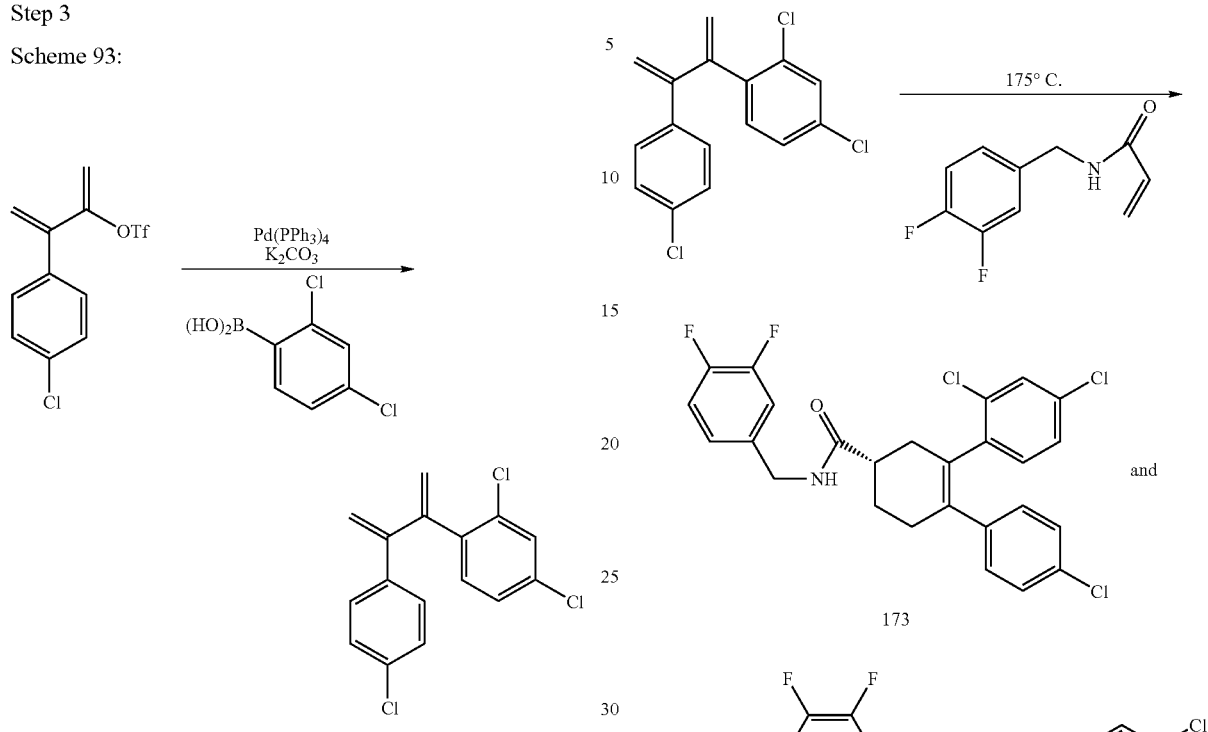

Trifluoro-methanesulfonic acid 2-(4-chloro-phenyl)-1-methylene-allyl ester was converted to 2,4-dichloro-1-[2-(4-chloro-phenyl)-1-methylene-allyl]-benzene by the Suzuki procedure shown above.

Step 4

Scheme 94:

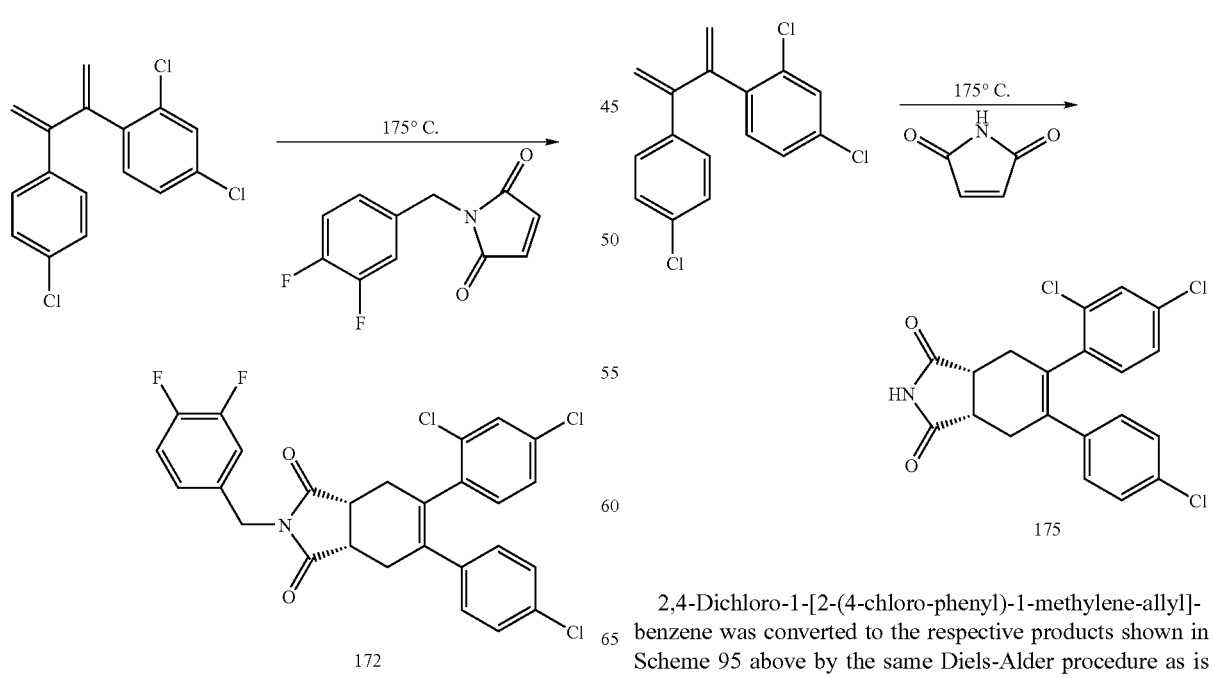

2,4-Dichloro-1-[2-(4-chloro-phenyl)-1-methylene-allyl]-benzene was converted to the respective products shown in Scheme 95 above by the same Diels-Alder procedure as is shown in Scheme 88.

Preparation of Compound 176

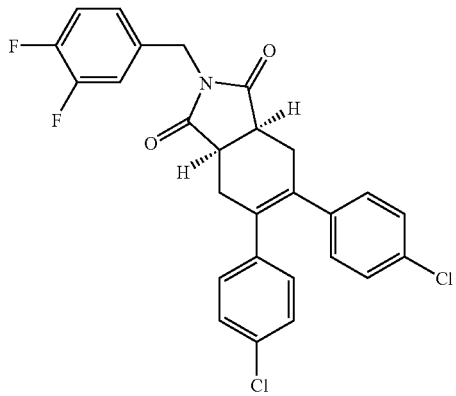

176

Substituted 5,6-diphenyl-isoindol-1-dione 176 was prepared using procedures similar to those used to prepare compound 172 except that diene 4-chloro-1-[2-(4-chloro-phenyl)-1-methylene-allyl]-benzene was used instead of 2,4-Dichloro-1-[2-(4-chloro-phenyl)-1-methylene-allyl]-benzene.

Preparation of Compound 177

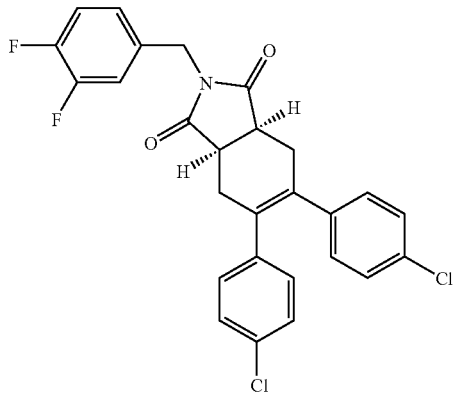

177

Compound 171 was prepared using procedures similar to those used to prepare compound 172 except that 4-chloro-1-[2-(4-chloro-phenyl)-1-methylene-allyl]-benzene was used instead of 2,4-dichloro-1-[2-(4-chloro-phenyl)-1-methylene-allyl]-benzene. (4-Chloro-1-[2-(4-chloro-phenyl)-1-methylene-allyl]-benzene was prepared using procedures similar to those used to prepare 2,4-dichloro-1-[2-(4-chloro-phenyl)-1-methylene-allyl]-benzene, as shown in Scheme 93, above.)

Preparation of Compounds 178-185

General Scheme K:

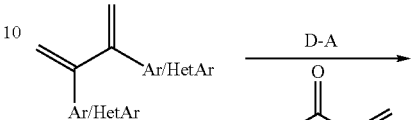

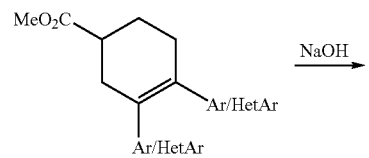

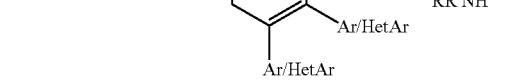

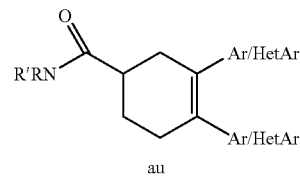

au

Di(hetero)aryl-cyclohex-3-ene carboxylic amides can be prepared by the intermolecular Diels-Alder reaction of a diaryl-, diheteroaryl-, or aryl-heteroaryl-substituted diene with an unsaturated amide, or alternatively by the intermolecular Diels-Alder reaction of a diaryl-, diheteroaryl-, or aryl-heteroaryl-substituted diene with an unsaturated ester which is subsequently converted to an amide, for example as shown in General Scheme K, above. Compounds prepared by the methods shown in General Scheme K are shown in the following Table:

| Compound | Structure | LCMS m/e (MH+) |
|---|---|---|
| 178 | 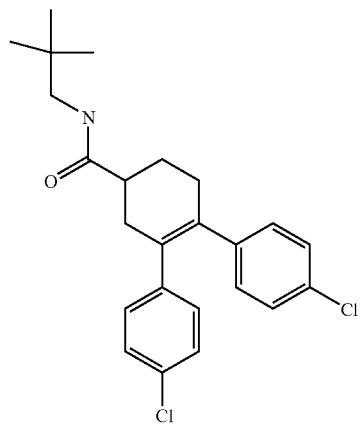 | 416 |
| 179 | 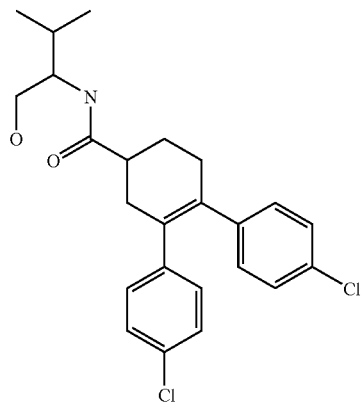 | 432 |
| 180 | 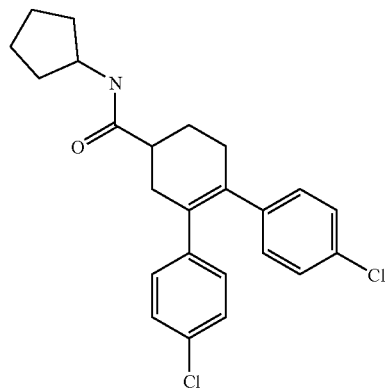 | 414 |

-continued

| Compound | Structure | LCMS m/e (MH+) |
|---|---|---|
| 181 | 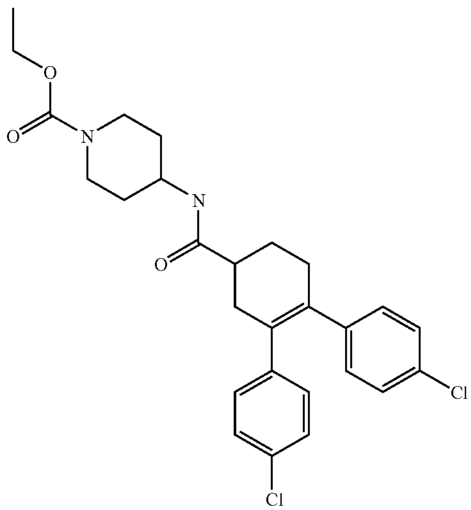 | 501 |
| 182 | 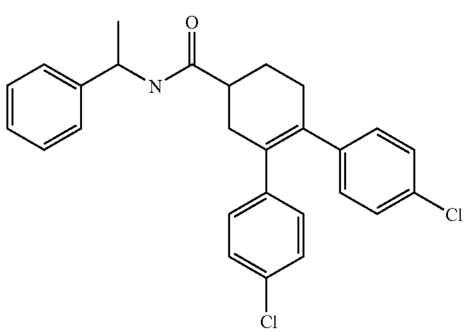 | 450 |
| 183 | 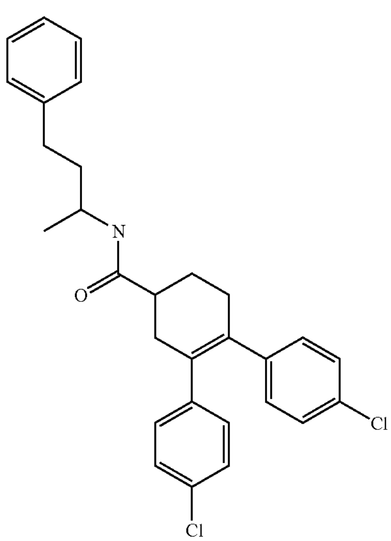 | 478 |

-continued
| Compound | Structure | LCMS m/e (MH+) |
|---|---|---|
| 184 | 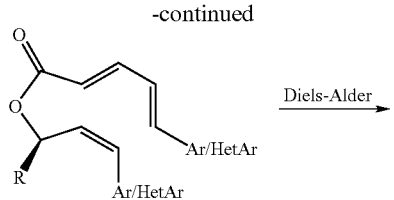 | 470 |
| 185 | 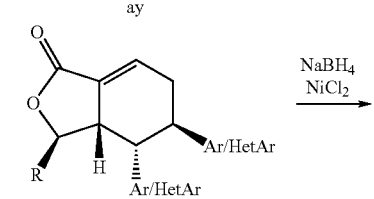 | 464 |
Preparation of Di(hetero)aryl-isobenzofuran-1-ones
General Scheme L:
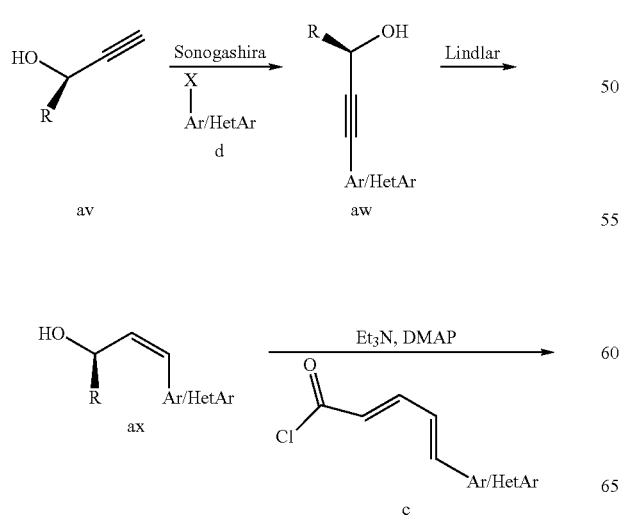
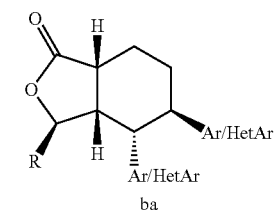
Di(hetero)aryl-isobenzofuran-1-ones can be prepared by a variety of methods. For example, an aryl- or heteroaryl-substituted unsaturated alcohol or acid can be condensed with an aryl- or heteroaryl-substituted diene acid or acid chloride c to provide a triene ester ay by the method shown above in General Scheme L. The triene ester ay can be cyclized via an intramolecular Diels-Alder reaction to form a di(hetero)aryl-tetrahydro-isobenzofuran-1-one az, that can be further modified (e.g., by reduction, etc.) to form the saturated di(hetero)aryl-isobenzofuran-1-one ba.

Preparation of Compounds 186-191

Step 1

Scheme 95:

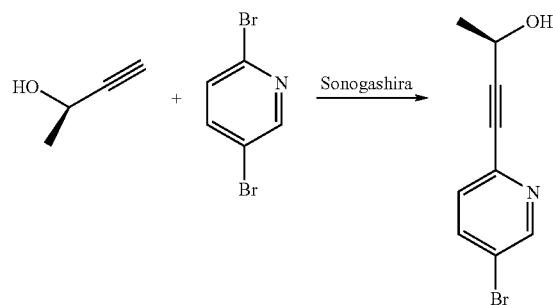

A mixture of but-3-yn-2-ol (7.0 g, 0.10 mol), 2,5-dibromopyridine (15.89 g, 0.067 mol), PdCl$_2$(PPh$_3$)$_2$ (2.35 g, 3.4 mmol), CuI (2.55 g, 0.013 mol), and diisopropylamine (300 mL) was stirred at RT for 1 h. The mixture was filtered through CELITE. The filtrate was concentrated in vacuo. The residue was dissolved in a CH$_2$Cl$_2$, washed with saturated NH$_4$Cl aqueous solution, dried (MgSO$_4$), and concentrated. The residue was chromatographed (SiO$_2$, 7:3 hexane/EtOAc) to afford the alkyne alcohol product 4-(5-bromo-pyridin-2-yl)-but-3-yn-2-ol as a tan solid (13.24 g, 87%).

Scheme 96:

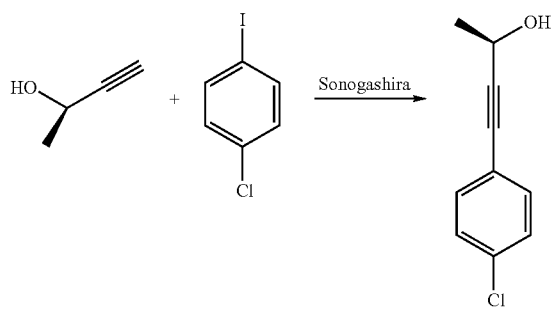

4-(4-Chloro-phenyl)-but-3-yn-2-ol was prepared as shown in Scheme 95.

Step 2

Scheme 97:

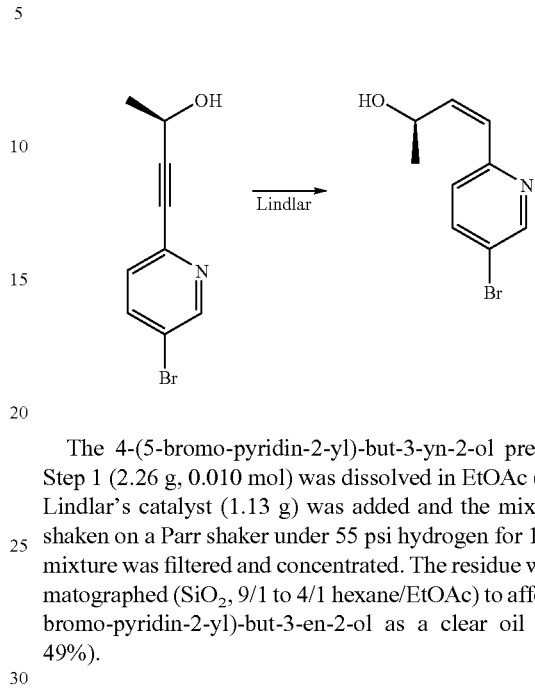

The 4-(5-bromo-pyridin-2-yl)-but-3-yn-2-ol prepared in Step 1 (2.26 g, 0.010 mol) was dissolved in EtOAc (50 mL). Lindlar's catalyst (1.13 g) was added and the mixture was shaken on a Parr shaker under 55 psi hydrogen for 16 h. The mixture was filtered and concentrated. The residue was chromatographed (SiO$_2$, 9/1 to 4/1 hexane/EtOAc) to afford 4-(5-bromo-pyridin-2-yl)-but-3-en-2-ol as a clear oil (1.12 g, 49%).

Scheme 98:

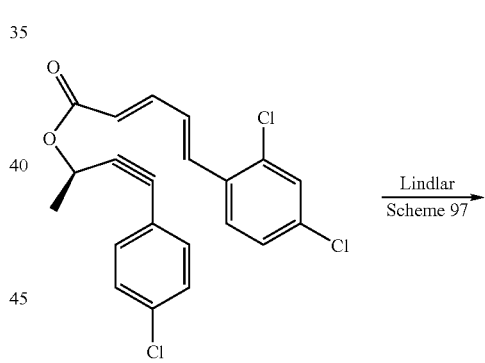

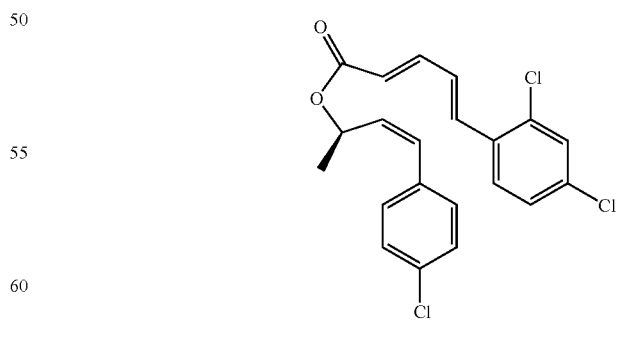

5-(2,4-Dichloro-phenyl)-penta-2,4-dienoic acid 3-(4-chloro-phenyl)-1-methyl-allyl ester was prepared as shown in Scheme 97 using 1 atmosphere hydrogen and 10-20% by weight Lindlar's catalyst.

Step 3

Scheme 99:

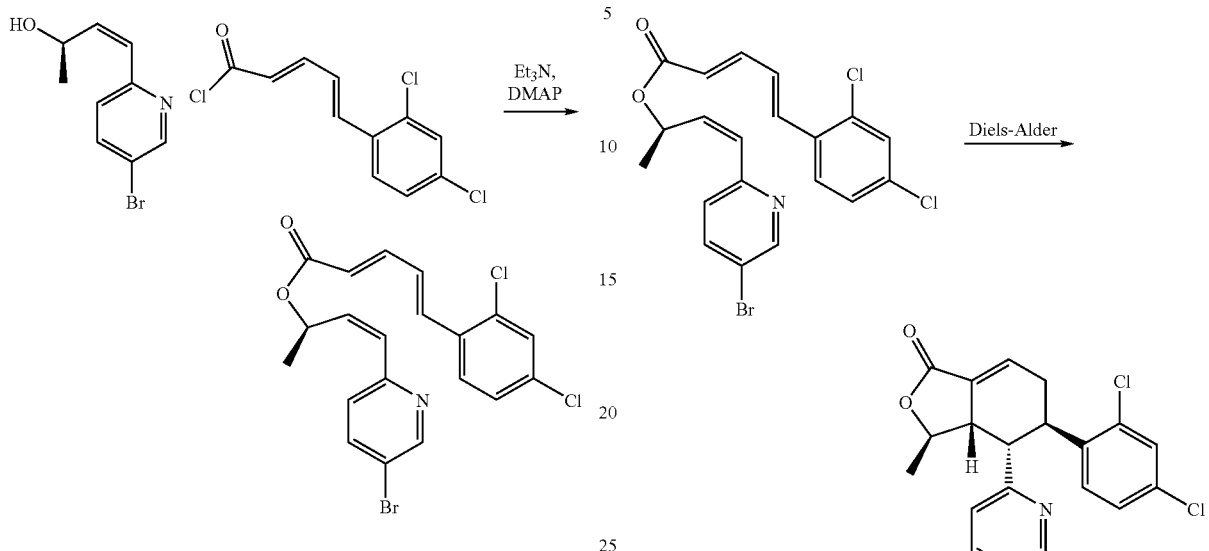

The 4-(5-bromo-pyridin-2-yl)-but-3-en-2-ol prepared in Step 2 was converted to 5-(2,4-dichloro-phenyl)-penta-2,4-dienoic acid 3-(5-bromo-pyridin-2-yl)-1-methyl-allyl ester in a manner similar to the procedure used to prepare 5-(2,4-dichloro-phenyl)-penta-2,4-dienoic acid [3-(4-chloro-phenyl)-allyl]-amide in Scheme 5 above.

Scheme 100:

5-(2,4-Dichloro-phenyl)-penta-2,4-dienoic acid 3-(4-chloro-phenyl)-1-methyl-prop-2-ynyl ester was similarly prepared as shown in Scheme 101.

Step 4:

Scheme 101:

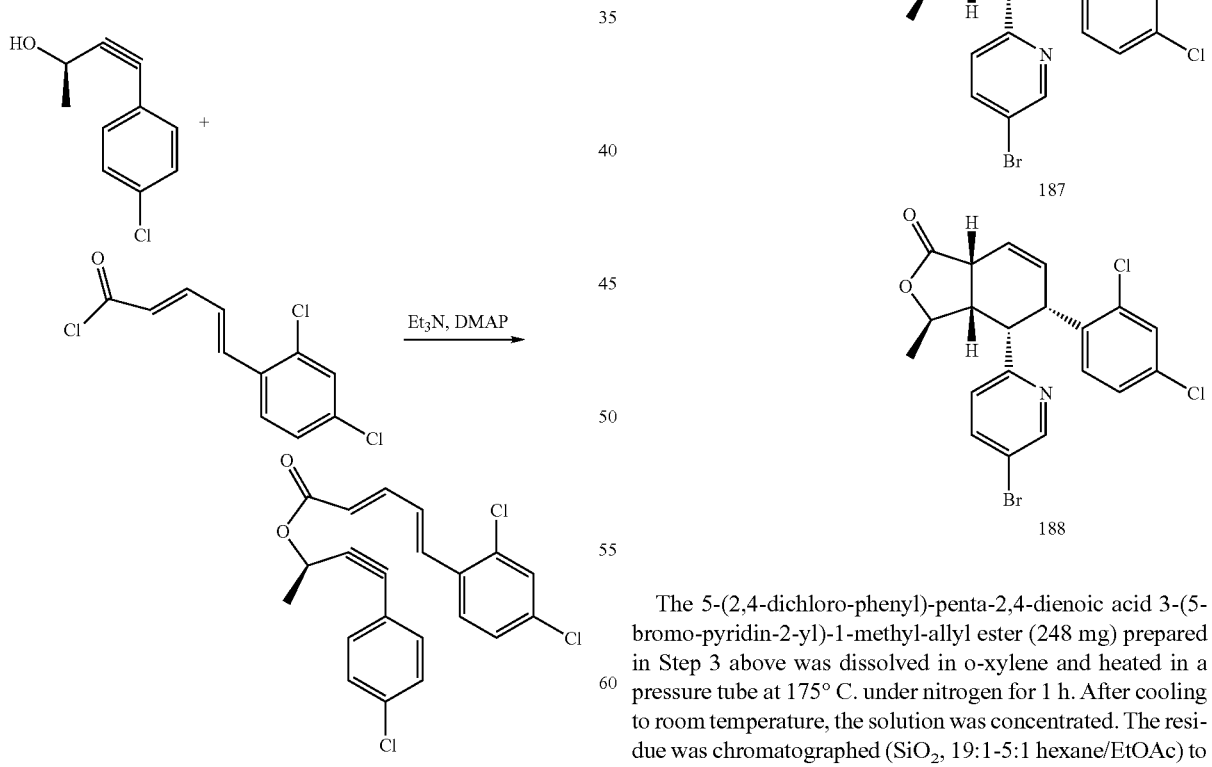

The 5-(2,4-dichloro-phenyl)-penta-2,4-dienoic acid 3-(5-bromo-pyridin-2-yl)-1-methyl-allyl ester (248 mg) prepared in Step 3 above was dissolved in o-xylene and heated in a pressure tube at 175° C. under nitrogen for 1 h. After cooling to room temperature, the solution was concentrated. The residue was chromatographed (SiO$_2$, 19:1-5:1 hexane/EtOAc) to give the cycloadduct 186 as an off-white solid (141 mg, 49%). LCMS: m/e 452.1 (MH$^+$). Also isolated were minor cycloadducts 187 (12 mg, 5%), LCMS: m/e 452.1 (MH$^+$), and 188 (35 mg, 14%), LCMS: m/e 452.1 (MH$^+$).

Scheme 102:

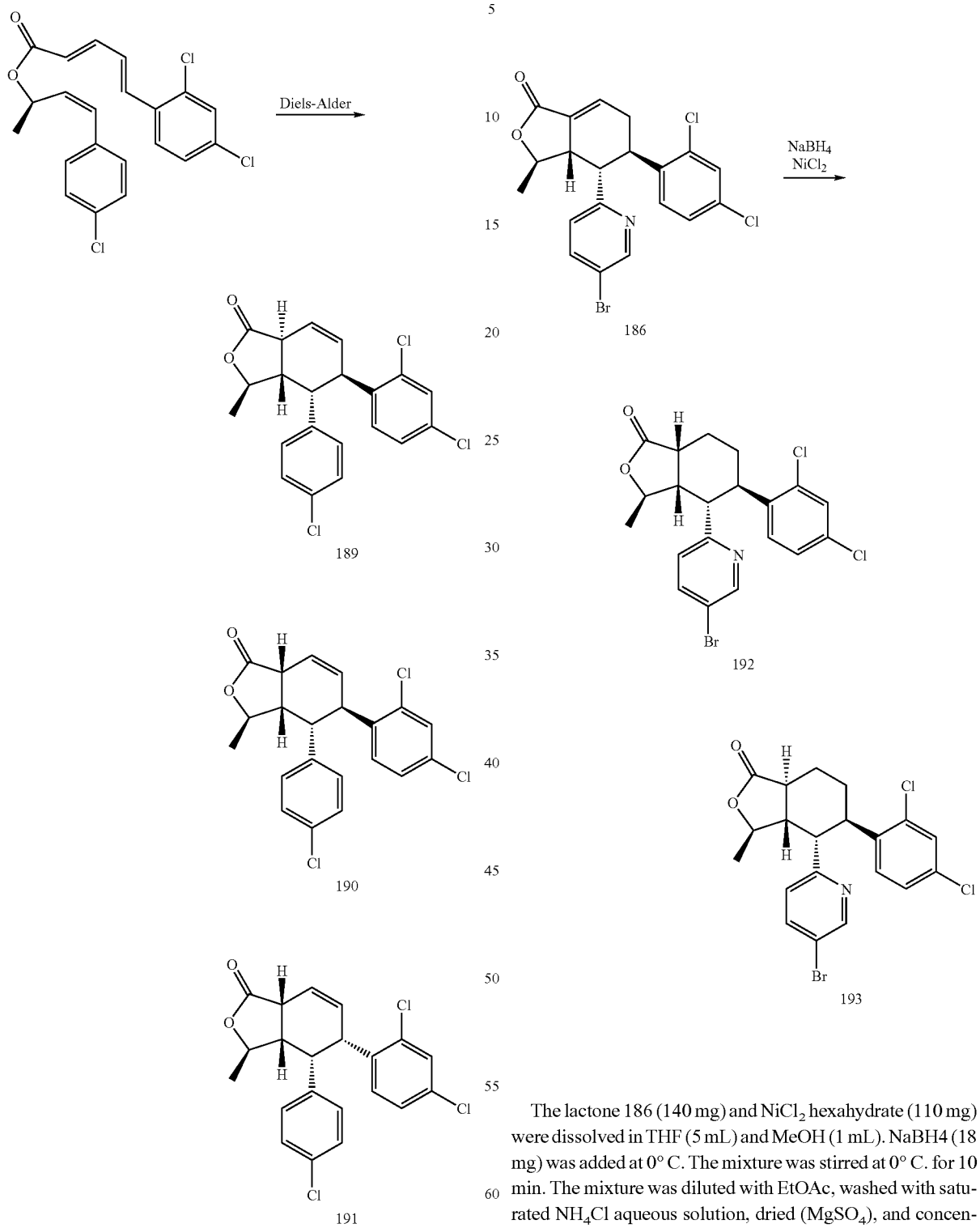

LCMS: m/e 407.2 (MH+)

Compounds 189-191 were prepared in a manner shown in Scheme 101.

Preparation of Compounds 192 and 193

Scheme 103:

The lactone 186 (140 mg) and NiCl$_2$ hexahydrate (110 mg) were dissolved in THF (5 mL) and MeOH (1 mL). NaBH4 (18 mg) was added at 0° C. The mixture was stirred at 0° C. for 10 min. The mixture was diluted with EtOAc, washed with saturated NH$_4$Cl aqueous solution, dried (MgSO$_4$), and concentrated. The residue was separated by preparative TLC (SiO$_2$, 3:1 hexane/EtOAc) to give the reduced product 192 as a white solid (35 mg, 25%). LCMS: m/e 454.1 (MH+). Also isolated was minor reduced product 193 (10 mg, 7%). LCMS: m/e 454.1 (MH+).

Preparation of Compound 194
Scheme 104:

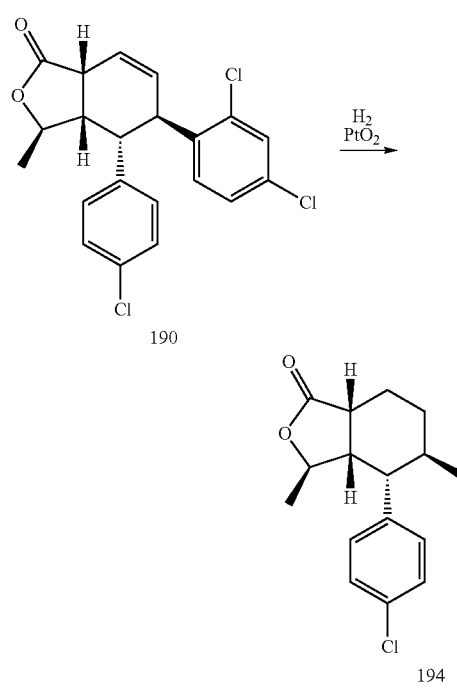

LCMS: m/e 409.2 (MH⁺)

Compound 192 was prepared by the reduction procedure described in Scheme 12.

Preparation of Compound 195
Scheme 105:

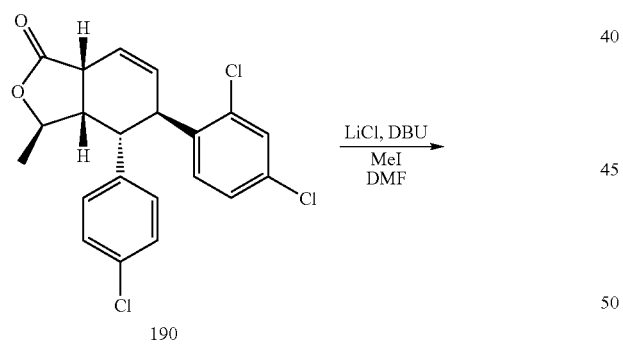

LCMS: m/e 421.2 (MH⁺)

Compound 193 was prepared by a procedure similar to that shown in Scheme 55, Step 2, except that methyl iodide was used instead of trisyl azide.

Preparation of Compound 195
Scheme 106:

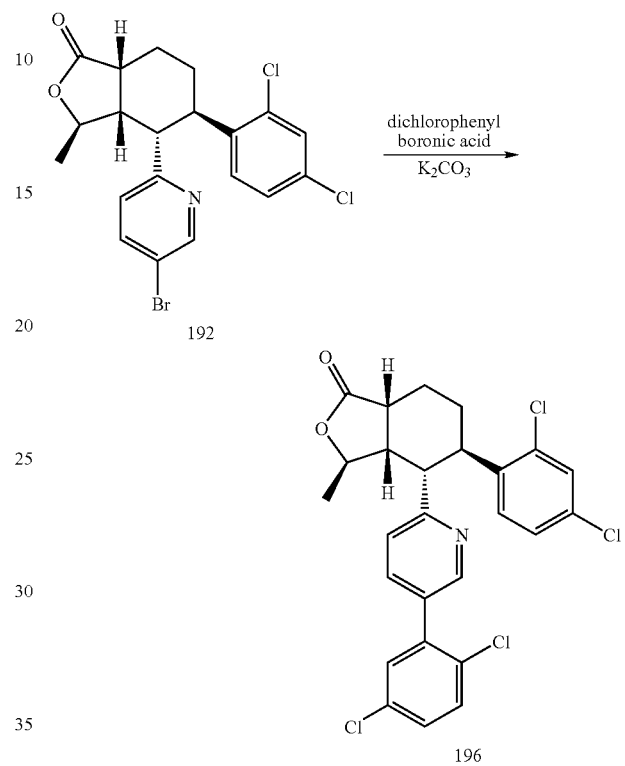

The bromopyridine 192 (6.5 mg), Pd(PPh₃)₄ (2 mg), 2,5-dichlorophenylboronic acid (7 mg), K₂CO₃ (22 mg), ethanol (0.2 mL), water (0.1 mL), and toluene (0.4 mL) was heated at 90° C. for 1 h. The reaction mixture was diluted with EtOAc, washed with saturated NH₄Cl aqueous solution, dried (MgSO₄), and concentrated. The residue was subjected to preparative TLC purification (SiO₂, 3:2 hexane/EtOAc) to afford 196 as a white solid (6 mg, 81%). LCMS: m/e 520.1 (MH⁺)

Preparation of Compounds 197 and 198

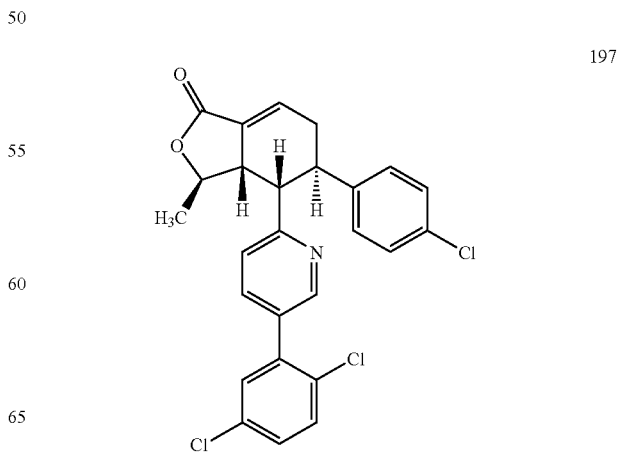

335
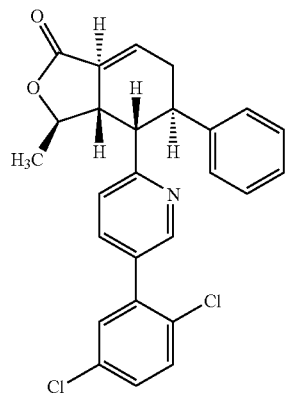
198
Substituted 4-pyridyl-5-phenyl-isobenzofuran-1-ones 197 and 198 were prepared using procedures similar to those used to prepare compound 196 using the appropriate dienoic acid chloride c as shown in General Scheme L.
Preparation of Compounds 199-201
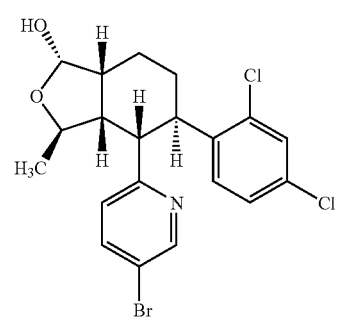
199
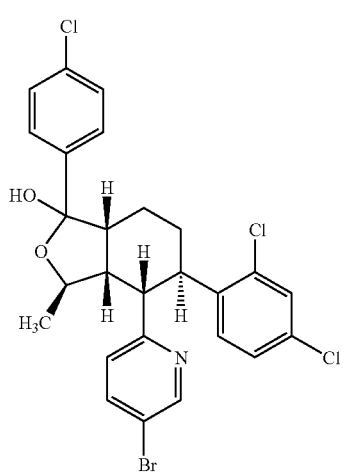
200
336
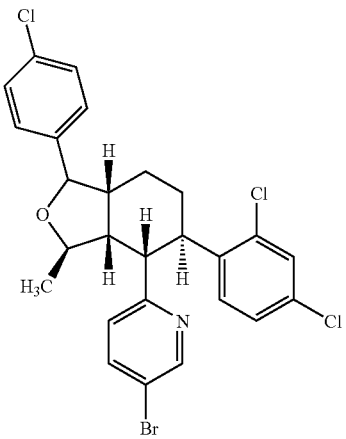
201
Compounds 199-201 were prepared as shown in Scheme 107, below:
Scheme 107:
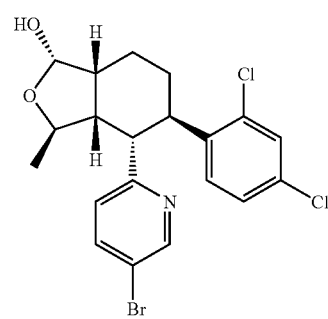

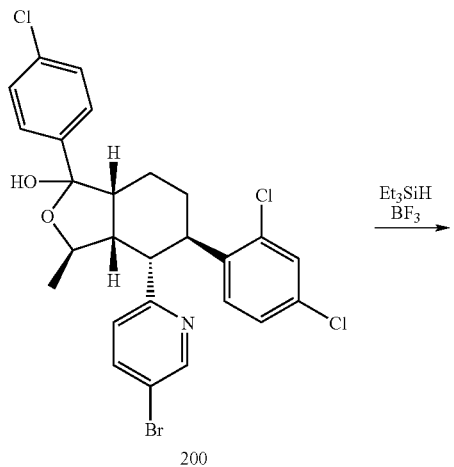
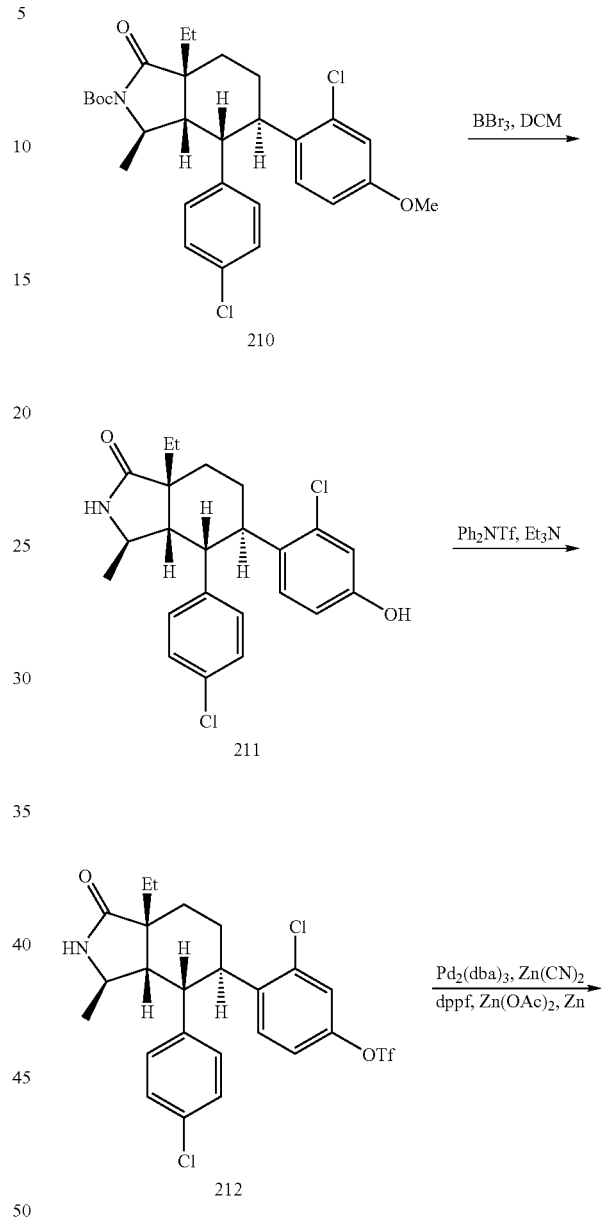
Scheme 108:
Similar to the methylation of 126 to provide 127 (see scheme 73), other alkyl groups can be introduced at the alpha-position of lactam carbonyl. For example, an ethyl group can be introduced as described below:
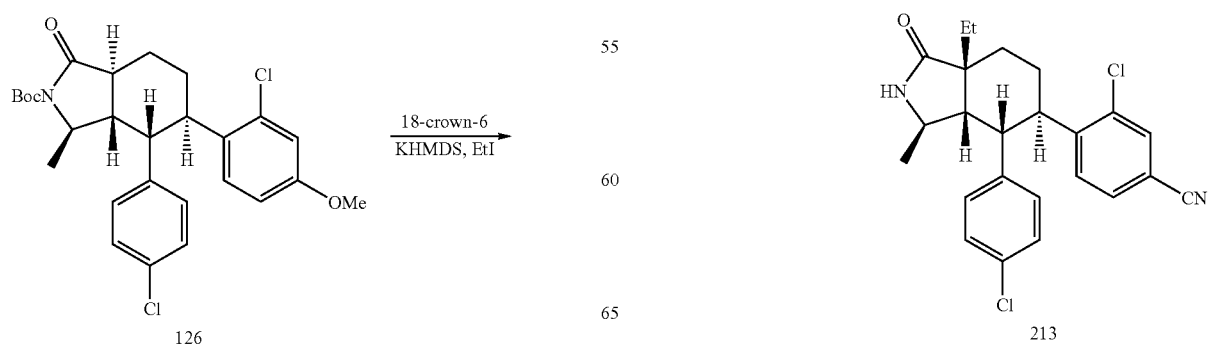

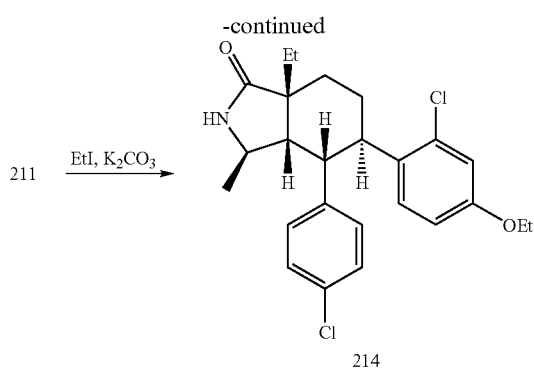

Preparation of Compound 210
Scheme 108:

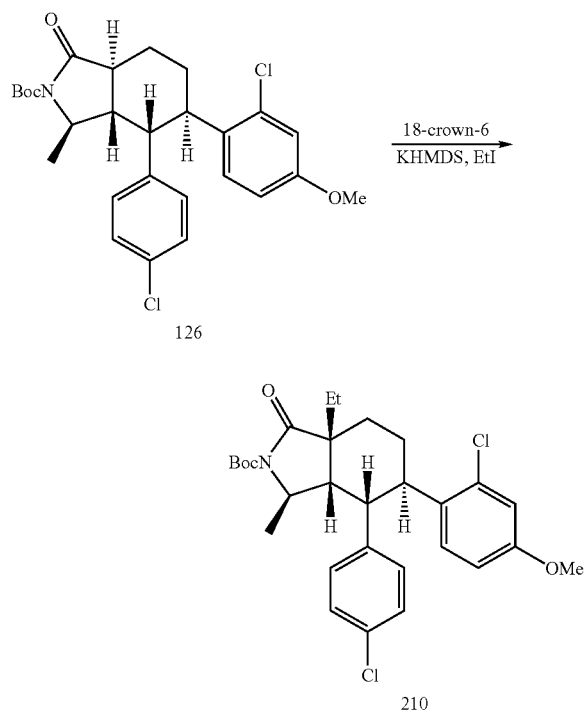

A degassed solution of 126 (1.16 g, 2.30 mmol) and 18-crown-6 (1.2 g, 4.54 mmol, 2 eq.) in 20 ml THF was cooled to −78° C. and a 0.5M solution of KHMDS in toluene (9.1 ml, 4.55 mmol, 2 eq.) was added and stirred for 1 hr. To this was added ethyl iodide (2.8 ml, 34.68 mmol, 15 eq.) and stirred for 2 hr at −78° C. then quenched with aq. NH₄Cl. The THF was evaporated and the aqueous slurry was extracted with 3× ethyl acetate. The combined organic layers washed with brine, dried over MgSO₄, filtered, concentrated and purified by chromatography using 0% to 20% ethyl acetate in hexanes to provide 1.04 g of 210 as white solid.

MS: 476.3 (M-$^t$Bu$^+$)

Preparation of Compounds 211, 212, 213 and 214
These analogs were prepared using a similar procedures described under scheme 73 and scheme 80.
MS for 211: 418.2 (MH$^+$)
MS for 212: 550.3 (MH$^+$)
MS for 213: 427.2 (MH$^+$)
MS for 214: 446.2 (MH$^+$)

Scheme 109:
The phenolic functionality of 128 (see scheme 73) can be used as a versatile handle to introduce a variety of other groups. For example the phenol can be alkylated with appropriate alkyl halides to provide the ethers as presented below.

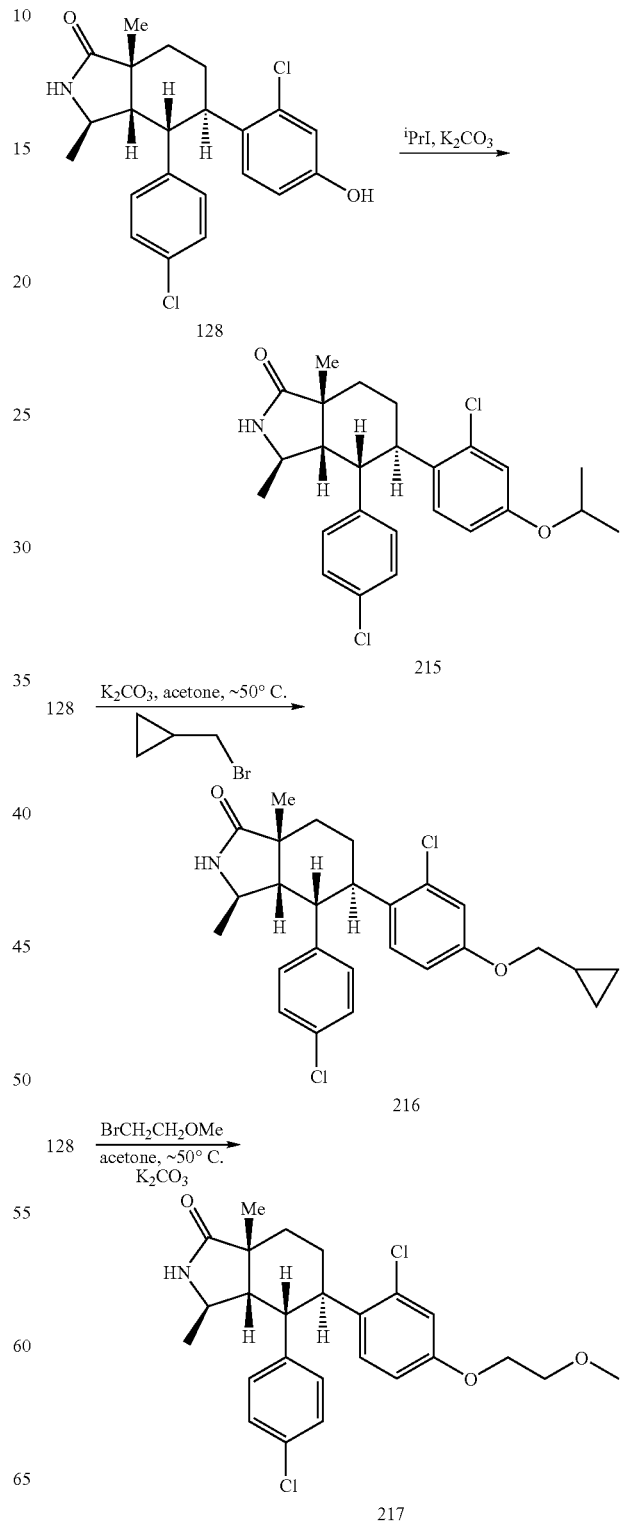

-continued

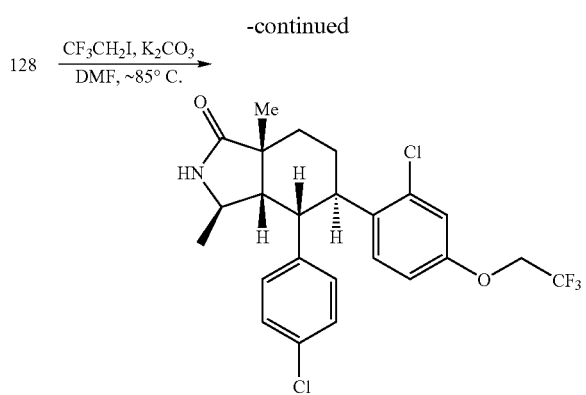

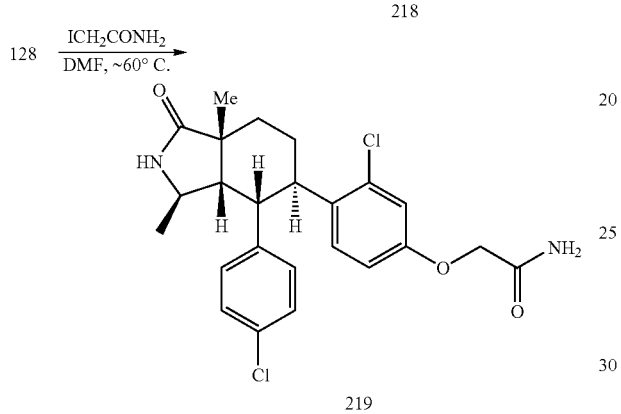

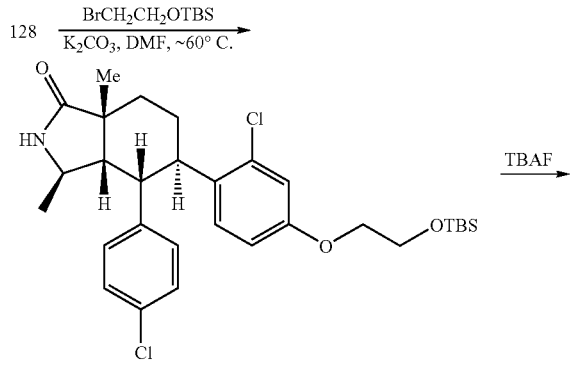

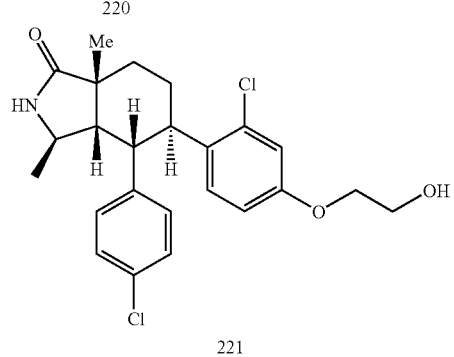

Preparation of Compounds 215, 216 and 217
These analogs were prepared using a procedure similar to the procedure used for the preparation of 131 (see scheme 80)
MS for 215: 446.2 (MH+)
MS for 216: 458.3 (MH+)
MS for 217: 462.3 (MH+)

Preparation of Compound 218
Scheme 110:

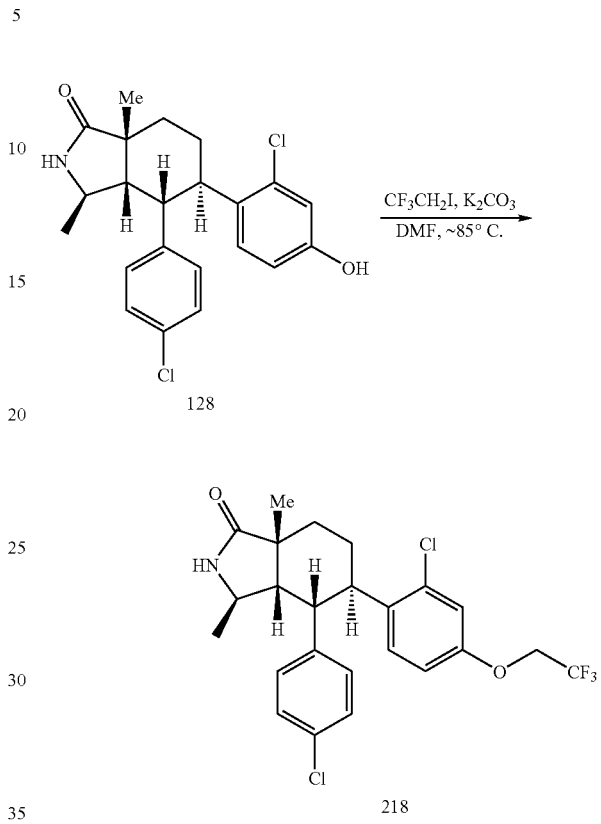

A mixture of 128 (50 mg, 0.12 mmol), trifluoroiodoethane (25 µL, 1.27 mmol, 10 eq.) and K$_2$CO$_3$ (50 mg, 0.36 mmol, 3 eq.) in 1 ml DMF in a sealed tube was heated overnight at ~85° C. The mixture was diluted with ethyl acetate, washed 3× with 1N HCl, brine, dried over MgSO$_4$, filtered, concentrated and purified by chromatography using 0% to 3% methanol in dichloromethane to provide 55 mg of 218.

MS: 486.3 (MH+)

Preparation of Compound 219
Scheme 111:

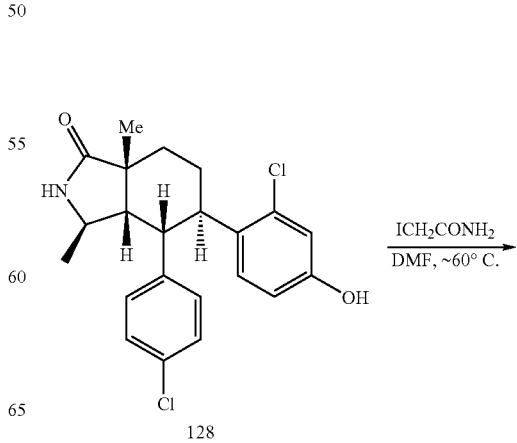

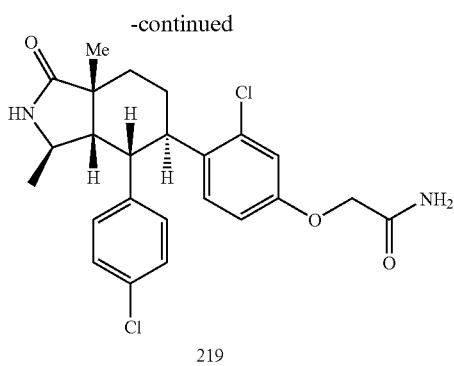

219

A mixture of 128 (30 mg, 0.072 mmol), iodoacetamide (67 mg, 0.36 mmol, 5 eq.) and K$_2$CO$_3$ (40 mg, 0.29 mmol, 4 eq.) in 1 ml DMF in a sealed tube was heated for 2.5 h at ~60° C. The mixture was diluted with ethyl acetate, washed 3× with 1N HCl, brine, dried over MgSO$_4$, filtered, concentrated and purified by chromatography using 0% to 4% methanol in dichloromethane to provide 32 mg of 219.

MS: 475.3 (MH$^+$)

Preparation of Compounds 220 and 221

Scheme 112:

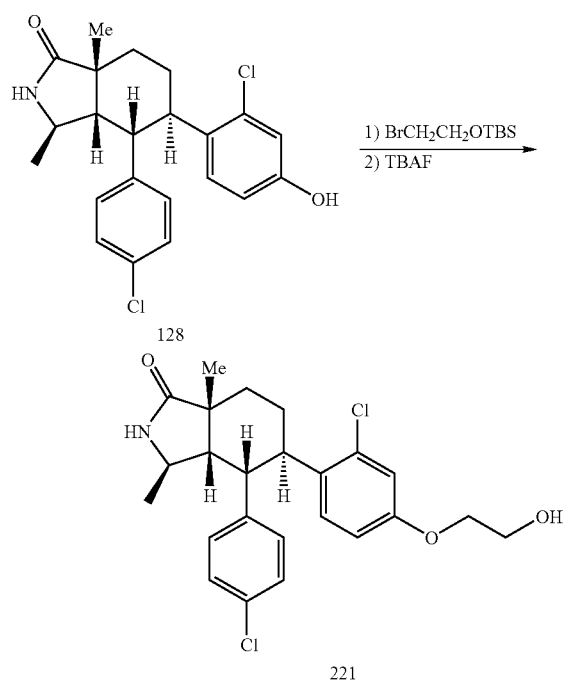

A mixture of 128 (25 mg, 0.044 mmol), (2-bromoethoxy)-tert-butyldimethylsilane (106 μL, 10 eq.) and K$_2$CO$_3$ (28 mg, 4 eq.) in 0.5 ml DMF in a sealed tube was heated for 2 h at ~65° C. The mixture was diluted with ethyl acetate, washed 3× with 1N HCl, brine, dried over MgSO$_4$, filtered, concentrated and purified by chromatography using 0% to 4% methanol in dichloromethane to provide 25 mg of 220.

This was dissolved in 0.5 ml THF and stirred with 0.14 ml of 1M solution of tetrabutylammonium fluoride in THF (0.14 mmol, 3 eq) for about 3 hr, diluted with ethyl acetate, washed 3× with 1N HCl, brine, dried over MgSO$_4$, filtered, concentrated and purified by chromatography using 0% to 4% methanol in dichloromethane to provide 20 mg of 221.

MS for 220: 562.3 (MH$^+$)
MS for 221: 448.2 (MH$^+$)

Preparation of Compound 222

Scheme 113:

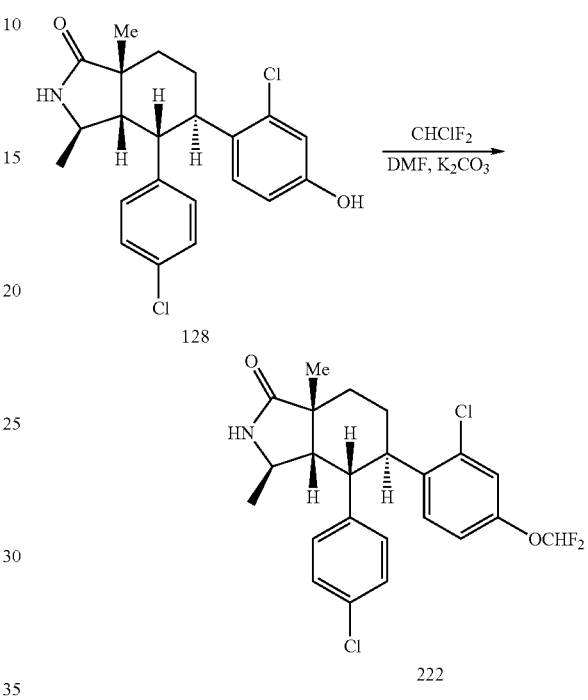

A two-necked round bottom flask containing a solution of 128 (50 mg, 0.124 mmol) and K$_2$CO$_3$ (68 mg, 0.49 mmol) in 2 ml DMF was fitted with a cold finger. The cold finger was cooled by dry ice—acetone mixture and chlorodifluoromethane gas was introduced from a cylinder and allowed to condense under the cold finger. The RB flask was immersed in an oil bath kept at ~40° C. and stirred for 5 hr. The mixture was diluted with ethyl acetate, washed with 3×1N HCl, brine, dried over MgSO$_4$, filtered and evaporated. The crude product was purified by chromatography using 0% to 3% methanol in dichloromethane to provide 22 mg of 222.

MS: 454.2 (MH$^+$)

Preparation of Compound 224

Scheme 114:

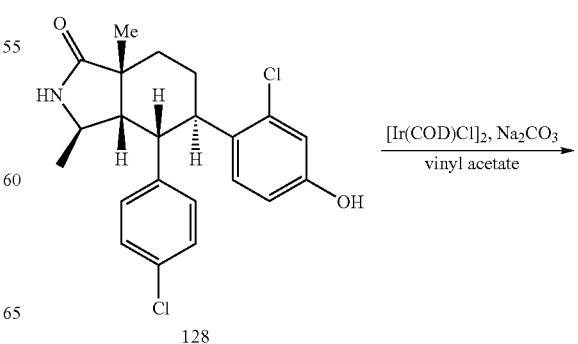

Preparation of Compounds 225-229

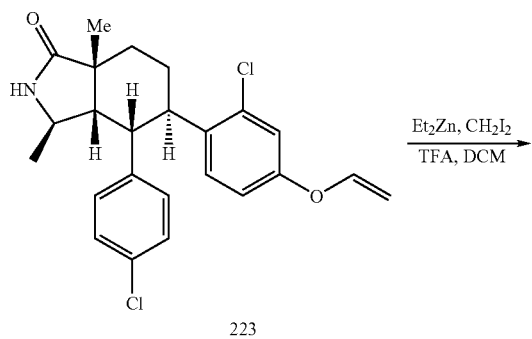

223

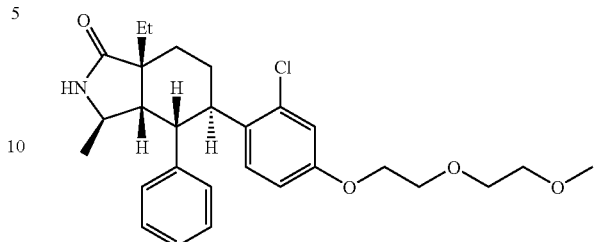

225

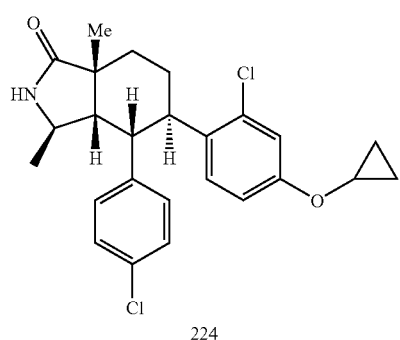

224

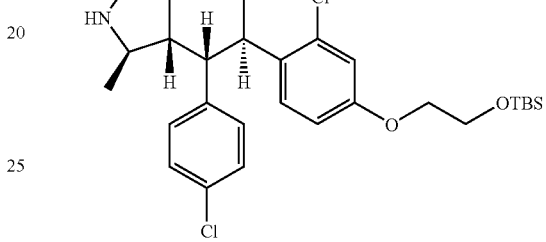

226

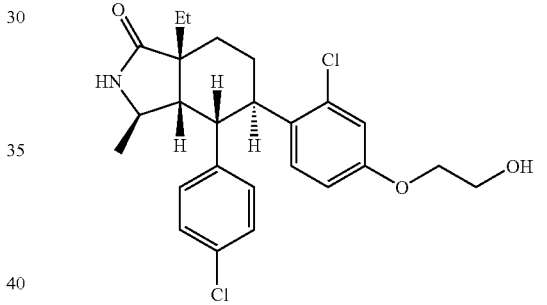

227

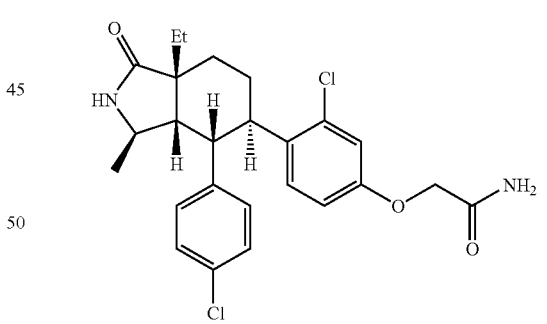

228

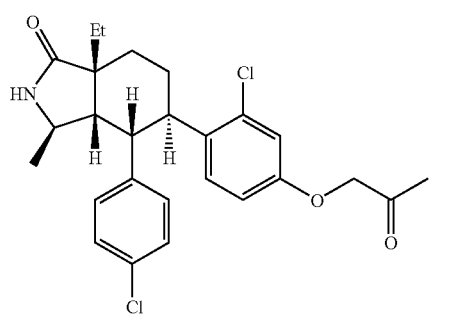

229

A mixture of 128 (50 mg, 0.124 mmol), Na$_2$CO$_3$ (8 mg, 0.076 mmol, 0.6 eq.), [Ir(COD)Cl]$_2$ (8 mg, 0.012 mmol, 0.1 eq.) and vinyl acetate (57 µl, 0.616 mmol, 5 eq.) in 1 ml toluene in a sealed tube was bubbled with argon and heated at ~105° C. for 8 hr. The mixture was diluted with ethyl acetate, washed 2× with water, brine, dried over MgSO$_4$, filtered and chromatographed with 0% to 3% methanol in dichloromethane to provide 45 mg of 223. (Refer to *Organic Synthesis*, volume 82, page 55-58 for literature procedure).

To a solution of 223 (45 mg, 0.105 mmol) in 2 ml dichloromethane at 0° C. was added a 1M solution of diethyl zinc in hexanes (0.52 mmol, 0.52 mmol, 5 eq.) followed by trifluoroacetic acid (39 µl, 0.52 mmol, 5 eq.) and stirred for 10 min. To this was added diiodomethane (42 µl, 0.52 mmol, 5 eq.) and mixture stirred overnight at rt. It was quenched with aq. NH$_4$Cl, extracted with 3× ethyl acetate and combined organic layer washed with brine, dried over MgSO$_4$, filtered, and chromatographed with 0% to 3% methanol in dichloromethane to provide 38 mg of product which contained some unreacted starting materials.

This product was once again treated with 10 eq. each of diethyl zinc, trifluoroacetic acid and diiodomethane under the above conditions and after work-up purified as above to provide 34 mg of 224.

MS: 444.2 (MH$^+$)

These compounds were prepared starting with 211 and using procedures described for the preparation of compounds under scheme 109.
MS for 225: 520.3 MS (MH+)
MS for 226: 576.3 MS (MH+)
MS for 227: 462.3 MS (MH+)
MS for 228: 475.3 MS (MH+)
MS for 229: 474.3 MS (MH+)
Scheme 115
Amide analog such as 232 can be prepared from the carboxylic acid 231. The carboxylic acid 231 in-turn can readily be obtained from the phenol 128.
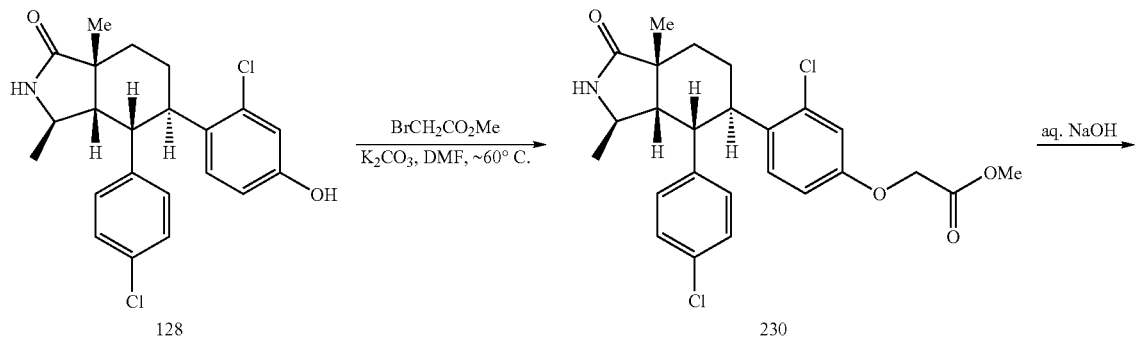
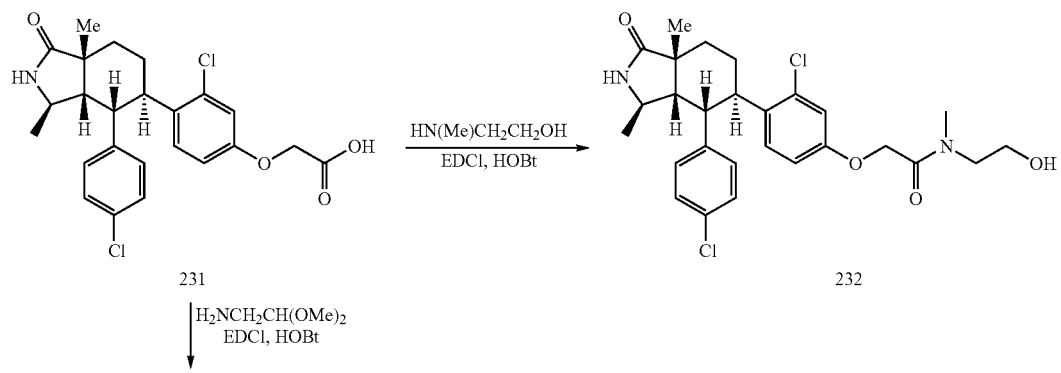
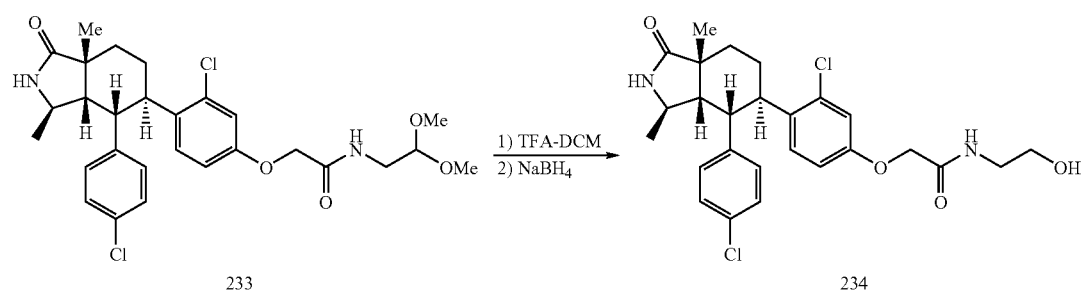

Preparation of Compound 230

Scheme 116:

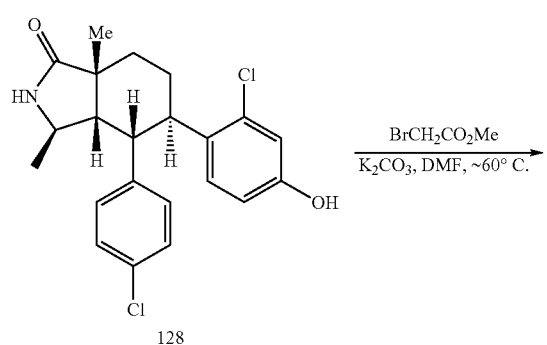

128

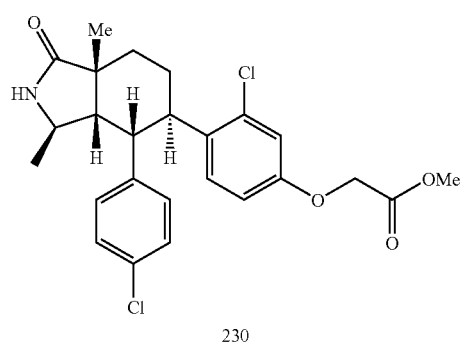

230

A mixture of 128 (300 mg, 0.742 mmol), methyl bromoacetate (350 µl, 3.7 mmol, 5 eq.) and K$_2$CO$_3$ (410 mg, 2.97 mmol, 4 eq.) in 5 ml DMF was heated for 4 h at ~60° C. The mixture was diluted with ethyl acetate, washed 3× with 1N HCl, brine, dried over MgSO$_4$, filtered, concentrated and purified by chromatography using 0% to 4% methanol in dichloromethane then filtered through a pad of basic alumina to provide 305 mg of 230.

MS: 476.3 (MH$^+$)

Preparation of Compound 231

Scheme 117:

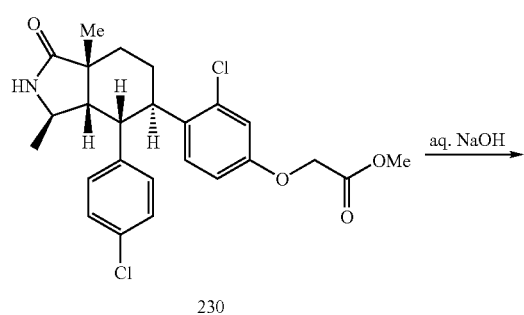

230

-continued

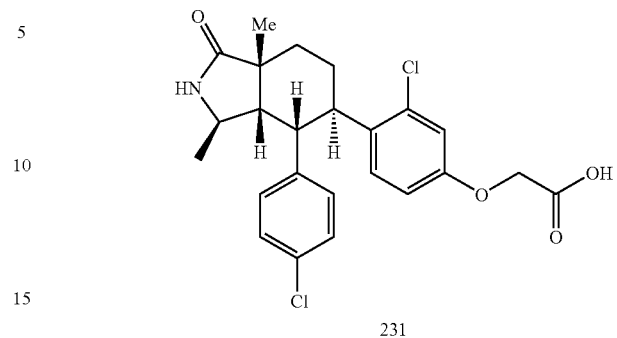

231

To a solution of 230 (300 mg, 0.63 mmol) in 2 ml each of methanol and THF was added 2 ml of 1M aq. NaOH solution and the mixture stirred at rt for 2 hr. It was diluted with water, acidified with 1N HCl and extracted with 3× ethyl acetate. The combined organic layers washed with brine, dried over MgSO$_4$, filtered and concentrated to provide 250 mg of 231.

MS: 462.3 (MH$^+$)

Preparation of Compound 232

Scheme 118:

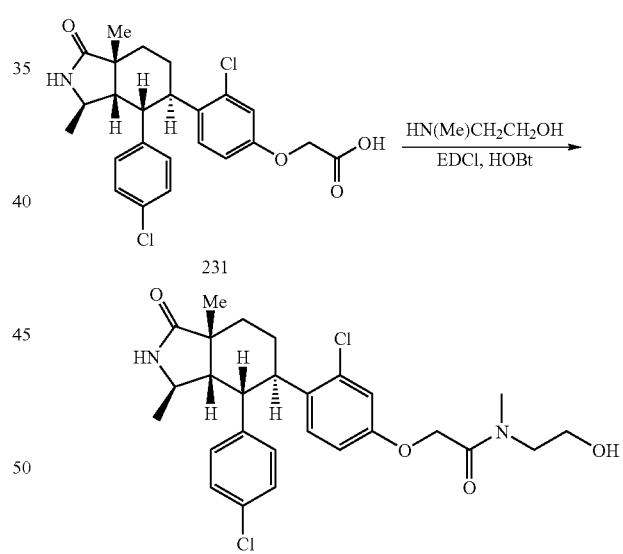

232

To solution of 231 (50 mg, 0.108 mmol), N-methyl ethanolamine (41 mg, 0.546 mmol, 5 eq.), HOBt (30 mg, 0.22 mmol, 2 eq.) in 1 ml DMF and 0.5 ml dichloromethane was added EDCl (42 mg, 0.219 mmol, 2 eq.) and the mixture stirred overnight at rt. The solution was diluted with ethyl acetate, washed 3× with 1N HCl, brine, dried over MgSO$_4$, filtered, concentrated and purified by chromatography using 0% to 5% methanol in dichloromethane to provide 52 mg of 232.

MS: 519.3 (MH$^+$)

Preparation of Compound 234

Scheme 119:

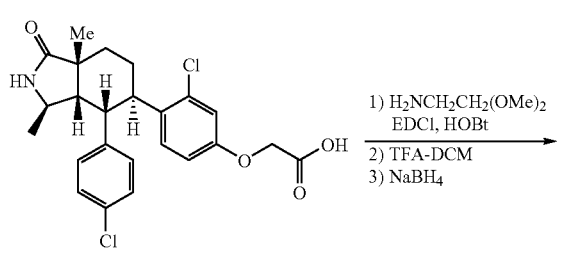

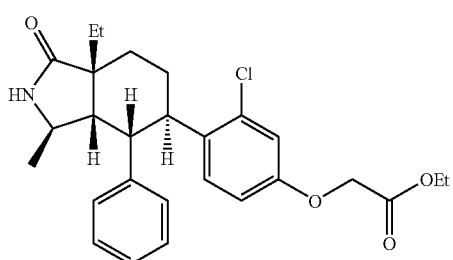

To solution of 231 (110 mg, 0.238 mmol), aminoacetaldehyde dimethyl acetal (125 mg, 1.19 mmol, 5 eq.), HOBt (65 mg, 0.48 mmol, 2 eq.) in 1.5 ml DMF and 0.5 ml dichloromethane was added EDCl (92 mg, 0.48 mmol, 2 eq.) and the mixture stirred overnight at rt. The solution was diluted with ethyl acetate, washed 3× with 1N HCl, brine, dried over MgSO$_4$, filtered, concentrated and purified by chromatography using 0% to 5% methanol in dichloromethane to provide 51 mg of 233.

This was stirred with 3 ml of 1:1 trifluoroacetic acid and dichloromethane and few drops of water at rt for 3 hr. It was diluted with ethyl acetate, washed 2× with water, brine, dried over MgSO$_4$, filtered and concentrated to provide 41 mg of aldehyde. This was dissolved in 1 ml of 1:1 methanol and dichloromethane, cooled to 0° C. and treated with sodium borohydride (4 mg, 0.10 mmol, 1 eq) for 2 min. It was quenched with aq. ammonium chloride, extracted 3× with ethyl acetate, combined organic layers washed with brine, dried over MgSO$_4$, filtered, evaporated and purified by preparative TLC using 5% methanol in dichloromethane to provide 38 mg of 234.

MS: 505.3 (MH$^+$)

Preparation of Compounds 235-237

Scheme 120:

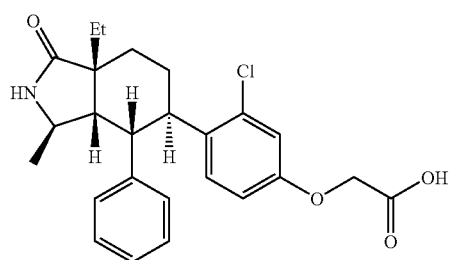

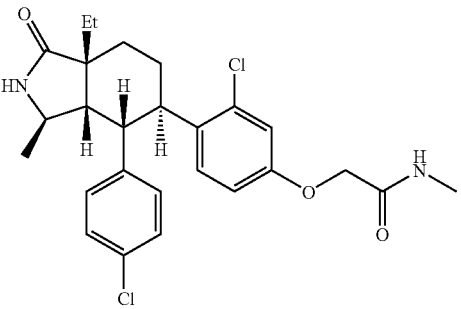

These compounds were prepared using similar procedures described under scheme 115.

MS for 235: 504.3 (MH$^+$)

MS for 236: 476.3 (MH$^+$)

MS for 237: 489.3 (MH$^+$)

Scheme 121:

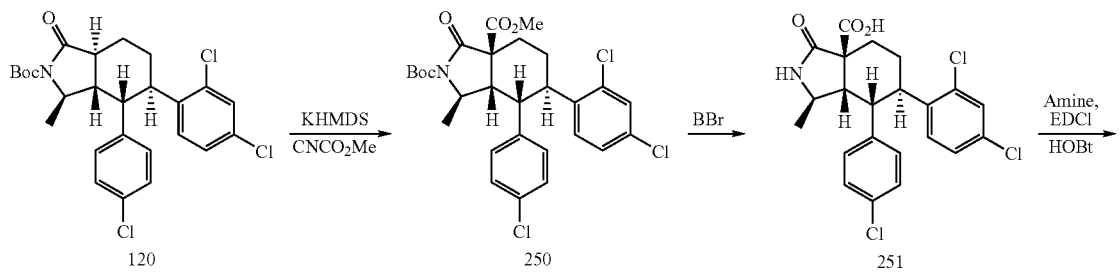

-continued

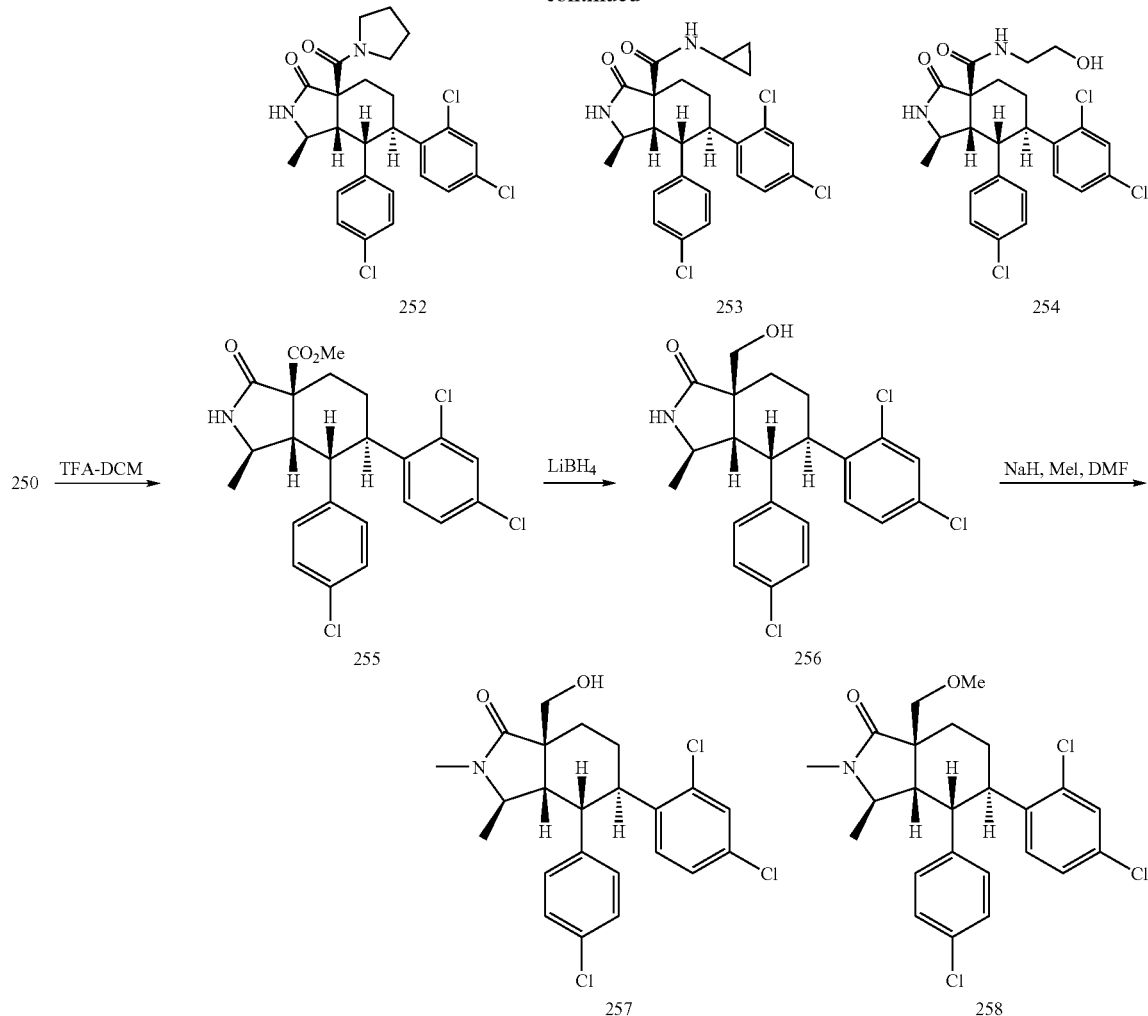

Preparation of 250:

To a degassed solution of 120 (400 mg, 0.786 mmol) in 5 ml THF at −78° C. was added 0.5M solution of KHMDS in toluene (2.4 ml, 1.2 mmol, 1.5 eq.) and stirred for 30 min. To this was added methyl cyanoformate (125 μl, 1.58 mmol, 2 eq.) and stirred for 30 min. The reaction was quenched with ferrous ammonium sulfate, and extracted with 3× ethyl acetate. The combined organic layers washed with brine, dried over $MgSO_4$, filtered, concentrated and chromatographed with 0% to 20% ethyl acetate in hexanes to provide 394 mg of 250.

MS: 566.3 ($MH^+$)

Preparation of 251:

To a solution of 250 (0.459 mmol) in 3 ml dichloromethane at rt was added 1M $BBr_3$ solution in dichloromethane (2.3 ml, 2.3 mmol, 5 eq.) and stirred for 2 hr. The reaction was quenched by the addition of water, extracted 3× with dichloromethane. The combined organic layer washed with brine, dried over $MgSO_4$, filtered and concentrated to provide 177 mg of 251 as a solid.

MS: 452.2 ($MH^+$)

Preparation of 252-254:

To a solution of 251 (20 mg, 0.044 mmol), pyrrolidine (11 μl, 0.134 mmol, 3 eq), HOBt (9 mg, 0.067 mmol, 1.5 eq) in 0.75 ml dichloromethane at rt was added EDCl (13 mg, 0.068 mmol, 1.5 eq) and stirred overnight at rt. It was diluted with ethyl acetate, washed with 2×1N HCl, brine, dried over $MgSO_4$, filtered, concentrated and chromatographed with 0% to 3% methanol in dichloromethane to provide 10 mg of 252.

Using a similar procedure, compounds 253 and 254 were prepared.

MS for 252: 505.3 ($MH^+$)
MS for 253: 491.3 ($MH^+$)
MS for 254: 495.3 ($MH^+$)

Preparation of 255:

A solution of 250 (390 mg, 0.688 mol) in 1:1 dichloromethane-trifluoroacetic acid was stirred at 0° C. for 1 hr and concentrated to provide 320 mg of 255.

MS: 466.3 ($MH^+$)

Preparation of 256:

To a solution of 255 (300 mg, 0.643 mmol) in 3 ml THF at rt was added 2M solution of $LiBH_4$ in THF (1 ml, 2 mmol, 3 eq.) and stirred for 1.5 hr. It was quenched with aq. $NH_4Cl$, and extracted 3× with ethyl acetate. The combined organic layer washed with brine, dried over MgSO$_4$, filtered, concentrated and chromatographed with 0% to 3% methanol in dichloromethane to provide 256 mg of 256.

MS: 438.2 (MH$^+$)

Preparation of 257 and 258:

To a solution of 256 (50 mg, 0.114 mmol) in 1 ml DMF at 0° C. was added 60% NaH in mineral oil (4.6 mg, 0.115 mmol, 1 eq) followed by iodomethane (35 µl, 0.562 mol, 5 eq).

The mixture was stirred for 2 hr at 0° C. and 1 hr at rt. It was diluted with ethyl acetate, washed 3× with water, brine, dried over MgSO$_4$, filtered, concentrated and chromatographed with 0% to 4% methanol in dichloromethane followed by preparative TCL purification of the overlapped fractions in 3% methanol in dichloromethane to obtain 14 mg of 257 and 16 mg of 258.

MS for 257: 452.2 (MH$^+$)
MS for 258: 466.3 (MH$^+$)

Scheme 122:

Compound 120 was converted to compounds 259, 260 and 261 using procedure similar to conversion of 81 to 84 (see scheme 47) using appropriate benzylic bromides.

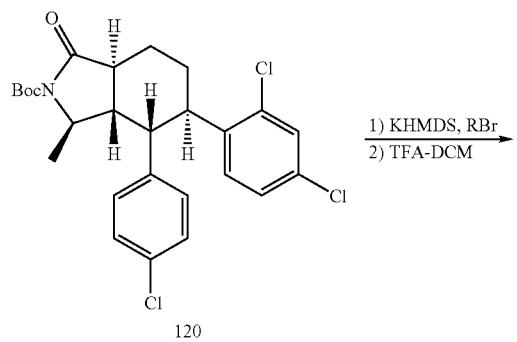

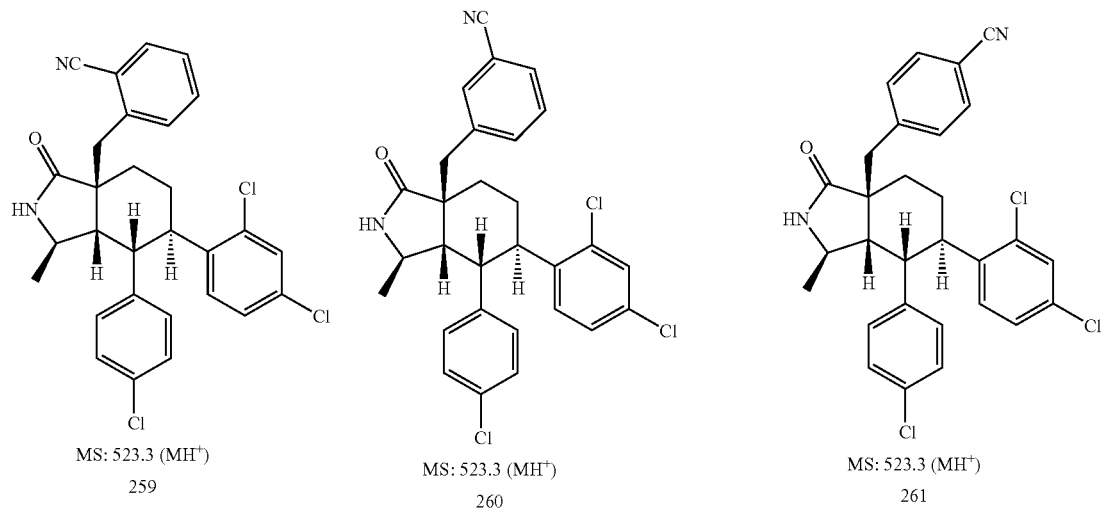

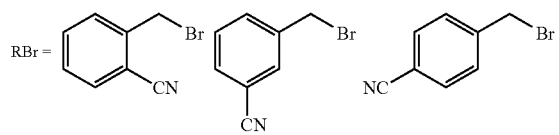

Scheme 123:

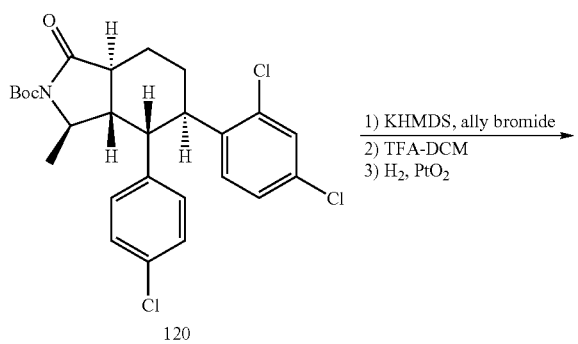

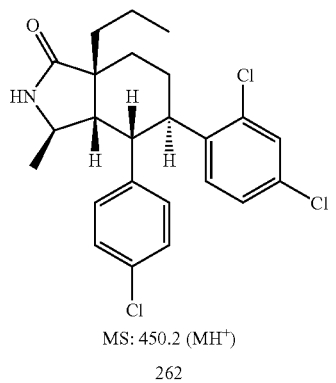
MS: 450.2 (MH+)
262

The intermediate 120 alkylated with allylbromide similar to the alkylation of 81 to give 86 then the double bond was reduced using conditions similar to the conversion of 79 to 80 (see scheme 47).

Scheme 124:

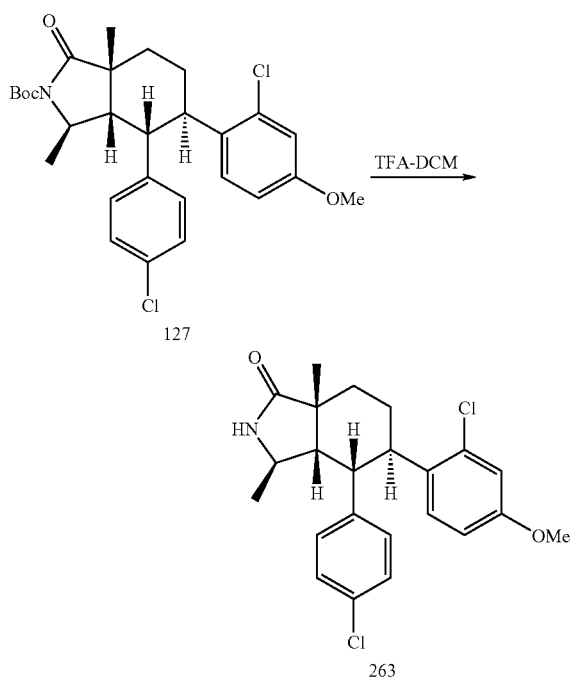

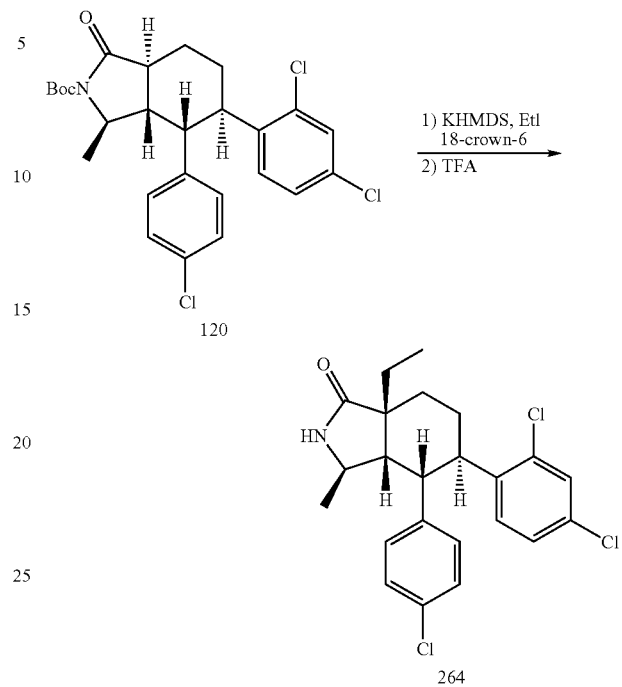

Preparation of 263 and 264:

A solution of 127 (30 mg) in 0.5 ml each of dichloromethane and trifluoroacetic acid was stirred at 0° C. for 40 min, concentrated and chromatographed with 0% to 3% methanol in dichloromethane to provide 21 mg of 263.

Intermediate 120 was ethylated using similar condition used in scheme 108 then the Boc group was cleaved using the above deprotection conditions to give 264.

MS for 263: 418.2 (MH+)
MS for 264: 432.2 (MH+)

Scheme 125:

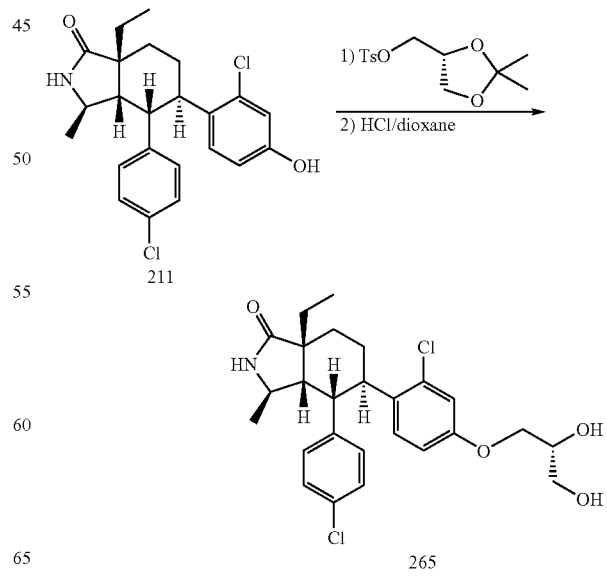

Preparation of 265:

A mixture of 211 (70 mg, 0.167 mmol), (R)-2,2-dimethyl-1,3-dioxolan-4-ylmethyl p-toluenesulfonate (145 mg, 0.506 mmol, 3 eq.), K₂CO₃ (93 mg, 0.67 mmol, 4 eq), NaI (25 mg, 0.166 mmol, 1 eq) in 2 ml DMF was heated at 80° C. in sealed tube for 2 days. It was diluted with ethyl acetate, washed with 1N HCl, brine, dried over MgSO₄, filtered, concentrated and chromatographed with 0% to 4% methanol in dichloromethane to provide 82 mg of a mixture of alkylated product and unreacted starting material. This was stirred with 1.5 ml of 1:3 v/v con. HCl and dioxane at rt for 4 hr. The mixture was diluted with ethyl acetate, washed with water, aq. NaHCO₃, and brine, dried over MgSO₄, filtered, concentrated and chromatographed with 0% to 5% methanol in dichloromethane to provide 31 mg of 265.

MS: 492.3 (MH⁺)

Using a similar procedure, the following compounds were prepared:

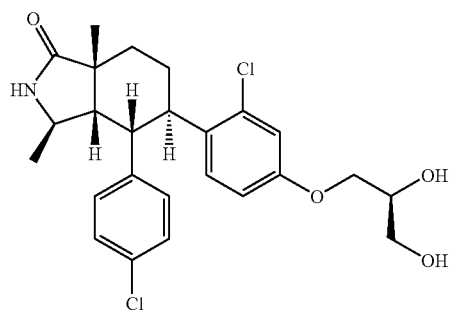

267

MS: 478.3 (MH⁺)

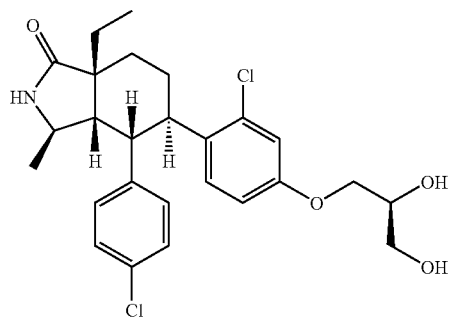

266

MS: 492.3 (MH⁺)

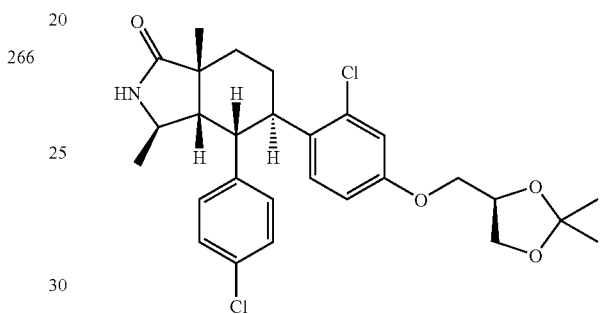

268

MS: 518.3 (MH⁺)

Scheme 126:

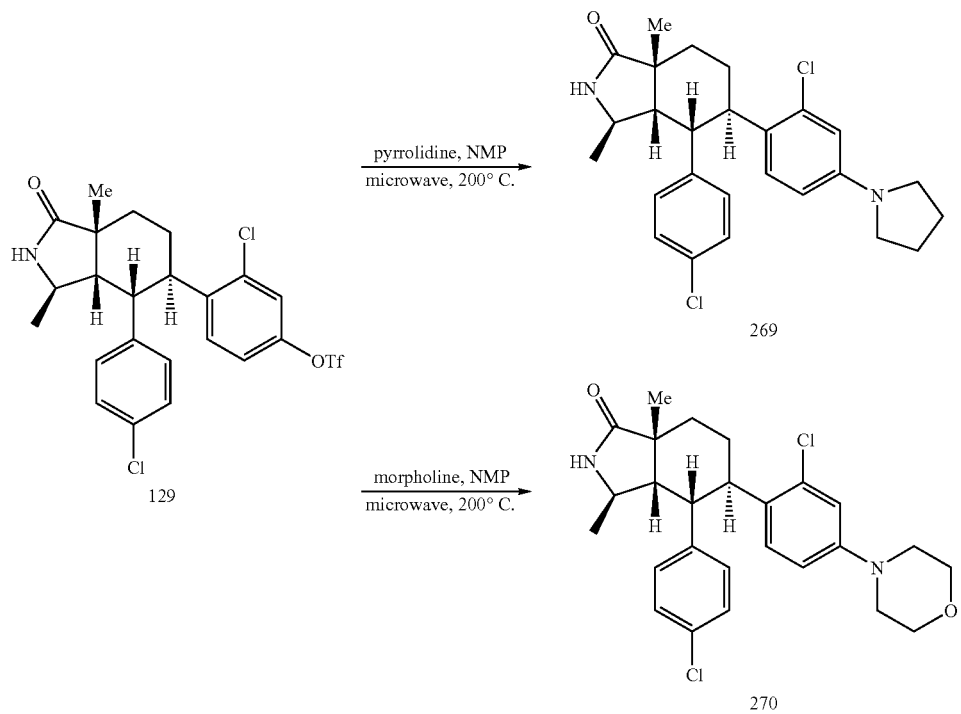

A mixture of 129 (30 mg, 0.056 mmol) and pyrrolidine (46 µl, 0.56 mmol, 10 eq.) in 1 ml NMP in a sealed tube was heated in a microwave reactor at 200° C. for 60 min. It was diluted with ethyl acetate, washed with water, brine, dried over MgSO$_4$, filtered, concentrated and purified by preparative TLC using 4% methanol in dichloromethane to provide 17 mg of 269.

Using a similar procedure 270 was prepared.
MS for 269: 457.3 (MH$^+$)
MS for 270: 473.3 (MH$^+$)

Scheme 127:

Scheme 128:

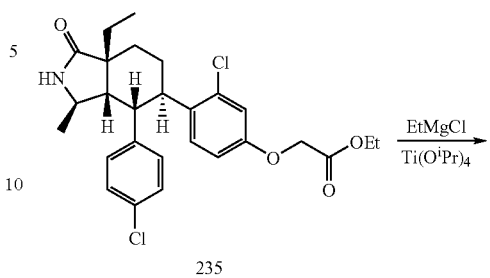

235

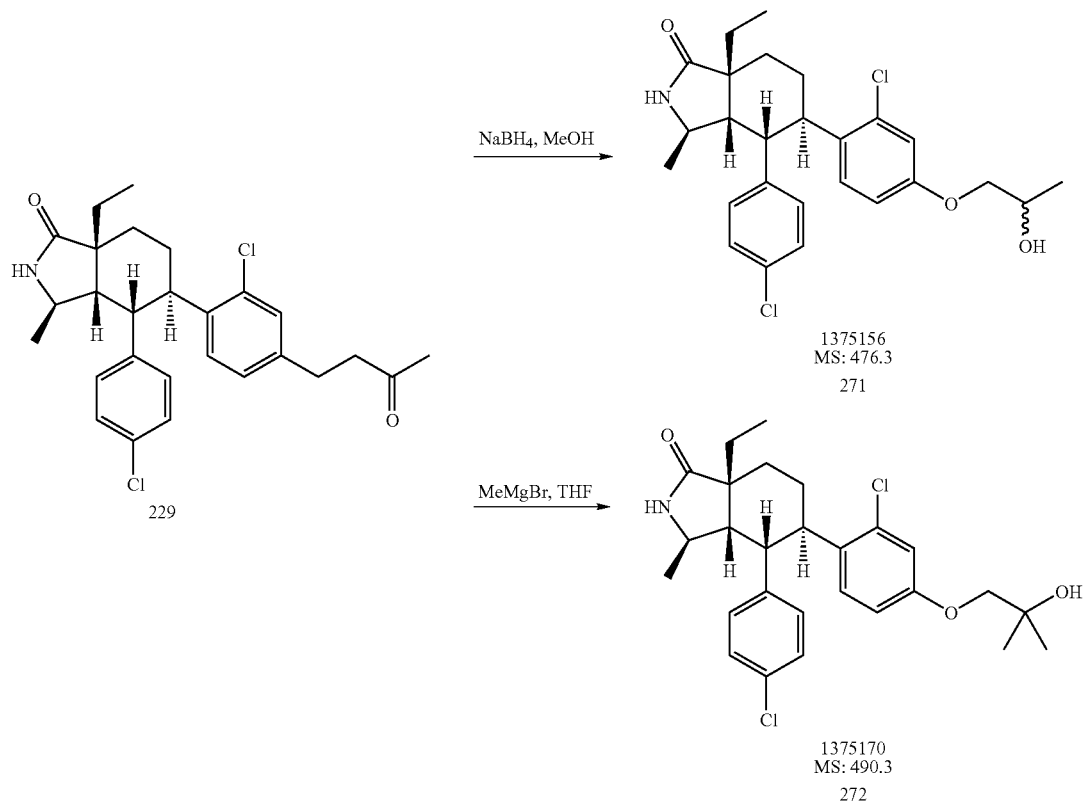

1375156
MS: 476.3
271

1375170
MS: 490.3
272

Preparation of 271:
To a solution of 229 (5 mg) in 1 ml of 1:1 v/v dichloromethane-methanol mixture at rt was added excess NaBH$_4$ and stirred at rt for 10 min. It was quenched with water, extracted with ethyl acetate, washed with brine, dried over MgSO$_4$, filtered, concentrated and purified by preparative TLC using 4% methanol in dichloromethane to provide 4 mg of 271.
MS: 476.3 (MH$^+$)

Preparation of 272:
To a solution of 229 (60 mg, 0.126 mmol) in 2 ml THF at −78° C. was added 1.4 M solution of MeMgBr in toluene/THF mixture. The reaction mixture was stirred at −78° C. for 30 min then at rt for 1.5 hr. It was quenched with aq. NH$_4$Cl, extracted 3× with ethyl acetate. The combined organic layer was washed with brine, dried over MgSO$_4$, filtered, concentrated and purified by preparative TLC using 4% methanol in dichloromethane to provide 20 mg of 272.
MS: 490.3 (MH$^+$)

-continued

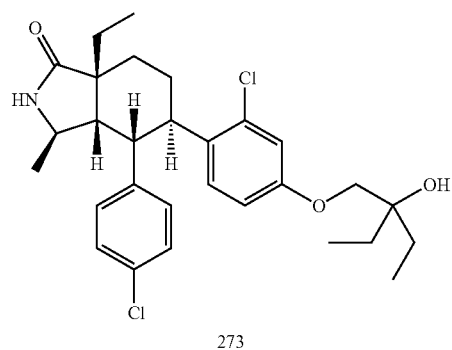

273

-continued

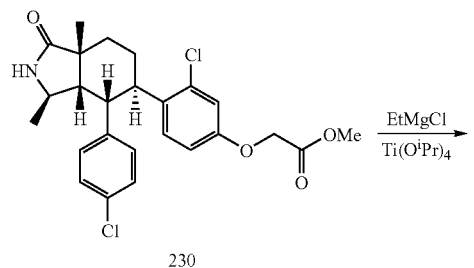
230

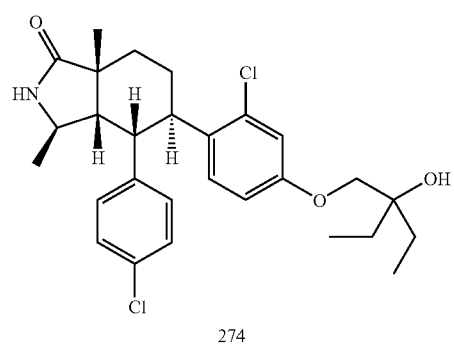
274

Preparation of 273 and 274:

To a solution of 235 (65 mg, 0.129 mmol) in 2 ml THF at −78° C. was added Ti(O$^i$Pr)$_4$ (115 µl, 0.388 mmol, 3 eq.) followed by 3M solution of EtMgCl in ether (0.39 ml, 1.17 mmol, 9 eq.). The mixture was stirred for 1 hr at −78° C. and 2 hr at rt. It was quenched by the addition of aq. NH$_4$Cl, stirred for 20 min and diluted with aq. sodium potassium tartrate. The slurry was extracted 3× with ethyl acetate, the combined organic layers washed with aq. sodium potassium tartrate followed by brine. It was dried over MgSO$_4$, filtered, concentrated and purified by preparative TLC using 4% methanol in dichloromethane to provide 33 mg of 273.

Similarly, 230 was converted to 274.

MS for 273: 518.3 (MH$^+$)

MS for 274: 504.3 (MH$^+$)

Scheme 129:

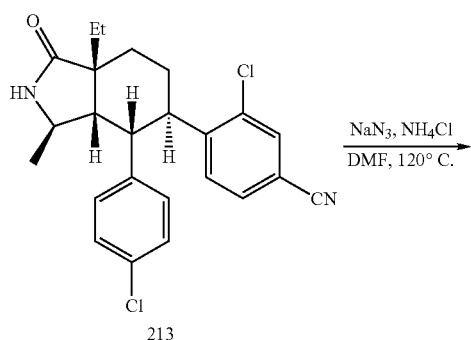
213

-continued

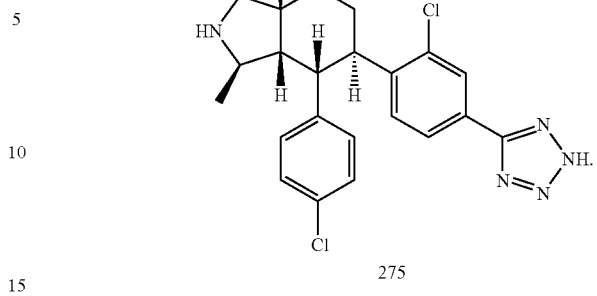
275

Preparation of 275:

A mixture of 213 (25 mg, 0.059 mmol), NaN$_3$ (39 mg, 0.60 mmol) and NH$_4$Cl (32 mg (0.59 mmol) in 0.5 ml DMF in a sealed tube was heated overnight at 120° C. The mixture was diluted with 1N HCl and extracted 3× with ethyl acetate. The combined organic layer washed with brine, dried over MgSO$_4$, filtered and concentrated to provide ~30 mg 275.

MS: 470.3 (MH$^+$)

Scheme 130:

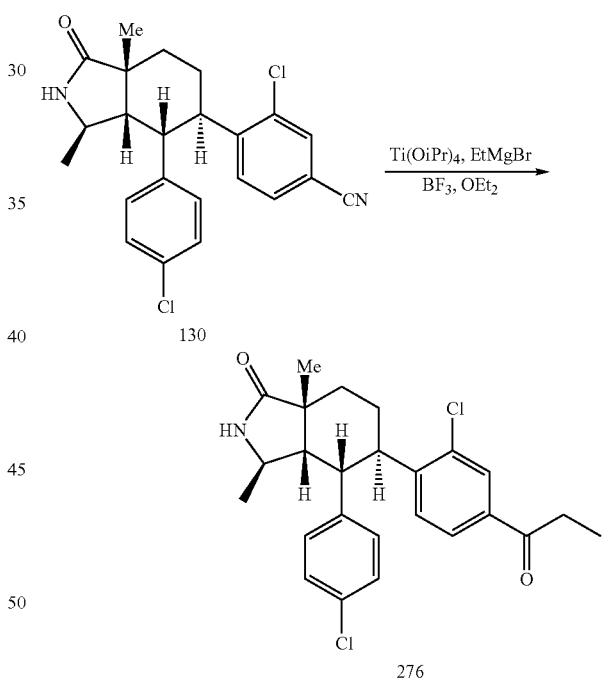

Preparation of 276:

To a solution of 130 (55 mg, 0.133 mmol), in 2 ml ether was added Ti(O$^i$Pr)$_4$ (120 µl, 0.401 mmol, 3 eq.) cooled to −78° C. and added 3M solution of EtMgBr in ether (0.27 ml, 0.81 mmol, 6 eq.) and stirred for 10 min at −78° C. and for 1 hr at rt. To this was added BF$_3$.OEt$_2$ (101 µl, 0.80 mmol, 6 eq) and stirred for 1 hr at rt. The mixture was poured in to aq. sodium potassium tartrate and extracted 3× with ethyl acetate. The combined organic layer was washed with brine, dried over MgSO$_4$, filtered concentrated and chromatographed with 0% to 4% methanol in dichloromethane to provide 26 mg of 276.

MS: 444.2 (MH$^+$)

Scheme 131:

Using chemistry similar to the alkylation conditions given under scheme 73 and scheme 109, intermediates 126 and 120 were transformed to compounds 277-281.

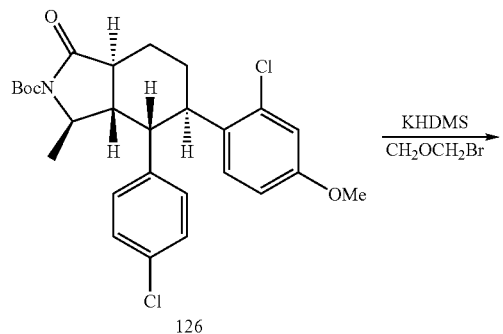

126

KHDMS
CH₂OCH₂Br
→

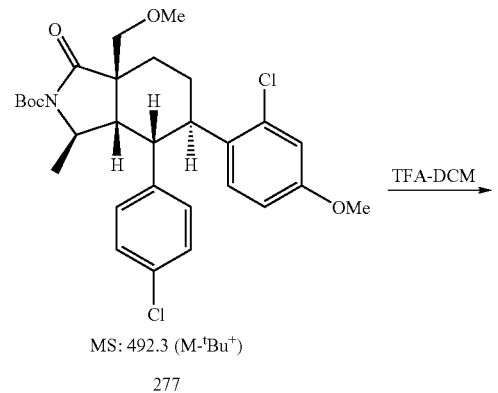

MS: 492.3 (M-ᵗBu⁺)
277

TFA-DCM
→

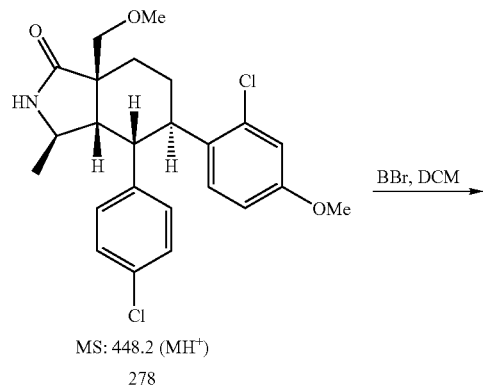

MS: 448.2 (MH⁺)
278

BBr, DCM
→

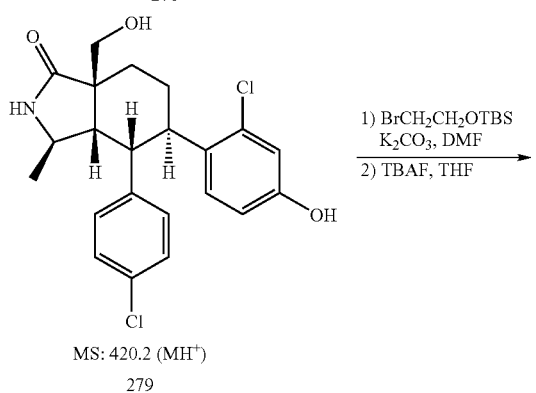

MS: 420.2 (MH⁺)
279

1) BrCH₂CH₂OTBS
K₂CO₃, DMF
2) TBAF, THF
→

-continued

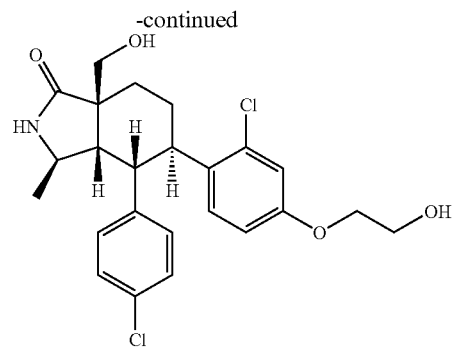

MS: 464.3 (MH⁺)
280

Similarity:

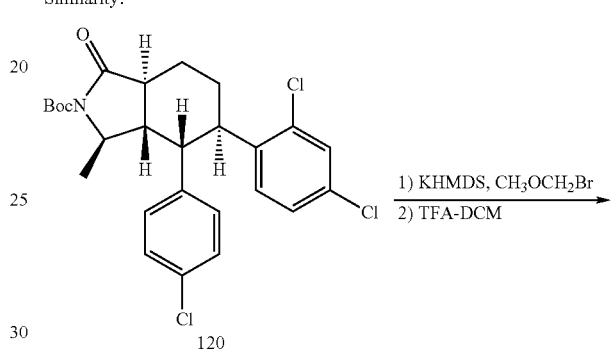

120

1) KHMDS, CH₃OCH₂Br
2) TFA-DCM
→

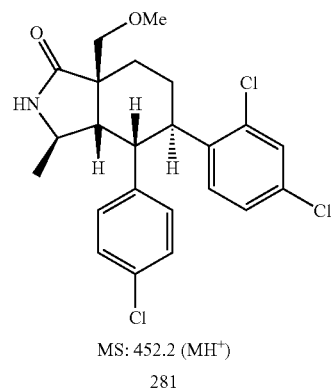

MS: 452.2 (MH⁺)
281

Scheme 132:

Using the conditions similar to the transformations described under scheme 109, intermediates 211 and 128 were converted to compounds 282-287.

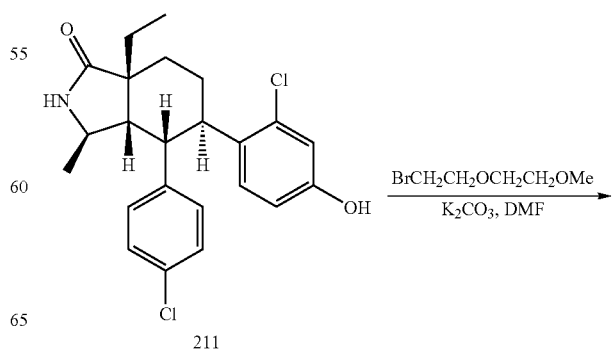

211

BrCH₂CH₂OCH₂CH₂OMe
K₂CO₃, DMF
→

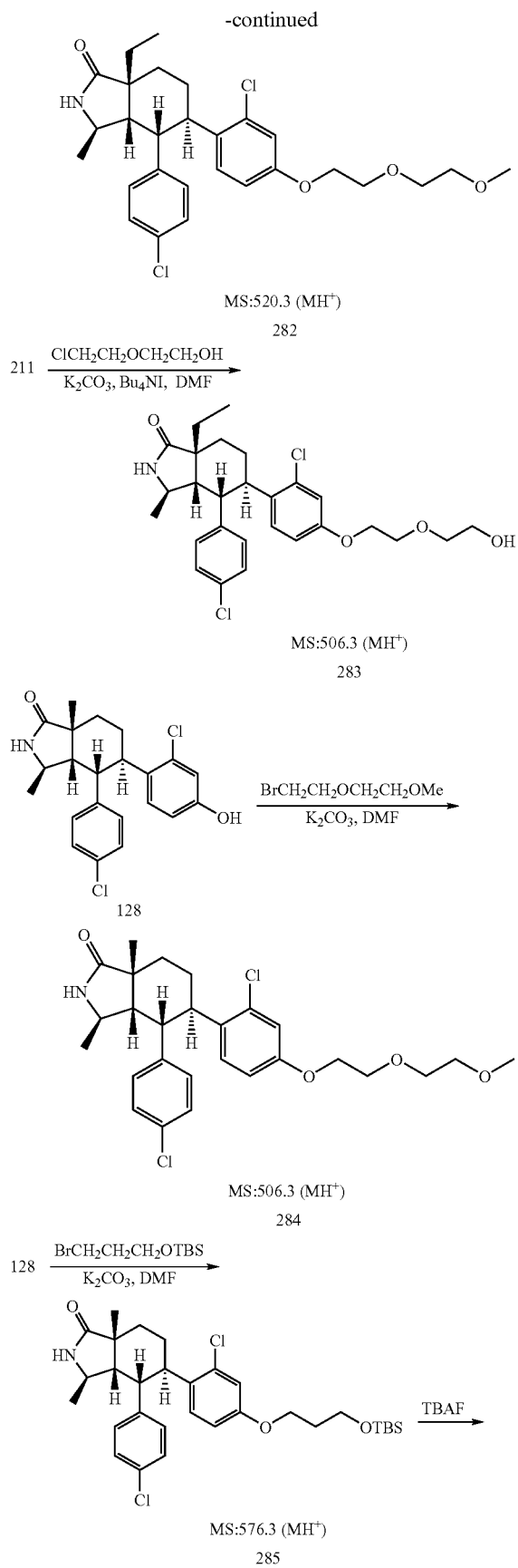
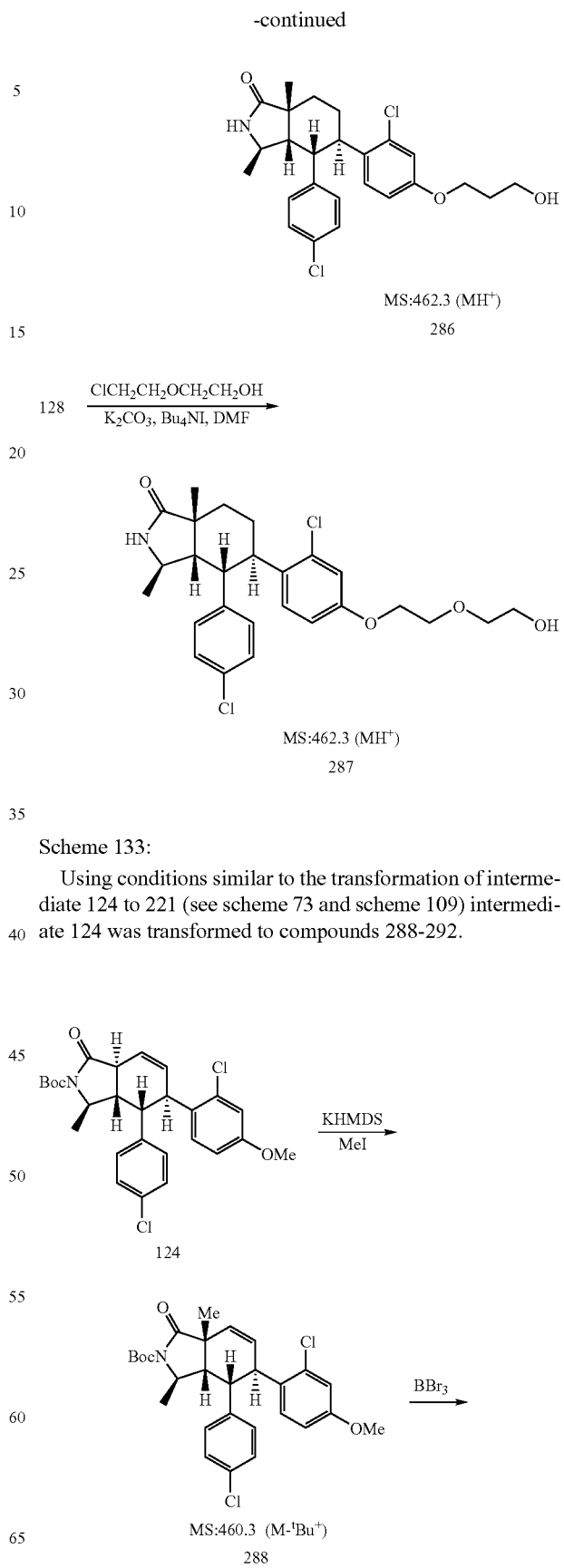
Scheme 133:
Using conditions similar to the transformation of intermediate 124 to 221 (see scheme 73 and scheme 109) intermediate 124 was transformed to compounds 288-292.

-continued
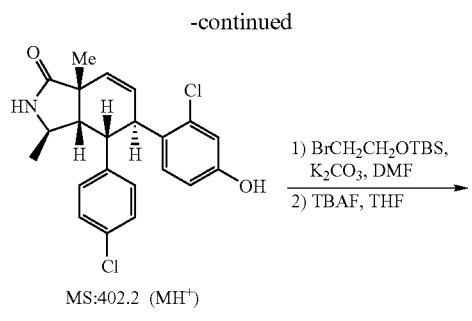
MS:402.2 (MH+)
289
1) BrCH₂CH₂OTBS, K₂CO₃, DMF
2) TBAF, THF
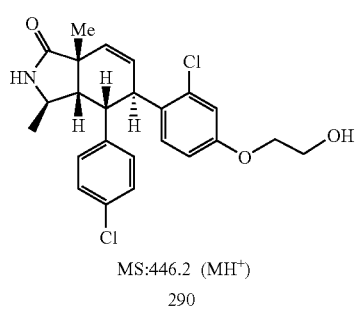
MS:446.2 (MH+)
290
Similarly:
124 →
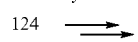
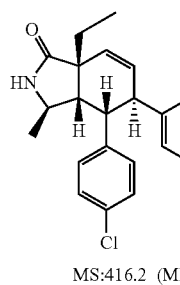
MS:416.2 (MH+)
291
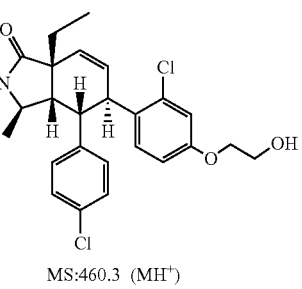
MS:460.3 (MH+)
292
Scheme 134:
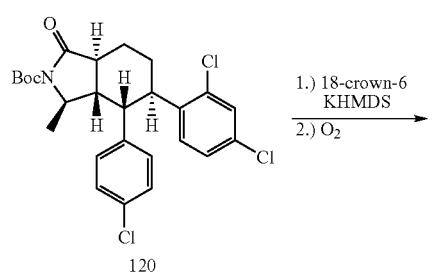
120
1.) 18-crown-6 KHMDS
2.) O₂
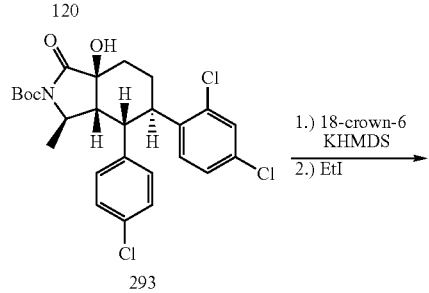
293
1.) 18-crown-6 KHMDS
2.) EtI
-continued
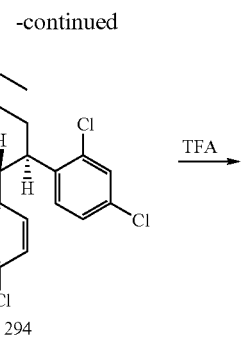
294
TFA →
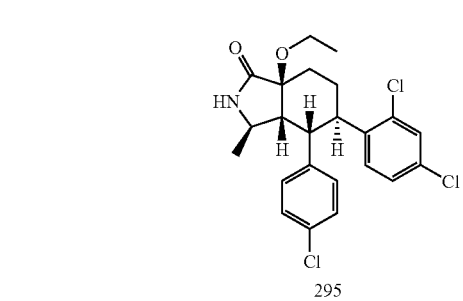
295
293 →  NaH / MeI
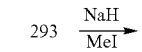
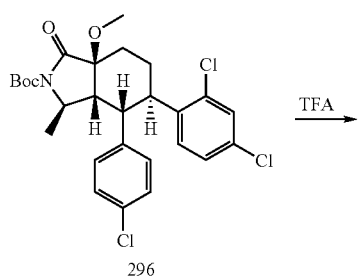
296
TFA →
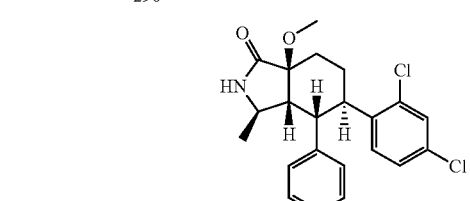
297
293 →  TFA
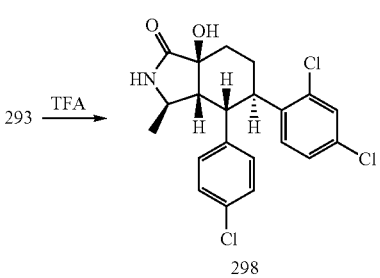
298
Preparation of Compound 295:
To 250 mg of compound 120 was added 18-crown-6 and the mixture twice dissolved in toluene and evaporated to dryness. To the residue in 3 ml of dry THF at −78° C. was added two equivalents of potassium hexamethyldisilylamide (as a 0.5M solution in toluene) and the mixture stirred under argon for 1.5 hours after which the reaction mixture was stirred under a balloon of O₂ for two hours. The mixture was then quenched with aqueous sodium sulfite and allowed to warm to room temperature. The mixture was then extracted three times with ethyl acetate and the combined organic phases were washed with brine, dried with MgSO₄, filtered and evaporated to dryness. Purification by flash chromatography (0-40% acetone in hexane) yielded 96 mg of compound 293.

To 45 mg of compound 293 was added 18-crown-6 and the mixture twice dissolved in toluene and evaporated to dryness. To the residue in 3 mL of dry THF at −78° C. was added two equivalents of potassium hexamethyldisilylamide (as a 0.5M solution in toluene) and the mixture stirred under argon for about one hour after which ten equivalents iodoethane was added and, after two hours, the mixture placed in a freezer overnight. The reaction mixture was quenched with aqueous ammonium chloride and extracted three times with ethyl acetate. The combined organic phases were washed with brine, dried with MgSO₄, filtered and evaporated to dryness. Purification by flash chromatography (0-50% ethyl acetate in hexane) yielded 12 mg of compound 294.

To 12 mg of compound 294 in 2 mL of dry dichloromethane at 0° C. was added 0.5 mL of trifluoroacetic acid and the mixture stirred under nitrogen. After one hour the mixture was evaporated to dryness and twice dissolved in toluene and evaporated to dryness yielding 10 mg of 295.

MS for 295: 452.2 (MH⁺)

Preparation of 296:

To 30 mg of 293 in 2 ml of dry DMF at 0° C. was added 2 equivalents of sodium hydride (5 mg of 60% NaH in mineral oil) and the mixture stirred under nitrogen. After 15 minutes 5 equivalents of iodomethane was added and the mixture slowly warmed to room temperature. After a further two hours the mixture was quenched with aqueous ammonium chloride and extracted with ethyl acetate three times. The combined organic extracts were washed with brine, dried with magnesium sulfate, filtered and evaporated to dryness. Purification by flash chromatography (0-30% EtOAc in hexane) yielded 15 mg of 296.

MS: 538.3 (MH⁺)

Preparation of 297:

To 13 mg of 296 in 1.5 ml of dichloromethane at 0° C. was added 1 ml of trifluoroacetic acid and the mixture stirred under nitrogen for two hours. The reaction mixture was then evaporated to dryness and twice dissolved in toluene and evaporated to dryness. The crude product was purified by reversed phase HPLC yielding 5 mg of 297.

MS: 438.2 (MH⁺)

Preparation of 298:

To 30 mg of 293 in 2 ml of dichloromethane at 0° C. was added 1 ml of trifluoroacetic acid and the mixture stirred under nitrogen for two hours. The reaction mixture was then evaporated to dryness and twice dissolved in toluene and evaporated to dryness yielding 24 mg of 298.

MS: 424.2 (MH⁺)

Scheme 135:

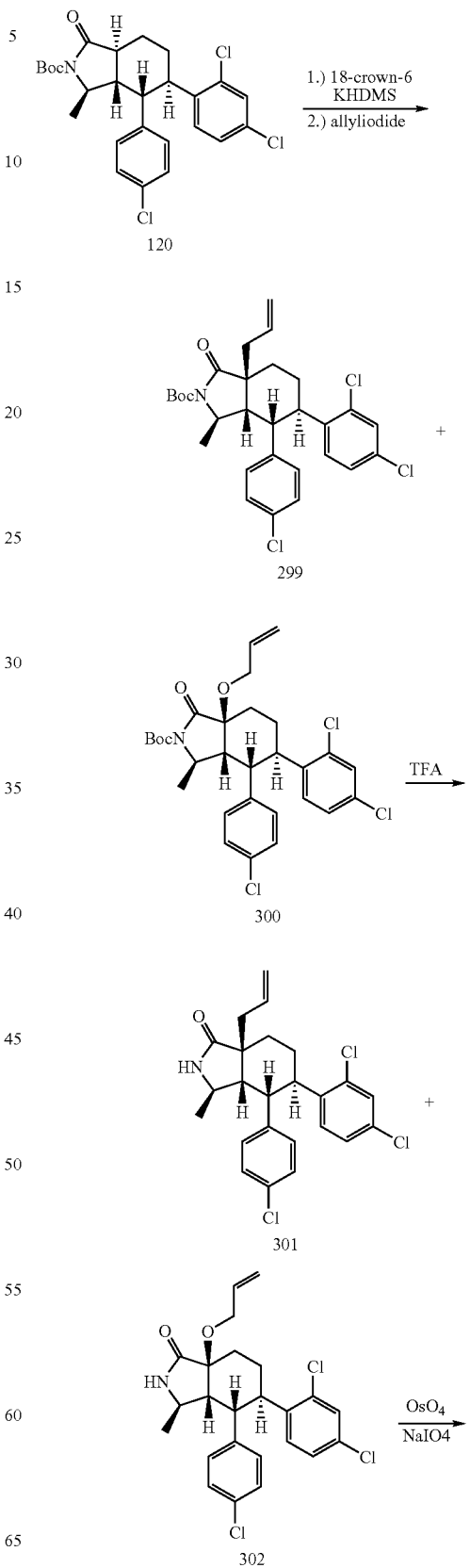

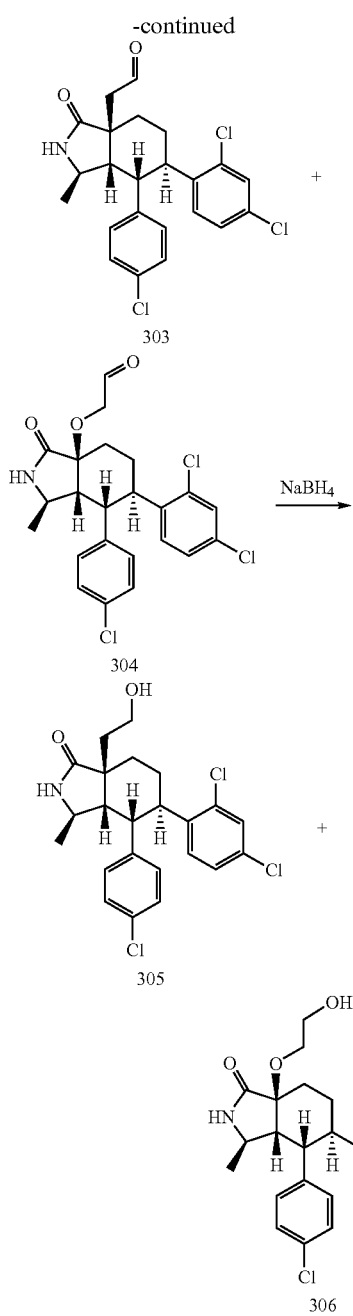

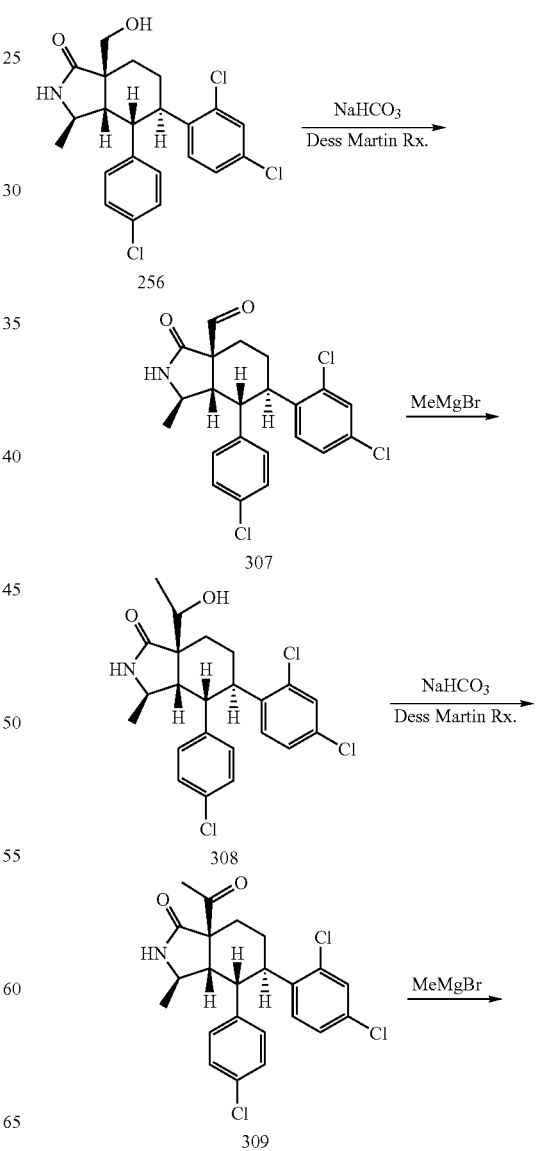

To 100 mg of 120 in 3 ml of dry THF at −78° C. was added 2 equivalents of 18-crown-6 and 2 equivalents of potassium hexamethyldisilylamide (as a 0.5M solution in toluene) and the mixture stirred under argon for 15 minutes after which 10 equivalents of allyl iodide was added. After 1.5 hours the mixture was poured onto aqueous ammonium chloride and extracted three times with ethyl acetate. The combined extracts were washed with brine, dried with MgSO$_4$, filtered and evaporated to dryness. The crude mixture was purified by flash chromatography (0 to 20% EtOAc in hexane) yielding 61 mg of a mixture of compounds 299 and 300.

To this mixture in 2 ml of dichloromethane at 0° C. was added 1 mL of trifluoroacetic acid and the mixture stirred under nitrogen for one hour. The reaction mixture was then evaporated to dryness and twice dissolved in toluene and evaporated to dryness yielding 60 mg of a mixture of compounds 301 and 302.

To the mixture of 301 and 302 in 3 mL of dioxane and 1 mL of water was added 2 equivalents of 2,6-lutidine, 4 equivalents of sodium periodate and 2% mole of osmium tetroxide (as a 2.5% solution in t-butanol) and the mixture stirred under nitrogen. After five hours the mixture was placed in a freezer for 16 hours after which the mixture was poured onto water and extracted three times with dichloromethane. The combined extracts were washed with brine, dried with MgSO$_4$, filtered and evaporated to dryness yielding 60 mg of a mixture of compounds 303 and 304.

To the mixture of 303 and 304 in 5 mL of methanol was added ~10 mg of sodium borohydride and the mixture stirred under nitrogen for 10 minutes then quenched with aqueous ammonium chloride and extracted three times with dichloromethane. The combined extracts were washed with brine, dried with MgSO$_4$, filtered and evaporated to dryness. The crude product was purified by reversed phase HPLC yielding 15 mg of 305 and 12 mg of 306.

MS for 305: 452.2 (MH$^+$)

MS for 306: 468.3 (MH$^+$)

Scheme 136:

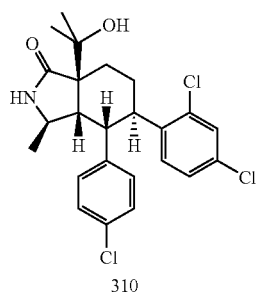

310

Preparation of 308:

To 98 mg of 256, in 5 mL of dry dichloromethane, was added two equivalents of sodium bicarbonate and 1.2 equivalents of Dess-Martin reagent and the mixture stirred under nitrogen. After one hour aqueous sodium bicarbonate and ether were added to the reaction mixture and allowed to stir for ten minutes. The phases were separated and the aqueous phase extracted with diethyl ether. The combined organic phased were washed with brine, dried with MgSO$_4$, filtered and evaporated to dryness yielding 90 mg of aldehyde 307.

To 90 mg of 307 in 5 mL of dry THF at 0° C. was added three equivalents of methyl magnesium bromide (as a 1.4M solution in toluene) and the mixture stirred under nitrogen. After one hour an additional equivalent of methyl magnesium bromide (as a 1.4M solution in toluene) was added and, after a further 20 minutes, the reaction mixture was quenched with aqueous ammonium chloride and extracted three times with ethyl acetate. The combined organic phases were washed with brine, dried with MgSO$_4$, filtered and evaporated to dryness yielding 100 mg of crude product. Purification by flash chromatography (0-2% MeOH in DCM) yielded 6 mg of 308.

MS: 452.2 (MH$^+$)

Preparation of 310:

To 22 mg of 308 in dry dichloromethane were added two equivalents of sodium bicarbonate and 1.2 equivalents of Des Martin reagent and the mixture stirred under nitrogen. After two hours the reaction mixture was poured onto aqueous sodium bicarbonate and extracted three times with ethyl acetate. The combined organic phases were washed with brine, dried with MgSO$_4$, filtered and evaporated to dryness yielding 26 mg of crude ketone 309.

To 26 mg of crude ketone 309 in 5 mL of dry THF at 0° C. was added five equivalents of methyl magnesium bromide (as a 1.4M solution in toluene) and the mixture stirred under nitrogen. After three hours the reaction mixture was quenched with aqueous ammonium chloride and extracted three times with ethyl acetate. The combined organic phases were washed with brine, dried with MgSO$_4$, filtered and evaporated to dryness. Purification by flash chromatography (0-2% MeOH in DCM) yielded 1.2 mg of 310.

MS: 466.3 (MH$^+$)

Scheme 137:

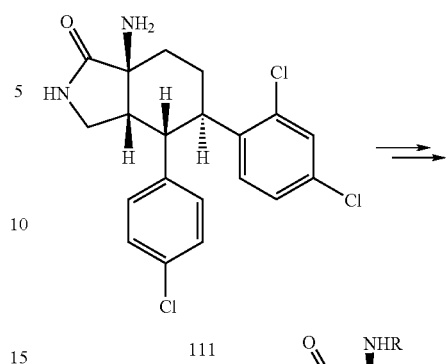

Similar to the preparation of amide 112 described under scheme 59 and scheme 63, a variety of amides, sulfonamides, ureas and carbamates were prepared using appropriate acid chlorides, sulfonyl chlorides, isocyanates and chloroformates to give 311A to 311BB.

| Compound# | Structure | M+H |
|---|---|---|
| 311A | 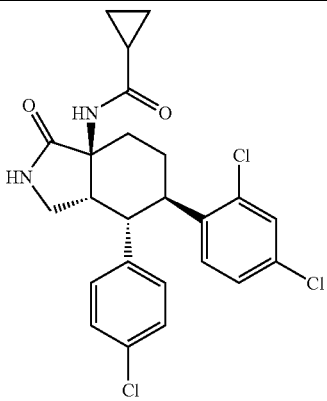 | 477.3 |
| 311B | 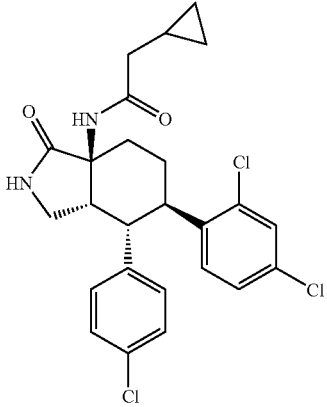 | 491.3 |

377
-continued
| Compound# | Structure | M+H |
|---|---|---|
| 311C | 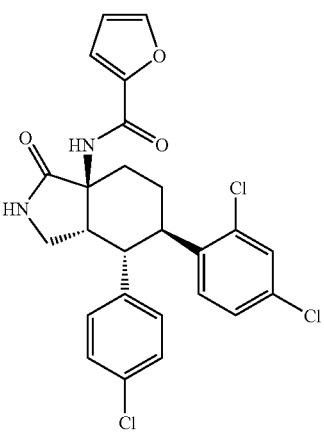 | 503.3 |
| 311D | 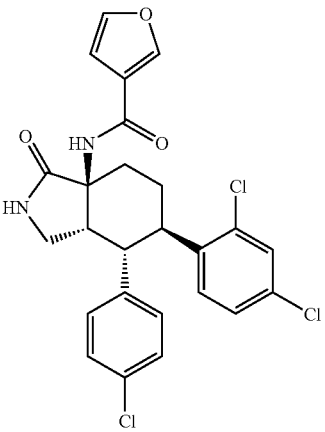 | 503.3 |
| 311E | 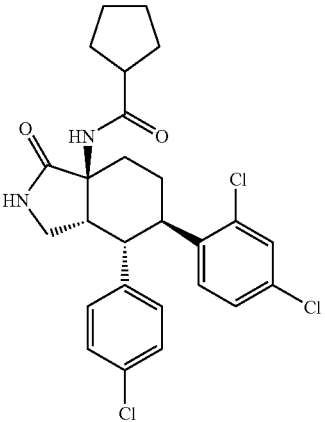 | 505.3 |
378
-continued
| Compound# | Structure | M+H |
|---|---|---|
| 311F | 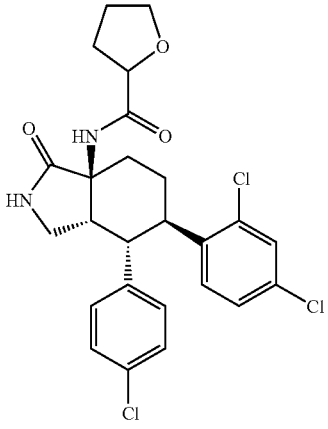 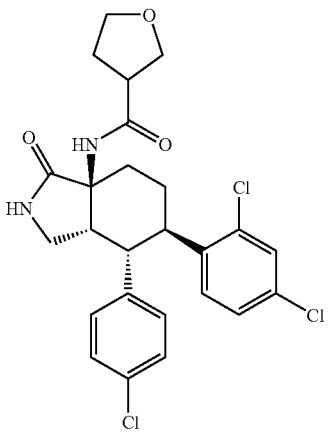 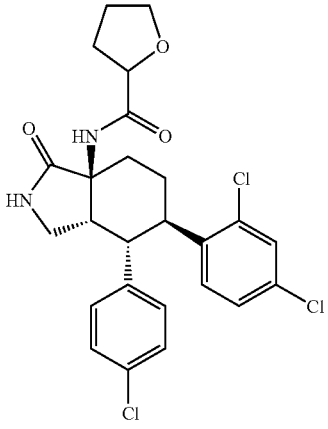 | 507.3 |
| 311G | 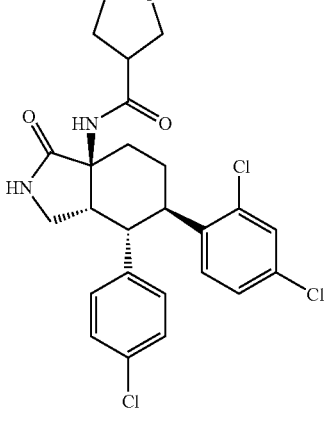 | 507.3 |
| 311H | 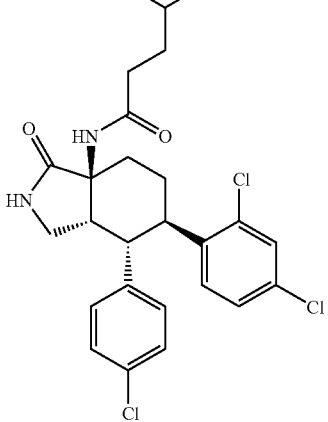 | 507.3 |

379
-continued
| Compound# | Structure | M+H |
|---|---|---|
| 311I | 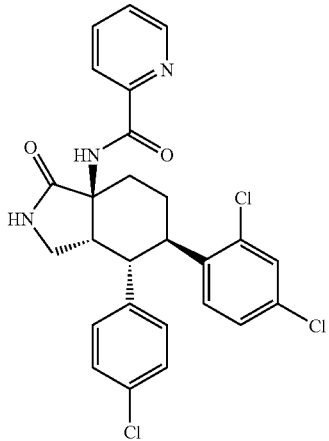 | 514.3 |
| 311J | 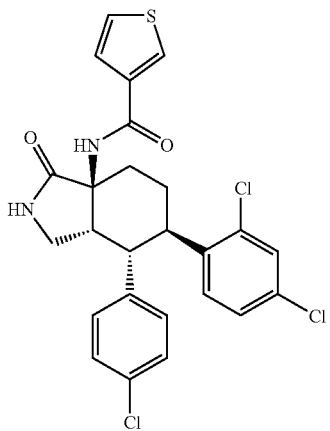 | 519.3 |
| 311K | 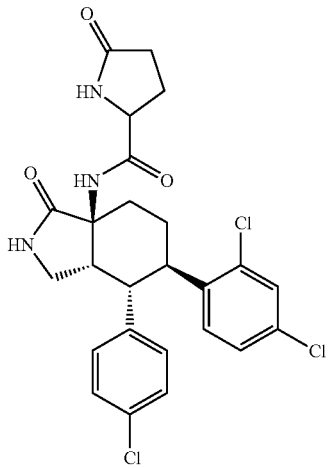 | 520.3 |
380
-continued
| Compound# | Structure | M+H |
|---|---|---|
| 311L | 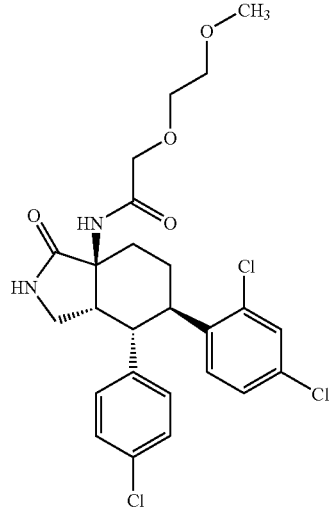 | 525.3 |
| 311M | 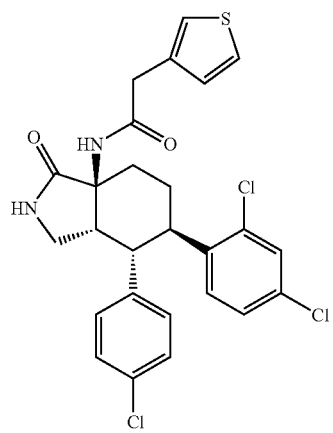 | 533.3 |
| 311N | 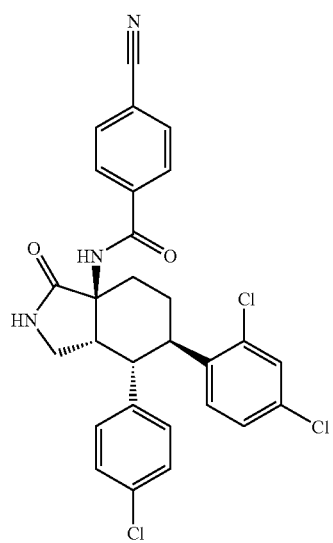 | 538.3 |

-continued
| Compound# | Structure | M+H |
|---|---|---|
| 311O | 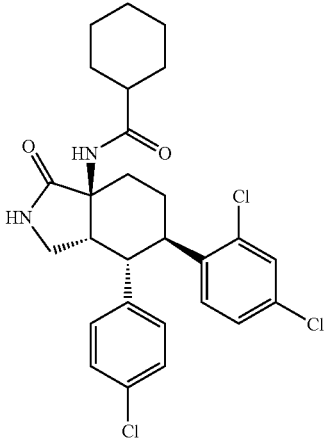 | 519.3 |
| 311P | 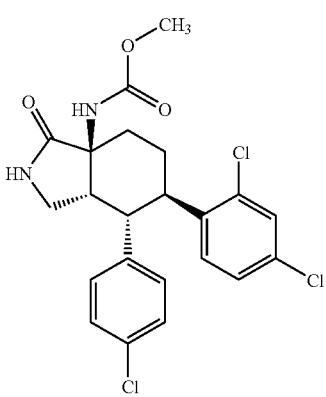 | 467.3 |
| 311Q | 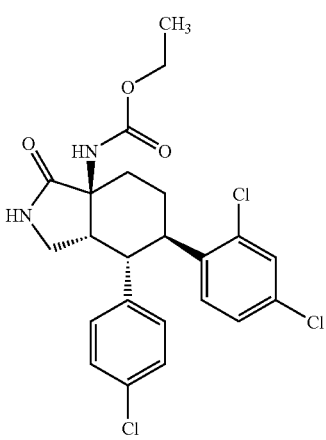 | 481.3 |
-continued
| Compound# | Structure | M+H |
|---|---|---|
| 311R | 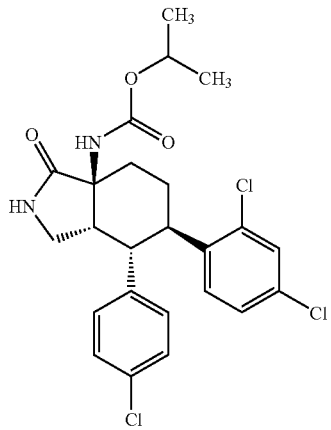 | 495.3 |
| 311S | 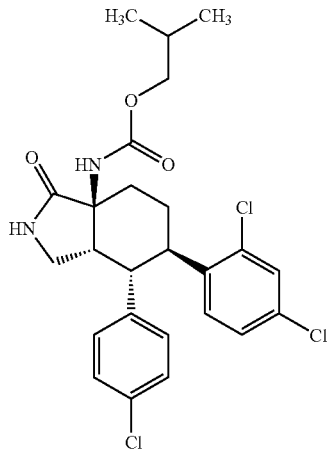 | 509.3 |
| 311T | 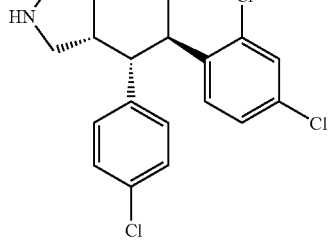 | 511.3 |

383
-continued
| Compound# | Structure | M+H |
|---|---|---|
| 311U | 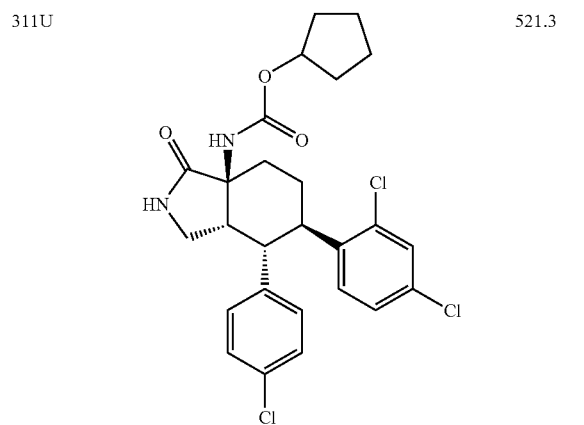 | 521.3 |
| 311V | 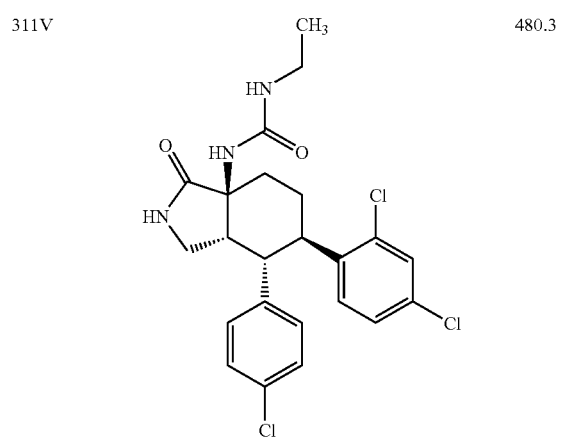 | 480.3 |
| 311W | 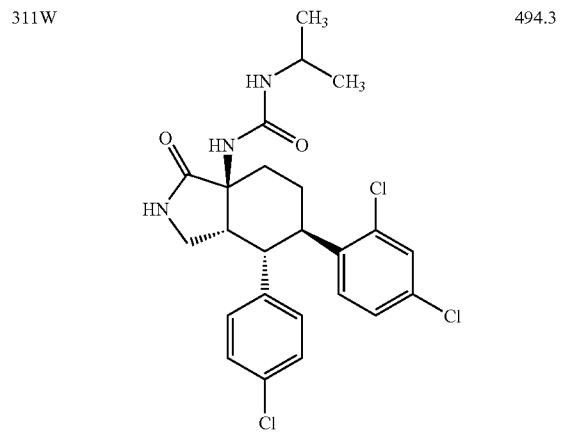 | 494.3 |
384
-continued
| Compound# | Structure | M+H |
|---|---|---|
| 311X | 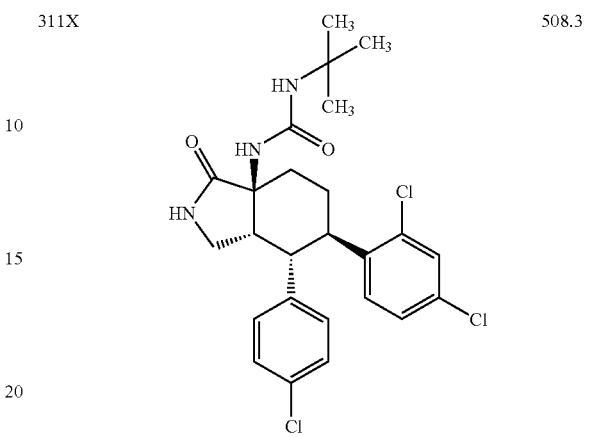 | 508.3 |
| 311Y | 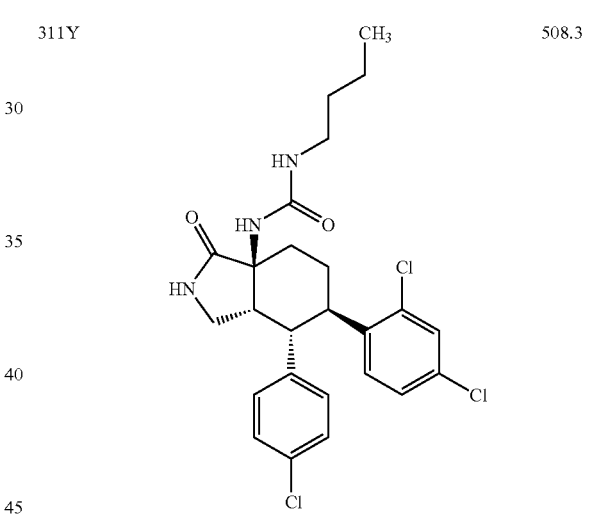 | 508.3 |
| 311Z | 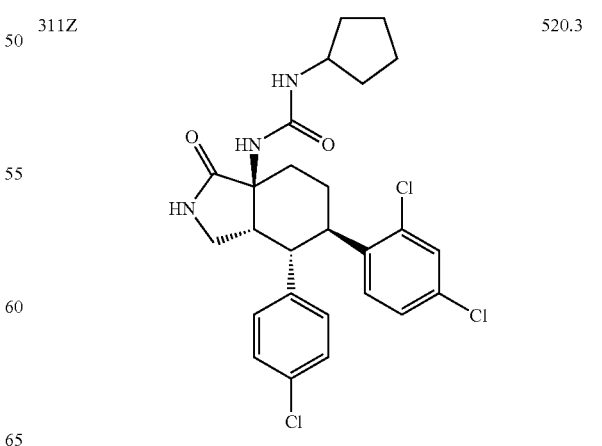 | 520.3 |

-continued
| Compound# | Structure | M+H |
|---|---|---|
| 311AA | 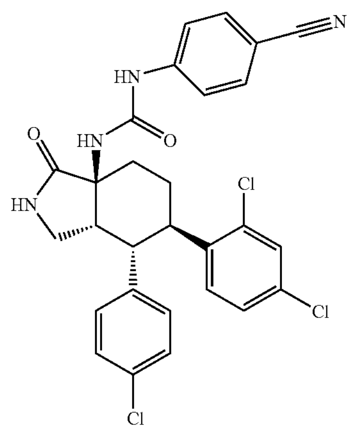 | 553.3 |
| 311BB | | 534.3 |
Scheme 138:
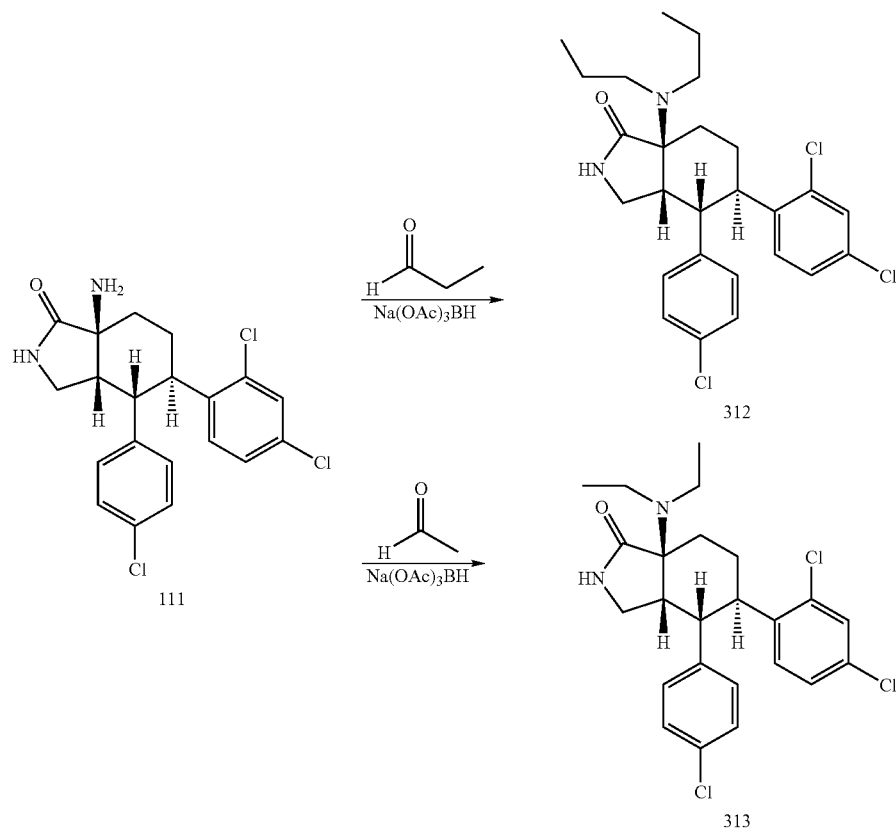

Preparation of 312:

To 111 in 2 mL of dry dichloroethane was added 5 equivalents of propionaldehyde and 5 equivalents of sodium triacetoxy borohydride and the mixture stirred under nitrogen. After about 16 hours the reaction mixture was poured onto aqueous potassium carbonate and extracted three times with ethyl acetate. The combined organic phases were washed with brine, dried with MgSO$_4$, filtered and evaporated to dryness. Purification by flash chromatography (0-35% ethyl acetate in hexane) yielded 25 mg of 312.

MS: 493.3 (MH$^+$)

Preparation of 313:

To 40 mg of 111 in 2 mL of dry dichloroethane was added 5 equivalents of acetaldehyde and 5 equivalents of sodium triacetoxy borohydride and the mixture stirred under nitrogen. After 16 hours the reaction mixture was poured onto aqueous potassium carbonate and extracted three times with ethyl acetate. The combined organic phases were washed with brine, dried with MgSO$_4$, filtered and evaporated to dryness. The crude product was purified by reversed phase HPLC yielding 5 mg of 313.

MS: 465.3 (MH$^+$)

Scheme 139:

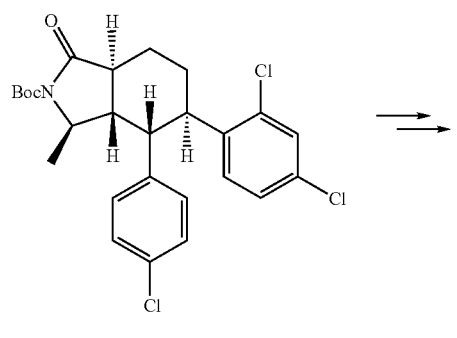

120

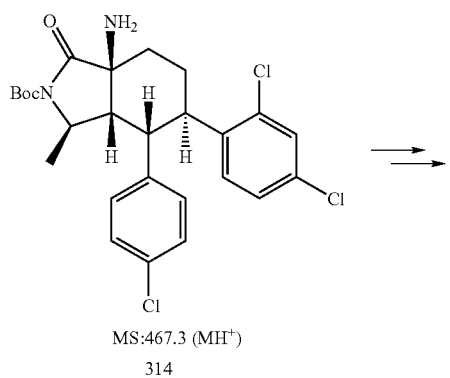

MS: 467.3 (MH$^+$)
314

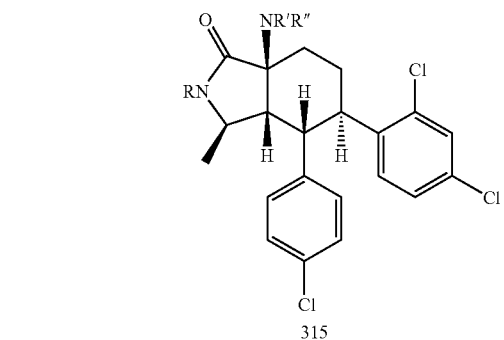

315

Intermediate 120 was converted to amine 314 then to a variety of amino derivatives 315A-315Q using a procedures similar to the transformation of 108 to 112 (see scheme 59)

| Compound # | R | R' | R" | MS (MH$^+$) |
|---|---|---|---|---|
| 315A | H | H | H | 423.2 |
| 315B | ![Boc] | ![CH2CH2OCH3 ester] | H | 625.3 |
| 315C | H | ![CH2CH2OCH3 ester] | H | 525.3 |
| 315D | ![Boc] | ![methanesulfonyl] | H | 601.3 |

-continued

| Compound # | R | R' | R" | MS (MH+) |
|---|---|---|---|---|
| 315E | H | *methylsulfonyl* | H | 501.3 |
| 315F | *tert-butyl ester* | *CH₂C(O)CH₂OCH₂CH₂OCH₃* | H | 639.4 |
| 315G | H | *CH₂C(O)CH₂OCH₂CH₂OCH₃* | H | 539.3 |
| 315H | *tert-butyl ester* | *ethylsulfonyl* | H | 615.3 |
| 315I | H | *ethylsulfonyl* | H | 515.3 |
| 315J | *tert-butyl ester* | *tetrahydropyran-4-yl* | H | 607.3 |
| 315K | H | *tetrahydropyran-4-yl* | H | 507.3 |
| 315L | *tert-butyl ester* | *cyclopentyl* | H | 591.3 |
| 315M | H | *cyclopentyl* | H | 491.3 |
| 315N | H | *cyclobutyl* | H | 477.3 |
| 315O | H | Me | H | 437.2 |
| 315P | H | Et | Et | 479.3 |
| 315Q | H | n-Pr | n-Pr | 507.3 |

Scheme 140:

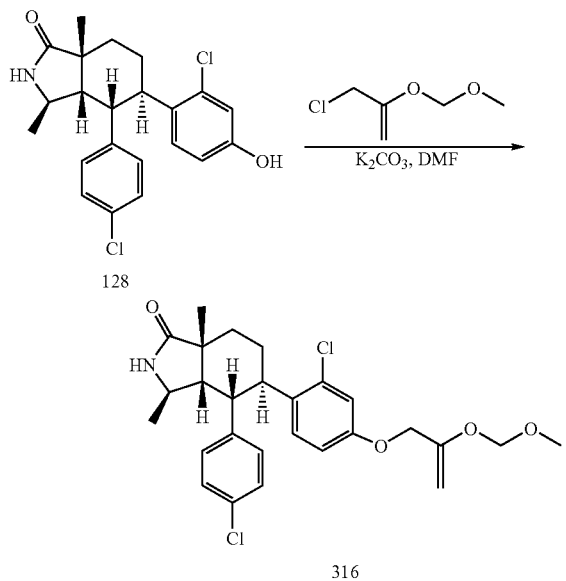

To 60 mg of 128 in 1 mL of dry DMF was added four equivalents of potassium carbonate and five equivalents of 2-(chloromethyl)-3,5-dioxahex-1-ene. After bubbling with argon for one minute, the mixture was heated to 65° C. in a pressure tube for three hours. The reaction mixture was diluted with ethyl acetate, washed three times with water, once with brine, dried with MgSO$_4$, filtered and evaporated to dryness. Purification by flash chromatography (hexane to 95:5 DCM/MeOH) yielded 61 mg of 316.

MS: 504.3 (MH$^+$)

Scheme 141:

Preparation of 318:

To 750 mg of 128 in 10 mL of dry DMF was added ten equivalents of potassium carbonate and ten equivalents of N(2-bromoethyl)phthalimide. After bubbling with argon for one minute, the mixture was heated to 75° C. in a pressure tube for eight hours. An additional five equivalents of potassium carbonate and five equivalents of N(2-bromoethyl)phthalamide were added and the mixture heated at 75° C. in a pressure tube overnight. The reaction mixture was diluted with ethyl acetate, washed three times with water, once with brine, dried with MgSO$_4$, filtered and evaporated to dryness. Purification by flash chromatography (hexane to 95:5 DCM/MeOH) yielded 1.08 g of compound 317.

To 30 mg of compound 317 in 2 mL of dichloromethane was added 300 µL of hydrazine and the mixture stirred under nitrogen overnight. The reaction mixture was then washed three times with water and then extracted with 1N aqueous HCl. The acidic aqueous phase washed three times with dichloromethane. The acidic aqueous phase was made basic with aqueous potassium carbonate then extracted three times with dichloromethane. The basic extracts were combined, dried with MgSO$_4$, filtered and evaporated to dryness yielding 5 mg of 318.

MS: 447.2 (MH$^+$)

Preparation of 319:

To 40 mg of 318 in 2 mL of dichloromethane and 2 mL of aqueous potassium carbonate was added five equivalents of acetyl chloride and the mixture stirred under nitrogen. After three hours the phases were separated and the aqueous phase extracted twice with dichloromethane. The combined organic phases were washed with brine, dried with MgSO$_4$, filtered and evaporated to dryness. The crude product was purified by reversed phase HPLC yielding 12 mg of 319.

MS: 489.3 (MH$^+$)

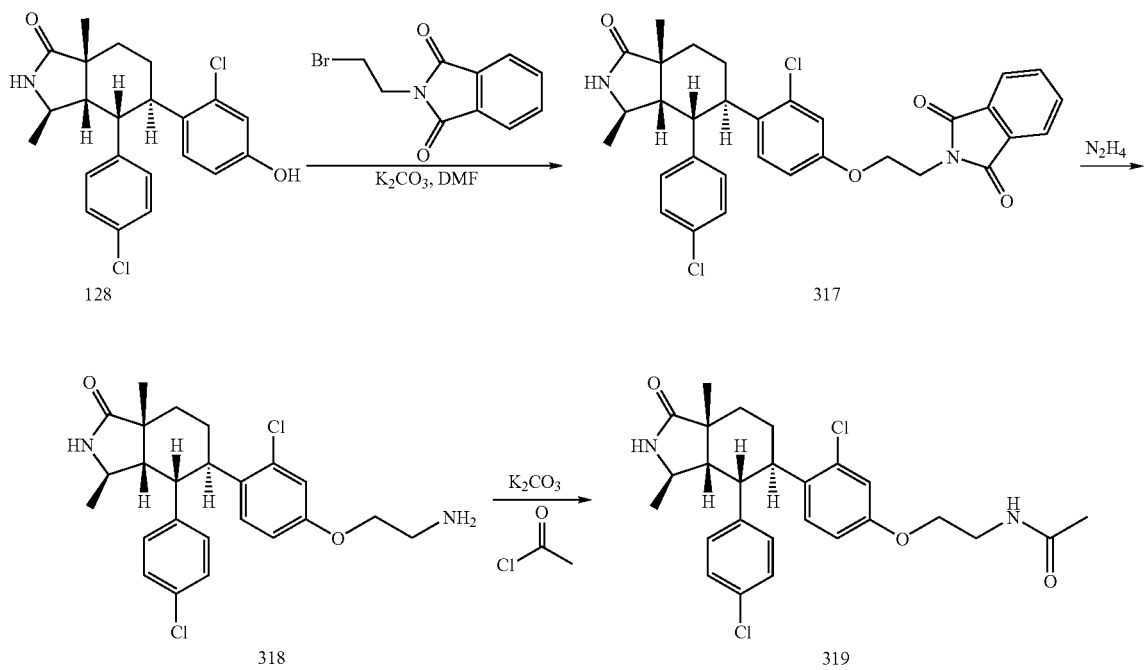

Compounds 320-326 were similarly prepared.
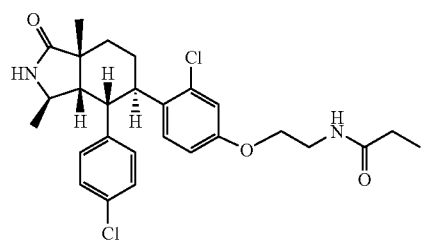
MS:503.3 (MH+)
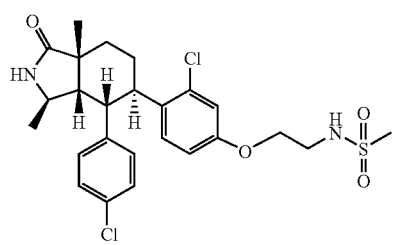
MS:525.3 (MH+)
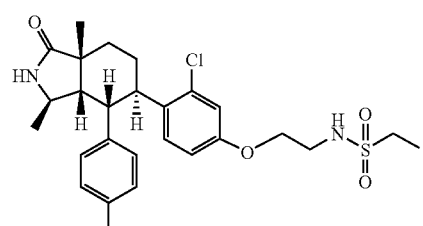
MS:539.3 (MH+)
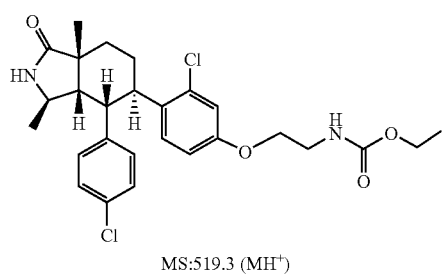
MS:519.3 (MH+)
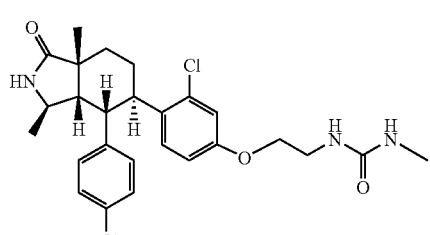
MS:504.3 (MH+)
320
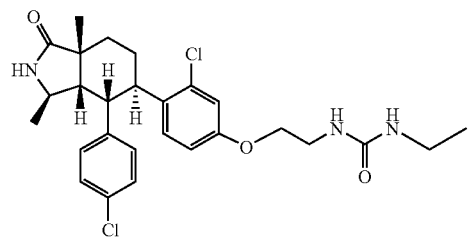
MS:518.3 (MH+)
321
326
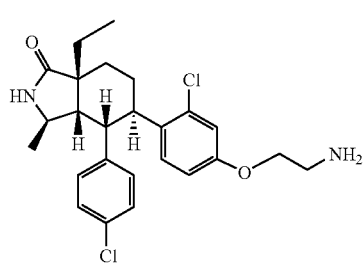
MS:461.3 (MH+)
322
Scheme 142:
Using procedures similar to those described under scheme 73 and scheme 109, compound 124 was converted to compounds 327-334.
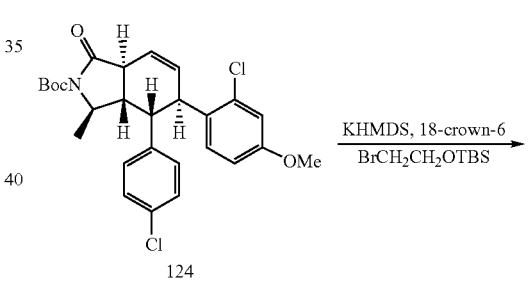
124
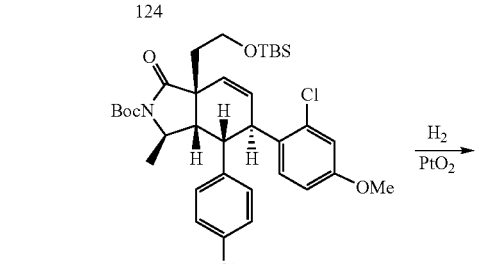
327
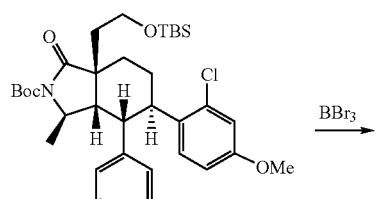
MS:662.4 (MH+)
328

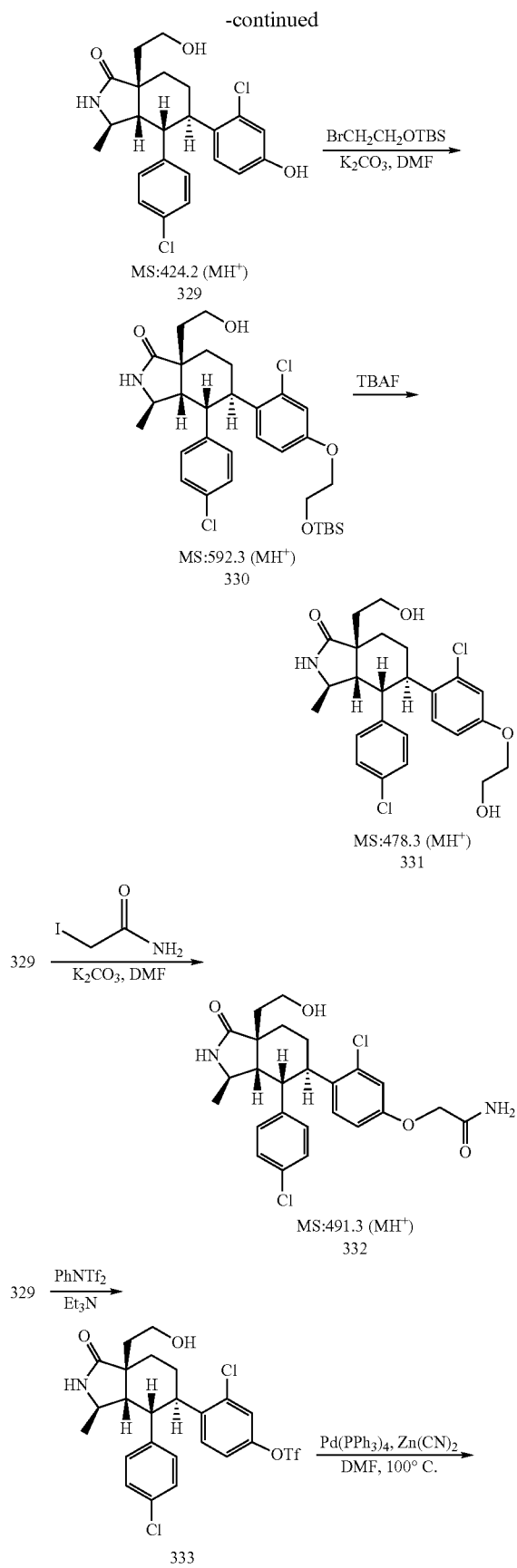
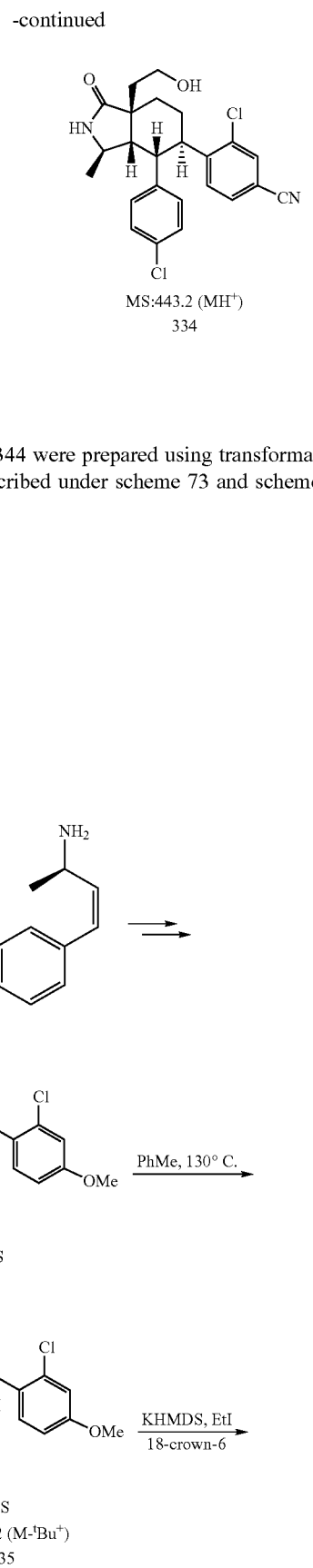
Scheme 143:
Compounds 335 to 344 were prepared using transformations similar those described under scheme 73 and scheme 109.

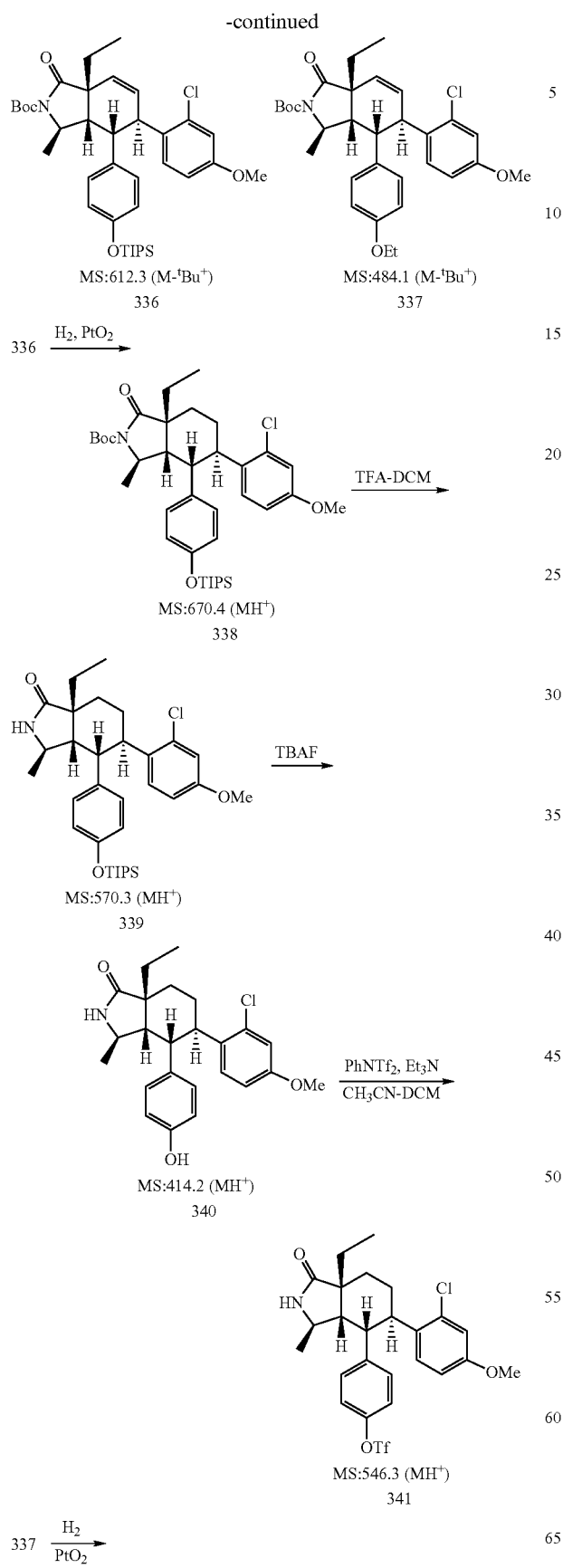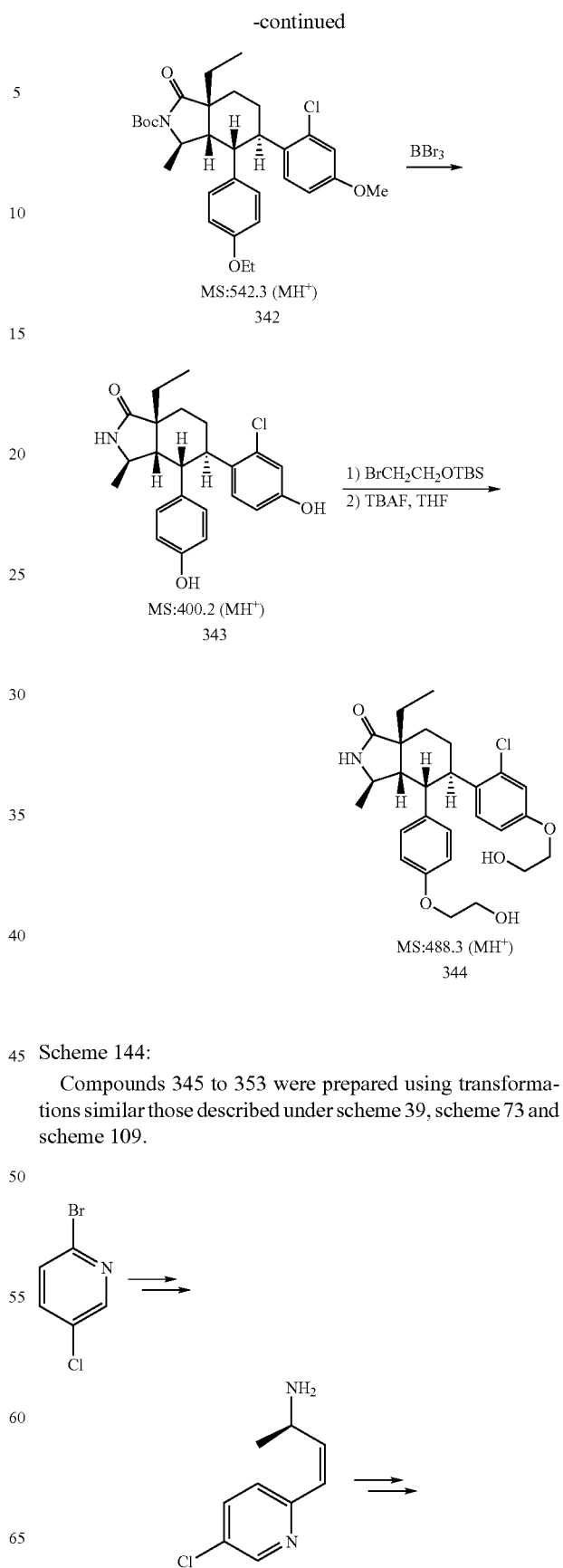
Scheme 144:
Compounds 345 to 353 were prepared using transformations similar those described under scheme 39, scheme 73 and scheme 109.
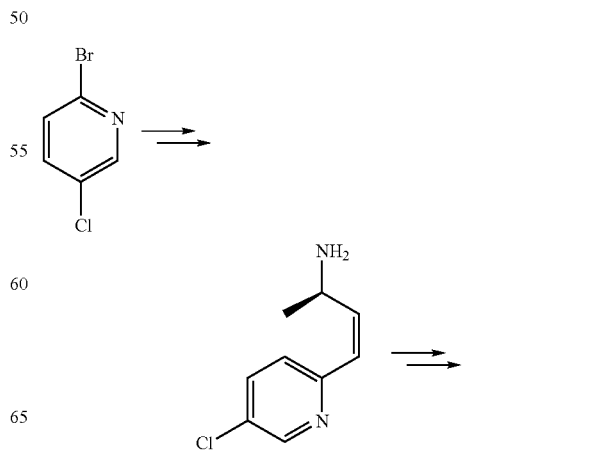

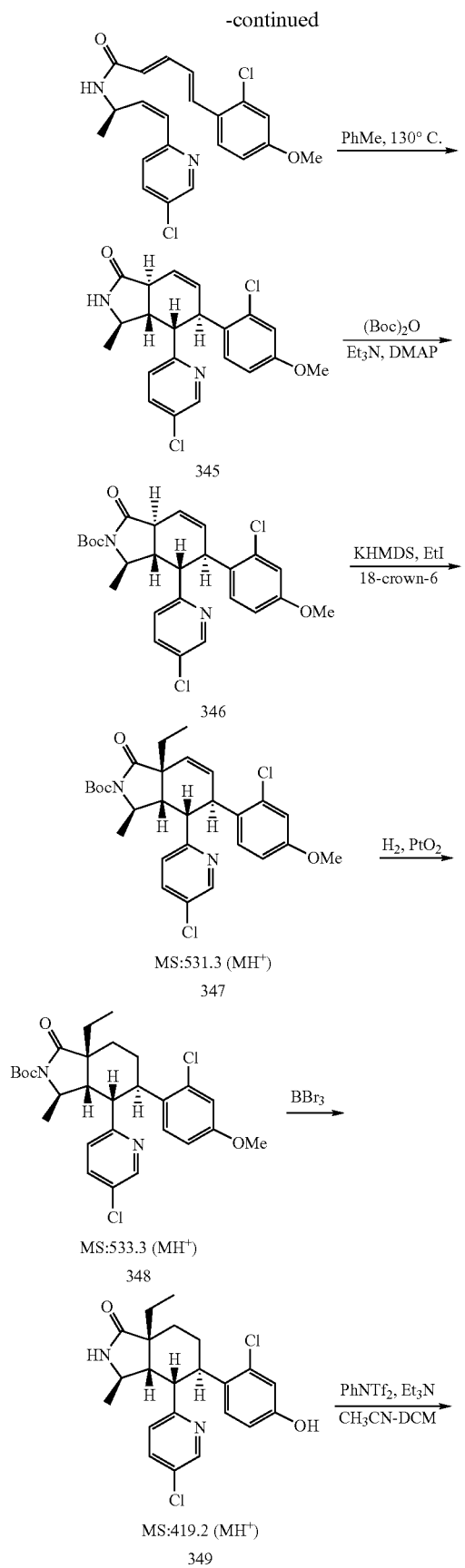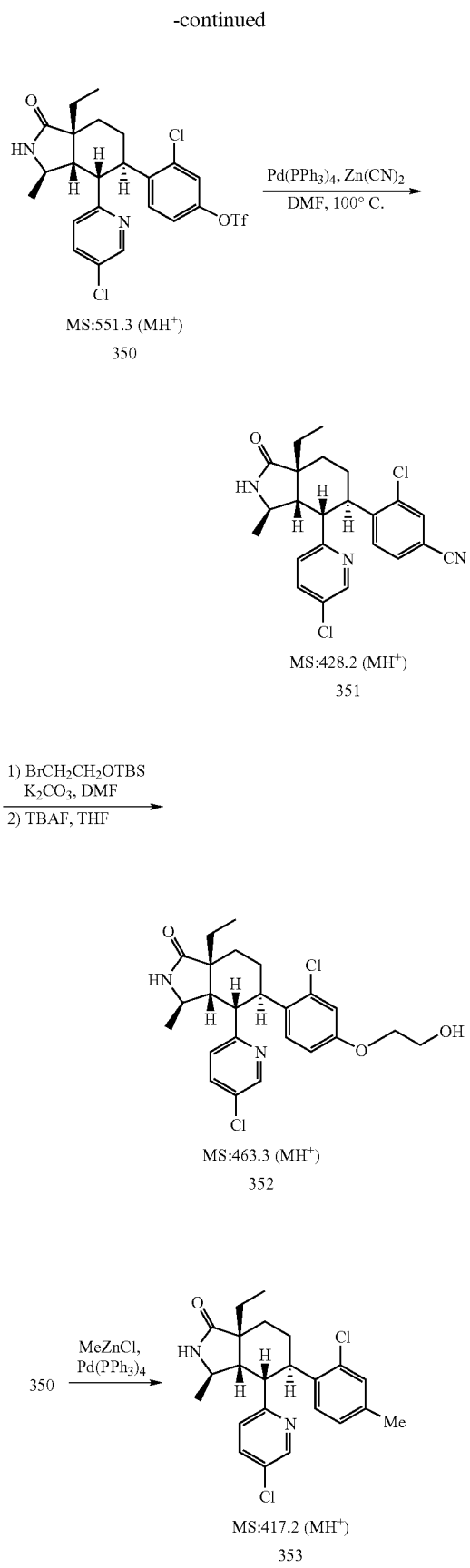

Similarly, the following compounds were prepared:

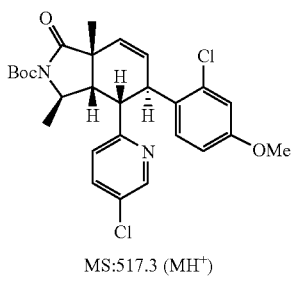

MS:517.3 (MH+)

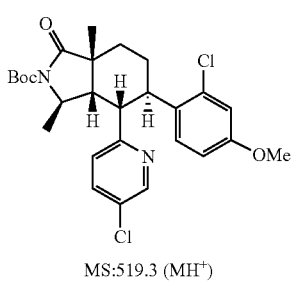

MS:519.3 (MH+)

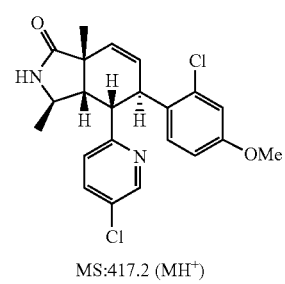

MS:417.2 (MH+)

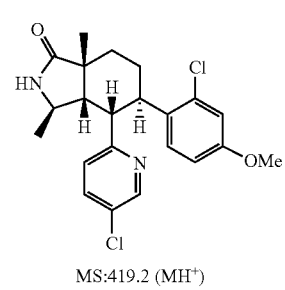

MS:419.2 (MH+)

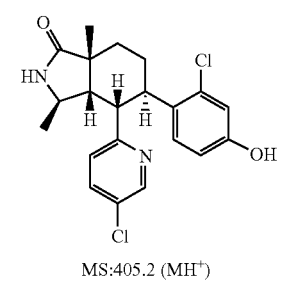

MS:405.2 (MH+)

-continued

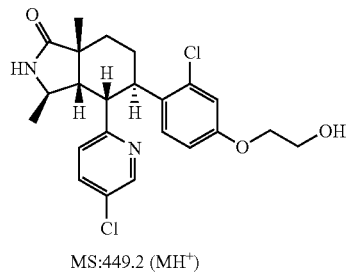

MS:449.2 (MH+)

Scheme 145:

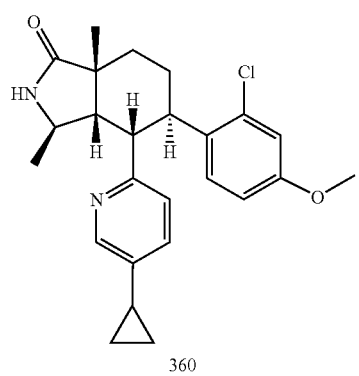

To 30 mg of 357 in 1 mL of toluene was added 50 µL of water, 1.3 equivalents of cyclopropane boronic acid, 10% mole of tricyclohexyl phosphine and 5% mole of palladium acetate. After bubbling with argon for 2 minutes the mixture was heated to 100° C. in a pressure tube. After heating overnight an additional 10% mole of tricyclohexyl phosphine and 5% mole of palladium acetate were added and the temperature was raised to 120° C. After a further 16 hours the reaction mixture was poured onto water and extracted three times with ethyl acetate. The combined organic phases were washed with brine, dried with MgSO4, filtered and evaporated to dryness. Purification by flash chromatography (045% ethyl acetate in hexane) yielded 22 mg of 360.

MS: 425.2 (MH+)

Scheme 146:

Compounds 361 to 370 were prepared using transformations similar those described under general scheme A, scheme 29, scheme 39, scheme 73 and scheme 109.

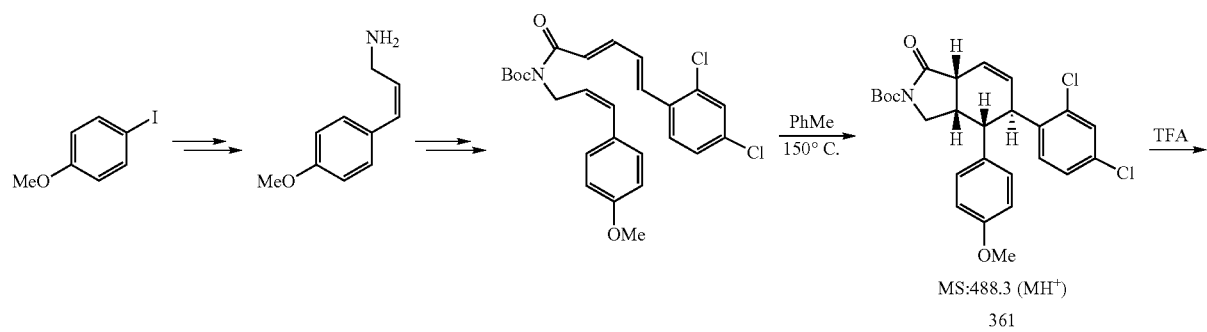
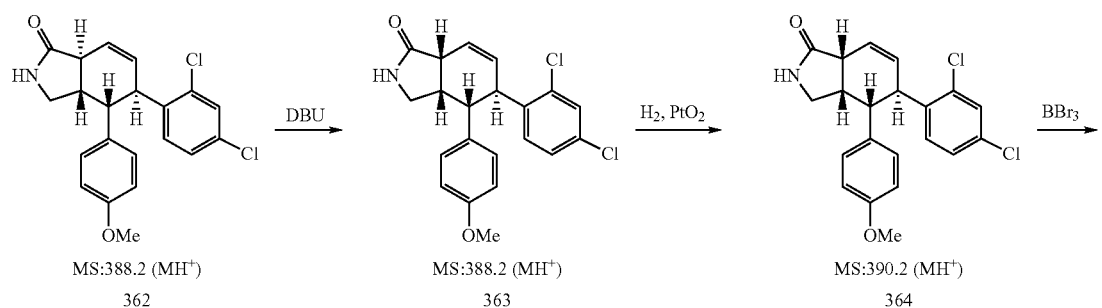
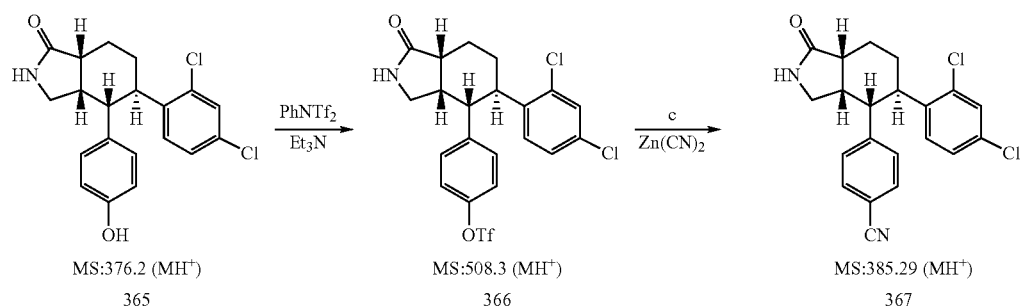
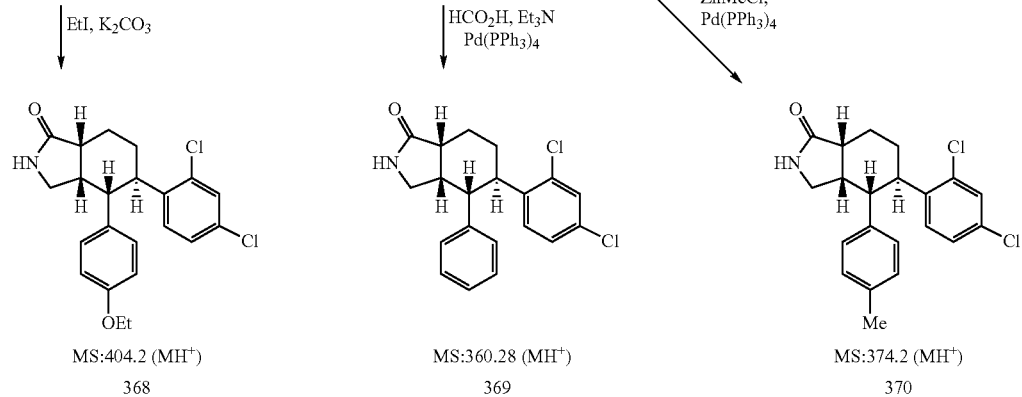

Scheme 147:

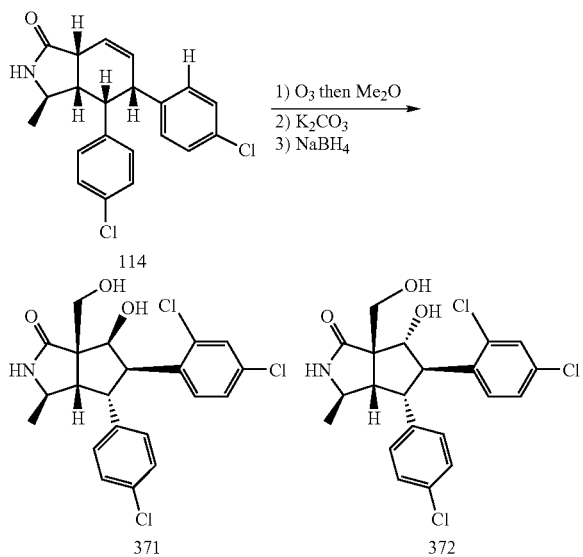

A solution of 114 (2.6 g, 6.39 mmol) in 50 ml of 1:1 v/v dichloromethane-methanol solution at −78° C. was bubbled with ozone until the blue color persisted. To excess ozone was bubbled off with nitrogen and 3 ml of dimethyl sulfide was added and stirred for 20 min at −78° C. and 30 min. at 0° C. To this mixture was added 3.5 g of $K_2CO_3$ and stirred for 1.5 hr at rt. The mixture was diluted with water, extracted 3× with ethyl acetate, the combined organic layers washed with brine, dried over $MgSO_4$, filtered and evaporated to give the crude aldehyde. This was dissolved in 30 ml of 2:1 v/v methanol-dichloromethane, cooled 0° C. and 240 mg of $NaBH_4$ was added. The mixture was stirred for 10 min then quenched with aq. $NH_4Cl$. The slurry was extracted 3× with ethyl acetate, combined organic layers washed with brine, dried over $MgSO_4$, filtered and evaporated to give the crude product. The crude product was stored as an ether solution in the refrigerator and the precipitated solids were filtered off to give 1.07 g of 371. The filtrate was concentrated and chromatographed with 0% to 5% methanol in dichloromethane to provide 0.65 g of 372.

MS for 371: 440.2 ($MH^+$)

MS for 372: 440.2 ($MH^+$)

Scheme 148:

Preparation of 380

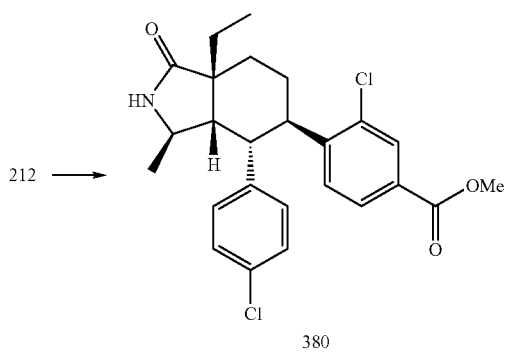

Compound 212 (860 mg, 0.000156 mol) was dissolved in DMF/MeOH (17 mL, 1.58 mL), dppp (65 mg, 10 mol %), $Pd(OAc)_2$ (35 mg, 10 mol %), and $Et_3N$ 0.463 mL, 2 eq) were added. The mixture was put under an atmosphere of CO and heated at 70° C. for 16 hours. The mixture was cooled to rt and $NH_4Cl_{(sat)}$ was added, the resulting mixture was extracted with EtOAc (×3), and the combined extracts were washed with water, dried ($MgSO_4$), and concentrated. The residue was purified by silica gel chromatography (1:3-3:1 EtOAc/Hexanes) to give 675 mg of the title compound. LCMS: 460.3 ($MH^+$)

Scheme 149:

Preparation of 381

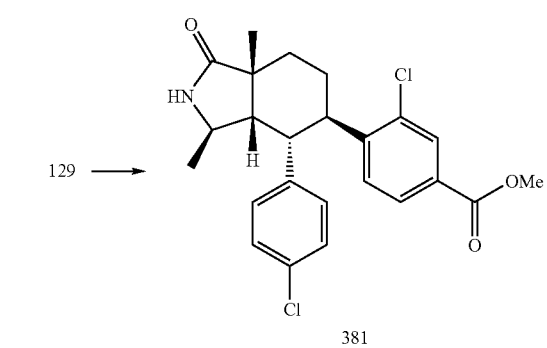

Compound 381 was prepared from compound 129 using a procedure similar to the procedure used for the preparation of 380. LCMS: 446.2 ($MH^+$)

Scheme 150:

Preparation of 382

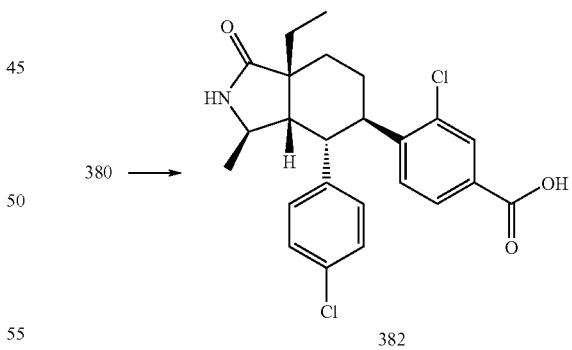

Compound 380, 675 mg (0.00147 mol) was dissolved in MeOH/THF (5.6 mL/5.6 mL), NaOH (3.37 mL of a 1 M solution) was added and the mixture stirred overnight. The organic solvents were removed under reduced pressure and the remaining solution diluted with water, after the mixture was acidified to PH2 the resulting solid was collected by filtration to give 573 mg of the title compound. LCMS: 446.2 ($MH^+$).

Scheme 151:

Preparation of 383

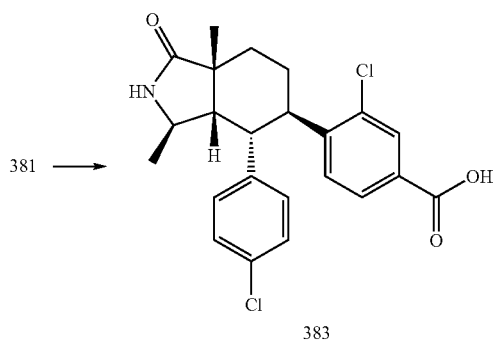

383

Compound 383 was prepared from compound 381 using a procedure similar to the procedure used for the preparation of 382. LCMS: 446.2 (MH+)

Scheme 152:

Preparation of 384

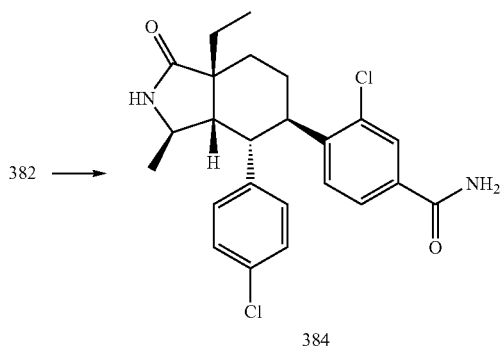

384

Compound 382 (50 mg, 0.112 mmol) was dissolved in DMF (2 mL), DIPEA (94 μL, 5 eq) and HATU (110 mg, 2.5 eq) was added. The mixture was stirred for 5 hours, diluted with EtOAc and washed with NH$_4$Cl$_{(sat)}$. The organic layer was dried over MgSO$_4$, concentrated under reduced pressure and purified by reverse phase HPLC, C18 (10:90:0.5 to 90:10: 0.5 MeCN/H$_2$O/HCO$_2$H) to give 36 mg of the title compound. LCMS: 445.2 (MH+).

Scheme 153:

Preparation of 385A-385AAA

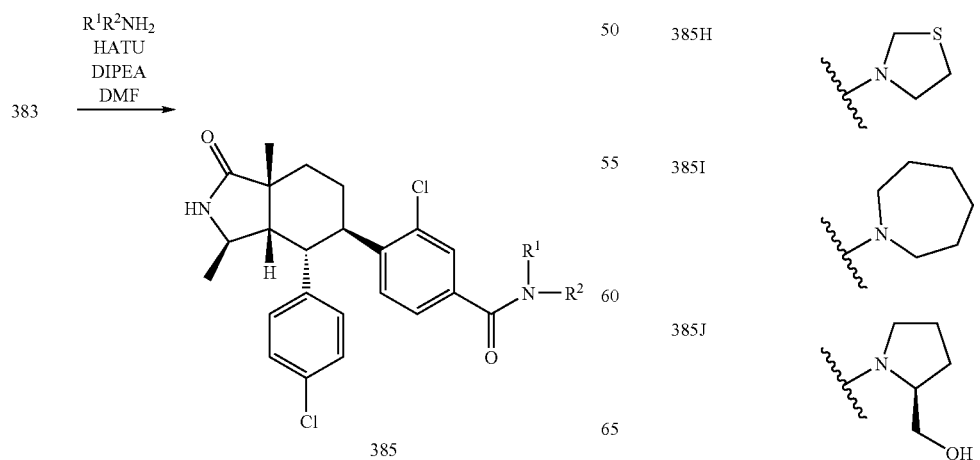

385

The following compounds were synthesized from compound 383 and the appropriate amine/amine hydrochloride using a procedure similar to the procedure used for the preparation of 384.

| Compound No | R$^1$/R$^2$ amine | LCMS MH+ |
|---|---|---|
| 385A | pyrrolidine | 485.3 |
| 385B | indoline | 533.3 |
| 385C | isoindoline | 533.3 |
| 385D | 4-hydroxypiperidine | 515.3 |
| 385E | piperidine | 499.3 |
| 385F | 3-hydroxypyrrolidine | 501.3 |
| 385G | morpholine | 501.3 |
| 385H | thiazolidine | 503.3 |
| 385I | azepane | 513.3 |
| 385J | 2-(hydroxymethyl)pyrrolidine | 515.3 |

-continued
| Compound No | 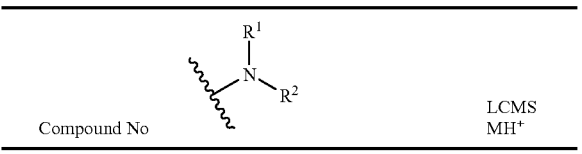 | LCMS MH+ |
|---|---|---|
| 385K | 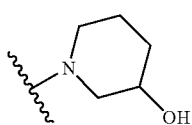 | 515.3 |
| 385L | 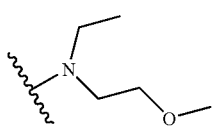 | 517.3 |
| 385M | 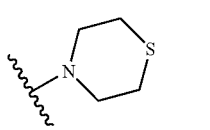 | 517.3 |
| 385N | 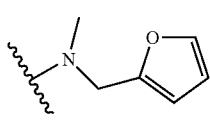 | 525.3 |
| 385O | 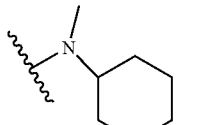 | 527.3 |
| 385P | 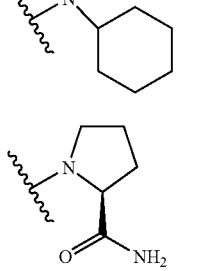 | 528.3 |
| 385Q | 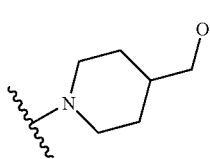 | 529.3 |
| 385R | 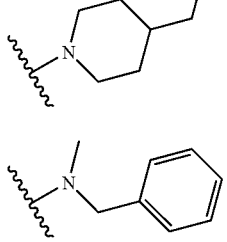 | 535.3 |
| 385S | 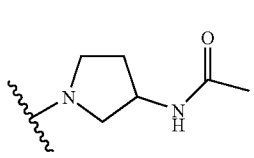 | 542.3 |
| 385T | 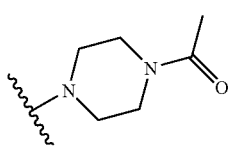 | 542.3 |
-continued
| Compound No | 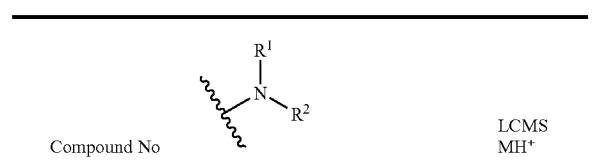 | LCMS MH+ |
|---|---|---|
| 385U | 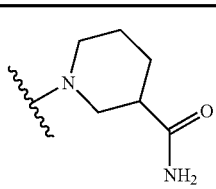 | 542.3 |
| 385V | 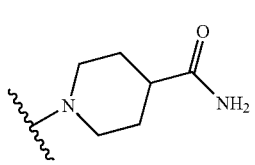 | 542.3 |
| 385W | 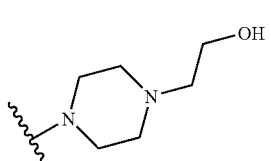 | 544.3 |
| 385X | 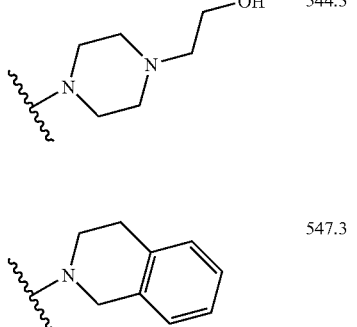 | 547.3 |
| 385Y | 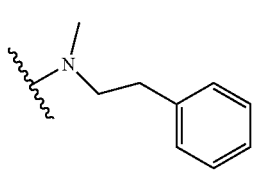 | 549.3 |
| 385Z | 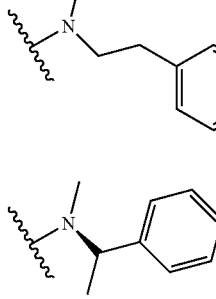 | 549.3 |
| 385AA | 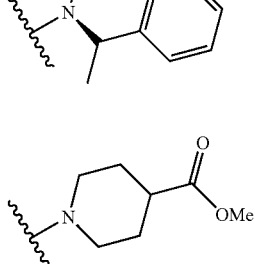 | 557.3 |
| 385BB | 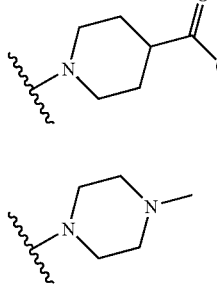 | 514.3 |

-continued
| Compound No | 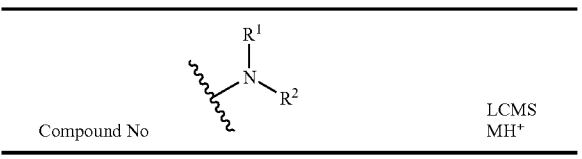 | LCMS MH+ |
|---|---|---|
| 385CC | 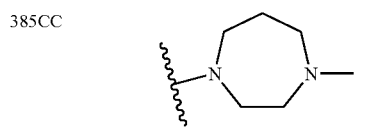 | 528.3 |
| 385DD | 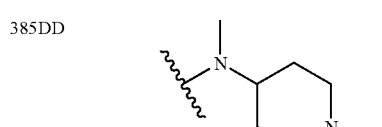 | 542.3 |
| 385EE | 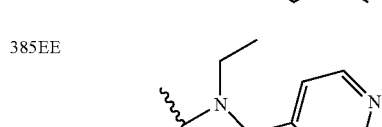 | 550.3 |
| 385FF | 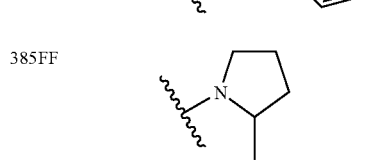 | 499.3 |
| 385GG | 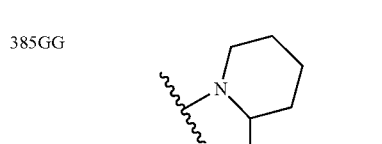 | 513.3 |
| 385HH | 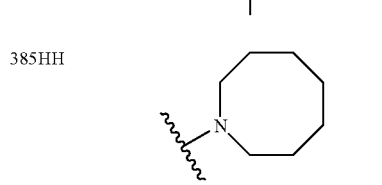 | 527.3 |
| 385II | 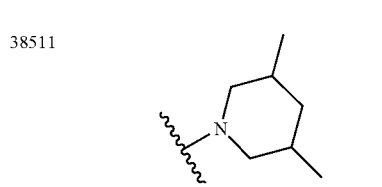 | 527.3 |
| 385JJ | 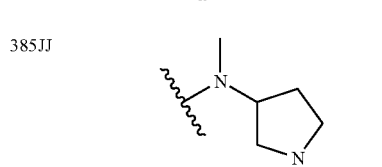 | 528.3 |
| 385KK | 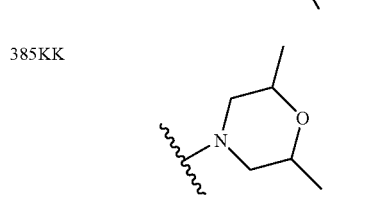 | 529.3 |
-continued
| Compound No | 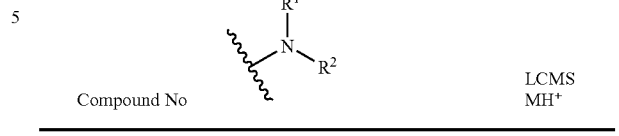 | LCMS MH+ |
|---|---|---|
| 385LL | 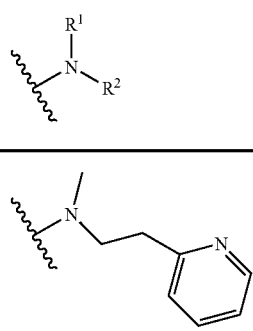 | 550.3 |
| 385MM | 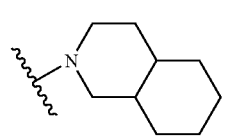 | 553.3 |
| 385NN | 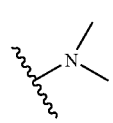 | 459.3 |
| 385OO | 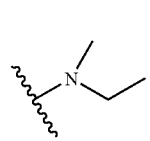 | 473.3 |
| 385PP | 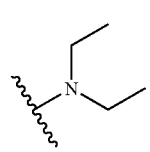 | 487.3 |
| 385QQ | 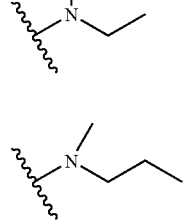 | 487.3 |
| 385RR | 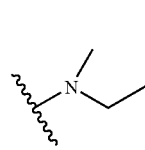 | 487.3 |
| 385SS | 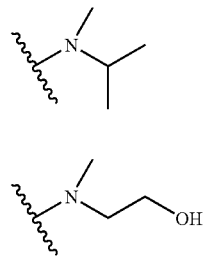 | 489.3 |
| 385TT | 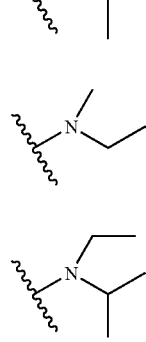 | 501.3 |

413

-continued

| Compound No | R¹ N R² | LCMS MH⁺ |
|---|---|---|
| 385UU | N-ethyl, N-(2-hydroxyethyl) | 503.3 |
| 385VV | N-propyl, N-(cyclopropylmethyl) | 527.3 |
| 385WW | N,N-dibutyl | 543.3 |
| 385XX | N-methyl, N-(1-phenylethyl) | 549.3 |
| 385YY | NH-(2-hydroxyethyl) | 475.3 |
| 385ZZ | 2-(hydroxymethyl)pyrrolidinyl | 515.3 |
| 385AAA | NH₂ | 431.2 |

Scheme 154:

Compounds 386A-386I

The following compounds were synthesized from compound 382 and the appropriate amine/amine hydrochloride using a procedure similar to the procedure used for the preparation of 384.

414

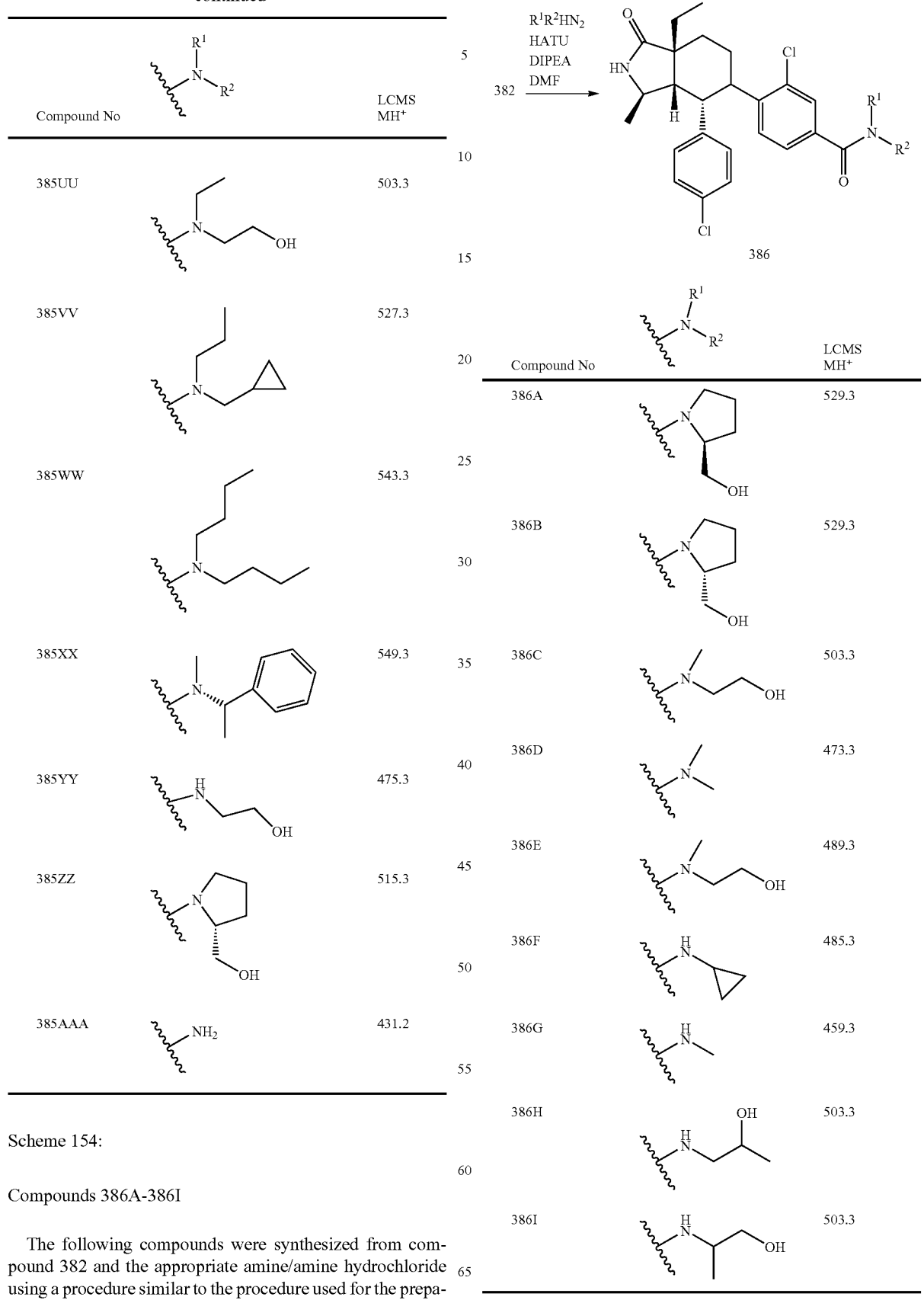

| Compound No | R¹ N R² | LCMS MH⁺ |
|---|---|---|
| 386A | 2-(hydroxymethyl)pyrrolidinyl | 529.3 |
| 386B | 2-(hydroxymethyl)pyrrolidinyl | 529.3 |
| 386C | N-methyl, N-(2-hydroxyethyl) | 503.3 |
| 386D | N,N-dimethyl | 473.3 |
| 386E | N-methyl, N-(2-hydroxyethyl) | 489.3 |
| 386F | NH-cyclopropyl | 485.3 |
| 386G | NH-methyl | 459.3 |
| 386H | NH-(2-hydroxypropyl) | 503.3 |
| 386I | NH-(1-hydroxypropan-2-yl) | 503.3 |

Scheme 155:

Preparation of 387

382 →

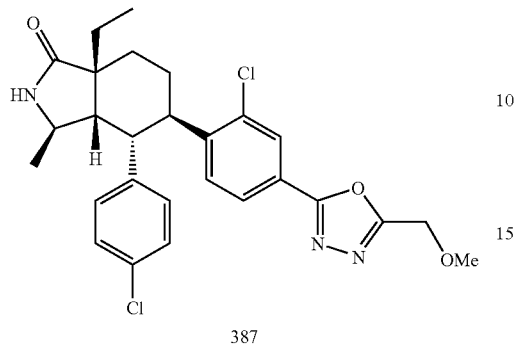

387

Compound 382 (25 mg, 0.056 mmol) was dissolved in DMF (1 mL), DIPEA (23 µL, 2.5 eq), methoxyacetic acid hydrazide (14.5 mg, 2.5 eq) then HATU (53 mg, 2.5 eq) were added. The mixture was stirred for 3 hours and then diluted with EtOAc. The mixture washed with $NH_4Cl_{(sat)}$, dried, concentrated, and dissolved in THF (3 mL). 2-tert-Butyl-imino-2-diethylamino-1,3-dimethyl-perhydro-1,3,2-diaza-phosphorine on polystyrene (PS-BEMP) (140 mg, 5 eq, 2.2 mmol base/g) and TsCl (13.5 mg, 1.2 eq) were added, the resulting mixture was heated at 120° C. for 15 minutes via microwave. Once the mixture was cooled to room temperature the mixture was filtered, concentrated, and purified by reverse phase HPLC, C18 (10:90:0.5 to 90:10:0.5 MeCN/$H_2O$/$HCO_2H$) to give 17 mg of the title compound. LCMS: 514.3 (MH$^+$).

Scheme 156:

Preparation of 388A-388D

The following compounds were synthesized from compound 382 using a procedure similar to the procedure used for the preparation of 387 substituting the appropriate carboxylic acid hydrazide.

382 →

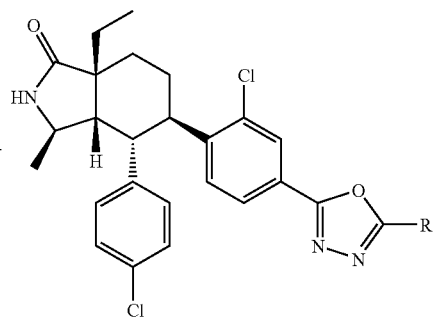

388

| Compound No | 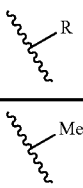 | LCMS MH$^+$ |
|---|---|---|
| 388A | Me | 484.3 |

382 →

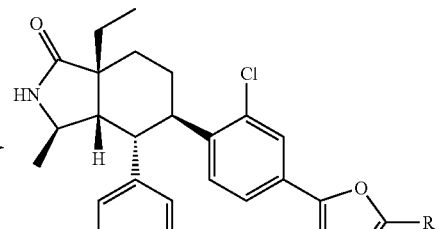

388

| Compound No | R | LCMS MH$^+$ |
|---|---|---|
| 388B | 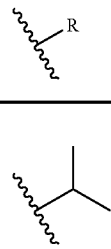 | 512.3 |
| 388C | 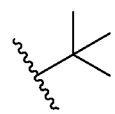 | 526.3 |
| 388D | 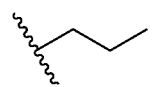 | 512.3 |
| 388E | 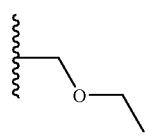 | 528.3 |
| 388F | 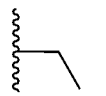 | 498.3 |
| 388G | 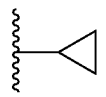 | 510.3 |
| 388H | 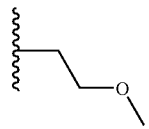 | 528.3 |

Scheme 157:

Preparation of 389A-389B

The following compounds were synthesized from compound 383 using a procedure similar to the procedure used for the preparation of 387 using the appropriate carboxylic acid hydrazide.

417

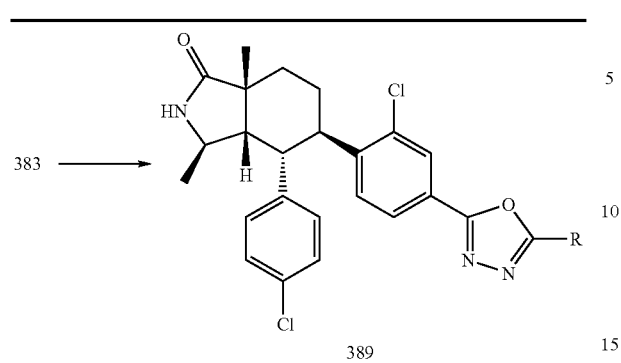

383 →

389

| Compound No | R | LCMS MH+ |
|---|---|---|
| 389A | Me | 470.3 |
| 389B | OMe | 500.3 |

Scheme 158:

Preparation of 390

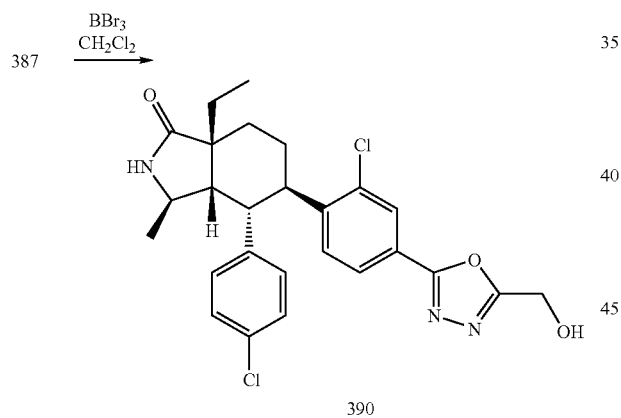

387 →(BBr₃, CH₂Cl₂)→ 390

Compound 387 (55 mg, 0.107 mmol) was dissolved in CH₂Cl₂ and cooled in an ice-water bath. BBr₃ (45 μL, 4.5 eq) was added and the mixture stirred for 4 hours. Water was added slowly and the resulting mixture stirred for 15 minutes. The mixture was extracted with EtOAc, washed with brine, concentrated, and purified by reverse phase HPLC, C18 (10: 90:0.5 to 90:10:0.5 MeCN/H₂O/HCO₂H) to give 25 mg of the title compound. LCMS: 500.3 (MH⁺).

Scheme 159:

Preparation of 391

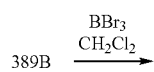

389B →(BBr₃, CH₂Cl₂)→

418

-continued

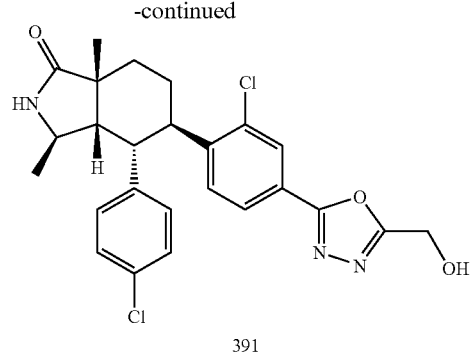

391

Compound 391 was synthesized from compound 389B using a procedure similar to the procedure used for the preparation of 390. LCMS: 486.3 (MH⁺).

Scheme 160:

Preparation of 392

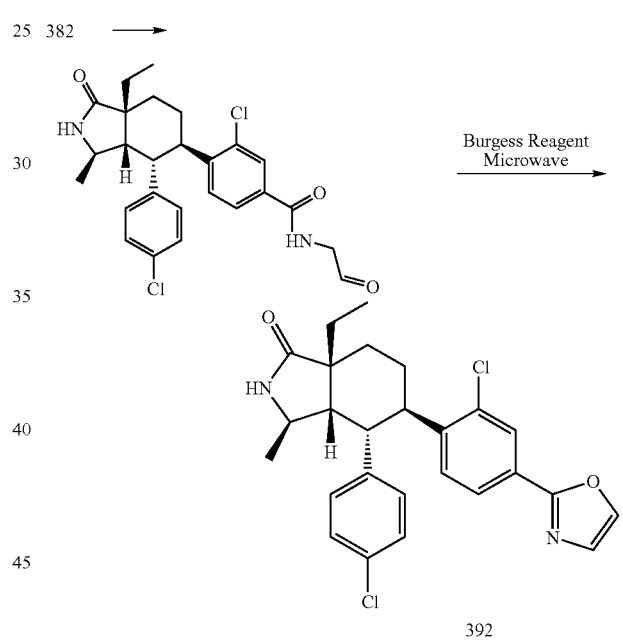

382 → → (Burgess Reagent, Microwave) → 392

Step 1

Compound 382 (50 mg, 0.112 mmol) was dissolved in DMF (1 mL), DIPEA (55 μL, 3 eq), aminoethanal dimethyl acetal (37 μg, 3 eq) then HATU (128 mg, 3 eq) were added. The mixture was stirred for 4 hours and then diluted with EtOAc. The mixture washed with NH₄Cl₍sat₎, dried (MgSO₄), concentrated, and dissolved in THF/1M HCl (3 mL/3 mL). The mixture was stirred for 4 hours then diluted with EtOAc. The mixture washed with NaHCO₃₍sat₎ dried (MgSO₄), and concentrated to give 50 mg of product.

Step 2

The product of step 1 (50 mg, 0.0113 mmol) was dissolved in THF (3 mL), Burgess reagent (54 mg, 2 eq) was added and the mixture heated in the microwave for 15 minutes at 120° C. The mixture was concentrated and purified by reverse phase HPLC, C18 (10:90:0.5 to 90:10:0.5 MeCN/H₂O/HCO₂H) to give 5 mg of the title compound. LCMS: 469.3 (MH⁺).

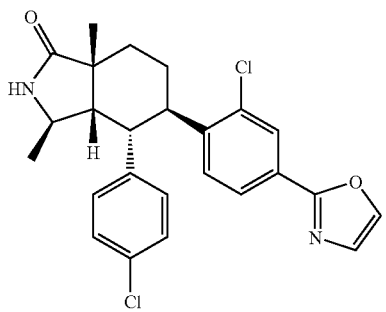

393

Compound 393 was synthesized from compound 383 using a procedure similar to the procedure used for the preparation of 392. LCMS: 455.3 (MH$^+$).

Scheme 161:

Preparation of 394

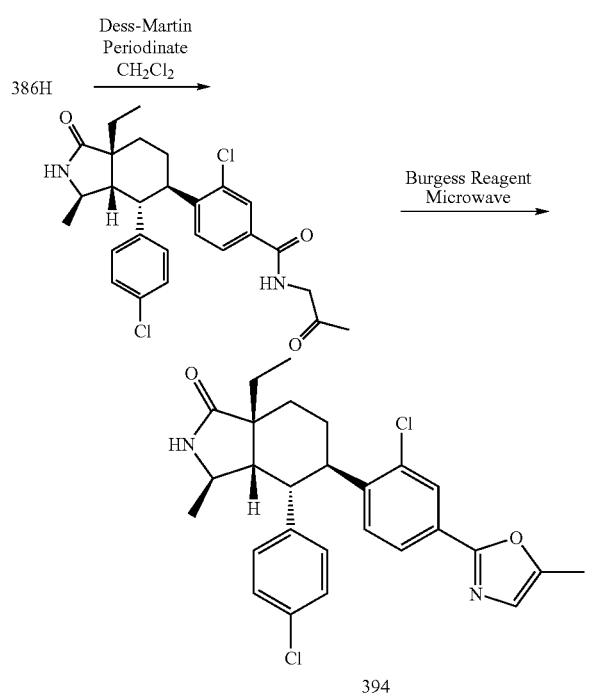

394

Step 1

Compound 386H (80 mg, 0.165 mmol) was dissolved in CH$_2$Cl$_2$, Dess-Martin Periodinate (88 mg) was added and the mixture stirred for 1 hour. EtOAc was added followed by NaHCO$_{3(sat)}$ and sodium thiosulphate$_{(sat)}$, the mixture was stirred for 1 hour and the organic layer collected, dried (MgSO$_4$), and concentrated to give 74 mg of product.

Step 2

The product of step 1 (74 mg, 0.0147 mmol) was dissolved in THF (3 mL), Burgess reagent (65 mg, 2 eq) was added and the mixture heated in the microwave for 15 minutes at 120° C. The mixture was concentrated and purified by reverse phase HPLC, C18 (10:90:0.5 to 90:10:0.5 MeCN/H$_2$O/HCO$_2$H) to give 7 mg of the title compound. LCMS: 484.3 (MH$^+$).

Scheme 162:

Preparation of 395

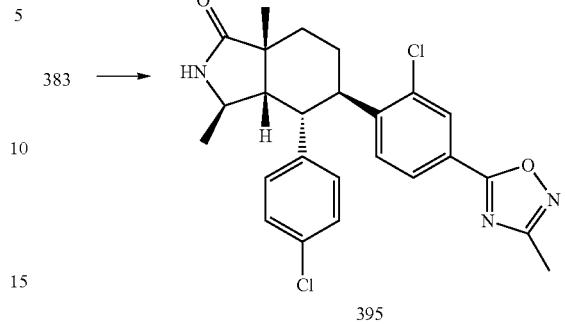

395

Compound 383 (55 mg, 0.127 mmol) was dissolved in DMF (2.5 mL), DIPEA (55 µL, 2.5 eq), acetamide oxime (24 mg, 2.5 eq) and HATU (121 mg, 2.5 eq) were added. The mixture was stirred at rt for 3 hours and then heated at 191° C. via microwave for 4 minutes. After cooling to rt the mixture was diluted with EtOAc, washed with NH$_4$Cl$_{(sat)}$, dried (MgSO$_4$), and concentrated. The residue was purified by reverse phase HPLC, C18 (10:90:0.5 to 90:10:0.5 MeCN/H$_2$O/HCO$_2$H) to give 17 mg of the title compound. LCMS: 470.3 (MH$^+$).

Scheme 163:

Preparation of 396

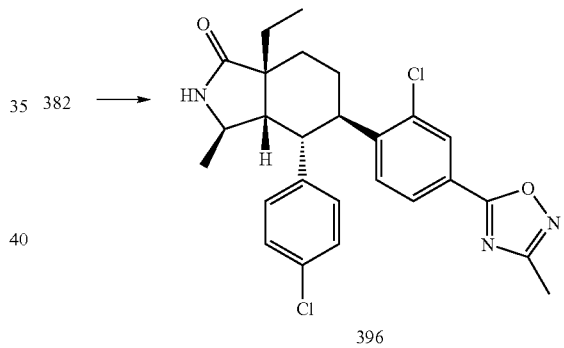

396

Compound 396 was synthesized from compound 382 using a procedure similar to the procedure used for the preparation of 395. LCMS: 484.3 (MH$^+$).

Scheme 164:

Preparation of 397

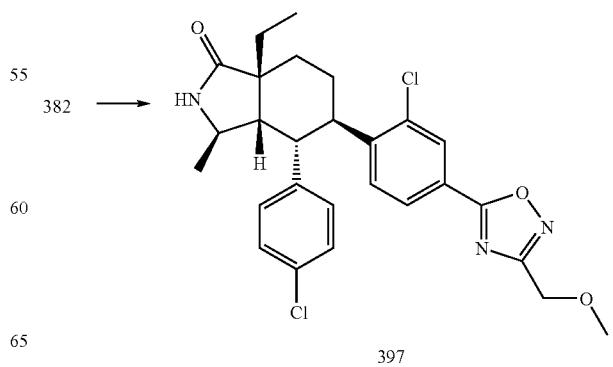

397

Compound 397 was synthesized from compound 382 using a procedure similar to the procedure used for the preparation of 395 substituting N-hydroxy-2-methoxyacetamidine in place of acetamide oxime. LCMS: 514.3 (MH+).

Scheme 165:

Preparation of 398

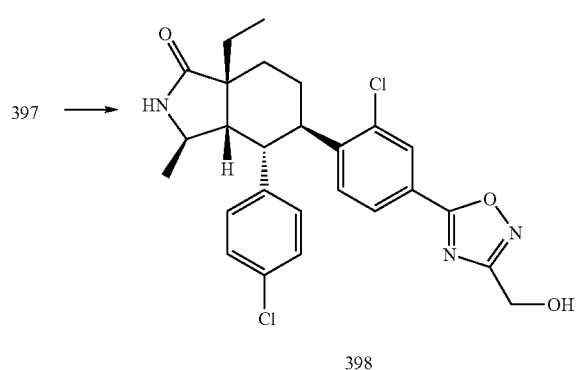

398

Compound 398 was synthesized from compound 397 using a procedure similar to the procedure used for the preparation of 390. LCMS: 500.3 (MH+).

Scheme 166:

Preparation of 399

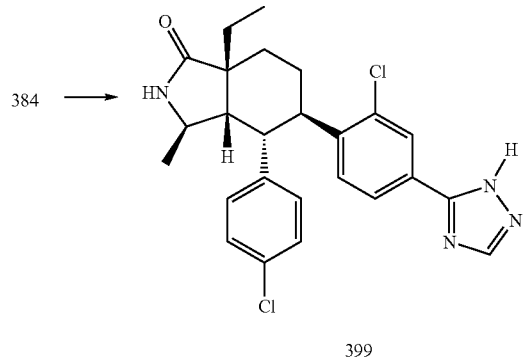

399

Compound 384 (55 mg, 0.123 mmol) was dissolved in N,N-dimethylformamide dimethyl acetal (2 mL) and heated at 120° C. for 1.5 hours. The excess reagent was removed under reduced pressure and the residue treated with hydrazine hydrate (7 µL, 1.1 eq) in acetic acid (1 mL) at 90° C. for 1.5 hours. The volatiles were removed under reduced pressure and the residue treated with NaHCO$_3$(sat), the mixture was extracted with EtOAc, dried (MgSO$_4$), concentrated, and purified by reverse phase HPLC, C18 (10:90:0.5 to 90:10:0.5 MeCN/H$_2$O/HCO$_2$H) to give 17 mg of the title compound. LCMS: 469.3 (MH+).

Scheme 167:

Preparation of 400

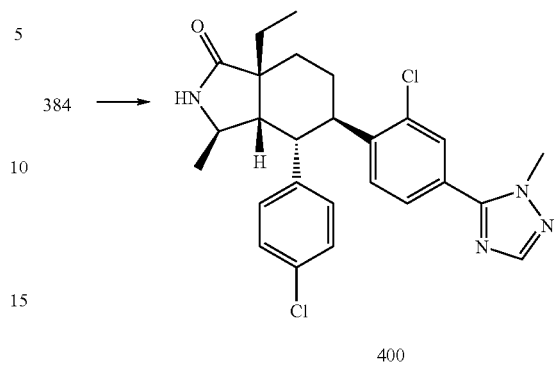

400

Compound 400 was synthesized from compound 384 using a procedure similar to the procedure used for the preparation of 399 by substituting methyl hydrazine for hydrazine hydrate. LCMS: 483.3 (MH+).

Scheme 168:

Preparation of 401

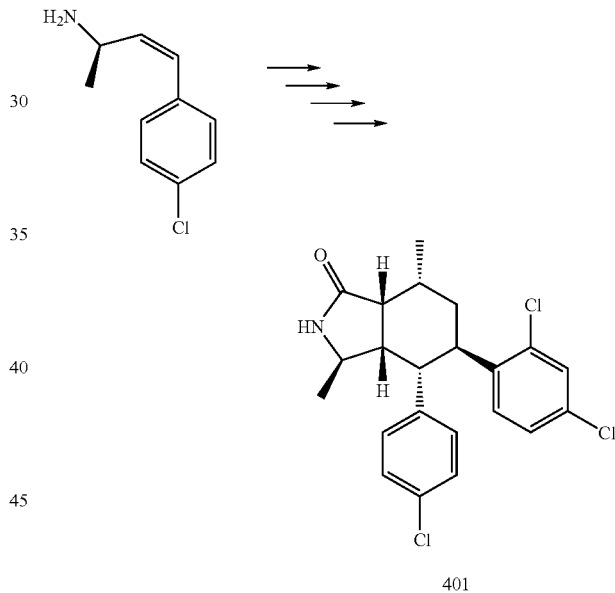

401

Compound 401 and was synthesized in an analogous manner to compound 153 substituting 3-(4-chlorophenyl)-1(R)-methylallylamine for 3-(4-chlorophenyl)allyl amine. LCMS: 422.2 (MH+).

Scheme 169:

Preparation of 402 and 403

Step 1

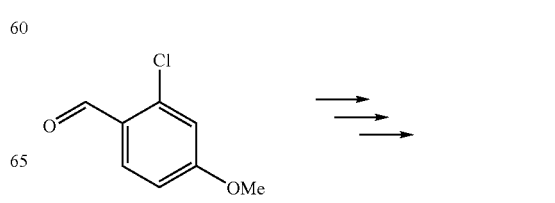

-continued

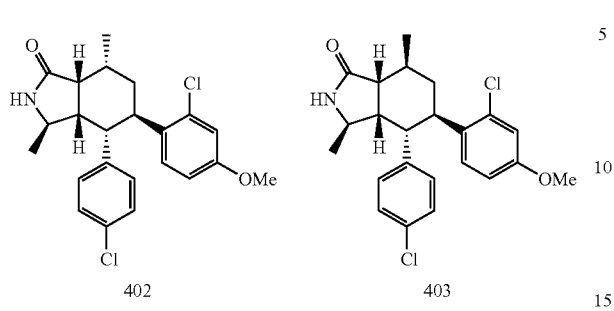

3-Chloro-4-bromoanisole (10 g, 0.045 mol) was dissolved in THF (200 mL) the mixture was cooled to −78° C. n-BuLi (18 mL of a 2.5 M solution in hexanes, 1 eq) was added over 5 minutes. After the resulting mixture was stirred at −78° C. for 30 minutes DMF (5.24 mL, 1.5 eq) was added. The mixture stirred for an additional 30 minutes then allowed to warm to rt. NH$_4$Cl$_{(sat)}$ was added and the mixture extracted with Ether. The combined extracts were washed with water, dried (MgSO$_4$), and concentrated to give the product of step 1.

Step 2

The product of step 1 was converted to compounds 402 and 403 using analogous procedures to those used for the synthesis of compounds 153 and 154 substituting 3-(4-chlorophenyl)-1(R)-methylallylamine for 3-(4-chlorophenyl)allyl amine. LCMS: 87a, 418.2 (MH$^+$), 88a, 418.2 (MH$^+$).

Scheme 170:

Preparation of 404

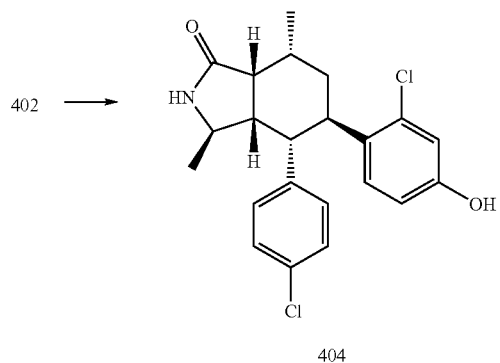

Compound 404 was prepared from compound 402 using a procedure similar to the procedure used for the preparation of 72. LCMS: 404.2 (MH$^+$)

Scheme 171:

Preparation of 405

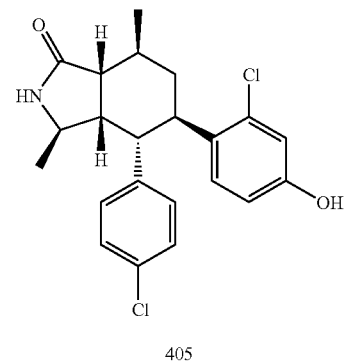

Compound 405 was prepared from compound 403 using a procedure similar to the procedure used for the preparation of 72. LCMS: 404.2 (MH$^+$)

Scheme 172:

Preparation of 406

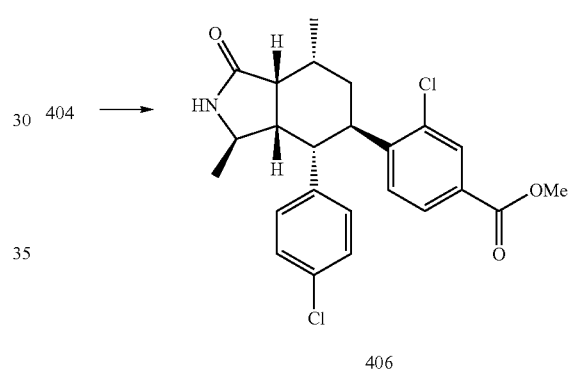

Compound 406 was prepared from compound 404 in two steps using the procedures described for compound 129 and compound 380. LCMS: 446.2 (MH$^+$)

Scheme 173:

Preparation of 407

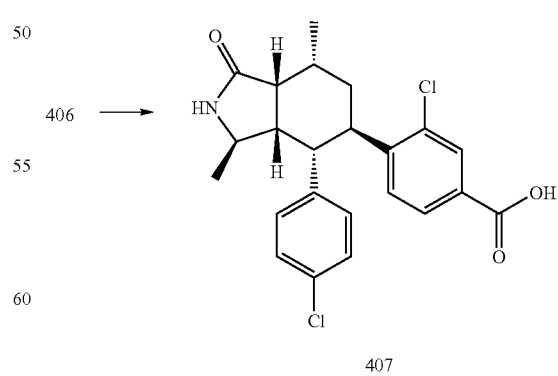

Compound 407 was prepared from compound 406 using a procedure similar to the procedure used for the preparation of 382. LCMS: 432.2 (MH$^+$)

Scheme 174:

Preparation of 408

404 →

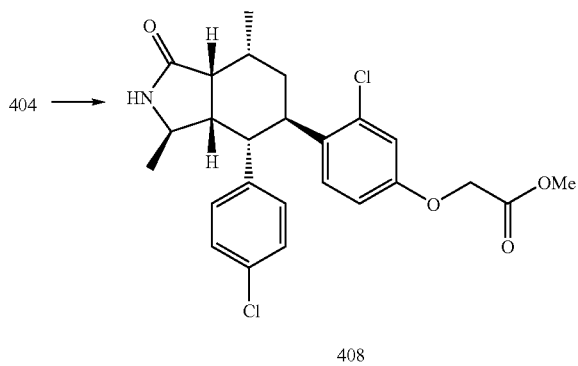

408

Compound 408 was prepared from compound 404 using a procedure similar to the procedure used for the preparation of 230. LCMS: 476.3 (MH+)

Scheme 175:

Preparation of 409

408 →

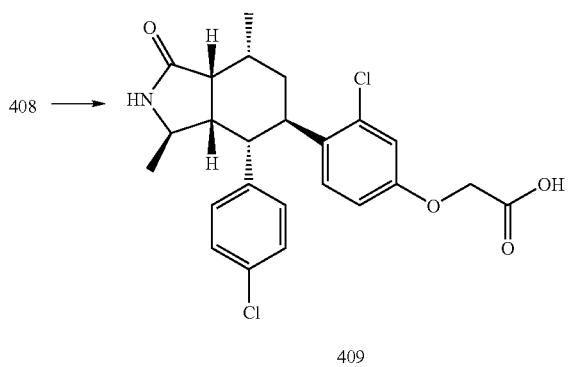

409

Compound 409 was prepared from compound 408 using procedures similar to the procedure used for the preparation of 231. LCMS: 462.3 (MH+)

Scheme 176:

Preparation of 410

404 →

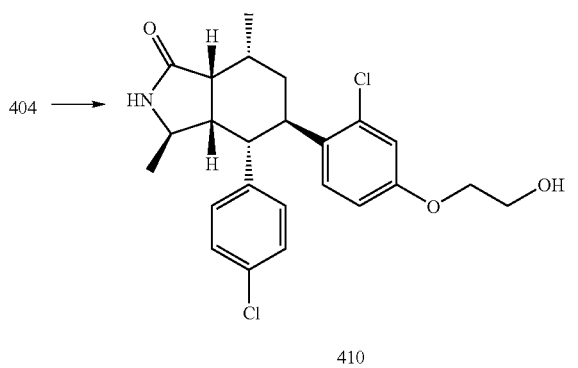

410

Compound 410 was prepared from compound 404 using procedures similar to the procedures used for the preparation of 221. LCMS: 448.2 (MH+)

Scheme 177:

Preparation of 411

404 →

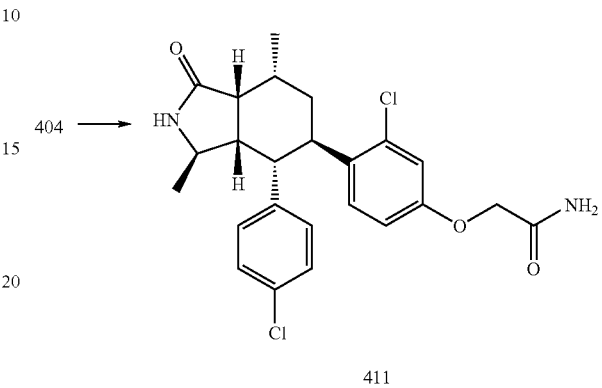

411

Compound 411 was prepared from compound 404 using a procedure similar to the procedure used for the preparation of 131. LCMS: 461.3 (MH+)

Scheme 178:

Preparation of 412

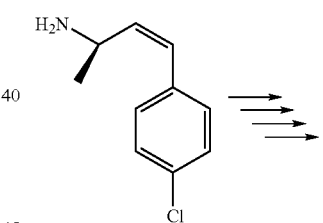

412

Compound 412 and was synthesized in an analogous manner to 137 substituting 3-(4-chlorophenyl)-1(R)-methylallylamine for 3-(4-chlorophenyl)allyl amine. LCMS: 424.2 (MH+).

Scheme 179:
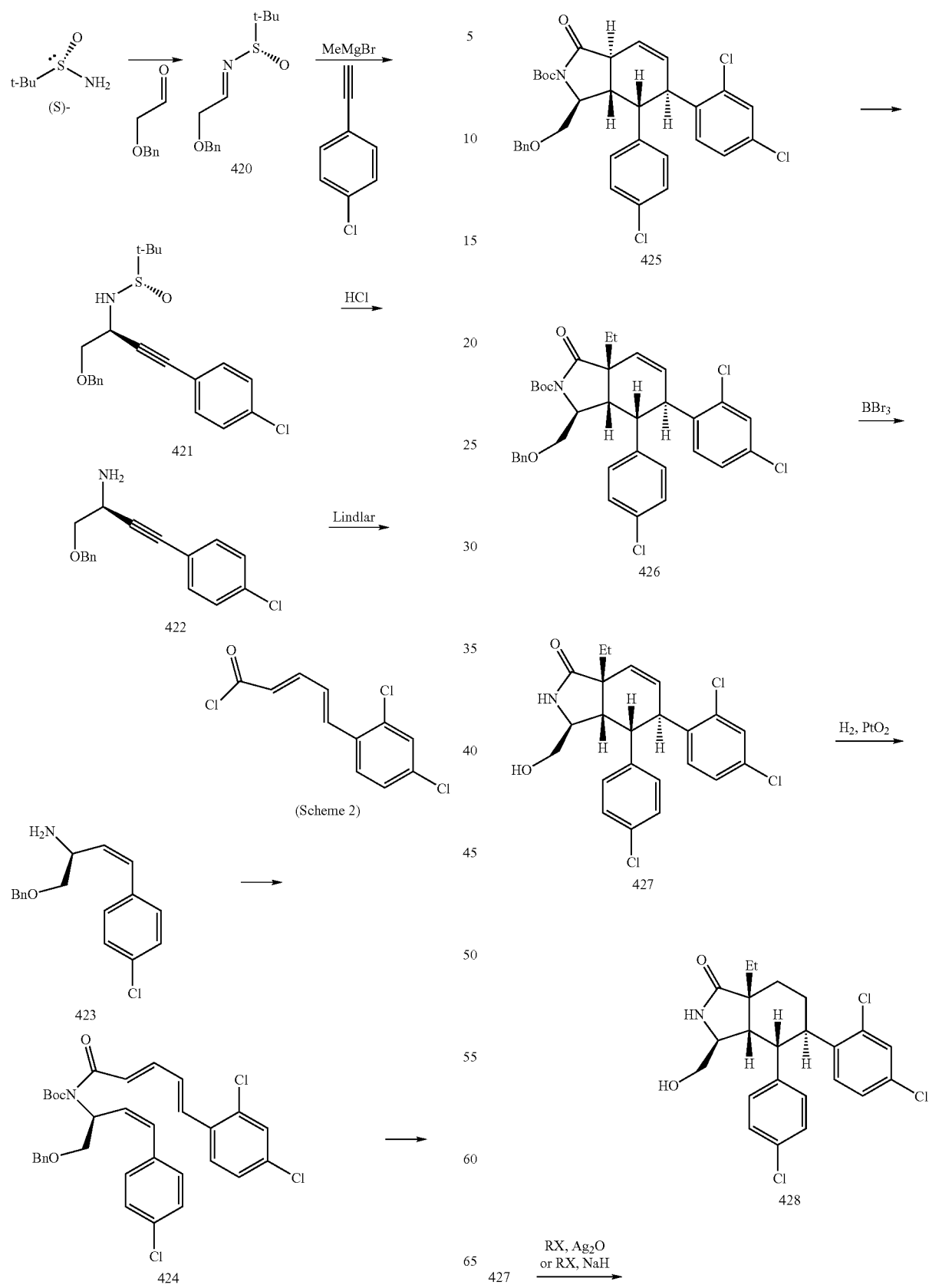

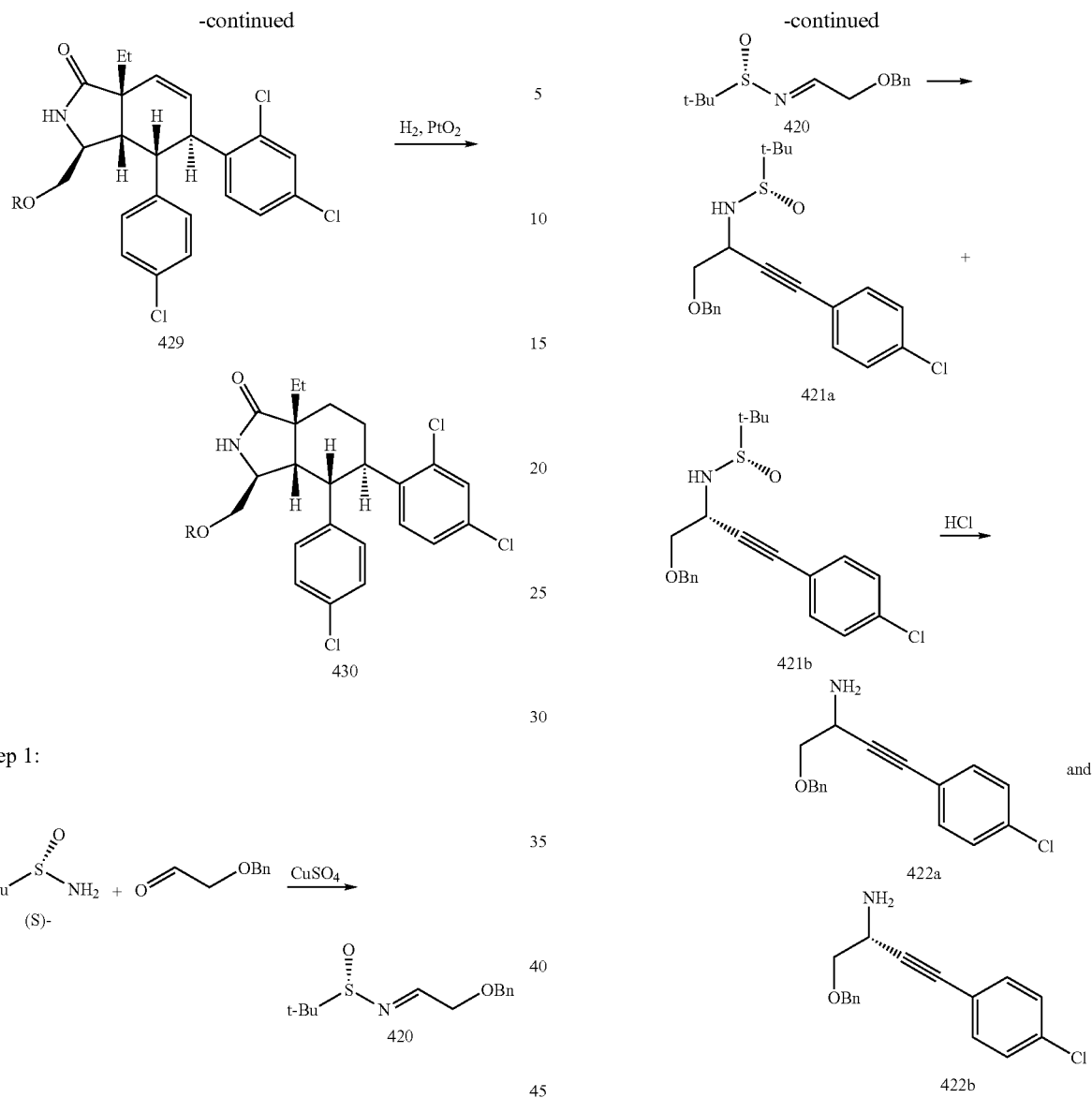

Step 1:

A mixture of (S)-2-methyl-2-propyl sulfinamide (19.4 g, 0.16 mol), benzyloxyacetaldehyde (20 g, 0.133 mol), and anhydrous CuSO$_4$ (12.8 g, 80 mmol) in DCM (170 mL) was stirred at room temperature under N$_2$ for 6 h. Another 30 g of anhydrous CuSO$_4$ (12.8 g, 80 mmol) was added and the mixture was stirred at room temperature for 16 h. The mixture was filtered through CELITE. The filtrate was concentrated in vacuo. The residue was chromatographed on a silica gel cartridge with EtOAc in hexane (0→50%) to afford 420 (27.5 g, 82%).

Racemic 420 was obtained similarly from racemic 2-methyl-2-propyl sulfonamide. From racemic 420, racemic final products such as racemic 428 were prepared.

Step 2:

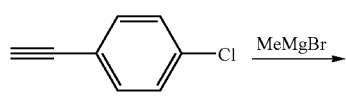

A solution of EtMgBr (31.5 mL, 3.0 M in ether, 0.102 mol) was added to a solution of 4-chlorophenylacetylene (15 g, 0.11 mol) in anhydrous ether (370 mL) under argon at 50° C. and refluxed for 1 h. The resulting Grignard solution was added to a solution of 420 (13 g, 0.051 mol) in DCM (150 mL) at −78° C. under argon. The mixture was stirred at −78° C. for 5 h and at room temperature for 16 h. The reaction was quenched with NH$_4$Cl (sat.) and extracted with EtOAc. The organic layer was dried (MgSO$_4$) and concentrated in vacuo. The crude product (24 g) was used for the next reaction.

A solution of HCl in dioxane (93 mL, 4.0 M, 0.372 mol) was added to a solution of the crude product (24 g) from the above reaction in MeOH at 0° C. and stirred for 1.5 h. The mixture was concentrated in vacuo. The residue was dissolved with EtOAc and washed with NaHCO$_3$ (sat.). The organic layer was dried (MgSO$_4$) and concentrated in vacuo. The residue was chromatographed on a silica gel cartridge with EtOAc in hexane (0→70%) to afford a mixture of 422a and 422b (7.3 g, 50%). The ratio of 422a and 422b is around 4 to 1 based on final product (e.g., 434) ratios.

Racemic 422 was obtained similarly from racemic 420. From racemic 422, racemic final products such as racemic 428 were prepared.

Step 3:

Scheme 4

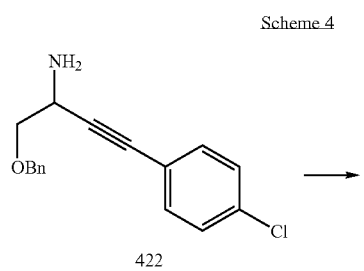

422

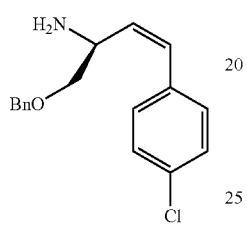

423

The alkyne 422 was reduced to give the cis-olefin 423 in a similar way as shown in Scheme 4.

Steps 4 and 5:

(Scheme 2)

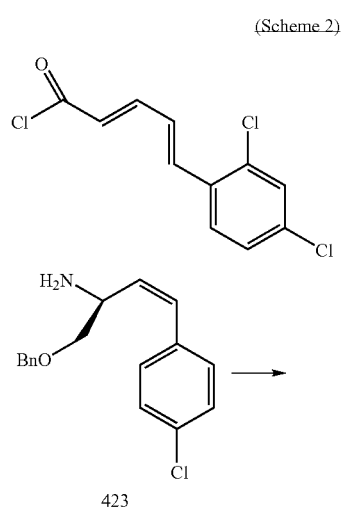

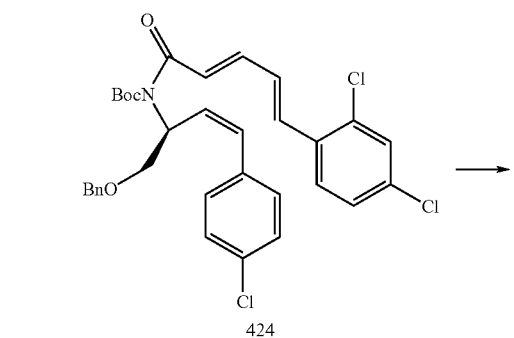

424

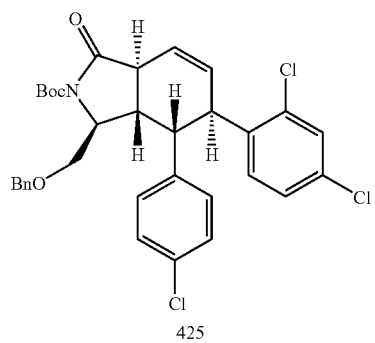

425

The cis-olefin 423 was converted to the Diels-Alder precursor 424 and then to the Diels-Alder product 425 in a similar way as shown in Scheme 73.

Step 6:

Scheme 52

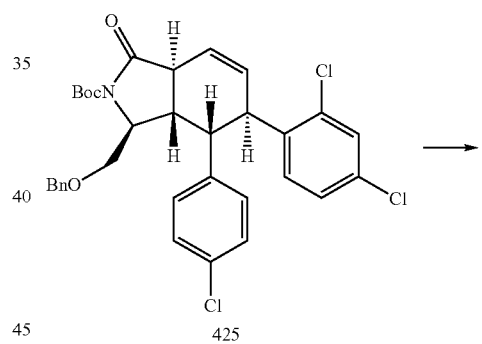

425

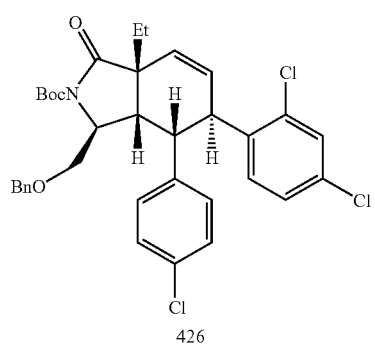

426

The Diels-Alder product 425 was ethylated to give 426 in a similar way as shown in Scheme 52.

Step 7:

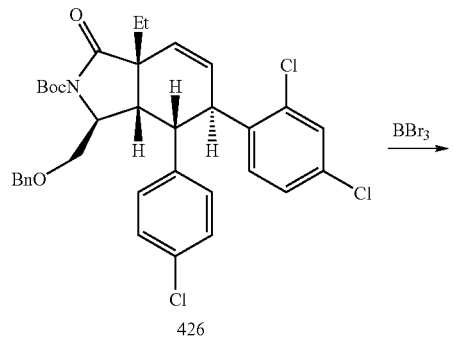

426

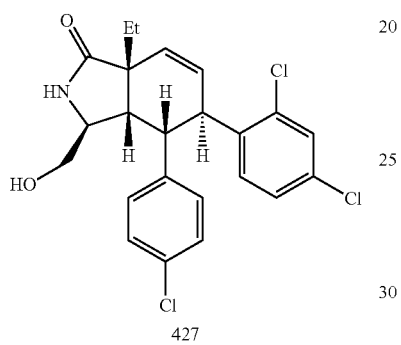

427

The intermediate 426 was converted to compound 427 in a similar way as shown in Scheme 77. Neat BBr₃ was used instead of 1 M solution.

LCMS for 427: 450.2 (MH⁺)

Compound 427 was separated to give single enantiomers 427a and 427b in a similar way as shown in Scheme 71. Chiralpac OD column was used for the chiral HPLC separation.

LCMS for 427a: 450.2 (MH⁺)
LCMS for 427b: 450.2 (MH⁺)

Step 8:

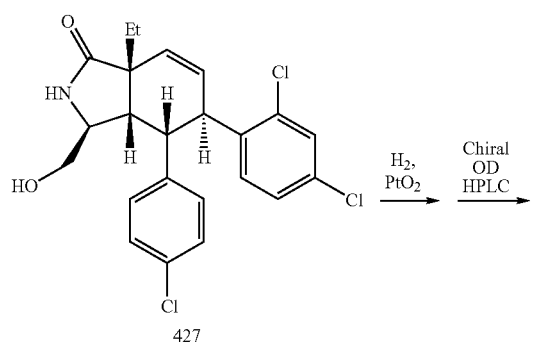

427

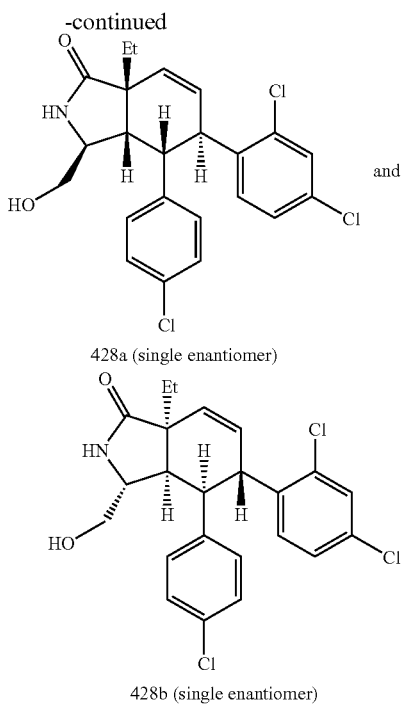

428a (single enantiomer)

428b (single enantiomer)

Compound 427 was converted to single enantiomers 428a and 428b and in a similar way as shown in Schemes 75 and 71. Chiralpac OD column was used for the chiral HPLC separation.

LCMS for 428a: 452.2 (MH⁺)
LCMS for 428b: 452.2 (MH⁺)

Step 9:

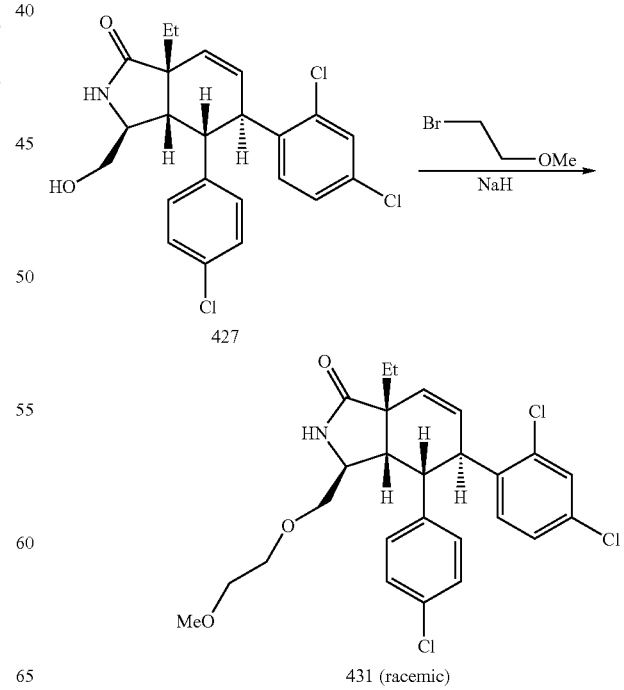

427

431 (racemic)

A solution of 427 (30 mg, 0.066 mmol) in anhydrous THF (1.3 mL) was added to NaH (15 mg, 0.33 mmol) at room temperature and stirred for 0.5 h. Bromoethyl methyl ether (0.20 mL, 0.22 mmol) was added and stirred for 16 h. The reaction was quenched with water and extracted with DCM. The organic layer was dried (MgSO$_4$) and concentrated in vacuo. The residue was chromatographed on a silica gel cartridge with EtOAc in DCM (0→60%) to afford racemic 431 (26 mg, 76%).

LCMS: 508.3 (MH$^+$)

The following compounds were similarly prepared from 427 using appropriate alkylating agents:

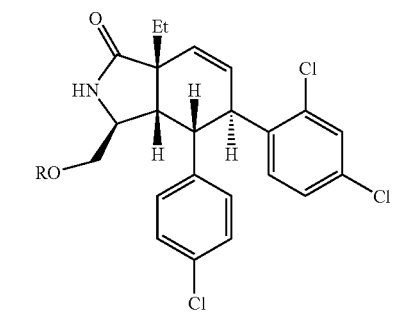

| Compound No | R | LCMS |
|---|---|---|
| 429A | Me | 464.3 |
| 429B | Et | 478.3 |
| 429C | n-Pr | 492.3 |

The following compounds were prepared from appropriate precursors (e.g. 430A from 429A) in a similar way as shown in Schemes 75.

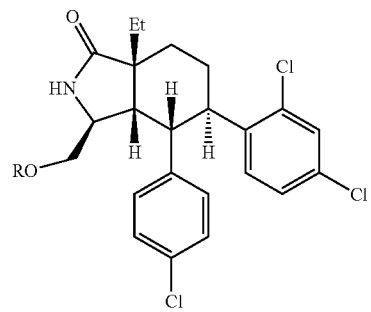

| Compound No | R | LCMS |
|---|---|---|
| 430A | Me | 466.3 |
| 430B | Et | 480.3 |
| 430C | —CH$_2$CH$_2$OMe | 510.3 |

The Diels-Alder product 425 was converted to give 432 in a similar way as shown in Scheme 52:

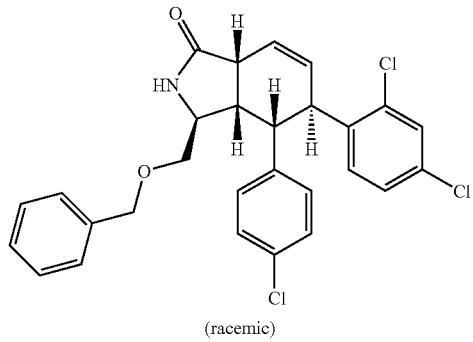

432

(racemic)

LCMS for 432: 512.3 (MH$^+$)

Scheme 180:

Synthesis of 433 and 434

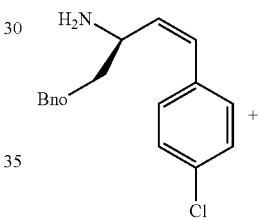

16

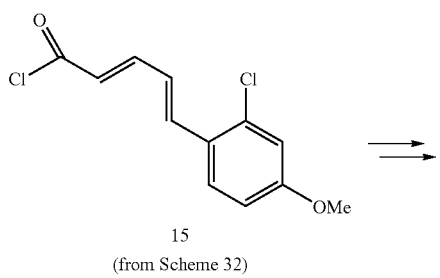

15
(from Scheme 32)

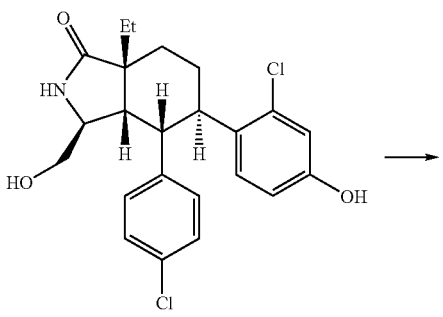

433 (racemic)

437

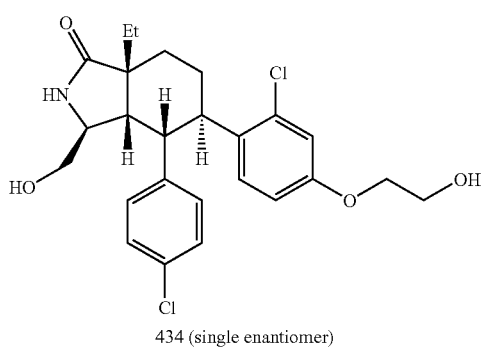

434 (single enantiomer)

The cis-olefin 16 was converted to racemic 433 in a similar way as shown for the synthesis of 428 above. Racemic 433 was converted to single enantiomer 434 in a similar way as shown for the synthesis of 221 given in scheme 109 followed by chiral HPLC separation as described in scheme 71. Chiralpac OD column was used for the chiral HPLC separation.

LCMS for 433: 434.2 (MH$^+$)
LCMS for 434: 478.3 (MH$^+$)

Scheme 181:

Synthesis of 436-438:

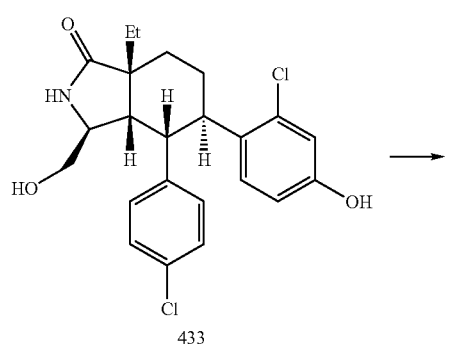

433

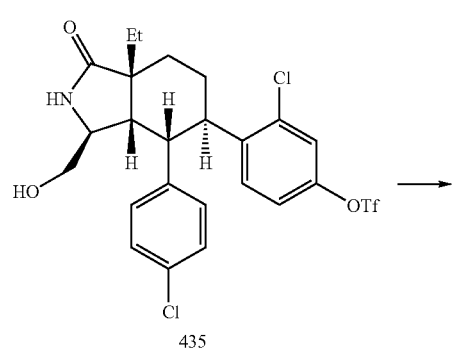

435

438

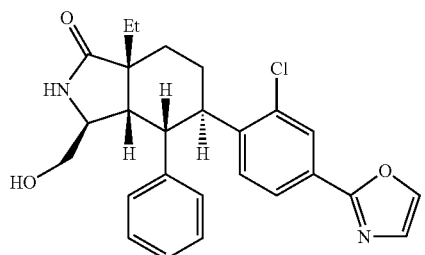

436 (single enantiomer)

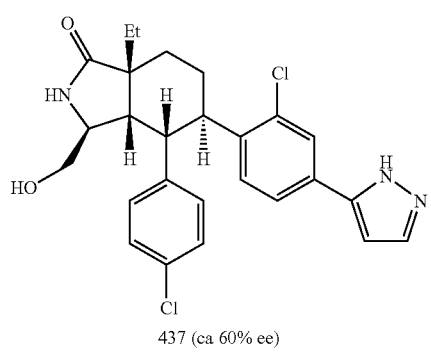

437 (ca 60% ee)

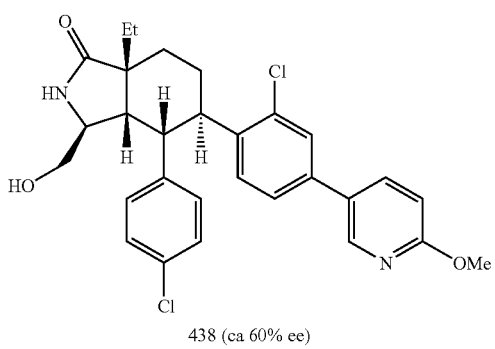

438 (ca 60% ee)

Compound 433 was converted to 436, 437 and 438 in a similar way as shown in Scheme 39.

LCMS for 436: 485.3 (MH$^+$)
LCMS for 437: 484.3 (MH$^+$)
LCMS for 438: 525.3 (MH$^+$)

Scheme 182:

Synthesis of 440:

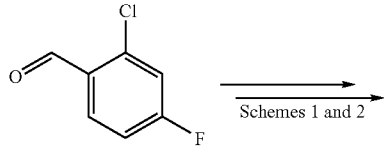

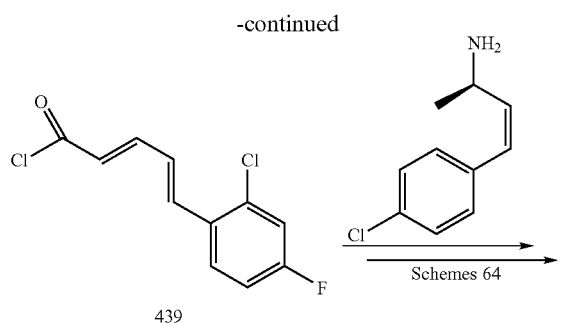
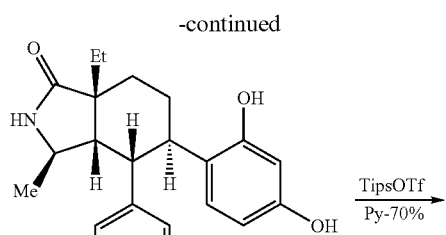
The commercially available 2-chloro-4-fluoro-benzaldehyde was converted to 440 in a similar way as shown in Schemes 1, 2, and 64.
LCMS: 420.2 (MH$^+$)
Scheme 183:
Synthesis of 443-446
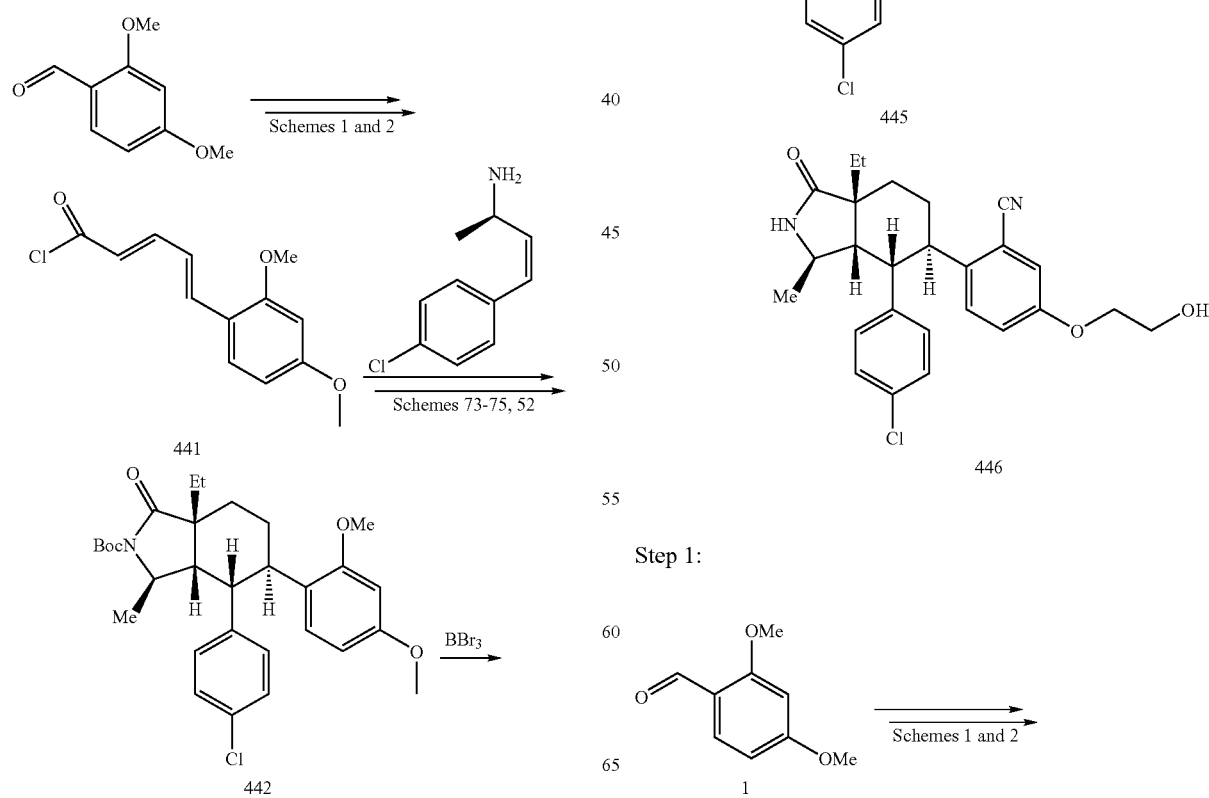
Step 1:

441

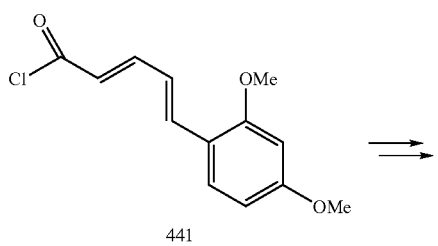

See Scheme 179

The commercially available 2,4-dimethoxy-benzaldehyde was converted to intermediate 443 in a similar way as shown in Schemes 1, 2, 179.

Step 2:

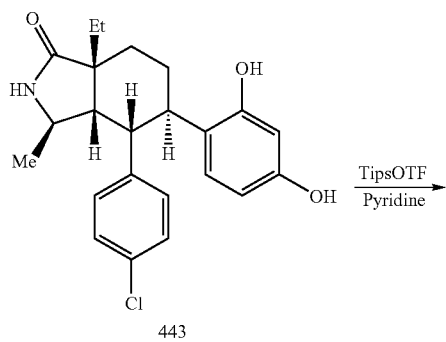

A mixture of intermediate 443 (241 mg, 0.624 mmol), triisopropylsilyl triflate (0.42 mL, 1.6 mmol), and pyridine

442

(0.25 mL, 3.1 mmol) in DCM (6 mL) was stirred at room temperature for 1.5 h. The solution washed with NH$_4$Cl (sat.). The organic layer was dried (MgSO$_4$) and concentrated in vacuo. The residue was chromatographed on a silica gel cartridge with MeOH in DCM (0→15%) to afford intermediate 444 (294 mg, 87%).

Step 3:

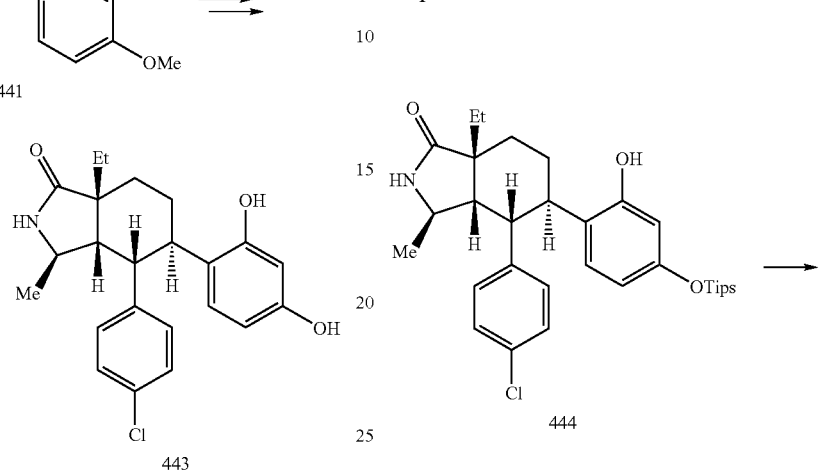

The intermediate 444 was converted to 445 in a similar way as shown in Scheme 39. During the conversion of the triflate to the nitrile group, the triisopropyl group was cleaved to give the phenol.

445, LCMS: 409.2 (MH$^+$)

Step 4:

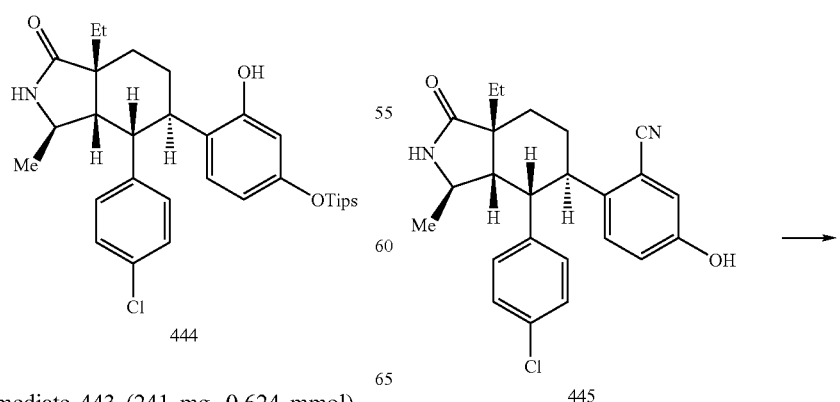

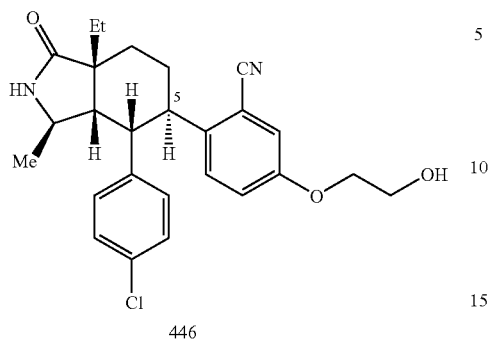
446
Compound 445 was converted to 446 in a similar way as shown for the synthesis of 221 (see scheme 109)
LCMS: 453.2 (MH$^+$)
Scheme 184:
Preparation of Compounds 450-452:
Using a procedure similar to the conversion of 73 to 78 (see scheme 46) compounds 450-452 were prepared from intermediates 212 and 341 and the appropriate boronic acid or boronate ester.
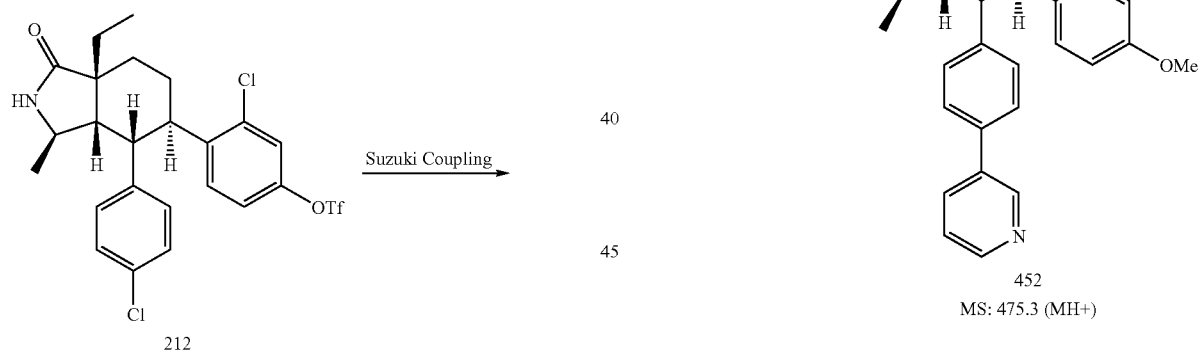
450
MS: 479.3
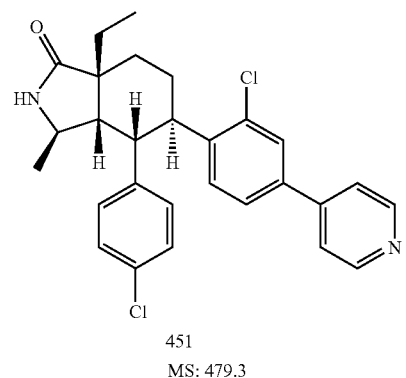
451
MS: 479.3
452
MS: 475.3 (MH+)
Scheme 185:
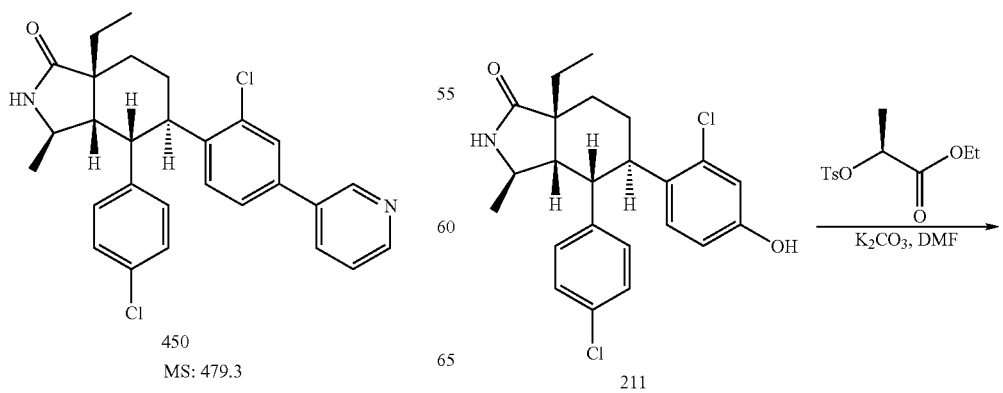
211

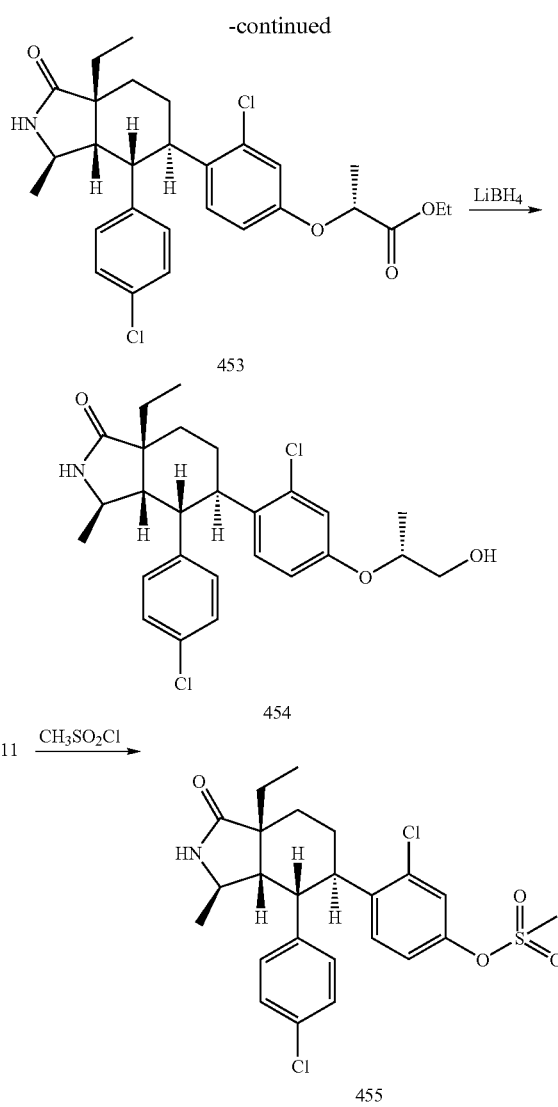

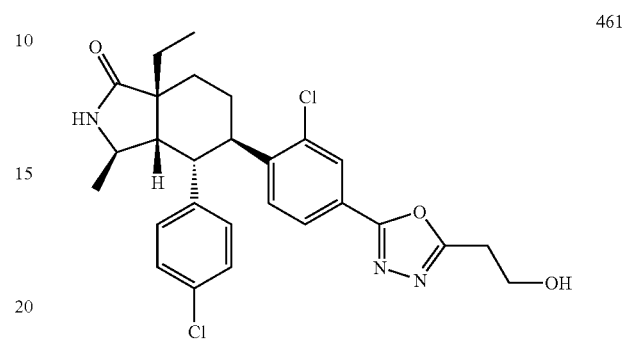

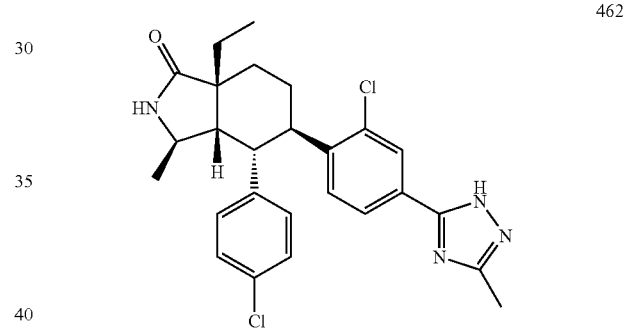

Preparation of 453:

A mixture of 211 (160 mg, 0.382 mmol), Ethyl O-(p-toluenesulfonyl)-L-(–)-lactate (520 mg, 1.91 mmol, 5 eq) (Ref: *Tetrahedron*, 1985, vol. 41, page 541-546) and K$_2$CO$_3$ (160 mg, 1.16 mmol, 3 eq.) in 3 ml DMF was heated overnight in a sealed tube at 100° C. The mixture was diluted with ethyl acetate, washed 3× with 1N HCl, brine, dried over MgSO$_4$, filtered, concentrated and chromatographed with 0% to 5% methanol in dichloromethane to provide 204 mg of 453.

MS: 518.3 (MH$^+$)

Preparation of 454:

To a solution of 453 (100 mg, 0.21 mmol) in 2 ml THF at rt was added 2M solution of LiBH$_4$ in THF (0.5 ml, 1 mmol) and the mixture was stirred at rt for 1 hr. It was poured in to aq. NH$_4$Cl, extracted 3× with ethyl acetate, the combined organic layers washed with brine, dried over MgSO$_4$, filtered, concentrated and chromatographed with 0% to 5% methanol in dichloromethane to provide 84 mg of 454.

MS: 476.3 (MH$^+$)

Preparation of 455:

A mixture of 211 (40 mg, 0.095 mmol), and ~7 equivalents of methane sulfonyl chloride in 1 ml pyridine was stirred overnight. It was diluted with ethyl acetate, washed 3× with 1N HCl, brine, dried over MgSO$_4$, filtered, concentrated and purified by preparative TLC using 4% methanol in dichloromethane as eluent to provide 16 mg of 455.

MS: 496.3 (MH$^+$)

Preparation of 461

Compound 461 was prepared from 388H using the procedure used for compound 390. LCMS: 514.3 (MH$^+$).

Preparation of 462

Compound 462 was prepared from compound 384 in a similar manner to compound 399 using dimethylacetamide dimethylacetal in place of dimethylformamide dimethylacetal. LCMS: 483.3 (MH$^+$).

Scheme 186:

Preparation of 463

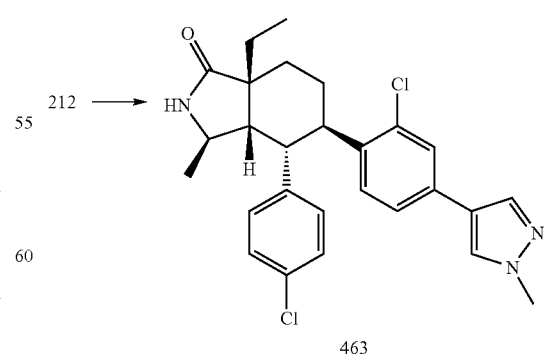

Compound 212 (110 mg, 0.2 mmol) was dissolved in PhMe/EtOH/H$_2$O (1.1 mL/1.1 mL/0.45 mL). Pd (dppf)

Cl₂.CH₂Cl₂ (15 mg, 10 mol %), Na₂CO₃ (64 mg, 3 eq), and 1-Methylpyrazole-4-boronic acid pinacol ester (62 mg, 1.5 eq) were added. The mixture was heated at 120° C. in a microwave for 20 minutes. NH₄Cl$_{(sat)}$ was added and the mixture extracted with EtOAc. The extracts were dried, concentrated, and then purified (SiO₂, hexane/EtOAc 2:1-1:2) to give the title compound, 28 mg, LCMS: 482.3 (MH⁺).

Scheme 187:

Preparation of 464

212 →

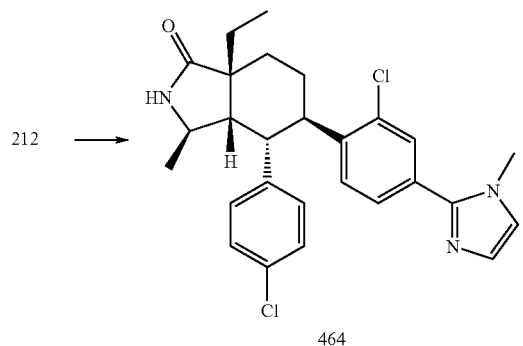

464

Compound 212 (94 mg, 0.171 mmol) and 1-methyl-2-(tributylstannyl)imidazole (317 mg, 5 eq) was dissolved in THF. Pd(Ph₃P)₄ (60 mg, 0.3 eq) was added and the mixture heated at 85° C. overnight. The mixture was diluted with EtOAc, washed with NH₄Cl$_{(sat)}$, brine, dried, and concentrated. Purification (SiO₂, hexane/EtOAc 2:1-1:2) gave the title compound, 20 mg, LCMS: 482.3 (MH⁺).

The following compounds were prepared in a similar manner to 463 using appropriate boronic acid pinacol esters.

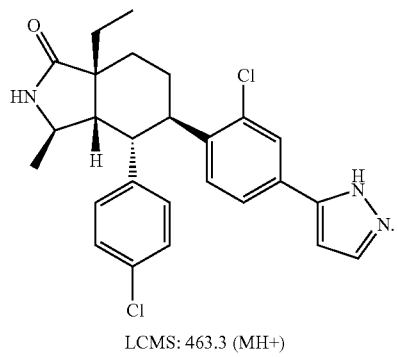

465

LCMS: 463.3 (MH+)

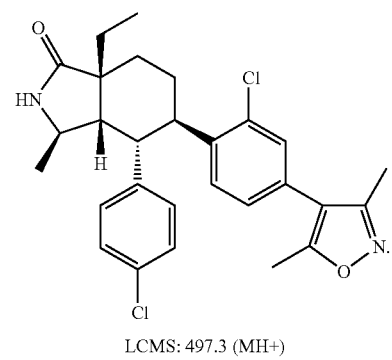

466

LCMS: 497.3 (MH+)

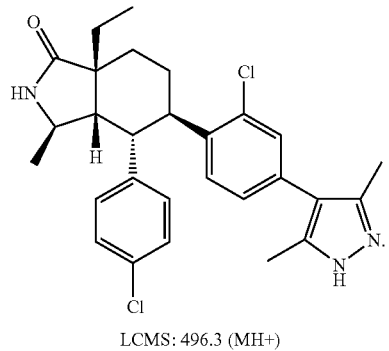

467

LCMS: 496.3 (MH+)

The following compounds were prepared in a similar manner to 464 using appropriate tributylstannanes.

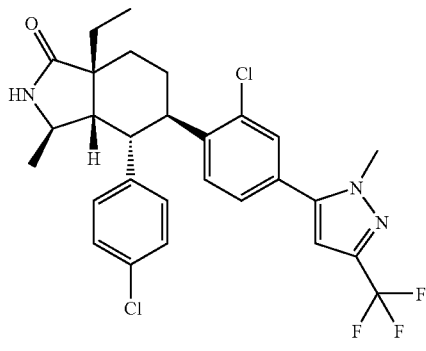

468

LCMS: 550.3 (MH⁺)

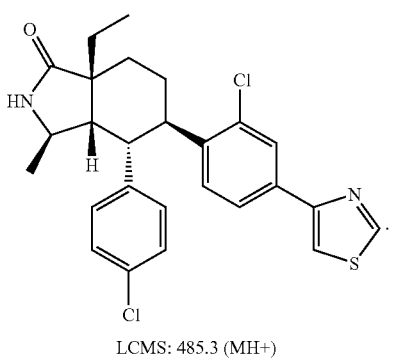

469

LCMS: 485.3 (MH+)

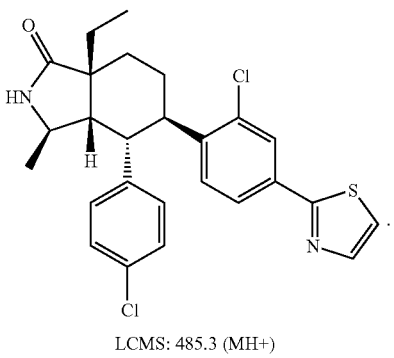

470

LCMS: 485.3 (MH+)

Preparation of 471
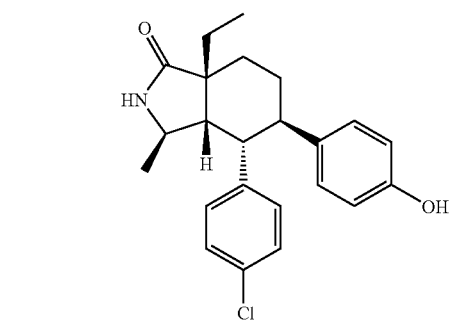
471
Compound 471 was prepared from 5-(4-methoxyphenyl)-2(E), 4(E)-pentadienoic acid in a similar manner to compound 211. LCMS 384.2 (MH+) The following compounds were prepared from 435 in a similar fashion as shown in Scheme 39 using appropriate organoboron or organotin reagents:
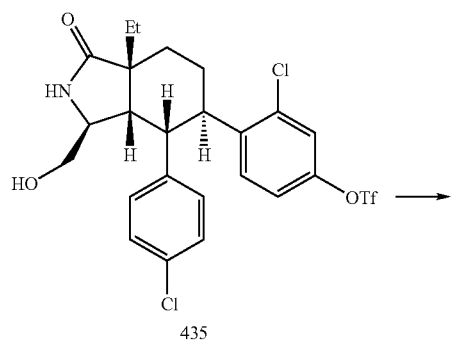
435
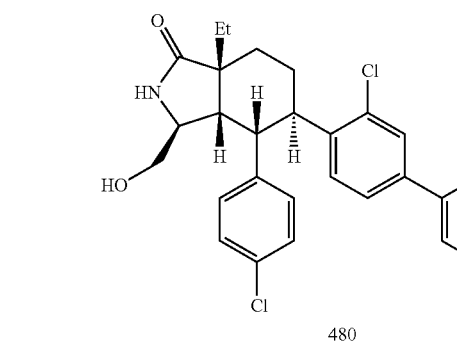
480
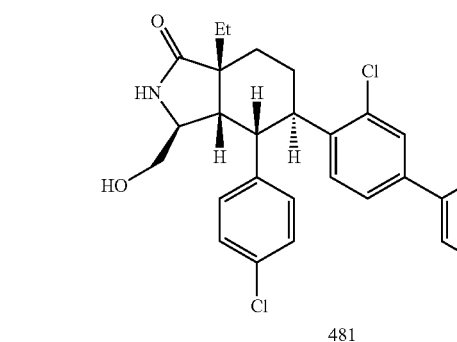
481
-continued
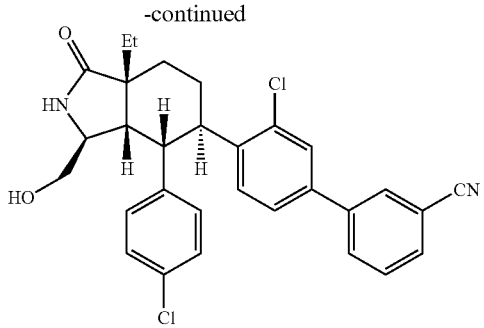
482
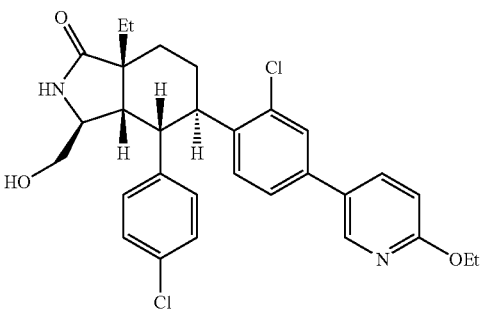
483
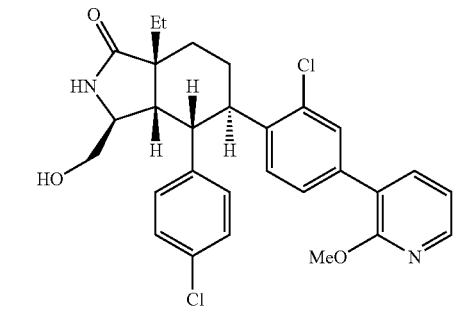
484
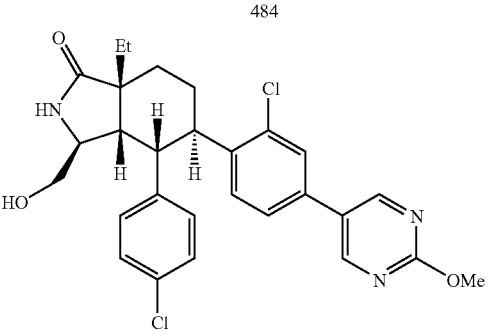
485
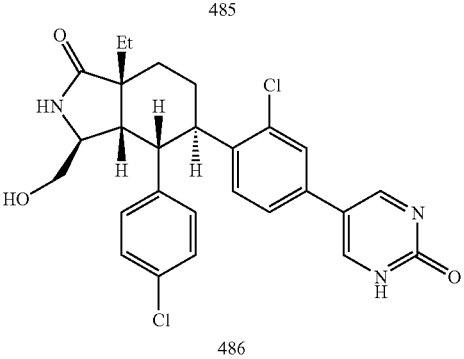
486

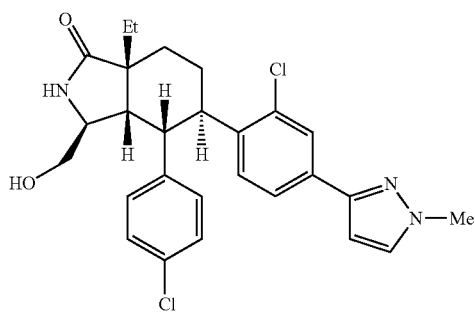

487

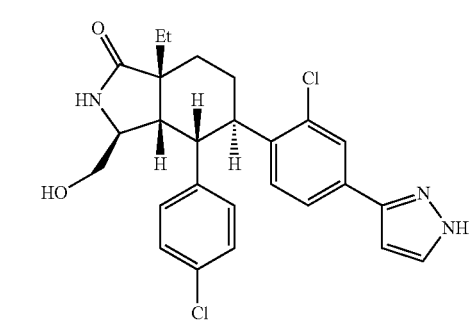

488

LCMS for 480: 524.3 (MH+)
LCMS for 481: 537.3 (MH+)
LCMS for 482: 519.3 (MH+)
LCMS for 483: 539.3 (MH+)
LCMS for 484: 525.3 (MH+)
LCMS for 485: 526.3 (MH+)
LCMS for 486: 512.3 (MH+)
LCMS for 487: 498.3 (MH+)
LCMS for 488: 484.3 (MH+)

Preparation of 4,5-Di(hetero)aryl-octahydro-benzo[1,2,5]thiadiazole 2,2-dioxides and 4,5-Di(hetero)aryl-octahydro-benzoimidazol-2-ones General Scheme M:

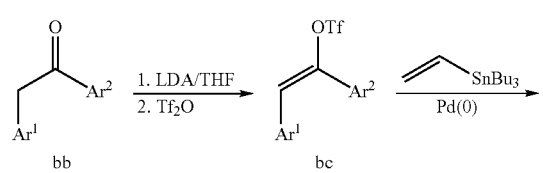

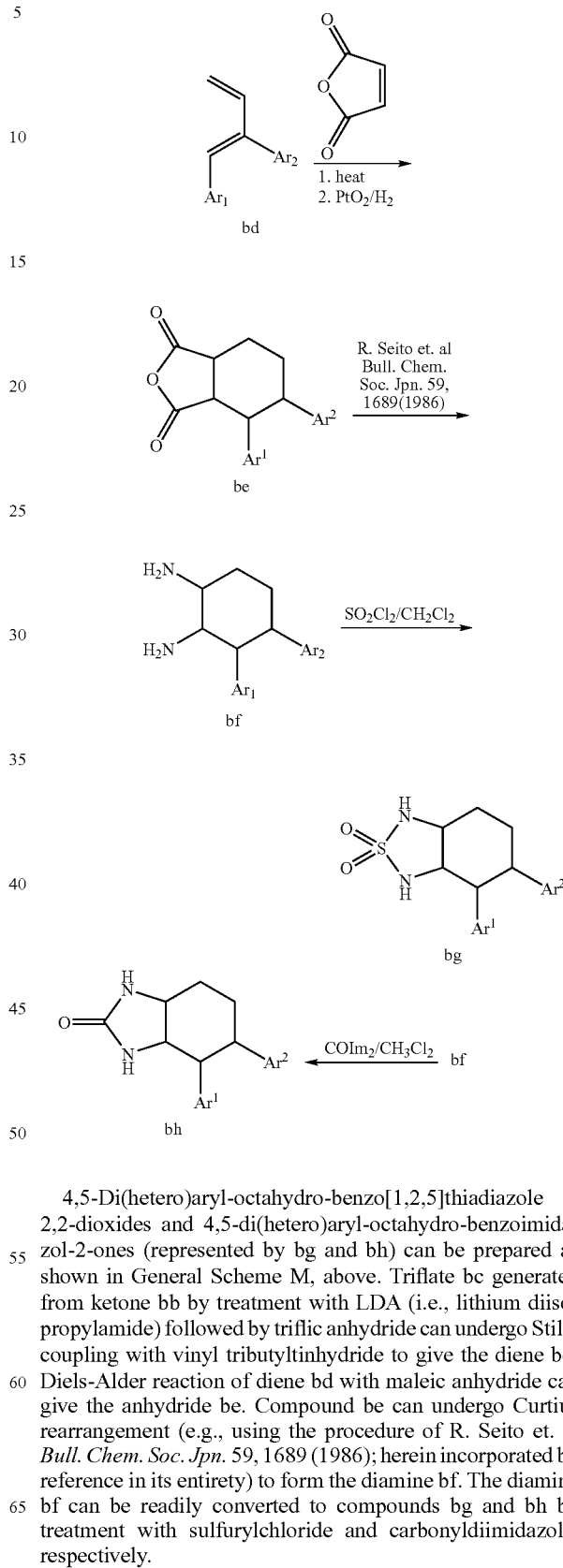

4,5-Di(hetero)aryl-octahydro-benzo[1,2,5]thiadiazole 2,2-dioxides and 4,5-di(hetero)aryl-octahydro-benzoimidazol-2-ones (represented by bg and bh) can be prepared as shown in General Scheme M, above. Triflate bc generated from ketone bb by treatment with LDA (i.e., lithium diisopropylamide) followed by triflic anhydride can undergo Stille coupling with vinyl tributyltinhydride to give the diene bd. Diels-Alder reaction of diene bd with maleic anhydride can give the anhydride be. Compound be can undergo Curtius rearrangement (e.g., using the procedure of R. Seito et. al Bull. Chem. Soc. Jpn. 59, 1689 (1986); herein incorporated by reference in its entirety) to form the diamine bf. The diamine bf can be readily converted to compounds bg and bh by treatment with sulfurylchloride and carbonyldiimidazole, respectively.

Synthesis of Isolactones and Isolactams bl and bp

General Scheme N:

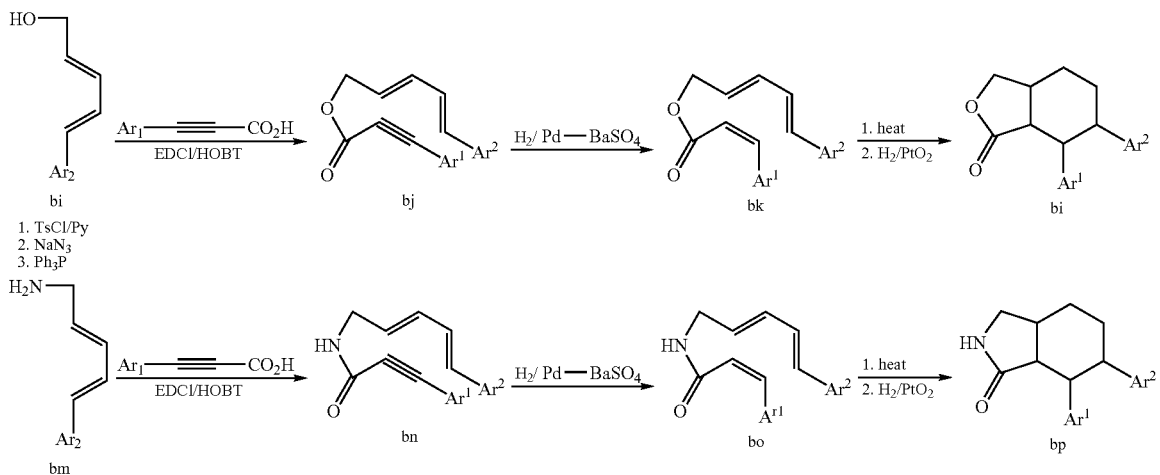

solactone bl and isolactam bp can be prepared according to General Scheme N, above. Cinnamyl alcohol bi can undergo coupling with a substituted propargylic acid to give the ester bj, which under selective hydrogenation conditions can yield bk. Standard Diels-Alder cyclization of bk and subsequent reduction of the internal double bond can provide compound bl. Similarly, bi can be converted to the amine bm. Amine bm can be converted to Diels-Alder precursor bo by reaction with a propargylic acid and subsequent selective reduction. Thermal Diels-Alder reaction of bo can give the lactam bp after reduction of the double bond.

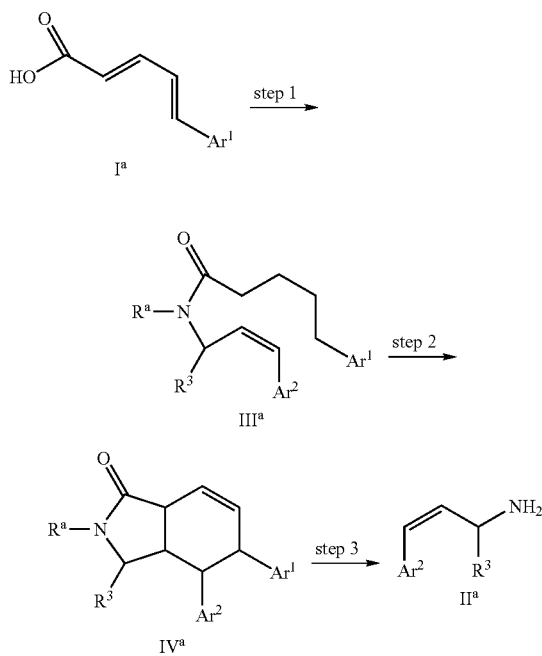

General Scheme:

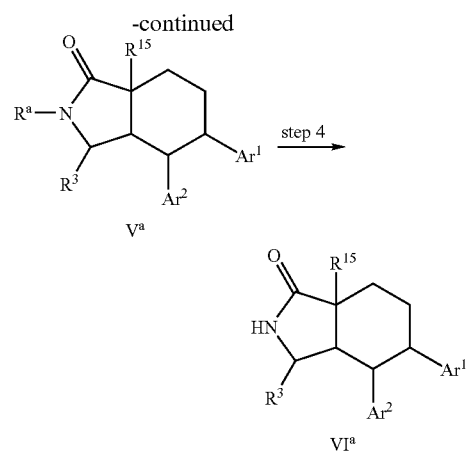

The synthesis of an embodiment of the formula I involves the application of Diels-Alder reaction. The Diels-Alder precursor $III^a$ can be readily prepared by coupling the dienoic acid $I^a$ and the allyl amine $II^a$. The amide can be either protected with an appropriate functional group ($R^a$ is a protecting group) or it can be used without any protection ($R^a$ is hydrogen). When $III^a$ is subjected to the Diels-Alder reaction it gives the cyclization product $IV^a$. The yield and selectivity of the products in this step can depend on a variety of reaction conditions such as the solvent used, the temperature employed for the cyclization, the additives used in the reaction medium such as Lewis acids etc. Following the Diels-Alder reaction an $R^{15}$ group can be introduced and the double bond reduced to provide $V^a$ which can be subjected to the deprotection conditions to cleave the protecting group to give $VI^a$. The substitution of $Ar^1$ or $Ar^2$ can be further functionalized or transformed. Non-limiting examples of protecting groups for $R^a$ include all those known to protect a nitrogen and examples may be found in Green et al., (Protective Groups in Organic Synthesis by T. W. Greene and P. G. Wuts; 1999, Third edition, John Wiley & Sons, Inc.) Preferred amide protecting groups include but are not limited to tert-butoxycarbonyl (Boc), benzyl oxycarbonyl (Cbz), para-methoxy benzyl, 3,4-dimethoxybenzyl, allyl, trimethylsilyl ethyl (TMSE), methoxy methyl (MOM), benzyloxymethyl (BOM), methoxy, tert-butyldimethylsilyl (TBDMS), Triisopropylsilyl (TIPS), methoxy carbonyl and ethoxycarbonyl, etc. Preferred electrophilic reagents include for example optionally substituted alkyl halides (e.g., methyl iodide, ethyl iodide, propyl iodide, Br—CH$_2$CH$_2$—OTBS), optionally substituted benzyl halides (e.g., benzyl bromide, para-cyano benzyl bromide, ortho-cyano benzyl bromide and meta-cyano benzyl bromide). Electrophilic reagents are electron deficient reagents that can react with another molecule by accepting a pair of electrons to form a new bond. The electrophiles (which are also a Lewis acids), can be positively charged, have an atom which carries a partial positive charge, or have an atom which does not have an octet of electrons [see Page 541 of Mechanism and Theory in Organic Chemistry by T. H. Lowry and K. S. Richardson, Third edition, Harper Collins Publishers].

In another embodiment is a process for preparing compounds of formula V$^a$

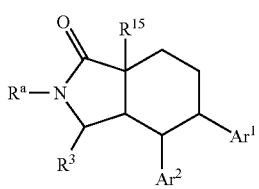

wherein R$^a$ is H or a protecting group and R$^3$, R$^{15}$, Ar$^1$ and Ar$^2$ are herein defined above, comprising a) coupling a compound of formula I$^a$

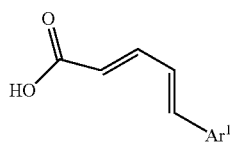

with a compound of formula II$^a$

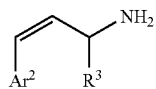

to obtain a compound of formula III$^a$

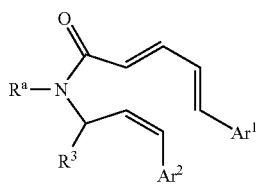

b) cyclizing the compound of formula III$^a$ to obtain a compound of formula IV$^a$

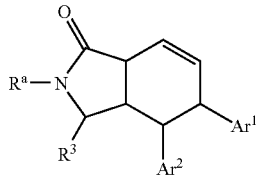

c) generating the enolate and reacting with an electrophilic reagent to introduce R$^{15}$ group to the compound of formula III$^a$ and d) reducing the double bond of the compound of formula IV$^a$ to obtain a compound of formula V$^a$

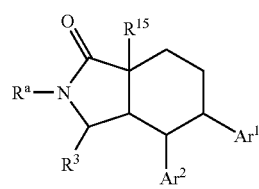

In an embodiment of the invention is the process to obtain a compound of formula V$^a$ wherein R$^a$ is H, tert-butoxycarbonyl (Boc), benzyl oxycarbonyl (Cbz), para-methoxy benzyl, 3,4-dimethoxybenzyl, allyl or trimethylsilyl ethyl (TMSE), methoxy methyl (MOM), benzyloxymethyl (BOM), methoxy, tert-butyldimethylsilyl (TBDMS), Triisopropylsilyl (TIPS), methoxy carbonyl or ethoxycarbonyl and wherein said electrophilic reagent is alkyl-iodide.

Assay

Method for Evaluating Cannabinioid CB$_1$ and CB$_2$ Affinity

Competition binding assays for cannabinoid CB$_1$ and CB$_2$ affinity were performed by incubating commercially purchased membranes prepared from cells expressing each receptor subtype (8 μg pro) with 0.5 nM $^3$H-CP55,940, a non-selective cannabinoid agonist, along with concentrations of drug ranging from 0.0001-3 μM in Buffer A (5 mM MgCl$_2$, 2.5 mM EDTA and 013% BSA). Non-specific binding was defined in the presence of 10 μM CP55,940. For saturation studies, concentrations of $^3$H-CP55,940 ranging from 0.1-5 nM were incubated with membranes in the presence and absence of 10 μM CP55,940. Assays were terminated after incubation for 1½ hours by rapid filtration onto 0.3% polyethylenamine treated GF/C filterplates using a BRANDEL cell harvester. The plates were dried and MICROSCINT scintillation cocktail was added, after which the bound radioactivity was quantified using a TOPCOUNT scintillation counter.

The dissociation constant (K$_d$) of $^3$H-CP55,940 at the CB$_1$ and CB$_2$ receptor were determined by plotting specific binding at each concentration of radioligand, and analysis by non-linear regression. For competition studies, the concentration of each drug that inhibited 50 percent of $^3$H-CP55,940 binding (IC$_{50}$) was determined by non-linear regression analysis of the radioligand displacement curves. Affinity constants ($K_i$) were calculated using the equation derived by Cheng and Prusoff (1973), defined as: $IC_{50}/1+[conc. ligand/K_d]$.

GTPγS Binding Protocol

The functional efficacy of compounds to activate second messengers within the cell was determined utilizing the GTPγS binding assay. Guanine nucleotides are phosphorylated within the plasma membrane of the cell following binding and activation by agonists. A radiolabelled derivative of guanine triphosphate (GTP) is utilized in this assay as it cannot be dephosphorylated and therefore accumulates following agonist binding. The simultaneous presence of an antagonist into this system will shift the agonist concentration curve to the right, with increasing concentrations of antagonist producing a greater rightward shift in the dose-response curve of the agonist.

Commercially purchased membranes were incubated with 10 mM GDP to allow sufficient substrate for phosphorylation in the presence of agonist. The membranes were then pre-incubated with increasing concentrations of test compound for 30 minutes to determine if they were capable of stimulating phosphorylation alone. Increasing concentrations of the non-selective cannabinoid agonist WIN55,122 were then added in the presence or absence of each concentration of test compound. The assay was then incubated for 1 hour at room temperature. To complete the assay, $^{35}$S-GTPγS was added and the assay incubated for another 30 minutes. Assays were terminated by rapid filtration onto 10 mM sodium phosphate-treated GF/C filterplates using a BRANDEL cell harvester. The plates were dried and Microscint scintillation cocktail was added, after which the bound radioactivity was quantified using a TOPCOUNT scintillation counter.

The stimulation of $^{35}$S-GTPγS binding as a function of the concentration of the agonist WIN55,122, in the absence and presence of test compound, was plotted and the $EC_{50}$ determined by nonlinear regression analysis using GraphPad Prism software. A Schild analysis of the rightward shift in the dose response curve of WIN55,122 in the presence of test compound was determined by plotting the concentration of test compound against the negative log of the dose ratio [1-($EC_{50}$ agonist+test compound/EC50 of agonist alone)]. A linear regression analysis yields the Kb, defined as the X-intercept of the linear equation.

Preferred compounds of Formula I of the present invention, and salts, solvates, or esters thereof, have $K_i$ values of about 200 nM or less. In another embodiment, the compounds of Formula (I) of the present invention, and salts, solvates, or esters thereof, have $K_i$ values of about 100 nM or less. In another embodiment, the compounds of Formula (I) of the present invention, and salts, solvates, or esters thereof, have $K_i$ values of about 50 nM or less. In another embodiment, the compounds of Formula (I) of the present invention, and salts, solvates, or esters thereof, have $K_i$ values of about 20 nM or less. In another embodiment, the compounds of Formula (I) of the present invention, and salts, solvates, or esters thereof, have $K_i$ values of about 10 nM or less. In another embodiment, the compounds of Formula (I) of the present invention, and salts, solvates, or esters thereof, have $K_i$ values of about 5 nM or less. In another embodiment, the compounds of Formula (I) of the present invention, and salts, solvates, or esters thereof, have $K_i$ values of about 10 to about 1 nM. In another embodiment, the compounds of Formula (I) of the present invention, and salts, solvates, or esters thereof, have $K_i$ values of about 10 to about 0.1 nM. In another embodiment, the compounds of Formula (I) of the present invention, and salts, solvates, or esters thereof, have $K_i$ values of about 10 to about 0.01 nM. Examples 40, 42, 169, 170, 174, 178, 180, 181, 183, 182, 185, 213, 221, 227, 228, 260, 282, 387, 397, 438, 451, 454, 463 and 483 have $K_i$ values in the range of about 10 to about 1 nM.

We claim:

1. A compound of Formula (I):

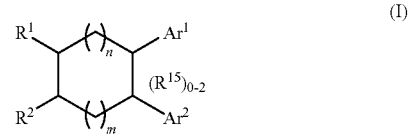

(I)

or a pharmaceutically acceptable salt, solvate, or ester thereof, wherein:

m is 0 or 1, n is 1 or 2, and m+n is 1 or 2;

$R^1$ and $R^2$ together with the carbon atoms to which they are shown attached in Formula (I) form a group Q as shown in Formula (IA):

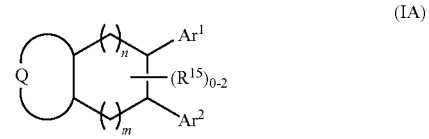

(IA)

wherein Q is selected from the group consisting of:

(a)

$Y^1$ is —O— or —N($R^7$)—;

$R^3$, and $R^4$, are each independently selected from the group consisting of H, —O—$R^9$, $R^{11}$, and —N($R^{16}$)$_2$;

$R^7$ is selected from the group consisting of H, alkyl, arylalkyl, alkenyl, -alkylene-N($R^9$)$_2$, -alkylene-O—$R^9$, -alkylene-$R^{12}$, —C(O)—$R^{14}$, -alkylene-C(O)H, —C(O)—O—$R^{11}$, and Boc;

$R^9$ is selected from the group consisting of H, TBS, TIPS, Tf and $R^{11}$;

$R^{11}$ is selected from the group consisting of unsubstituted alkyl, alkyl substituted with one or more U groups, -alkylene-O-alkyl, -alkylene-O-aryl, unsubstituted aryl, and aryl substituted with one or more $X^1$ groups;

$R^{12}$ is selected from the group consisting of unsubstituted aryl and aryl substituted with one or more $X^1$ groups;

$R^{13}$ is selected from the group consisting of unsubstituted heteroaryl and heteroaryl substituted with one or more $X^2$ groups;

$R^{14}$ is selected from the group consisting of unsubstituted cycloalkyl, cycloalkyl substituted with one or more $X^4$ groups unsubstituted alkyl, and alkyl substituted with one or more U groups;

each $R^{15}$ is independently selected from the group consisting of H, —$N_3$, halogen, alkenyl, -alkylene-$R^{12}$, -alkylene-O—$R^9$, -alkylene-N($R^{18}$)$_2$, -alkylene-C(O)H, —OH, —CN, —O-alkyl, —C(O)N($R^{18}$)$_2$, —N($R^{18}$)$_2$, —$NR^{18}$C(O)$R^{18}$, —$NR^{18}$C(O)$_{2R}{}^{18}$, —$NR^{18}$C(O)N($R^{18}$)$_2$, —$_{NR}{}^{18}$S(O)$_2R^{18}$, —O-alkenyl, —C(O)$_2R^{18}$; unsubstituted alkyl, alkyl substituted with one or more U groups, —O-alkylene-C(O)$R^{18}$, or —C(O)$R^{18}$;

with the proviso wherein the group —N($R^{18}$)$_2$, both $R^{18}$ groups taken together with the N atom to which they are bonded form an unsubstituted heterocycloalkyl, heterocycloalkyl substituted with one or more $X^3$ groups, or said substituted or unsubstituted heterocycloalkyl group is fused with aryl, heteroaryl, cycloalkyl or heterocycloalkyl;

is selected from the group consisting of $R^9$ and —C(O)—$R^{12}$;

each $R^{18}$ is independently selected from the group consisting of H, unsubstituted heterocycloalkyl, heterocycloalkyl substituted with one or more $X^3$ groups, $R^{12}$, $R^{13}$ and $R^{14}$;

with the proviso that when $R^{18}$ is attached to N, then each $R^{18}$ is independently selected from the group consisting of H, unsubstituted heterocycloalkyl, heterocycloalkyl substituted with one or more $W^3$ groups, —C(O)$R^{21}$, $R^{12}$, $R^{13}$ and $R^{14}$;

$R^{19}$ is selected from the group consisting of H, TBS, TIPS, Tf and $R^{21}$;

each $R^{20}$ is independently selected from the group consisting of H, unsubstituted alkyl, alkyl substituted with one or more U groups, -alkylene-$R^{22}$, -alkylene-$R^{23}$, -alkylene-$R^{24}$, —C(O)—$R^{24}$, -alkylene-O—$R^{19}$, $R^{24}$, unsubstituted heterocycloalkyl, heterocycloalkyl substituted with one or more $W^3$ groups, and benzo-fused cycloalkyl;

$R^{21}$ is selected from the group consisting of unsubstituted alkyl, alkyl substituted with one or more U groups, -alkylene-O-alkyl, -alkylene-O-aryl, unsubstituted aryl, aryl substituted with one or more $W^1$ groups;

unsubstituted heteroaryl, heteroaryl substituted with one or more $W^2$ groups, unsubstituted cycloalkyl, cycloalkyl substituted with one or more $W^4$ groups, unsubstituted heterocycloalkyl, heterocycloalkyl substituted with one or more $W^3$ groups, —O-alkylene-O—$R^{24}$, —C(O)—O-alkylene-O—$R^{24}$; —C(O)-alkylene-$R^{23}$, —C(O)—$R^{22}$, —C(O)—$R^{24}$, —C(O)—O—$R^{22}$, —C(O)—O—$R^{24}$, —NH$R^{22}$, —NH$R^{24}$, —S(O)$_2$—$R^{24}$, and -alkylene-O-alkylene-O—$R^{24}$, with the proviso that —O—O— cannot be formed with $R^{21}$ and the atom said $R^{21}$ is attached to;

$R^{22}$ is selected from the group consisting of unsubstituted aryl and aryl substituted with one or more $W^1$ groups;

$R^{23}$ is selected from the group consisting of unsubstituted heteroaryl and heteroaryl substituted with one or more $W^2$ groups;

$R^{24}$ is selected from the group consisting of alkyl, unsubstituted cycloalkyl, cycloalkyl substituted with one or more $W^4$ groups, unsubstituted alkyl, and alkyl substituted with one or more U groups;

each $R^{25}$ is independently selected from the group consisting of H, $R^{22}$, $R^{23}$, unsubstituted alkyl, alkyl substituted with one or more U groups, unsubstituted cycloalkyl, cycloalkyl substituted with one or more $W^4$ groups, -alkylene-O$R^{19}$, -alkylene-N$R^{19}R^{19}$, -alkylene-S$R^{19}$, -alkylene-$R^{23}$, -alkylene-$R^{22}$, unsubstituted heterocycloalkyl, heterocycloalkyl substituted with one or more $W^3$ groups, -alkylene-heterocycloalkyl, -alkylene-heterocycloalkyl substituted with one or more $W^3$ groups, —C(O)—$R^{24}$, —C(O)—$R^{22}$, —C(O)—$R^{24}$, —C(O)—O—$R^{22}$, —C(O)—O—$R^{24}$, —NH$R^{22}$, —NH$R^{24}$, —S(O)$_2$—$R^{24}$, —C(O)—NH—$R^{22}$ and —C(O)—NH—$R^{24}$;

with the proviso wherein the group —N($R^{25}$)$_2$, both $R^{25}$ groups taken together with the N atom to which they are bonded form an unsubstituted heterocycloalkyl, heterocycloalkyl substituted with one or more $X^3$ groups, or said substituted or unsubstituted heterocycloalkyl group is fused with aryl, heteroaryl, cycloalkyl or heterocycloalkyl;

each $W^1$ is independently selected from the group consisting of halogen, —CN, —OH, —O—S(O)$_2$-haloalkyl, unsubstituted aryl, aryl substituted with one or more Z groups, unsubstituted heteroaryl, heteroaryl substituted with one or more Z groups, and —O-alkyl;

each $W^2$ is independently selected from the group consisting of halogen, unsubstituted aryl, and aryl substituted with one or more Z groups;

each $W^3$ is independently selected from the group consisting of —OH, alkyl, -alkylene-OH, —O-alkyl, —C(O)-alkyl, —C(O)NH$_2$, —NHC(O)alkyl, —NHC(O)H, -NHC(O)—O-alkyl and —C(O)—O-alkyl; or two $W^3$ groups together with the ring carbon atom to which they are attached form a carbonyl group;

each $W^4$ is independently halogen or alkyl;

$Ar^1$ is selected from the group consisting of unsubstituted phenyl and phenyl substituted with one or more $X^1$ groups;

$Ar^2$ is selected from the group consisting of unsubstituted phenyl, phenyl substituted with one or more $X^1$ groups, pyridyl-2-yl and pyridyl-2-yl substituted with one or more $X^2$ groups;

each $X^1$ is independently selected from the group consisting of halogen, —CN, —O—$R^{19}$, —OH, —O—S(O)$_2$-haloalkyl, unsubstituted aryl, aryl substituted with one or more Z groups, unsubstituted heteroaryl, heteroaryl substituted with one or more Z groups, —O-cycloalkyl, —O-cycloalkylalkyl, —O-alkylene-O$R^{19}$, —O-alkylene-C(O)N($R^{20}$)$_2$, —O-alkylene-O—$R^{19}$, unsubstituted —O-alkyl, —O-alkyl substituted with one or more U groups, —O-alkenyl, —O-alkylene-O-alkylene-O$R^{19}$, —O-alkylene-C(O)$R^{24}$, —O-alkylene-C(O)O$R^{19}$, —O-alkyl, —N($R^{25}$)$_2$, —C(O)alkyl, —C(O)OH, —C(O)O-alkyl, —C(O)O-cycloalkyl, —C(O)N($R^{25}$)$_2$, —O-alkylene-heterocycloalkyl, —O-alkylene-heterocycloalkyl substituted with one or more $W^3$ groups, unsubstituted heterocycloalkyl, -heterocycloalkyl substituted with one or more $W^3$ groups, —O-alkenylene-O-alkylene-O—$R^{24}$, —O-alkylene-N($R^{25}$)$_2$, —O-alkylene-C(O)N($R^{25}$)$_2$, unsubstituted cycloalkyl, cycloalkyl substituted with one or more $W^4$ groups, —S(O)—$R^{24}$, —S(O)$_2$—$R^{24}$, and alkenyl;

with the proviso wherein the group —N($R^{20}$)$_2$ or —N($R^{25}$)$_2$, both $R^2$ or $R^{25}$ groups taken together with the N atom to which they are bonded form an unsubstituted heterocycloalkyl, heterocycloalkyl substituted with one or more $X^3$ groups, or said substituted or unsubstituted heterocycloalkyl group is fused with aryl, heteroaryl, cycloalkyl or heterocycloalkyl;

each $X^2$ is independently selected from the group consisting of halogen, —CN, —O—$R^{19}$, —OH, —O—S(O)$_2$-haloalkyl, unsubstituted aryl, aryl substituted with one or more Z groups, unsubstituted heteroaryl, heteroaryl substituted with one or more Z groups, —O-cycloalkyl, —O-cycloalkylalkyl, —O-alkylene-O$R^{19}$, —O-alkylene-C(O)N($R^{20}$)$_2$, —O-alkylene-O—$R^{19}$, unsubstituted —O-alkyl, —O-alkyl substituted with one or more U groups, —O-alkenyl, —O-alkylene-O-alkylene-OR$^{19}$, —O-alkylene-C(O)R$^{24}$, —O-alkylene-C(O)OR$^{19}$, —O-alkyl, —N(R$^{25}$)$_2$, —C(O)alkyl, —C(O)OH, —C(O)O-alkyl, —C(O)O-cycloalkyl, —C(O)N(R$^{25}$)$_2$, —O-alkylene-heterocycloalkyl, —O-alkylene-heterocycloalkyl substituted with one or more W$^3$ groups, unsubstituted heterocycloalkyl, -heterocycloalkyl substituted with one or more W$^3$ groups, —O-alkenylene-O-alkylene-O—R$^{24}$, —O-alkylene-N(R$^{25}$)$_2$, —O-alkylene-C(O)N(R$^{25}$)$_2$, unsubstituted cycloalkyl, cycloalkyl substituted with one or more W$^4$ groups, —S(O)—R$^{24}$, —S(O)$_2$—R$^{24}$, and alkenyl;

with the proviso wherein the group —N(R$^{20}$)$_2$ or —N(R$^{25}$)$_2$ both R$^2$ or R$^{25}$ groups taken together with the N atom to which they are bonded form an unsubstituted heterocycloalkyl, heterocycloalkyl substituted with one or more X$^3$ groups, or said substituted or unsubstituted heterocycloalkyl group is fused with aryl, heteroaryl, cycloalkyl or heterocycloalkyl;

each X$^3$ is independently selected from the group consisting of —OH, alkyl, -alkylene-OH, —O-alkyl, —C(O)-alkyl, —C(O)NH$_2$, —NHC(O)alkyl, —NHC(O)H, —NHC(O)—O-alkyl and —C(O)—O-alkyl; or two X$^3$ groups together with the ring carbon atom to which they are attached form a carbonyl group;

each X$^4$ is independently halogen or alkyl;

each U is independently selected from the group consisting of —OH, —O-alkyl, —O-aryl, —O-alkylene-aryl, —O-alkylene-O-alkyl, —O-alkylene-O-haloalkyl, —O-alkylene-O-aryl, halogen, —CN, cycloalkyl, heterocycloalkyl, aryl, heteroaryl, OTBS, OTIPS and OTf; and each Z is independently selected from the group consisting of —OH; —O-alkyl; halogen; alkyl; —CN; —CF$_3$; cycloalkyl; -alkylene-OH; -alkylene-O-alkyl; -alkylene-O-alkyl substituted with one or more groups selected from the group consisting of —OH, —O-alkyl, halogen, —CN, cycloalkyl, heterocycloalkyl, aryl, heteroaryl; -alkylene-O-alkylene-O-alkyl; -alkylene-O-alkylene-O-aryl; -alkylene-O-aryl; and -alkylene-O-aryl substituted with one or more groups selected from the group consisting of halogen, —CN, —OH, —O—S(O)$_2$-haloalkyl, aryl, heteroaryl and —O-alkyl; or two Z groups together with the ring carbon atom to which they are attached form a carbonyl group.

2. The compound of claim 1, or a pharmaceutically acceptable salt, solvate or ester thereof, wherein:

m is 0 or 1, n is 1 or 2, and m+n is 1 or 2;

R$^1$ and R$^2$ together with the carbon atoms to which they are shown attached in Formula (I) form a group Q as shown in Formula (IA):

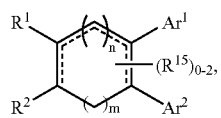

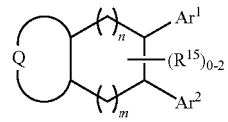
(IA)

wherein Q is selected from the group consisting of:

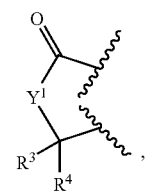
(a)

Y$^1$ is —O— or —N(R$^7$)—;

R$^3$, and R$^4$, are each independently selected from the group consisting of H, —O—R$^9$, R$^{11}$, and —N(R$^{16}$)$_2$;

R$^7$ is selected from the group consisting of H, (C$_1$-C$_6$)alkyl, (C$_6$-C$_{12}$)aryl(C$_1$-C$_6$)alkyl, (C$_2$-C$_6$)alkenyl, —(C$_1$-C$_6$)alkylene-N(R$^9$)$_2$, —(C$_1$-C$_6$)alkylene-O—R$^9$, —(C$_1$-C$_6$)alkylene-R$^{12}$, —C(O)—R$^{14}$, —(C$_1$-C$_6$)alkylene-C(O)H, —C(O)—O—R$^{11}$, and Boc;

R$^9$ is selected from the group consisting of H, TBS, TIPS, Tf and R$^{11}$;

R$^{11}$ is selected from the group consisting of unsubstituted (C$_1$-C$_6$)alkyl, (C$_1$-C$_6$)alkyl substituted with one or more U groups, —(C$_1$-C$_6$)alkylene-O—(C$_1$-C$_6$)alkyl, —(C$_1$-C$_6$)alkylene-O—(C$_6$-C$_{12}$)aryl, unsubstituted (C$_6$-C$_{12}$)aryl, and (C$_6$-C$_{12}$)aryl substituted with one or more X$^1$ groups;

R$^{12}$ is selected from the group consisting of unsubstituted (C$_6$-C$_{12}$)aryl and (C$_6$-C$_{12}$)aryl substituted with one or more X$^1$ groups;

R$^{13}$ is selected from the group consisting of unsubstituted (C$_2$-C$_{10}$)heteroaryl and (C$_2$-C$_{10}$)heteroaryl substituted with one or more X$^2$ groups;

R$^{14}$ is selected from the group consisting of unsubstituted (C$_3$-C$_7$)cycloalkyl, (C$_3$-C$_7$)cycloalkyl substituted with one or more X$^4$ groups unsubstituted (C$_1$-C$_6$) alkyl and (C$_1$-C$_6$)alkyl substituted with one or more U groups;

each R$^{15}$ is independently selected from the group consisting of H, —N$_3$, halogen, (C$_2$-C$_6$)alkenyl, —(C$_1$-C$_6$)alkylene-R$^{12}$, —(C$_1$-C$_6$)alkylene-O—R$^9$, —(C$_1$-C$_6$)alkylene-N(R$^{18}$)$_2$, —(C$_1$-C$_6$)alkylene-C(O)H, —OH, —CN, —O—(C$_1$-C$_6$)alkyl, —C(O)N(R$^{18}$)$_2$, —N(R$^{18}$)$_2$, NR$^{18}$C(O)R$^{18}$, —NR$^{18}$C(O)$_2$R$^{18}$, —NR$^{18}$C(O)N(R$^{18}$)$_2$, —NR$^{18}$S(O)$_2$R$^{18}$, —O—(C$_2$-C$_6$)alkenyl, —C(O)$_2$R$^{18}$, unsubstituted (C$_1$-C$_6$)alkyl, (C$_1$-C$_6$)alkyl substituted with one or more U groups, —O—(C$_1$-C$_6$)alkylene-C(O)R$^{18}$, or —C(O)R$^{18}$;

with the proviso wherein the group —N(R$^{18}$)$_2$, both R$^{18}$ groups taken together with the N atom to which they are bonded form an unsubstituted (C$_3$-C$_5$)heterocycloalkyl, (C$_3$-C$_5$)heterocycloalkyl substituted with one or more X$^3$ groups, or said substituted or unsubstituted (C$_3$-C$_5$) heterocycloalkyl group is fused with (C$_6$-C$_{12}$)aryl, (C$_2$-C$_{10}$)heteroaryl, (C$_3$-C$_7$)cycloalkyl or (C$_3$-C$_5$)heterocycloalkyl;

R$^{16}$ is selected from the group consisting of R$^9$ and —C(O)—R$^{12}$;

each $R^{18}$ is independently selected from the group consisting of H, unsubstituted $(C_3-C_5)$heterocycloalkyl, $(C_3-C_5)$heterocycloalkyl substituted with one or more $X^3$ groups, $R^{12}$, $R^{13}$ and $R^{14}$;

with the proviso that when $R^{18}$ is attached to N, then each $R^{18}$ is independently selected from the group consisting of H, unsubstituted $(C_3-C_5)$heterocycloalkyl, $(C_3-C_5)$heterocycloalkyl substituted with one or more $W^3$ groups, —C(O)$R^{21}$, $R^{12}$, $R^{13}$ and $R^{14}$;

$R^{19}$ is selected from the group consisting of H, TBS, TIPS, Tf and $R^{21}$;

each $R^{20}$ is independently selected from the group consisting of H, unsubstituted $(C_1-C_6)$alkyl, $(C_1-C_6)$alkyl substituted with one or more U groups, —$(C_1-C_6)$alkylene-$R^{22}$, —$(C_1-C_6)$alkylene-$R^{23}$, —$(C_1-C_6)$alkylene-$R^{24}$, —C(O)—$R^{24}$, —$(C_1-C_6)$alkylene-O—$R^{19}$, $R^{24}$, unsubstituted $(C_3-C_5)$heterocycloalkyl, $(C_3-C_5)$heterocycloalkyl substituted with one or more $W^3$ groups, and benzo-fused $(C_3-C_7)$cycloalkyl;

$R^{21}$ is selected from the group consisting of unsubstituted $(C_1-C_6)$alkyl, $(C_1-C_6)$alkyl substituted with one or more U groups, —$(C_1-C_6)$alkylene-O—$(C_1-C_6)$alkyl, —$(C_1-C_6)$alkylene-O—$(C_6-C_{12})$aryl, unsubstituted $(C_6-C_{12})$aryl, and $(C_6-C_{12})$aryl substituted with one or more $W^1$ groups, unsubstituted $(C_2-C_{10})$heteroaryl, $(C_2-C_{10})$heteroaryl substituted with one or more $W^2$ groups, unsubstituted $(C_3-C_7)$cycloalkyl, $(C_3-C_7)$cycloalkyl substituted with one or more $W^4$ groups, unsubstituted $(C_3-C_5)$heterocycloalkyl, $(C_3-C_5)$heterocycloalkyl with one or more $W^3$ groups, —O—$(C_1-C_6)$alkylene-O—$R^{24}$, —C(O)—O—$(C_1-C_6)$alkylene-O—$R^{24}$; —C(O)—$(C_1-C_6)$alkylene—$R^{23}$, —C(O)—$R^{22}$, C(O)—$R^{24}$, —C(O)—O—$R^{22}$, —C(O)—O—$R^{24}$, —NH$R^{22}$, —NH$R^{24}$, —S(O)$_2$—$R^{24}$, and —$(C_1-C_6)$alkylene-O—$(C_1-C_6)$alkylene-O—$R^{24}$, with the proviso that —O—O— cannot be formed with $R^{21}$ and the atom said $R^{21}$ is attached to;

$R^{22}$ is selected from the group consisting of unsubstituted $(C_6-C_{12})$aryl and $(C_6-C_{12})$aryl substituted with one or more $W^1$ groups;

$R^{23}$ is selected from the group consisting of unsubstituted $(C_2-C_{10})$heteroaryl and $(C_2-C_{10})$heteroaryl substituted with one or more $W^2$ groups;

$R^{24}$ is selected from the group consisting of unsubstituted $(C_3-C_7)$cycloalkyl, $(C_3-C_7)$cycloalkyl substituted with one or more $X^4$ groups, unsubstituted $(C_1-C_6)$alkyl and $(C_1-C_6)$alkyl substituted with one or more U groups;

each $R^{25}$ is independently selected from the group consisting of H, $R^{22}$, $R^{23}$, unsubstituted $(C_1-C_6)$alkyl, $(C_1-C_6)$alkyl substituted with one or more U groups, unsubstituted $(C_3-C_7)$cycloalkyl, $(C_3-C_7)$cycloalkyl substituted with one or more $W^4$ groups, —$(C_1-C_6)$alkylene-O$R^{19}$, —$(C_1-C_6)$alkylene-N$R^{19}R^{19}$, —$(C_1-C_6)$alkylene-S$R^{19}$, —$(C_1-C_6)$alkylene-$R^{23}$, —$(C_1-C_6)$alkylene-$R^{22}$, unsubstituted $(C_3-C_5)$heterocycloalkyl, $(C_3-C_5)$heterocycloalkyl substituted with one or more $W^3$ groups, —$(C_1-C_6)$alkylene-$(C_3-C_5)$heterocycloalkyl, —$(C_1-C_6)$alkylene-$(C_3-C_5)$heterocycloalkyl substituted with one or more $W^3$ groups, —C(O)—$R^{24}$, —C(O)—$R^{22}$, —C(O)—$R^{24}$, —C(O)—O—$R^{22}$, —C(O)—O—$R^{24}$, —NH$R^{22}$, —NH$R^{24}$, —S(O)$_2$—$R^{24}$, —C(O)—NH—$R^{22}$ and —C(O)—NH—$R^{24}$;

with the proviso wherein the group —N($R^{25}$)$_2$ both $R^{25}$ groups taken together with the N atom to which they are bonded form an unsubstituted $(C_3-C_5)$heterocycloalkyl, $(C_3-C_5)$heterocycloalkyl substituted with one or more $X^3$ groups, or said substituted or unsubstituted $(C_3-C_5)$heterocycloalkyl group is fused with $(C_6-C_{12})$aryl, $(C_2-C_{10})$heteroaryl, $(C_3-C_7)$cycloalkyl or $(C_3-C_5)$heterocycloalkyl;

each $W^1$ is independently selected from the group consisting of halogen, —CN, —OH, —O—S(O)$_2$-$C_1-C_6$haloalkyl, unsubstituted $(C_6-C_{12})$aryl, $(C_6-C_{12})$aryl substituted with one or more Z groups, unsubstituted $(C_2-C_{10})$heteroaryl, $(C_2-C_{10})$heteroaryl substituted with one or more Z groups, and —O—$(C_1-C_6)$alkyl;

each $W^2$ is independently selected from the group consisting of halogen, unsubstituted $(C_6-C_{12})$aryl, and $(C_6-C_{12})$aryl substituted with one or more Z groups;

each $W^3$ is independently selected from the group consisting of —OH, $(C_1-C_6)$alkyl, —$(C_1-C_6)$alkylene-OH, —O—$(C_1-C_6)$alkyl, —C(O)—$(C_1-C_6)$alkyl, —C(O)NH$_2$, —NHC(O) $(C_1-C_6)$alkyl, —NHC(O)H, —NHC(O)—O—$(C_1-C_6)$alkyl and —C(O)—O—$(C_1-C_6)$alkyl; or two $W^3$ groups together with the ring carbon atom to which they are attached form a carbonyl group;

each $W^4$ is independently halogen or $(C_1-C_6)$alkyl;

Ar$^1$ is selected from the group consisting of unsubstituted phenyl and phenyl substituted with one or more $X^1$ groups;

Ar$^2$ is selected from the group consisting of unsubstituted phenyl, phenyl substituted with one or more $X^1$ groups, pyridyl-2-yl and pyridyl-2-yl substituted with one or more $X^2$ groups;

each $X^1$ is independently selected from the group consisting of halogen, —CN, —O—$R^{19}$, —OH, —O—S(O)$_2$-$(C_1-C_6)$haloalkyl, unsubstituted $(C_6-C_{12})$aryl, $(C_6-C_{12})$aryl substituted with one or more Z groups, unsubstituted $(C_2-C_{10})$heteroaryl, $(C_2-C_{10})$heteroaryl substituted with one or more Z groups, —O—$(C_3-C_7)$cycloalkyl, —O—$(C_3-C_7)$cycloalkyl$(C_1-C_6)$alkyl, —O—$(C_1-C_6)$alkylene-O$R^{19}$, —O—$(C_1-C_6)$alkylene-C(O)N($R^{20}$)$_2$, —O—$(C_1-C_6)$alkylene-O—$R^{19}$, unsubstituted —O—$(C_1-C_6)$alkyl, —O—$(C_1-C_6)$alkyl substituted with one or more U groups, —O—$(C_2-C_7)$alkenyl, —O—$(C_1-C_6)$alkylene-O—$(C_1-C_6)$alkylene-O$R^{19}$, —O—$(C_1-C_6)$alkylene-C(O)$R^{24}$, —O—$(C_1-C_6)$alkylene-C(O)O$R^{19}$, —O—$(C_1-C_6)$alkyl, —N($R^{25}$)$_2$, —C(O)$(C_1-C_6)$alkyl, —C(O)OH, —C(O)O—$(C_1-C_6)$alkyl, —C(O)O—$(C_3-C_7)$cycloalkyl, —C(O)N($R^{25}$)$_2$, —O—$(C_1-C_6)$alkylene-$(C_3-C_5)$heterocycloalkyl, —O—$(C_1-C_6)$alkylene-$(C_3-C_5)$heterocycloalkyl substituted with one or more $W^3$ groups, unsubstituted $(C_3-C_5)$heterocycloalkyl, —$(C_3-C_5)$heterocycloalkyl substituted with one or more $W^3$ groups, —O—$(C_2-C_7)$alkenylene-O—$(C_1-C_6)$alkylene-O—$R^{24}$, —O—$(C_1-C_6)$alkylene-N($R^{25}$)$_2$, —O—$(C_1-C_6)$alkylene-C(O)N($R^{25}$)$_2$, unsubstituted $(C_3-C_7)$cycloalkyl, $(C_3-C_7)$cycloalkyl substituted with one or more $W^4$ groups, —S(O)—$R^{24}$, —S(O)$_2$—$R^{24}$, and $(C_2-C_7)$alkenyl;

with the proviso wherein the group —N($R^{20}$)$_2$ or —N($R^{25}$)$_2$ both $R^{20}$ or $R^{25}$ groups taken together with the N atom to which they are bonded form an unsubstituted $(C_3-C_5)$heterocycloalkyl, $(C_3-C_5)$heterocycloalkyl substituted with one or more $X^3$ groups, or said substituted or unsubstituted $(C_3-C_5)$heterocycloalkyl group is fused with $(C_6-C_{12})$aryl, $(C_2-C_1$ heteroaryl, $(C_3-C_7)$cycloalkyl or $(C_3-C_5)$ heterocycloalkyl;

each $X^2$ is independently selected from the group consisting of halogen, —CN, —O—$R^{19}$, —OH, —O—S(O)$_2$—$(C_1-C_6)$haloalkyl, unsubstituted $(C_6-C_{12})$aryl, $(C_6-C_{12})$aryl substituted with one or more Z groups, unsubstituted $(C_2-C_{10})$heteroaryl, $(C_2-C_{10})$heteroaryl substituted with one or more Z groups, —O—($C_3$-$C_7$)cycloalkyl, —O—($C_3$-$C_7$)cycloalkyl($C_1$-$C_6$)alkyl, —O—($C_1$-$C_6$)alkylene-$OR^{19}$, —O—($C_1$-$C_6$)alkylene-C(O)N($R^{20}$)$_2$, —O—($C_1$-$C_6$)alkylene-O—$R^{19}$, unsubstituted —O—($C_1$-$C_6$)alkyl, —O—($C_1$-$C_6$)alkyl substituted with one or more U groups, —O—($C_2$-$C_7$)alkenyl, —O—($C_1$-$C_6$)alkylene-O—($C_1$-$C_6$)alkylene-$OR^{19}$, —O—($C_1$-$C_6$)alkylene-C(O)$R^{24}$, —O—($C_1$-$C_6$)alkylene-C(O)$OR^{19}$, —O—($C_1$-$C_6$)alkyl, —N($R^{25}$)$_2$, —C(O)($C_1$-$C_6$)alkyl, —C(O)OH, —C(O)O—($C_1$-$C_6$)alkyl, —C(O)O—($C_3$-$C_7$)cycloalkyl, —C(O)N($R^{25}$)$_2$, —O—($C_1$-$C_6$)alkylene-($C_3$-$C_5$)heterocycloalkyl, —O—($C_1$-$C_6$)alkylene-($C_3$-$C_5$)heterocycloalkyl substituted with one or more $W^3$ groups, unsubstituted($C_3$-$C_5$)heterocycloalkyl, —($C_3$-$C_5$)heterocycloalkyl substituted with one or more $W^3$ groups, —O—($C_2$-$C_7$)alkenylene-O—($C_1$-$C_6$)alkylene-O—$R^{24}$, —O—($C_1$-$C_6$)alkylene-N($R^{25}$)$_2$, —O—($C_1$-$C_6$)alkylene-C(O)N($R^{25}$)$_2$, unsubstituted ($C_3$-$C_7$)cycloalkyl, ($C_3$-$C_7$)cycloalkyl substituted with one or more $W^4$ groups, —S(O)—$R^{24}$, —S(O)$_2$—$R^{24}$, and ($C_2$-$C_7$)alkenyl;

with the proviso wherein the group —N($R^{20}$)$_2$ or —N($R^{25}$)$_2$ both $R^{20}$ or $R^{25}$ groups taken together with the N atom to which they are bonded form an unsubstituted ($C_3$-$C_5$)heterocycloalkyl, ($C_3$-$C_5$)heterocycloalkyl substituted with one or more $X^3$ groups, or said substituted or unsubstituted ($C_3$-$C_5$)heterocycloalkyl group is fused with ($C_6$-$C_{12}$)aryl, ($C_2$-$C_{10}$)heteroaryl, ($C_3$-$C_7$)cycloalkyl or ($C_3$-$C_5$)heterocycloalkyl;

each $X^3$ is independently selected from the group consisting of —OH, ($C_1$-$C_6$)alkyl, —($C_1$-$C_6$)alkylene-OH, —O—($C_1$-$C_6$)alkyl, —C(O)—($C_1$-$C_6$)alkyl, —C(O)NH$_2$, —NHC(O) ($C_1$-$C_6$)alkyl, —NHC(O)H, —NHC(O)—O—($C_1$-$C_6$)alkyl and —C(O)—O—($C_1$-$C_6$)alkyl; or two $X^3$ groups together with the ring carbon atom to which they are attached form a carbonyl group;

each $X^4$ is independently halogen or ($C_1$-$C_6$)alkyl;

each U is independently selected from the group consisting of —OH, —O—($C_1$-$C_6$)alkyl, —O—($C_6$-$C_{12}$)aryl, —O—($C_1$-$C_6$)alkylene-($C_6$-$C_{12}$)aryl, —O—($C_1$-$C_6$)alkylene-O—($C_1$-$C_6$)alkyl, —O—($C_1$-$C_6$)alkylene-O—($C_1$-$C_6$)haloalkyl, —O—($C_1$-$C_6$)alkylene-O—($C_6$-$C_{12}$)aryl, halogen, —CN, ($C_3$-$C_7$)cycloalkyl, ($C_3$-$C_5$)heterocycloalkyl, ($C_6$-$C_{12}$)aryl, ($C_2$-$C_{10}$)heteroaryl, OTBS, OTIPS and OTf; and each Z is independently selected from the group consisting of —OH; —O—($C_1$-$C_6$)alkyl; halogen; ($C_1$-$C_6$)alkyl; —CN; —$CF_3$; ($C_3$-$C_7$)cycloalkyl; —($C_1$-$C_6$)alkylene-OH; —($C_1$-$C_6$)alkylene-O—($C_1$-$C_6$)alkyl; —($C_1$-$C_6$)alkylene-O—($C_1$-$C_6$)alkyl substituted with one or more groups selected from the group consisting of —OH, —O—($C_1$-$C_6$)alkyl, halogen, —CN, ($C_3$-$C_7$)cycloalkyl, ($C_3$-$C_5$)heterocycloalkyl, ($C_6$-$C_{12}$)aryl, ($C_2$-$C_{10}$)heteroaryl; —($C_1$-$C_6$)alkylene-O—($C_1$-$C_6$)alkylene-O—($C_1$-$C_6$)alkyl; —($C_1$-$C_6$)alkylene-O—($C_1$-$C_6$)alkylene-O—($C_6$-$C_{12}$)aryl; —($C_1$-$C_6$)alkylene-O—($C_6$-$C_{12}$)aryl; and —($C_1$-$C_6$)alkylene-O—($C_6$-$C_{12}$)aryl substituted with one or more groups selected from the group consisting of halogen, —CN, —OH, —O—S(O)$_2$—($C_1$-$C_6$)haloalkyl, ($C_6$-$C_{12}$)aryl, ($C_2$-$C_{10}$)heteroaryl and —O—($C_1$-$C_6$)alkyl; or two Z groups together with the ring carbon atom to which they are attached form a carbonyl group.

3. The compound of claim 1, or a pharmaceutically acceptable salt, solvate or ester thereof having the following Formula (II):

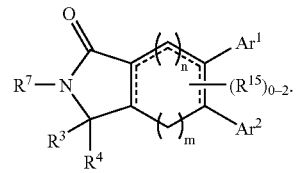

(II)

4. The compound of claim 3, or a pharmaceutically acceptable salt, solvate or ester thereof having the following Formula (IIA):

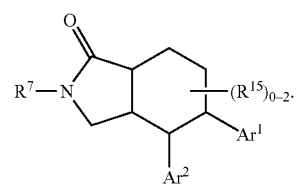

(IIA)

5. The compound of claim 4, or a pharmaceutically acceptable salt, solvate or ester thereof having the following Formula (IIB):

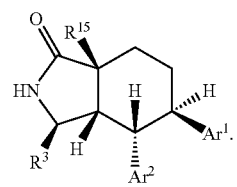

(IIB)

6. The compound of claim 4, or a pharmaceutically acceptable salt, solvate or ester thereof, wherein:

$Ar^1$ is selected from the group consisting of unsubstituted phenyl and phenyl substituted with one or more $X^1$ groups;

$Ar^2$ is selected from the grow consisting of unsubstituted Phenyl, phenyl substituted with one or more $X^1$ groups, pyridyl-2-yl and pyridyl-2-yl substituted with one or more $X^2$ groups;

$R^7$ is selected from the group consisting of H, alkyl, alkenyl, -alkylene-N($R^9$)$_2$, -alkylene-O—$R^9$, -alkylene-$R^{12}$, —C(O)—$R^{14}$, -alkylene-C(O)H, and —C(O)—O—$R^{11}$;

$R^9$ is selected from the group consisting of H and alkyl;

$R^{14}$ is selected from the group consisting of alkyl, unsubstituted cycloalkyl, or cycloalkyl substituted with one or more $X^4$ groups; and each $R^{15}$ is independently selected from the group consisting of H, alkyl, alkenyl, -alkylene-$R^{12}$, and —O-alkenyl.

7. The compound of claim 6, or a pharmaceutically acceptable salt, solvate or ester thereof, wherein:

$Ar^1$ is phenyl substituted with one or more $X^1$ groups;

$Ar^2$ is phenyl substituted with one or more $X^1$ groups or pyridyl substituted with one or more $X^2$ groups;

$R^7$ is H; and
$R^{15}$ is alkyl.

8. The compound of claim 1, or a pharmaceutically acceptable salt, solvate or ester thereof, having the following Formula (III):

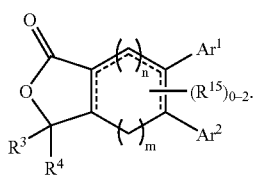
(III)

9. The compound of claim 8, or a pharmaceutically acceptable salt, solvate or ester thereof, having the following Formula (IIIA):

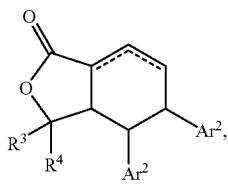
(IIIA)

wherein:
$Ar^1$ is selected from the group consisting of unsubstituted phenyl and phenyl substituted with one or more $X^1$ groups;
$Ar^2$ is selected from the group consisting of unsubstituted phenyl, phenyl substituted with one or more $X^1$ groups, pyridyl-2-yl and pyridyl-2-yl substituted with one or more $X^2$ groups; and
$R^3$ and $R^4$ are each independently H or alkyl.

10. The compound of claim 9, or a pharmaceutically acceptable salt, solvate or ester thereof, wherein:
$R^3$ and $R^4$ are each independently H or —$CH_3$;
$Ar^1$ is unsubstituted phenyl or phenyl substituted with one or more halogens; and
$Ar^2$ is selected from the group consisting of unsubstituted phenyl, phenyl substituted with one or more halogens, unsubstituted pyridyl, and pyridyl substituted with one or more $X^2$ groups.

11. The compound of claim 1, or a pharmaceutically acceptable salt, solvate or ester thereof, having the following Formula (V):

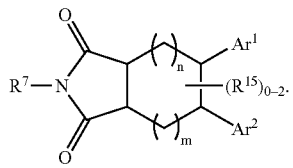
(V)

12. The compound of claim 1, or a pharmaceutically acceptable salt, solvate or ester thereof, having the following Formula (ID):

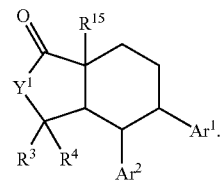
(ID)

13. The compound of claim 12, or a pharmaceutically acceptable salt, solvate or ester thereof, having the following Formula (IE):

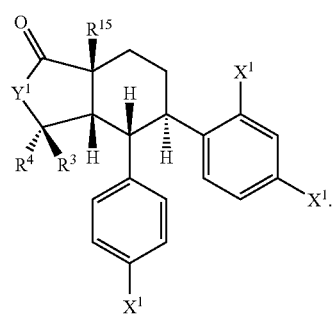
(IE)

14. The compound of claim 12, or a pharmaceutically acceptable salt, solvate or ester thereof, wherein:
$Y^1$ is NH or N-Boc;
$R^3$ is H or alkyl;
$R^4$ is H or alkyl;
$R^{15}$ is alkyl;
and
$Ar^1$ and $Ar^2$ are selected from the group consisting of unsubstituted phenyl and phenyl substituted with one or more $X^1$ groups.

15. The compound of claim 14, or a pharmaceutically acceptable salt, solvate or ester thereof, wherein:
each $X^1$ is independently selected from the group consisting of halogen, —CN, —OH, —O-cycloalkyl, O-cycloalkylalkyl, —O-alkylene-$OR^{19}$, —O-alkylene-C(O)N$(R^{20})_2$, —O-alkylene-O—$R^{19}$, unsubstituted unsubstituted—O-alkyl, —O-alkyl substituted with one or more U groups, —O-alkenyl,—O-alkylene-O-alkylene-$OR^{19}$, —O-alkylene-C(O)$R^{24}$, —O-alkylene-C(O)$OR^{19}$ and —O-alkyl.

16. The compound of claim 14, or a pharmaceutically acceptable salt, solvate or ester thereof, wherein:
each $X^1$ is independently selected from the group consisting of —$OCH_3$, —OH, —OTf, —CN, —$OCH_2CH_3$, —$OCH(CH_3)_2$,

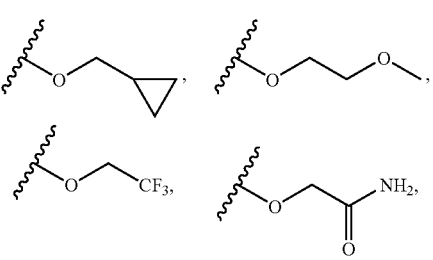

-continued

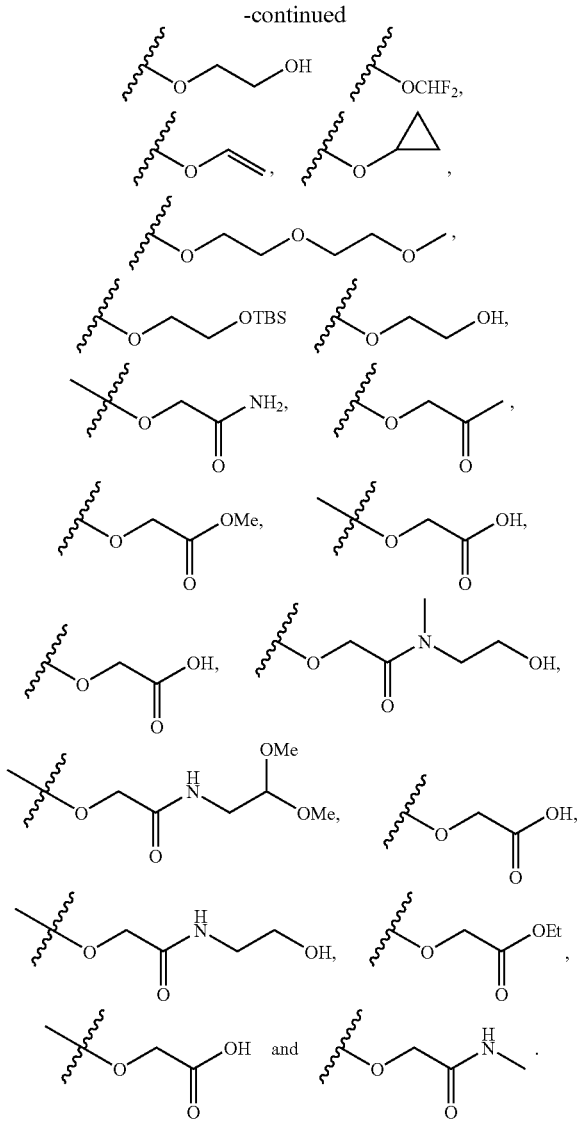

17. A compound of Formula (ID),

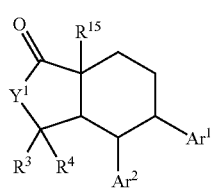

(ID)

or a pharmaceutically acceptable salt, solvate or ester thereof, wherein:

$Y^1$ is NH or N-Boc;
$R^3$ is H or alkyl;
$R^4$ is H or alkyl;
$R^{15}$ is alkyl;
$Ar^1$ and $Ar^2$ are selected from the group consisting of unsubstituted phenyl and phenyl substituted with one or more $X^1$ groups;

and
each $X^1$ is independently selected from the group consisting of —$OCH_3$, —OH, —OTf, —CN, —$OCH_2CH_3$, —$OCH(CH_3)_2$,

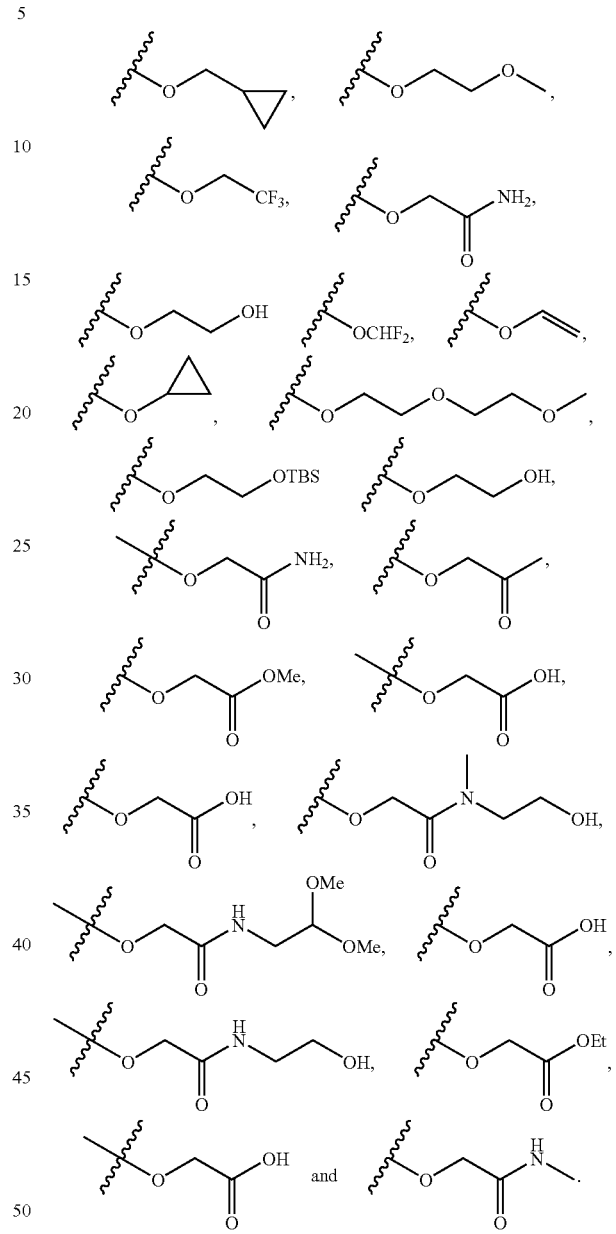

18. A compound of Formula (IE),

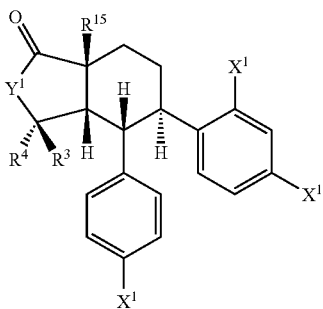

(IE)

or a pharmaceutically acceptable salt, solvate or ester thereof, wherein:

Y¹ is NH or N-Boc;

R³ is H or alkyl;

R⁴ is H or alkyl;

R¹⁵ is alkyl;

and each X¹ is independently selected from the group consisting of —OCH₃, —OH, —OTf, —CN, —OCH₂CH₃, —OCH(CH₃)₂,

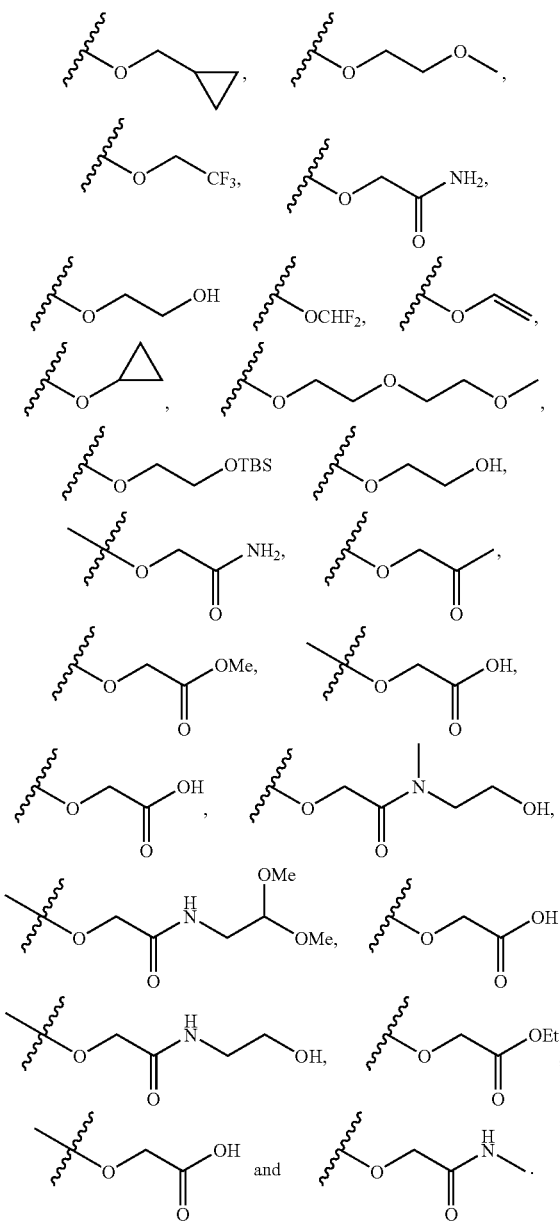

19. The compound of claim 1, or a pharmaceutically acceptable salt, solvate or ester thereof, wherein:

each R¹⁵ is independently selected from the group consisting of H, —N₃, halogen, alkenyl, -alkylene-R¹², -alkylene-O—R⁹, -alkylene-N(R¹⁸)₂, -alkylene-C(O)H, —OH, —CN, —O-alkyl, —C(O)N(R¹⁸)₂, —N(R¹⁸)₂, —NHC(O)R¹⁸, —NHC(O)₂R¹⁸, —NR¹⁸C(O)N(R¹⁸)₂, —NHS(O)₂R¹⁸, —O-alkenyl, —C(O)₂R¹⁸, unsubstituted alkyl, alkyl substituted with one or more U groups, —O-alkylene-C(O)R¹⁸, or —C(O)R¹⁸;

with the proviso wherein the group —N(R¹⁸)₂, both R¹⁸ groups taken together with the N atom to which they are bonded form an unsubstituted heterocycloalkyl, heterocycloalkyl substituted with one or more X³ groups, or said substituted or unsubstituted heterocycloalkyl group is fused with aryl, heteroaryl, cycloalkyl or heterocycloalkyl.

20. The compound of claim 1, or a pharmaceutically acceptable salt, solvate or ester thereof, wherein:

each R¹⁵ is independently selected from the group consisting of H, —OH, —OCH₃, —OCH₂CH₃, —CH₃, —CH₂CH₃, —CH₂CH₂CH₃, —N₃, —NH₂, —CO₂H, —CO₂CH₃, —CH₂OH, —CH₂CH₂OH, —CH₂CH₂OTBS, —CH₂OCH₃, —OCH₂CH₂OH,

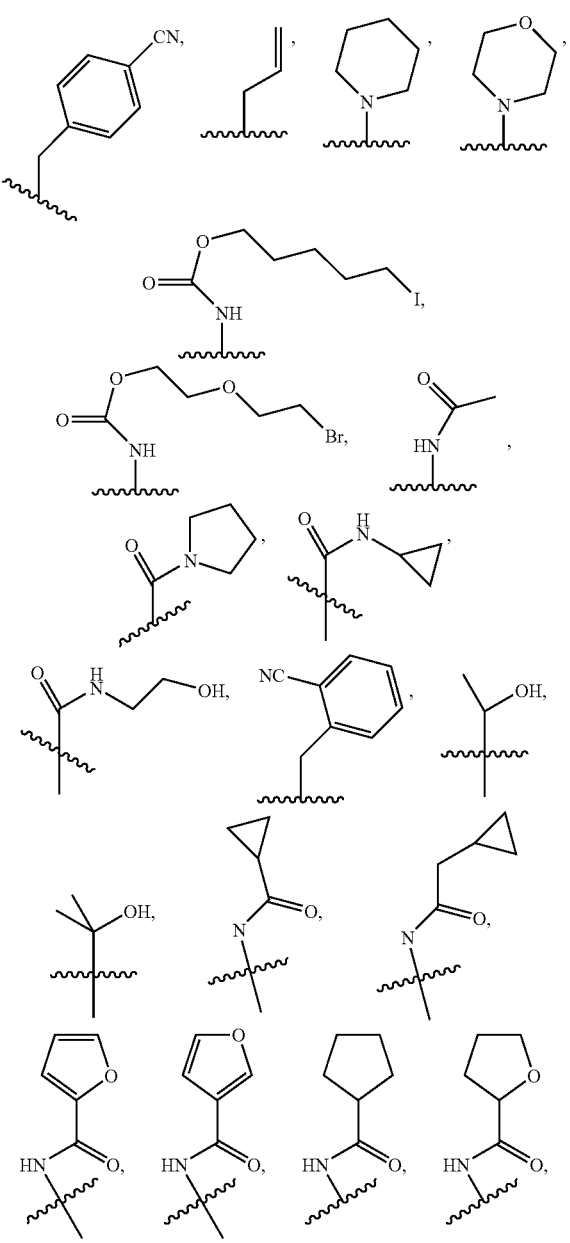

-continued

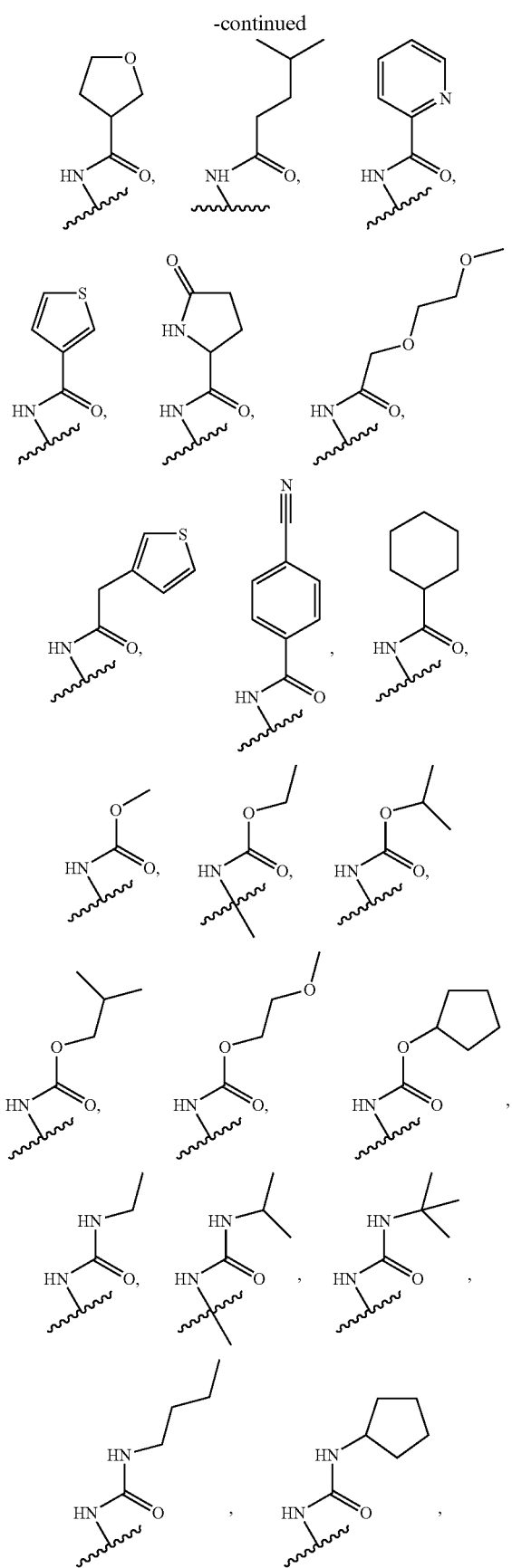

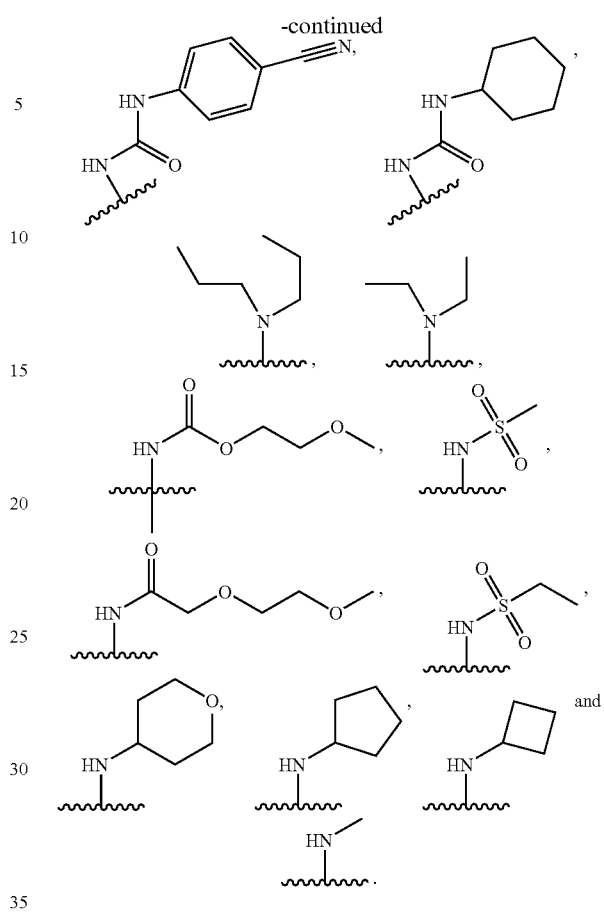

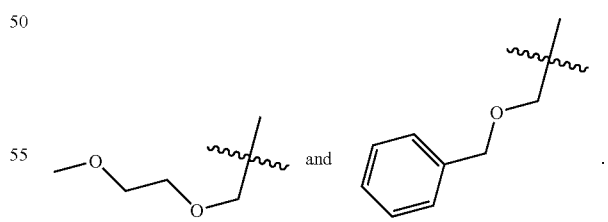 and

21. The compound of claim 1, or a pharmaceutically acceptable salt, solvate or ester thereof, wherein:
$R^3$ and $R^4$ are each independently selected from the group consisting of H, —O—$R^9$, $R^{11}$, and —N($R^{16}$)$_2$.

22. The compound of claim 1, or a pharmaceutically acceptable salt, solvate or ester thereof, wherein:
each $R^3$ and $R^4$ is independently selected from the group consisting of H, —CH$_3$, —CH$_2$OH, —CH$_2$OCH$_2$CH$_2$OCH$_3$, —CH$_2$OCH$_3$, —CH$_2$OCH$_2$CH$_3$, —CH$_2$OCH$_2$CH$_2$CH$_3$, —CH$_2$CH$_2$OH,

23. The compound of claim 1, or a pharmaceutically acceptable salt, solvate or ester thereof, wherein
$R^7$ is selected from the group consisting of H, alkyl, arylalkyl, alkenyl, -alkylene-N($R^9$)$_2$, -alkylene-O—$R^9$, -alkylene-$R^{12}$, —C(O)—$R^{14}$, -alkylene-C(O)H, —C(O)—O—$R^{11}$, and Boc.

24. The compound of claim 1, or a pharmaceutically acceptable salt, solvate or ester thereof, wherein $R^7$ is H, —$CH_3$, Boc,

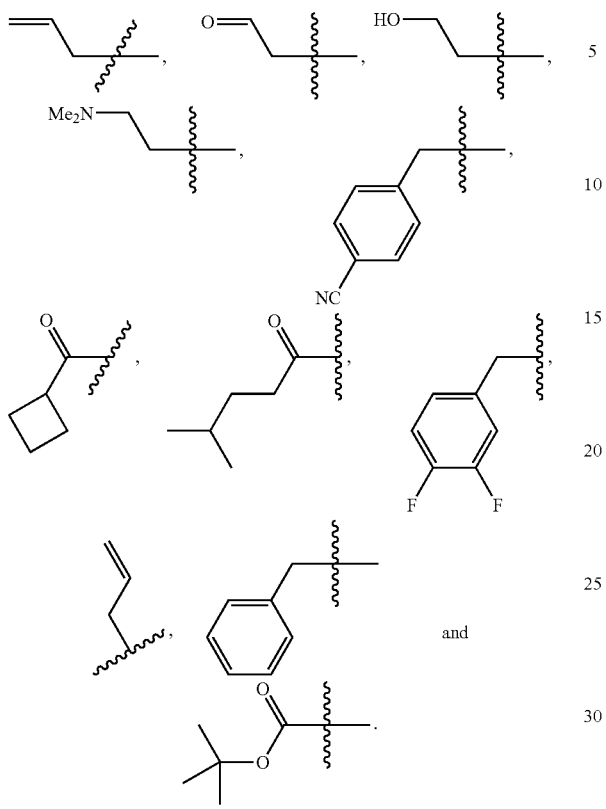

25. The compound of claim 1, or a pharmaceutically acceptable salt, solvate or ester thereof, wherein $Ar^1$ is phenyl substituted with one or more $X^1$ groups; and each $X^1$ is independently selected from the group consisting of halogen, —CN, —O—$R^{19}$, —OH, —O—$S(O)_2$-haloalkyl, unsubstituted aryl, aryl substituted with one or more Z groups, unsubstituted heteroaryl, heteroaryl substituted with one or more Z groups, —O-cycloalkyl, —O-cycloalkylalkyl, —O-alkylene-$OR^{19}$, —O-alkylene-$C(O)N(R^{20})_2$, —O-alkylene-O—$R^{19}$, unsubstituted —O-alkyl, —O-alkyl substituted with one or more U groups, —O-alkenyl, —O-alkylene-O-alkylene-$OR^{19}$, —O-alkylene-$C(O)R^{24}$, —O-alkylene-$C(O)OR^{19}$, —O-alkyl, —$N(R^{25})_2$, —C(O)alkyl, —C(O)OH, —C(O)O-alkyl, —C(O)O-cycloalkyl, —$C(O)N(R^{25})_2$, —O-alkylene-heterocycloalkyl, —O-alkylene-heterocycloalkyl substituted with one or more $W^3$ groups, unsubstituted heterocycloalkyl, -heterocycloalkyl substituted with one or more $W^3$ groups, —O-alkenylene-O-alkylene-O—$R^{24}$, —O-alkylene-N$(R^{25})_2$, —O-alkylene-$C(O)N(R^{25})_2$, unsubstituted cycloalkyl, cycloalkyl substituted with one or more $W^4$ groups, —S(O)—$R^{24}$, —$S(O)_2$—$R^{24}$, and alkenyl;

with the proviso wherein the group —$N(R^{20})_2$ or —$N(R^{25})_2$ both $R^{20}$ or $R^{25}$ groups taken together with the N atom to which they are bonded form an unsubstituted heterocycloalkyl, heterocycloalkyl substituted with one or more $X^3$ groups, or said substituted or unsubstituted heterocycloalkyl group is fused with aryl, heteroaryl, cycloalkyl or heterocycloalkyl.

26. The compound of claim 1, or a pharmaceutically acceptable salt, solvate or ester thereof, wherein:

each $X^1$ is independently selected from the group consisting of Cl, F, —$OCH_3$, —$OCH_2CH_3$, —OH, —OTf, —CN, —$OCH_2CH_3$, —$OCH(CH_3)_2$,

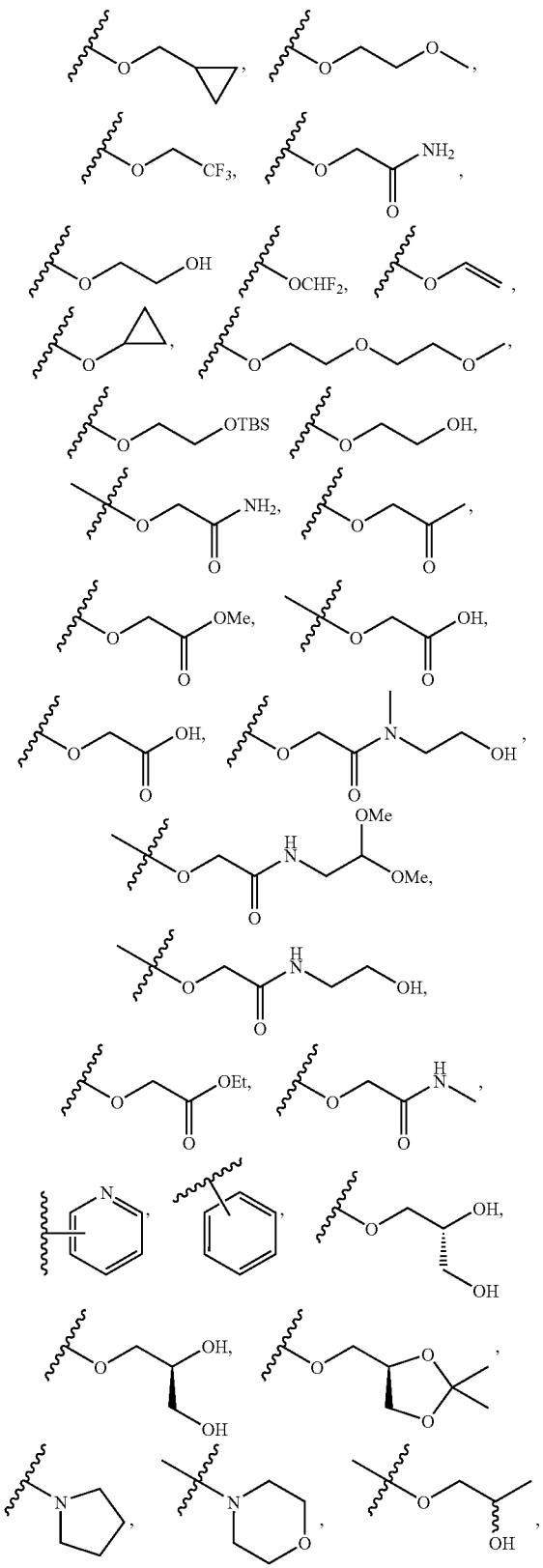

477
-continued
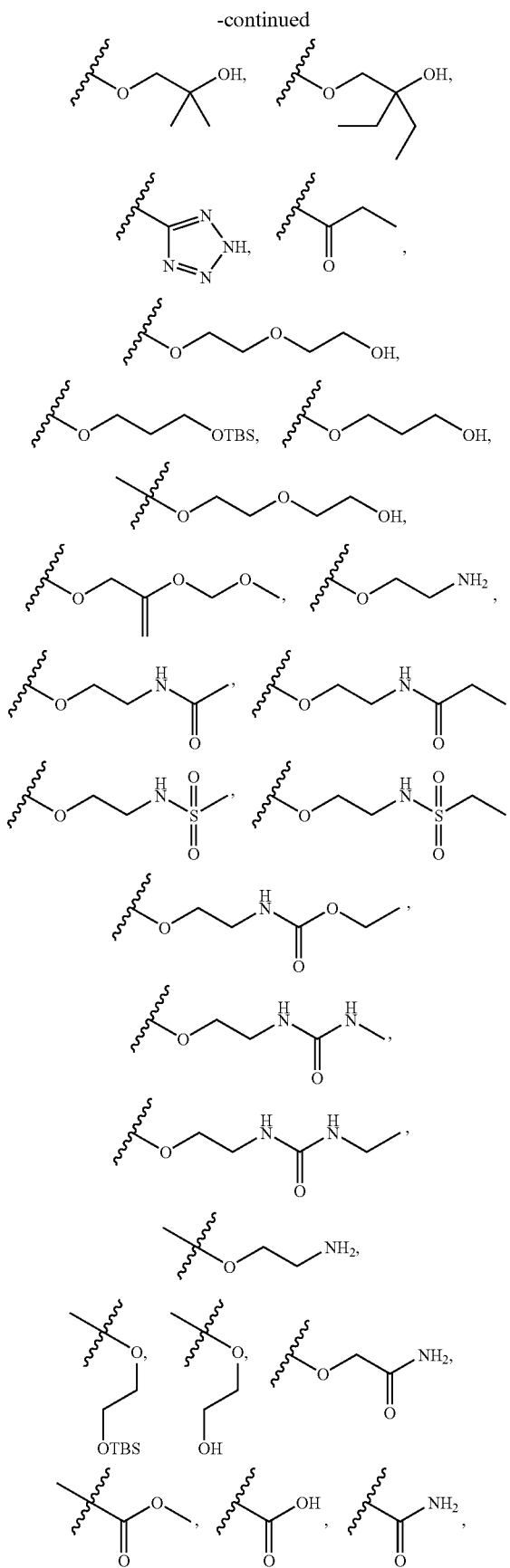
478
-continued
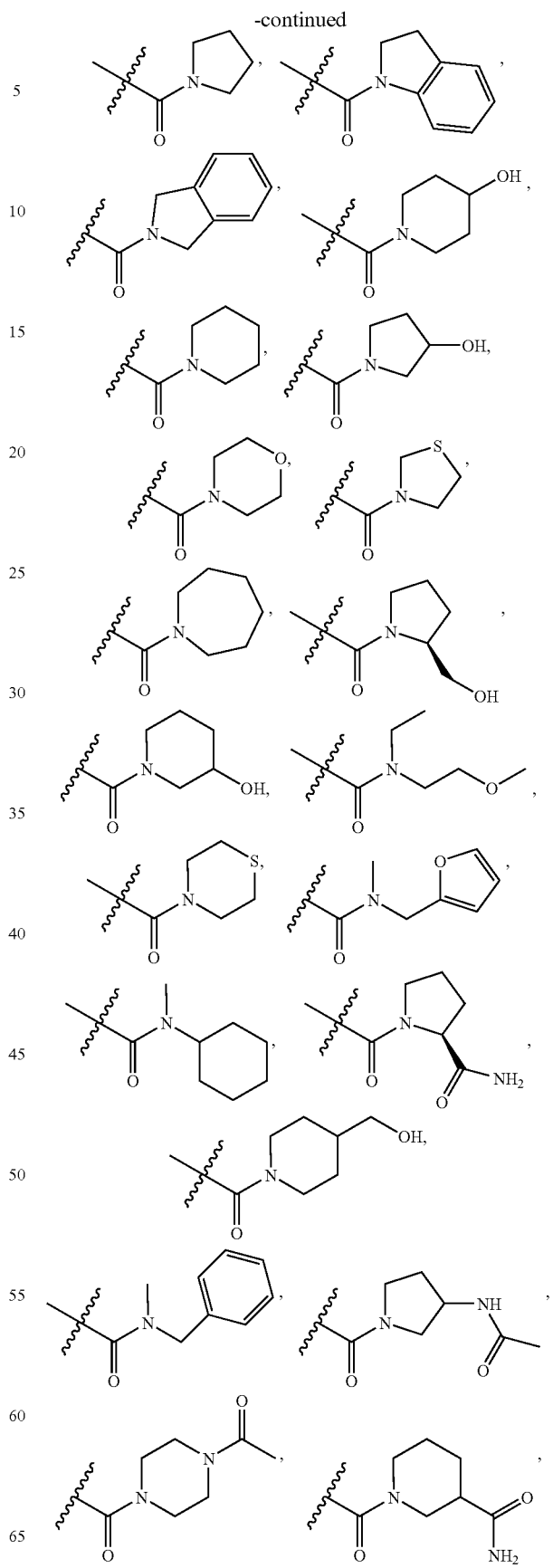

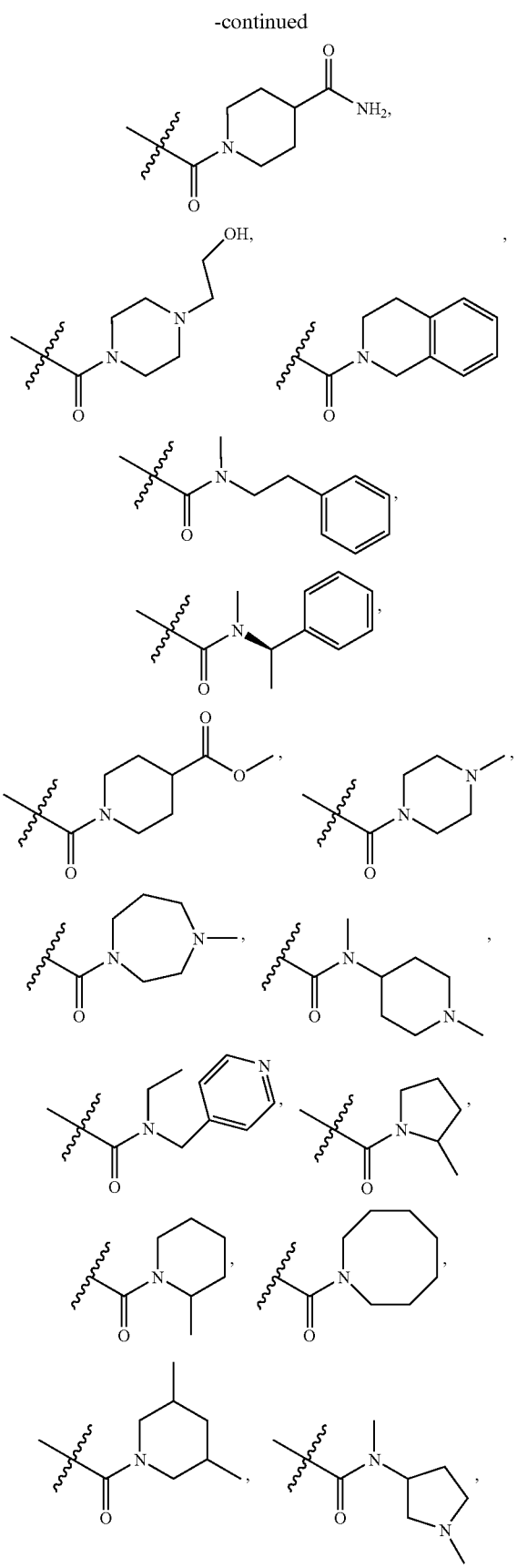
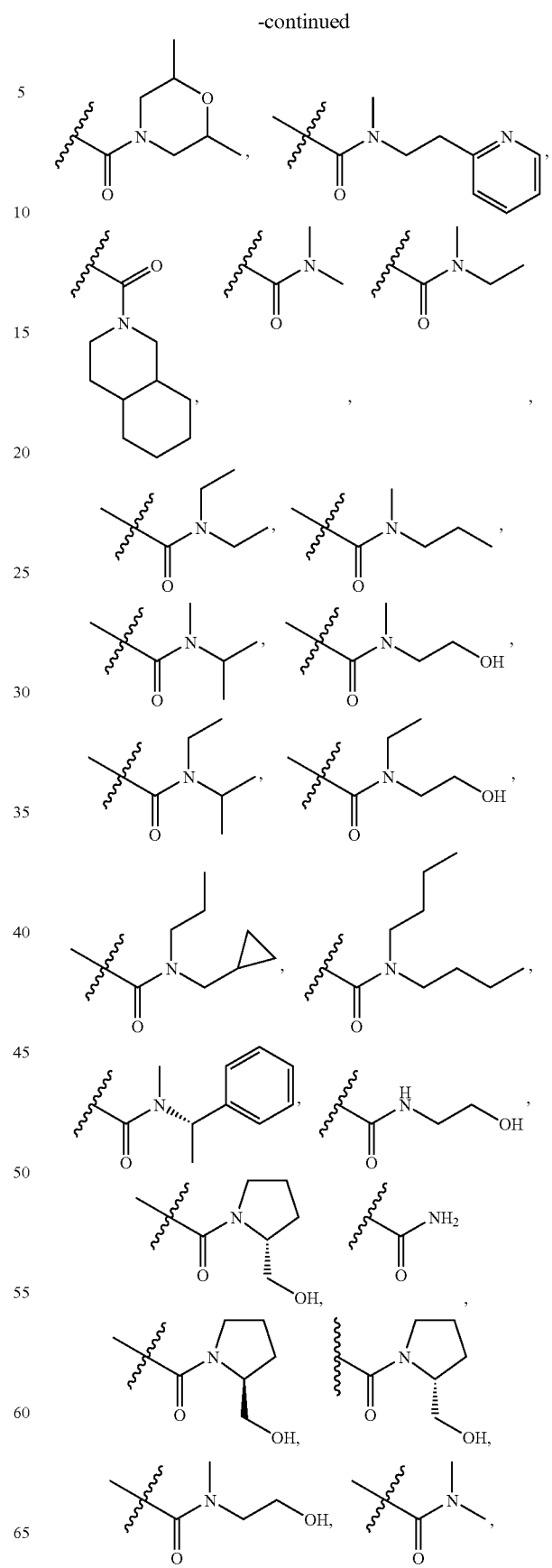

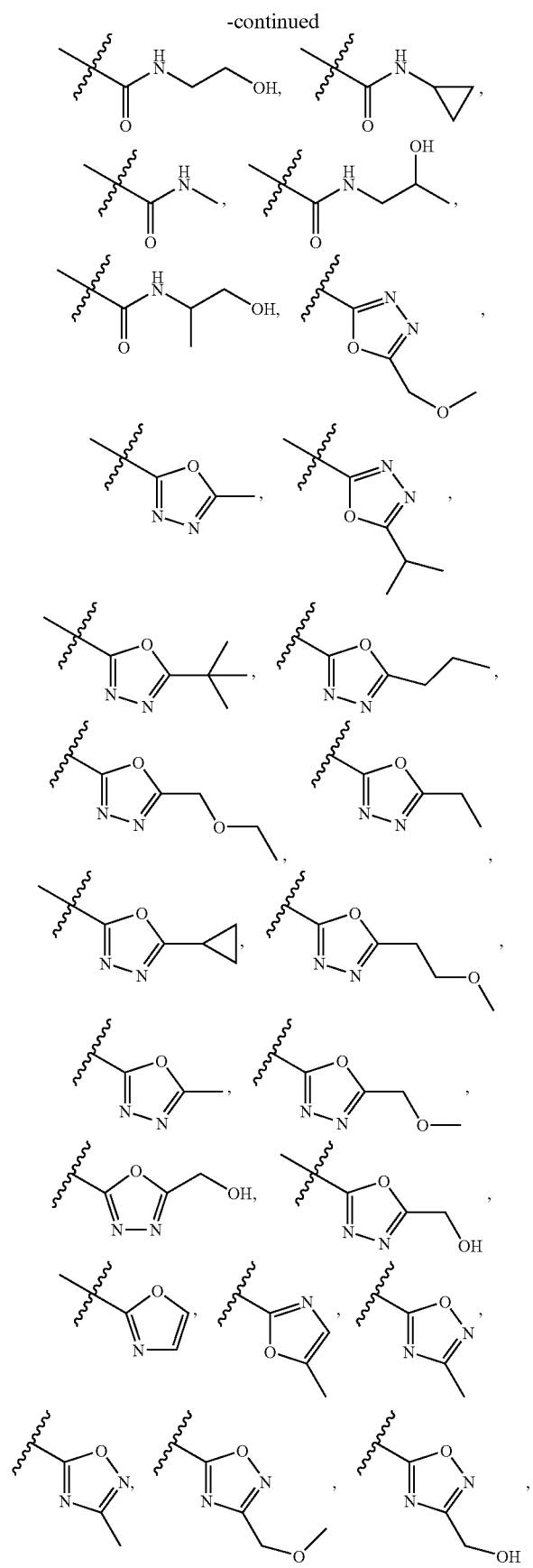
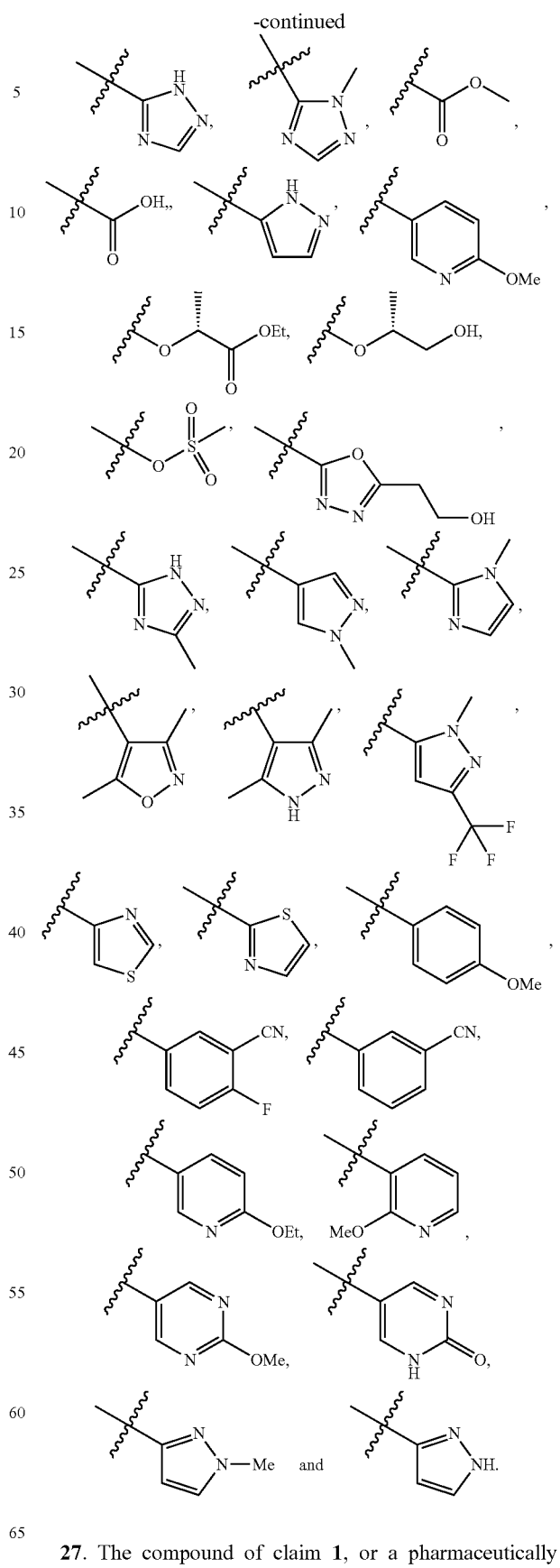
27. The compound of claim 1, or a pharmaceutically acceptable salt, solvate or ester thereof, wherein Ar² is phenyl substituted with one or more X¹ groups or pyridyl substituted with one or more X² groups;

X¹ is selected from the group consisting of —OH, —CN, halogen, —OTIPS, —OTf, —O-alkyl, —O-alkyl-OH and heteroaryl; and X² is selected from the group consisting of halogen and cycloalkyl.

28. The compound of claim 1, or a pharmaceutically acceptable salt, solvate or ester thereof, wherein Ar² is phenyl substituted with one or more X¹ groups or pyridyl substituted with one or more X² groups, X¹ is selected from the group consisting of —OH, —CN, Cl, —OTIPS, —OCH₃, —OCH₂CH₃, —OTf and

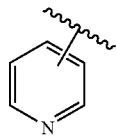

; and x² is selected from the group consisting of Cl, Br and

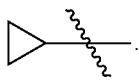

29. The compound of claim 1 or a pharmaceutically acceptable salt, solvate or ester thereof having the following Formulas (IF) or (IFa):

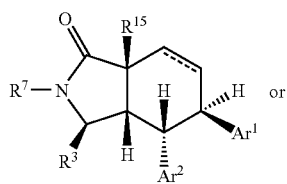

(IIF)

or (IIFa)

30. The compound of claim 1, or a pharmaceutically acceptable salt, solvate or ester thereof having the following Formula (IG):

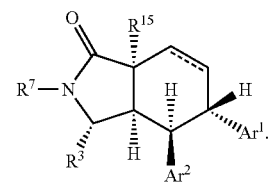

(IG)

31. The compound of claim 1, or a pharmaceutically acceptable salt, solvate or ester thereof having the following Formula (IH):

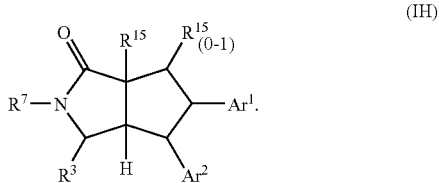

(IH)

32. A compound, or a pharmaceutically acceptable salt, solvate, ester or stereoisomer thereof, selected from the group consisting of:

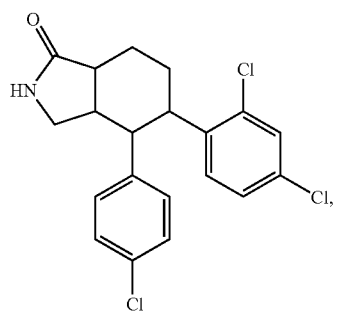

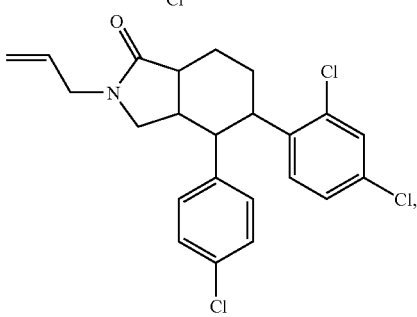

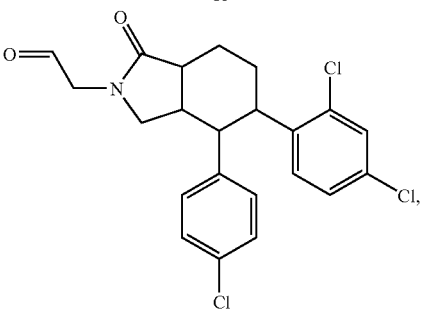

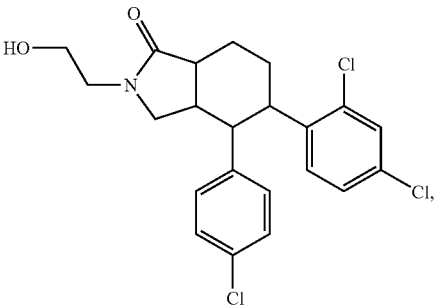

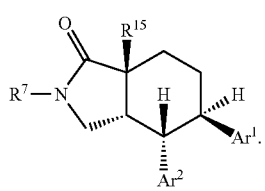

-continued
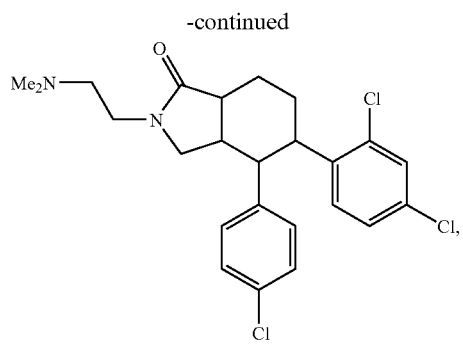
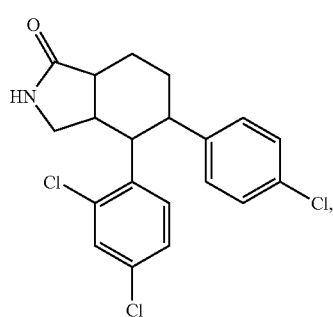
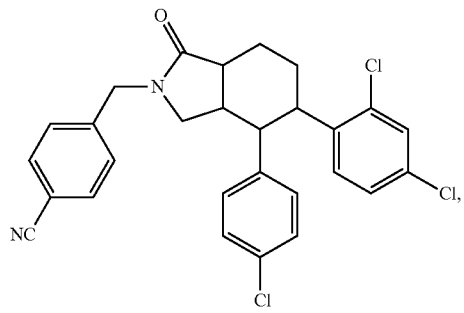
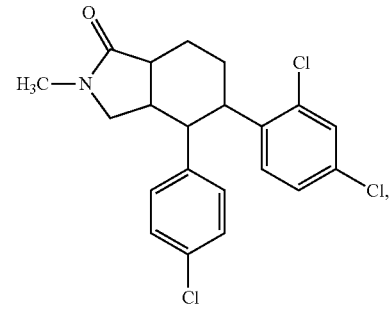
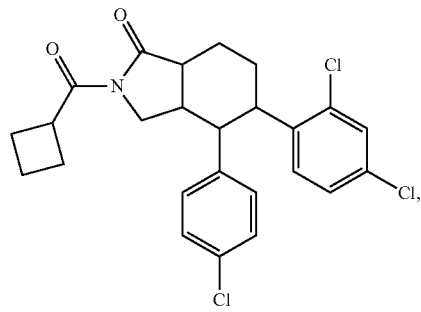
-continued
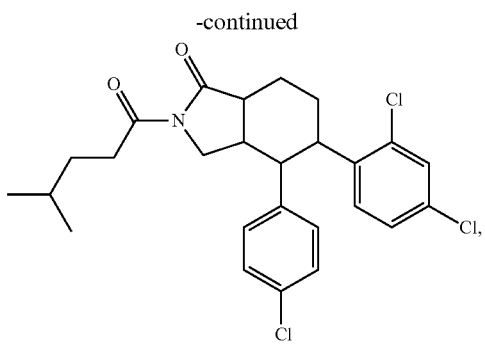
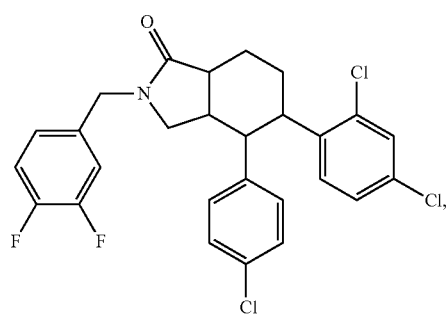
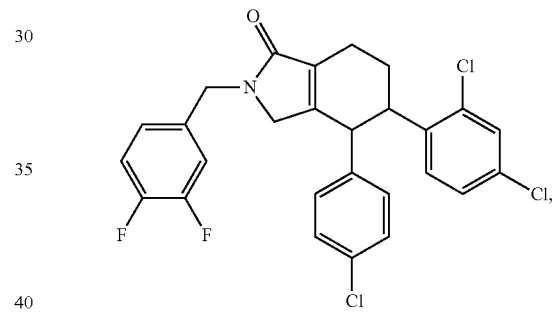
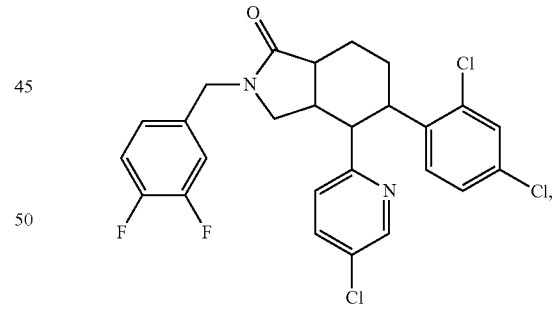
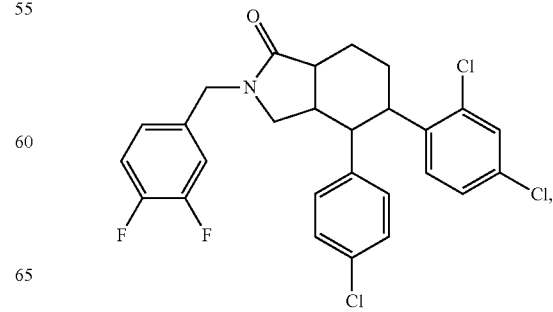

487
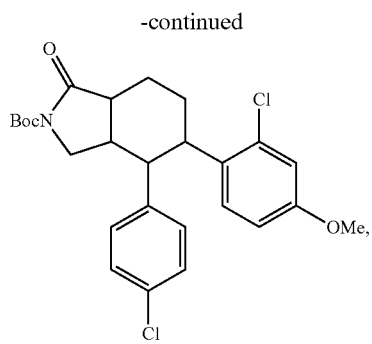
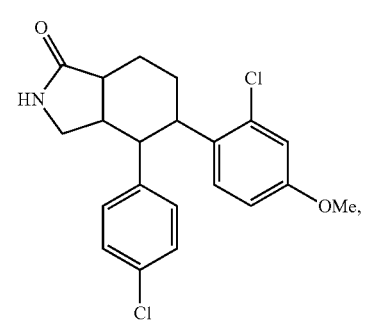
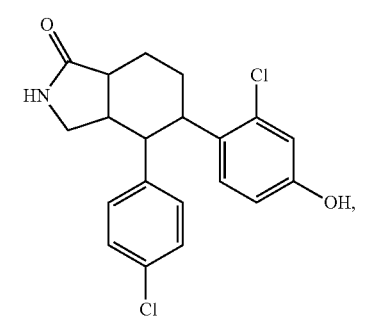
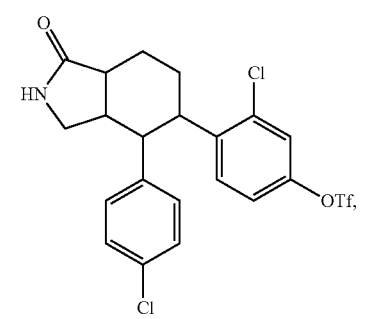
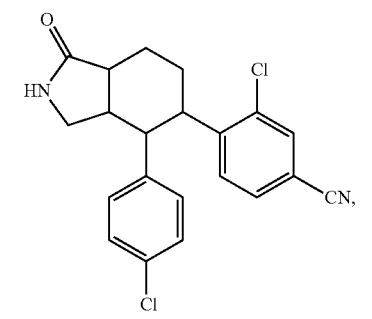
488
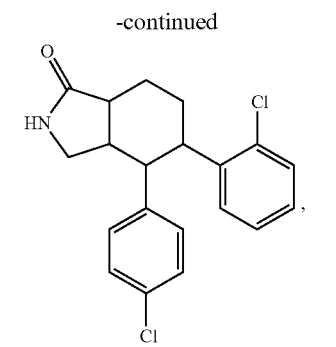
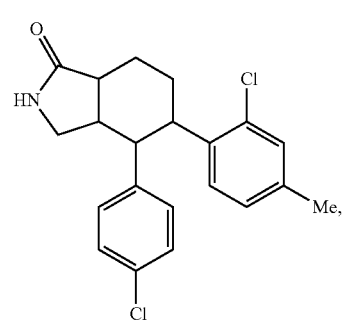
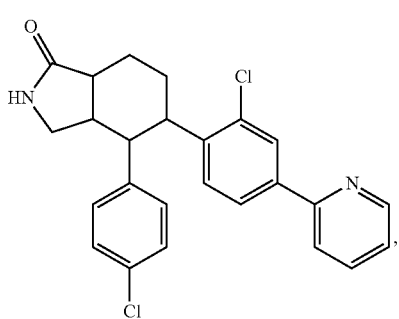
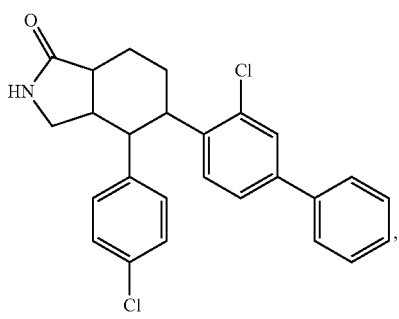
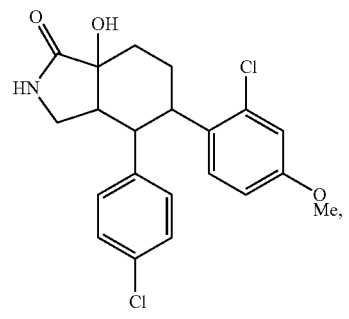

-continued
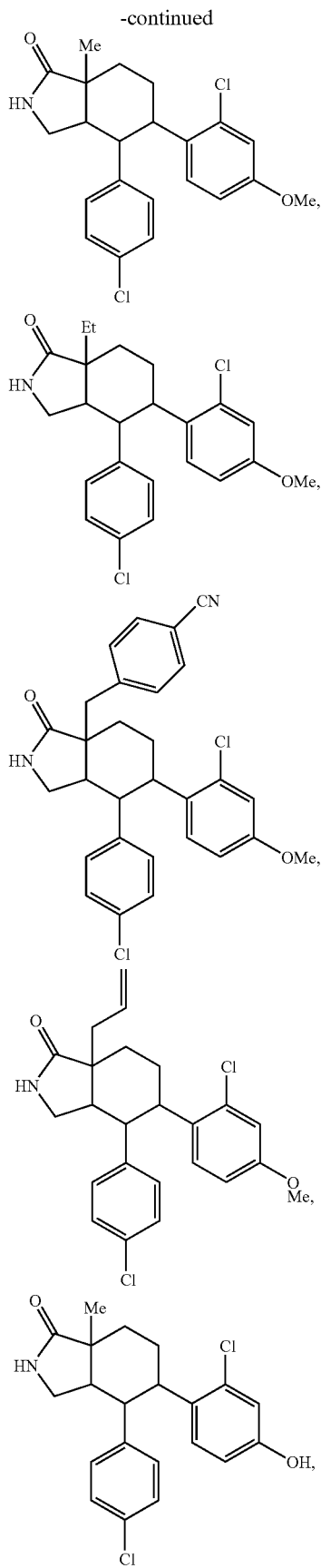
-continued
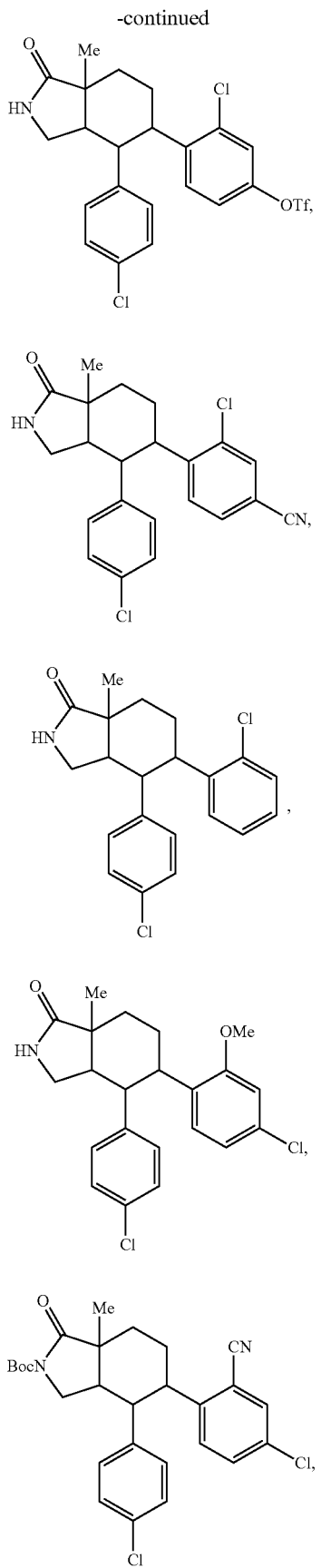

491
-continued
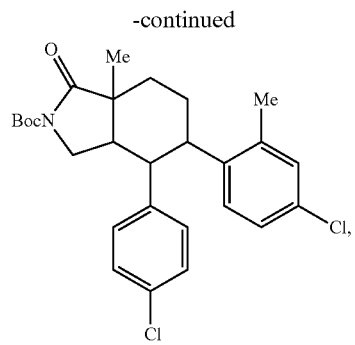
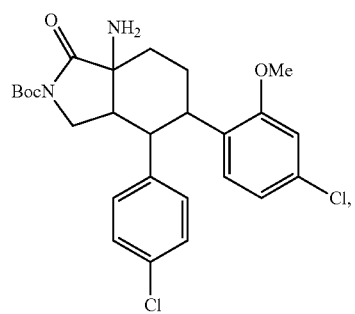
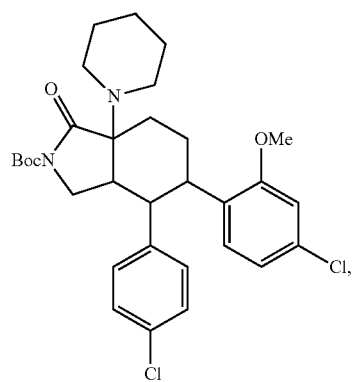
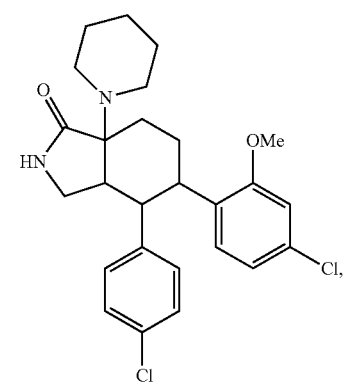
492
-continued
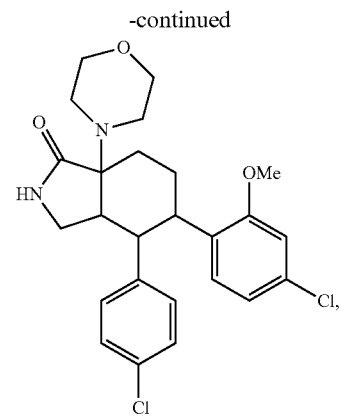
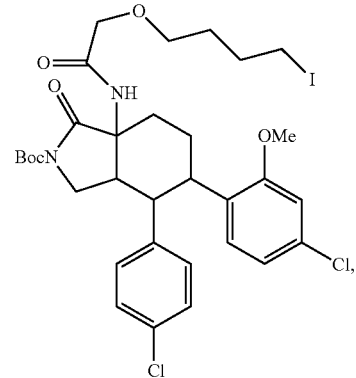
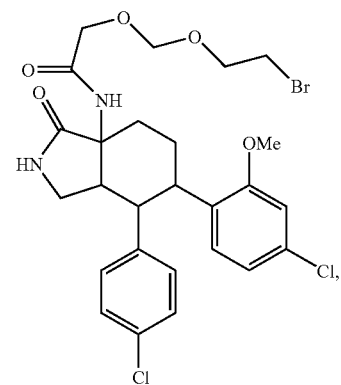
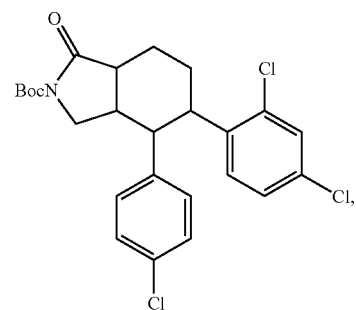

-continued
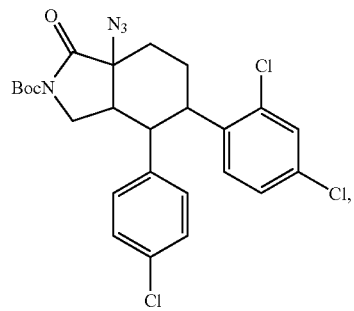
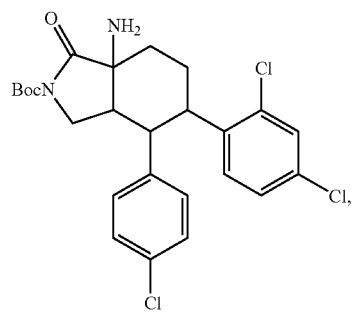
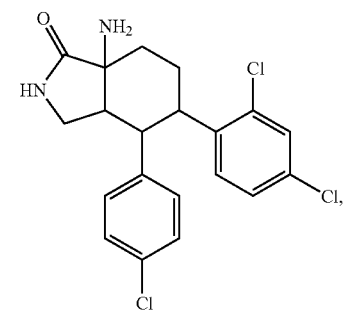
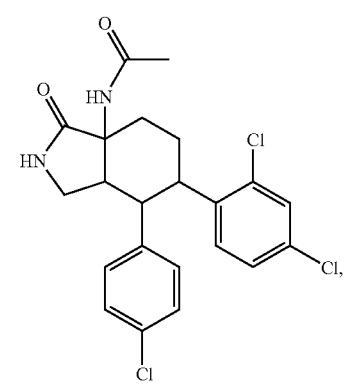
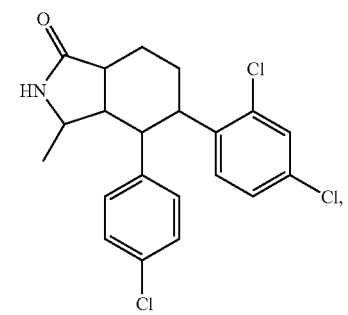
-continued
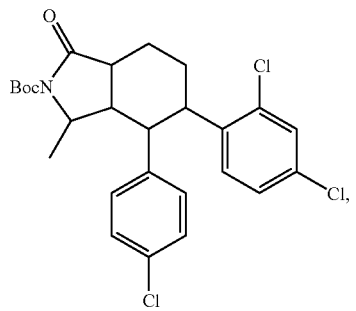
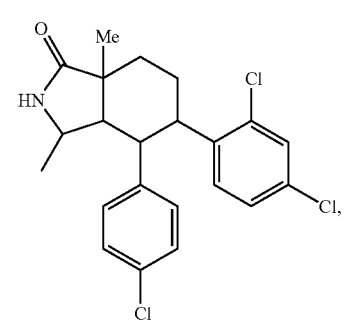
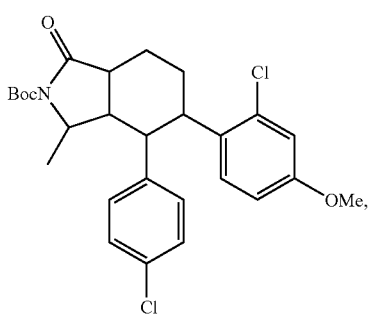
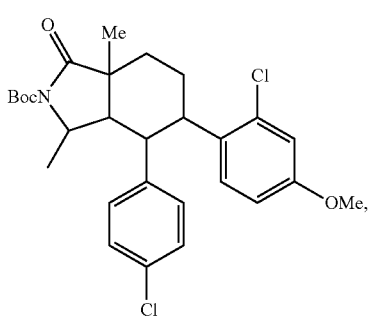
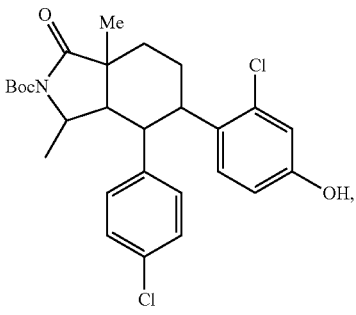

-continued
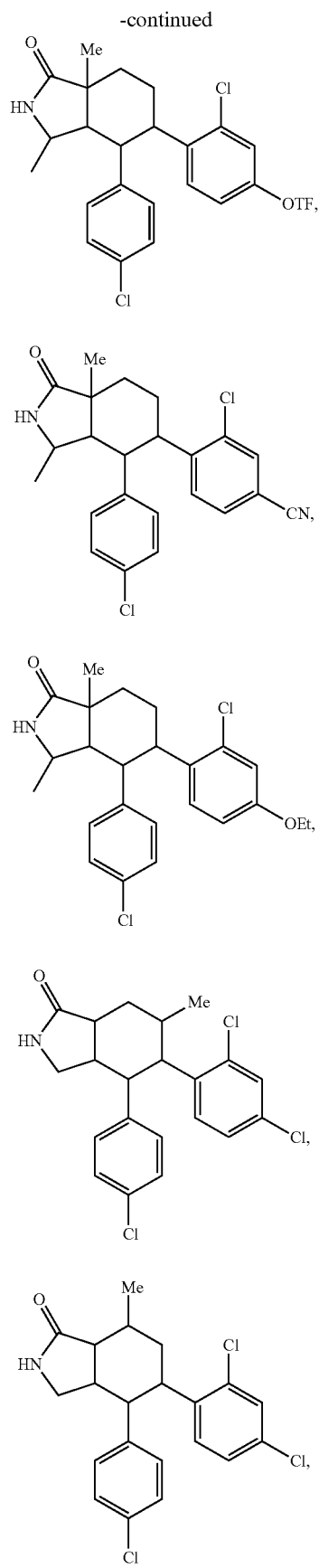
-continued
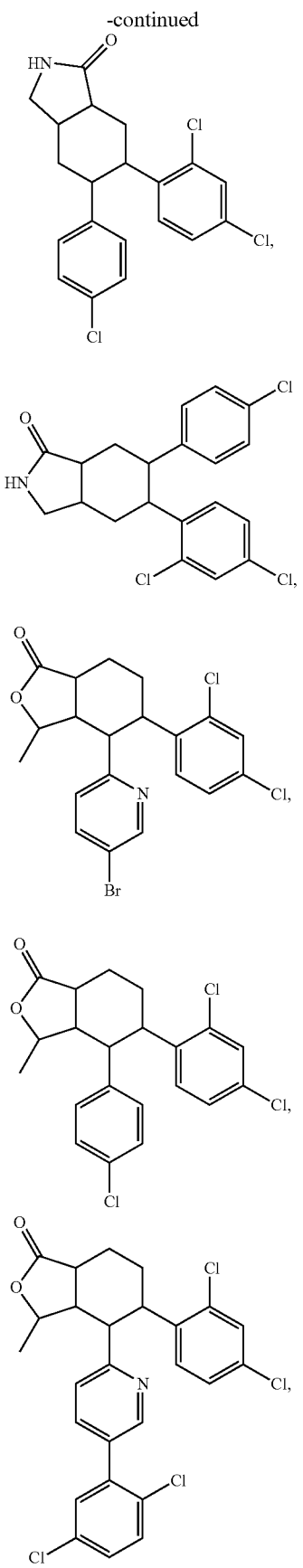

-continued
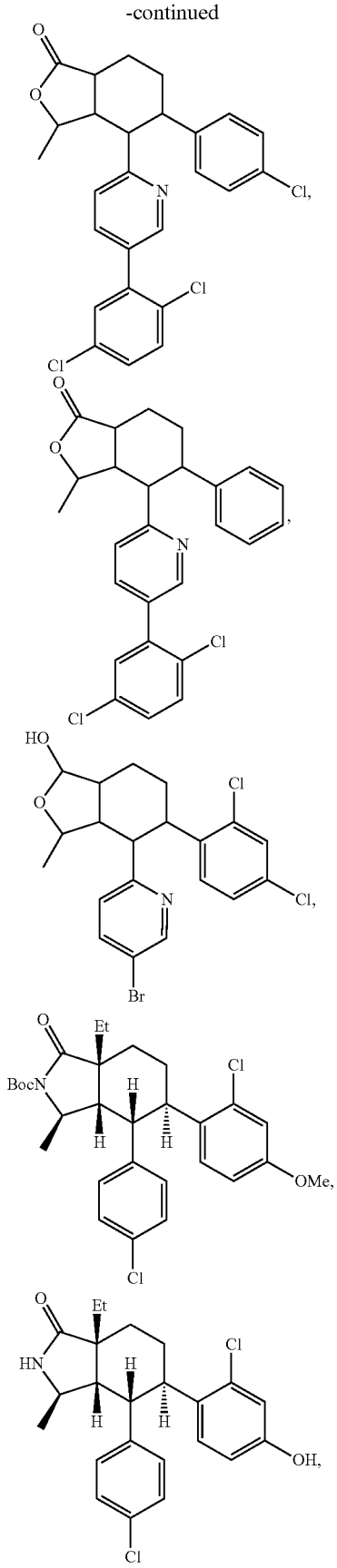
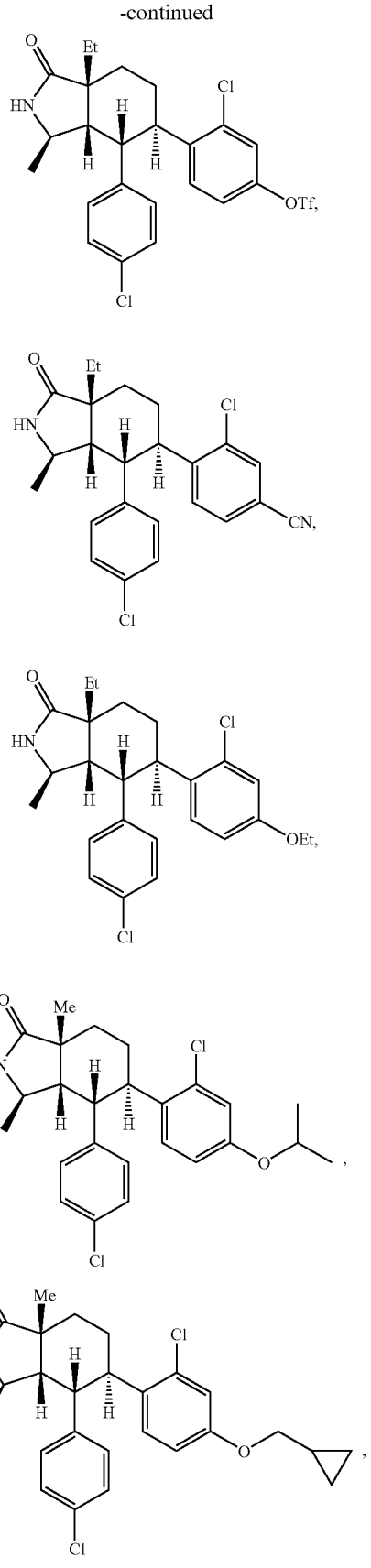

-continued
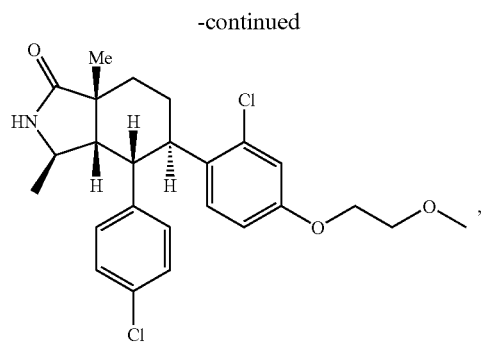
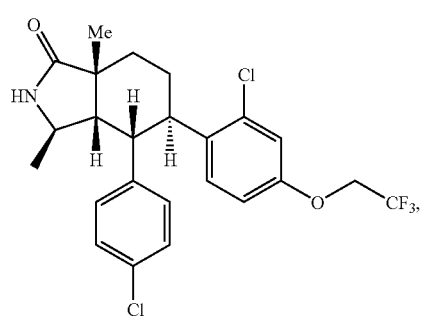
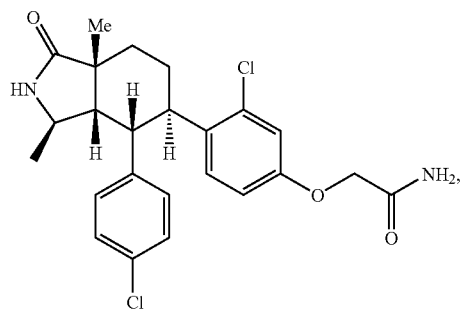
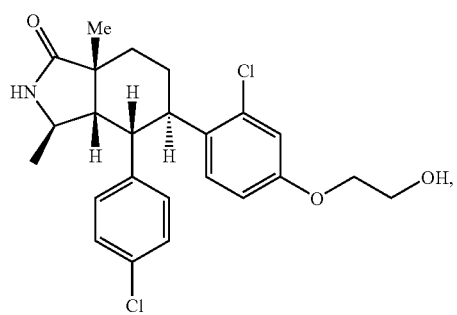
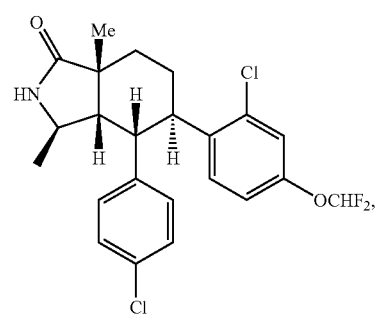
-continued
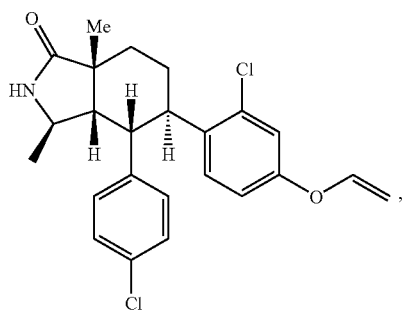
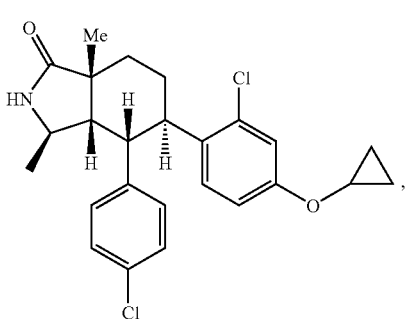
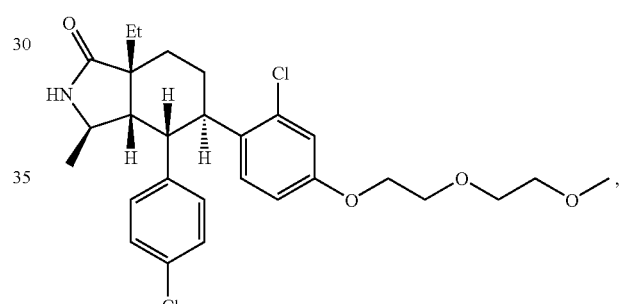
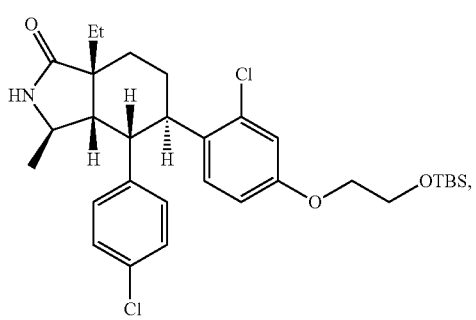
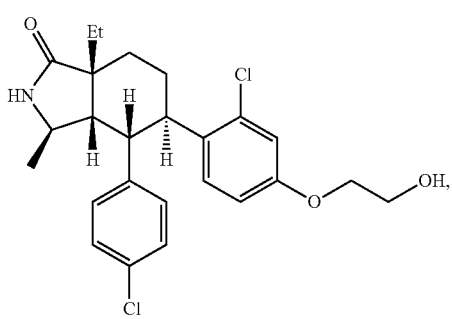

501
-continued
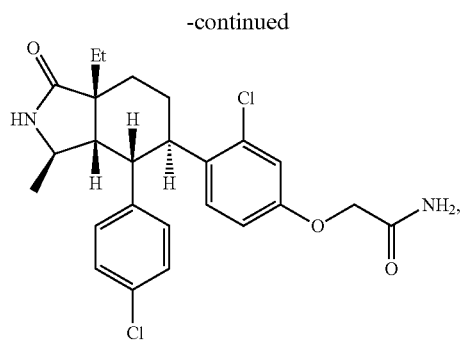
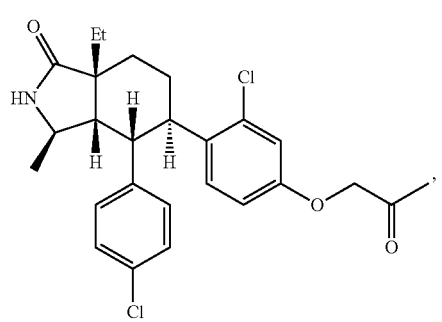
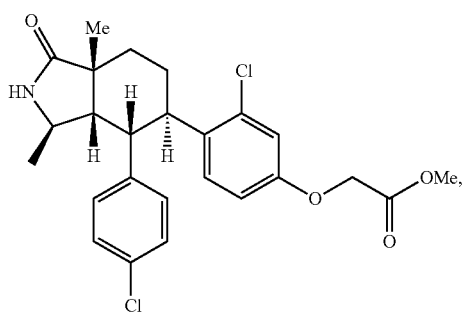
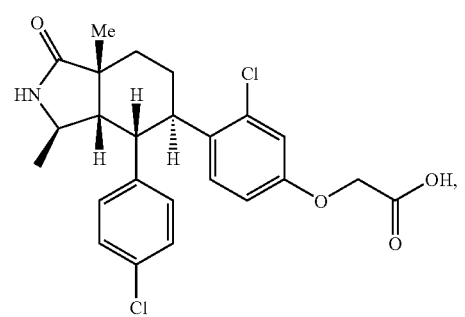
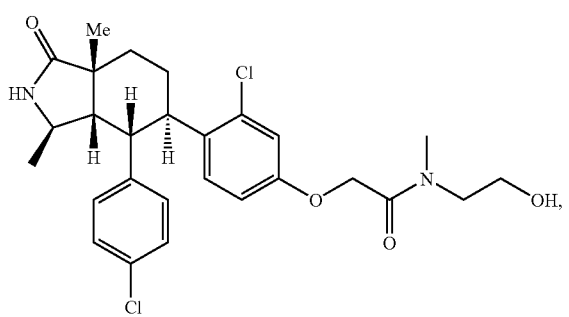
502
-continued
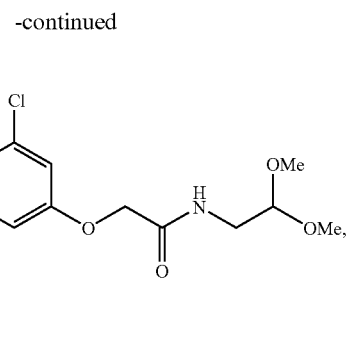
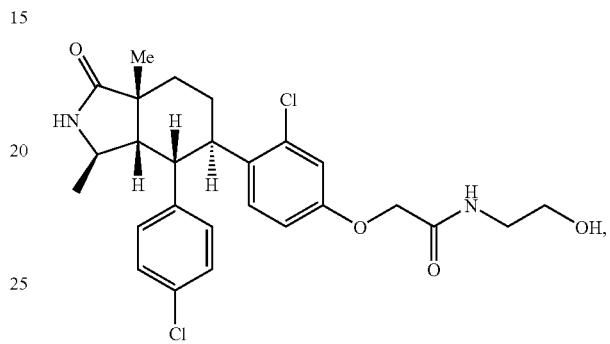
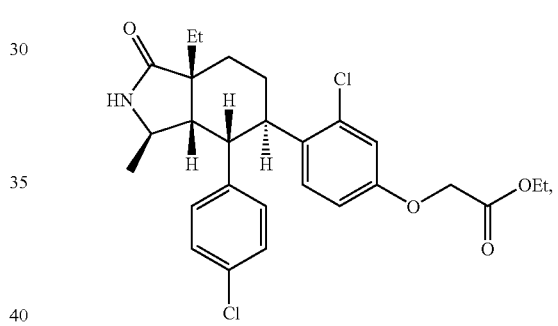
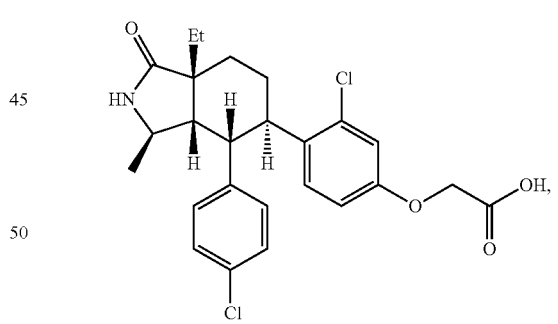
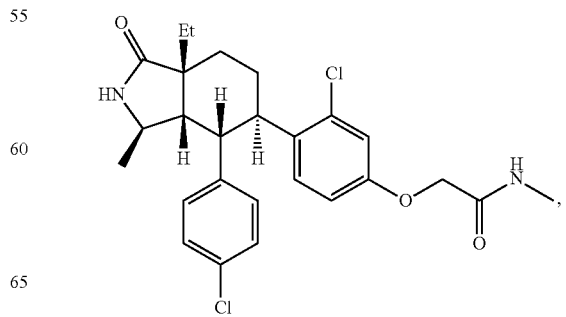

503 -continued
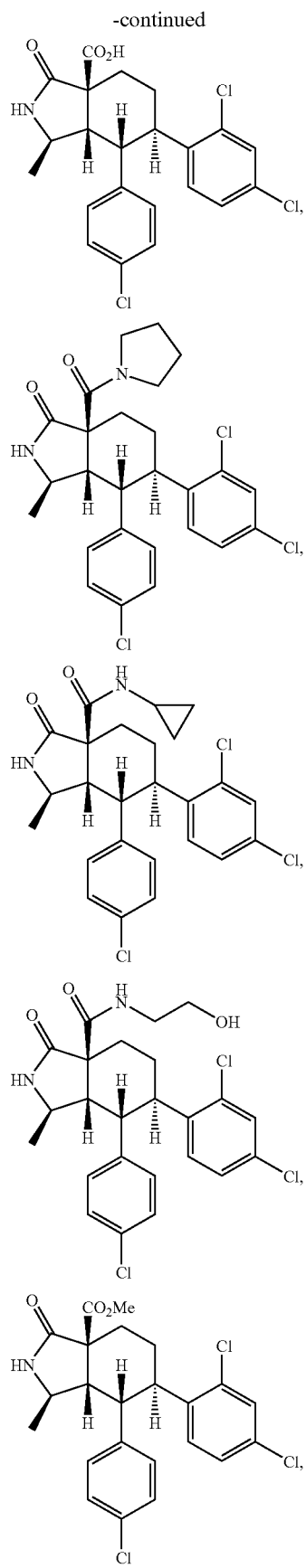
504 -continued
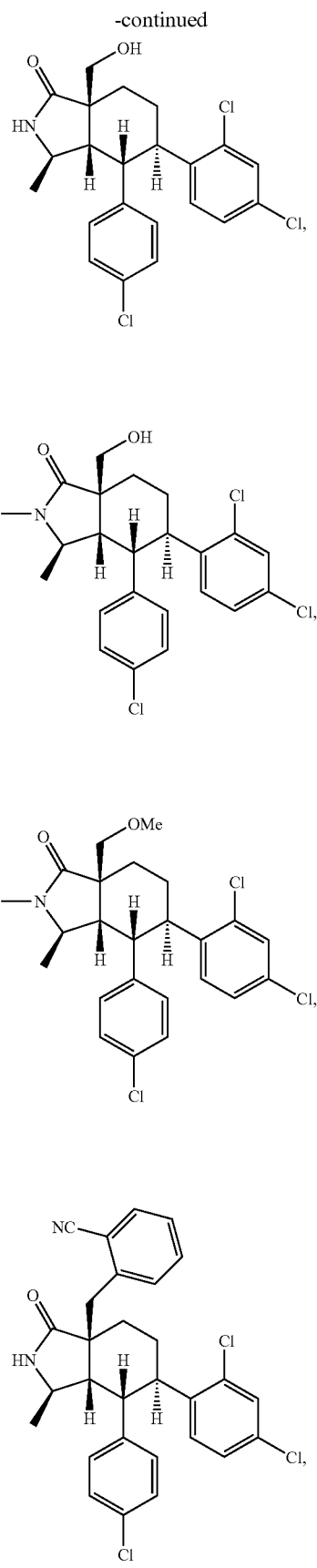

-continued
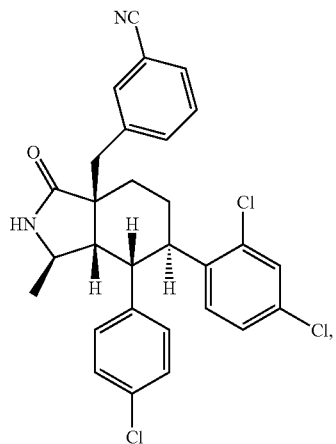
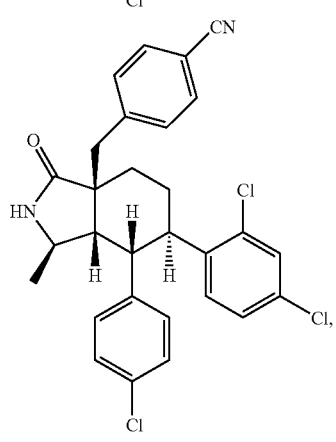
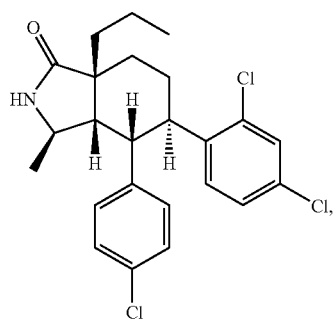
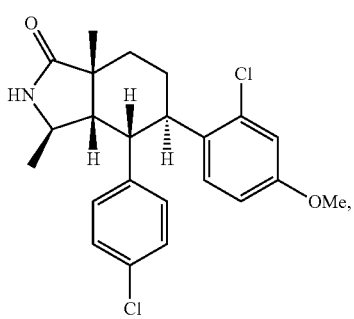
-continued
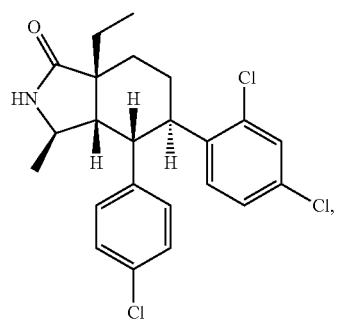
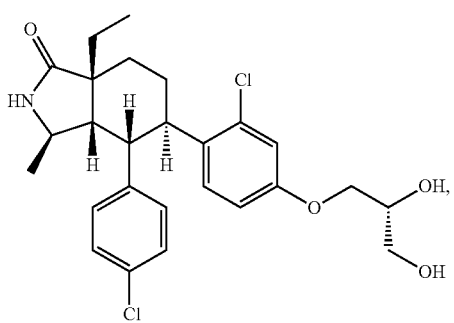
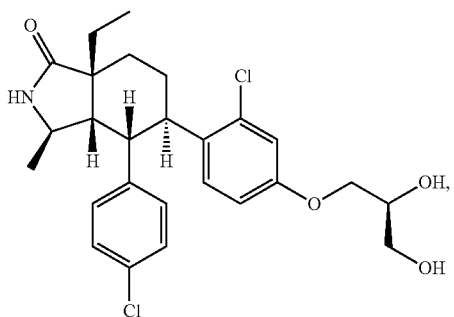
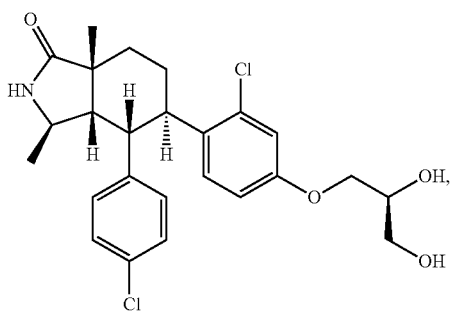
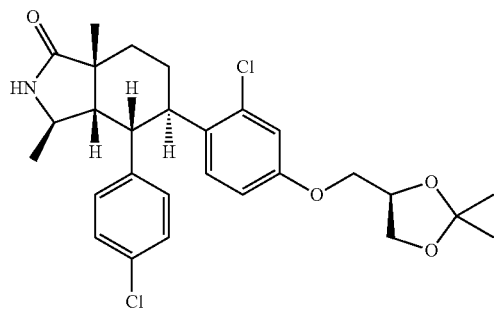

507
-continued
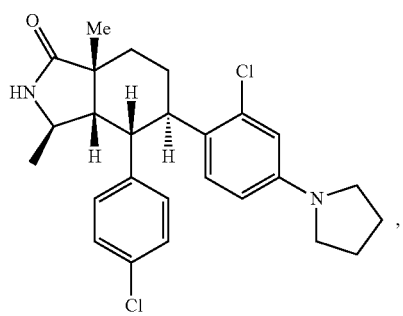
508
-continued
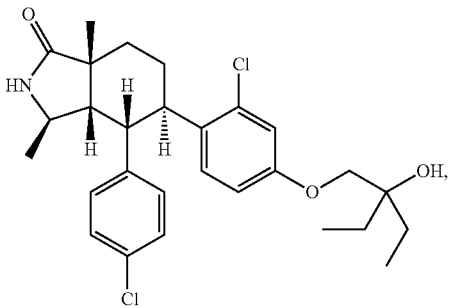
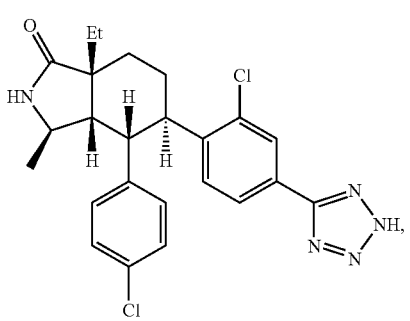
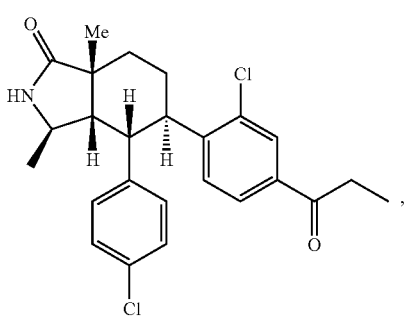
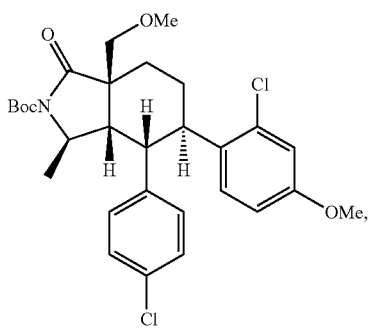
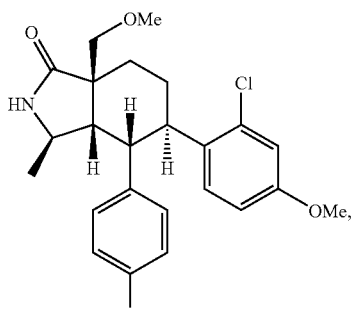

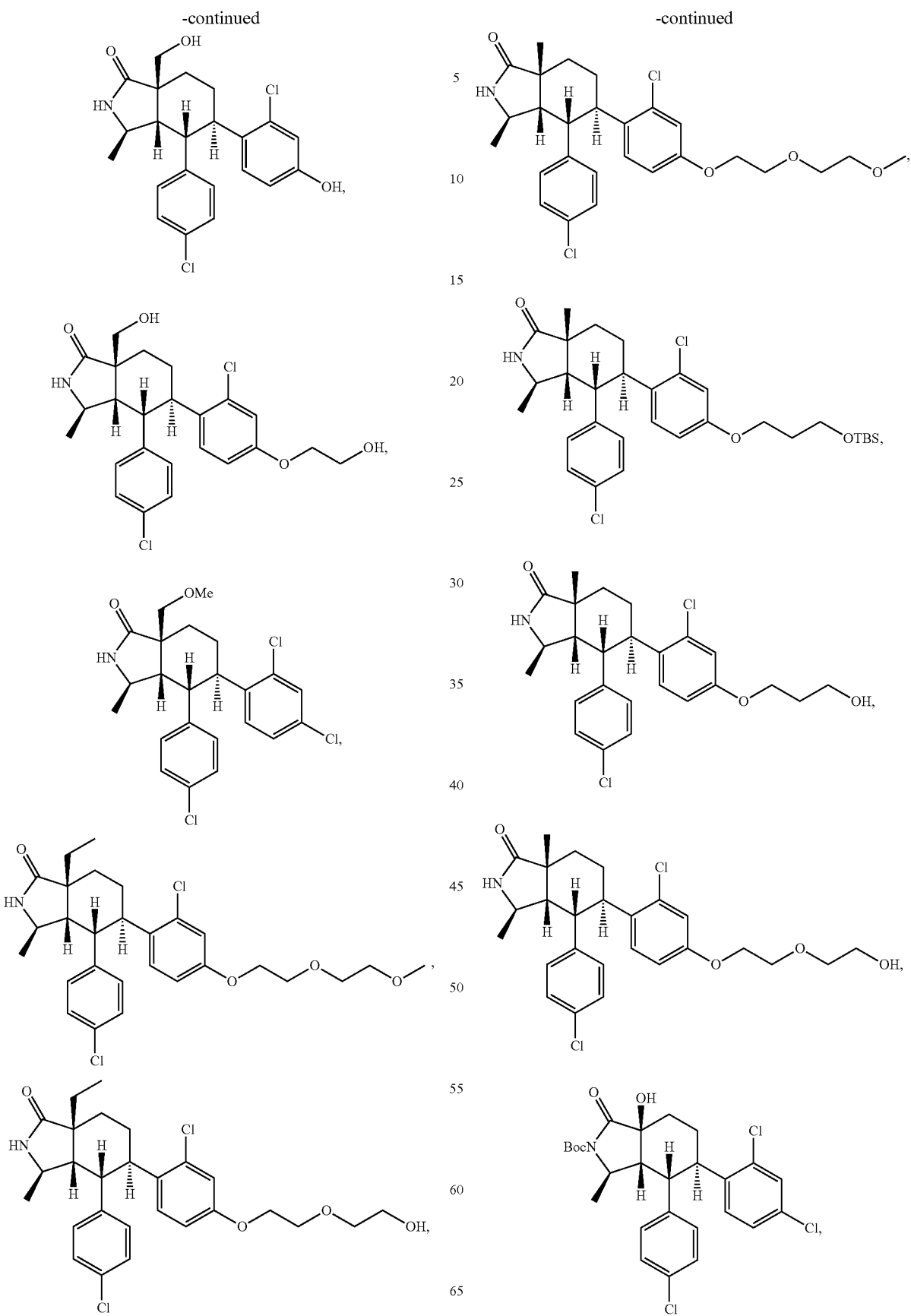

511 512
-continued -continued
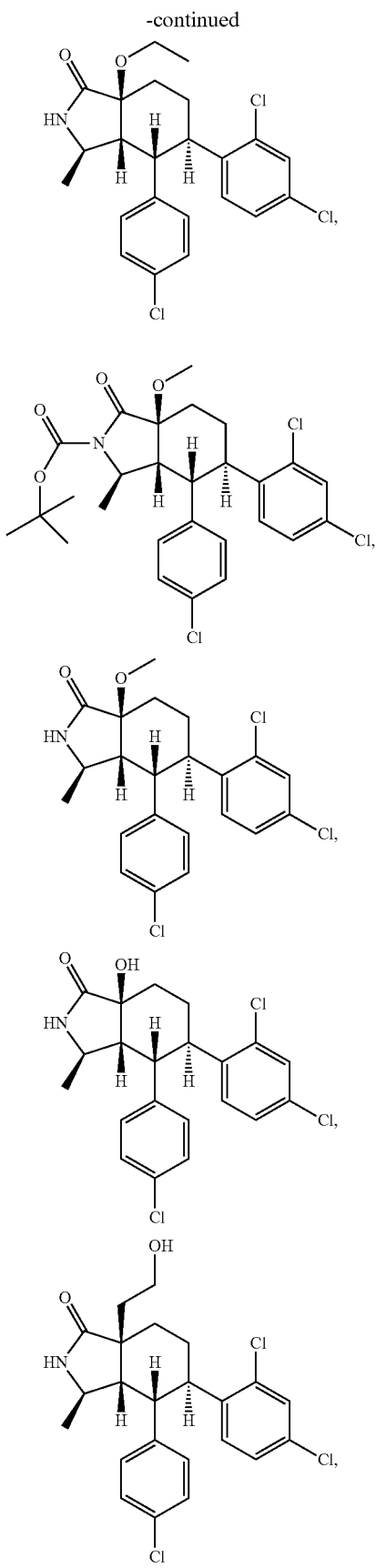
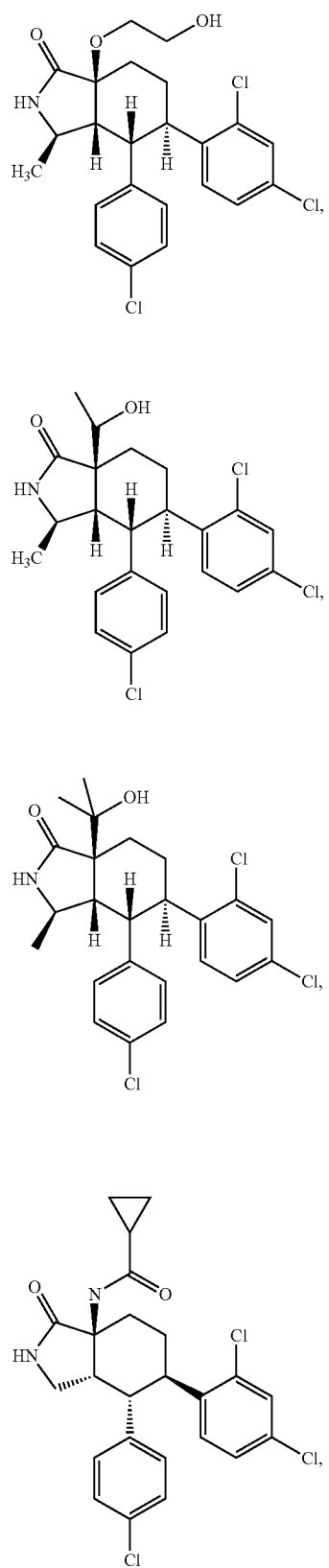

513 514
-continued -continued
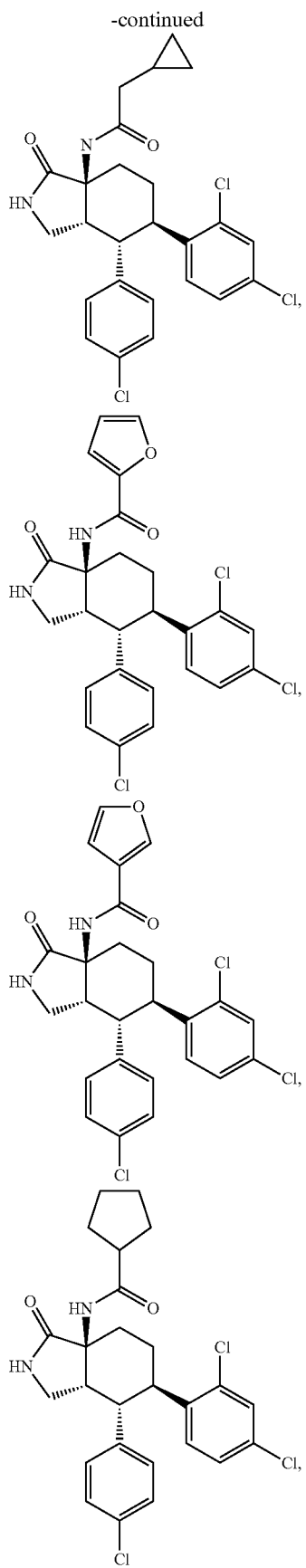
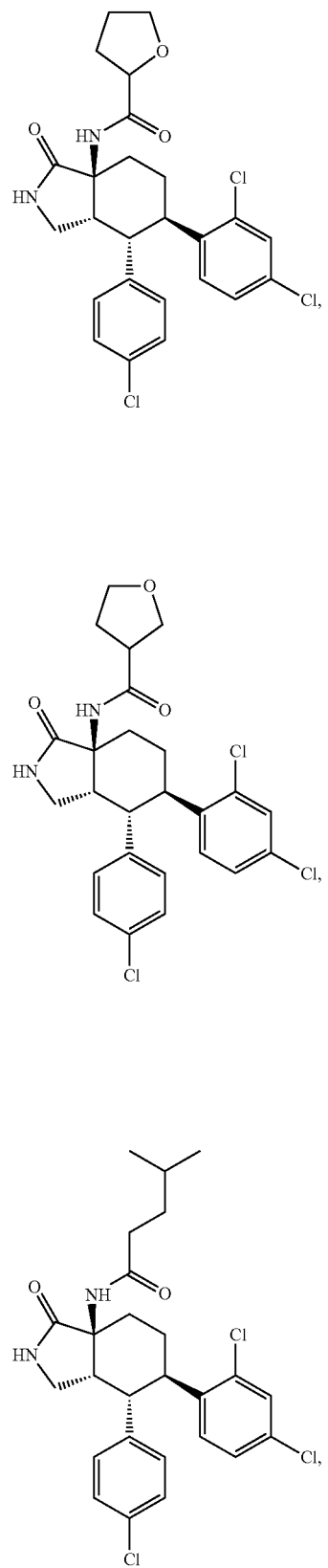

515
-continued
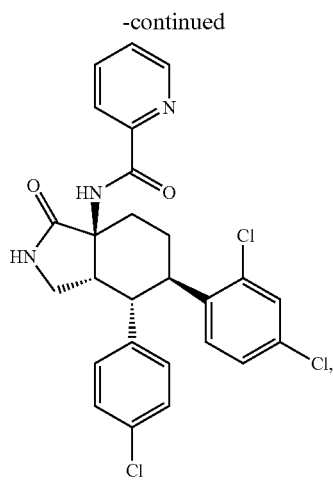
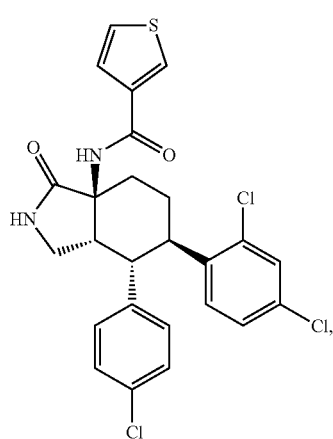
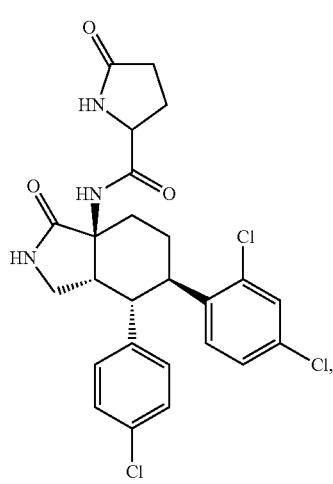
516
-continued
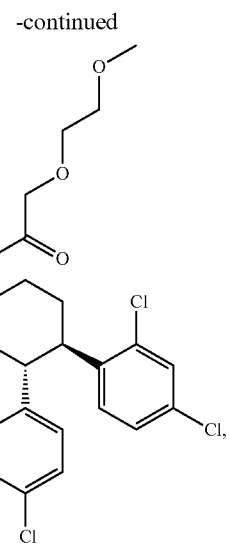
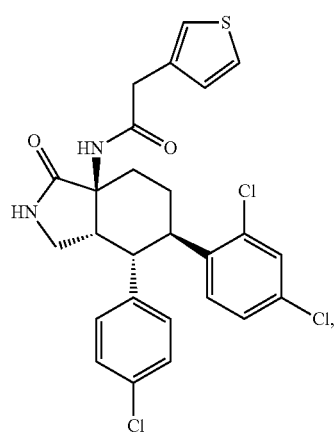
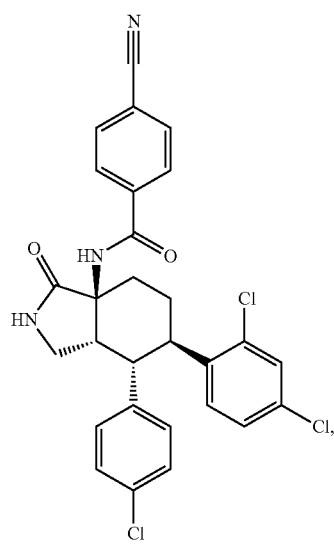

| 517 | 518 |
|---|---|
| -continued | -continued |
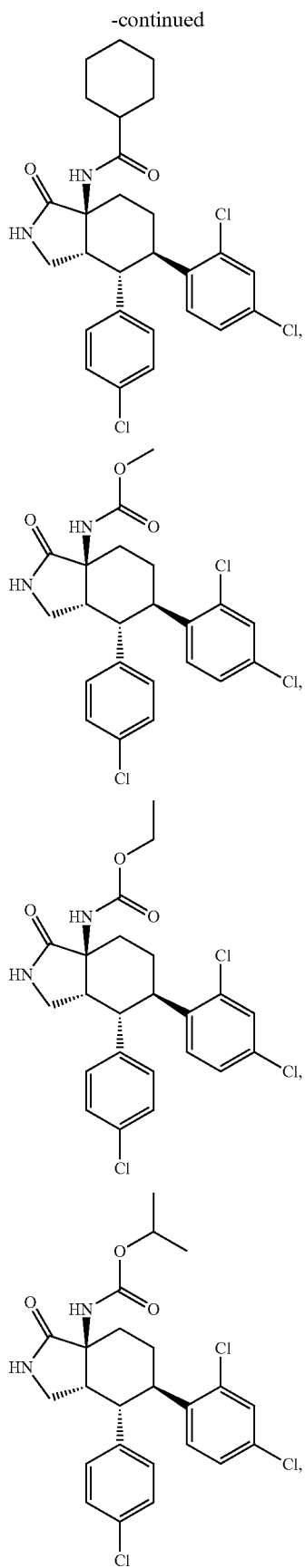
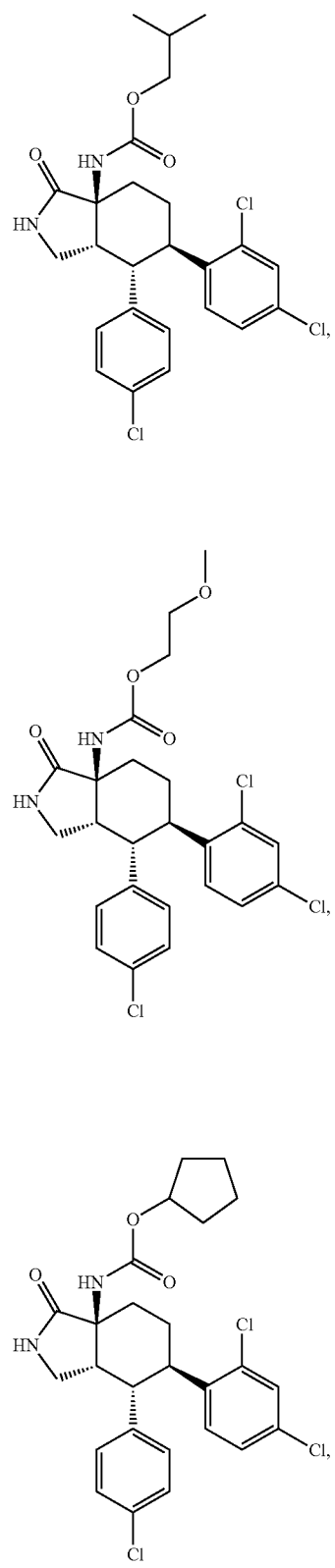

519
-continued
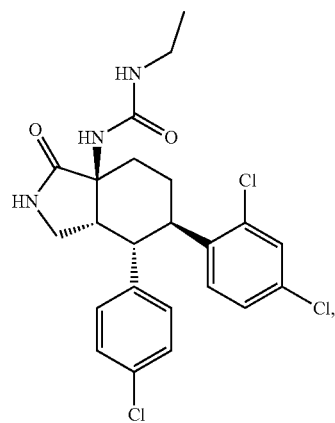
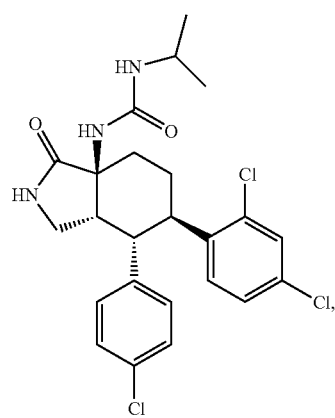
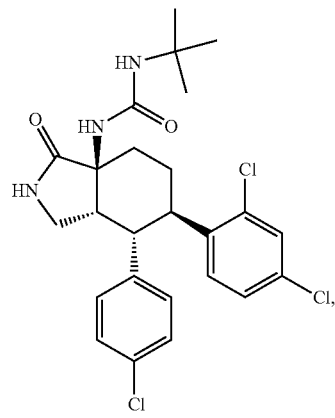
520
-continued
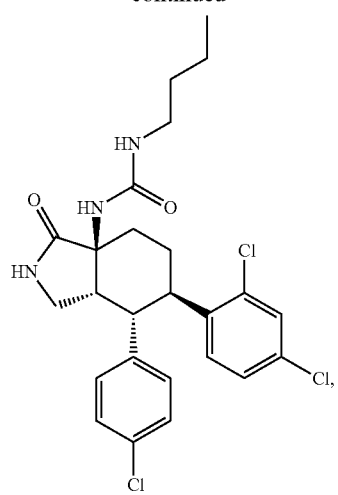
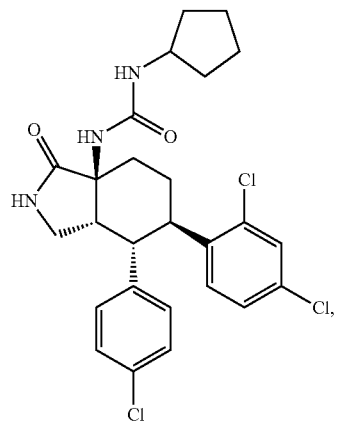
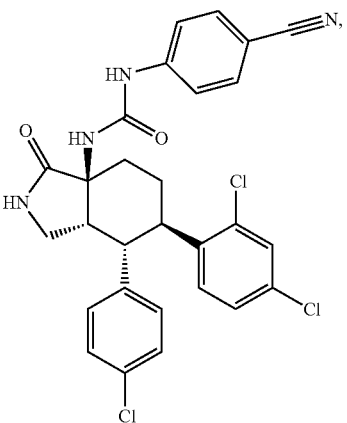

-continued
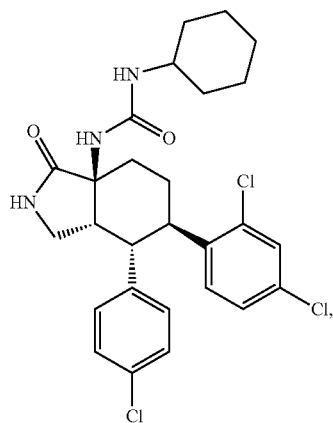
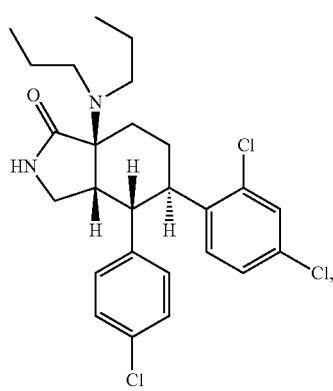
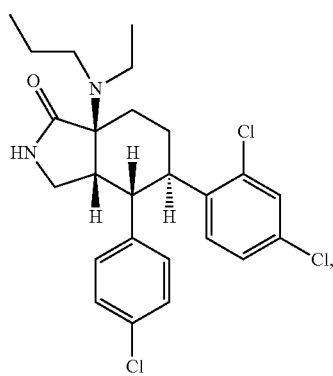
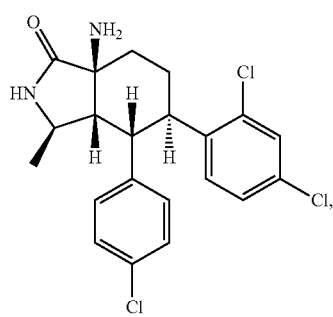
-continued
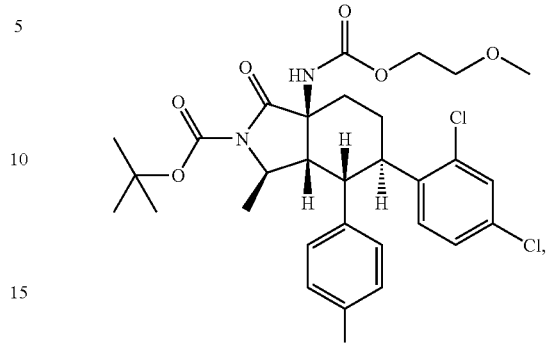
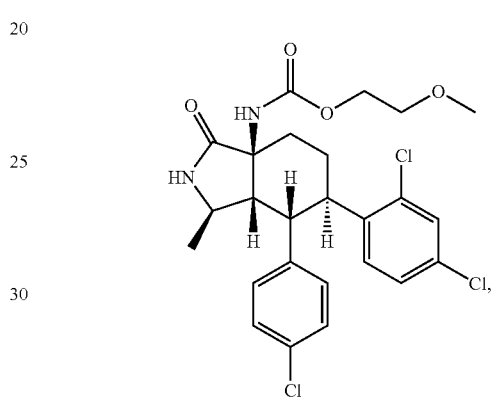
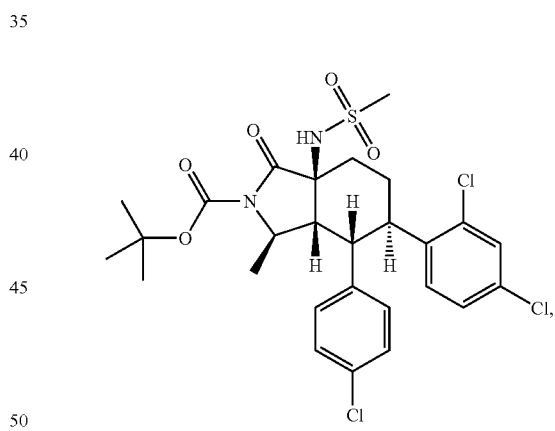
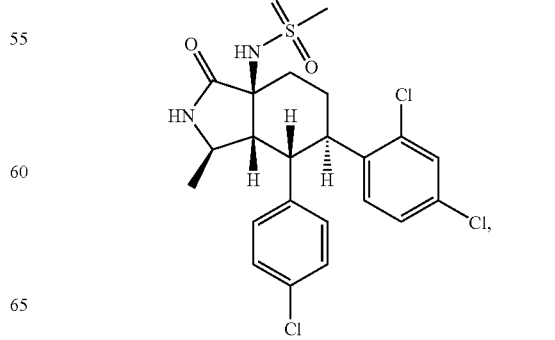

523
-continued
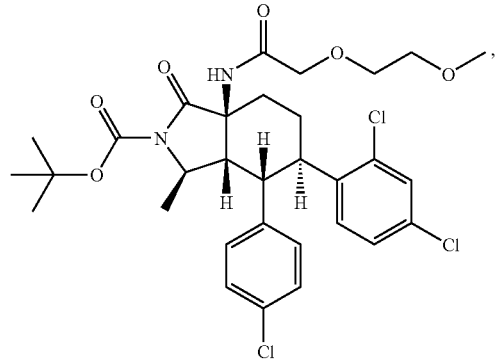
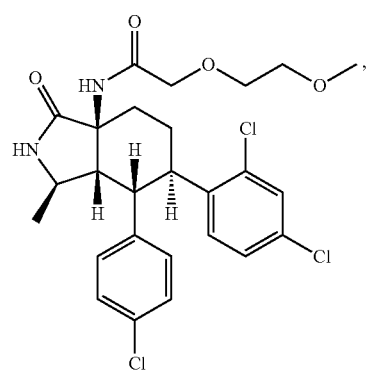
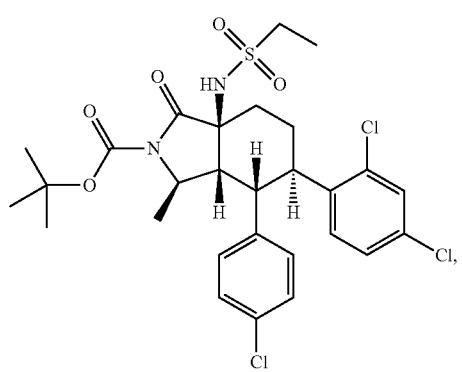
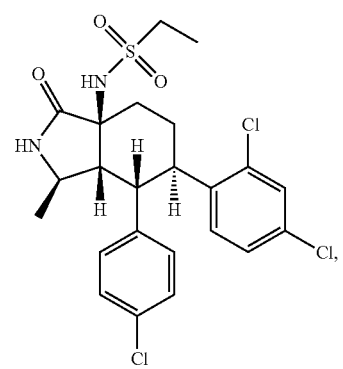
524
-continued
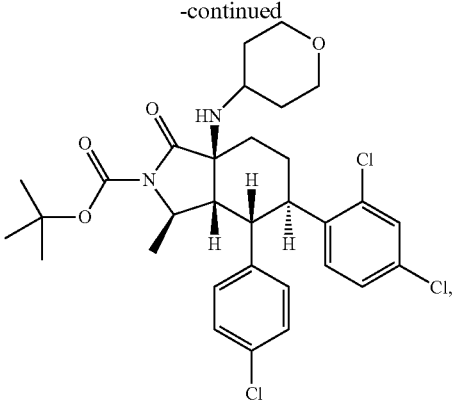
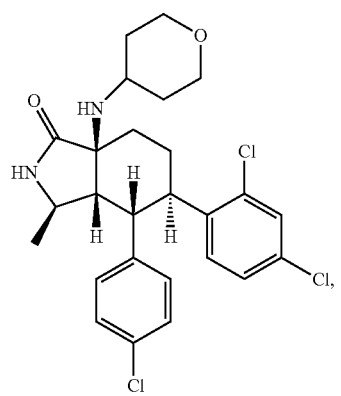
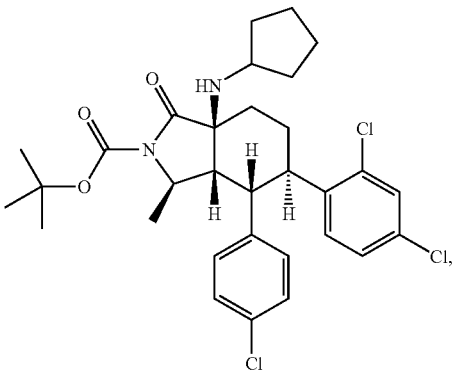
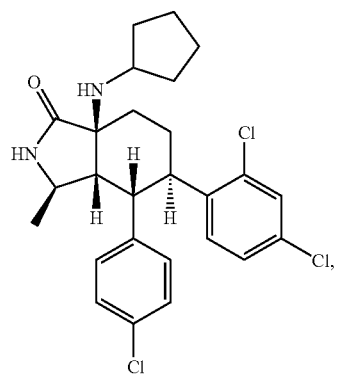

-continued
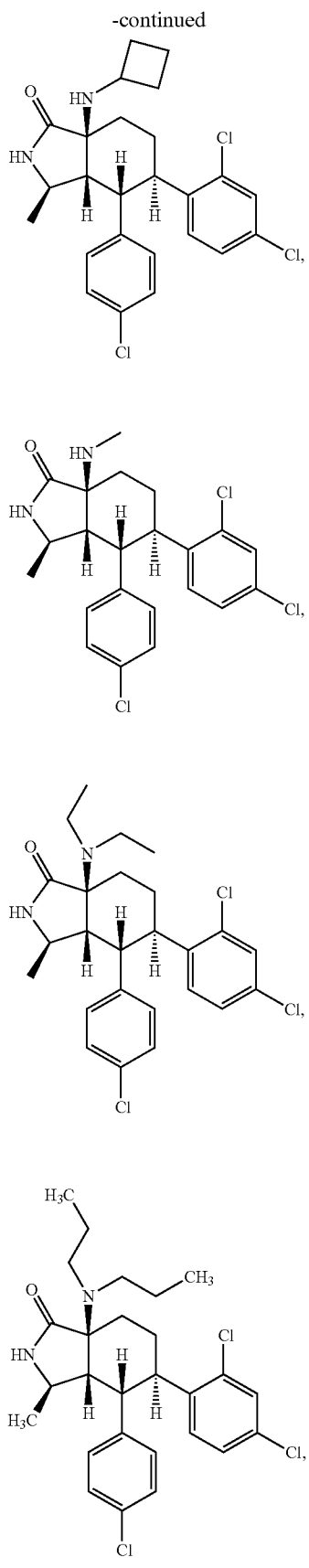
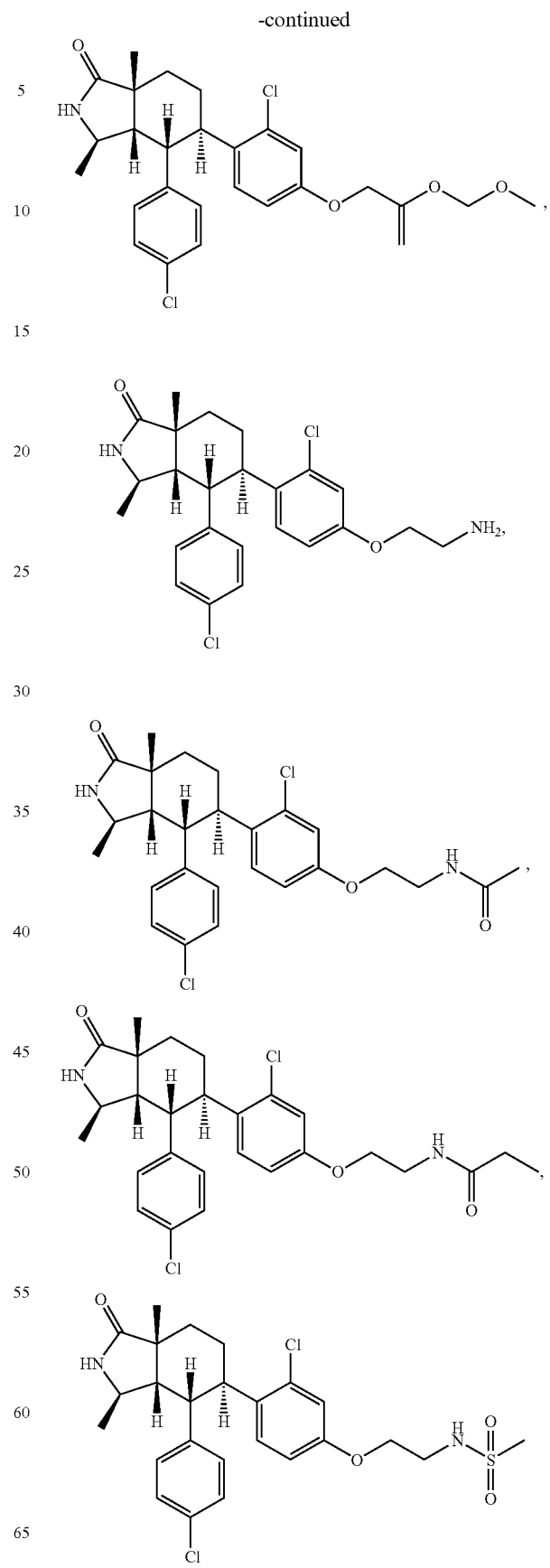

527
-continued
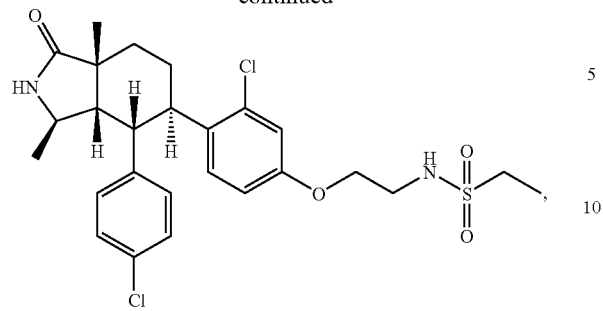
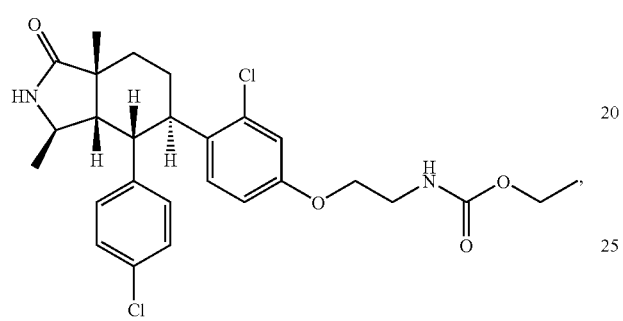
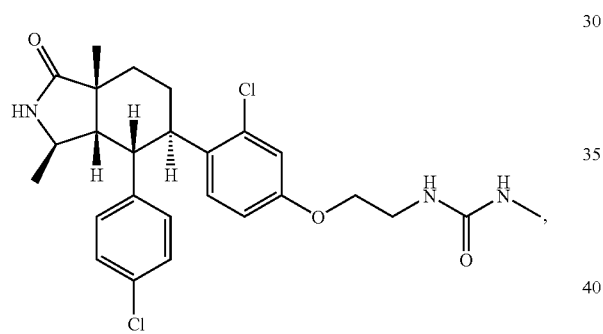
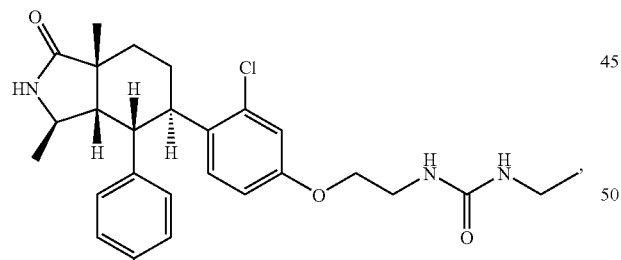
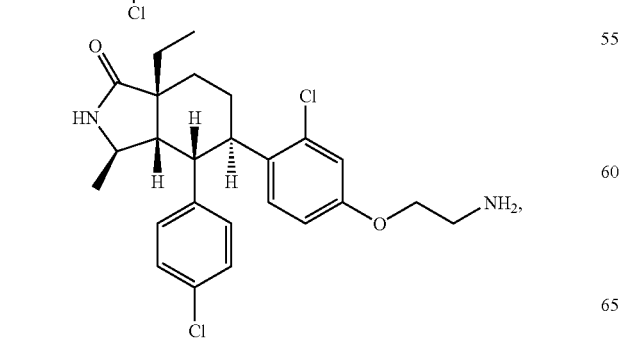
528
-continued
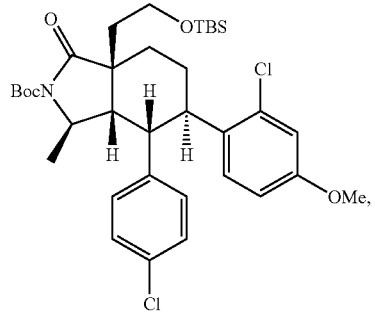
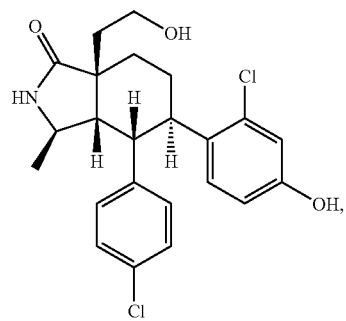
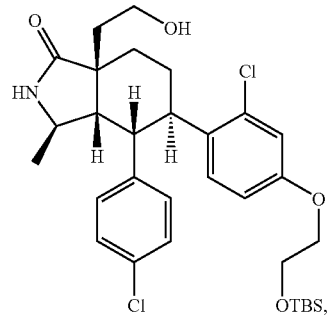
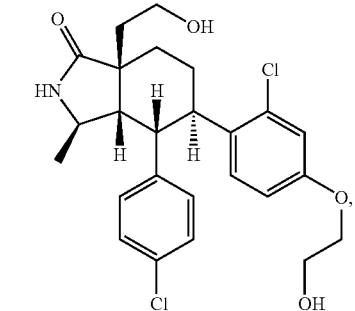
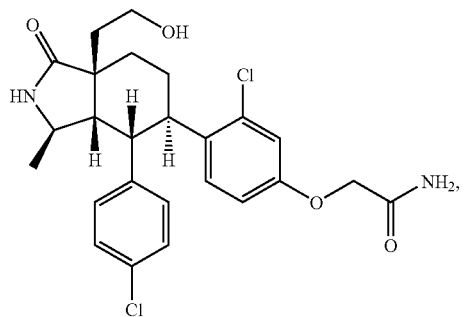

-continued
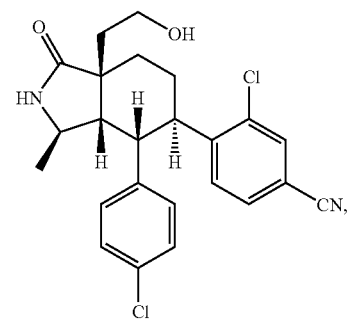
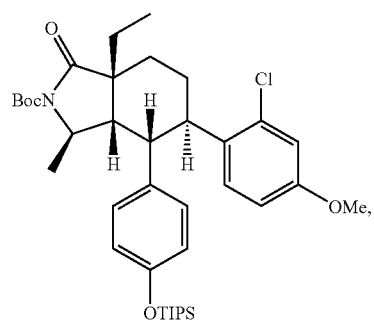
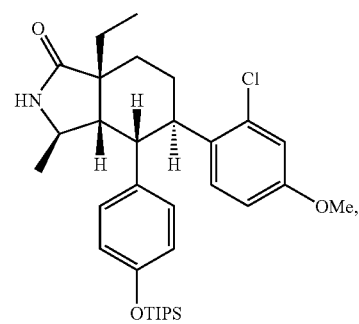
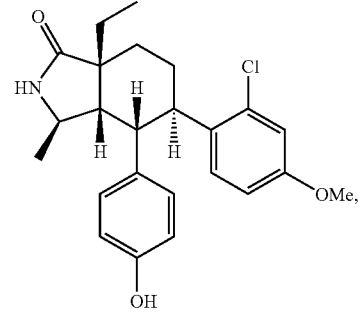
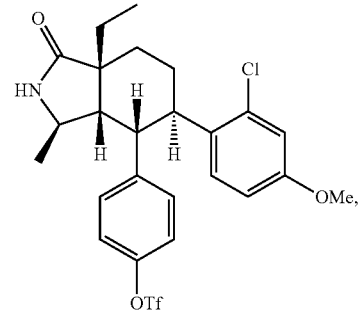
-continued
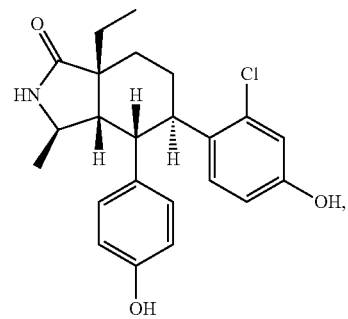
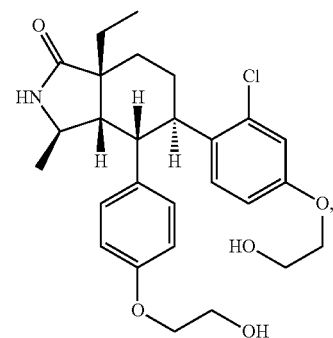
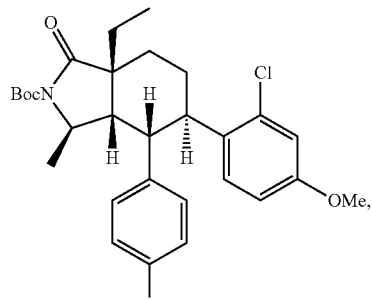
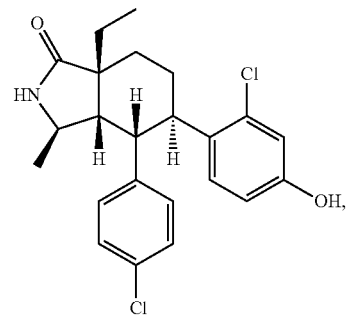
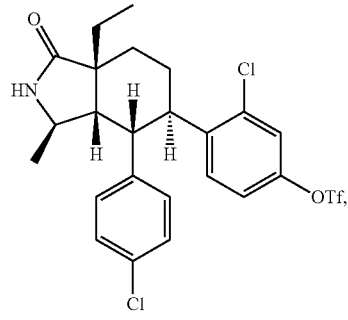

-continued
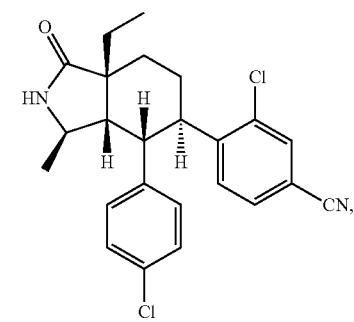
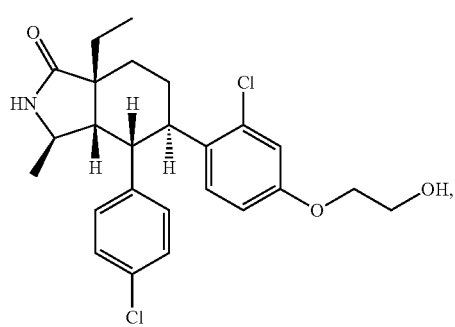
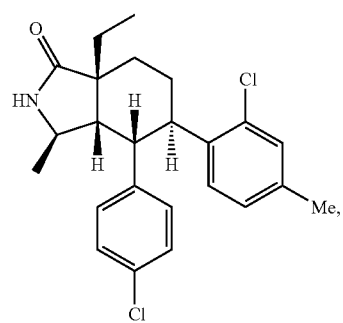
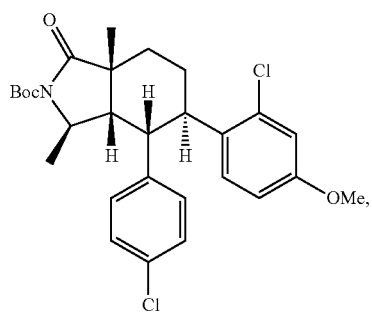
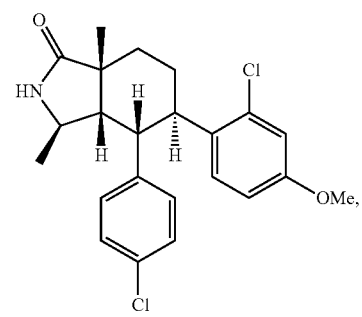
-continued
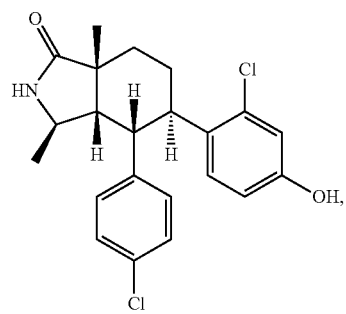
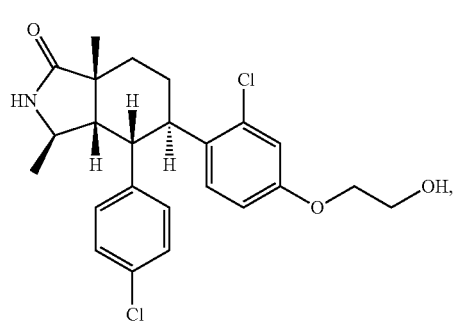
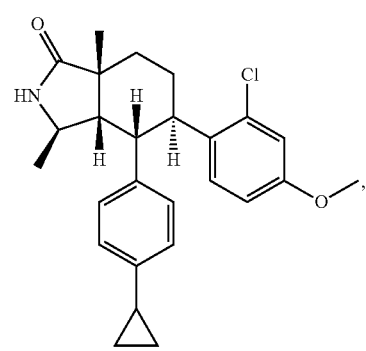
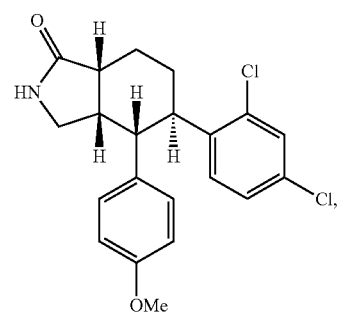
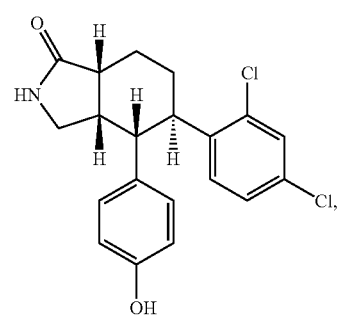

-continued
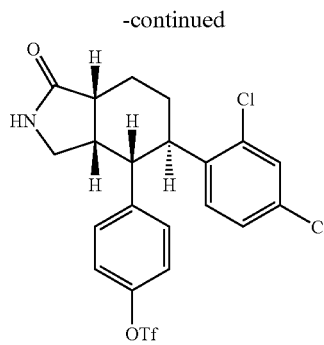
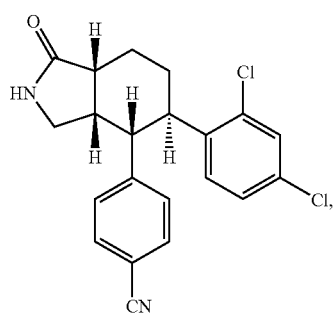
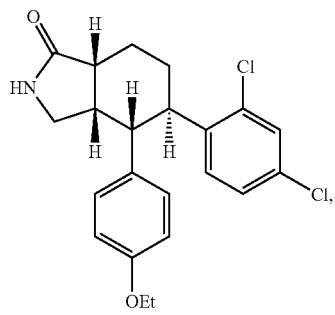
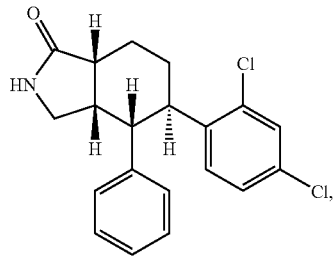
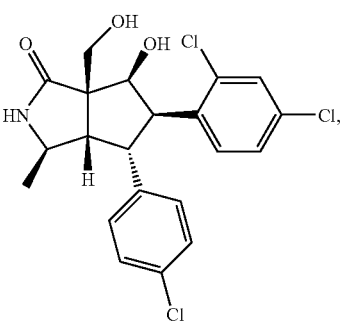
-continued
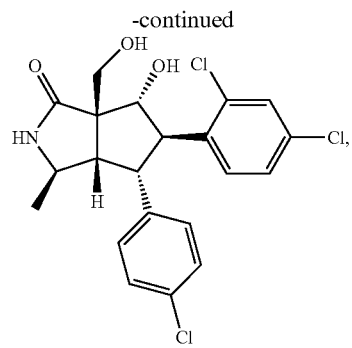
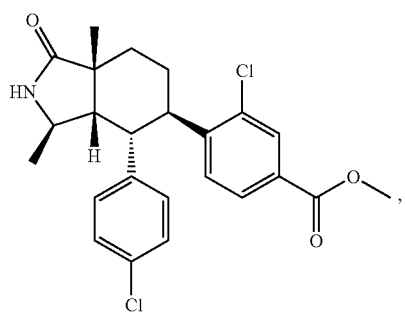
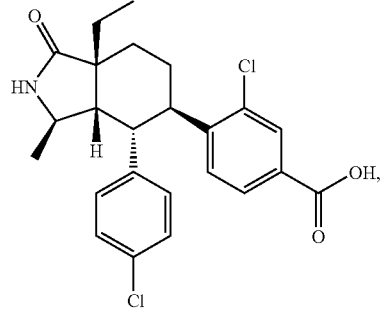
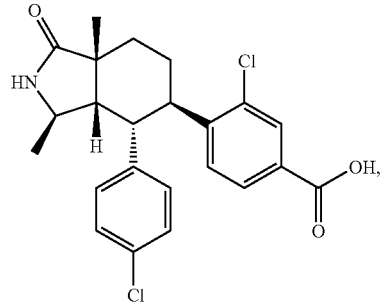
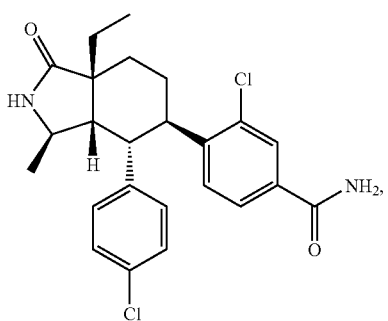

535
-continued
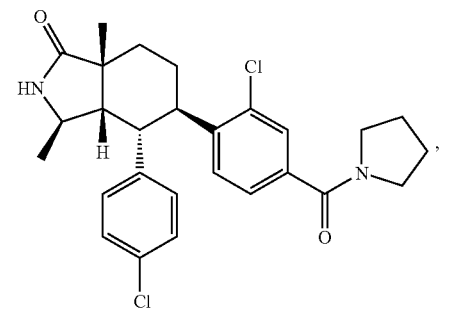
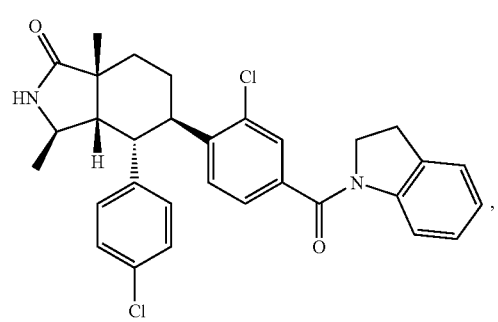
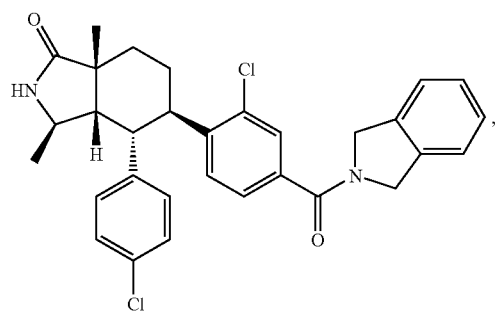
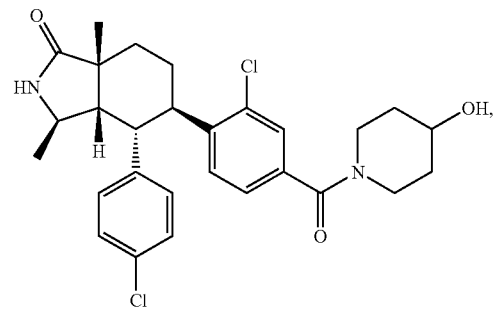
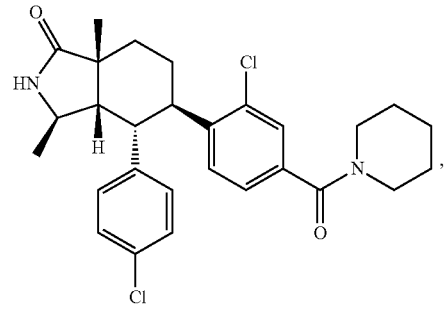
536
-continued
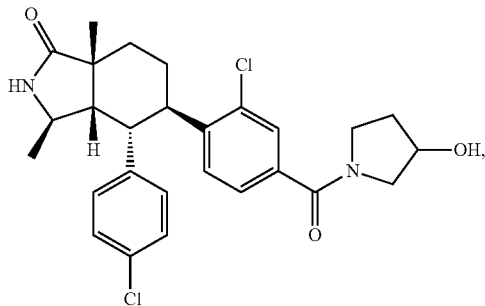
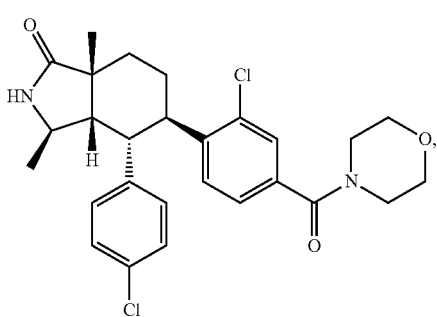
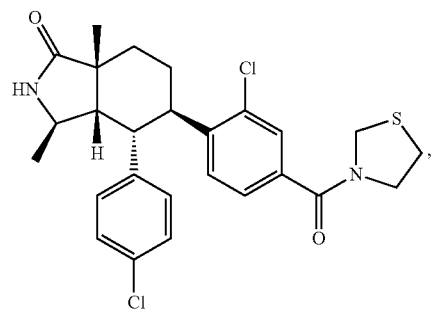
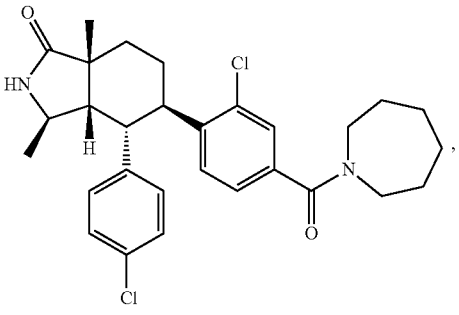
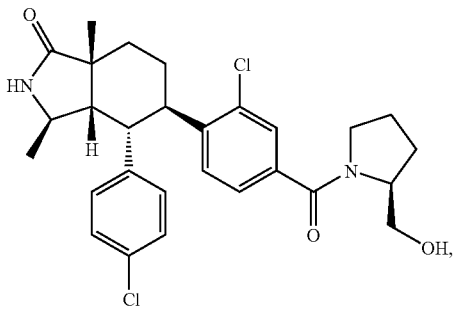

| 537 | 538 |
|---|---|
| 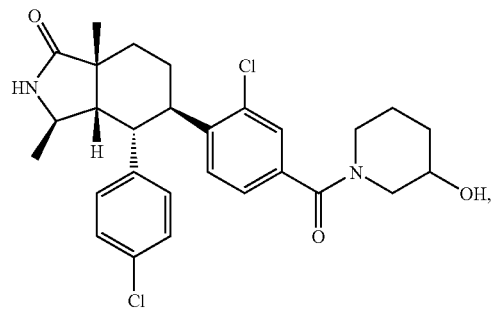 | 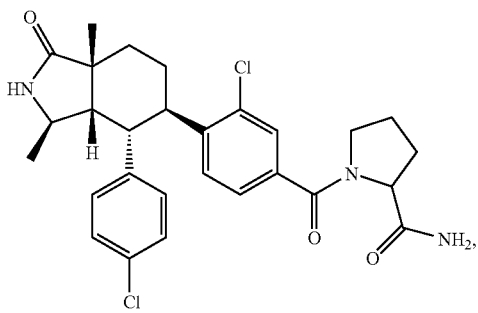 |
| 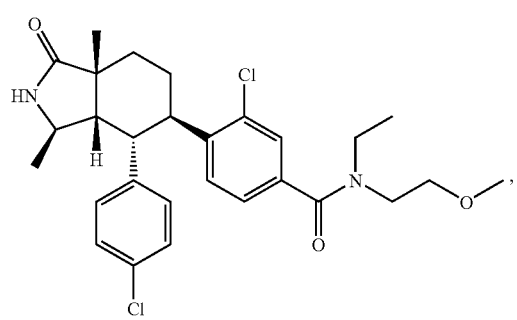 | 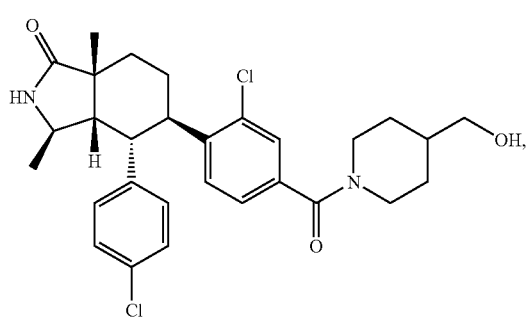 |
| 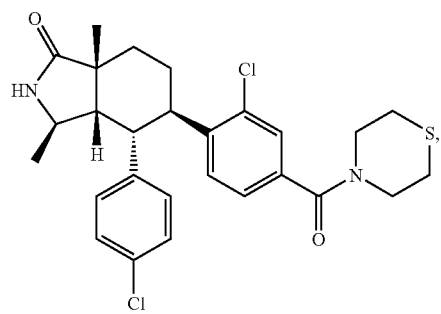 | 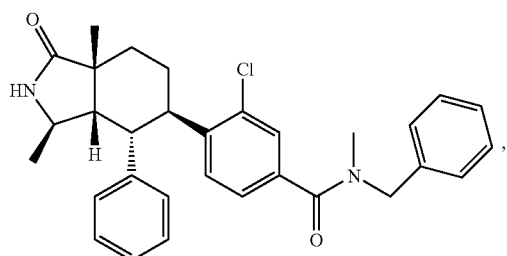 |
| 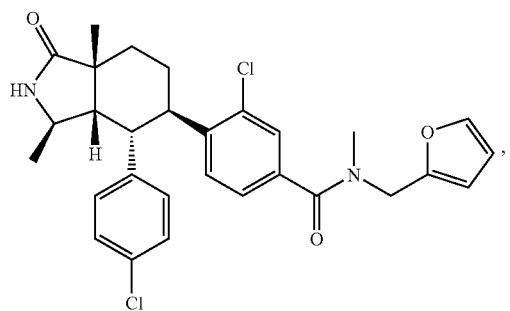 | 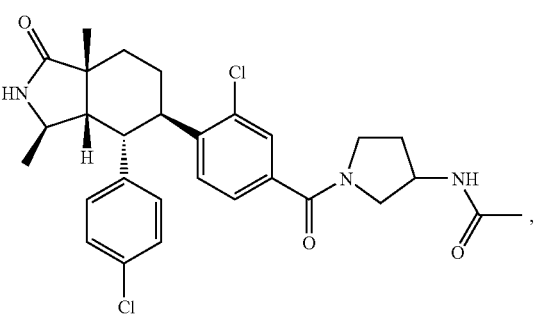 |
| 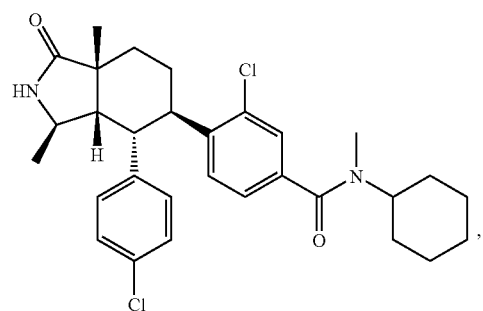 | 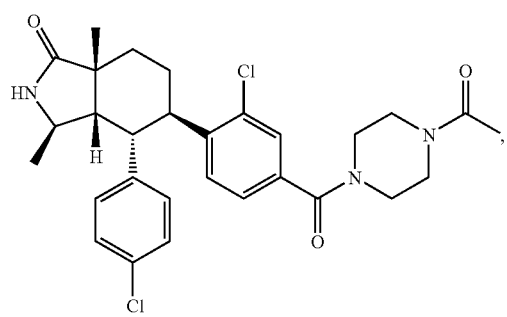 |

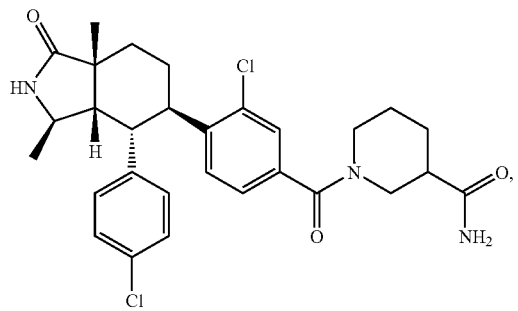
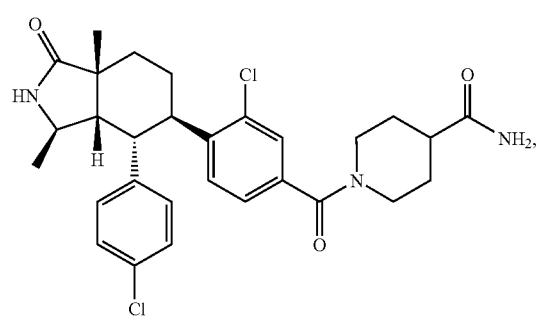
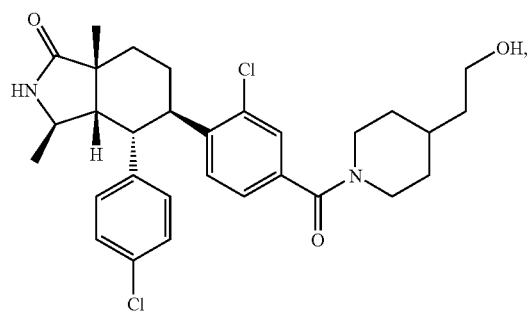
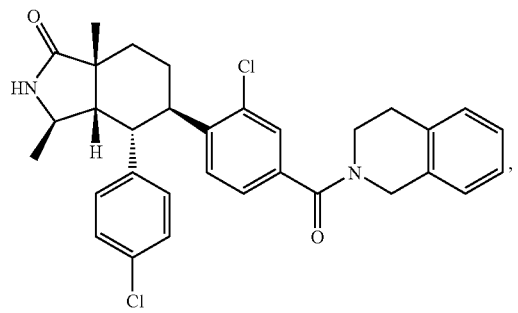
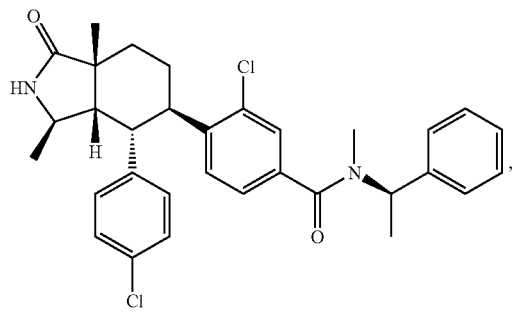
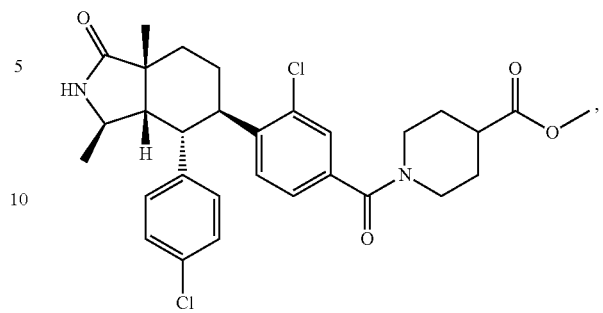
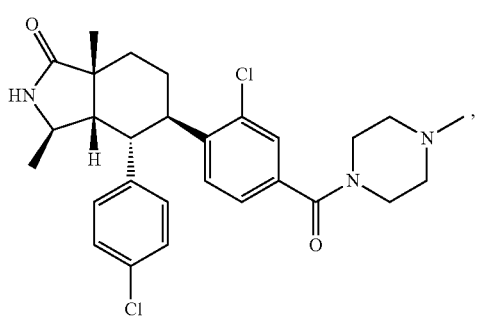
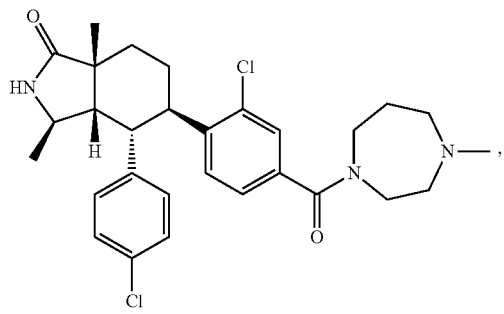
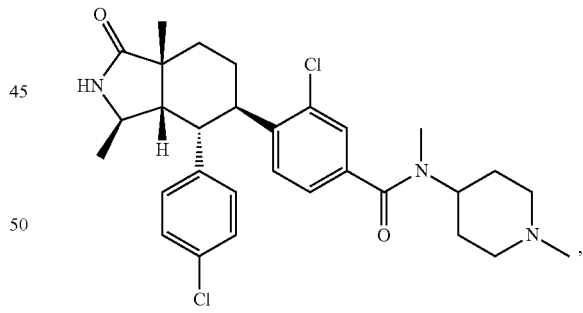
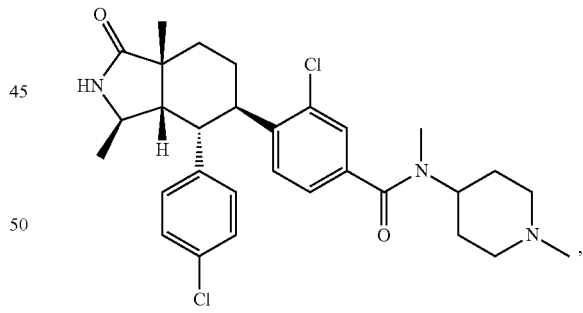

-continued
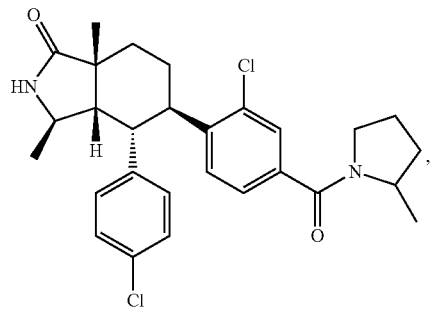
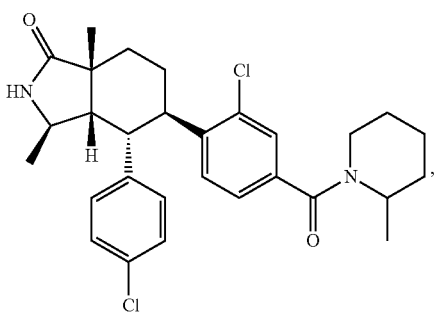
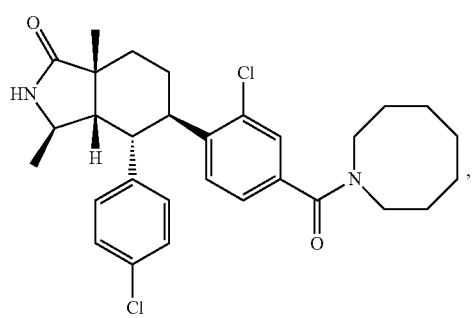
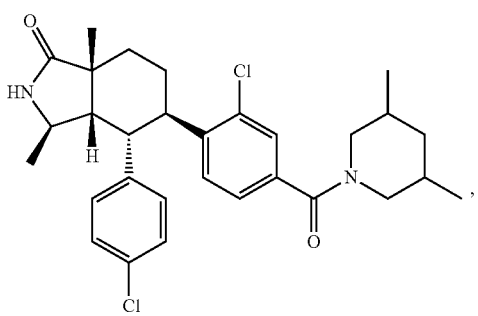
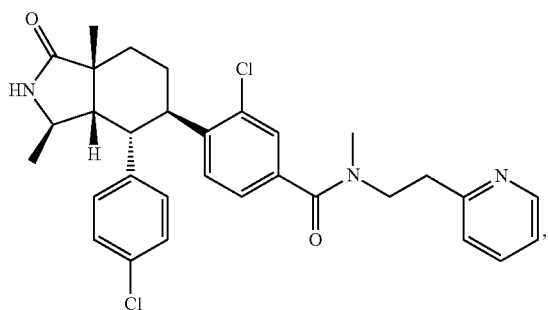
-continued
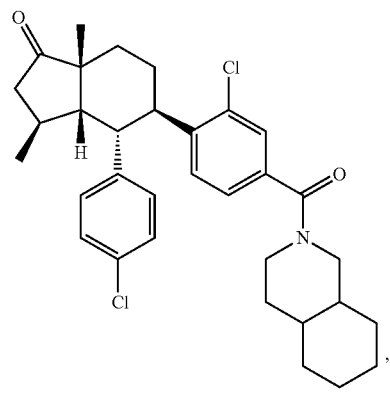
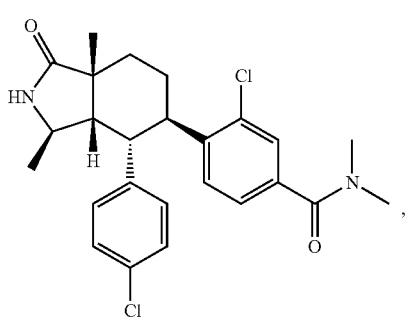
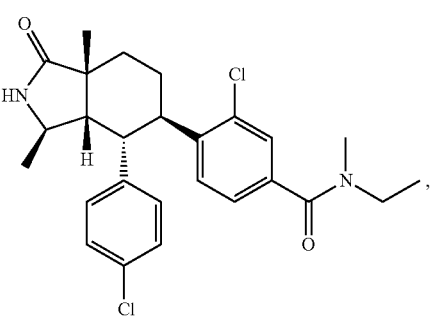
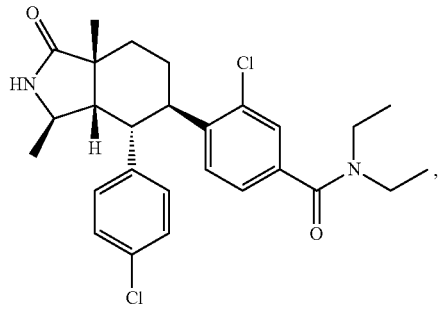
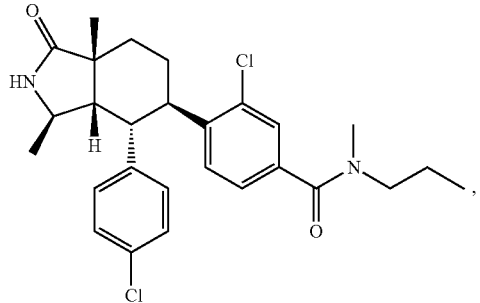

543
-continued
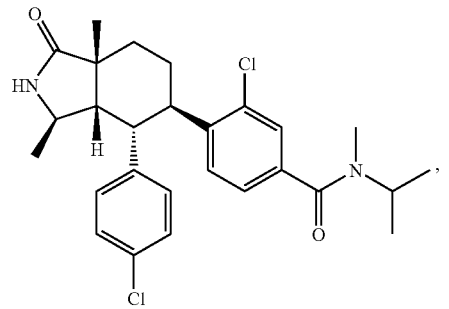
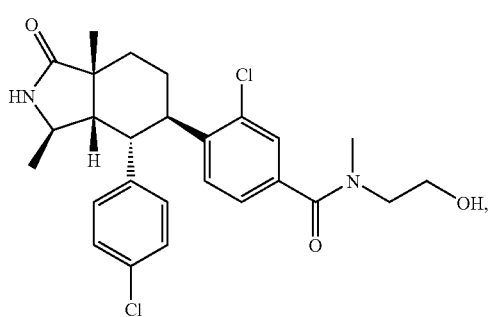
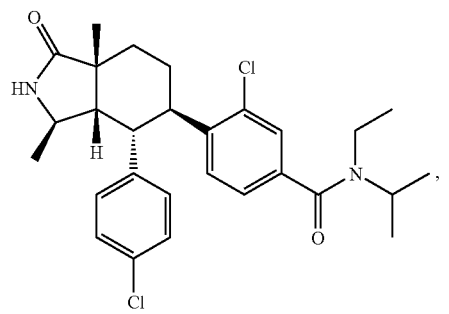
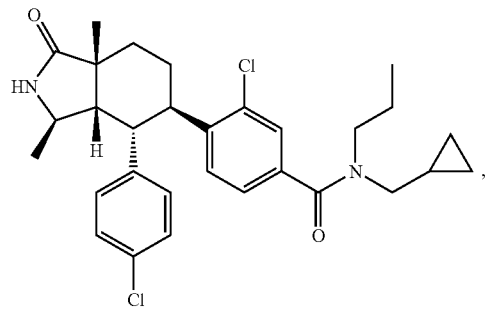
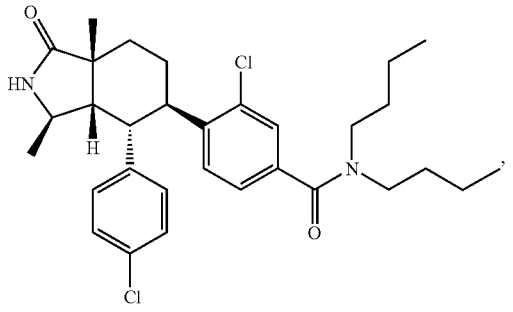
544
-continued
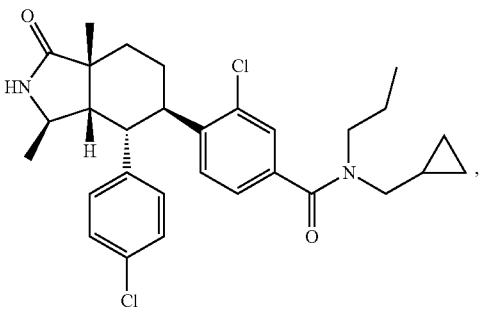
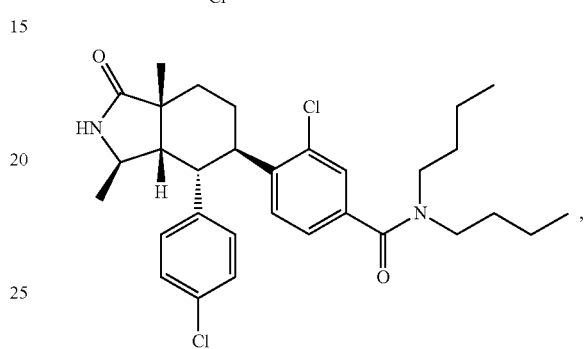
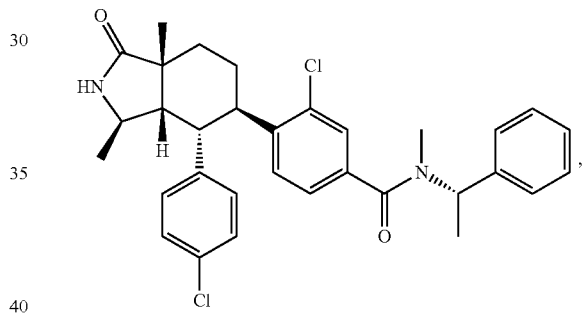
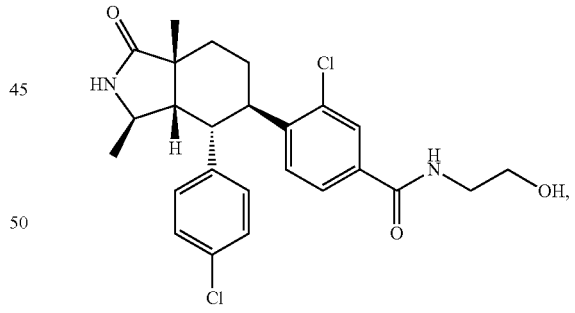
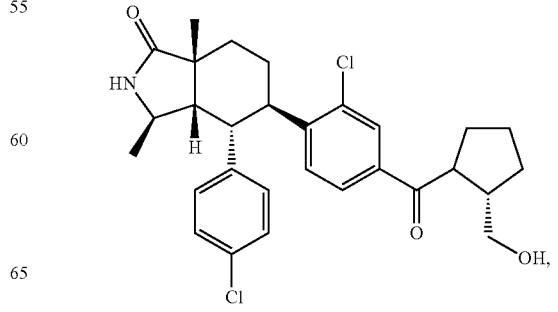

545
-continued
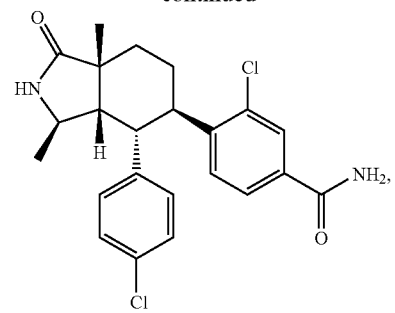
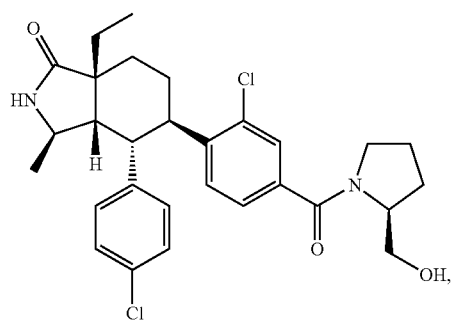
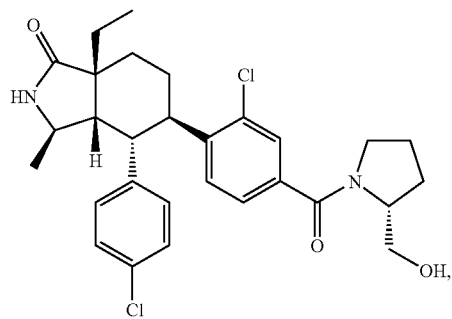
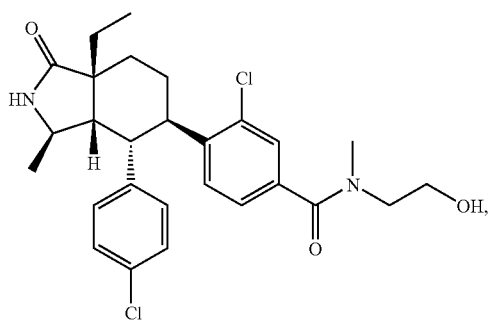
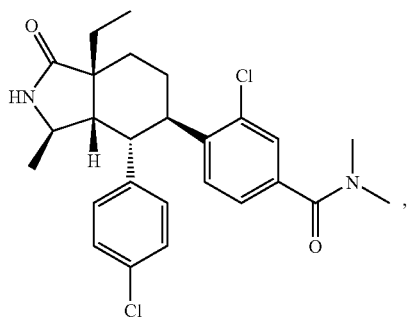
546
-continued
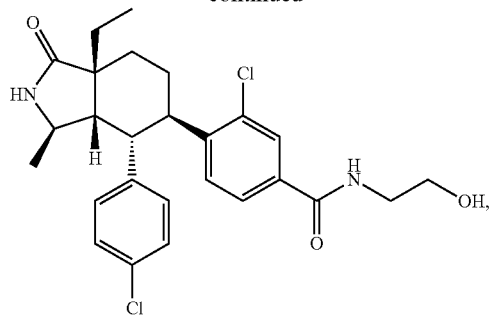
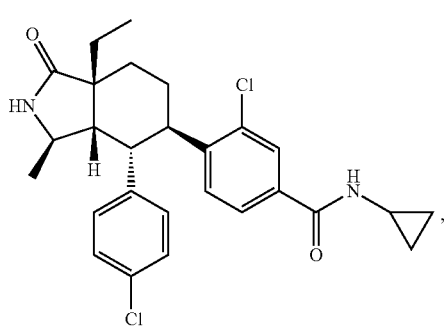
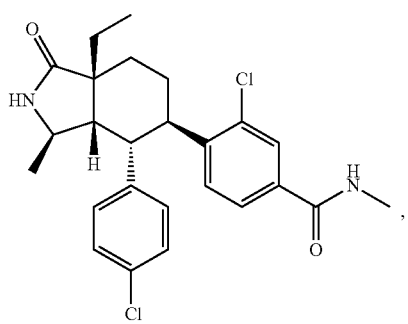
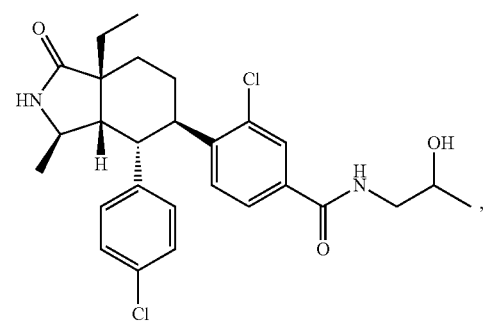
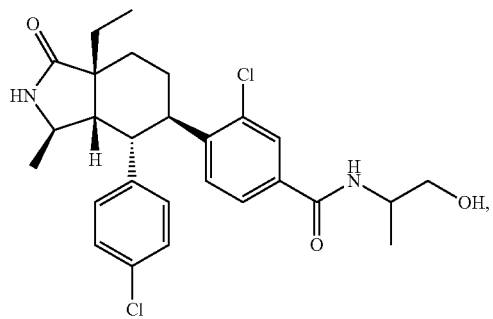

547
-continued
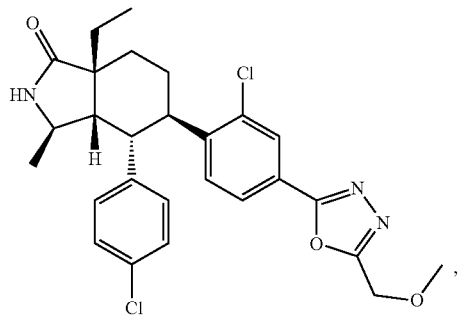
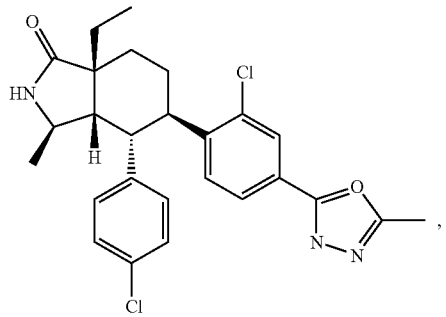
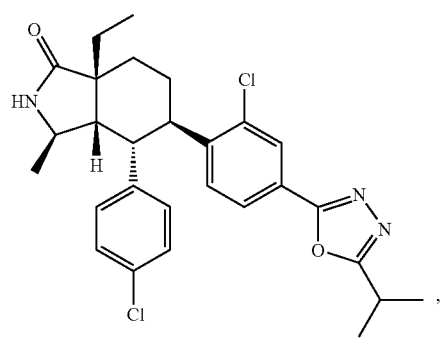
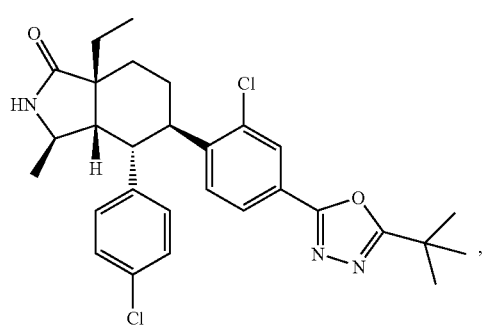
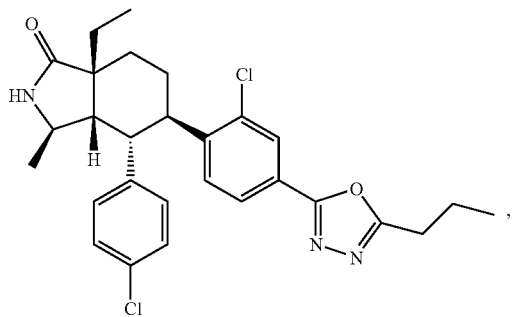
548
-continued
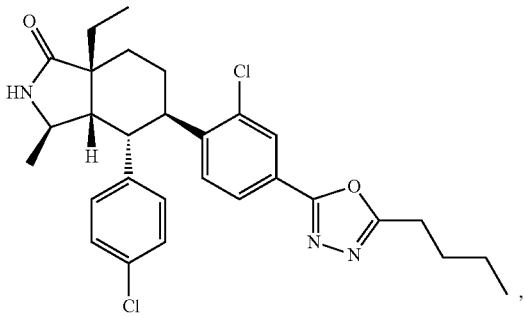
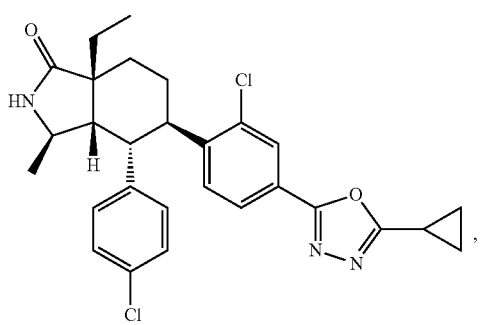
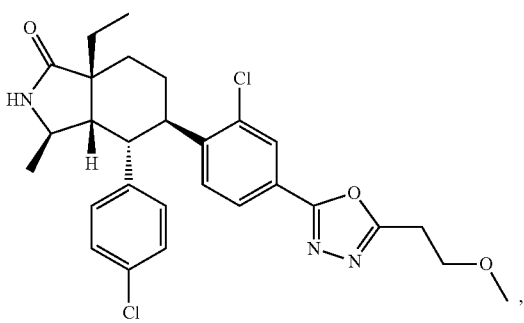
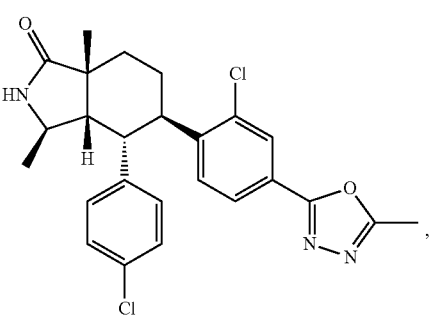
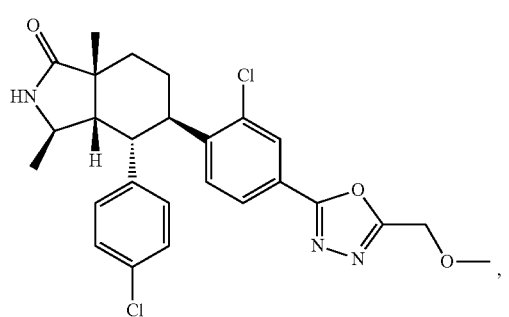

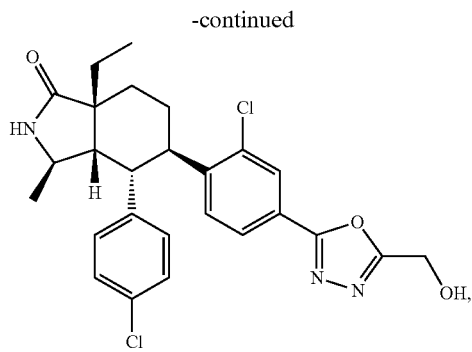
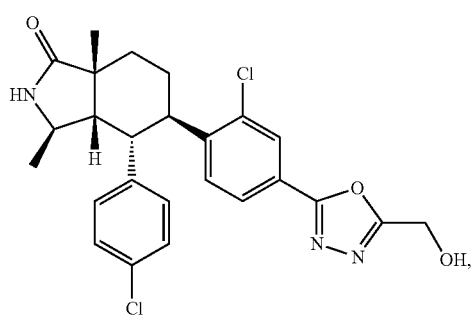
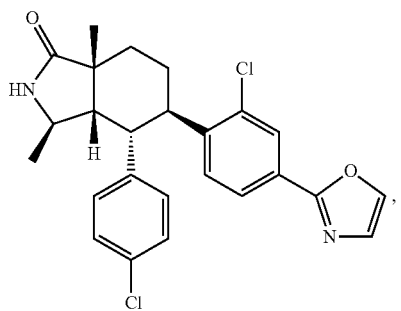
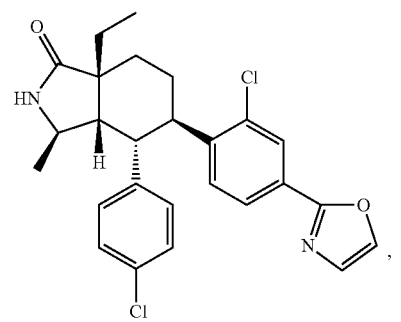
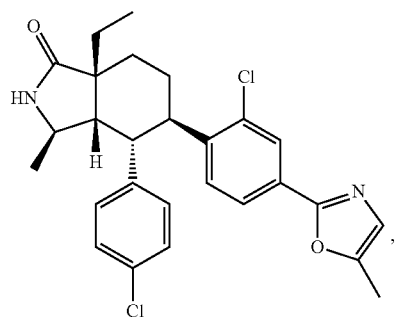
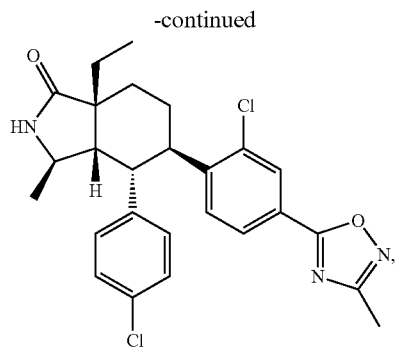
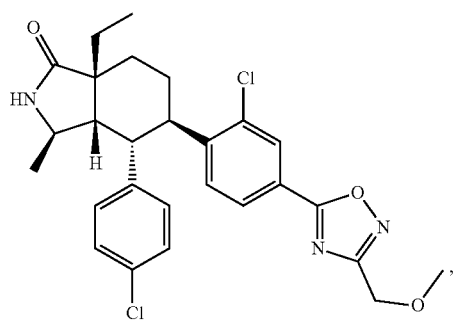
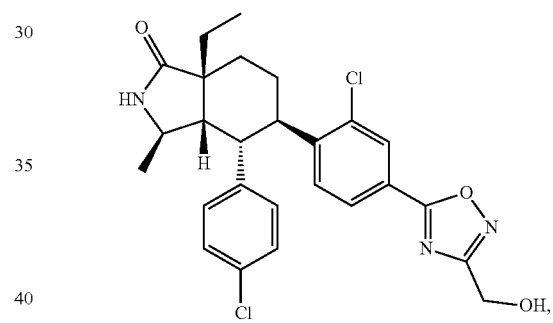
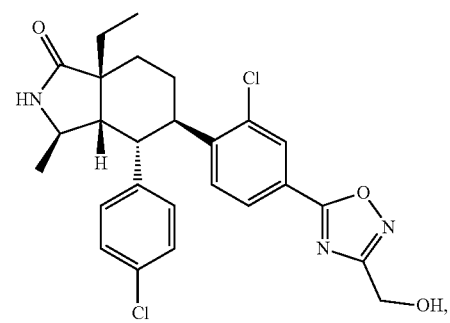
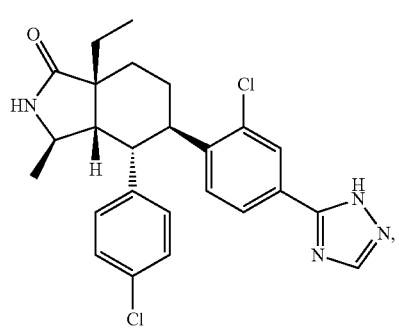
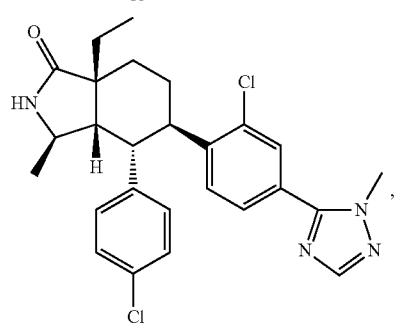

551
-continued
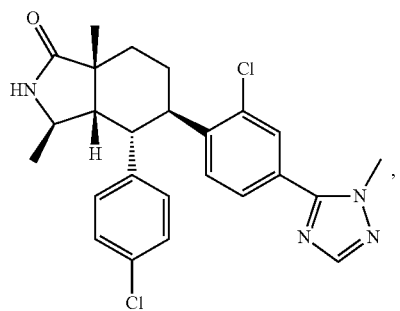
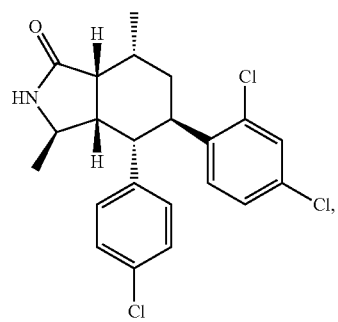
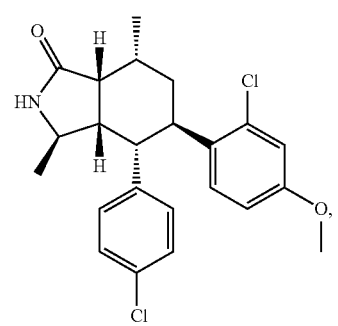
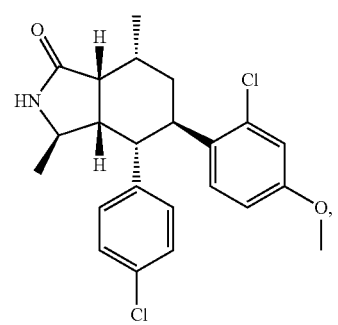
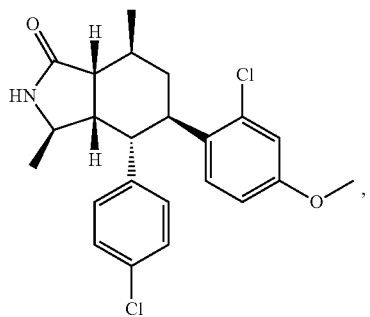
552
-continued
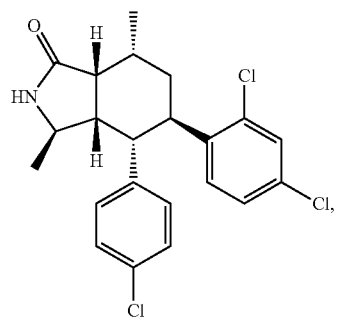
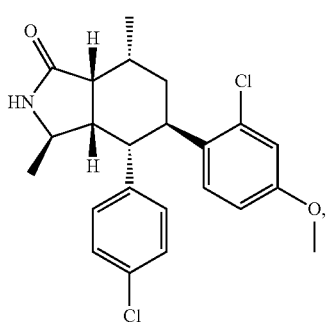
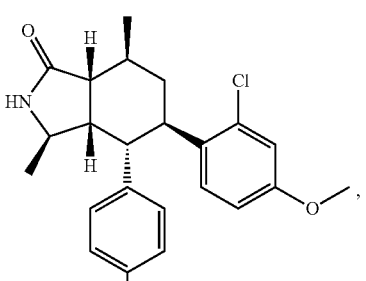
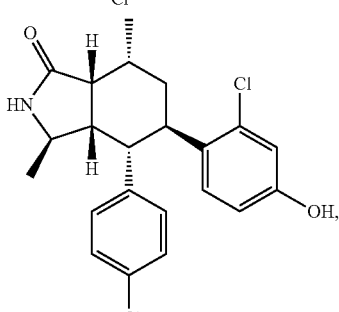
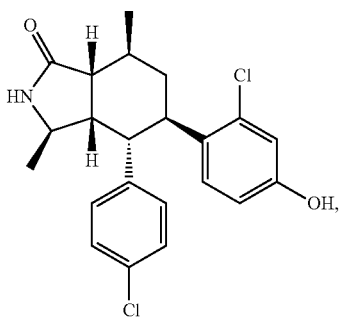

-continued
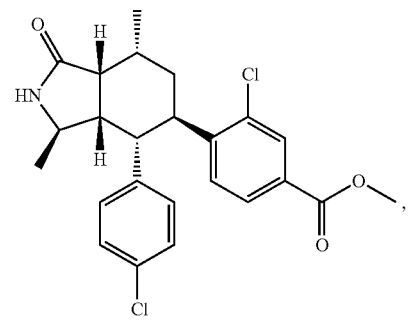
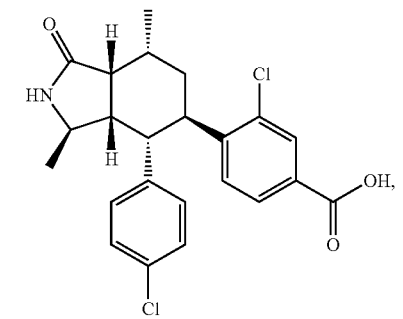
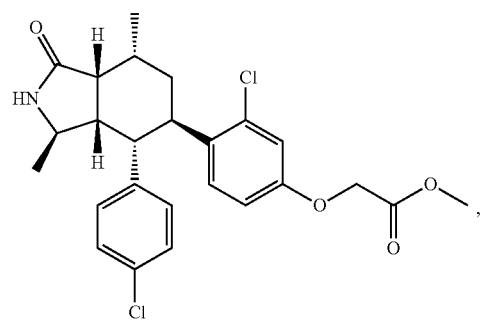
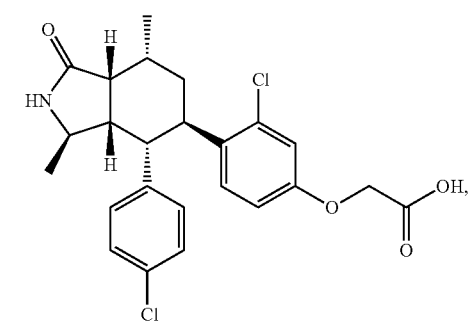
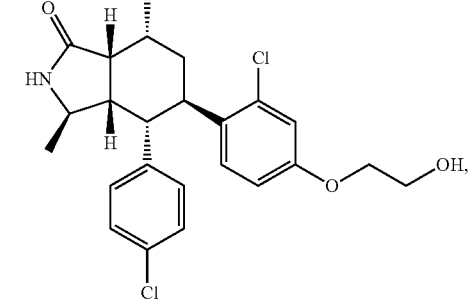
-continued
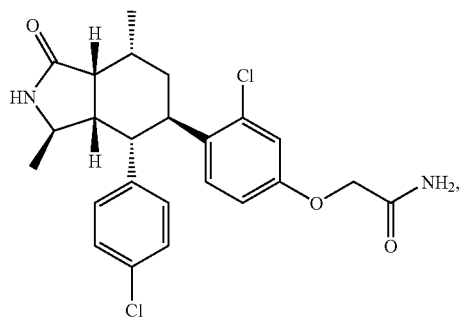
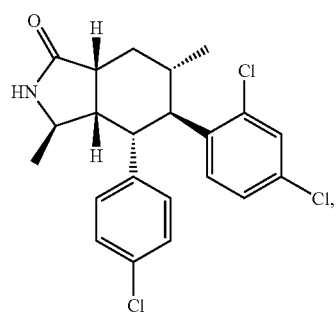
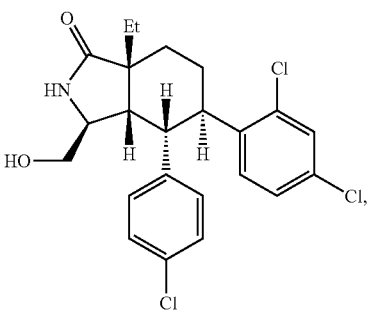
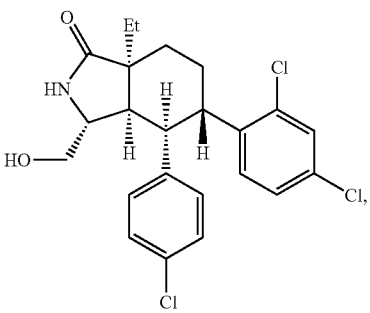
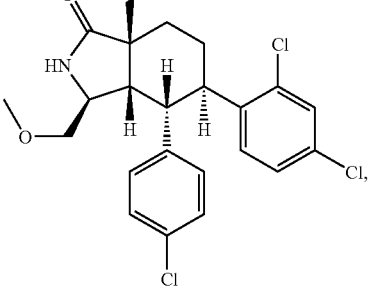

555
-continued
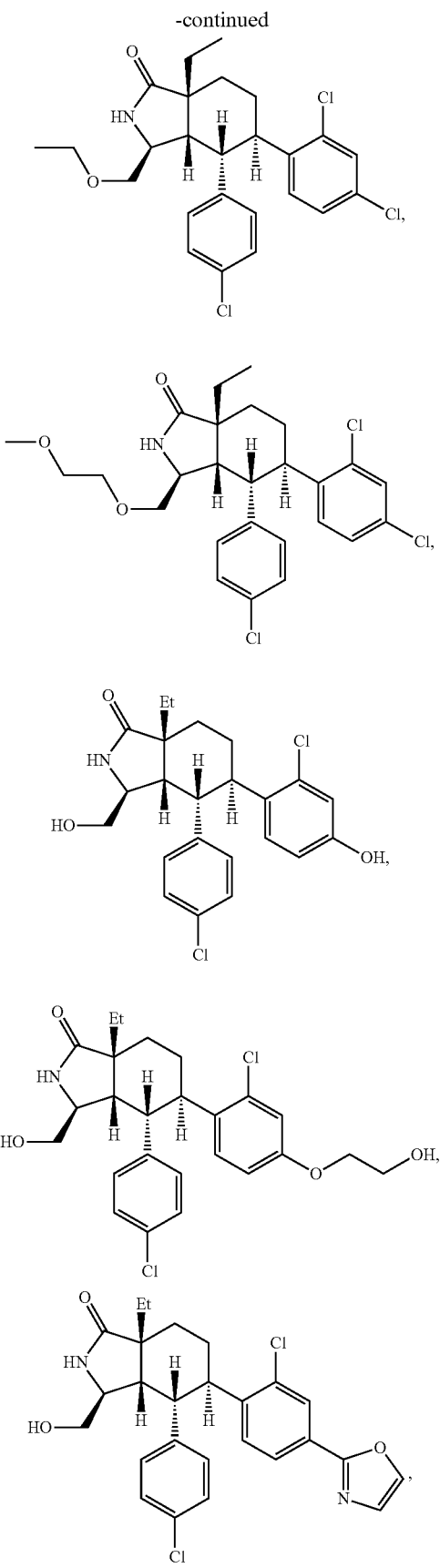
556
-continued
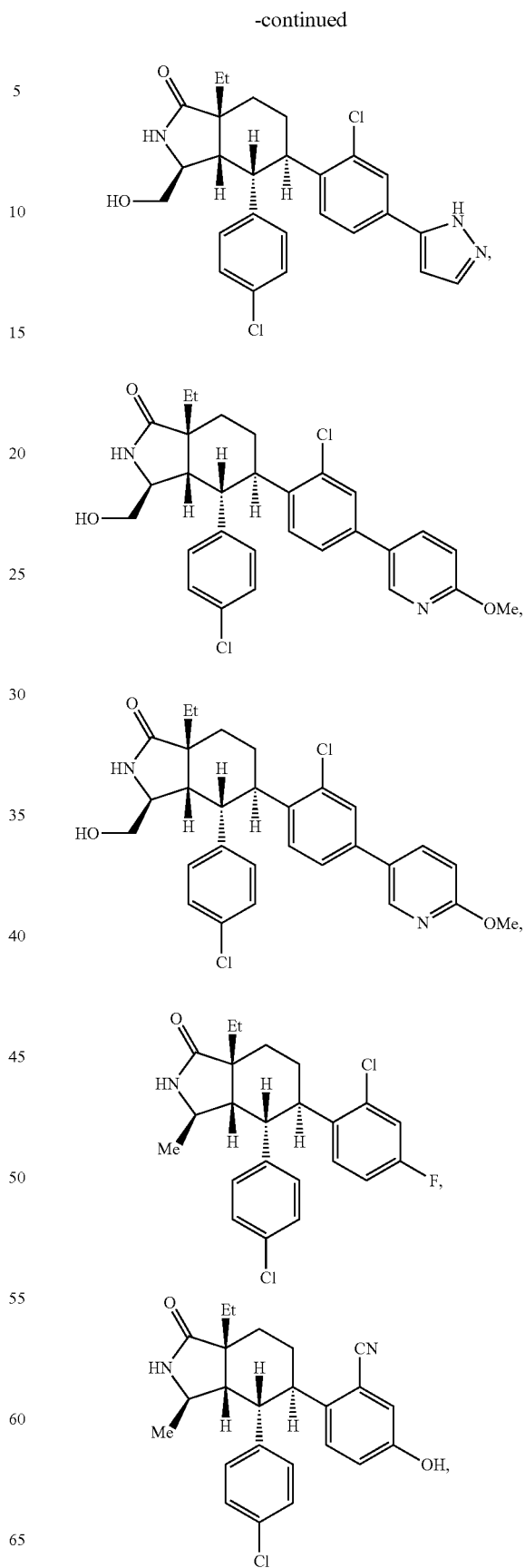

557
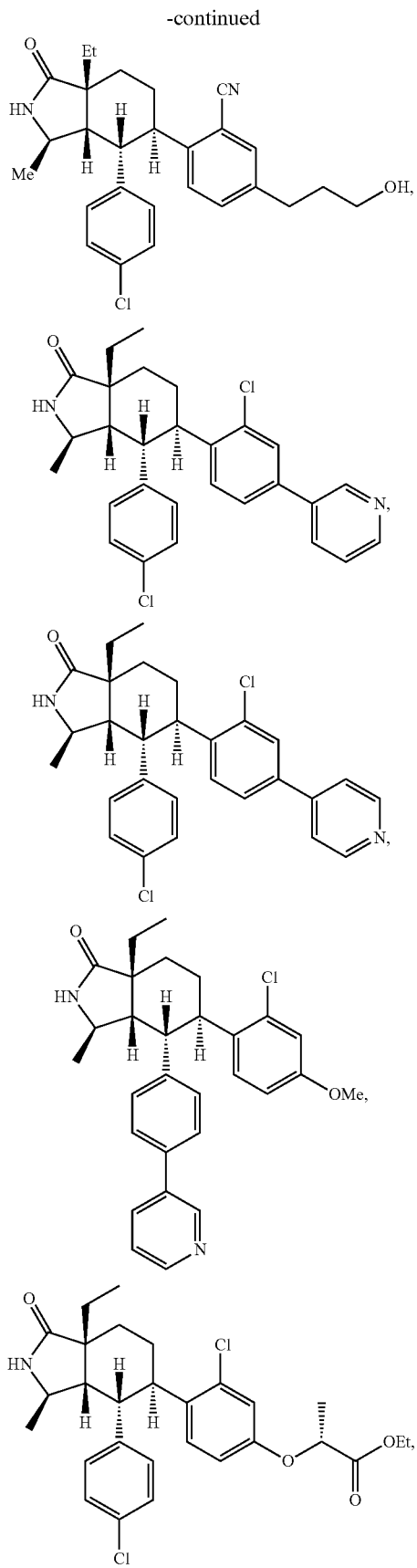
558
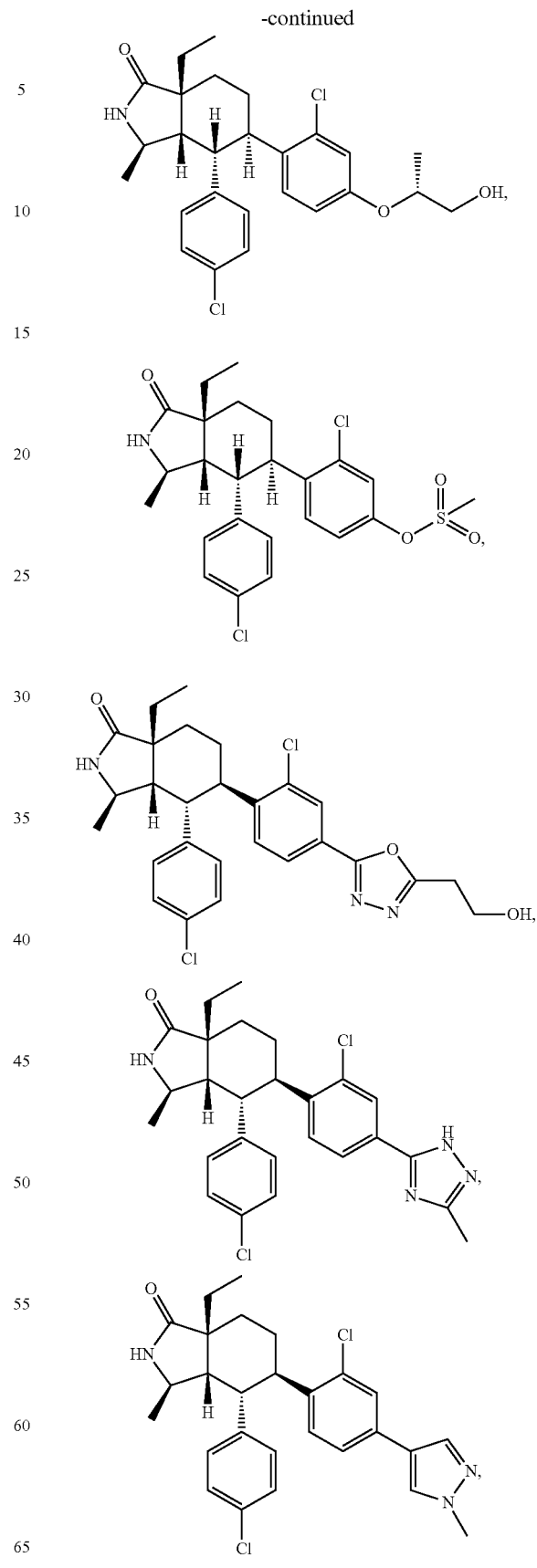

-continued
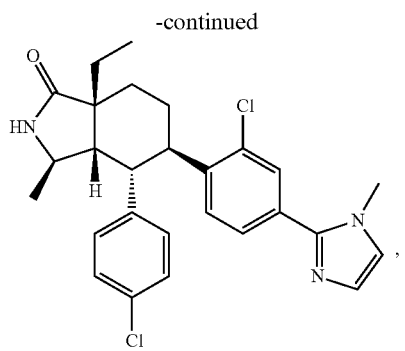,
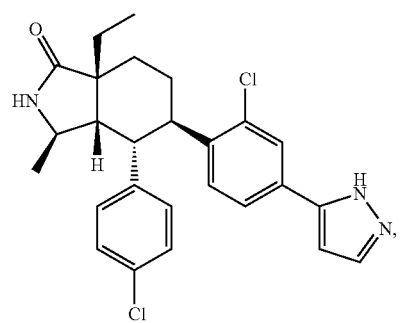,
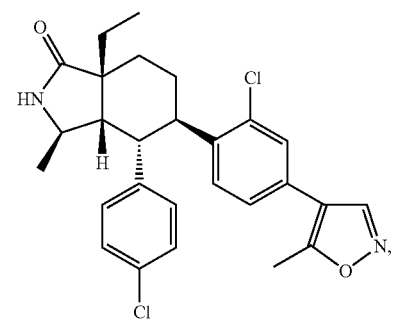,
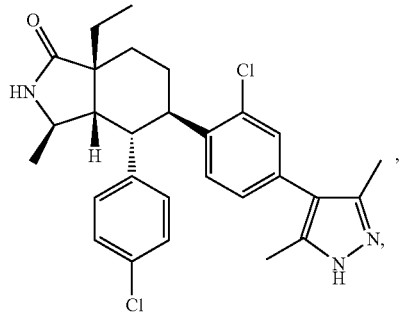,
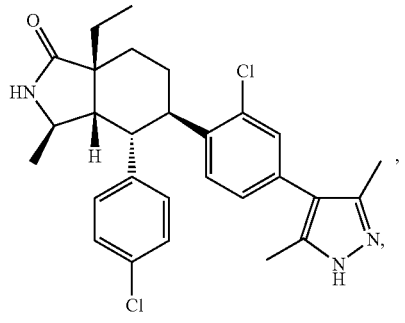,
-continued
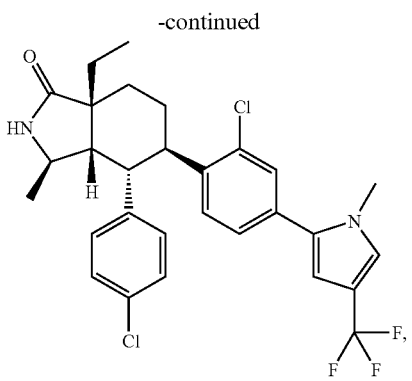,
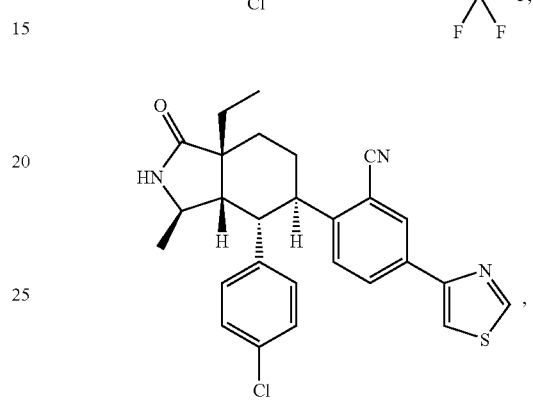,
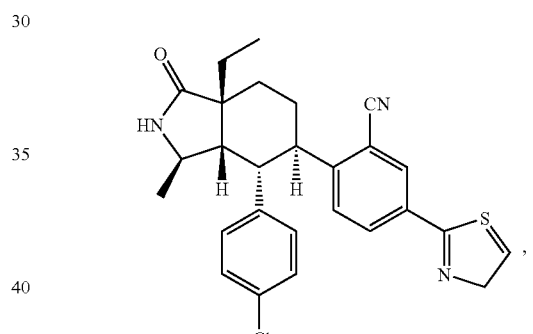,
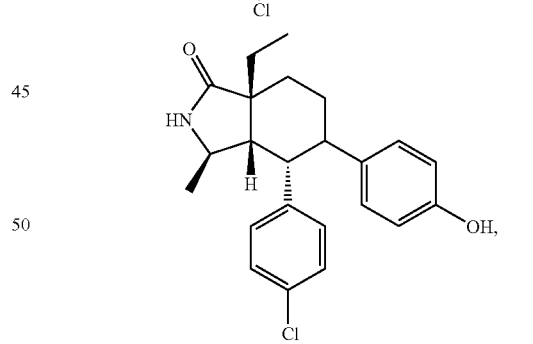,
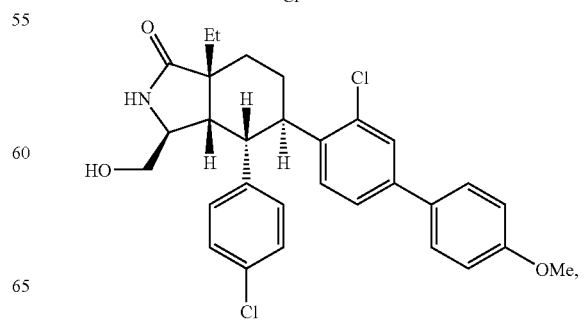,

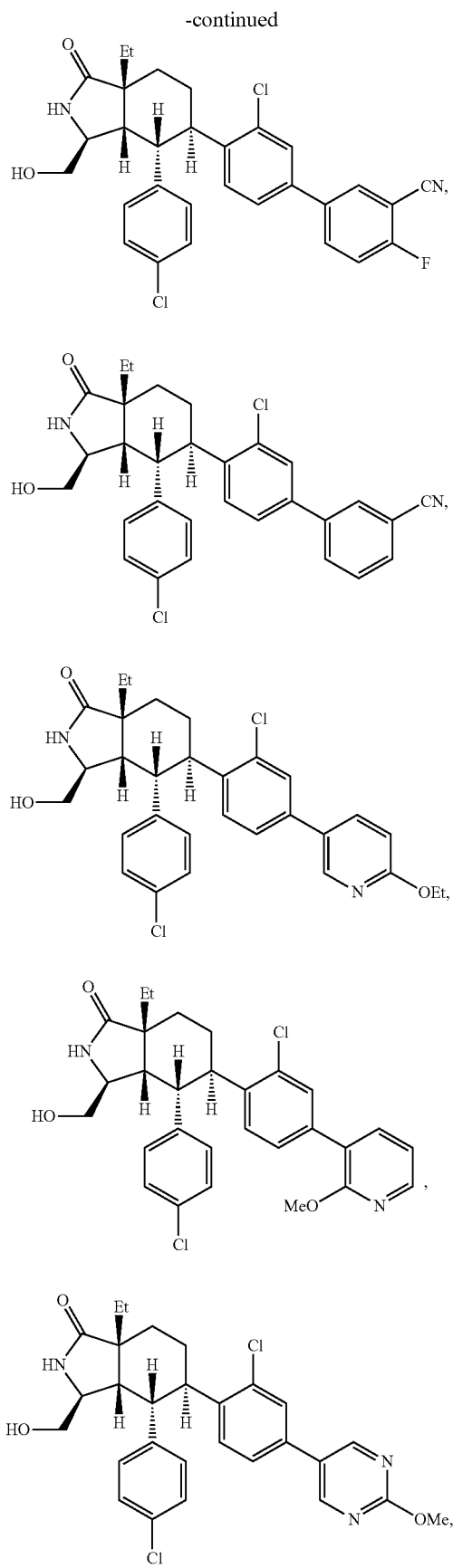
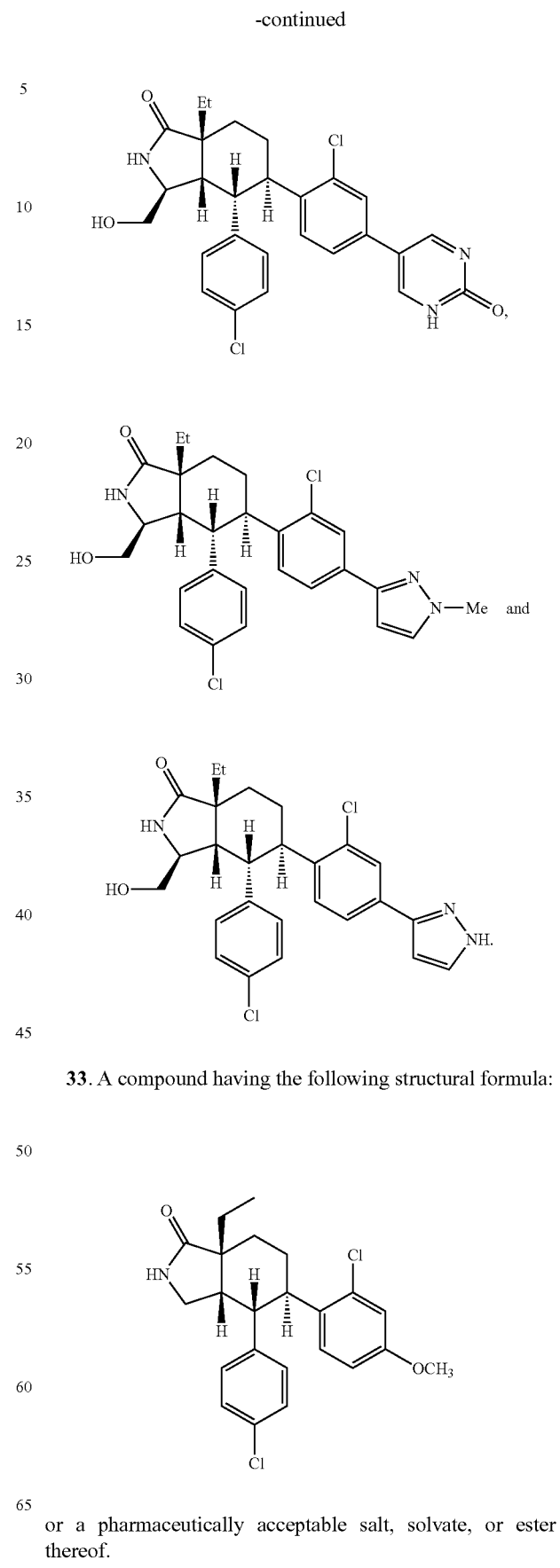
33. A compound having the following structural formula:
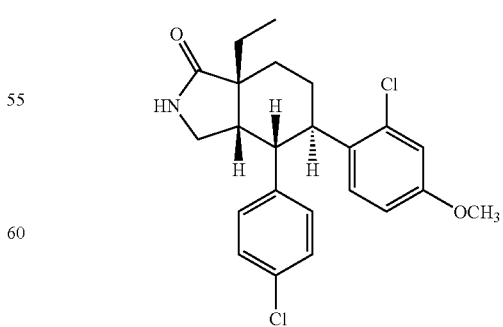
or a pharmaceutically acceptable salt, solvate, or ester thereof.

34. A compound having the following structural formula:

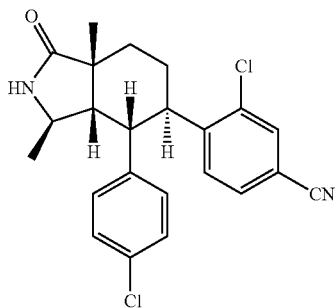

or a pharmaceutically acceptable salt, solvate, or ester thereof.

35. A compound having the following structural formula:

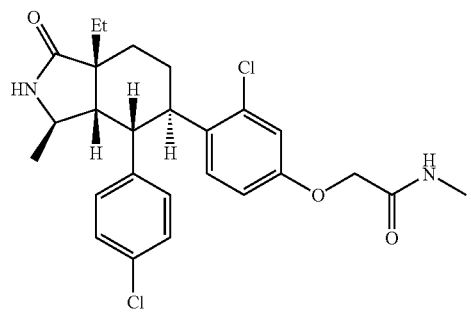

or a pharmaceutically acceptable salt, solvate, or ester thereof.

36. A compound having the following structural formula:

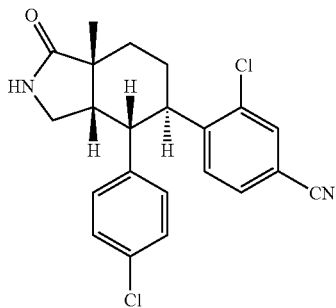

or a pharmaceutically acceptable salt, solvate, or ester thereof.

37. A compound having the following structural formula:

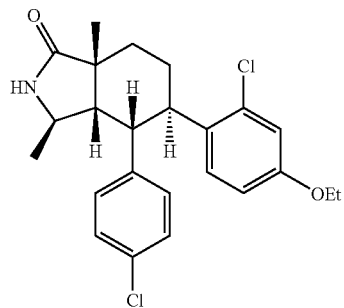

or a pharmaceutically acceptable salt, solvate, or ester thereof.

38. A compound having the following structural formula:

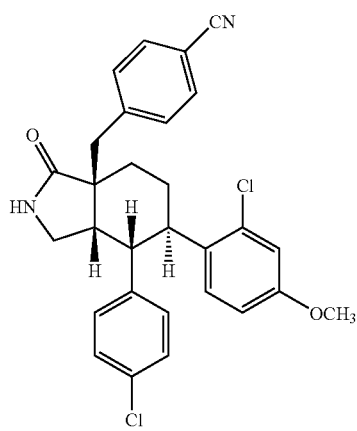

or a pharmaceutically acceptable salt, solvate, or ester thereof.

39. A compound having the following structural formula:

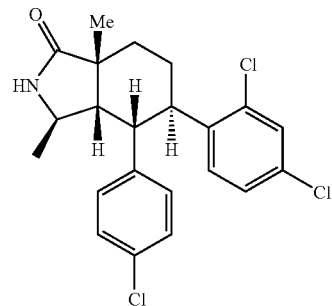

or a pharmaceutically acceptable salt, solvate, or ester thereof.

40. A compound having the following structural formula:

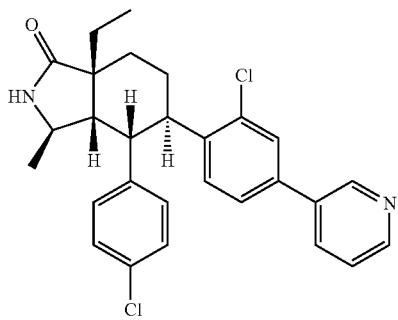

or a pharmaceutically acceptable salt, solvate, or ester thereof.

41. A compound having the following structural formula:

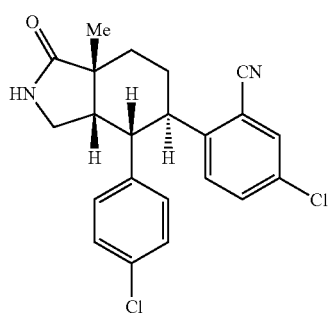

or a pharmaceutically acceptable salt, solvate, or ester thereof.

42. A compound having the following structural formula:

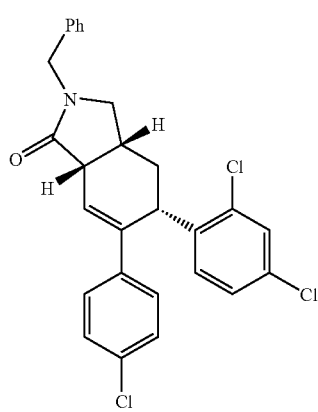

or a pharmaceutically acceptable salt, solvate, or ester thereof.

43. A compound having the following structural formula:

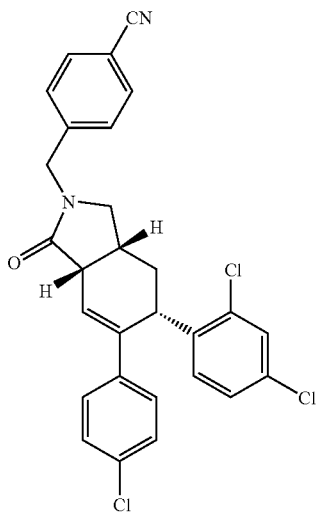

or a pharmaceutically acceptable salt, solvate, or ester thereof.

44. A compound having the following structural formula:

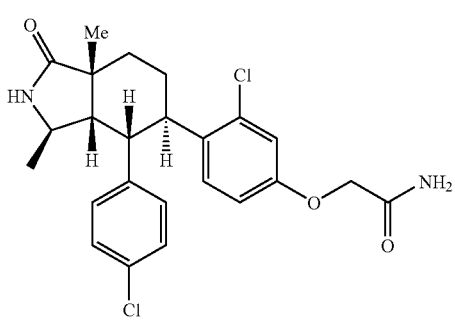

or a pharmaceutically acceptable salt, solvate, or ester thereof.

45. A compound having the following structural formula:

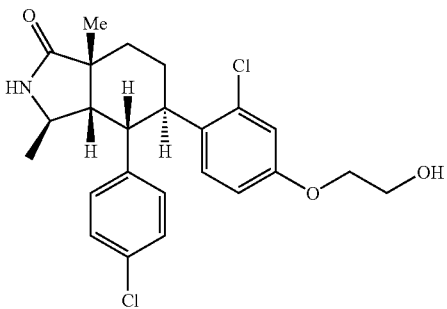

or a pharmaceutically acceptable salt, solvate, or ester thereof.

46. A compound having the following structural formula:

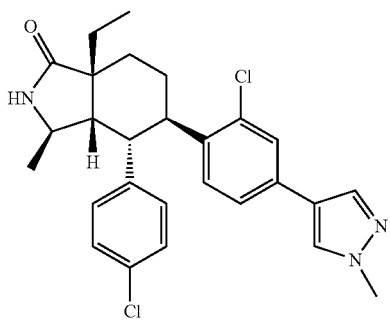

or a pharmaceutically acceptable salt, solvate, or ester thereof.

47. A compound having the following structural formula:

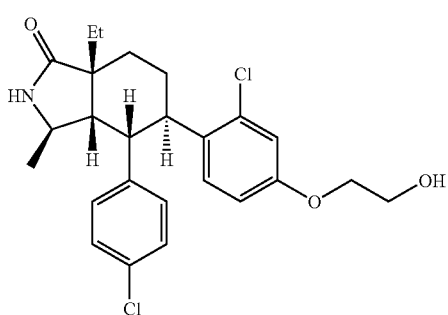

or a pharmaceutically acceptable salt, solvate, or ester thereof.

48. A compound having the following structural formula:

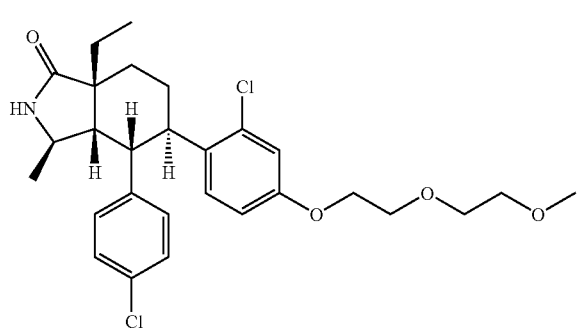

or a pharmaceutically acceptable salt, solvate, or ester thereof.

49. A compound having the following structural formula:

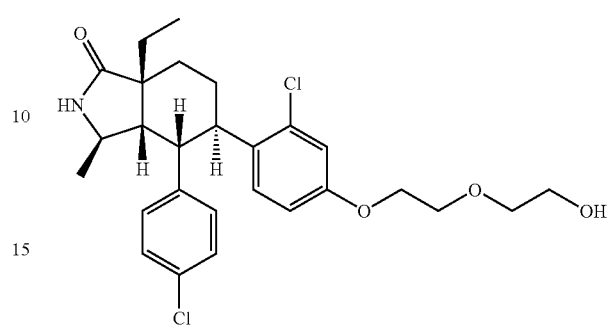

or a pharmaceutically acceptable salt, solvate, or ester thereof.

50. A compound having the following structural formula:

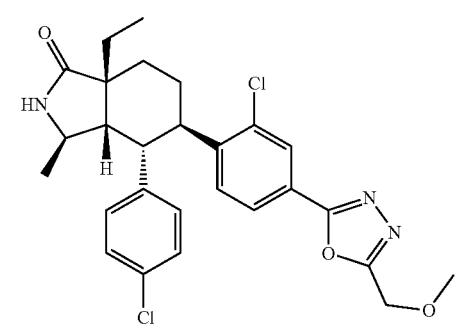

or a pharmaceutically acceptable salt, solvate, or ester thereof.

51. A compound having the following structural formula:

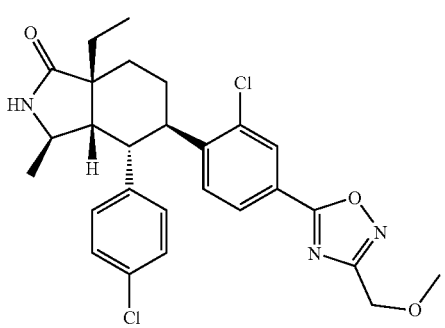

or a pharmaceutically acceptable salt, solvate, or ester thereof.

52. A compound having the following structural formula:

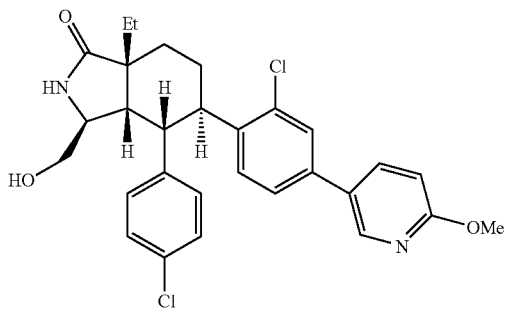

or a pharmaceutically acceptable salt, solvate, or ester thereof.

53. A compound having the following structural formula:

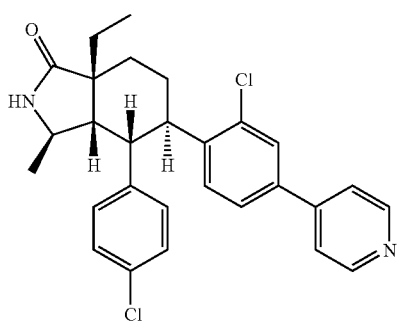

or a pharmaceutically acceptable salt, solvate, or ester thereof.

54. A compound having the following structural formula:

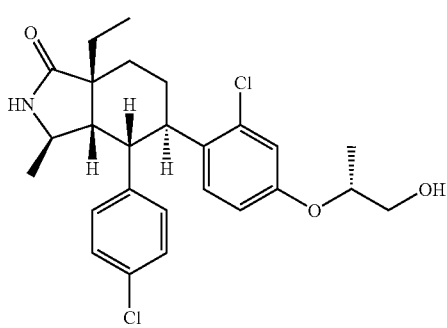

or a pharmaceutically acceptable salt, solvate, or ester thereof.

55. A compound having the following structural formula:

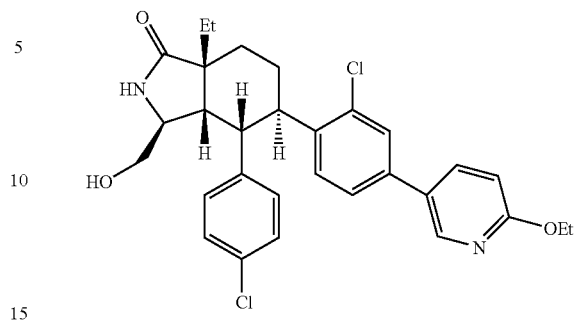

or a pharmaceutically acceptable salt, solvate, or ester thereof.

56. A compound having the following structural formula:

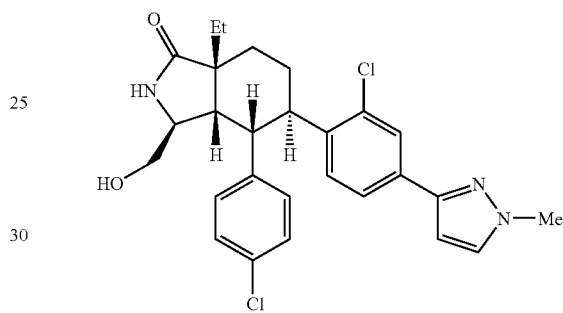

or a pharmaceutically acceptable salt, solvate, or ester thereof.

57. A composition comprising:
at least one compound of Formula (I) according to claim 1, or a pharmaceutically acceptable salt, solvate, or ester thereof; and
at least one cholesterol lowering compound.

58. The composition of claim 57, wherein said at least one cholesterol lowering compound is at least one sterol absorption inhibitor or at least one 5α-stanol absorption inhibitor.

59. The composition of claim 57, wherein said at least one cholesterol lowering compound is at least one substituted azetidinone compound or substituted β-lactam compound or a pharmaceutically acceptable salt, solvate, or ester thereof.

60. The composition of claim 57, wherein said at least one cholesterol lowering compound is ezetimibe.

61. A method of treating a disease, disorder, or condition comprising:
administering to a patient in need thereof a therapeutically effective amount of at least one compound of claim 1, or a pharmaceutically acceptable salt, solvate, or ester thereof; wherein said disease, disorder, or condition is selected from the group consisting of obesity, metabolic disorders, addiction, and diabetes.

62. The method of claim 61, wherein said disease, disorder, or condition is metabolic syndrome.

63. The method of claim 61, further comprising administering at least one additional active ingredient.

64. The method of claim 63 wherein at least one additional active ingredient is a cholesterol lowering compound.

65. The method of claim 63 wherein at least one additional active ingredient is at least one sterol absorption inhibitor or at least one 5α-stanol absorption inhibitor.

66. The method of claim 64 wherein said at least one cholesterol lowering compound is at least one substituted azetidinone compound or substituted β-lactam compound or a pharmaceutically acceptable salt, solvate, or ester thereof.

67. The method of claim 63, wherein said additional active ingredient is ezetimibe.

* * * * *